(12) United States Patent
Soong et al.

(10) Patent No.: US 12,398,407 B2
(45) Date of Patent: Aug. 26, 2025

(54) YEAST EXPRESSING A HETEROLOGOUS PHOSPHOLIPASE FOR ETHANOL PRODUCTION

(71) Applicant: Novozymes A/S, Bagsvaerd (DK)

(72) Inventors: Chee-Leong Soong, Raleigh, NC (US); James Ron Huffman, Wake Forest, NC (US); Monica Tassone, West Sacramento, CA (US); Jung Yi, Sacramento, CA (US); Hanlin Ouyang, Raleigh, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 18/484,322

(22) Filed: Oct. 10, 2023

(65) Prior Publication Data
US 2024/0110204 A1 Apr. 4, 2024

Related U.S. Application Data

(62) Division of application No. 17/283,760, filed as application No. PCT/US2019/054996 on Oct. 7, 2019, now Pat. No. 11,807,889.

(60) Provisional application No. 62/742,805, filed on Oct. 8, 2018.

(51) Int. Cl.
| | |
|---|---|
| *C12P 7/06* | (2006.01) |
| *C12N 9/16* | (2006.01) |
| *C12N 9/18* | (2006.01) |
| *C12N 9/34* | (2006.01) |

(52) U.S. Cl.
CPC .............. *C12P 7/06* (2013.01); *C12N 9/16* (2013.01); *C12N 9/18* (2013.01); *C12N 9/2428* (2013.01); *C12Y 301/01004* (2013.01); *C12Y 301/04003* (2013.01); *C12Y 302/01001* (2013.01); *C12Y 302/01003* (2013.01)

(58) Field of Classification Search
None
See application file for complete search history.

(56) References Cited

U.S. PATENT DOCUMENTS

| | | | |
|---|---|---|---|
| 10,745,676 B2 * | 8/2020 | Sun | ........................ C11B 3/04 |
| 2015/0368627 A1 | 12/2015 | Sun et al. | |
| 2018/0155744 A1 | 6/2018 | Cripwell et al. | |

FOREIGN PATENT DOCUMENTS

| | | |
|---|---|---|
| WO | 1996040939 A2 | 12/1996 |
| WO | 2008135547 A1 | 11/2008 |
| WO | 2011128712 A1 | 10/2011 |
| WO | 2011153516 A2 | 12/2011 |
| WO | 2014090161 A1 | 6/2014 |
| WO | 2014147219 A1 | 9/2014 |
| WO | 2015140275 A1 | 9/2015 |
| WO | 2017037614 A1 | 3/2017 |
| WO | 2017077504 A1 | 5/2017 |
| WO | 2017087330 A1 | 5/2017 |
| WO | 2018075430 A1 | 4/2018 |
| WO | 2018098381 A1 | 5/2018 |

OTHER PUBLICATIONS

Accession BBO52657. Nov. 20, 2014 (Year: 2014).*
Aon, 2001, Metabolic engineering, 3, 250-264.
Chica et al., Current Opinion in Biotechnology, 2005, 378-384, 16(4).
Keun, 2012, Biochemistry molecular biology, Abstract.
Liu et al, 2014, WO2014090161—Accession No. BBI75668.
Singh et al., Current Protein and Peptide Science, 2017, 1-11, 18.

* cited by examiner

*Primary Examiner* — Christian L Fronda
(74) *Attorney, Agent, or Firm* — Eric J. Fechter

(57) ABSTRACT

Described herein are recombinant fermenting organisms having a heterologous polynucleotide encoding a phospholipase. Also described are processes for producing a fermentation product, such as ethanol, from starch or cellulosic-containing material with the recombinant fermenting organisms.

20 Claims, 4 Drawing Sheets
Specification includes a Sequence Listing.

YEAST EXPRESSING A HETEROLOGOUS PHOSPHOLIPASE FOR ETHANOL PRODUCTION

CROSS-REFERENCE TO RELATED APPLICATIONS

This application is a divisional of U.S. patent application Ser. No. 17/283,760 which is a 35 U.S.C. 371 national application of PCT/US2019/054996, filed Oct. 7, 2019, which claims priority or the benefit from U.S. Provisional Application Ser. No. 62/742,805, filed Oct. 8, 2018. The contents of these applications are fully incorporated herein by reference.

REFERENCE TO A SEQUENCE LISTING

This application contains a Sequence Listing in computer readable form, that was submitted as an xml file named SQ_ST26 (created on Oct. 3, 2023, containing 665 kb), which is incorporated herein by reference.

BACKGROUND

Production of ethanol from starch and cellulosic containing materials is well-known in the art.

The most commonly industrially used commercial process for starch-containing material, often referred to as a "conventional process", includes liquefying gelatinized starch at high temperature (about 85° C.) using typically a bacterial alpha-amylase, followed by simultaneous saccharification and fermentation (SSF) carried out anaerobically in the presence of typically a glucoamylase and a *Saccharomyces cerevisae* yeast.

Yeasts which are used for production of ethanol for use as fuel, such as in the corn ethanol industry, require several characteristics to ensure cost effective production of the ethanol. These characteristics include ethanol tolerance, low by-product yield, rapid fermentation, and the ability to limit the amount of residual sugars remaining in the ferment. Such characteristics have a marked effect on the viability of the industrial process.

Yeast of the genus *Saccharomyces* exhibits many of the characteristics required for production of ethanol. In particular, strains of *Saccharomyces cerevisiae* are widely used for the production of ethanol in the fuel ethanol industry. Strains of *Saccharomyces cerevisiae* that are widely used in the fuel ethanol industry have the ability to produce high yields of ethanol under fermentation conditions found in, for example, the fermentation of corn mash. An example of such a strain is the yeast used in commercially available ethanol yeast product called ETHANOL RED®.

*Saccharomyces cerevisae* yeast have been genetically engineered to express alpha-amylase and/or glucoamylase to improve yield and decrease the amount of exogenously added enzymes necessary during SSF (e.g., WO2018/098381, WO2017/087330, WO2017/037614, WO2011/128712, WO2011/153516, US2018/0155744). Yeast have also been engineered to express trehalase in an attempt to increase fermentation yield by breaking down residual trehalose (e.g., WO2017/077504).

WO2008/135547 concerns reducing foam in processes for production of a fermentation product by contacting the fermentation media comprising a fermenting organism with a lipolytic enzyme selected from the group consisting of phospholipase, lyso-phospholipase and lipase, and a metal salt.

WO2014/147219 concerns a phospholipase A from *Talaromyces leycettanus*.

WO2015/140275 discloses a phospholipase C from *Bacillus thuringiensis*.

Despite significant improvement of ethanol production processes over the past decade there is still a desire and need for providing improved processes of ethanol fermentation from starch and cellulosic containing material in an economically and commercially relevant scale.

For example, foam generation during ethanol fermentation is a major problem, especially in ethanol production processes where starch-containing material is liquefied with an alpha-amylase and a protease before saccharification and fermentation. Additionally, the use of nitrogen supplements (e.g., urea) is an added expense during fermentation. Therefore, there is a desire to, inter alia, reduce foam and/or reduce supplemental nitrogen requirements in ethanol fermentation.

SUMMARY

Described herein are, inter alia, methods for producing a fermentation product, such as ethanol, from starch or cellulosic-containing material, and yeast suitable for use in such processes. The Applicant has surprisingly found that yeasts expressing a phospholipase provide beneficial properties during fermentation, such as reduced foaming, improved oil extraction yield, and improved ethanol yield.

A first aspect relates to methods of producing a fermentation product from a starch-containing or cellulosic-containing material comprising: (a) saccharifying the starch-containing or cellulosic-containing material; and (b) fermenting the saccharified material of step (a) with a fermenting organism; wherein the fermenting organism comprises a heterologous polynucleotide encoding a phospholipase. In some embodiments, the phospholipase is a Phospholipase A or a Phospholipase C.

In some embodiments of the methods, fermentation and saccharification are performed simultaneously in a simultaneous saccharification and fermentation (SSF). In other embodiments, fermentation and saccharification are performed sequentially (SHF).

In some embodiments of the methods, the method comprises recovering the fermentation product from the from the fermentation (e.g., by distillation).

In some embodiments of the methods, the fermentation product is ethanol.

In some embodiments of the methods, fermentation is performed under reduced nitrogen conditions (e.g., less than 1000 ppm urea or ammonium hydroxide, such as less than 750 ppm, less than 500 ppm, less than 400 ppm, less than 300 ppm, less than 250 ppm, less than 200 ppm, less than 150 ppm, less than 100 ppm, less than 75 ppm, less than 50 ppm, less than 25 ppm, or less than 10 ppm).

In some embodiments of the methods, the method results in higher yield of fermentation product (e.g., ethanol) and/or reduced foam accumulation when compared to the same process using an identical cell without the heterologous polynucleotide encoding the phospholipase under the same conditions (e.g., at about or after 54 hours fermentation, such as the conditions described in Examples 3 or 4). In some embodiments, the method results in at least 0.25% (e.g., 0.5%, 0.75%, 1.0%, 1.25%, 1.5%, 1.75%, 2%, 3% or 5%) higher yield of fermentation product.

In some embodiments of the methods, the phospholipase has a mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 235-242 and 252-342. In some embodiments of the methods, the phospholipase has a mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 235, 236, 237, 238, 239, 240, 241 and 242. In some embodiments of the methods, the heterologous polynucleotide encodes a phospholipase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 235-242 and 252-342 (e.g., any one of SEQ ID NOs: 235, 236, 237, 238, 239, 240, 241 and 242). In some embodiments of the methods, the heterologous polynucleotide encodes a phospholipase having a mature polypeptide sequence comprising or consisting of the amino acid sequence of any one of SEQ ID NOs: 235-242 and 252-342 (e.g., any one of SEQ ID NOs: SEQ ID NOs: 235, 236, 237, 238, 239, 240, 241 and 242).

In some embodiments of the methods, saccharification of step occurs on a starch-containing material, and wherein the starch-containing material is either gelatinized or ungelatinized starch.

In some embodiments of the methods, the method comprises liquefying the starch-containing material by contacting the material with an alpha-amylase prior to saccharification.

In some embodiments of the methods, liquefying the starch-containing material and/or saccharifying the starch-containing material is conducted in presence of exogenously added protease.

In some embodiments of the methods, the fermenting organism comprises a heterologous polynucleotide encoding a glucoamylase, such as a glucoamylase having a mature polypeptide sequence with 60%, e.g., at least 65%, 70%, 75%, 80%, 85%, 90%, 95%, 97%, 98%, 99%, or 100% sequence identity, to the amino acid sequence of a *Pycnoporus* glycoamylase (e.g., a *Pycnoporus sanguineus* glucoamylase of SEQ ID NO: 229), a *Gloeophyllum* glucoamylase (e.g. a *Gloeophyllum sepiarium* of SEQ ID NO: 8), or a glucoamylase of any one of SEQ ID NOs: 102-113 (e.g., a *Saccharomycopsis fibuligera* glucoamylase of SEQ ID NO: 103 or 104, or a *Trichoderma reesei* glucoamylase of SEQ ID NO: 230).

In some embodiments of the methods, the fermenting organism comprises a heterologous polynucleotide encoding an alpha-amylase, such as an alpha-amylase having a mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 76-101, 121-174 and 231. In some embodiments of the methods, the heterologous polynucleotide encodes an alpha-amylase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 76-101, 121-174 and 231. In some embodiments of the methods, the heterologous polynucleotide encodes an alpha-amylase having a mature polypeptide sequence comprising or consisting of the amino acid sequence of any one of SEQ ID NOs: SEQ ID NOs: 76-101, 121-174 and 231.

In some embodiments of the methods, the fermenting organism comprises a heterologous polynucleotide encoding a trehalase, such as a trehalase having a mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 175-226. In some embodiments of the methods, the heterologous polynucleotide encodes a trehalase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 175-226. In some embodiments of the methods, the heterologous polynucleotide encodes a trehalase having a mature polypeptide sequence comprising or consisting of the amino acid sequence of any one of SEQ ID NOs: SEQ ID NOs: 175-226.

In some embodiments of the methods, the fermenting organism comprises a heterologous polynucleotide encoding a protease, such as a protease having a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 9-73 (e.g., any one of SEQ ID NOs: 9, 14, 16, 21, 22, 33, 41, 45, 61, 62, 66, 67, and 69; such as any one of SEQ NOs: 9, 14, 16, and 69).

In some embodiments of the methods, saccharification of step occurs on a cellulosic-containing material, and wherein the cellulosic-containing material is pretreated (e.g. a dilute acid pretreatment).

In some embodiments of the methods, saccharification occurs on a cellulosic-containing material, and wherein the enzyme composition comprises one or more enzymes selected from a cellulase (e.g., endoglucanase, a cellobiohydrolase, or a beta-glucosidase), an AA9 polypeptide, a hemicellulase (e.g., a xylanase, an acetylxylan esterase, a feruloyl esterase, an arabinofuranosidase, a xylosidase, or a glucuronidase), a CIP, an esterase, an expansin, a ligninolytic enzyme, an oxidoreductase, a pectinase, a protease, and a swollenin.

In some embodiments of the methods, the fermenting organism is a *Saccharomyces, Rhodotorula, Schizosaccharomyces, Kluyveromyces, Pichia, Hansenula, Rhodosporidium, Candida, Yarrowia, Lipomyces, Cryptococcus,* or *Dekkera* sp. cell. In some embodiments, the fermenting organism is a *Saccharomyces cerevisiae* cell.

Another aspect relates to a recombinant yeast cell comprising a heterologous polynucleotide encoding a phospholipase. In some embodiments, the phospholipase is a Phospholipase A or a Phospholipase C.

In some embodiments of the yeast cell, the cell is capable of higher yield of fermentation product and/or reduced foam accumulation when compared to fermentation using the same process and an identical cell without the heterologous polynucleotide encoding the phospholipase under the same conditions (e.g., at about or after 54 hours fermentation, such as the conditions described in Examples 3 or 4). In some embodiments, the cell is capable of at least 0.25% (e.g., 0.5%, 0.75%, 1.0%, 1.25%, 1.5%, 1.75%, 2%, 3% or 5%) higher yield of fermentation product.

In some embodiments, the recombinant yeast cell is a *Saccharomyces, Rhodotorula, Schizosaccharomyces, Kluyveromyces, Pichia, Hansenula, Rhodosporidium, Candida, Yarrowia, Lipomyces, Cryptococcus,* or *Dekkera* sp. cell. In some embodiments, the recombinant yeast cell is a *Saccharomyces cerevisiae* cell.

In some embodiments of the yeast cell, the fermenting organism comprises a heterologous polynucleotide encoding a glucoamylase, such as a glucoamylase having a mature polypeptide sequence with 60%, e.g., at least 65%, 70%, 75%, 80%, 85%, 90%, 95%, 97%, 98%, 99%, or 100% sequence identity, to the amino acid sequence of a *Pycnoporus* glycoamylase (e.g., a *Pycnoporus sanguineus* glucoamylase of SEQ ID NO: 229), a *Gloeophyllum* glucoamylase (e.g. a *Gloeophyllum sepiarium* of SEQ ID NO: 8), or a glucoamylase of any one of SEQ ID NOs: 102-113 (e.g., a *Saccharomycopsis fibuligera* glucoamylase of SEQ ID NO: 103 or 104, or a *Trichoderma reesei* glucoamylase of SEQ ID NO: 230).

In some embodiments of the yeast cell, the fermenting organism comprises a heterologous polynucleotide encoding an alpha-amylase, wherein the alpha-amylase has a mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 76-101, 121-174 and 231. In some embodiments of the methods, the heterologous polynucleotide encodes an alpha-amylase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 76-101, 121-174 and 231. In some embodiments of the methods, the heterologous polynucleotide encodes an alpha-amylase having a mature polypeptide sequence comprising or consisting of the amino acid sequence of any one of SEQ ID NOs: SEQ ID NOs: 76-101, 121-174 and 231.

In some embodiments of the yeast cell, the fermenting organism comprises a heterologous polynucleotide encoding a trehalase, wherein the trehalase has mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 175-226. In some embodiments of the methods, the heterologous polynucleotide encodes a trehalase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 175-226. In some embodiments of the methods, the heterologous polynucleotide encodes a trehalase having a mature polypeptide sequence comprising or consisting of the amino acid sequence of any one of SEQ ID NOs: SEQ ID NOs: 175-226.

In some embodiments of the yeast cell, the fermenting organism comprises a heterologous polynucleotide encoding a protease, such as a protease having a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 9-73 (e.g., any one of SEQ ID NOs: 9, 14, 16, 21, 22, 33, 41, 45, 61, 62, 66, 67, and 69; such as any one of SEQ ID NOs: 9, 14, 16, and 69).

DEFINITIONS

Figure 1:
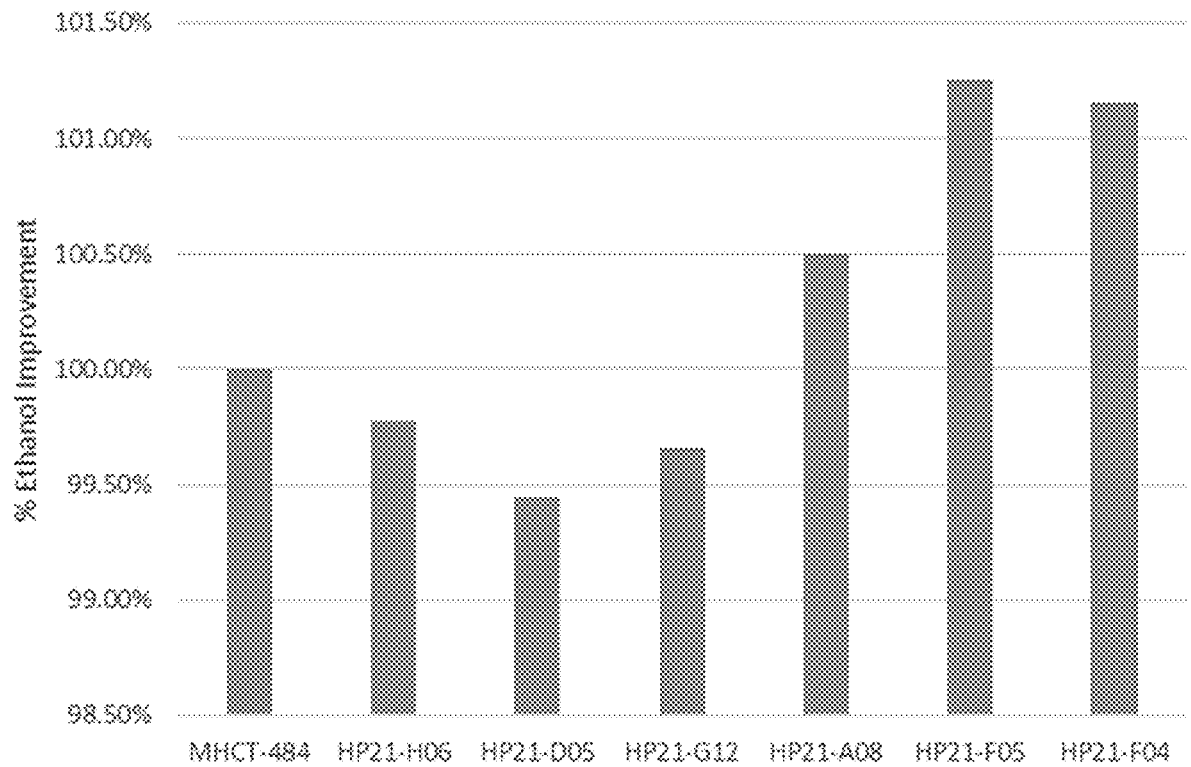
FIG. 1 shows % ethanol improvement for phospholipase-expressing yeast strains and control strain MHCT-484 described in Example 3.

Unless defined otherwise or clearly indicated by context, all technical and scientific terms used herein have the same meaning as commonly understood by one of ordinary skill in the art.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-amylase: The term "alpha amylase" means an 1,4-alpha-D-glucan glucanohydrolase, EC. 3.2.1.1, which catalyze hydrolysis of starch and other linear and branched 1,4-glucosidic oligo- and polysaccharides. For purposes of the present invention, alpha amylase activity can be determined using an alpha amylase assay described in the examples section below.

Auxiliary Activity 9: The term "Auxiliary Activity 9" or "AA9" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic-containing material by an enzyme having cellulolytic activity. Cellulolytic enhancing activity can be determined by measuring the increase in reducing sugars or the increase of the total of cellobiose and glucose from the hydrolysis of a cellulosic-containing material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40 C-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST® 1.5 L (Novozymes A/S, Bagsværd, Denmark) and beta-glucosidase as the source of the cellulolytic activity, wherein the beta-glucosidase is present at a weight of at least 2-5% protein of the cellulase protein loading. In one embodiment, the beta-glucosidase is an *Aspergillus oryzae* beta-glucosidase (e.g., recombinantly produced in *Aspergillus oryzae* according to WO 02/095014). In another embodiment, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/mL of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic-containing material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

Catalase: The term "catalase" means a hydrogen-peroxide:hydrogen-peroxide oxidoreductase (EC 1.11.1.6) that catalyzes the conversion of 2 $H_2O_2$ to $O_2$+2 $H_2O$. For purposes of the present invention, catalase activity is determined according to U.S. Pat. No. 5,646,025. One unit of catalase activity equals the amount of enzyme that catalyzes the oxidation of 1 μmole of hydrogen peroxide under the assay conditions.

Catalytic domain: The term "catalytic domain" means the region of an enzyme containing the catalytic machinery of the enzyme.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teen et al., 1998, *Biochem. Soc. Trans.* 26:173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic-containing material. Such enzymes include endoglucanase(s), cellobiohydrolase (s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic-containing material by cellulolytic enzyme(s) under the following conditions: 1-50 mg of cellulolytic enzyme protein/g of cellulose in pretreated corn stover (PCS) (or other pretreated cellulosic-containing material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 mL reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, CA, USA).

Coding sequence: The term "coding sequence" or "coding region" means a polynucleotide sequence, which specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a sequence of genomic DNA, cDNA, a synthetic polynucleotide, and/or a recombinant polynucleotide.

Control sequence: The term "control sequence" means a nucleic acid sequence necessary for polypeptide expression. Control sequences may be native or foreign to the polynucleotide encoding the polypeptide, and native or foreign to each other. Such control sequences include, but are not limited to, a leader sequence, polyadenylation sequence, propeptide sequence, promoter sequence, signal peptide sequence, and transcription terminator sequence. The control sequences may be provided with linkers for the purpose of introducing specific restriction sites facilitating ligation of the control sequences with the coding region of the polynucleotide encoding a polypeptide.

Disruption: The term "disruption" means that a coding region and/or control sequence of a referenced gene is partially or entirely modified (such as by deletion, insertion, and/or substitution of one or more nucleotides) resulting in the absence (inactivation) or decrease in expression, and/or the absence or decrease of enzyme activity of the encoded polypeptide. The effects of disruption can be measured using techniques known in the art such as detecting the absence or decrease of enzyme activity using from cell-free extract measurements referenced herein; or by the absence or decrease of corresponding mRNA (e.g., at least 25% decrease, at least 50% decrease, at least 60% decrease, at least 70% decrease, at least 80% decrease, or at least 90% decrease); the absence or decrease in the amount of corresponding polypeptide having enzyme activity (e.g., at least 25% decrease, at least 50% decrease, at least 60% decrease, at least 70% decrease, at least 80% decrease, or at least 90% decrease); or the absence or decrease of the specific activity of the corresponding polypeptide having enzyme activity (e.g., at least 25% decrease, at least 50% decrease, at least 60% decrease, at least 70% decrease, at least 80% decrease, or at least 90% decrease). Disruptions of a particular gene of interest can be generated by methods known in the art, e.g., by directed homologous recombination (see *Methods in Yeast Genetics* (1997 edition), Adams, Gottschling, Kaiser, and Stems, Cold Spring Harbor Press (1998)).

Endogenous gene: The term "endogenous gene" means a gene that is native to the referenced host cell. "Endogenous gene expression" means expression of an endogenous gene.

Endoglucanase: The term "endoglucanase" means a 4-(1, 3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of the polypeptide including, but not limited to, transcription, post-transcriptional modification, translation, post-translational modification, and secretion. Expression can be measured—for example, to detect increased expression—by techniques known in the art, such as measuring levels of mRNA and/or translated polypeptide.

Expression vector: The term "expression vector" means a linear or circular DNA molecule that comprises a polynucleotide encoding a polypeptide and is operably linked to control sequences that provide for its expression.

Fermentable medium: The term "fermentable medium" or "fermentation medium" refers to a medium comprising one or more (e.g., two, several) sugars, such as glucose, fructose, sucrose, cellobiose, xylose, xylulose, arabinose, mannose, galactose, and/or soluble oligosaccharides, wherein the medium is capable, in part, of being converted (fermented) by a host cell into a desired product, such as ethanol. In some instances, the fermentation medium is derived from a natural source, such as sugar cane, starch, or cellulose, and may be the result of pretreating the source by enzymatic hydrolysis (saccharification). The term fermentation medium is understood herein to refer to a medium before the fermenting organism is added, such as, a medium resulting from a saccharification process, as well as a medium used in a simultaneous saccharification and fermentation process (SSF).

Glucoamylase: The term "glucoamylase" (1,4-alpha-D-glucan glucohydrolase, EC 3.2.1.3) is defined as an enzyme that catalyzes the release of D-glucose from the non-reducing ends of starch or related oligo- and polysaccharide molecules. For purposes of the present invention, glucoamylase activity may be determined according to the procedures known in the art, such as those described in the Examples of U.S. Provisional Patent Application No. 62/703,103, filed Jul. 25, 2018.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

Heterologous polynucleotide: The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign) promoter; or a native polynucleotide in a host cell having one or more extra copies of the polynucleotide to quantitatively alter expression. A "heterologous gene" is a gene comprising a heterologous polynucleotide.

High stringency conditions: The term "high stringency conditions" means for probes of at least 100 nucleotides in length, prehybridization and hybridization at 42° C. in 5×SSPE, 0.3% SDS, 200 micrograms/mL sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, and the like with a nucleic acid construct or expression vector comprising a polynucleotide described herein (e.g., a polynucleotide encoding an alpha-amylase and/or trehalase). The term "host cell" encompasses any progeny of a parent cell that is not identical to the parent cell due to mutations that occur during replication. The term "recombinant cell" is defined herein as a non-naturally occurring host cell comprising one or more (e.g., two, several) heterologous polynucleotides.

Low stringency conditions: The term "low stringency conditions" means for probes of at least 100 nucleotides in length, prehybridization and hybridization at 42° C. in 5×SSPE, 0.3% SDS, 200 micrograms/mL sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" is defined herein as a polypeptide having biological activity that is in its final form following translation and any post-translational modifications, such as N-terminal processing, C-terminal truncation, glycosylation, phosphorylation, etc. The mature polypeptide sequence lacks a signal sequence, which may be determined using techniques known in the art (See, e.g., Zhang and Henzel, 2004, *Protein Science* 13: 2819-2824).

Medium stringency conditions: The term "medium stringency conditions" means for probes of at least 100 nucleotides in length, prehybridization and hybridization at 42° C. in 5×SSPE, 0.3% SDS, 200 micrograms/mL sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/mL sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Nucleic acid construct: The term "nucleic acid construct" means a polynucleotide comprises one or more (e.g., two, several) control sequences. The polynucleotide may be single-stranded or double-stranded, and may be isolated from a naturally occurring gene, modified to contain segments of nucleic acids in a manner that would not otherwise exist in nature, or synthetic.

Operably linked: The term "operably linked" means a configuration in which a control sequence is placed at an appropriate position relative to the coding sequence of a polynucleotide such that the control sequence directs expression of the coding sequence.

Phospholipase: The term "phospholipase" means an enzyme that catalyzes the conversion of phospholipids into fatty acids and other lipophilic substances, such as phospholipase A (EC numbers 3.1.1.4, 3.1.1.5 and 3.1.1.32) or phospholipase C (EC numbers 3.1.4.3 and 3.1.4.11). For purposes of the present invention, phospholipase activity may be determined using activity assays known in the art, or according to the procedures described in the Examples herein (Example 2).

Pretreated corn stover: The term "Pretreated Corn Stover" or "PCS" means a cellulosic-containing material derived from corn stover by treatment with heat and dilute sulfuric acid, alkaline pretreatment, neutral pretreatment, or any pretreatment known in the art.

Protease: The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, California, including supplements 1-5 published in *Eur. J. Biochem.* 223: 1-5 (1994); *Eur. J. Biochem.* 232: 1-6 (1995); *Eur. J. Biochem.* 237: 1-5 (1996); *Eur. J. Biochem.* 250: 1-6 (1997); and *Eur. J. Biochem.* 264: 610-650 (1999); respectively. The term "subtilases" refer to a sub-group of serine protease according to Siezen et al., 1991, *Protein Engng.* 4: 719-737 and Siezen et al., 1997, *Protein Science* 6: 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue. The subtilases may be divided into 6 sub-divisions, i.e. the Subtilisin family, the Thermitase family, the Proteinase K family, the Lantibiotic peptidase family, the Kexin family and the Pyrolysin family. The term "protease activity" means a proteolytic activity (EC 3.4). Protease activity may be determined using methods described in the art (e.g., US 2015/0125925) or using commercially available assay kits (e.g., Sigma-Aldrich).

Pullulanase: The term "pullulanase" means a starch debranching enzyme having pullulan 6-glucano-hydrolase activity (EC 3.2.1.41) that catalyzes the hydrolysis the α-1,6-glycosidic bonds in pullulan, releasing maltotriose with reducing carbohydrate ends. For purposes of the present invention, pullulanase activity can be determined according to a PHADEBAS assay or the sweet potato starch assay described in WO2016/087237.

Sequence Identity: The relatedness between two amino acid sequences or between two nucleotide sequences is described by the parameter "sequence identity".

For purposes described herein, the degree of sequence identity between two amino acid sequences is determined using the Needleman-Wunsch algorithm (Needleman and Wunsch, *J. Mol. Biol.* 1970, 48, 443-453) as implemented in the Needle program of the EMBOSS package (EMBOSS: The European Molecular Biology Open Software Suite, Rice et al., *Trends Genet* 2000, 16, 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of the Referenced Sequence−Total Number of Gaps in Alignment)

For purposes described herein, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Referenced Sequence−Total Number of Gaps in Alignment)

Signal peptide: The term "signal peptide" is defined herein as a peptide linked (fused) in frame to the amino terminus of a polypeptide having biological activity and directs the polypeptide into the cell's secretory pathway. Signal sequences may be determined using techniques known in the art (See, e.g., Zhang and Henzel, 2004, *Protein Science* 13: 2819-2824). The polypeptides described herein may comprise any suitable signal peptide known in the art, or any signal peptide described herein (e.g., the *S. cerevisiae* MFα1 signal peptide of SEQ ID NO: 7, the *S. cerevisiae* EXG1 signal peptide of SEQ ID NO: 227, or the *S. cerevisiae* AG2 signal peptide of SEQ ID NO: 234, or a signal peptide having at least 80%, 85%, 90%, 95%, 96%, 97%, 98% or 99% sequence identity thereof).

Trehalase: The term "trehalase" means an enzyme which degrades trehalose into its unit monosaccharides (i.e., glucose). Trehalases are classified in EC 3.2.1.28 (alpha,alpha-trehalase) and EC. 3.2.1.93 (alpha,alpha-phosphotrehalase). The EC classes are based on recommendations of the Nomenclature Committee of the International Union of Biochemistry and Molecular Biology (IUBMB). Description of EC classes can be found on the internet, e.g., on "http://www.expasy.org/enzyme/". Trehalases are enzymes that catalyze the following reactions:

EC 3.2.1.28: Alpha,alpha-trehalose+$H_2O$⇔2 D-glucose;
EC 3.2.1.93: Alpha,alpha-trehalose 6-phosphate+$H_2O$⇔D-glucose+D-glucose 6-phosphate.

For purposes of the present invention, trehalase activity may be determined according to the trehalase activity assay described herein in the experimental section.

Very high stringency conditions: The term "very high stringency conditions" means for probes of at least 100 nucleotides in length, prehybridization and hybridization at 42° C. in 5×SSPE, 0.3% SDS, 200 micrograms/mL sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/mL sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylose Isomerase: The term "Xylose Isomerase" or "XI" means an enzyme which can catalyze D-xylose into D-xylulose in vivo, and convert D-glucose into D-fructose in vitro. Xylose isomerase is also known as "glucose isomerase" and is classified as E.C. 5.3.1.5. As the structure of the enzyme is very stable, the xylose isomerase is a good model for studying the relationships between protein structure and functions (Karimaki et al., Protein Eng Des Sel, 12004, 17 (12):861-869). Xylose Isomerase activity may be determined using techniques known in the art (e.g., a coupled enzyme assay using D-sorbitol dehygrogenase, as described by Verhoeven et. al., 2017, *Sci Rep* 7, 46155).

Reference to "about" a value or parameter herein includes embodiments that are directed to that value or parameter per se. For example, description referring to "about X" includes the embodiment "X". When used in combination with measured values, "about" includes a range that encompasses at least the uncertainty associated with the method of measuring the particular value, and can include a range of plus or minus two standard deviations around the stated value.

Likewise, reference to a gene or polypeptide that is "derived from" another gene or polypeptide X, includes the gene or polypeptide X.

As used herein and in the appended claims, the singular forms "a," "or," and "the" include plural referents unless the context clearly dictates otherwise.

It is understood that the embodiments described herein include "consisting" and/or "consisting essentially of" embodiments. As used herein, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

DETAILED DESCRIPTION

Described herein, inter alia, are methods for producing a fermentation product, such as ethanol, from starch or cellulosic containing material.

During industrial scale fermentation, yeast encounter various physiological challenges including variable concentrations of sugars, high concentrations of yeast metabolites such as ethanol, glycerol, organic acids, osmotic stress, as well as potential competition from contaminating microbes such as wild yeasts and bacteria. As a consequence, many yeasts are not suitable for use in industrial fermentation. The most widely used commercially available industrial strain of *Saccharomyces* (i.e. for industrial scale fermentation) is the *Saccharomyces cerevisiae* strain used, for example, in the product ETHANOL RED®. This strain is well suited to industrial ethanol production; however, it remains unclear how modifications to the yeast will impact performance. In particular, the functional expression of heterologous enzymes by an industrially-relevant *Saccharomyces cerevisiae* yeast is uncertain (See, for example U.S. Pat. No. 9,206,444 where the applicant was unable to functionally express numerous enzymes/enzyme classes).

The Applicant has surprisingly found that yeast expressing a phospholipase provide beneficial properties that may be useful for ethanol fermentation, such as reduced need for supplemental nitrogen.

In one aspect is a method of producing a fermentation product from a starch-containing or cellulosic-containing material comprising:
   (a) saccharifying the starch-containing or cellulosic-containing material; and
   (b) fermenting the saccharified material of step (a) with a fermenting organism;
   wherein the fermenting organism comprises a heterologous polynucleotide encoding a phospholipase.

Steps of saccharifying and fermenting are carried out either sequentially or simultaneously (SSF). In one embodiment, steps of saccharifying and fermenting are carried out simultaneously (SSF). In another embodiment, steps of saccharifying and fermenting are carried out sequentially.

Fermenting Organism

The fermenting organism described herein may be derived from any host cell known to the skilled artisan capable of producing a fermentation product, such as ethanol. As used herein, a "derivative" of strain is derived from a referenced strain, such as through mutagenesis, recombinant DNA technology, mating, cell fusion, or cytoduction between yeast strains. Those skilled in the art will understand that the genetic alterations, including metabolic modifications exemplified herein, may be described with reference to a suitable host organism and their corresponding metabolic reactions or a suitable source organism for desired genetic material such as genes for a desired metabolic pathway. However, given the complete genome sequencing of a wide variety of organisms and the high level of skill in the area of genomics, those skilled in the art can apply the teachings and guidance provided herein to other organisms. For example, the metabolic alterations exemplified herein can readily be applied to other species by incorporating the same or analogous encoding nucleic acid from species other than the referenced species.

The host cells for preparing the recombinant cells described herein can be from any suitable host, such as a yeast strain, including, but not limited to, a *Saccharomyces, Rhodotorula, Schizosaccharomyces, Kluyveromyces, Pichia, Hansenula, Rhodosporidium, Candida, Yarrowia, Lipomyces, Cryptococcus*, or *Dekkera* sp. cell. In particular, *Saccharomyces* host cells are contemplated, such as *Saccharomyces cerevisiae, bayanus* or *carlsbergensis* cells. Preferably, the yeast cell is a *Saccharomyces cerevisiae* cell. Suitable cells can, for example, be derived from commercially available strains and polyploid or aneuploid industrial strains, including but not limited to those from Superstart™, THERMOSACC®, C5 FUEL™, XyloFerm®, etc. (Lallemand); RED STAR and ETHANOL RED® (Fermentis/Lesaffre); FALI (AB Mauri); Baker's Best Yeast, Baker's Compressed Yeast, etc. (Fleishmann's Yeast); BIOFERM AFT, XP, CF, and XR (North American Bioproducts Corp.); Turbo Yeast (Gert Strand AB); and FERMIOL® (DSM Specialties). Other useful yeast strains are available from biological depositories such as the American Type Culture Collection (ATCC) or the Deutsche Sammlung von Mikroorganismen und Zellkulturen GmbH (DSMZ), such as, e.g., BY4741 (e.g., ATCC 201388); Y108-1 (ATCC PTA. 10567) and NRRL YB-1952 (ARS Culture Collection). Still other *S. cerevisiae* strains suitable as host cells DBY746, [Alpha][Eta]22, S150-2B, GPY55-15Ba, CEN.PK, USM21, TMB3500, TMB3400, VTT-A-63015, VTT-A-85068, VTT-c-79093 and their derivatives as well as *Saccharomyces* sp. 1400, 424A (LNH-ST), 259A (LNH-ST) and derivatives thereof. In one embodiment, the recombinant cell is a derivative of a strain *Saccharomyces cerevisiae* CIBTS1260 (deposited under Accession No. NRRL Y-50973 at the Agricultural Research Service Culture Collection (NRRL), Illinois 61604 U.S.A.).

The fermenting organism may be *Saccharomyces* strain, e.g., *Saccharomyces cerevisiae* strain produced using the method described and concerned in U.S. Pat. No. 8,257,959-BB.

The strain may also be a derivative of *Saccharomyces cerevisiae* strain NMI V14/004037 (See, WO2015/143324 and WO2015/143317 each incorporated herein by reference), strain nos. V15/004035, V15/004036, and V15/004037 (See, WO 2016/153924 incorporated herein by reference), strain nos. V15/001459, V15/001460, V15/001461 (See, WO2016/138437 incorporated herein by reference), strain no. NRRL Y67342 (See, WO2017/063159 incorporated herein by reference), or any strain described in WO2017/087330 (incorporated herein by reference).

The fermenting organisms according to the invention have been generated in order to, e.g., improve fermentation yield and to improve process economy by cutting enzyme costs since part or all of the necessary enzymes needed to improve method performance are be produced by the fermenting organism.

The fermenting organisms described herein may utilize expression vectors comprising the coding sequence of one or more (e.g., two, several) heterologous genes linked to one or more control sequences that direct expression in a suitable cell under conditions compatible with the control sequence(s). Such expression vectors may be used in any of the cells and methods described herein. The polynucleotides described herein may be manipulated in a variety of ways to provide for expression of a desired polypeptide. Manipulation of the polynucleotide prior to its insertion into a vector may be desirable or necessary depending on the expression vector. The techniques for modifying polynucleotides utilizing recombinant DNA methods are well known in the art.

A construct or vector (or multiple constructs or vectors) comprising the one or more (e.g., two, several) heterologous genes may be introduced into a cell so that the construct or vector is maintained as a chromosomal integrant or as a self-replicating extra-chromosomal vector as described earlier.

The various nucleotide and control sequences may be joined together to produce a recombinant expression vector that may include one or more (e.g., two, several) convenient restriction sites to allow for insertion or substitution of the polynucleotide at such sites. Alternatively, the polynucleotide(s) may be expressed by inserting the polynucleotide(s) or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the cell, or a transposon, may be used.

The expression vector may contain any suitable promoter sequence that is recognized by a cell for expression of a gene described herein. The promoter sequence contains transcriptional control sequences that mediate the expression of the polypeptide. The promoter may be any polynucleotide that shows transcriptional activity in the cell of choice including mutant, truncated, and hybrid promoters, and may be obtained from genes encoding extracellular or intracellular polypeptides either homologous or heterologous to the cell.

Each heterologous polynucleotide described herein may be operably linked to a promoter that is foreign to the polynucleotide. For example, in one embodiment, the heterologous polynucleotide encoding the hexose transporter is operably linked to a promoter foreign to the polynucleotide. The promoters may be identical to or share a high degree of sequence identity (e.g., at least about 80%, at least about 85%, at least about 90%, at least about 95%, at least about 96%, at least about 97%, at least about 98%, or at least about 99%) with a selected native promoter.

Examples of suitable promoters for directing the transcription of the nucleic acid constructs in a yeast cells, include, but are not limited to, the promoters obtained from the genes for enolase, (e.g., *S. cerevisiae* enolase or *I. orientalis* enolase (ENO1)), galactokinase (e.g., *S. cerevisiae* galactokinase or *I. orientalis* galactokinase (GAL1)), alcohol dehydrogenase/glyceraldehyde-3-phosphate dehydrogenase (e.g., *S. cerevisiae* alcohol dehydrogenase/glyceraldehyde-3-phosphate dehydrogenase or *I. orientalis* alcohol dehydrogenase/glyceraldehyde-3-phosphate dehydrogenase (ADH1, ADH2/GAP)), triose phosphate isomerase (e.g., *S. cerevisiae* triose phosphate isomerase or *I. orientalis* triose phosphate isomerase (TPI)), metallothionein (e.g., *S. cerevisiae* metallothionein or *I. orientalis* metallothionein (CUP1)), 3-phosphoglycerate kinase (e.g., *S. cerevisiae* 3-phosphoglycerate kinase or *I. orientalis* 3-phosphoglycerate kinase (PGK)), PDC1, xylose reductase (XR), xylitol dehydrogenase (XDH), L-(+)-lactate-cytochrome c oxidoreductase (CYB2), translation elongation factor-1 (TEF1), translation elongation factor-2 (TEF2), glyceraldehyde-3-phosphate dehydrogenase (GAPDH), and orotidine 5'-phosphate decarboxylase (URA3) genes. Other suitable promoters may be obtained from *S. cerevisiae* TDH3, HXT7, PGK1, RPL18B and CCW12 genes. Additional useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the yeast cell of choice may be used. The terminator may be identical to or share a high degree of sequence identity (e.g., at least about 80%, at least about 85%, at least about 90%, at least about 95%, at least about 96%, at least about 97%, at least about 98%, or at least about 99%) with the selected native terminator.

Suitable terminators for yeast host cells may be obtained from the genes for enolase (e.g., *S. cerevisiae* or *I. orientalis* enolase cytochrome C (e.g., *S. cerevisiae* or *I. orientalis* cytochrome (CYC1)), glyceraldehyde-3-phosphate dehydrogenase (e.g., *S. cerevisiae* or *I. orientalis* glyceraldehyde-3-phosphate dehydrogenase (gpd)), PDC1, XR, XDH, transaldolase (TAL), transketolase (TKL), ribose 5-phosphate ketol-isomerase (RKI), CYB2, and the galactose family of genes (especially the GAL10 terminator). Other suitable terminators may be obtained from *S. cerevisiae* ENO2 or TEF1 genes. Additional useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the yeast cell of choice may be used.

Suitable leaders for yeast host cells are obtained from the genes for enolase (e.g., *S. cerevisiae* or *I. orientalis* enolase (ENO-1)), 3-phosphoglycerate kinase (e.g., *S. cerevisiae* or *I. orientalis* 3-phosphoglycerate kinase), alpha-factor (e.g., *S. cerevisiae* or *I. orientalis* alpha-factor), and alcohol dehydrogenase/glyceraldehyde-3-phosphate dehydrogenase (e.g., *S. cerevisiae* or *I. orientalis* alcohol dehydrogenase/glyceraldehyde-3-phosphate dehydrogenase (ADH2/GAP)).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used. Useful polyadenylation sequences for yeast cells are described by Guo and Sherman, 1995, *Mol. Cellular Biol.* 15: 5983-5990.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used.

The vectors may contain one or more (e.g., two, several) selectable markers that permit easy selection of transformed, transfected, transduced, or the like cells. A selectable marker is a gene the product of which provides for biocide or viral resistance, resistance to heavy metals, prototrophy to auxotrophs, and the like. Suitable markers for yeast host cells include, but are not limited to, ADE2, HIS3, LEU2, LYS2, MET3, TRP1, and URA3.

The vectors may contain one or more (e.g., two, several) elements that permit integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination. Potential integration loci include those described in the art (e.g., See US2012/0135481).

For autonomous replication, the vector may further comprise an origin of replication enabling the vector to replicate autonomously in the yeast cell. The origin of replication may be any plasmid replicator mediating autonomous replication that functions in a cell. The term "origin of replication" or "plasmid replicator" means a polynucleotide that enables a plasmid or vector to replicate in vivo. Examples of origins of replication for use in a yeast host cell are the 2 micron origin of replication, ARS1, ARS4, the combination of ARS1 and CEN3, and the combination of ARS4 and CEN6.

More than one copy of a polynucleotide described herein may be inserted into a host cell to increase production of a polypeptide. An increase in the copy number of the polynucleotide can be obtained by integrating at least one additional copy of the sequence into the yeast cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors described herein are well known to one skilled in the art (see, e.g., Sambrook et al., 1989, *Molecular Cloning, A Laboratory Manual*, 2d edition, Cold Spring Harbor, New York).

Additional procedures and techniques known in the art for the preparation of recombinant cells for ethanol fermentation, are described in, e.g., WO 2016/045569, the content of which is hereby incorporated by reference.

The fermenting organism may be in the form of a composition comprising a fermenting organism (e.g., a yeast strain described herein) and a naturally occurring and/or a none naturally occurring component.

The fermenting organism described herein may be in any viable form, including crumbled, dry, including active dry and instant, compressed, cream (liquid) form etc. In one embodiment, the fermenting organism (e.g., a *Saccharomyces cerevisiae* yeast strain) is dry yeast, such as active dry yeast or instant yeast. In one embodiment, the fermenting organism (e.g., a *Saccharomyces cerevisiae* yeast strain) is crumbled yeast. In one embodiment, the fermenting organism (e.g., a *Saccharomyces cerevisiae* yeast strain) is compressed yeast. In one embodiment, the fermenting organism (e.g., a *Saccharomyces cerevisiae* yeast strain) is cream yeast.

In one embodiment is a composition comprising a fermenting organism described herein (e.g., a *Saccharomyces cerevisiae* yeast strain), and one or more of the component selected from the group consisting of: surfactants, emulsifiers, gums, swelling agent, and antioxidants and other processing aids.

The compositions described herein may comprise a fermenting organism described herein (e.g., a *Saccharomyces cerevisiae* yeast strain) and any suitable surfactants. In one embodiment, the surfactant(s) is/are an anionic surfactant, cationic surfactant, and/or nonionic surfactant.

The compositions described herein may comprise a fermenting organism described herein (e.g., a *Saccharomyces cerevisiae* yeast strain) and any suitable emulsifier. In one embodiment, the emulsifier is a fatty-acid ester of sorbitan. In one embodiment, the emulsifier is selected from the group of sorbitan monostearate (SMS), citric acid esters of monodiglycerides, polyglycerolester, fatty acid esters of propylene glycol.

In one embodiment, the composition comprises a fermenting organism described herein (e.g., a *Saccharomyces cerevisiae* yeast strain), and Olindronal SMS, Olindronal SK, or Olindronal SPL including composition concerned in European Patent No. 1,724,336 (hereby incorporated by reference). These products are commercially available from Bussetti, Austria, for active dry yeast.

The compositions described herein may comprise a fermenting organism described herein (e.g., a *Saccharomyces cerevisiae* yeast strain) and any suitable gum. In one embodiment, the gum is selected from the group of carob, guar, tragacanth, arabic, xanthan and acacia gum, in particular for cream, compressed and dry yeast.

The compositions described herein may comprise a fermenting organism described herein (e.g., a *Saccharomyces cerevisiae* yeast strain) and any suitable swelling agent. In one embodiment, the swelling agent is methyl cellulose or carboxymethyl cellulose.

The compositions described herein may comprise a fermenting organism described herein (e.g., a *Saccharomyces cerevisiae* yeast strain) and any suitable anti-oxidant. In one embodiment, the antioxidant is butylated hydroxyanisol (BHA) and/or butylated hydroxytoluene (BHT), or ascorbic acid (vitamin C), particular for active dry yeast.

Gene Disruptions

The fermenting organisms described herein may also comprise one or more (e.g., two, several) gene disruptions, e.g., to divert sugar metabolism from undesired products to ethanol. In some aspects, the recombinant host cells produce a greater amount of ethanol compared to the cell without the one or more disruptions when cultivated under identical conditions. In some aspects, one or more of the disrupted endogenous genes is inactivated.

In certain embodiments, the fermenting organism provided herein comprises a disruption of one or more endogenous genes encoding enzymes involved in producing alternate fermentative products such as glycerol or other byproducts such as acetate or diols. For example, the cells provided herein may comprise a disruption of one or more of glycerol 3-phosphate dehydrogenase (GPD, catalyzes reaction of dihydroxyacetone phosphate to glycerol 3-phosphate), glycerol 3-phosphatase (GPP, catalyzes conversion of glycerol-3 phosphate to glycerol), glycerol kinase (catalyzes conversion of glycerol 3-phosphate to glycerol), dihydroxyacetone kinase (catalyzes conversion of dihydroxyacetone phosphate to dihydroxyacetone), glycerol dehydrogenase (catalyzes conversion of dihydroxyacetone to glycerol), and aldehyde dehydrogenase (ALD, e.g., converts acetaldehyde to acetate).

Modeling analysis can be used to design gene disruptions that additionally optimize utilization of the pathway. One exemplary computational method for identifying and designing metabolic alterations favoring biosynthesis of a desired product is the OptKnock computational framework, Burgard et al., 2003, *Biotechnol. Bioeng.* 84: 647-657.

The fermenting organisms comprising a gene disruption may be constructed using methods well known in the art, including those methods described herein. A portion of the gene can be disrupted such as the coding region or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification include, but are not limited to, a leader, propeptide sequence, signal sequence, transcription terminator, and transcriptional activator.

The fermenting organisms comprising a gene disruption may be constructed by gene deletion techniques to eliminate or reduce expression of the gene. Gene deletion techniques enable the partial or complete removal of the gene thereby eliminating their expression. In such methods, deletion of the gene is accomplished by homologous recombination using a plasmid that has been constructed to contiguously contain the 5' and 3' regions flanking the gene.

The fermenting organisms comprising a gene disruption may also be constructed by introducing, substituting, and/or removing one or more (e.g., two, several) nucleotides in the gene or a control sequence thereof required for the transcription or translation thereof. For example, nucleotides may be inserted or removed for the introduction of a stop codon, the removal of the start codon, or a frame-shift of the open reading frame. Such a modification may be accomplished by site-directed mutagenesis or PCR generated mutagenesis in accordance with methods known in the art. See, for example, Botstein and Shortle, 1985, *Science* 229: 4719; Lo et al., 1985, *Proc. Natl. Acad. Sci. U.S.A.* 81: 2285; Higuchi et al., 1988, *Nucleic Acids Res* 16: 7351; Shimada, 1996, *Meth. Mol. Biol.* 57: 157; Ho et al., 1989, *Gene* 77: 61; Horton et al., 1989, *Gene* 77: 61; and Sarkar and Sommer, 1990, *BioTechniques* 8: 404.

The fermenting organisms comprising a gene disruption may also be constructed by inserting into the gene a disruptive nucleic acid construct comprising a nucleic acid fragment homologous to the gene that will create a duplication of the region of homology and incorporate construct DNA between the duplicated regions. Such a gene disruption can eliminate gene expression if the inserted construct separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

The fermenting organisms comprising a gene disruption may also be constructed by the process of gene conversion (see, for example, Iglesias and Trautner, 1983, *Molecular General Genetics* 189: 73-76). For example, in the gene conversion method, a nucleotide sequence corresponding to the gene is mutagenized in vitro to produce a defective nucleotide sequence, which is then transformed into the recombinant strain to produce a defective gene. By homologous recombination, the defective nucleotide sequence replaces the endogenous gene. It may be desirable that the defective nucleotide sequence also comprises a marker for selection of transformants containing the defective gene.

The fermenting organisms comprising a gene disruption may be further constructed by random or specific mutagenesis using methods well known in the art, including, but not limited to, chemical mutagenesis (see, for example, Hopwood, *The Isolation of Mutants in Methods in Microbiology* (J. R. Norris and D. W. Ribbons, eds.) pp. 363-433, Academic Press, New York, 1970). Modification of the gene may be performed by subjecting the parent strain to mutagenesis and screening for mutant strains in which expression of the gene has been reduced or inactivated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the parent strain to be mutagenized in the presence of the mutagenizing agent of choice under suitable conditions, and selecting for mutants exhibiting reduced or no expression of the gene.

A nucleotide sequence homologous or complementary to a gene described herein may be used from other microbial sources to disrupt the corresponding gene in a recombinant strain of choice.

In one aspect, the modification of a gene in the recombinant cell is unmarked with a selectable marker. Removal of the selectable marker gene may be accomplished by culturing the mutants on a counter-selection medium. Where the selectable marker gene contains repeats flanking its 5' and 3' ends, the repeats will facilitate the looping out of the selectable marker gene by homologous recombination when the mutant strain is submitted to counter-selection. The selectable marker gene may also be removed by homologous recombination by introducing into the mutant strain a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

Methods Using a Starch-Containing Material

In some aspects, the methods described herein produce a fermentation product from a starch-containing material. Starch-containing material is well-known in the art, containing two types of homopolysaccharides (amylose and amylopectin) and is linked by alpha-(1-4)-D-glycosidic bonds. Any suitable starch-containing starting material may be used. The starting material is generally selected based on the desired fermentation product, such as ethanol. Examples of starch-containing starting materials include cereal, tubers or grains. Specifically, the starch-containing material may be corn, wheat, barley, rye, milo, sago, cassava, tapioca, sorghum, oat, rice, peas, beans, or sweet potatoes, or mixtures thereof. Contemplated are also waxy and non-waxy types of corn and barley.

In one embodiment, the starch-containing starting material is corn. In one embodiment, the starch-containing starting material is wheat. In one embodiment, the starch-containing starting material is barley. In one embodiment, the starch-containing starting material is rye. In one embodiment, the starch-containing starting material is milo. In one embodiment, the starch-containing starting material is sago. In one embodiment, the starch-containing starting material is cassava. In one embodiment, the starch-containing starting material is tapioca. In one embodiment, the starch-containing starting material is sorghum. In one embodiment, the starch-containing starting material is rice. In one embodiment, the starch-containing starting material is peas. In one embodiment, the starch-containing starting material is beans. In one embodiment, the starch-containing starting material is sweet potatoes. In one embodiment, the starch-containing starting material is oats.

The methods using a starch-containing material may include a conventional process (e.g., including a liquefaction step described in more detail below) or a raw starch hydrolysis process. In some embodiments using a starch-containing material, saccharification of the starch-containing material is at a temperature above the initial gelatinization temperature. In some embodiments using a starch-containing material, saccharification of the starch-containing material is at a temperature below the initial gelatinization temperature.

Liquefaction

In aspects using a starch-containing material, the methods may further comprise a liquefaction step carried out by subjecting the starch-containing material at a temperature above the initial gelatinization temperature to an alpha-amylase and optionally a protease and/or a glucoamylase. Other enzymes such as a pullulanase and phytase may also be present and/or added in liquefaction. In some embodiments, the liquefaction step is carried out prior to steps a) and b) of the described methods.

Liquefaction step may be carried out for 0.5-5 hours, such as 1-3 hours, such as typically about 2 hours.

The term "initial gelatinization temperature" means the lowest temperature at which gelatinization of the starch-containing material commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. The initial gelatinization temperature of a given starch-containing material may be determined as the temperature at which birefringence is lost in 5% of the starch granules using the method described by Gorinstein and Lii, 1992, *Starch/Stärke* 44(12): 461-466.

Liquefaction is typically carried out at a temperature in the range from 70-100° C. In one embodiment, the temperature in liquefaction is between 75-95° C., such as between 75-90° C., between 80-90° C., or between 82-88° C., such as about 85° C.

A jet-cooking step may be carried out prior to liquefaction in step, for example, at a temperature between 110-145° C., 120-140° C., 125-135° C., or about 130° C. for about 1-15 minutes, for about 3-10 minutes, or about 5 minutes.

The pH during liquefaction may be between 4 and 7, such as pH 4.5-6.5, pH 5.0-6.5, pH 5.0-6.0, pH 5.2-6.2, or about 5.2, about 5.4, about 5.6, or about 5.8.

In one embodiment, the process further comprises, prior to liquefaction, the steps of:
 i) reducing the particle size of the starch-containing material, preferably by dry milling;
 ii) forming a slurry comprising the starch-containing material and water.

The starch-containing starting material, such as whole grains, may be reduced in particle size, e.g., by milling, in order to open up the structure, to increase surface area, and allowing for further processing. Generally, there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry milling and wet milling are well known in the art of starch processing. In one embodiment the starch-containing material is subjected to dry milling. In one embodiment, the particle size is reduced to between 0.05 to 3.0 mm, e.g., 0.1-0.5 mm, or so that at least 30%, at least 50%, at least 70%, or at least 90% of the starch-containing material fit through a sieve with a 0.05 to 3.0 mm screen, e.g., 0.1-0.5 mm screen. In another embodiment, at least 50%, e.g., at least 70%, at least 80%, or at least 90% of the starch-containing material fit through a sieve with #6 screen.

The aqueous slurry may contain from 10-55 w/w-% dry solids (DS), e.g., 25-45 w/w-% dry solids (DS), or 30-40 w/w-% dry solids (DS) of starch-containing material.

The alpha-amylase, optionally a protease, and optionally a glucoamylase may initially be added to the aqueous slurry to initiate liquefaction (thinning). In one embodiment, only a portion of the enzymes (e.g., about ⅓) is added to the aqueous slurry, while the rest of the enzymes (e.g., about ⅔) are added during liquefaction step.

A non-exhaustive list of alpha-amylases used in liquefaction can be found below in the "Alpha-Amylases" section. Examples of suitable proteases used in liquefaction include any protease described supra in the "Proteases" section. Examples of suitable glucoamylases used in liquefaction include any glucoamylase found in the "Glucoamylases" section.

Saccharification and Fermentation of Starch-Containing Material

In aspects using a starch-containing material, a glucoamylase may be present and/or added in saccharification step a) and/or fermentation step b) or simultaneous saccharification and fermentation (SSF). The glucoamylase of the saccharification step a) and/or fermentation step b) or simultaneous saccharification and fermentation (SSF) is typically different from the glucoamylase optionally added to any liquefaction step described supra. In one embodiment, the glucoamylase is present and/or added together with a fungal alpha-amylase.

In some aspects, the fermenting organism comprises a heterologous polynucleotide encoding a glucoamylase, for example, as described in WO2017/087330, the content of which is hereby incorporated by reference.

Examples of glucoamylases can be found in the "Glucoamylases" section below.

When doing sequential saccharification and fermentation, saccharification step a) may be carried out under conditions well-known in the art. For instance, saccharification step a) may last up to from about 24 to about 72 hours. In one embodiment, pre-saccharification is done. Pre-saccharification is typically done for 40-90 minutes at a temperature between 30-65° C., typically about 60° C. Pre-saccharification is, in one embodiment, followed by saccharification during fermentation in simultaneous saccharification and fermentation (SSF). Saccharification is typically carried out at temperatures from 20-75° C., preferably from 40-70° C., typically about 60° C., and typically at a pH between 4 and 5, such as about pH 4.5.

Fermentation is carried out in a fermentation medium, as known in the art and, e.g., as described herein. The fermentation medium includes the fermentation substrate, that is, the carbohydrate source that is metabolized by the fermenting organism. With the processes described herein, the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Generally, fermenting organisms such as yeast, including *Saccharomyces cerevisiae* yeast, require an adequate source of nitrogen for propagation and fermentation. Many sources of supplemental nitrogen, if necessary, can be used and such sources of nitrogen are well known in the art. The nitrogen source may be organic, such as urea, DDGs, wet cake or corn mash, or inorganic, such as ammonia or ammonium hydroxide. In one embodiment, the nitrogen source is urea.

Fermentation can be carried out under low nitrogen conditions, e.g., when using a protease-expressing yeast. In some embodiments, the fermentation step is conducted with less than 1000 ppm supplemental nitrogen (e.g., urea or ammonium hydroxide), such as less than 750 ppm, less than 500 ppm, less than 400 ppm, less than 300 ppm, less than 250 ppm, less than 200 ppm, less than 150 ppm, less than 100 ppm, less than 75 ppm, less than 50 ppm, less than 25 ppm, or less than 10 ppm, supplemental nitrogen. In some embodiments, the fermentation step is conducted with no supplemental nitrogen.

Simultaneous saccharification and fermentation ("SSF") is widely used in industrial scale fermentation product production processes, especially ethanol production processes. When doing SSF the saccharification step a) and the fermentation step b) are carried out simultaneously. There is no holding stage for the saccharification, meaning that a fermenting organism, such as yeast, and enzyme(s), may be added together. However, it is also contemplated to add the fermenting organism and enzyme(s) separately. SSF is typically carried out at a temperature from 25° C. to 40° C., such as from 28° C. to 35° C., such as from 30° C. to 34° C., or about 32° C. In one embodiment, fermentation is ongoing for 6 to 120 hours, in particular 24 to 96 hours. In one embodiment, the pH is between 4-5.

In one embodiment, a cellulolytic enzyme composition is present and/or added in saccharification, fermentation or simultaneous saccharification and fermentation (SSF). Examples of such cellulolytic enzyme compositions can be found in the "Cellulolytic Enzymes and Compositions" section below. The cellulolytic enzyme composition may be present and/or added together with a glucoamylase, such as one disclosed in the "Glucoamylases" section below.

Phospholipases

The expressed phospholipase may be any phospholipase that is suitable for the host cells and/or the methods described herein, such as a naturally occurring phospholipase (e.g., a native phospholipase from another species or an endogenous phospholipase expressed from a modified expression vector) or a variant thereof that retains phospholipase activity.

In some embodiments, the fermenting organism comprises a heterologous polynucleotide encoding a phospholipase, for example, as described in WO2018/075430, the content of which is hereby incorporated by reference. In some embodiments, the phospholipase is classified as a phospholipase A. In other embodiments, the phospholipase is classified as a phospholipase C. Any phospholipase described or referenced herein is contemplated for expression in the fermenting organism.

In some embodiments, the fermenting organism comprising a heterologous polynucleotide encoding a phospholipase has an increased level of phospholipase activity compared to the host cells without the heterologous polynucleotide encoding the phospholipase, when cultivated under the same conditions. In some embodiments, the fermenting organism has an increased level of phospholipase activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the phospholipase, when cultivated under the same conditions.

Exemplary phospholipases that can be used with the host cells and/or the methods described herein include bacterial, yeast, or filamentous fungal phospholipases, e.g., derived from any of the microorganisms described or referenced herein.

Additional phospholipases that may be expressed with the fermenting organisms and used with the methods described herein are described in the examples, and include, but are not limited to phospholipases shown in Table 1 (or derivatives thereof).

TABLE 1

| Donor Organism (catalytic domain) | SEQ ID NO: (mature polypeptide) |
|---|---|
| Thermomyces lanuginosus | 235 |
| Talaromyces leycettanus | 236 |
| Penicillium emersonii | 237 |
| Bacillus thuringiensis | 238 |
| Pseudomonas sp. | 239 |
| Kionochaeta sp. | 240 |
| Mariannaea pinicola | 241 |
| Fictibacillus macauensis | 242 |
| Aspergillus wentii | 252 |
| Penicillium cylindrosporum | 253 |
| Penicillium meridianum | 254 |
| Penicillium bialowiezense | 255 |
| Penicillium sclerotiorum | 256 |
| Rasamsonia byssochlamydoides | 257 |
| Rasamsonia eburnea | 258 |
| Penicillium brefeldianum | 259 |
| Penicillium adametzii | 260 |
| Rasamsonia brevistipitata | 261 |
| Penicillium scabrosum | 262 |
| Penicillium manginii | 263 |
| Penicillium emersonii | 264 |
| Rasamsonia argillacea | 265 |
| Penicillium parviverrucosum | 266 |
| Penicillium flavescens | 267 |
| Penicillium hispanicum | 268 |
| Penicillium simplicissimum | 269 |
| Penicillium vasconiae | 270 |
| Talaromyces columbinus | 271 |
| Talaromyces variabilis | 272 |
| Talaromyces rugulosus | 273 |
| Hamigera terricola | 274 |
| Penicillium piscarium | 275 |
| Talaromyces bacillisporus | 276 |
| Galactomyces candidus | 277 |
| Penicillium megasporum | 278 |
| Penicillium jensenii | 279 |
| Aspergillus stramenius | 280 |
| Bacillus pseudomycoides | 281 |
| Bacillus mycoides | 282 |
| Bacillus thuringiensis | 283 |
| Listeria innocua | 284 |
| Aspergillus egyptiacus | 285 |
| Aspergillus tamarii | 286 |
| Aspergillus niger | 287 |
| Bacillus luciferensis | 288 |
| Bacillus mycoides | 289 |
| Bacillus mycoides | 290 |
| Bacillus sp. | 291 |
| Bacillus drentensis | 292 |
| Aspergillus turcosus | 293 |
| Talaromyces subinflatus | 294 |
| Aspergillus tubingensis | 295 |
| Bacillus acidiceler | 296 |
| Lysinibacillus xylanilyticus | 297 |
| Bacillus toyonensis | 298 |
| Bacillus wiedmannii | 299 |
| Listeria seeligeri | 300 |
| Penicillium swiecickii | 301 |
| Talaromyces boninensis | 302 |
| Hamigera striata | 303 |
| Bacillus sp. | 304 |
| Bacillus thuringiensis | 305 |
| Bacillus mycoides | 306 |
| Fictibacillus macauensis | 307 |
| Listeria seeligeri | 308 |
| Penicillium donkii | 309 |

TABLE 1-continued

| Donor Organism (catalytic domain) | SEQ ID NO: (mature polypeptide) |
|---|---|
| Hamigera paravellanea | 310 |
| Talaromyces lecycettanus | 311 |
| Paenibacillus sp. | 312 |
| Bacillus toyonensis | 313 |
| Bacillus thuringiensis | 314 |
| Bacillus thuringiensis | 315 |
| Talaromyces rugulosus | 316 |
| Penicillium sp. | 317 |
| Hamigera avellanea | 318 |
| Penicillium spikei | 319 |
| Paenibacillus alginolyticus | 320 |
| Bacillus mycoides | 321 |
| Bacillus bingmayongensis | 322 |
| Bacillus mycoides | 323 |
| Brevibacillus sp. | 324 |
| Penicillium vasconiae | 325 |
| Talaromyces diversus | 326 |
| Aspergillus wentii | 327 |
| Bacillus acidiceler | 328 |
| Bacillus luti | 329 |
| Bacillus pseudomycoides | 330 |
| Bacillus mycoides | 331 |
| Penicillium cinnamopurpureum | 332 |
| Talaromyces verruculosus | 333 |
| Talaromyces cellulolyticus | 334 |
| Penicillium megasporum | 335 |
| Bacillus toyonensis | 336 |
| Bacillus sp. | 337 |
| Bacillus manliponensis | 338 |
| Penicillium simplicissimum | 339 |
| Penicillium arenicola | 340 |
| Aspergillus aculeatus | 341 |
| Bacillus acidiceler | 342 |

Additional phospholipases contemplated for use with the present invention can be found in WO2018/075430 (the content of which is incorporated herein).

Additional polynucleotides encoding suitable phospholipases may be obtained from microorganisms of any genus, including those readily available within the UniProtKB database (www.uniprot.org).

The phospholipase may be a bacterial phospholipase. For example, the phospholipase may be derived from a Gram-positive bacterium such as a *Bacillus, Clostridium, Enterococcus, Geobacillus, Lactobacillus, Lactococcus, Oceanobacillus, Staphylococcus, Streptococcus,* or *Streptomyces,* or a Gram-negative bacterium such as a *Campylobacter, E. coli, Flavobacterium, Fusobacterium, Helicobacter, Ilyobacter, Neisseria, Pseudomonas, Salmonella,* or *Ureaplasma.*

In one embodiment, the phospholipase is derived from *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis.*

In another embodiment, the phospholipase is derived from *Streptococcus equisimilis, Streptococcus pyogenes, Streptococcus uberis,* or *Streptococcus equi* subsp. *Zooepidemicus.*

In another embodiment, the phospholipase is derived from *Streptomyces achromogenes, Streptomyces avermitilis, Streptomyces coelicolor, Streptomyces griseus,* or *Streptomyces lividans.*

The phospholipase may be a fungal phospholipase. For example, the phospholipase may be derived from a yeast such as a *Candida, Kluyveromyces, Pichia, Saccharomyces, Schizosaccharomyces, Yarrowia* or *Issatchenkia;* or derived from a filamentous fungus such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria.*

In another embodiment, the phospholipase is derived from *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis.*

In another embodiment, the phospholipase is derived from *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride.*

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The phospholipase coding sequences described or referenced herein, or a subsequence thereof, as well as the phospholipases described or referenced herein, or a fragment thereof, may be used to design nucleic acid probes to identify and clone DNA encoding a phospholipase from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin).

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with a coding sequence, or a subsequence thereof, the carrier material is used in a Southern blot.

In one embodiment, the nucleic acid probe is a polynucleotide, or subsequence thereof, that encodes the phospholipase of any one of SEQ ID NOs: 235-242 and 252-342 (such as the coding sequence of SEQ ID NOs: 244-251 and 343-433, respectively), or a fragment thereof.

In one embodiment, the nucleic acid probe is a polynucleotide, or subsequence thereof, that encodes the phospholipase of any one of SEQ ID NOs: 235, 236, 237, 238, 239, 240, 241 and 242 (such as the coding sequence of SEQ ID NO: 244, 245, 246, 247, 248, 249, 250 or 251, respectively), or a fragment thereof.

For purposes of the probes described above, hybridization indicates that the polynucleotide hybridizes to a labeled nucleic acid probe, or the full-length complementary strand thereof, or a subsequence of the foregoing; under very low to very high stringency conditions. Molecules to which the nucleic acid probe hybridizes under these conditions can be detected using, for example, X-ray film. Stringency and washing conditions are defined as described supra.

In one embodiment, the phospholipase is encoded by a polynucleotide that hybridizes under at least low stringency conditions, e.g., medium stringency conditions, medium-high stringency conditions, high stringency conditions, or very high stringency conditions with the full-length complementary strand of the coding sequence for any one of the phospholipases described or referenced herein (e.g., the coding sequence that encodes any one of SEQ ID NOs: 235-242 and 252-342; such as the corresponding coding sequence of SEQ ID NO: 244-251 or 343-433, respectively, or the coding sequence that encodes any one of SEQ ID NOs: 235, 236, 237, 238, 239, 240, 241 and 242; such as the corresponding coding sequence of SEQ ID NO: 244, 245, 246, 247, 248, 249, 250 or 251, respectively). (Sambrook et al., 1989, *Molecular Cloning, A Laboratory Manual*, 2d edition, Cold Spring Harbor, New York).

The phospholipase may also be identified and obtained from other sources including microorganisms isolated from nature (e.g., soil, composts, water, silage, etc.) or DNA samples obtained directly from natural materials (e.g., soil, composts, water, silage, etc.) using the above-mentioned probes. Techniques for isolating microorganisms and DNA directly from natural habitats are well known in the art. The polynucleotide encoding a phospholipase may then be derived by similarly screening a genomic or cDNA library of another microorganism or mixed DNA sample.

Once a polynucleotide encoding a phospholipase has been detected with a suitable probe as described herein, the sequence may be isolated or cloned by utilizing techniques that are known to those of ordinary skill in the art (see, e.g., Sambrook et al., 1989, *Molecular Cloning, A Laboratory Manual*, 2d edition, Cold Spring Harbor, New York). Techniques used to isolate or clone polynucleotides encoding alpha-amylases include isolation from genomic DNA, preparation from cDNA, or a combination thereof. The cloning of the polynucleotides from such genomic DNA can be effected, e.g., by using the well-known polymerase chain reaction (PCR) or antibody screening of expression libraries to detect cloned DNA fragments with shares structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used.

In one embodiment, the phospholipase has a mature polypeptide sequence that comprises or consists of the amino acid sequence of any one of the phospholipases described or referenced herein (e.g., any one of SEQ ID NOs: 235-242 and 252-342, such as any one of SEQ ID NOs: 235, 236, 237, 238, 239, 240, 241 and 242). In another embodiment, the phospholipase has a mature polypeptide sequence that is a fragment of the any one of the phospholipases described or referenced herein (e.g., any one of SEQ ID NOs: 235-242 and 252-342, such as any one of SEQ ID NOs: 235, 236, 237, 238, 239, 240, 241 and 242). In one embodiment, the number of amino acid residues in the fragment is at least 75%, e.g., at least 80%, 85%, 90%, or 95% of the number of amino acid residues in referenced full length phospholipase (e.g., any one of SEQ ID NOs: 235-242 and 252-342, such as any one of SEQ ID NOs: 235, 236, 237, 238, 239, 240, 241 and 242). In other embodiments, the phospholipase may comprise the catalytic domain of any phospholipase described or referenced herein (e.g., the catalytic domain of any one of SEQ ID NOs: 235-242 and 252-342, such as any one of SEQ ID NOs: 235, 236, 237, 238, 239, 240, 241 and 242).

The phospholipase may be a variant of any one of the phospholipases described supra (e.g., any one of SEQ ID NOs: 235-242 and 252-342, such as any one of SEQ ID NOs: 235, 236, 237, 238, 239, 240, 241 and 242). In one embodiment, the phospholipase has a mature polypeptide sequence of at least 60%, e.g., at least 65%, 70%, 75%, 80%, 85%, 90%, 95%, 97%, 98%, 99%, or 100% sequence identity to any one of the phospholipases described supra (e.g., any one of SEQ ID NOs: 235-242 and 252-342, such as any one of SEQ ID NOs: 235, 236, 237, 238, 239, 240, 241 and 242).

In one embodiment, the phospholipase has a mature polypeptide sequence that differs by no more than ten amino acids, e.g., by no more than five amino acids, by no more than four amino acids, by no more than three amino acids, by no more than two amino acids, or by one amino acid from the amino acid sequence of any one of the phospholipases described supra (e.g., any one of SEQ ID NOs: 235-242 and 252-342, such as any one of SEQ ID NOs: 235, 236, 237, 238, 239, 240, 241 and 242). In one embodiment, the phospholipase has an amino acid substitution, deletion, and/or insertion of one or more (e.g., two, several) of amino acid sequence of any one of the phospholipases described supra (e.g., any one of SEQ ID NOs: 235-242 and 252-342, such as any one of SEQ ID NOs: 235, 236, 237, 238, 239, 240, 241 and 242). In some embodiments, the total number of amino acid substitutions, deletions and/or insertions is not more than 10, e.g., not more than 9, 8, 7, 6, 5, 4, 3, 2, or 1.

The amino acid changes are generally of a minor nature, that is conservative amino acid substitutions or insertions that do not significantly affect the folding and/or activity of the protein; small deletions, typically of one to about 30 amino acids; small amino-terminal or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the phospholipase, alter the substrate specificity, change the pH optimum, and the like.

Essential amino acids can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for activity to identify amino acid residues that are critical to the activity of the molecule. See also, Hilton et al., 1996, *J. Biol. Chem.* 271: 4699-4708. The active site or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with other phospholipases that are related to the referenced phospholipase.

Additional guidance on the structure-activity relationship of the polypeptides herein can be determined using multiple sequence alignment (MSA) techniques well-known in the art. Based on the teachings herein, the skilled artisan could make similar alignments with any number of phospholipases described herein or known in the art. Such alignments aid the skilled artisan to determine potentially relevant domains (e.g., binding domains or catalytic domains), as well as which amino acid residues are conserved and not conserved among the different alpha-amylase sequences. It is appreciated in the art that changing an amino acid that is conserved at a particular position between disclosed polypeptides will more likely result in a change in biological activity (Bowie et al., 1990, *Science* 247: 1306-1310: "Residues that are directly involved in protein functions such as binding or catalysis will certainly be among the most conserved"). In contrast, substituting an amino acid that is not highly conserved among the polypeptides will not likely or significantly alter the biological activity.

Even further guidance on the structure-activity relationship for the skilled artisan can be found in published x-ray crystallography studies known in the art.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7:127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active alpha-amylases can be recovered from the host cells and rapidly sequenced using standard methods in the art. These methods allow the rapid determination of the importance of individual amino acid residues in a polypeptide.

In some embodiments, the phospholipase has at least 20%, e.g., at least 40%, at least 50%, at least 60%, at least 70%, at least 80%, at least 90%, at least 95%, at least 96%, at least 97%, at least 98%, at least 99%, or 100% of the phospholipase activity of any phospholipase described or referenced herein (e.g., any one of SEQ ID NOs: 235-242 and 252-342, such as any one of SEQ ID NOs: 235, 236, 237, 238, 239, 240, 241 and 242) under the same conditions.

In one embodiment, the phospholipase coding sequence hybridizes under at least low stringency conditions, e.g., medium stringency conditions, medium-high stringency conditions, high stringency conditions, or very high stringency conditions with the full-length complementary strand of the coding sequence from any phospholipase described or referenced herein (e.g., a coding sequence for the phospholipase of any one of SEQ ID NOs: 235-242 and 252-342; such as the corresponding coding sequence of SEQ ID NO: 244-251 or 343-433, respectively; or the phospholipase of any one of SEQ ID NO: 235, 236, 237, 238, 239, 240, 241 or 242; such as the corresponding coding sequence of SEQ ID NO: 244, 245, 246, 247, 248, 249, 250 or 251, respectively). In one embodiment, the phospholipase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any phospholipase described or referenced herein (e.g., a coding sequence for the phospholipase of any one of SEQ ID NOs: 235-242 and 252-342; such as the corresponding coding sequence of SEQ ID NO: 244-251 or 343-433, respectively; or the phospholipase of any one of SEQ ID NO: 235, 236, 237, 238, 239, 240, 241 or 242; such as the corresponding coding sequence of SEQ ID NO: 244, 245, 246, 247, 248, 249, 250 or 251, respectively).

In one embodiment, the phospholipase comprises the coding sequence of any phospholipase described or referenced herein (e.g., a coding sequence for the phospholipase of any one of SEQ ID NOs: 235-242 and 252-342; such as the corresponding coding sequence of SEQ ID NO: 244-251 or 343-433, respectively; or the phospholipase of any one of SEQ ID NO: 235, 236, 237, 238, 239, 240, 241 or 242; such as the corresponding coding sequence of SEQ ID NO: 244, 245, 246, 247, 248, 249, 250 or 251, respectively). In one embodiment, the phospholipase comprises a coding sequence that is a subsequence of the coding sequence from any phospholipase described or referenced herein, wherein the subsequence encodes a polypeptide having phospholipase activity. In one embodiment, the number of nucleotides residues in the subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for use in a particular host cell (e.g., optimized for expression in Saccharomyces cerevisiae).

The phospholipase may be a fused polypeptide or cleavable fusion polypeptide in which another polypeptide is fused at the N-terminus or the C-terminus of the alpha-amylase. A fused polypeptide may be produced by fusing a polynucleotide encoding another polypeptide to a polynucleotide encoding the phospholipase. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

Alpha-Amylases

The expressed and/or exogenous alpha-amylase may be any alpha-amylase that is suitable for the host cells and/or the methods described herein, such as a naturally occurring alpha-amylase (e.g., a native alpha-amylase from another species or an endogenous alpha-amylase expressed from a modified expression vector) or a variant thereof that retains alpha-amylase activity. Any alpha-amylase contemplated for expression by a fermenting organism described below is also contemplated for aspects of the invention involving exogenous addition of an alpha-amylase.

In some embodiments, the fermenting organism comprises a heterologous polynucleotide encoding an alpha-amylase, for example, as described in WO2017/087330, the content of which is hereby incorporated by reference. Any alpha-amylase described or referenced herein is contemplated for expression in the fermenting organism.

In some embodiments, the fermenting organism comprising a heterologous polynucleotide encoding an alpha-amylase has an increased level of alpha-amylase activity compared to the host cells without the heterologous polynucleotide encoding the alpha-amylase, when cultivated under the same conditions. In some embodiments, the fermenting organism has an increased level of alpha-amylase activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the alpha-amylase, when cultivated under the same conditions.

Exemplary alpha-amylases that can be used with the host cells and/or the methods described herein include bacterial, yeast, or filamentous fungal alpha-amylases, e.g., derived from any of the microorganisms described or referenced herein.

The term "bacterial alpha-amylase" means any bacterial alpha-amylase classified under EC 3.2.1.1. A bacterial alpha-amylase used herein may, e.g., be derived from a strain of the genus *Bacillus*, which is sometimes also referred to as the genus *Geobacillus*. In one embodiment, the *Bacillus* alpha-amylase is derived from a strain of *Bacillus amyloliquefaciens, Bacillus licheniformis, Bacillus stearothermophilus,* or *Bacillus subtilis*, but may also be derived from other *Bacillus* sp.

Specific examples of bacterial alpha-amylases include the *Bacillus stearothermophilus* alpha-amylase (BSG) of SEQ ID NO: 3 in WO 99/19467, the *Bacillus amyloliquefaciens* alpha-amylase (BAN) of SEQ ID NO: 5 in WO 99/19467, and the *Bacillus licheniformis* alpha-amylase (BLA) of SEQ ID NO: 4 in WO 99/19467 (all sequences are hereby incorporated by reference). In one embodiment, the alpha-amylase may be an enzyme having a mature polypeptide sequence with a degree of identity of at least 60%, e.g., at least 70%, at least 80%, at least 90%, at least 95%, at least 96%, at least 97%, at least 98% or at least 99% to any of the sequences shown in SEQ ID NOs: 3, 4 or 5, in WO 99/19467.

In one embodiment, the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be a truncated at the C-terminal, so that it is from 480-495 amino acids long, such as about 491 amino acids long, e.g., so that it lacks a functional starch binding domain (compared to SEQ ID NO: 3 in WO 99/19467).

The *Bacillus* alpha-amylase may also be a variant and/or hybrid. Examples of such a variant can be found in any of WO 96/23873, WO 96/23874, WO 97/41213, WO 99/19467, WO 00/60059, and WO 02/10355 (each hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, I181 and/or G182, preferably a double deletion disclosed in WO 96/23873—see, e.g., page 20, lines 1-10 (hereby incorporated by reference), such as corresponding to deletion of positions I181 and G182 compared to the amino acid sequence of *Bacillus stearothermophilus* alpha-amylase set forth in SEQ ID NO: 3 disclosed in WO 99/19467 or the deletion of amino acids R179 and G180 using SEQ ID NO: 3 in WO 99/19467 for numbering (which reference is hereby incorporated by reference). In some embodiments, the *Bacillus* alpha-amylases, such as *Bacillus stearothermophilus* alpha-amylases, have a double deletion corresponding to a deletion of positions 181 and 182 and further optionally comprise a N193F substitution (also denoted I181*+G182*+N193F) compared to the wild-type BSG alpha-amylase amino acid sequence set forth in SEQ ID NO: 3 disclosed in WO 99/19467. The bacterial alpha-amylase may also have a substitution in a position corresponding to S239 in the *Bacillus licheniformis* alpha-amylase shown in SEQ ID NO: 4 in WO 99/19467, or a S242 and/or E188P variant of the *Bacillus stearothermophilus* alpha-amylase of SEQ ID NO: 3 in WO 99/19467.

In one embodiment, the variant is a S242A, E or Q variant, e.g., a S242Q variant, of the *Bacillus stearothermophilus* alpha-amylase.

In one embodiment, the variant is a position E188 variant, e.g., E188P variant of the *Bacillus stearothermophilus* alpha-amylase.

The bacterial alpha-amylase may, in one embodiment, be a truncated *Bacillus* alpha-amylase. In one embodiment, the truncation is so that, e.g., the *Bacillus stearothermophilus* alpha-amylase shown in SEQ ID NO: 3 in WO 99/19467, is about 491 amino acids long, such as from 480 to 495 amino acids long, or so it lacks a functional starch bind domain.

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In one embodiment, this hybrid has one or more, especially all, of the following substitutions: G48A+T49I+G107A+H156Y+A181T+N190F+I201F+A209V+Q264S (using the *Bacillus licheniformis* numbering in SEQ ID NO: 4 of WO 99/19467). In some embodiments, the variants have one or more of the following mutations (or corresponding mutations in other *Bacillus* alpha-amylases): H154Y, A181T, N190F, A209V and Q264S and/or the deletion of two residues between positions 176 and 179, e.g., deletion of E178 and G179 (using SEQ ID NO: 5 of WO 99/19467 for position numbering).

In one embodiment, the bacterial alpha-amylase is the mature part of the chimeric alpha-amylase disclosed in Richardson et al. (2002), The Journal of Biological Chemistry, Vol. 277, No 29, Issue 19 July, pp. 267501-26507, referred to as BD5088 or a variant thereof. This alpha-amylase is the same as the one shown in SEQ ID NO: 2 in WO 2007/134207. The mature enzyme sequence starts after the initial "Met" amino acid in position 1.

The alpha-amylase may be a thermostable alpha-amylase, such as a thermostable bacterial alpha-amylase, e.g., from *Bacillus stearothermophilus*. In one embodiment, the alpha-amylase used in a process described herein has a T½ (min) at pH 4.5, 85° C., 0.12 mM CaCl$_2$ of at least 10 determined as described in Example 1 of WO2018/098381.

In one embodiment, the thermostable alpha-amylase has a T½ (min) at pH 4.5, 85° C., 0.12 mM CaCl$_2$, of at least 15. In one embodiment, the thermostable alpha-amylase has a T½ (min) at pH 4.5, 85° C., 0.12 mM CaCl$_2$, of as at least 20. In one embodiment, the thermostable alpha-amylase has a T½ (min) at pH 4.5, 85° C., 0.12 mM CaCl$_2$, of as at least 25. In one embodiment, the thermostable alpha-amylase has a T½ (min) at pH 4.5, 85° C., 0.12 mM CaCl$_2$, of as at least 30. In one embodiment, the thermostable alpha-amylase has a T½ (min) at pH 4.5, 85° C., 0.12 mM CaCl$_2$, of as at least 40.

In one embodiment, the thermostable alpha-amylase has a T½ (min) at pH 4.5, 85° C., 0.12 mM CaCl$_2$, of at least 50. In one embodiment, the thermostable alpha-amylase has a T½ (min) at pH 4.5, 85° C., 0.12 mM CaCl$_2$, of at least 60. In one embodiment, the thermostable alpha-amylase has a T½ (min) at pH 4.5, 85° C., 0.12 mM CaCl$_2$, between 10-70. In one embodiment, the thermostable alpha-amylase has a T½ (min) at pH 4.5, 85° C., 0.12 mM CaCl$_2$, between 15-70. In one embodiment, the thermostable alpha-amylase has a T½ (min) at pH 4.5, 85° C., 0.12 mM CaCl$_2$, between 20-70. In one embodiment, the thermostable alpha-amylase has a T½ (min) at pH 4.5, 85° C., 0.12 mM CaCl$_2$, between 25-70.

In one embodiment, the thermostable alpha-amylase has a T½ (min) at pH 4.5, 85° C., 0.12 mM CaCl$_2$, between 30-70. In one embodiment, the thermostable alpha-amylase has a T½ (min) at pH 4.5, 85° C., 0.12 mM CaCl$_2$, between 40-70. In one embodiment, the thermostable alpha-amylase has a T½ (min) at pH 4.5, 85° C., 0.12 mM CaCl$_2$, between 50-70. In one embodiment, the thermostable alpha-amylase has a T½ (min) at pH 4.5, 85° C., 0.12 mM CaCl$_2$, between 60-70.

In one embodiment, the alpha-amylase is a bacterial alpha-amylase, e.g., derived from the genus *Bacillus*, such as a strain of *Bacillus stearothermophilus*, e.g., the *Bacillus stearothermophilus* as disclosed in WO 99/019467 as SEQ ID NO: 3 with one or two amino acids deleted at positions R179, G180, I181 and/or G182, in particular with R179 and G180 deleted, or with I181 and G182 deleted, with mutations in below list of mutations.

In some embodiment, the *Bacillus stearothermophilus* alpha-amylases have double deletion I181+G182, and optional substitution N193F, further comprising one of the following substitutions or combinations of substitutions:

V59A+Q89R+G112D+E129V+K177L+R179E+K220P+N224L+Q254S;
V59A+Q89R+E129V+K177L+R179E+H208Y+K220P+N224L+Q254S;
V59A+Q89R+E129V+K177L+R179E+K220P+N224L+Q254S+D269E+D281N;
V59A+Q89R+E129V+K177L+R179E+K220P+N224L+Q254S+I270L;
V59A+Q89R+E129V+K177L+R179E+K220P+N224L+Q254S+H274K;
V59A+Q89R+E129V+K177L+R179E+K220P+N224L+Q254S+Y276F;
V59A+E129V+R157Y+K177L+R179E+K220P+N224L+S242Q+Q254S;
V59A+E129V+K177L+R179E+H208Y+K220P+N224L+S242Q+Q254S;
V59A+E129V+K177L+R179E+K220P+N224L+S242Q+Q254S;
V59A+E129V+K177L+R179E+K220P+N224L+S242Q+Q254S+H274K;
V59A+E129V+K177L+R179E+K220P+N224L+S242Q+Q254S+Y276F;
V59A+E129V+K177L+R179E+K220P+N224L+S242Q+Q254S+D281N;
V59A+E129V+K177L+R179E+K220P+N224L+S242Q+Q254S+M284T;
V59A+E129V+K177L+R179E+K220P+N224L+S242Q+Q254S+G416V;
V59A+E129V+K177L+R179E+K220P+N224L+Q254S;
V59A+E129V+K177L+R179E+K220P+N224L+Q254S+M284T;
A91L+M96I+E129V+K177L+R179E+K220P+N224L+S242Q+Q254S;
E129V+K177L+R179E;
E129V+K177L+R179E+K220P+N224L+S242Q+Q254S;
E129V+K177L+R179E+K220P+N224L+S242Q+Q254S+Y276F+L427M;
E129V+K177L+R179E+K220P+N224L+S242Q+Q254S+M284T;
E129V+K177L+R179E+K220P+N224L+S242Q+Q254S+N376*+I377*;
E129V+K177L+R179E+K220P+N224L+Q254S;
E129V+K177L+R179E+K220P+N224L+Q254S+M284T;
E129V+K177L+R179E+S242Q;

E129V+K177L+R179V+K220P+N224L+S242Q+
   Q254S;
K220P+N224L+S242Q+Q254S;
M284V;
V59A+Q89R+E129V+K177L+R179E+Q254S+M284V;
   and
V59A+E129V+K177L+R179E+Q254S+M284V;

In one embodiment, the alpha-amylase is selected from the group of *Bacillus stearothermophilus* alpha-amylase variants with double deletion I181*+G182*, and optionally substitution N193F, and further one of the following substitutions or combinations of substitutions:
E129V+K177L+R179E;
V59A+Q89R+E129V+K177L+R179E+H208Y+K220P+
   N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S
   (using SEQ ID NO: 1 herein for numbering).

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467, or variants thereof, are truncated in the C-terminal and are typically from 480-495 amino acids long, such as about 491 amino acids long, e.g., so that it lacks a functional starch binding domain.

In one embodiment, the alpha-amylase variant may be an enzyme having a mature polypeptide sequence with a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the sequence shown in SEQ ID NO: 3 in WO 99/19467.

In one embodiment, the bacterial alpha-amylase, e.g., *Bacillus* alpha-amylase, such as especially *Bacillus stearothermophilus* alpha-amylase, or variant thereof, is dosed to liquefaction in a concentration between 0.01-10 KNU-A/g DS, e.g., between 0.02 and 5 KNU-A/g DS, such as 0.03 and 3 KNU-A, preferably 0.04 and 2 KNU-A/g DS, such as especially 0.01 and 2 KNU-A/g DS. In one embodiment, the bacterial alpha-amylase, e.g., *Bacillus* alpha-amylase, such as especially *Bacillus stearothermophilus* alpha-amylases, or variant thereof, is dosed to liquefaction in a concentration of between 0.0001-1 mg EP (Enzyme Protein)/g DS, e.g., 0.0005-0.5 mg EP/g DS, such as 0.001-0.1 mg EP/g DS.

In one embodiment, the bacterial alpha-amylase is derived from the *Bacillus subtilis* alpha-amylase of SEQ ID NO: 76, the *Bacillus subtilis* alpha-amylase of SEQ ID NO: 82, the *Bacillus subtilis* alpha-amylase of SEQ ID NO: 83, the *Bacillus subtilis* alpha-amylase of SEQ ID NO: 84, or the *Bacillus licheniformis* alpha-amylase of SEQ ID NO: 85, the *Clostridium phytofermentans* alpha-amylase of SEQ ID NO: 89, the *Clostridium phytofermentans* alpha-amylase of SEQ ID NO: 90, the *Clostridium phytofermentans* alpha-amylase of SEQ ID NO: 91, the *Clostridium phytofermentans* alpha-amylase of SEQ ID NO: 92, the *Clostridium phytofermentans* alpha-amylase of SEQ ID NO: 93, the *Clostridium phytofermentans* alpha-amylase of SEQ ID NO: 94, the *Clostridium thermocellum* alpha-amylase of SEQ ID NO: 95, the *Thermobifida fusca* alpha-amylase of SEQ ID NO: 96, the *Thermobifida fusca* alpha-amylase of SEQ ID NO: 97, the *Anaerocellum thermophilum* of SEQ ID NO: 98, the *Anaerocellum thermophilum* of SEQ ID NO: 99, the *Anaerocellum thermophilum* of SEQ ID NO: 100, the *Streptomyces avermitilis* of SEQ ID NO: 101, or the *Streptomyces avermitilis* of SEQ ID NO: 88.

In one embodiment, the alpha-amylase is derived from *Bacillus amyloliquefaciens*, such as the *Bacillus amyloliquefaciens* alpha-amylase of SEQ ID NO: 231 (e.g., as described in WO2018/002360, or variants thereof as described in WO2017/037614).

In one embodiment, the alpha-amylase is derived from a yeast alpha-amylase, such as the *Saccharomycopsis fibuligera* alpha-amylase of SEQ ID NO: 77, the *Debaryomyces occidentalis* alpha-amylase of SEQ ID NO: 78, the *Debaryomyces occidentalis* alpha-amylase of SEQ ID NO: 79, the *Lipomyces kononenkoae* alpha-amylase of SEQ ID NO: 80, the *Lipomyces kononenkoae* alpha-amylase of SEQ ID NO: 81.

In one embodiment, the alpha-amylase is derived from a filamentous fungal alpha-amylase, such as the *Aspergillus niger* alpha-amylase of SEQ ID NO: 86, or the *Aspergillus niger* alpha-amylase of SEQ ID NO: 87.

Additional alpha-amylases that may be expressed with the fermenting organisms and used with the methods described herein are described in the examples, and include, but are not limited to alpha-amylases shown in Table 2 (or derivatives thereof).

TABLE 2

| Donor Organism (catalytic domain) | SEQ ID NO: (mature polypeptide) |
|---|---|
| Rhizomucor pusillus | 121 |
| Bacillus licheniformis | 122 |
| Aspergillus niger | 123 |
| Aspergillus tamarii | 124 |
| Acidomyces richmondensis | 125 |
| Aspergillus bombycis | 126 |
| Alternaria sp | 127 |
| Rhizopus microsporus | 128 |
| Syncephalastrum racemosum | 129 |
| Rhizomucor pusillus | 130 |
| Dichotomocladium hesseltinei | 131 |
| Lichtheimia ramosa | 132 |
| Penicillium aethiopicum | 133 |
| Subulispora sp | 134 |
| Trichoderma paraviridescens | 135 |
| Byssoascus striatosporus | 136 |
| Aspergillus brasiliensis | 137 |
| Penicillium subspinulosum | 138 |
| Penicillium antarcticum | 139 |
| Penicillium coprophilum | 140 |
| Penicillium olsonii | 141 |
| Penicillium vasconiae | 142 |
| Penicillium sp | 143 |
| Heterocephalum aurantiacum | 144 |
| Neosartorya massa | 145 |
| Penicillium janthinellum | 146 |
| Aspergillus brasiliensis | 147 |
| Aspergillus westerdijkiae | 148 |
| Hamigera avellanea | 149 |
| Hamigera avellanea | 150 |
| Meripilus giganteus | 151 |
| Cerrena unicolor | 152 |
| Physalacria cryptomeriae | 153 |
| Lenzites betulinus | 154 |
| Trametes ljubarskyi | 155 |
| Bacillus subtilis | 156 |
| Bacillus subtilis subsp. subtilis | 157 |
| Schwanniomyces occidentalis | 158 |
| Rhizomucor pusillus | 159 |
| Aspergillus niger | 160 |
| Bacillus stearothermophilus | 161 |
| Bacillus halmapalus | 162 |
| Aspergillus oryzae | 163 |
| Bacillus amyloliquefaciens | 164 |

TABLE 2-continued

| Donor Organism (catalytic domain) | SEQ ID NO: (mature polypeptide) |
|---|---|
| Rhizomucor pusillus | 165 |
| Kionochaeta ivoriensis | 166 |
| Aspergillus niger | 167 |
| Aspergillus oryzae | 168 |
| Penicillium canescens | 169 |
| Acidomyces acidothermus | 170 |
| Kinochaeta ivoriensis | 171 |
| Aspergillus terreus | 172 |
| Thamnidium elegans | 173 |
| Meripilus giganteus | 174 |

Additional alpha-amylases contemplated for use with the present invention can be found in WO2011/153516 (the content of which is incorporated herein).

Additional polynucleotides encoding suitable alpha-amylases may be obtained from microorganisms of any genus, including those readily available within the UniProtKB database (www.uniprot.org).

The alpha-amylase coding sequences can also be used to design nucleic acid probes to identify and clone DNA encoding trehalases from strains of different genera or species, as described supra.

The polynucleotides encoding alpha-amylases may also be identified and obtained from other sources including microorganisms isolated from nature (e.g., soil, composts, water, etc.) or DNA samples obtained directly from natural materials (e.g., soil, composts, water, etc) as described supra.

Techniques used to isolate or clone polynucleotides encoding alpha-amylases are described supra.

In one embodiment, the alpha-amylase has a mature polypeptide sequence that comprises or consists of the amino acid sequence of any one of the alpha-amylases described or referenced herein (e.g., any one of SEQ ID NOs: 76-101, 121-174 and 231). In another embodiment, the alpha-amylase has a mature polypeptide sequence that is a fragment of the any one of the alpha-amylases described or referenced herein (e.g., any one of SEQ ID NOs: 76-101, 121-174 and 231). In one embodiment, the number of amino acid residues in the fragment is at least 75%, e.g., at least 80%, 85%, 90%, or 95% of the number of amino acid residues in referenced full length alpha-amylase (e.g. any one of SEQ ID NOs: 76-101, 121-174 and 231). In other embodiments, the alpha-amylase may comprise the catalytic domain of any alpha-amylase described or referenced herein (e.g., the catalytic domain of any one of SEQ ID NOs: 76-101, 121-174 and 231).

The alpha-amylase may be a variant of any one of the alpha-amylases described supra (e.g., any one of SEQ ID NOs: 76-101, 121-174 and 231). In one embodiment, the alpha-amylase has a mature polypeptide sequence of at least 60%, e.g., at least 65%, 70%, 75%, 80%, 85%, 90%, 95%, 97%, 98%, 99%, or 100% sequence identity to any one of the alpha-amylases described supra (e.g., any one of SEQ ID NOs: 76-101, 121-174 and 231).

In one embodiment, the alpha-amylase has a mature polypeptide sequence that differs by no more than ten amino acids, e.g., by no more than five amino acids, by no more than four amino acids, by no more than three amino acids, by no more than two amino acids, or by one amino acid from the amino acid sequence of any one of the alpha-amylases described supra (e.g., any one of SEQ ID NOs: 76-101, 121-174 and 231). In one embodiment, the alpha-amylase has an amino acid substitution, deletion, and/or insertion of one or more (e.g., two, several) of amino acid sequence of any one of the alpha-amylases described supra (e.g., any one of SEQ ID NOs: 76-101, 121-174 and 231). In some embodiments, the total number of amino acid substitutions, deletions and/or insertions is not more than 10, e.g., not more than 9, 8, 7, 6, 5, 4, 3, 2, or 1.

In some embodiments, the alpha-amylase has at least 20%, e.g., at least 40%, at least 50%, at least 60%, at least 70%, at least 80%, at least 90%, at least 95%, at least 96%, at least 97%, at least 98%, at least 99%, or 100% of the alpha-amylase activity of any alpha-amylase described or referenced herein (e.g., any one of SEQ ID NOs: 76-101, 121-174 and 231) under the same conditions.

In one embodiment, the alpha-amylase coding sequence hybridizes under at least low stringency conditions, e.g., medium stringency conditions, medium-high stringency conditions, high stringency conditions, or very high stringency conditions with the full-length complementary strand of the coding sequence from any alpha-amylase described or referenced herein (e.g., any one of SEQ ID NOs: 76-101, 121-174 and 231). In one embodiment, the alpha-amylase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any alpha-amylase described or referenced herein (e.g., any one of SEQ ID NOs: 76-101, 121-174 and 231).

In one embodiment, the alpha-amylase comprises the coding sequence of any alpha-amylase described or referenced herein (any one of SEQ ID NOs: 76-101, 121-174 and 231). In one embodiment, the alpha-amylase comprises a coding sequence that is a subsequence of the coding sequence from any alpha-amylase described or referenced herein, wherein the subsequence encodes a polypeptide having alpha-amylase activity. In one embodiment, the number of nucleotides residues in the subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for use in a particular host cell (e.g., optimized for expression in *Saccharomyces cerevisiae*).

The alpha-amylase can also include fused polypeptides or cleavable fusion polypeptides, as described supra.

Trehalases

The expressed and/or exogenous trehalase can be any trehalase that is suitable for the fermenting organisms and/or their methods of use described herein, such as a naturally occurring trehalase or a variant thereof that retains trehalase activity. Any trehalase contemplated for expression by a fermenting organism described below is also contemplated for aspects of the invention involving exogenous addition of a trehalase (e.g., added before, during or after liquefaction and/or saccharification).

In some embodiments, the fermenting organism comprising a heterologous polynucleotide encoding a trehalase has an increased level of trehalase activity compared to the host cells without the heterologous polynucleotide encoding the trehalase, when cultivated under the same conditions. In some embodiments, the fermenting organism has an increased level of trehalase activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the trehalase, when cultivated under the same conditions.

Trehalases that may be expressed with the fermenting organisms and used with the methods described herein include, but are not limited to, trehalases shown in Table 3 (or derivatives thereof).

TABLE 3

| Donor Organism (catalytic domain) | SEQ ID NO: (mature polypeptide) |
|---|---|
| Chaetomium megalocarpum | 175 |
| Lecanicillium psalliotae | 176 |
| Doratomyces sp | 177 |
| Mucor moelleri | 178 |
| Phialophora cyclaminis | 179 |
| Thielavia arenaria | 180 |
| Thielavia antarctica | 181 |
| Chaetomium sp | 182 |
| Chaetomium nigricolor | 183 |
| Chaetomium jodhpurense | 184 |
| Chaetomium piluliferum | 185 |
| Myceliophthora hinnulea | 186 |
| Chloridium virescens | 187 |
| Gelasinospora cratophora | 188 |
| Acidobacteriaceae bacterium | 189 |
| Acidobacterium capsulatum | 190 |
| Acidovorax wautersii | 191 |
| Xanthomonas arboricola | 192 |
| Kosakonia sacchari | 193 |
| Enterobacter sp | 194 |
| Saitozyma flava | 195 |
| Phaeotremella skinneri | 196 |
| Trichoderma asperellum | 197 |
| Corynascus sepedonium | 198 |
| Myceliophthora thermophila | 199 |
| Trichoderma reesei | 200 |
| Chaetomium virescens | 201 |
| Rhodothermus marinus | 202 |
| Myceliophthora sepedonium | 203 |
| Moelleriella libera | 204 |
| Acremonium dichromosporum | 205 |
| Fusarium sambucinum | 206 |
| Phoma sp | 207 |
| Lentinus similis | 208 |
| Diaporthe nobilis | 209 |
| Solicoccozyma terricola | 210 |
| Dioszegia cryoxerica | 211 |
| Talaromyces funiculosus | 212 |
| Hamigera avellanea | 213 |
| Talaromyces ruber | 214 |
| Trichoderma lixii | 215 |
| Aspergillus cervinus | 216 |
| Rasamsonia brevistipitata | 217 |
| Acremonium curvulum | 218 |
| Talaromyces piceae | 219 |
| Penicillium sp | 220 |
| Talaromyces aurantiacus | 221 |
| Talaromyces pinophilus | 222 |
| Talaromyces leycettanus | 223 |
| Talaromyces variabilis | 224 |
| Aspergillus niger | 225 |
| Trichoderma reesei | 226 |

Additional polynucleotides encoding suitable trehalases may be derived from microorganisms of any suitable genus, including those readily available within the UniProtKB database (www.uniprot.org).

The trehalase coding sequences can also be used to design nucleic acid probes to identify and clone DNA encoding trehalases from strains of different genera or species, as described supra.

The polynucleotides encoding trehalases may also be identified and obtained from other sources including microorganisms isolated from nature (e.g., soil, composts, water, etc.) or DNA samples obtained directly from natural materials (e.g., soil, composts, water, etc) as described supra.

Techniques used to isolate or clone polynucleotides encoding trehalases are described supra.

In one embodiment, the trehalase has a mature polypeptide sequence that comprises or consists of the amino acid sequence of any one of the trehalases described or referenced herein (e.g., any one of SEQ ID NOs: 175-226). In another embodiment, the trehalase has a mature polypeptide sequence that is a fragment of the any one of the trehalases described or referenced herein (e.g., any one of SEQ ID NOs: 175-226). In one embodiment, the number of amino acid residues in the fragment is at least 75%, e.g., at least 80%, 85%, 90%, or 95% of the number of amino acid residues in referenced full length trehalase (e.g. any one of SEQ ID NOs: 175-226). In other embodiments, the trehalase may comprise the catalytic domain of any trehalase described or referenced herein (e.g., the catalytic domain of any one of SEQ ID NOs: 175-226).

The trehalase may be a variant of any one of the trehalases described supra (e.g., any one of SEQ ID NOs: 175-226). In one embodiment, the trehalase has a mature polypeptide sequence of at least 60%, e.g., at least 65%, 70%, 75%, 80%, 85%, 90%, 95%, 97%, 98%, 99%, or 100% sequence identity to any one of the trehalases described supra (e.g., any one of SEQ ID NOs: 175-226).

In one embodiment, the trehalase has a mature polypeptide sequence that differs by no more than ten amino acids, e.g., by no more than five amino acids, by no more than four amino acids, by no more than three amino acids, by no more than two amino acids, or by one amino acid from the amino acid sequence of any one of the trehalases described supra (e.g., any one of SEQ ID NOs: 175-226). In one embodiment, the trehalase has an amino acid substitution, deletion, and/or insertion of one or more (e.g., two, several) of amino acid sequence of any one of the trehalases described supra (e.g., any one of SEQ ID NOs: 175-226). In some embodiments, the total number of amino acid substitutions, deletions and/or insertions is not more than 10, e.g., not more than 9, 8, 7, 6, 5, 4, 3, 2, or 1.

In some embodiments, the trehalase has at least 20%, e.g., at least 40%, at least 50%, at least 60%, at least 70%, at least 80%, at least 90%, at least 95%, at least 96%, at least 97%, at least 98%, at least 99%, or 100% of the trehalase activity of any trehalase described or referenced herein (e.g., any one of SEQ ID NOs: 175-226) under the same conditions.

In one embodiment, the trehalase coding sequence hybridizes under at least low stringency conditions, e.g., medium stringency conditions, medium-high stringency conditions, high stringency conditions, or very high stringency conditions with the full-length complementary strand of the coding sequence from any trehalase described or referenced herein (e.g., any one of SEQ ID NOs: 175-226). In one embodiment, the trehalase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any trehalase described or referenced herein (e.g., any one of SEQ ID NOs: 175-226).

In one embodiment, the trehalase comprises the coding sequence of any trehalase described or referenced herein (any one of SEQ ID NOs: 175-226). In one embodiment, the trehalase comprises a coding sequence that is a subsequence of the coding sequence from any trehalase described or referenced herein, wherein the subsequence encodes a polypeptide having trehalase activity. In one embodiment, the number of nucleotides residues in the subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for use in a particular host cell (e.g., optimized for expression in *Saccharomyces cerevisiae*).

The trehalase can also include fused polypeptides or cleavable fusion polypeptides, as described supra.

Glucoamylases

The expressed and/or exogenous glucoamylase can be any glucoamylase that is suitable for the fermenting organisms and/or their methods of use described herein, such as a naturally occurring glucoamylase or a variant thereof that retains glucoamylase activity. Any glucoamylase contemplated for expression by a fermenting organism described below is also contemplated for aspects of the invention involving exogenous addition of a glucoamylase (e.g., added before, during or after liquefaction and/or saccharification).

In some embodiments, the fermenting organism comprises a heterologous polynucleotide encoding a glucoamylase, for example, as described in WO2017/087330, the content of which is hereby incorporated by reference. Any glucoamylase described or referenced herein is contemplated for expression in the fermenting organism.

In some embodiments, the fermenting organism comprising a heterologous polynucleotide encoding an glucoamylase has an increased level of glucoamylase activity compared to the host cells without the heterologous polynucleotide encoding the glucoamylase, when cultivated under the same conditions. In some embodiments, the fermenting organism has an increased level of glucoamylase activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the glucoamylase, when cultivated under the same conditions.

Exemplary glucoamylases that can be used with the host cells and/or the methods described herein include bacterial, yeast, or filamentous fungal glucoamylases, e.g., obtained from any of the microorganisms described or referenced herein, as described supra under the sections related to alpha-amylases.

The glucoamylase may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). In one embodiment, the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831).

Contemplated fungal glucoamylases include *Trametes cingulate, Pachykytospora papyracea*; and *Leucopaxillus giganteus* all disclosed in WO 2006/069289; or *Peniophora rufomarginata* disclosed in WO2007/124285; or a mixture thereof. Also hybrid glucoamylase are contemplated. Examples include the hybrid glucoamylases disclosed in WO 2005/045018.

In one embodiment, the glucoamylase is derived from a strain of the genus *Pycnoporus*, in particular a strain of *Pycnoporus* as described in WO 2011/066576 (SEQ ID NO: 2, 4 or 6 therein), including the *Pycnoporus sanguineus* glucoamylase, or from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16 therein). In one embodiment, the glucoamylase is SEQ ID NO: 2 in WO 2011/068803 (i.e. *Gloeophyllum sepiarium* glucoamylase). In one embodiment, the glucoamylase is the *Gloeophyllum sepiarium* glucoamylase of SEQ ID NO: 8. In one embodiment, the glucoamylase is the *Pycnoporus sanguineus* glucoamylase of SEQ ID NO: 229.

In one embodiment, the glucoamylase is a *Gloeophyllum trabeum* glucoamylase (disclosed as SEQ ID NO: 3 in WO2014/177546). In another embodiment, the glucoamylase is derived from a strain of the genus *Nigrofomes*, in particular a strain of *Nigrofomes* sp. disclosed in WO 2012/064351 (disclosed as SEQ ID NO: 2 therein).

Also contemplated are glucoamylases with a mature polypeptide sequence which exhibit a high identity to any of the above mentioned glucoamylases, i.e., at least 60%, such as at least 70%, at least 75%, at least 80%, at least 85%, at least 90%, at least 95%, at least 96%, at least 97%, at least 98%, at least 99% or even 100% identity to any one of the mature polypeptide sequences mentioned above.

Glucoamylases may be added to the saccharification and/or fermentation in an amount of 0.0001-20 AGU/g DS, such as 0.001-10 AGU/g DS, 0.01-5 AGU/g DS, or 0.1-2 AGU/g DS.

Glucoamylases may be added to the saccharification and/or fermentation in an amount of 1-1,000 μg EP/g DS, such as 10-500 μg/g DS, or 25-250 μg/g DS.

Glucoamylases may be added to liquefaction in an amount of 0.1-100 μg EP/g DS, such as 0.5-50 μg EP/g DS, 1-25 μg EP/g DS, or 2-12 μg EP/g DS.

In one embodiment, the glucoamylase is added as a blend further comprising an alpha-amylase (e.g., any alpha-amylase described herein). In one embodiment, the alpha-amylase is a fungal alpha-amylase, especially an acid fungal alpha-amylase. The alpha-amylase is typically a side activity.

In one embodiment, the glucoamylase is a blend comprising *Talaromyces emersonii* glucoamylase disclosed in WO 99/28448 as SEQ ID NO: 34 and *Trametes cingulata* glucoamylase disclosed as SEQ ID NO: 2 in WO 06/069289.

In one embodiment, the glucoamylase is a blend comprising *Talaromyces emersonii* glucoamylase disclosed in WO 99/28448, *Trametes cingulata* glucoamylase disclosed as SEQ ID NO: 2 in WO 06/69289, and an alpha-amylase.

In one embodiment, the glucoamylase is a blend comprising *Talaromyces emersonii* glucoamylase disclosed in WO99/28448, *Trametes cingulata* glucoamylase disclosed in WO 06/69289, and *Rhizomucor pusillus* alpha-amylase with *Aspergillus niger* glucoamylase linker and SBD disclosed as V039 in Table 5 in WO 2006/069290.

In one embodiment, the glucoamylase is a blend comprising *Gloeophyllum sepiarium* glucoamylase shown as SEQ ID NO: 2 in WO 2011/068803 and an alpha-amylase, in particular *Rhizomucor pusillus* alpha-amylase with an *Aspergillus niger* glucoamylase linker and starch-binding domain (SBD), disclosed SEQ ID NO: 3 in WO 2013/006756, in particular with the following substitutions: G128D+D143N.

In one embodiment, the alpha-amylase may be derived from a strain of the genus *Rhizomucor*, preferably a strain the *Rhizomucor pusillus*, such as the one shown in SEQ ID NO: 3 in WO2013/006756, or the genus *Meripilus*, preferably a strain of *Meripilus giganteus*. In one embodiment, the alpha-amylase is derived from a *Rhizomucor pusillus* with an *Aspergillus niger* glucoamylase linker and starch-binding domain (SBD), disclosed as V039 in Table 5 in WO 2006/069290.

In one embodiment, the *Rhizomucor pusillus* alpha-amylase or the *Rhizomucor pusillus* alpha-amylase with an *Aspergillus niger* glucoamylase linker and starch-binding domain (SBD) has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; and G128D+Y141W+D143N+K192R; or G128D+Y141W+D143N+K192R+P219C (using SEQ ID NO: 3 in WO 2013/006756 for numbering).

In one embodiment, the glucoamylase blend comprises *Gloeophyllum sepiarium* glucoamylase (e.g., SEQ ID NO: 2 in WO 2011/068803) and *Rhizomucor pusillus* alpha-amylase.

In one embodiment, the glucoamylase blend comprises *Gloeophyllum sepiarium* glucoamylase shown as SEQ ID NO: 2 in WO 2011/068803 and *Rhizomucor pusillus* with an *Aspergillus niger* glucoamylase linker and starch-binding domain (SBD), disclosed SEQ ID NO: 3 in WO 2013/006756 with the following substitutions: G128D+D143N.

Commercially available compositions comprising glucoamylase include AMG 200L; AMG 300 L; SAN™ SUPER, SAN™ EXTRA L, SPIRIZYME® PLUS, SPIRIZYME® FUEL, SPIRIZYME® B4U, SPIRIZYME® ULTRA, SPIRIZYME® EXCEL, SPIRIZYME ACHIEVE®, and AMG® E (from Novozymes A/S); OPTIDEX™ 300, GC480, GC417 (from DuPont-Danisco); AMIGASE™ and AMIGASE™ PLUS (from DSM); G-ZYME™ G900, G-ZYME™ and G990 ZR (from DuPont-Danisco).

In one embodiment, the glucoamylase is derived from the *Debaryomyces occidentalis* glucoamylase of SEQ ID NO: 102. In one embodiment, the glucoamylase is derived from the *Saccharomycopsis fibuligera* glucoamylase of SEQ ID NO: 103. In one embodiment, the glucoamylase is derived from the *Saccharomycopsis fibuligera* glucoamylase of SEQ ID NO: 104. In one embodiment, the glucoamylase is derived from the *Saccharomyces cerevisiae* glucoamylase of SEQ ID NO: 105. In one embodiment, the glucoamylase is derived from the *Aspergillus niger* glucoamylase of SEQ ID NO: 106. In one embodiment, the glucoamylase is derived from the *Aspergillus oryzae* glucoamylase of SEQ ID NO: 107. In one embodiment, the glucoamylase is derived from the *Rhizopus oryzae* glucoamylase of SEQ ID NO: 108. In one embodiment, the glucoamylase is derived from the *Clostridium thermocellum* glucoamylase of SEQ ID NO: 109. In one embodiment, the glucoamylase is derived from the *Clostridium thermocellum* glucoamylase of SEQ ID NO: 110. In one embodiment, the glucoamylase is derived from the Arxula adeninivorans glucoamylase of SEQ ID NO: 111. In one embodiment, the glucoamylase is derived from the *Hormoconis resinae* glucoamylase of SEQ ID NO: 112. In one embodiment, the glucoamylase is derived from the *Aureobasidium pullulans* glucoamylase of SEQ ID NO: 113.

In one embodiment, the glucoamylase is a *Trichoderma reesei* glucoamylase, such as the *Trichoderma reesei* glucoamylase of SEQ ID NO: 230.

In one embodiment, the glucoamylase has a Relative Activity heat stability at 85° C. of at least 20%, at least 30%, or at least 35% determined as described in Example 4 of WO2018/098381 (heat stability).

In one embodiment, the glucoamylase has a relative activity pH optimum at pH 5.0 of at least 90%, e.g., at least 95%, at least 97%, or 100% determined as described in Example 4 of WO2018/098381 (pH optimum).

In one embodiment, the glucoamylase has a pH stability at pH 5.0 of at least 80%, at least 85%, at least 90% determined as described in Example 4 of WO2018/098381 (pH stability).

In one embodiment, the glucoamylase used in liquefaction, such as a *Penicillium oxalicum* glucoamylase variant, has a thermostability determined as DSC Td at pH 4.0 as described in Example 15 of WO2018/098381 of at least 70° C., preferably at least 75° C., such as at least 80° C., such as at least 81° C., such as at least 82° C., such as at least 83° C., such as at least 84° C., such as at least 85° C., such as at least 86° C., such as at least 87%, such as at least 88° C., such as at least 89° C., such as at least 90° C. In one embodiment, the glucoamylase, such as a *Penicillium oxalicum* glucoamylase variant, has a thermostability determined as DSC Td at pH 4.0 as described in Example 15 of WO2018/098381 in the range between 70° C. and 95° C., such as between 80° C. and 90° C.

In one embodiment, the glucoamylase, such as a *Penicillium oxalicum* glucoamylase variant, used in liquefaction has a thermostability determined as DSC Td at pH 4.8 as described in Example 15 of WO2018/098381 of at least 70° C., preferably at least 75° C., such as at least 80° C., such as at least 81° C., such as at least 82° C., such as at least 83° C., such as at least 84° C., such as at least 85° C., such as at least 86° C., such as at least 87%, such as at least 88° C., such as at least 89° C., such as at least 90° C., such as at least 91° C. In one embodiment, the glucoamylase, such as a *Penicillium oxalicum* glucoamylase variant, has a thermostability determined as DSC Td at pH 4.8 as described in Example 15 of WO2018/098381 in the range between 70° C. and 95° C., such as between 80° C. and 90° C.

In one embodiment, the glucoamylase, such as a *Penicillium oxalicum* glucoamylase variant, used in liquefaction has a residual activity determined as described in Example 16 of WO2018/098381, of at least 100% such as at least 105%, such as at least 110%, such as at least 115%, such as at least 120%, such as at least 125%. In one embodiment, the glucoamylase, such as a *Penicillium oxalicum* glucoamylase variant, has a thermostability determined as residual activity as described in Example 16 of WO2018/098381, in the range between 100% and 130%.

In one embodiment, the glucoamylase, e.g., of fungal origin such as a filamentous fungi, from a strain of the genus *Penicillium*, e.g., a strain of *Penicillium oxalicum*, in particular the *Penicillium oxalicum* glucoamylase disclosed as SEQ ID NO: 2 in WO 2011/127802 (which is hereby incorporated by reference).

In one embodiment, the glucoamylase has a mature polypeptide sequence of at least 80%, e.g., at least 85%, at least 90%, at least 91%, at least 92%, at least 93%, at least 94%, at least 95%, at least 96%, at least 97%, at least 98%, at least 99% or 100% identity to the mature polypeptide shown in SEQ ID NO: 2 in WO 2011/127802.

In one embodiment, the glucoamylase is a variant of the *Penicillium oxalicum* glucoamylase disclosed as SEQ ID NO: 2 in WO 2011/127802, having a K79V substitution. The K79V glucoamylase variant has reduced sensitivity to protease degradation relative to the parent as disclosed in WO 2013/036526 (which is hereby incorporated by reference).

In one embodiment, the glucoamylase is derived from *Penicillium oxalicum*.

In one embodiment, the glucoamylase is a variant of the *Penicillium oxalicum* glucoamylase disclosed as SEQ ID NO: 2 in WO 2011/127802. In one embodiment, the *Penicillium oxalicum* glucoamylase is the one disclosed as SEQ ID NO: 2 in WO 2011/127802 having Val (V) in position 79.

Contemplated *Penicillium oxalicum* glucoamylase variants are disclosed in WO 2013/053801 which is hereby incorporated by reference.

In one embodiment, these variants have reduced sensitivity to protease degradation.

In one embodiment, these variant have improved thermostability compared to the parent.

In one embodiment, the glucoamylase has a K79V substitution (using SEQ ID NO: 2 of WO 2011/127802 for numbering), corresponding to the PE001 variant, and further comprises one of the following alterations or combinations of alterations T65A; Q327F; E501V; Y504T; Y504*; T65A+Q327F; T65A+E501V; T65A+Y504T; T65A+Y504*; Q327F+E501V; Q327F+Y504T; Q327F+Y504*; E501V+Y504T; E501V+Y504*; T65A+Q327F+E501V; T65A+Q327F+Y504T; T65A+E501V+Y504T; Q327F+E501V+Y504T; T65A+Q327F+Y504*; T65A+E501V+Y504*; Q327F+E501V+Y504*; T65A+Q327F+E501V+Y504T; T65A+Q327F+E501V+Y504*; E501V+Y504T; T65A+K161S; T65A+Q405T; T65A+Q327W; T65A+Q327F; T65A+Q327Y; P11F+T65A+Q327F; R1K+D3W+K5Q+G7V+N8S+T10K+P11S+T65A+Q327F; P2N+P4S+P11F+T65A+Q327F; P11F+D26C+K33C+T65A+Q327F; P2N+P4S+P11F+T65A+Q327W+E501V+Y504T; R1E+D3N+P4G+G6R+G7A+N8A+T10D+P11D+T65A+Q327F; P11F+T65A+Q327W; P2N+P4S+P11F+T65A+Q327F+E501V+Y504T; P11F+T65A+Q327W+E501V+Y504T; T65A+Q327F+E501V+Y504T; T65A+S105P+Q327W; T65A+S105P+Q327F; T65A+Q327W+S364P; T65A+Q327F+S364P; T65A+S103N+Q327F; P2N+P4S+P11F+K34Y+T65A+Q327F; P2N+P4S+P11F+T65A+Q327F+D445N+V447S; P2N+P4S+P11F+T65A+I172V+Q327F; P2N+P4S+P11F+T65A+Q327F+N502*; P2N+P4S+P11F+T65A+Q327F+N502T+P563S+K571E; P2N+P4S+P11F+R31S+K33V+T65A+Q327F+N564D+K571S; P2N+P4S+P11F+T65A+Q327F+S377T; P2N+P4S+P11F+T65A+V325T+Q327W; P2N+P4S+P11F+T65A+Q327F+D445N+V447S+E501V+Y504T; P2N+P4S+P11F+T65A+I172V+Q327F+E501V+Y504T; P2N+P4S+P11F+T65A+Q327F+S377T+E501V+Y504T; P2N+P4S+P11F+D26N+K34Y+T65A+Q327F; P2N+P4S+P11F+T65A+Q327F+I375A+E501V+Y504T; P2N+P4S+P11F+T65A+K218A+K221D+Q327F+E501V+Y504T; P2N+P4S+P11F+T65A+S103N+Q327F+E501V+Y504T; P2N+P4S+T10D+T65A+Q327F+E501V+Y504T; P2N+P4S+F12Y+T65A+Q327F+E501V+Y504T; K5A+P11F+T65A+Q327F+E501V+Y504T; P2N+P4S+T10E+E18N+T65A+Q327F+E501V+Y504T; P2N+T10E+E18N+T65A+Q327F+E501V+Y504T; P2N+P4S+P11F+T65A+Q327F+E501V+Y504T+T568N; P2N+P4S+P11F+T65A+Q327F+E501V+Y504T+K524T+G526A; P2N+P4S+P11F+K34Y+T65A+Q327F+D445N+V447S+E501V+Y504T; P2N+P4S+P11F+R31S+K33V+T65A+Q327F+D445N+V447S+E501V+Y504T; P2N+P4S+P11F+D26N+K34Y+T65A+Q327F+E501V+Y504T; P2N+P4S+P11F+T65A+F80*+Q327F+E501V+Y504T; P2N+P4S+P11F+T65A+K112S+Q327F+E501V+Y504T; P2N+P4S+P11F+T65A+Q327F+E501V+Y504T+T516P+K524T+G526A; P2N+P4S+P11F+T65A+Q327F+E501V+N502T+Y504*; P2N+P4S+P11F+T65A+Q327F+E501V+Y504T; P2N+P4S+P11F+T65A+S103N+Q327F+E501V+Y504T; K5A+P11F+T65A+Q327F+E501V+Y504T; P2N+P4S+P11F+T65A+Q327F+E501V+Y504T+T516P+K524T+G526A; P2N+P4S+P11F+T65A+V79A+Q327F+E501V+Y504T; P2N+P4S+P11F+T65A+V79G+Q327F+E501V+Y504T; P2N+P4S+P11F+T65A+V79I+Q327F+E501V+Y504T; P2N+P4S+P11F+T65A+V79L+Q327F+E501V+Y504T; P2N+P4S+P11F+T65A+V79S+Q327F+E501V+Y504T; P2N+P4S+P11F+T65A+L72V+Q327F+E501V+Y504T; S255N+Q327F+E501V+Y504T; P2N+P4S+P11F+T65A+E74N+V79K+Q327F+E501V+Y504T; P2N+P4S+P11F+T65A+G220N+Q327F+E501V+Y504T; P2N+P4S+P11F+T65A+Y245N+Q327F+E501V+Y504T; P2N+P4S+P11F+T65A+Q253N+Q327F+E501V+Y504T; P2N+P4S+P11F+T65A+D279N+Q327F+E501V+Y504T; P2N+P4S+P11F+T65A+Q327F+S359N+E501V+Y504T; P2N+P4S+P11F+T65A+Q327F+D370N+E501V+Y504T; P2N+P4S+P11F+T65A+Q327F+V460S+E501V+Y504T; P2N+P4S+P11F+T65A+Q327F+V460T+P468T+E501V+Y504T; P2N+P4S+P11F+T65A+Q327F+T463N+E501V+Y504T; P2N+P4S+P11F+T65A+Q327F+S465N+E501V+Y504T; and P2N+P4S+P11F+T65A+Q327F+T477N+E501V+Y504T.

In one embodiment, the *Penicillium oxalicum* glucoamylase variant has a K79V substitution (using SEQ ID NO: 2 of WO 2011/127802 for numbering), corresponding to the PE001 variant, and further comprises one of the following substitutions or combinations of substitutions:

P11F+T65A+Q327F;
P2N+P4S+P11F+T65A+Q327F;
P11F+D26C+K33C+T65A+Q327F;
P2N+P4S+P11F+T65A+Q327W+E501V+Y504T;

P2N+P4S+P11F+T65A+Q327F+E501V+Y504T; and
P11F+T65A+Q327W+E501V+Y504T.

Additional glucoamylases contemplated for use with the present invention can be found in WO2011/153516 (the content of which is incorporated herein).

Additional polynucleotides encoding suitable glucoamylases may be obtained from microorganisms of any genus, including those readily available within the UniProtKB database (www.uniprot.org).

The glucoamylase coding sequences can also be used to design nucleic acid probes to identify and clone DNA encoding glucoamylases from strains of different genera or species, as described supra.

The polynucleotides encoding glucoamylases may also be identified and obtained from other sources including microorganisms isolated from nature (e.g., soil, composts, water, etc.) or DNA samples obtained directly from natural materials (e.g., soil, composts, water, etc) as described supra.

Techniques used to isolate or clone polynucleotides encoding glucoamylases are described supra.

In one embodiment, the glucoamylase has a mature polypeptide sequence that comprises or consists of the amino acid sequence of any one of the glucoamylases described or referenced herein (e.g., any one of SEQ ID NOs: 8, 102-113, 229 and 230). In another embodiment, the glucoamylase has a mature polypeptide sequence that is a fragment of the any one of the glucoamylases described or referenced herein (e.g., any one of SEQ ID NOs: 8, 102-113, 229 and 230). In one embodiment, the number of amino acid residues in the fragment is at least 75%, e.g., at least 80%, 85%, 90%, or 95% of the number of amino acid residues in referenced full length glucoamylase (e.g. any one of SEQ ID NOs: 8, 102-113, 229 and 230). In other embodiments, the glucoamylase may comprise the catalytic domain of any glucoamylase described or referenced herein (e.g., the catalytic domain of any one of SEQ ID NOs: 8, 102-113, 229 and 230).

The glucoamylase may be a variant of any one of the glucoamylases described supra (e.g., any one of SEQ ID NOs: 8, 102-113, 229 and 230). In one embodiment, the glucoamylase has a mature polypeptide sequence of at least 60%, e.g., at least 65%, 70%, 75%, 80%, 85%, 90%, 95%, 97%, 98%, 99%, or 100% sequence identity to any one of the glucoamylases described supra (e.g., any one of SEQ ID NOs: 8, 102-113, 229 and 230).

In one embodiment, the glucoamylase has a mature polypeptide sequence that differs by no more than ten amino acids, e.g., by no more than five amino acids, by no more than four amino acids, by no more than three amino acids, by no more than two amino acids, or by one amino acid from the amino acid sequence of any one of the glucoamylases described supra (e.g., any one of SEQ ID NOs: 8, 102-113, 229 and 230). In one embodiment, the glucoamylase has an amino acid substitution, deletion, and/or insertion of one or more (e.g., two, several) of amino acid sequence of any one of the glucoamylases described supra (e.g., any one of SEQ ID NOs: 8, 102-113, 229 and 230). In some embodiments, the total number of amino acid substitutions, deletions and/or insertions is not more than 10, e.g., not more than 9, 8, 7, 6, 5, 4, 3, 2, or 1.

In some embodiments, the glucoamylase has at least 20%, e.g., at least 40%, at least 50%, at least 60%, at least 70%, at least 80%, at least 90%, at least 95%, at least 96%, at least 97%, at least 98%, at least 99%, or 100% of the glucoamylase activity of any glucoamylase described or referenced herein (e.g., any one of SEQ ID NOs: 8, 102-113, 229 and 230) under the same conditions.

In one embodiment, the glucoamylase coding sequence hybridizes under at least low stringency conditions, e.g., medium stringency conditions, medium-high stringency conditions, high stringency conditions, or very high stringency conditions with the full-length complementary strand of the coding sequence from any glucoamylase described or referenced herein (e.g., any one of SEQ ID NOs: 8, 102-113, 229 and 230). In one embodiment, the glucoamylase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any glucoamylase described or referenced herein (e.g., any one of SEQ ID NOs: 8, 102-113, 229 and 230).

In one embodiment, the glucoamylase comprises the coding sequence of any glucoamylase described or referenced herein (any one of SEQ ID NOs: 8, 102-113, 229 and 230). In one embodiment, the glucoamylase comprises a coding sequence that is a subsequence of the coding sequence from any glucoamylase described or referenced herein, wherein the subsequence encodes a polypeptide having glucoamylase activity. In one embodiment, the number of nucleotides residues in the subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for use in a particular host cell (e.g., optimized for expression in *Saccharomyces cerevisiae*).

The glucoamylase can also include fused polypeptides or cleavable fusion polypeptides, as described supra.

Proteases

The expressed and/or exogenous protease can be any protease that is suitable for the fermenting organisms and/or their methods of use described herein, such as a naturally occurring protease or a variant thereof that retains protease activity. Any protease contemplated for expression by a fermenting organism described below is also contemplated for aspects of the invention involving exogenous addition of a protease.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

In some aspects, the fermenting organism comprising a heterologous polynucleotide encoding a protease has an increased level of protease activity compared to the fermenting organism without the heterologous polynucleotide encoding the protease, when cultivated under the same conditions. In some aspects, the fermenting organism has an increased level of protease activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the protease, when cultivated under the same conditions.

Exemplary proteases that may be expressed with the fermenting organisms and used with the methods described herein include, but are not limited to, proteases shown in Table 4 (or derivatives thereof).

TABLE 4

| Donor Organism (catalytic domain) | SEQ ID NO: (mature polypeptide) | Family |
|---|---|---|
| *Aspergillus niger* | 9 | A1 |
| *Trichoderma reesei* | 10 | |
| *Thermoascus aurantiacus* | 11 | M35 |
| *Dichomitus squalens* | 12 | S53 |
| *Nocardiopsis prasina* | 13 | S1 |
| *Penicillium simplicissimum* | 14 | S10 |
| *Aspergillus niger* | 15 | |
| *Meriphilus giganteus* | 16 | S53 |
| *Lecanicillium* sp. WMM742 | 17 | S53 |
| *Talaromyces proteolyticus* | 18 | S53 |
| *Penicillium ranomafanaense* | 19 | A1A |
| *Aspergillus oryzae* | 20 | S53 |
| *Talaromyces liani* | 21 | S10 |
| *Thermoascus thermophilus* | 22 | S53 |
| *Pyrococcus furiosus* | 23 | |
| *Trichoderma reesei* | 24 | |
| *Rhizomucor miehei* | 25 | |
| *Lenzites betulinus* | 26 | S53 |
| *Neolentinus lepideus* | 27 | S53 |
| *Thermococcus* sp. | 28 | S8 |
| *Thermococcus* sp. | 29 | S8 |
| *Thermomyces lanuginosus* | 30 | S53 |
| *Thermococcus thioreducens* | 31 | S53 |
| *Polyporus arcularius* | 32 | S53 |
| *Ganoderma lucidum* | 33 | S53 |
| *Ganoderma lucidum* | 34 | S53 |
| *Ganoderma lucidum* | 35 | S53 |
| *Trametes* sp. AH28-2 | 36 | S53 |
| *Cinereomyces lindbladii* | 37 | S53 |
| *Trametes versicolor* O82DDP | 38 | S53 |
| *Paecilomyces hepiali* | 39 | S53 |
| *Isaria tenuipes* | 40 | S53 |
| *Aspergillus tamarii* | 41 | S53 |
| *Aspergillus brasiliensis* | 42 | S53 |
| *Aspergillus iizukae* | 43 | S53 |
| *Penicillium* sp-72364 | 44 | S10 |
| *Aspergillus denticulatus* | 45 | S10 |
| *Hamigera* sp. t184-6 | 46 | S10 |
| *Penicillium janthinellum* | 47 | S10 |
| *Penicillium vasconiae* | 48 | S10 |
| *Hamigera paravellanea* | 49 | S10 |
| *Talaromyces variabilis* | 50 | S10 |
| *Penicillium arenicola* | 51 | S10 |
| *Nocardiopsis kunsanensis* | 52 | S1 |
| *Streptomyces parvulus* | 53 | S1 |
| *Saccharopolyspora endophytica* | 54 | S1 |
| *luteus* cellwall enrichments K | 55 | S1 |
| *Saccharothrix australiensis* | 56 | S1 |
| *Nocardiopsis baichengensis* | 57 | S1 |
| *Streptomyces* sp. SM15 | 58 | S1 |
| *Actinoalloteichus spitiensis* | 59 | S1 |
| *Byssochlamys verrucosa* | 60 | M35 |
| *Hamigera terricola* | 61 | M35 |
| *Aspergillus tamarii* | 62 | M35 |
| *Aspergillus niveus* | 63 | M35 |
| *Penicillium sclerotiorum* | 64 | A1 |
| *Penicillium bilaiae* | 65 | A1 |
| *Penicillium antarcticum* | 66 | A1 |
| *Penicillium sumatrense* | 67 | A1 |
| *Trichoderma lixii* | 68 | A1 |
| *Trichoderma brevicompactum* | 69 | A1 |
| *Penicillium cinnamopurpureum* | 70 | A1 |
| *Bacillus licheniformis* | 71 | S8 |
| *Bacillus subtilis* | 72 | S8 |
| *Trametes* cf *versicol* | 73 | S53 |

Additional polynucleotides encoding suitable proteases may be derived from microorganisms of any suitable genus, including those readily available within the UniProtKB database (www.uniprot.org).

In one embodiment, the protease is derived from *Aspergillus*, such as the *Aspergillus niger* protease of SEQ ID NO: 9, the *Aspergillus tamarii* protease of SEQ ID NO: 41, or the *Aspergillus denticulatus* protease of SEQ ID NO: 45. In one embodiment, the protease is derived from *Dichomitus*, such as the *Dichomitus squalens* protease of SEQ ID NO: 12. In one embodiment, the protease is derived from *Penicillium*, such as the *Penicillium simplicissimum* protease of SEQ ID NO: 14, the *Penicillium antarcticum* protease of SEQ ID NO: 66, or the *Penicillium sumatrense* protease of SEQ ID NO: 67. In one aspect, the protease is derived from *Meriphilus*, such as the *Meriphilus giganteus* protease of SEQ ID NO: 16. In one aspect, the protease is derived from *Talaromyces*, such as the *Talaromyces liani* protease of SEQ ID NO: 21. In one aspect, the protease is derived from *Thermoascus*, such as the *Thermoascus thermophilus* protease of SEQ ID NO: 22. In one aspect, the protease is derived from *Ganoderma*, such as the *Ganoderma lucidum* protease of SEQ ID NO: 33. In one aspect, the protease is derived from *Hamigera*, such as the *Hamigera terricola* protease of SEQ ID NO: 61. In one aspect, the protease is derived from *Trichoderma*, such as the *Trichoderma brevicompactum* protease of SEQ ID NO: 69.

The protease coding sequences can also be used to design nucleic acid probes to identify and clone DNA encoding proteases from strains of different genera or species, as described supra.

The polynucleotides encoding proteases may also be identified and obtained from other sources including microorganisms isolated from nature (e.g., soil, composts, water, etc.) or DNA samples obtained directly from natural materials (e.g., soil, composts, water, etc) as described supra.

Techniques used to isolate or clone polynucleotides encoding proteases are described supra.

In one embodiment, the protease has a mature polypeptide sequence that comprises or consists of the amino acid sequence of any one of SEQ ID NOs: 9-73 (e.g., any one of SEQ ID NOs: 9, 14, 16, 21, 22, 33, 41, 45, 61, 62, 66, 67, and 69; such as any one of SEQ NOs: 9, 14, 16, and 69). In another embodiment, the protease has a mature polypeptide sequence that is a fragment of the protease of any one of SEQ ID NOs: 9-73 (e.g., wherein the fragment has protease activity). In one embodiment, the number of amino acid residues in the fragment is at least 75%, e.g., at least 80%, 85%, 90%, or 95% of the number of amino acid residues in referenced full length protease (e.g. any one of SEQ ID NOs: 9-73). In other embodiments, the protease may comprise the catalytic domain of any protease described or referenced herein (e.g., the catalytic domain of any one of SEQ ID NOs: 9-73).

The protease may be a variant of any one of the proteases described supra (e.g., any one of SEQ ID NOs: 9-73. In one embodiment, the protease has a mature polypeptide sequence of at least 60%, e.g., at least 65%, 70%, 75%, 80%, 85%, 90%, 95%, 97%, 98%, 99%, or 100% sequence identity to any one of the proteases described supra (e.g., any one of SEQ ID NOs: 9-73).

In one embodiment, the protease has a mature polypeptide sequence that differs by no more than ten amino acids, e.g., by no more than five amino acids, by no more than four amino acids, by no more than three amino acids, by no more than two amino acids, or by one amino acid from the amino acid sequence of any one of the proteases described supra (e.g., any one of SEQ ID NOs: 9-73). In one embodiment, the protease has an amino acid substitution, deletion, and/or insertion of one or more (e.g., two, several) of amino acid sequence of any one of the proteases described supra (e.g., any one of SEQ ID NOs: 9-73). In some embodiments, the total number of amino acid substitutions, deletions and/or insertions is not more than 10, e.g., not more than 9, 8, 7, 6, 5, 4, 3, 2, or 1.

In one embodiment, the protease coding sequence hybridizes under at least low stringency conditions, e.g., medium stringency conditions, medium-high stringency conditions, high stringency conditions, or very high stringency conditions with the full-length complementary strand of the coding sequence from any protease described or referenced herein (e.g., any one of SEQ ID NOs: 9-73). In one embodiment, the protease coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any protease described or referenced herein (e.g., any one of SEQ ID NOs: 9-73).

In one embodiment, the protease comprises the coding sequence of any protease described or referenced herein (any one of SEQ ID NOs: 9-73). In one embodiment, the protease comprises a coding sequence that is a subsequence of the coding sequence from any protease described or referenced herein, wherein the subsequence encodes a polypeptide having protease activity. In one embodiment, the number of nucleotides residues in the subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for use in a particular host cell (e.g., optimized for expression in *Saccharomyces cerevisiae*).

The protease can also include fused polypeptides or cleavable fusion polypeptides, as described supra.

In one embodiment, the protease used according to a process described herein is a Serine proteases. In one particular embodiment, the protease is a serine protease belonging to the family 53, e.g., an endo-protease, such as S53 protease from *Meripilus giganteus, Dichomitus squalens Trametes versicolor, Polyporus arcularius, Lenzites betulinus, Ganoderma lucidum, Neolentinus lepideus,* or *Bacillus* sp. 19138, in a process for producing ethanol from a starch-containing material, the ethanol yield was improved, when the S53 protease was present/or added during saccharification and/or fermentation of either gelatinized or un-gelatinized starch. In one embodiment, the proteases is selected from: (a) proteases belonging to the EC 3.4.21 enzyme group; and/or (b) proteases belonging to the EC 3.4.14 enzyme group; and/or (c) Serine proteases of the peptidase family S53 that comprises two different types of peptidases: tripeptidyl aminopeptidases (exo-type) and endo-peptidases; as described in 1993, *Biochem. J.* 290:205-218 and in MEROPS protease database, release, 9.4 (31 Jan. 2011) (www.merops.ac.uk). The database is described in Rawlings, N. D., Barrett, A. J. and Bateman, A., 2010, "MEROPS: the peptidase database", *Nucl. Acids Res.* 38: D227-D233.

For determining whether a given protease is a Serine protease, and a family S53 protease, reference is made to the above Handbook and the principles indicated therein. Such determination can be carried out for all types of proteases, be it naturally occurring or wild-type proteases; or genetically engineered or synthetic proteases.

Peptidase family S53 contains acid-acting endopeptidases and tripeptidyl-peptidases. The residues of the catalytic triad are Glu, Asp, Ser, and there is an additional acidic residue, Asp, in the oxyanion hole. The order of the residues is Glu, Asp, Asp, Ser. The Ser residue is the nucleophile equivalent to Ser in the Asp, His, Ser triad of subtilisin, and the Glu of the triad is a substitute for the general base, His, in subtilisin.

The peptidases of the S53 family tend to be most active at acidic pH (unlike the homologous subtilisins), and this can be attributed to the functional importance of carboxylic residues, notably Asp in the oxyanion hole. The amino acid sequences are not closely similar to those in family S8 (i.e. serine endopeptidase subtilisins and homologues), and this, taken together with the quite different active site residues and the resulting lower pH for maximal activity, provides for a substantial difference to that family. Protein folding of the peptidase unit for members of this family resembles that of subtilisin, having the clan type SB.

In one embodiment, the protease used according to a process described herein is a Cysteine proteases.

In one embodiment, the protease used according to a process described herein is a Aspartic proteases. Aspartic acid proteases are described in, for example, Hand-book of Proteolytic En-zymes, Edited by A. J. Barrett, N. D. Rawlings and J. F. Woessner, Aca-demic Press, San Diego, 1998, Chapter 270). Suitable examples of aspartic acid protease include, e.g., those disclosed in R. M. Berka et al. Gene, 96, 313 (1990)); (R. M. Berka et al. Gene, 125, 195-198 (1993)); and Gomi et al. Biosci. Biotech. Biochem. 57, 1095-1100 (1993), which are hereby incorporated by reference.

The protease also may be a metalloprotease, which is defined as a protease selected from the group consisting of:
 (a) proteases belonging to EC 3.4.24 (metalloendopeptidases); preferably EC 3.4.24.39 (acid metallo proteinases);
 (b) metalloproteases belonging to the M group of the above Handbook;
 (c) metalloproteases not yet assigned to clans (designation: Clan MX), or belonging to either one of clans MA, MB, MC, MD, ME, MF, MG, MH (as defined at pp. 989-991 of the above Handbook);
 (d) other families of metalloproteases (as defined at pp. 1448-1452 of the above Handbook);
 (e) metalloproteases with a HEXXH motif;
 (f) metalloproteases with an HEFTH motif;
 (g) metalloproteases belonging to either one of families M3, M26, M27, M32, M34, M35, M36, M41, M43, or M47 (as defined at pp. 1448-1452 of the above Handbook);
 (h) metalloproteases belonging to the M28E family; and
 (i) metalloproteases belonging to family M35 (as defined at pp. 1492-1495 of the above Handbook).

In other particular embodiments, metalloproteases are hydrolases in which the nucleophilic attack on a peptide bond is mediated by a water molecule, which is activated by a divalent metal cation. Examples of divalent cations are zinc, cobalt or manganese. The metal ion may be held in place by amino acid ligands. The number of ligands may be five, four, three, two, one or zero. In a particular embodiment the number is two or three, preferably three.

There are no limitations on the origin of the metalloprotease used in a process of the invention. In an embodiment the metalloprotease is classified as EC 3.4.24, preferably EC 3.4.24.39. In one embodiment, the metalloprotease is an acid-stable metalloprotease, e.g., a fungal acid-stable metalloprotease, such as a metalloprotease derived from a strain of the genus *Thermoascus*, preferably a strain of *Thermoascus aurantiacus*, especially *Thermoascus aurantiacus* CGMCC No. 0670 (classified as EC 3.4.24.39). In another embodiment, the metalloprotease is derived from a strain of the genus *Aspergillus*, preferably a strain of *Aspergillus oryzae*.

In one embodiment the metalloprotease has a degree of sequence identity to amino acids −178 to 177, −159 to 177, or preferably amino acids 1 to 177 (the mature polypeptide) of SEQ ID NO: 1 of WO 2010/008841 (a *Thermoascus aurantiacus* metalloprotease) of at least 80%, at least 82%, at least 85%, at least 90%, at least 95%, or at least 97%; and which have metalloprotease activity. In particular embodiments, the metalloprotease consists of an amino acid sequence with a degree of identity to SEQ ID NO: 1 as mentioned above.

The *Thermoascus aurantiacus* metalloprotease is a preferred example of a metalloprotease suitable for use in a process of the invention. Another metalloprotease is derived from *Aspergillus oryzae* and comprises the sequence of SEQ ID NO: 11 disclosed in WO 2003/048353, or amino acids −23-353; −23-374; −23-397; 1-353; 1-374; 1-397; 177-353; 177-374; or 177-397 thereof, and SEQ ID NO: 10 disclosed in WO 2003/048353.

Another metalloprotease suitable for use in a process of the invention is the *Aspergillus oryzae* metalloprotease comprising SEQ ID NO: 5 of WO 2010/008841, or a metalloprotease is an isolated polypeptide which has a degree of identity to SEQ ID NO: 5 of at least about 80%, at least 82%, at least 85%, at least 90%, at least 95%, or at least 97%; and which have metalloprotease activity. In particular embodiments, the metalloprotease consists of the amino acid sequence of SEQ ID NO: 5 of WO 2010/008841.

In a particular embodiment, a metalloprotease has an amino acid sequence that differs by forty, thirty-five, thirty, twenty-five, twenty, or by fifteen amino acids from amino acids −178 to 177, −159 to 177, or +1 to 177 of the amino acid sequences of the *Thermoascus aurantiacus* or *Aspergillus oryzae* metalloprotease.

In another embodiment, a metalloprotease has an amino acid sequence that differs by ten, or by nine, or by eight, or by seven, or by six, or by five amino acids from amino acids −178 to 177, −159 to 177, or +1 to 177 of the amino acid sequences of these metalloproteases, e.g., by four, by three, by two, or by one amino acid.

In particular embodiments, the metalloprotease a) comprises or b) consists of
  i) the amino acid sequence of amino acids −178 to 177, −159 to 177, or +1 to 177 of SEQ ID NO: 1 of WO 2010/008841;
  ii) the amino acid sequence of amino acids −23-353, −23-374, −23-397, 1-353, 1-374, 1-397, 177-353, 177-374, or 177-397 of SEQ ID NO: 3 of WO 2010/008841;
  iii) the amino acid sequence of SEQ ID NO: 5 of WO 2010/008841; or allelic variants, or fragments, of the sequences of i), ii), and iii) that have protease activity.

A fragment of amino acids −178 to 177, −159 to 177, or +1 to 177 of SEQ ID NO: 1 of WO 2010/008841 or of amino acids −23-353, −23-374, −23-397, 1-353, 1-374, 1-397, 177-353, 177-374, or 177-397 of SEQ ID NO: 3 of WO 2010/008841; is a polypeptide having one or more amino acids deleted from the amino and/or carboxyl terminus of these amino acid sequences. In one embodiment a fragment contains at least 75 amino acid residues, or at least 100 amino acid residues, or at least 125 amino acid residues, or at least 150 amino acid residues, or at least 160 amino acid residues, or at least 165 amino acid residues, or at least 170 amino acid residues, or at least 175 amino acid residues.

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

The protease may be a variant of, e.g., a wild-type protease, having thermostability properties defined herein. In one embodiment, the thermostable protease is a variant of a metallo protease. In one embodiment, the thermostable protease used in a process described herein is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In one embodiment, the thermostable protease is a variant of the mature part of the metallo protease shown in SEQ ID NO: 2 disclosed in WO 2003/048353 or the mature part of SEQ ID NO: 1 in WO 2010/008841 further with one of the following substitutions or combinations of substitutions:
  S5*+D79L+S87P+A112P+D142L;
  D79L+S87P+A112P+T124V+D142L;
  S5*+N26R+D79L+S87P+A112P+D142L;
  N26R+T46R+D79L+S87P+A112P+D142L;
  T46R+D79L+S87P+T116V+D142L;
  D79L+P81 R+S87P+A112P+D142L;
  A27K+D79L+S87P+A112P+T124V+D142L;
  D79L+Y82F+S87P+A112P+T124V+D142L;
  D79L+Y82F+S87P+A112P+T124V+D142L;
  D79L+S87P+A112P+T124V+A126V+D142L;
  D79L+S87P+A112P+D142L;
  D79L+Y82F+S87P+A112P+D142L;
  S38T+D79L+S87P+A112P+A126V+D142L;
  D79L+Y82F+S87P+A112P+A126V+D142L;
  A27K+D79L+S87P+A112P+A126V+D142L;
  D79L+S87P+N98C+A112P+G135C+D142L;
  D79L+S87P+A112P+D142L+T141C+M161C;
  S36P+D79L+S87P+A112P+D142L;
  A37P+D79L+S87P+A112P+D142L;
  S49P+D79L+S87P+A112P+D142L;
  S50P+D79L+S87P+A112P+D142L;
  D79L+S87P+D104P+A112P+D142L;
  D79L+Y82F+S87G+A112P+D142L;
  S70V+D79L+Y82F+S87G+Y97W+A112P+D142L;
  D79L+Y82F+S87G+Y97W+D104P+A112P+D142L;
  S70V+D79L+Y82F+S87G+A112P+D142L;
  D79L+Y82F+S87G+D104P+A112P+D142L;
  D79L+Y82F+S87G+A112P+A126V+D142L;
  Y82F+S87G+S70V+D79L+D104P+A112P+D142L;
  Y82F+S87G+D79L+D104P+A112P+A126V+D142L;
  A27K+D79L+Y82F+S87G+D104P+A112P+A126V+D142L;
  A27K+Y82F+S87G+D104P+A112P+A126V+D142L;
  A27K+D79L+Y82F+D104P+A112P+A126V+D142L;
  A27K+Y82F+D104P+A112P+A126V+D142L;
  A27K+D79L+S87P+A112P+D142L; and
  D79L+S87P+D142L.

In one embodiment, the thermostable protease is a variant of the metallo protease disclosed as the mature part of SEQ ID NO: 2 disclosed in WO 2003/048353 or the mature part of SEQ ID NO: 1 in WO 2010/008841 with one of the following substitutions or combinations of substitutions:
  D79L+S87P+A112P+D142L;
  D79L+S87P+D142L; and

A27K+D79L+Y82F+S87G+D104P+A112P+A126V+ D142L.

In one embodiment, the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841.

The thermostable protease may also be derived from any bacterium as long as the protease has the thermostability properties.

In one embodiment, the thermostable protease is derived from a strain of the bacterium *Pyrococcus*, such as a strain of *Pyrococcus furiosus* (pfu protease).

In one embodiment, the protease is one shown as SEQ ID NO: 1 in U.S. Pat. No. 6,358,726-E1 (Takara Shuzo Company).

In one embodiment, the thermostable protease is a protease having a mature polypeptide sequence of at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1. The *Pyrococcus furiosus* protease can be purchased from Takara Bio, Japan.

The *Pyrococcus furiosus* protease may be a thermostable protease as described in SEQ ID NO: 13 of WO2018/098381. This protease (PfuS) was found to have a thermostability of 110% (80° C./70° C.) and 103% (90° C./70° C.) at pH 4.5 determined.

In one embodiment a thermostable protease used in a process described herein has a thermostability value of more than 20% determined as Relative Activity at 80° C./70° C. determined as described in Example 2 of WO2018/098381.

In one embodiment, the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

In one embodiment, protease has a thermostability of between 20 and 50%, such as between 20 and 40%, such as 20 and 30% determined as Relative Activity at 80° C./70° C. In one embodiment, the protease has a thermostability between 50 and 115%, such as between 50 and 70%, such as between 50 and 60%, such as between 100 and 120%, such as between 105 and 115% determined as Relative Activity at 80° C./70° C.

In one embodiment, the protease has a thermostability value of more than 10% determined as Relative Activity at 85° C./70° C. determined as described in Example 2 of WO2018/098381.

In one embodiment, the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In one embodiment, the protease has a thermostability of between 10% and 50%, such as between 10% and 30%, such as between 10% and 25% determined as Relative Activity at 85° C./70° C.

In one embodiment, the protease has more than 20%, more than 30%, more than 40%, more than 50%, more than 60%, more than 70%, more than 80%, more than 90% determined as Remaining Activity at 80° C.; and/or the protease has more than 20%, more than 30%, more than 40%, more than 50%, more than 60%, more than 70%, more than 80%, more than 90% determined as Remaining Activity at 84° C.

Determination of "Relative Activity" and "Remaining Activity" is done as described in Example 2 of WO2018/098381.

In one embodiment, the protease may have a thermostability for above 90, such as above 100 at 85° C. as determined using the Zein-BCA assay as disclosed in Example 3 of WO2018/098381.

In one embodiment, the protease has a thermostability above 60%, such as above 90%, such as above 100%, such as above 110% at 85° C. as determined using the Zein-BCA assay of WO2018/098381.

In one embodiment, protease has a thermostability between 60-120, such as between 70-120%, such as between 80-120%, such as between 90-120%, such as between 100-120%, such as 110-120% at 85° C. as determined using the Zein-BCA assay of WO2018/098381.

In one embodiment, the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay of WO2018/098381, and described herein.

In one embodiment, the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the Protease 196 variant or Protease Pfu determined by the AZCL-casein assay of WO2018/098381, and described herein.

Pullulanases

In some embodiments, a pullulanase is present and/or added in liquefaction step and/or saccharification step, or simultaneous saccharification and fermentation (SSF).

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

In some embodiments, the fermenting organism comprises a heterologous polynucleotide encoding a pullulanase. Any pullulanase described or referenced herein is contemplated for expression in the fermenting organism.

The pullulanase may be any pullulanase that is suitable for the host cells and/or the methods described herein, such as a naturally occurring pullulanase or a variant thereof that retains pullulanase activity.

In some embodiments, the fermenting organism comprising a heterologous polynucleotide encoding a pullulanase has an increased level of pullulanase activity compared to the host cells without the heterologous polynucleotide encoding the pullulanase, when cultivated under the same conditions. In some embodiments, the fermenting organism has an increased level of pullulanase activity of at least 5%, e.g., at least 10%, at least 15%, at least 20%, at least 25%, at least 50%, at least 100%, at least 150%, at least 200%, at least 300%, or at least 500% compared to the fermenting organism without the heterologous polynucleotide encoding the pullulanase, when cultivated under the same conditions.

Exemplary pullulanases that can be used with the host cells and/or the methods described herein include bacterial, yeast, or filamentous fungal pullulanases, e.g., obtained from any of the microorganisms described or referenced herein, as described supra under the sections related to alpha-amylases.

Contemplated pullulanases include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

Additional pullulanases contemplated include the pullulanases from *Pyrococcus woesei*, specifically from *Pyrococcus woesei* DSM No. 3773 disclosed in WO92/02614.

In one embodiment, the pullulanase is a family GH57 pullulanase. In one embodiment, the pullulanase includes an X47 domain as disclosed in U.S. 61/289,040 published as WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase truncated at site X4 right after the X47 domain (i.e., amino acids 1-782). The pullulanase may also be a hybrid of the *Thermococcus litoralis* and *Thermococcus hydrothermalis* pullulanases or a *T. hydrothermalis/T. litoralis* hybrid enzyme with truncation site X4 disclosed in U.S. 61/289,040 published as WO 2011/087836 (which is hereby incorporated by reference).

In another embodiment, the pullulanase is one comprising an X46 domain disclosed in WO 2011/076123 (Novozymes).

The pullulanase may be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in WO2018/098381.

Suitable commercially available pullulanase products include PROMOZYME D, PROMOZYME™ D2 (Novozymes A/S, Denmark), OPTIMAX L-300 (DuPont-Danisco, USA), and AMANO 8 (Amano, Japan).

In one embodiment, the pullulanase is derived from the *Bacillus subtilis* pullulanase of SEQ ID NO: 114. In one embodiment, the pullulanase is derived from the *Bacillus licheniformis* pullulanase of SEQ ID NO: 115. In one embodiment, the pullulanase is derived from the *Oryza sativa* pullulanase of SEQ ID NO: 116. In one embodiment, the pullulanase is derived from the *Triticum aestivum* pullulanase of SEQ ID NO: 117. In one embodiment, the pullulanase is derived from the *Clostridium phytofermentans* pullulanase of SEQ ID NO: 118. In one embodiment, the pullulanase is derived from the *Streptomyces avermitilis* pullulanase of SEQ ID NO: 119. In one embodiment, the pullulanase is derived from the *Klebsiella pneumoniae* pullulanase of SEQ ID NO: 120.

Additional pullulanases contemplated for use with the present invention can be found in WO2011/153516 (the content of which is incorporated herein).

Additional polynucleotides encoding suitable pullulanases may be obtained from microorganisms of any genus, including those readily available within the UniProtKB database (www.uniprot.org).

The pullulanase coding sequences can also be used to design nucleic acid probes to identify and clone DNA encoding pullulanases from strains of different genera or species, as described supra.

The polynucleotides encoding pullulanases may also be identified and obtained from other sources including microorganisms isolated from nature (e.g., soil, composts, water, etc.) or DNA samples obtained directly from natural materials (e.g., soil, composts, water, etc) as described supra.

Techniques used to isolate or clone polynucleotides encoding pullulanases are described supra.

In one embodiment, the pullulanase has a mature polypeptide sequence that comprises or consists of the amino acid sequence of any one of the pullulanases described or referenced herein (e.g., any one of SEQ ID NOs: 114-120). In another embodiment, the pullulanase has a mature polypeptide sequence that is a fragment of the any one of the pullulanases described or referenced herein (e.g., any one of SEQ ID NOs: 114-120). In one embodiment, the number of amino acid residues in the fragment is at least 75%, e.g., at least 80%, 85%, 90%, or 95% of the number of amino acid residues in referenced full length pullulanase. In other embodiments, the pullulanase may comprise the catalytic domain of any pullulanase described or referenced herein (e.g., any one of SEQ ID NOs: 114-120).

The pullulanase may be a variant of any one of the pullulanases described supra (e.g., any one of SEQ ID NOs: 114-120). In one embodiment, the pullulanase has a mature polypeptide sequence of at least 60%, e.g., at least 65%, 70%, 75%, 80%, 85%, 90%, 95%, 97%, 98%, 99%, or 100% sequence identity to any one of the pullulanases described supra (e.g., any one of SEQ ID NOs: 114-120).

In one embodiment, the pullulanase has a mature polypeptide sequence that differs by no more than ten amino acids, e.g., by no more than five amino acids, by no more than four amino acids, by no more than three amino acids, by no more than two amino acids, or by one amino acid from the amino acid sequence of any one of the pullulanases described supra (e.g., any one of SEQ ID NOs: 114-120). In one embodiment, the pullulanase has an amino acid substitution, deletion, and/or insertion of one or more (e.g., two, several) of amino acid sequence of any one of the pullulanases described supra (e.g., any one of SEQ ID NOs: 114-120). In some embodiments, the total number of amino acid substitutions, deletions and/or insertions is not more than 10, e.g., not more than 9, 8, 7, 6, 5, 4, 3, 2, or 1.

In some embodiments, the pullulanase has at least 20%, e.g., at least 40%, at least 50%, at least 60%, at least 70%, at least 80%, at least 90%, at least 95%, at least 96%, at least 97%, at least 98%, at least 99%, or 100% of the pullulanase activity of any pullulanase described or referenced herein under the same conditions (e.g., any one of SEQ ID NOs: 114-120).

In one embodiment, the pullulanase coding sequence hybridizes under at least low stringency conditions, e.g., medium stringency conditions, medium-high stringency conditions, high stringency conditions, or very high stringency conditions with the full-length complementary strand of the coding sequence from any pullulanase described or referenced herein (e.g., any one of SEQ ID NOs: 114-120). In one embodiment, the pullulanase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any pullulanase described or referenced herein (e.g., any one of SEQ ID NOs: 114-120).

In one embodiment, the pullulanase comprises the coding sequence of any pullulanase described or referenced herein (e.g., any one of SEQ ID NOs: 114-120). In one embodiment, the pullulanase comprises a coding sequence that is a subsequence of the coding sequence from any pullulanase described or referenced herein, wherein the subsequence encodes a polypeptide having pullulanase activity. In one embodiment, the number of nucleotides residues in the subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for use in a particular host cell (e.g., optimized for expression in *Saccharomyces cerevisiae*).

The pullulanase can also include fused polypeptides or cleavable fusion polypeptides, as described supra.

Methods Using a Cellulosic-Containing Material

In some aspects, the methods described herein produce a fermentation product from a cellulosic-containing material. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic-containing material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one embodiment, the cellulosic-containing material is any biomass material. In another embodiment, the cellulosic-containing material is lignocellulose, which comprises cellulose, hemicelluloses, and lignin.

In one embodiment, the cellulosic-containing material is agricultural residue, herbaceous material (including energy crops), municipal solid waste, pulp and paper mill residue, waste paper, or wood (including forestry residue).

In another embodiment, the cellulosic-containing material is *arundo*, bagasse, bamboo, corn cob, corn fiber, corn stover, *miscanthus*, rice straw, switchgrass, or wheat straw.

In another embodiment, the cellulosic-containing material is aspen, *eucalyptus*, fir, pine, poplar, spruce, or willow.

In another embodiment, the cellulosic-containing material is algal cellulose, bacterial cellulose, cotton linter, filter paper, microcrystalline cellulose (e.g., AVICEL®), or phosphoric-acid treated cellulose.

In another embodiment, the cellulosic-containing material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic-containing material may be used as is or may be subjected to pretreatment, using conventional methods known in the art, as described herein. In a preferred embodiment, the cellulosic-containing material is pretreated.

The methods of using cellulosic-containing material can be accomplished using methods conventional in the art. Moreover, the methods of can be implemented using any conventional biomass processing apparatus configured to carry out the processes.

Cellulosic Pretreatment

In one embodiment the cellulosic-containing material is pretreated before saccharification.

In practicing the processes described herein, any pretreatment process known in the art can be used to disrupt plant cell wall components of the cellulosic-containing material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic-containing material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

In a one embodiment, the cellulosic-containing material is pretreated before saccharification (i.e., hydrolysis) and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

In one embodiment, the cellulosic-containing material is pretreated with steam. In steam pretreatment, the cellulosic-containing material is heated to disrupt the plant cell wall components, including lignin, hemicellulose, and cellulose to make the cellulose and other fractions, e.g., hemicellulose, accessible to enzymes. The cellulosic-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

In one embodiment, the cellulosic-containing material is subjected to a chemical pretreatment. The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, *Bioresource Technology* 855: 1-33; Schell et al., 2004, *Bioresource Technology* 91: 179-188; Lee et al., 1999, *Adv. Biochem. Eng. Biotechnol.* 65: 93-115). In a specific embodiment the dilute acid pretreatment of cellulosic-containing material is carried out using 4% w/w sulfuric acid at 180° C. for 5 minutes.

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment. Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one embodiment, the chemical pretreatment is carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic-containing material and held at a temperature in the range of preferably 140-200° C., e.g., 165-190° C., for periods ranging from 1 to 60 minutes.

In another embodiment, pretreatment takes place in an aqueous slurry. In preferred aspects, the cellulosic-containing material is present during pretreatment in amounts preferably between 10-80 wt. %, e.g., 20-70 wt. % or 30-60 wt. %, such as around 40 wt. %. The pretreated cellulosic-containing material can be unwashed or washed using any method known in the art, e.g., washed with water.

In one embodiment, the cellulosic-containing material is subjected to mechanical or physical pretreatment. The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in one embodiment, the cellulosic-containing material is subjected to physical (mechanical) or chemical pretreatment, or any combination thereof, to promote the separation and/or release of cellulose, hemicellulose, and/or lignin.

In one embodiment, the cellulosic-containing material is subjected to a biological pretreatment. The term "biological pretreatment" refers to any biological pretreatment that promotes the separation and/or release of cellulose, hemicellulose, and/or lignin from the cellulosic-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, DC, 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, DC, chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification and Fermentation of Cellulosic-Containing Material

Saccharification (i.e., hydrolysis) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF).

SHF uses separate process steps to first enzymatically hydrolyze the cellulosic-containing material to fermentable sugars, e.g., glucose, cellobiose, and pentose monomers, and then ferment the fermentable sugars to ethanol. In SSF, the enzymatic hydrolysis of the cellulosic-containing material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, DC, 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation organism can tolerate. It is understood herein that any method known in the art comprising pretreatment, enzymatic hydrolysis (saccharification), fermentation, or a combination thereof, can be used in the practicing the processes described herein.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

In the saccharification step (i.e., hydrolysis step), the cellulosic and/or starch-containing material, e.g., pretreated, is hydrolyzed to break down cellulose, hemicellulose, and/or starch to fermentable sugars, such as glucose, cellobiose, xylose, xylulose, arabinose, mannose, galactose, and/or soluble oligosaccharides. The hydrolysis is performed enzymatically e.g., by a cellulolytic enzyme composition. The enzymes of the compositions can be added simultaneously or sequentially.

Enzymatic hydrolysis may be carried out in a suitable aqueous environment under conditions that can be readily determined by one skilled in the art. In one aspect, hydrolysis is performed under conditions suitable for the activity of the enzymes(s), i.e., optimal for the enzyme(s). The hydrolysis can be carried out as a fed batch or continuous process where the cellulosic and/or starch-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 4.5 to about 5.5. The dry solids content is in the range of preferably about 5 to about 50 wt. %, e.g., about 10 to about 40 wt. % or about 20 to about 30 wt. %.

Saccharification in may be carried out using a cellulolytic enzyme composition. Such enzyme compositions are described below in the "Cellulolytic Enzyme Composition"-section below. The cellulolytic enzyme compositions can comprise any protein useful in degrading the cellulosic-containing material. In one aspect, the cellulolytic enzyme composition comprises or further comprises one or more (e.g., several) proteins selected from the group consisting of a cellulase, an AA9 (GH61) polypeptide, a hemicellulase, an esterase, an expansin, a ligninolytic enzyme, an oxidoreductase, a pectinase, a protease, and a swollenin.

In another embodiment, the cellulase is preferably one or more (e.g., several) enzymes selected from the group consisting of an endoglucanase, a cellobiohydrolase, and a beta-glucosidase.

In another embodiment, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another embodiment, the oxidoreductase is one or more (e.g., several) enzymes selected from the group consisting of a catalase, a laccase, and a peroxidase. The enzymes or enzyme compositions used in a processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

In one embodiment, an effective amount of cellulolytic or hemicellulolytic enzyme composition to the cellulosic-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic-containing material.

In one embodiment, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO 2012/021401, and the soluble contents thereof. A liquor for cellulolytic enhancement of an AA9 polypeptide (GH61 polypeptide) can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme preparation. The liquor can be separated from the treated material using a method standard in the art, such as filtration, sedimentation, or centrifugation.

In one embodiment, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In the fermentation step, sugars, released from the cellulosic-containing material, e.g., as a result of the pretreatment and enzymatic hydrolysis steps, are fermented to ethanol, by a fermenting organism, such as yeast described herein. Hydrolysis (saccharification) and fermentation can be separate or simultaneous.

Any suitable hydrolyzed cellulosic-containing material can be used in the fermentation step in practicing the processes described herein. Such feedstocks include, but are not limited to carbohydrates (e.g., lignocellulose, xylans, cellulose, starch, etc.). The material is generally selected based on economics, i.e., costs per equivalent sugar potential, and recalcitrance to enzymatic conversion.

Production of ethanol by a fermenting organism using cellulosic-containing material results from the metabolism of sugars (monosaccharides). The sugar composition of the hydrolyzed cellulosic-containing material and the ability of the fermenting organism to utilize the different sugars has a direct impact in process yields. Prior to Applicant's disclosure herein, strains known in the art utilize glucose efficiently but do not (or very limitedly) metabolize pentoses like xylose, a monosaccharide commonly found in hydrolyzed material.

Compositions of the fermentation media and fermentation conditions depend on the fermenting organism and can easily be determined by one skilled in the art. Typically, the fermentation takes place under conditions known to be suitable for generating the fermentation product. In some embodiments, the fermentation process is carried out under aerobic or microaerophilic (i.e., where the concentration of oxygen is less than that in air), or anaerobic conditions. In some embodiments, fermentation is conducted under anaerobic conditions (i.e., no detectable oxygen), or less than about 5, about 2.5, or about 1 mmol/L/h oxygen. In the absence of oxygen, the NADH produced in glycolysis cannot be oxidized by oxidative phosphorylation. Under anaerobic conditions, pyruvate or a derivative thereof may be utilized by the host cell as an electron and hydrogen acceptor in order to generate NAD+.

The fermentation process is typically run at a temperature that is optimal for the recombinant fungal cell. For example, in some embodiments, the fermentation process is performed at a temperature in the range of from about 25° C. to about 42° C. Typically the process is carried out a temperature that is less than about 38° C., less than about 35° C., less than about 33° C., or less than about 38° C., but at least about 20° C., 22° C., or 25° C.

A fermentation stimulator can be used in a process described herein to further improve the fermentation, and in particular, the performance of the fermenting organism, such as, rate enhancement and product yield (e.g., ethanol yield). A "fermentation stimulator" refers to stimulators for growth of the fermenting organisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Cellulolytic Enzymes and Compositions

A cellulolytic enzyme or cellulolytic enzyme composition may be present and/or added during saccharification. A cellulolytic enzyme composition is an enzyme preparation containing one or more (e.g., several) enzymes that hydrolyze cellulosic-containing material. Such enzymes include endoglucanase, cellobiohydrolase, beta-glucosidase, and/or combinations thereof.

In some embodiments, the fermenting organism comprises one or more (e.g., several) heterologous polynucleotides encoding enzymes that hydrolyze cellulosic-containing material (e.g., an endoglucanase, cellobiohydrolase, beta-glucosidase or combinations thereof). Any enzyme described or referenced herein that hydrolyzes cellulosic-containing material is contemplated for expression in the fermenting organism.

The cellulolytic enzyme may be any cellulolytic enzyme that is suitable for the host cells and/or the methods described herein (e.g., an endoglucanase, cellobiohydrolase, beta-glucosidase), such as a naturally occurring cellulolytic enzyme or a variant thereof that retains cellulolytic enzyme activity.

In some embodiments, the fermenting organism comprising a heterologous polynucleotide encoding a cellulolytic enzyme has an increased level of cellulolytic enzyme activity (e.g., increased endoglucanase, cellobiohydrolase, and/or beta-glucosidase) compared to the host cells without the heterologous polynucleotide encoding the cellulolytic enzyme, when cultivated under the same conditions. In some embodiments, the fermenting organism has an increased level of cellulolytic enzyme activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the cellulolytic enzyme, when cultivated under the same conditions.

Exemplary cellulolytic enzymes that can be used with the host cells and/or the methods described herein include bacterial, yeast, or filamentous fungal cellulolytic enzymes, e.g., obtained from any of the microorganisms described or referenced herein, as described supra under the sections related to proteases.

The cellulolytic enzyme may be of any origin. In an embodiment the cellulolytic enzyme is derived from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*. In a preferred embodiment the cellulolytic enzyme is derived from a strain of *Trichoderma reesei*.

The cellulolytic enzyme composition may further comprise one or more of the following polypeptides, such as enzymes: AA9 polypeptide (GH61 polypeptide) having cellulolytic enhancing activity, beta-glucosidase, xylanase, beta-xylosidase, CBH I, CBH II, or a mixture of two, three, four, five or six thereof.

The further polypeptide(s) (e.g., AA9 polypeptide) and/or enzyme(s) (e.g., beta-glucosidase, xylanase, beta-xylosidase, CBH I and/or CBH II may be foreign to the cellulolytic enzyme composition producing organism (e.g., *Trichoderma reesei*).

In an embodiment the cellulolytic enzyme composition comprises an AA9 polypeptide having cellulolytic enhancing activity and a beta-glucosidase.

In another embodiment the cellulolytic enzyme composition comprises an AA9 polypeptide having cellulolytic enhancing activity, a beta-glucosidase, and a CBH I.

In another embodiment the cellulolytic enzyme composition comprises an AA9 polypeptide having cellulolytic enhancing activity, a beta-glucosidase, a CBH I and a CBH II.

Other enzymes, such as endoglucanases, may also be comprised in the cellulolytic enzyme composition.

As mentioned above the cellulolytic enzyme composition may comprise a number of difference polypeptides, including enzymes.

In one embodiment, the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., WO 2005/074656), and *Aspergillus oryzae* beta-glucosidase fusion protein (e.g., one disclosed in WO 2008/057637, in particular shown as SEQ ID NOs: 59 and 60).

In another embodiment the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., SEQ ID NO: 2 in WO 2005/074656), and *Aspergillus fumigatus* beta-glucosidase (e.g., SEQ ID NO: 2 of WO 2005/047499).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO 2011/041397, and *Aspergillus fumigatus* beta-glucosidase (e.g., SEQ ID NO: 2 of WO 2005/047499).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO 2011/041397, and *Aspergillus fumigatus* beta-glucosidase (e.g., SEQ ID NO: 2 of WO 2005/047499) or a variant disclosed in WO 2012/044915 (hereby incorporated by reference), in particular one comprising one or more such as all of the following substitutions: F100D, S283G, N456E, F512Y.

In an embodiment the cellulolytic enzyme composition is a *Trichoderma reesei* cellulolytic composition, further comprising an AA9 (GH61A) polypeptide having cellulolytic enhancing activity, in particular the one derived from a strain of *Penicillium emersonii* (e.g., SEQ ID NO: 2 in WO 2011/041397), *Aspergillus fumigatus* beta-glucosidase (e.g., SEQ ID NO: 2 in WO 2005/047499) variant with one or more, in particular all of the following substitutions: F100D, S283G, N456E, F512Y and disclosed in WO 2012/044915; *Aspergillus fumigatus* Cel7A CBH1, e.g., the one disclosed as SEQ ID NO: 6 in WO2011/057140 and *Aspergillus fumigatus* CBH II, e.g., the one disclosed as SEQ ID NO: 18 in WO 2011/057140.

In a preferred embodiment the cellulolytic enzyme composition is a *Trichoderma reesei*, cellulolytic enzyme composition, further comprising a hemicellulase or hemicellulolytic enzyme composition, such as an *Aspergillus fumigatus* xylanase and *Aspergillus fumigatus* beta-xylosidase.

In an embodiment the cellulolytic enzyme composition also comprises a xylanase (e.g., derived from a strain of the genus *Aspergillus*, in particular *Aspergillus aculeatus* or *Aspergillus fumigatus*; or a strain of the genus *Talaromyces*, in particular *Talaromyces leycettanus*) and/or a beta-xylosidase (e.g., derived from *Aspergillus*, in particular *Aspergillus fumigatus*, or a strain of *Talaromyces*, in particular *Talaromyces emersonii*).

In an embodiment the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., WO 2005/074656), *Aspergillus oryzae* beta-glucosidase fusion protein (e.g., one disclosed in WO 2008/057637, in particular as SEQ ID NOs: 59 and 60), and *Aspergillus aculeatus* xylanase (e.g., Xyl II in WO 94/21785).

In another embodiment the cellulolytic enzyme composition comprises a *Trichoderma reesei* cellulolytic preparation, further comprising *Thermoascus aurantiacus* GH61A polypeptide having cellulolytic enhancing activity (e.g., SEQ ID NO: 2 in WO 2005/074656), *Aspergillus fumigatus* beta-glucosidase (e.g., SEQ ID NO: 2 of WO 2005/047499) and *Aspergillus aculeatus* xylanase (Xyl II disclosed in WO 94/21785).

In another embodiment the cellulolytic enzyme composition comprises a *Trichoderma reesei* cellulolytic enzyme composition, further comprising *Thermoascus aurantiacus* AA9 (GH61A) polypeptide having cellulolytic enhancing activity (e.g., SEQ ID NO: 2 in WO 2005/074656), *Aspergillus fumigatus* beta-glucosidase (e.g., SEQ ID NO: 2 of WO 2005/047499) and *Aspergillus aculeatus* xylanase (e.g., Xyl II disclosed in WO 94/21785).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO 2011/041397, *Aspergillus fumigatus* beta-glucosidase (e.g., SEQ ID NO: 2 of WO 2005/047499) and *Aspergillus fumigatus* xylanase (e.g., Xyl III in WO 2006/078256).

In another embodiment the cellulolytic enzyme composition comprises a *Trichoderma reesei* cellulolytic enzyme composition, further comprising *Penicillium emersonii* AA9 (GH61A) polypeptide having cellulolytic enhancing activity, in particular the one disclosed in WO 2011/041397, *Aspergillus fumigatus* beta-glucosidase (e.g., SEQ ID NO: 2 of WO 2005/047499), *Aspergillus fumigatus* xylanase (e.g., Xyl III in WO 2006/078256), and CBH I from *Aspergillus fumigatus*, in particular Cel7A CBH1 disclosed as SEQ ID NO: 2 in WO2011/057140.

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO 2011/041397, *Aspergillus fumigatus* beta-glucosidase (e.g., SEQ ID NO: 2 of WO 2005/047499), *Aspergillus fumigatus* xylanase (e.g., Xyl III in WO 2006/078256), CBH I from *Aspergillus fumigatus*, in particular Cel7A CBH1 disclosed as SEQ ID NO: 2 in WO 2011/057140, and CBH II derived from *Aspergillus fumigatus* in particular the one disclosed as SEQ ID NO: 4 in WO 2013/028928.

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO 2011/041397, *Aspergillus fumigatus* beta-glucosidase (e.g., SEQ ID NO: 2 of WO 2005/047499) or variant thereof with one or more, in particular all, of the following substitutions: F100D, S283G, N456E, F512Y; *Aspergillus fumigatus* xylanase (e.g., Xyl III in WO 2006/078256), CBH I from *Aspergillus fumigatus*, in particular Cel7A CBH I disclosed as SEQ ID NO: 2 in WO 2011/057140, and CBH II derived from *Aspergillus fumigatus*, in particular the one disclosed in WO 2013/028928.

In another embodiment the cellulolytic enzyme composition is a *Trichoderma reesei* cellulolytic enzyme composition comprising the CBH I (GENSEQP Accession No. AZY49536 (WO2012/103293); a CBH II (GENSEQP Accession No. AZY49446 (WO2012/103288); a beta-glucosidase variant (GENSEQP Accession No. AZU67153 (WO 2012/44915)), in particular with one or more, in particular all, of the following substitutions: F100D, S283G, N456E, F512Y; and AA9 (GH61 polypeptide) (GENSEQP Accession No. BAL61510 (WO 2013/028912)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288); a GH10 xylanase (GENSEQP Accession No. BAK46118 (WO 2013/019827)); and a beta-xylosidase (GENSEQP Accession No. AZI04896 (WO 2011/057140)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288)); and an AA9 (GH61 polypeptide; GENSEQP Accession No. BAL61510 (WO 2013/028912)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288)), an AA9 (GH61 polypeptide; GENSEQP Accession No. BAL61510 (WO 2013/028912)), and a catalase (GENSEQP Accession No. BAC11005 (WO 2012/130120)).

In an embodiment the cellulolytic enzyme composition is a *Trichoderma reesei* cellulolytic enzyme composition comprising a CBH I (GENSEQP Accession No. AZY49446 (WO2012/103288); a CBH II (GENSEQP Accession No. AZY49446 (WO2012/103288)), a beta-glucosidase variant (GENSEQP Accession No. AZU67153 (WO 2012/44915)), with one or more, in particular all, of the following substitutions: F100D, S283G, N456E, F512Y; an AA9 (GH61 polypeptide; GENSEQP Accession No. BAL61510 (WO 2013/028912)), a GH10 xylanase (GENSEQP Accession No. BAK46118 (WO 2013/019827)), and a beta-xylosidase (GENSEQP Accession No. AZI04896 (WO 2011/057140)).

In an embodiment the cellulolytic composition is a *Trichoderma reesei* cellulolytic enzyme preparation comprising an EG I (Swissprot Accession No. P07981), EG II (EMBL Accession No. M19373), CBH I (supra); CBH II (supra); beta-glucosidase variant (supra) with the following substitutions: F100D, S283G, N456E, F512Y; an AA9 (GH61 polypeptide; supra), GH10 xylanase (supra); and beta-xylosidase (supra).

All cellulolytic enzyme compositions disclosed in WO 2013/028928 are also contemplated and hereby incorporated by reference.

The cellulolytic enzyme composition comprises or may further comprise one or more (several) proteins selected from the group consisting of a cellulase, a AA9 (i.e., GH61) polypeptide having cellulolytic enhancing activity, a hemicellulase, an expansin, an esterase, a laccase, a ligninolytic enzyme, a pectinase, a peroxidase, a protease, and a swollenin.

In one embodiment the cellulolytic enzyme composition is a commercial cellulolytic enzyme composition. Examples of commercial cellulolytic enzyme compositions suitable for use in a process of the invention include: CELLIC® CTec (Novozymes A/S), CELLIC® CTec2 (Novozymes A/S), CELLIC® CTec3 (Novozymes A/S), CELLUCLAST™ (Novozymes A/S), SPEZYME™ CP (Genencor Int.), ACCELLERASE™ 1000, ACCELLERASE 1500, ACCELLERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme composition may be added in an amount effective from about 0.001 to about 5.0 wt. % of solids, e.g., about 0.025 to about 4.0 wt. % of solids or about 0.005 to about 2.0 wt. % of solids.

Additional enzymes, and compositions thereof can be found in WO2011/153516 and WO2016/045569 (the contents of which are incorporated herein).

Additional polynucleotides encoding suitable cellulolytic enzymes may be obtained from microorganisms of any genus, including those readily available within the UniProtKB database (www.uniprot.org).

The cellulolytic enzyme coding sequences can also be used to design nucleic acid probes to identify and clone DNA encoding cellulolytic enzymes from strains of different genera or species, as described supra.

The polynucleotides encoding cellulolytic enzymes may also be identified and obtained from other sources including microorganisms isolated from nature (e.g., soil, composts, water, etc.) or DNA samples obtained directly from natural materials (e.g., soil, composts, water, etc) as described supra.

Techniques used to isolate or clone polynucleotides encoding cellulolytic enzymes are described supra.

In one embodiment, the cellulolytic enzyme has a mature polypeptide sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any cellulolytic enzyme described or referenced herein (e.g., any endoglucanase, cellobiohydrolase, or beta-glucosidase). In one aspect, the cellulolytic enzyme has a mature polypeptide sequence that differs by no more than ten amino acids, e.g., by no more than five amino acids, by no more than four amino acids, by no more than three amino acids, by no more than two amino acids, or by one amino acid from any cellulolytic enzyme described or referenced herein. In one embodiment, the cellulolytic enzyme has a mature polypeptide sequence that comprises or consists of the amino acid sequence of any cellulolytic enzyme described or referenced herein, allelic variant, or a fragment thereof having cellulolytic enzyme activity. In one embodiment, the cellulolytic enzyme has an amino acid substitution, deletion, and/or insertion of one or more (e.g., two, several) amino acids. In some embodiments, the total number of amino acid substitutions, deletions and/or insertions is not more than 10, e.g., not more than 9, 8, 7, 6, 5, 4, 3, 2, or 1.

In some embodiments, the cellulolytic enzyme has at least 20%, e.g., at least 40%, at least 50%, at least 60%, at least 70%, at least 80%, at least 90%, at least 95%, at least 96%, at least 97%, at least 98%, at least 99%, or 100% of the cellulolytic enzyme activity of any cellulolytic enzyme described or referenced herein (e.g., any endoglucanase, cellobiohydrolase, or beta-glucosidase) under the same conditions.

In one embodiment, the cellulolytic enzyme coding sequence hybridizes under at least low stringency conditions, e.g., medium stringency conditions, medium-high stringency conditions, high stringency conditions, or very high stringency conditions with the full-length complementary strand of the coding sequence from any cellulolytic enzyme described or referenced herein (e.g., any endoglucanase, cellobiohydrolase, or beta-glucosidase). In one embodiment, the cellulolytic enzyme coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any cellulolytic enzyme described or referenced herein.

In one embodiment, the polynucleotide encoding the cellulolytic enzyme comprises the coding sequence of any cellulolytic enzyme described or referenced herein (e.g., any endoglucanase, cellobiohydrolase, or beta-glucosidase). In one embodiment, the polynucleotide encoding the cellulolytic enzyme comprises a subsequence of the coding sequence from any cellulolytic enzyme described or referenced herein, wherein the subsequence encodes a polypeptide having cellulolytic enzyme activity. In one embodiment, the number of nucleotides residues in the subsequence is at least 75%, e.g., at least 80%, 85%, 90%, or 95% of the number of the referenced coding sequence.

The cellulolytic enzyme can also include fused polypeptides or cleavable fusion polypeptides, as described supra.

Xylose Metabolism

In one aspect, the fermenting organism (e.g., yeast cell) further comprises a heterologous polynucleotide encoding a xylose isomerase (XI). The xylose isomerase may be any xylose isomerase that is suitable for the host cells and the methods described herein, such as a naturally occurring xylose isomerase or a variant thereof that retains xylose isomerase activity. In one embodiment, the xylose isomerase is present in the cytosol of the host cells.

In some embodiments, the fermenting organism comprising a heterologous polynucleotide encoding a xylose isomerase has an increased level of xylose isomerase activity compared to the host cells without the heterologous polynucleotide encoding the xylose isomerase, when cultivated under the same conditions. In some embodiments, the fermenting organisms have an increased level of xylose isomerase activity of at least 5%, e.g., at least 10%, at least 15%, at least 20%, at least 25%, at least 50%, at least 100%, at least 150%, at least 200%, at least 300%, or at 500% compared to the host cells without the heterologous polynucleotide encoding the xylose isomerase, when cultivated under the same conditions.

Exemplary xylose isomerases that can be used with the recombinant host cells and methods of use described herein include, but are not limited to, XIs from the fungus *Piromyces* sp. (WO2003/062430) or other sources (Madhavan et al., 2009, *Appl Microbiol Biotechnol.* 82(6), 1067-1078) have been expressed in *S. cerevisiae* host cells. Still other XIs suitable for expression in yeast have been described in US 2012/0184020 (an XI from *Ruminococcus flavefaciens*), WO2011/078262 (several XIs from *Reticulitermes speratus* and *Mastotermes darwiniensis*) and WO2012/009272 (constructs and fungal cells containing an XI from *Abiotrophia defectiva*). U.S. Pat. No. 8,586,336 describes a *S. cerevisiae* host cell expressing an XI obtained by bovine rumen fluid (shown herein as SEQ ID NO: 74).

Additional polynucleotides encoding suitable xylose isomerases may be obtained from microorganisms of any genus, including those readily available within the UniProtKB database (www.uniprot.org). In one embodiment, the xylose isomerases is a bacterial, a yeast, or a filamentous fungal xylose isomerase, e.g., obtained from any of the microorganisms described or referenced herein, as described supra.

The xylose isomerase coding sequences can also be used to design nucleic acid probes to identify and clone DNA encoding xylose isomerases from strains of different genera or species, as described supra.

The polynucleotides encoding xylose isomerases may also be identified and obtained from other sources including microorganisms isolated from nature (e.g., soil, composts, water, etc.) or DNA samples obtained directly from natural materials (e.g., soil, composts, water, etc) as described supra.

Techniques used to isolate or clone polynucleotides encoding xylose isomerases are described supra.

In one embodiment, the xylose isomerase has a mature polypeptide sequence of having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any xylose isomerase described or referenced herein (e.g., the xylose isomerase of SEQ ID NO: 74). In one aspect, the xylose isomerase has a mature polypeptide sequence that differs by no more than ten amino acids, e.g., by no more than five amino acids, by no more than four amino acids, by no more than three amino acids, by no more than two amino acids, or by one amino acid from any xylose isomerase described or referenced herein (e.g., the xylose isomerase of SEQ ID NO: 74). In one embodiment, the xylose isomerase has a mature polypeptide sequence that comprises or consists of the amino acid sequence of any xylose isomerase described or referenced herein (e.g., the xylose isomerase of SEQ ID NO: 74), allelic variant, or a fragment thereof having xylose isomerase activity. In one embodiment, the xylose isomerase has an amino acid substitution, deletion, and/or insertion of one or more (e.g., two, several) amino acids. In some embodiments, the total number of amino acid substitutions, deletions and/or insertions is not more than 10, e.g., not more than 9, 8, 7, 6, 5, 4, 3, 2, or 1.

In some embodiments, the xylose isomerase has at least 20%, e.g., at least 40%, at least 50%, at least 60%, at least 70%, at least 80%, at least 90%, at least 95%, at least 96%, at least 97%, at least 98%, at least 99%, or 100% of the xylose isomerase activity of any xylose isomerase described or referenced herein (e.g., the xylose isomerase of SEQ ID NO: 74) under the same conditions.

In one embodiment, the xylose isomerase coding sequence hybridizes under at least low stringency conditions, e.g., medium stringency conditions, medium-high stringency conditions, high stringency conditions, or very high stringency conditions with the full-length complementary strand of the coding sequence from any xylose isomerase described or referenced herein (e.g., the xylose isomerase of SEQ ID NO: 74). In one embodiment, the xylose isomerase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any xylose isomerase described or referenced herein (e.g., the xylose isomerase of SEQ ID NO: 74).

In one embodiment, the heterologous polynucleotide encoding the xylose isomerase comprises the coding sequence of any xylose isomerase described or referenced herein (e.g., the xylose isomerase of SEQ ID NO: 74). In one embodiment, the heterologous polynucleotide encoding the xylose isomerase comprises a subsequence of the coding sequence from any xylose isomerase described or referenced herein, wherein the subsequence encodes a polypeptide having xylose isomerase activity. In one embodiment, the number of nucleotides residues in the subsequence is at least 75%, e.g., at least 80%, 85%, 90%, or 95% of the number of the referenced coding sequence.

The xylose isomerases can also include fused polypeptides or cleavable fusion polypeptides, as described supra.

In one aspect, the fermenting organism (e.g., yeast cell) further comprises a heterologous polynucleotide encoding a xylulokinase (XK). A xylulokinase, as used herein, provides enzymatic activity for converting D-xylulose to xylulose 5-phosphate. The xylulokinase may be any xylulokinase that is suitable for the host cells and the methods described herein, such as a naturally occurring xylulokinase or a variant thereof that retains xylulokinase activity. In one embodiment, the xylulokinase is present in the cytosol of the host cells.

In some embodiments, the fermenting organisms comprising a heterologous polynucleotide encoding a xylulokinase have an increased level of xylulokinase activity compared to the host cells without the heterologous polynucleotide encoding the xylulokinase, when cultivated under the same conditions. In some embodiments, the host cells have an increased level of xylose isomerase activity of at least 5%, e.g., at least 10%, at least 15%, at least 20%, at least 25%, at least 50%, at least 100%, at least 150%, at least 200%, at least 300%, or at 500% compared to the host cells without the heterologous polynucleotide encoding the xylulokinase, when cultivated under the same conditions.

Exemplary xylulokinases that can be used with the fermenting organisms and methods of use described herein include, but are not limited to, the *Saccharomyces cerevisiae* xylulokinase of SEQ ID NO: 75. Additional polynucleotides encoding suitable xylulokinases may be obtained from microorganisms of any genus, including those readily available within the UniProtKB database (www.uniprot.org). In one embodiment, the xylulokinases is a bacterial, a yeast, or a filamentous fungal xylulokinase, e.g., obtained from any of the microorganisms described or referenced herein, as described supra.

The xylulokinase coding sequences can also be used to design nucleic acid probes to identify and clone DNA encoding xylulokinases from strains of different genera or species, as described supra.

The polynucleotides encoding xylulokinases may also be identified and obtained from other sources including microorganisms isolated from nature (e.g., soil, composts, water, etc.) or DNA samples obtained directly from natural materials (e.g., soil, composts, water, etc) as described supra.

Techniques used to isolate or clone polynucleotides encoding xylulokinases are described supra.

In one embodiment, the xylulokinase has a mature polypeptide sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any xylulokinase described or referenced herein (e.g., the *Saccharomyces cerevisiae* xylulokinase of SEQ ID NO: 75). In one embodiment, the xylulokinase has a mature polypeptide sequence that differs by no more than ten amino acids, e.g., by no more than five amino acids, by no more than four amino acids, by no more than three amino acids, by no more than two amino acids, or by one amino acid from any xylulokinase described or referenced herein (e.g., the *Saccharomyces cerevisiae* xylulokinase of SEQ ID NO: 75). In one embodiment, the xylulokinase has a mature polypeptide sequence that comprises or consists of the amino acid sequence of any xylulokinase described or referenced herein (e.g., the *Saccharomyces cerevisiae* xylulokinase of SEQ ID NO: 75), allelic variant, or a fragment thereof having xylulokinase activity. In one embodiment, the xylulokinase has an amino acid substitution, deletion, and/or insertion of one or more (e.g., two, several) amino acids. In some embodiments, the total number of amino acid substitutions, deletions and/or insertions is not more than 10, e.g., not more than 9, 8, 7, 6, 5, 4, 3, 2, or 1.

In some embodiments, the xylulokinase has at least 20%, e.g., at least 40%, at least 50%, at least 60%, at least 70%, at least 80%, at least 90%, at least 95%, at least 96%, at least 97%, at least 98%, at least 99%, or 100% of the xylulokinase activity of any xylulokinase described or referenced herein (e.g., the *Saccharomyces cerevisiae* xylulokinase of SEQ ID NO: 75) under the same conditions.

In one embodiment, the xylulokinase coding sequence hybridizes under at least low stringency conditions, e.g., medium stringency conditions, medium-high stringency conditions, high stringency conditions, or very high stringency conditions with the full-length complementary strand of the coding sequence from any xylulokinase described or referenced herein (e.g., the *Saccharomyces cerevisiae* xylulokinase of SEQ ID NO: 75). In one embodiment, the xylulokinase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any xylulokinase described or referenced herein (e.g., the *Saccharomyces cerevisiae* xylulokinase of SEQ ID NO: 75).

In one embodiment, the heterologous polynucleotide encoding the xylulokinase comprises the coding sequence of any xylulokinase described or referenced herein (e.g., the *Saccharomyces cerevisiae* xylulokinase of SEQ ID NO: 75). In one embodiment, the heterologous polynucleotide encoding the xylulokinase comprises a subsequence of the coding sequence from any xylulokinase described or referenced herein, wherein the subsequence encodes a polypeptide having xylulokinase activity. In one embodiment, the number of nucleotides residues in the subsequence is at least 75%, e.g., at least 80%, 85%, 90%, or 95% of the number of the referenced coding sequence.

The xylulokinases can also include fused polypeptides or cleavable fusion polypeptides, as described supra.

In one aspect, the fermenting organism (e.g., yeast cell) further comprises a heterologous polynucleotide encoding a ribulose 5 phosphate 3-epimerase (RPE1). A ribulose 5 phosphate 3-epimerase, as used herein, provides enzymatic activity for converting L-ribulose 5-phosphate to L-xylulose 5-phosphate (EC 5.1.3.22). The RPE1 may be any RPE1 that is suitable for the host cells and the methods described herein, such as a naturally occurring RPE1 or a variant thereof that retains RPE1 activity. In one embodiment, the RPE1 is present in the cytosol of the host cells.

In one embodiment, the recombinant cell comprises a heterologous polynucleotide encoding a ribulose 5 phosphate 3-epimerase (RPE1), wherein the RPE1 is *Saccharomyces cerevisiae* RPE1, or an RPE1 having at least 60%, e.g., at least 65%, 70%, 75%, 80%, 85%, 90%, 95%, 97%, 98%, 99%, or 100% sequence identity to a *Saccharomyces cerevisiae* RPE1.

In one aspect, the fermenting organism (e.g., yeast cell) further comprises a heterologous polynucleotide encoding a ribulose 5 phosphate isomerase (RKI1). A ribulose 5 phosphate isomerase, as used herein, provides enzymatic activity for converting ribose-5-phophate to ribulose 5-phosphate. The RKI1 may be any RKI1 that is suitable for the host cells and the methods described herein, such as a naturally occurring RKI1 or a variant thereof that retains RKI1 activity. In one embodiment, the RKI1 is present in the cytosol of the host cells.

In one embodiment, the fermenting organism comprises a heterologous polynucleotide encoding a ribulose 5 phosphate isomerase (RKI1), wherein the RKI1 is a *Saccharomyces cerevisiae* RKI1, or an RKI1 having a mature polypeptide sequence of at least 60%, e.g., at least 65%, 70%, 75%, 80%, 85%, 90%, 95%, 97%, 98%, 99%, or 100% sequence identity to a *Saccharomyces cerevisiae* RKI1.

In one aspect, the fermenting organism (e.g., yeast cell) further comprises a heterologous polynucleotide encoding a transketolase (TKL1). The TKL1 may be any TKL1 that is suitable for the host cells and the methods described herein, such as a naturally occurring TKL1 or a variant thereof that retains TKL1 activity. In one embodiment, the TKL1 is present in the cytosol of the host cells.

In one embodiment, the fermenting organism comprises a heterologous polynucleotide encoding a transketolase (TKL1), wherein the TKL1 is a *Saccharomyces cerevisiae* TKL1, or a TKL1 having a mature polypeptide sequence of at least 60%, e.g., at least 65%, 70%, 75%, 80%, 85%, 90%, 95%, 97%, 98%, 99%, or 100% sequence identity to a *Saccharomyces cerevisiae* TKL1.

In one aspect, the fermenting organism (e.g., yeast cell) further comprises a heterologous polynucleotide encoding a transaldolase (TAL1). The TAL1 may be any TAL1 that is suitable for the host cells and the methods described herein, such as a naturally occurring TAL1 or a variant thereof that retains TAL1 activity. In one embodiment, the TAL1 is present in the cytosol of the host cells.

In one embodiment, the fermenting organism comprises a heterologous polynucleotide encoding a transketolase (TAL1), wherein the TAL1 is a *Saccharomyces cerevisiae* TAL1, or a TAL1 having a mature polypeptide sequence of at least 60%, e.g., at least 65%, 70%, 75%, 80%, 85%, 90%, 95%, 97%, 98%, 99%, or 100% sequence identity to a *Saccharomyces cerevisiae* TAL1.

Fermentation Products

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

In one aspect, the fermentation product is an alcohol. The term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603. In one embodiment, the fermentation product is ethanol.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene. In another aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another aspect, the fermentation product is a gas. The gas can be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another aspect, the fermentation product is isoprene.

In another aspect, the fermentation product is a ketone. The term "ketone" encompasses a substance that contains one or more ketone moieties. The ketone can be, but is not limited to, acetone.

In another aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another aspect, the fermentation product is polyketide.

In some aspects, the fermenting organism (or processes thereof), provide higher yield of fermentation product (e.g., ethanol) when compared to the same process using an identical cell without the heterologous polynucleotide encoding the phospholipase under the same conditions (e.g., at about or after 54 hours fermentation, such as the conditions described in Example 3 or 4). In some embodiments, the process results in at least 0.25%, such as 0.5%, 0.75%, 1.0%, 1.25%, 1.5%, 1.75%, 2%, 3% or 5% higher yield of the fermentation product (e.g., ethanol).

Recovery

The fermentation product, e.g., ethanol, can optionally be recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

In some aspects of the methods, the fermentation product after being recovered is substantially pure. With respect to the methods herein, "substantially pure" intends a recovered preparation that contains no more than 15% impurity, wherein impurity intends compounds other than the fermentation product (e.g., ethanol). In one variation, a substantially pure preparation is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

Suitable assays to test for the production of ethanol and contaminants, and sugar consumption can be performed using methods known in the art. For example, ethanol product, as well as other organic compounds, can be analyzed by methods such as HPLC (High Performance Liquid Chromatography), GC-MS (Gas Chromatography Mass Spectroscopy) and LC-MS (Liquid Chromatography-Mass Spectroscopy) or other suitable analytical methods using routine procedures well known in the art. The release of ethanol in the fermentation broth can also be tested with the culture supernatant. Byproducts and residual sugar in the fermentation medium (e.g., glucose orxylose) can be quantified by HPLC using, for example, a refractive index detector for glucose and alcohols, and a UV detector for organic acids (Lin et al., *Biotechnol. Bioeng.* 90:775-779 (2005)), or using other suitable assay and detection methods well known in the art.

The invention may further be described in the following numbered paragraphs:

Paragraph [1]. A method of producing a fermentation product from a starch-containing or cellulosic-containing material comprising:
(a) saccharifying the starch-containing or cellulosic-containing material; and
(b) fermenting the saccharified material of step (a) with a fermenting organism;
wherein the fermenting organism comprises a heterologous polynucleotide encoding a phospholipase.

Paragraph [2]. The method of paragraph [1], wherein the phospholipase is a Phospholipase A or a Phospholipase C.

Paragraph [3]. The method of paragraph [1] or [2], wherein the phospholipase has a mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 235-242 and 252-342 (e.g., any one of SEQ ID NOs: 235, 236, 237, 238, 239, 240, 241 and 242).

Paragraph [4]. The method of any one of paragraphs [1]-[3], wherein the heterologous polynucleotide encodes a phospholipase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 235-242 and 252-342 (e.g., any one of SEQ ID NOs: 235, 236, 237, 238, 239, 240, 241 and 242).

Paragraph [5]. The method of any one of paragraphs [1]-[4], wherein the heterologous polynucleotide encodes a phospholipase having a mature polypeptide sequence comprising or consisting of the amino acid sequence of any one of SEQ ID NOs: 235-242 and 252-342 (e.g., any one of SEQ ID NOs: 235, 236, 237, 238, 239, 240, 241 and 242).

Paragraph [6]. The method of any one of paragraphs [1]-[5], wherein saccharification of step (a) occurs on a starch-containing material, and wherein the starch-containing material is either gelatinized or ungelatinized starch.

Paragraph [7]. The method of paragraph [6], comprising liquefying the starch-containing material by contacting the material with an alpha-amylase prior to saccharification.

Paragraph [8]. The method of paragraph [7], wherein liquefying the starch-containing material and/or saccharifying the starch-containing material is conducted in presence of exogenously added protease.

Paragraph [9]. The method of any one of paragraphs [1]-[8], wherein fermentation is performed under reduced nitrogen conditions (e.g., less than 1000 ppm urea or ammonium hydroxide, such as less than 750 ppm, less than 500 ppm, less than 400 ppm, less than 300 ppm, less than 250 ppm, less than 200 ppm, less than 150 ppm, less than 100 ppm, less than 75 ppm, less than 50 ppm, less than 25 ppm, or less than 10 ppm).

Paragraph [10]. The method of any one of paragraphs [1]-[9], wherein fermentation and saccharification are performed simultaneously in a simultaneous saccharification and fermentation (SSF).

Paragraph [11]. The method of any one of paragraphs [1]-[9], wherein fermentation and saccharification are performed sequentially (SHF).

Paragraph [12]. The method of any one of paragraphs paragraph [1]-[11], comprising recovering the fermentation product from the fermentation.

Paragraph [13]. The method of paragraph [12], wherein recovering the fermentation product from the from the fermentation comprises distillation.

Paragraph [14]. The method of any one of paragraphs [1]-[13], wherein the fermentation product is ethanol.

Paragraph [15]. The method of any one of paragraphs [1]-[14], wherein the fermenting organism comprises a heterologous polynucleotide encoding a glucoamylase.

Paragraph [16]. The method of paragraph [15], wherein the glucoamylase has a mature polypeptide sequence with 60%, e.g., at least 65%, 70%, 75%, 80%, 85%, 90%, 95%, 97%, 98%, 99%, or 100% sequence identity, to the amino acid sequence of a *Pycnoporus* glycoamylase (e.g., a *Pycnoporus sanguineus* glucoamylase of SEQ ID NO: 229), a *Gloeophyllum* glucoamylase (e.g. a *Gloeophyllum sepiarium* of SEQ ID NO: 8), or a glucoamylase of any one of SEQ ID NOs: 102-113 (e.g., a *Saccharomycopsis fibuligera* glucoamylase of SEQ ID NO: 103 or 104, or a *Trichoderma reesei* glucoamylase of SEQ ID NO: 230).

Paragraph [17]. The method of any one of paragraphs [1]-[16], wherein the fermenting organism comprises a heterologous polynucleotide encoding an alpha-amylase.

Paragraph [18]. The method of paragraph [17], wherein the alpha-amylase has a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 76-101, 121-174 and 231.

Paragraph [19]. The method of any one of paragraphs [1]-[18], wherein the fermenting organism comprises a heterologous polynucleotide encoding a protease.

Paragraph [20]. The method of paragraph [19], wherein the protease has a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 9-73 (e.g., any one of SEQ ID NOs: 9, 14, 16, 21, 22, 33, 41, 45, 61, 62, 66, 67, and 69; such as any one of SEQ NOs: 9, 14, 16, and 69).

Paragraph [21]. The method of any one of paragraphs [1]-[20], wherein the fermenting organism comprises a heterologous polynucleotide encoding a trehalase.

Paragraph [22]. The method of paragraph [21], wherein the trehalase has a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 175-226.

Paragraph [23]. The method of any one of paragraphs [1]-[22], wherein saccharification of step occurs on a cellulosic-containing material, and wherein the cellulosic-containing material is pretreated.

Paragraph [24]. The method of paragraph [23], wherein the pretreatment is a dilute acid pretreatment.

Paragraph [25]. The method of any one of paragraphs [1]-[24], wherein saccharification occurs on a cellulosic-containing material, and wherein the enzyme composition comprises one or more enzymes selected from a cellulase, an AA9 polypeptide, a hemicellulase, a CIP, an esterase, an expansin, a ligninolytic enzyme, an oxidoreductase, a pectinase, a protease, and a swollenin.

Paragraph [26]. The method of paragraph [25], wherein the cellulase is one or more enzymes selected from an endoglucanase, a cellobiohydrolase, and a beta-glucosidase.

Paragraph [27]. The method of paragraph [25] or [26], wherein the hemicellulase is one or more enzymes selected a xylanase, an acetylxylan esterase, a feruloyl esterase, an arabinofuranosidase, a xylosidase, and a glucuronidase.

Paragraph [28]. The method of any one of paragraphs [1]-[27], wherein the fermenting organism is a *Saccharomyces, Rhodotorula, Schizosaccharomyces, Kluyveromyces, Pichia, Hansenula, Rhodosporidium, Candida, Yarrowia, Lipomyces, Cryptococcus,* or *Dekkera* sp. cell.

Paragraph [29]. The method of any one of paragraphs [1]-[28], wherein the fermenting organism is a *Saccharomyces cerevisiae* cell.

Paragraph [30]. The method of any one of paragraphs [1]-[29], wherein the method results in higher yield of fermentation product and/or reduced foam accumulation when compared to the same process using an identical cell without the heterologous polynucleotide encoding the phospholipase under the same conditions (e.g., at about or after 54 hours fermentation, such as the conditions described in Examples 3 or 4).

Paragraph [31]. The method of paragraph [30], wherein the method results in at least 0.25% (e.g., 0.5%, 0.75%, 1.0%, 1.25%, 1.5%, 1.75%, 2%, 3% or 5%) higher yield of fermentation product.

Paragraph [32]. A recombinant yeast cell comprising a heterologous polynucleotide encoding a phospholipase.

Paragraph [33]. The recombinant yeast cell of paragraph [32], wherein the phospholipase is a Phospholipase A or a Phospholipase C.

Paragraph [34]. The recombinant yeast cell of paragraph [32] or [33], wherein the phospholipase has a mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 235-242 and 252-342 (e.g., any one of SEQ ID NOs: 235, 236, 237, 238, 239, 240, 241 and 242).

Paragraph [35]. The recombinant yeast cell of any one of paragraphs [32]-[34], wherein the heterologous polynucleotide encodes a phospholipase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 235-242 and 252-342 (e.g., any one of SEQ ID NOs: 235, 236, 237, 238, 239, 240, 241 and 242).

Paragraph [36]. The recombinant yeast cell of any one of paragraphs [32]-[35], wherein the heterologous polynucleotide encodes a phospholipase having a mature polypeptide sequence comprising or consisting of the amino acid sequence of any one of SEQ ID NOs: 235-242 and 252-342 (e.g., any one of SEQ ID NOs: 235, 236, 237, 238, 239, 240, 241 and 242.

Paragraph [37]. The recombinant yeast cell of any one of paragraphs [32]-[36], wherein the fermenting organism comprises a heterologous polynucleotide encoding a glucoamylase.

Paragraph [38]. The recombinant yeast cell of paragraph [37], wherein the glucoamylase has a mature polypeptide sequence with 60%, e.g., at least 65%, 70%, 75%, 80%, 85%, 90%, 95%, 97%, 98%, 99%, or 100% sequence identity, to the amino acid sequence of a *Pycnoporus* glucoamylase (e.g., a *Pycnoporus sanguineus* glucoamylase of SEQ ID NO: 229), a *Gloeophyllum* glucoamylase (e.g. a *Gloeophyllum sepiarium* of SEQ ID NO: 8), or a glucoamylase of any one of SEQ ID NOs: 102-113 (e.g., a *Saccharomycopsis fibuligera* glucoamylase of SEQ ID NO: 103 or 104, or a *Trichoderma reesei* glucoamylase of SEQ ID NO: 230).

Paragraph [39]. The recombinant yeast cell of any one of paragraphs [32]-[38], wherein the fermenting organism comprises a heterologous polynucleotide encoding an alpha-amylase.

Paragraph [40]. The recombinant yeast cell of paragraph [39], wherein the alpha-amylase has a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 76-101, 121-174 and 231.

Paragraph [41]. The recombinant yeast cell of any one of paragraphs [32]-[40], wherein the fermenting organism comprises a heterologous polynucleotide encoding a protease.

Paragraph [42]. The recombinant yeast cell of paragraph [41], wherein the protease has a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 9-73 (e.g., any one of SEQ ID NOs: 9, 14, 16, 21, 22, 33, 41, 45, 61, 62, 66, 67, and 69; such as any one of SEQ NOs: 9, 14, 16, and 69).

Paragraph [43]. The recombinant yeast cell of any one of paragraphs [32]-[42], wherein the fermenting organism comprises a heterologous polynucleotide encoding a trehalase.

Paragraph [44]. The recombinant yeast cell of paragraph [43], wherein the trehalase has a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 175-226.

Paragraph [45]. The recombinant yeast of any one of paragraphs [32]-[44], wherein the cell is a *Saccharomyces, Rhodotorula, Schizosaccharomyces, Kluyveromyces, Pichia, Hansenula, Rhodosporidium, Candida, Yarrowia, Lipomyces, Cryptococcus*, or *Dekkera* sp. cell.

Paragraph [46]. The recombinant yeast of paragraph [45], wherein the cell is a *Saccharomyces cerevisiae* cell.

Paragraph [47]. The recombinant cell of any one of paragraphs [32]-[46], wherein the cell is capable of higher yield of fermentation product and/or reduced foam accumulation when compared to fermentation using the same process and an identical cell without the heterologous polynucleotide encoding the phospholipase under the same conditions (e.g., at about or after 54 hours fermentation, such as the conditions described in Examples 3 or 4).

Paragraph [48]. The recombinant cell of paragraph [47], wherein the cell is capable of at least 0.25% (e.g., 0.5%, 0.75%, 1.0%, 1.25%, 1.5%, 1.75%, 2%, 3% or 5%) higher yield of fermentation product.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. All references are specifically incorporated by reference for that which is described.

The following examples are offered to illustrate certain aspects of the present invention, but not in any way intended to limit the scope of the invention as claimed.

EXAMPLES

Materials and Methods

Chemicals used as buffers and substrates were commercial products of at least reagent grade.

ETHANOL RED® ("ER"): *Saccharomyces cerevisiae* yeast available from Fermentis/Lesaffre, USA.

YPD+clonNAT plates were composed of 10 g of yeast extract, 20 g of peptone, 20 g bacto agar, and deionized water to 960 ml, followed by autoclave treatment. 40 mL sterile 50% glucose and 1 mL clonNAT stock solution was added, followed by mixing and pouring.

clonNAT stock solution was composed of 2 g nourseothricin sulfate and deionized water to 20 ml.

Example 1: Construction of Yeast Strains Expressing a Heterologous Phospholipase This example describes the construction of yeast cells containing a heterologous phospholipase under control of a *S. cerevisiae* TDH3, TEF2, PGK1, ADH1 or RPL18B promoter. Three pieces of DNA containing the promoter, gene and terminator were designed to allow for homologous recombination between the three DNA fragments and into the X-3 locus of the yeast MHCT-484 (WO2018/222990). The resulting strain has one promoter-containing fragment (left fragment), one gene-containing fragment (middle fragment) and one PRM9 terminator fragment (right fragment) integrated into the *S. cerevisiae* genome at the X-3 locus.

Construction of the Promoter Containing Fragments (Left Fragments)

Synthetic linear uncloned DNA containing 60 bp homology to the X-3 site, *S. cerevisiae* promoter TDH3, TEF2, PGK1, ADH1 or RPL18B (SEQ ID NOs: 1, 2, 4, 5, and 6, respectively) and coding sequence for the *S. cerevisiae* MF1α signal peptide (SEQ ID NO: 7) were synthesized by Thermo Fisher Scientific (Waltham, MA). To generate additional linear DNA for transformation into yeast, each of the five linear DNAs containing the left cassette above was PCR amplified.

Construction of the Terminator Containing Fragment (Right Fragment)

Synthetic linear uncloned DNA containing the *S. cerevisiae* PRM9 terminator (SEQ ID NO: 243) and 300 bp homology to the X-3 site was synthetized by Thermo Fisher Scientific.

Construction of the Gene Containing Fragment (Middle Fragment)

Synthetic linear uncloned DNA containing coding sequence for the *S. cerevisiae* MF1α signal peptide, coding sequence for the mature polypeptide and 50 bp PRM9 terminator was synthetized by Thermo Fisher Scientific.

Integration of the Left, Middle and Right-Hand Fragments to Generate Yeast Strains with a Heterologous Phospholipase The yeast MHCT-484 (WO2018/222990) was transformed with the left, middle and right integration fragments described above. In each transformation pool a fixed left fragment and right fragment were used as well as a fixed middle fragment containing the phospholipase gene with 100 ng of each fragment. To aid homologous recombination of the left, middle and right fragments at the genomic X-3 sites a plasmid containing Cas9 and guide RNA specific to X-3 (pMcTs442) was also used in the transformation. These four components were transformed into the *S. cerevisiae* strain MHCT-484 following a yeast electroporation protocol. Transformants were selected on YPD+cloNAT to select for transformants that contain the CRISPR/Cas9 plasmid pMcTs442. Transformants were picked using a Q-pix Colony Picking System (Molecular Devices; San Jose, CA) to inoculate one well of 96-well plate containing YPD+ cloNAT media. The plates were grown for 2 days then glycerol was added to 20% final concentration and the plates were stored at −80° C. until needed. Integration of specific phospholipase construct was verified by PCR with locus specific primers and subsequent sequencing. The strains generated in this example are shown in Table 5.

TABLE 5

| Strain Name | Promoter | SEQ ID NO: (mature polypeptide) | Donor Organism (catalytic domain) |
|---|---|---|---|
| HP21-B03 | pADH1v1 | 236 | *Talaromyces leycettanus* |
| HP21-C03 | pADH1v1 | 236 | *Talaromyces leycettanus* |
| HP21-D04 | pTEF2 | 236 | *Talaromyces leycettanus* |
| HP21-D05 | pTDH3 | 236 | *Talaromyces leycettanus* |
| HP21-E01 | pPGK1 | 236 | *Talaromyces leycettanus* |
| HP21-F01 | pPGK1 | 236 | *Talaromyces leycettanus* |
| HP21-G06 | pRPL18B | 236 | *Talaromyces leycettanus* |
| HP21-A02 | pADH1v1 | 237 | *Penicillium emersonii* |
| HP21-F04 | pTDH3 | 237 | *Penicillium emersonii* |
| HP21-F05 | pRPL18B | 237 | *Penicillium emersonii* |
| HP21-A04 | pTEF2 | 240 | *Kionochaeta* sp. |
| HP21-B01 | pPGK1 | 240 | *Kionochaeta* sp. |
| HP21-C05 | pTDH3 | 240 | *Kionochaeta* sp. |
| HP21-G02 | pADH1v1 | 240 | *Kionochaeta* sp. |
| HP21-B05 | pTDH3 | 241 | *Mariannaea pinicola* |
| HP21-B06 | pRPL18B | 241 | *Mariannaea pinicola* |
| HP21-C06 | pRPL18B | 241 | *Mariannaea pinicola* |
| HP21-F02 | pADH1v1 | 241 | *Mariannaea pinicola* |
| HP21-H03 | pTEF2 | 241 | *Mariannaea pinicola* |
| HP21-G04 | pTDH3 | 239 | *Pseudomonas* sp. 62186 |
| HP21-G05 | pRPL18B | 239 | *Pseudomonas* sp. 62186 |
| HP21-H05 | pRPL18B | 239 | *Pseudomonas* sp. 62186 |
| HP21-A03 | pADH1v1 | 238 | *Bacillus thuringiensis* |
| HP21-B04 | pTEF2 | 238 | *Bacillus thuringiensis* |
| HP21-C01 | pPGK1 | 238 | *Bacillus thuringiensis* |
| HP21-C04 | pTEF2 | 238 | *Bacillus thuringiensis* |
| HP21-D01 | pPGK1 | 238 | *Bacillus thuringiensis* |
| HP21-D06 | pRPL18B | 238 | *Bacillus thuringiensis* |
| HP21-E06 | pRPL18B | 238 | *Bacillus thuringiensis* |
| HP21-F06 | pRPL18B | 238 | *Bacillus thuringiensis* |
| HP21-H02 | pADH1v1 | 238 | *Bacillus thuringiensis* |
| HP21-D03 | pADH1v1 | 235 | *Thermomyces lanuginosus* |
| HP21-E04 | pTEF2 | 235 | *Thermomyces lanuginosus* |
| HP21-E05 | pTDH3 | 235 | *Thermomyces lanuginosus* |
| HP21-G01 | pPGK1 | 235 | *Thermomyces lanuginosus* |
| HP21-H06 | pRPL18B | 235 | *Thermomyces lanuginosus* |
| HP21-A01 | pPGK1 | 242 | *Fictibacillus macauensis* |
| HP21-A05 | pTDH3 | 242 | *Fictibacillus macauensis* |
| HP21-A06 | pRPL18B | 242 | *Fictibacillus macauensis* |
| HP21-F03 | pTEF2 | 242 | *Fictibacillus macauensis* |
| HP21-G03 | pTEF2 | 242 | *Fictibacillus macauensis* |
| HP21-H04 | pTDH3 | 242 | *Fictibacillus macauensis* |

Example 2: Activity Assay and Small-Scale Fermentation of Yeast Strains Expressing Phospholipase Preparation of Yeast Cells for Activity Assays Yeast strains were cultivated for 24 hours in standard YPD media containing 2% glucose. After the cultivation, samples were centrifuged, and the supernatants assayed for enzyme activity as described below.

PLA (Phospholipase A) Activity Assay

PLA activity was detected by using the EnzChek® PLA1 Kit from Invitrogen (Carlsbad, CA). The EnzChek® Direct Phospholipase A Assay Kit measures phosphatidylcholine-specific phospholipase C (PC-PLC) activity. PLA1 hydrolyzes the ester linkage of phospholipids and fatty acids. The EnzChek® Phospholipase A1 substrate (PED-A1) is a dye-labeled glycerophosphoethanolamines with BODIPY® FL dye-labeled acyl chain. PLA assay measures the release of the dye at a fluorescence emission at 515 nm. Reaction conditions are described in Table 6.

Initial Preparation of Solutions for PLA1 Activity Assay:
 1. Reaction Buffer: 100 mM MOPS+0.5 mM Zn pH 7
 2. PLA substrate:
  a. 40 ul DMSO (Comp E) to one vial PLA sub (Comp A)
  b. Protected from light
  c. Sufficient volume for 100 rxns 3. 500 U/mL stock of positive control PLA (Comp D)
   a. Dissolved Comp D vial in 100 uL of reaction buffer
4. 10 mM DOPC (Comp B)
   a. Dissolved Comp B vial in 100 ul of ETOH
5. 10 mM DOPG (Comp C)
   a. Dissolved Comp C vial in 100 ul of ETOH Final Preparation of Solutions and Samples for PLA1 Activity Assay:
1. 10 U/mL positive control made by diluting 500 U/mL stock positive control in reaction buffer
   a. Example: added 20 ul of 500 U/mL positive control to 980 mL of Reaction buffer
2. Serial dilutions of positive control to obtain 8-point standard curve with initial concentration beginning at 10 U/ml
   a. Final positive control concentration two-fold lower (5 U/ml) when substrate added
3. When necessary, samples diluted in reaction buffer
4. Lipid Mix: 30 ul 10 mM DOPC, 30 ul 10 mM DOPG, 30 ul 1 mM PLA substrate
5. PLA substrate
   a. 50 ul lipid mixed slowly to 5 mL reaction buffer in a smaller beaker containing a stir bar.
   b. Stirred for ~2-5 minutes Assay Protocol for PLA1 Activity Assay:
1. 50 ul of 8-point standard curve to columns 10, 11, 12
   a. last row left blank for buffer
2. Added 50 ul of samples to remaining wells
3. Added 50 ul of PLA-lipid substrate to wells containing samples and controls. Mixed well without introducing bubbles.
4. Read a T0 at 505EX/515EM (450EX/515EM is ok as well)
5. Covered plate and incubate protected from light
6. Read after 5 hours of incubation

TABLE 6

| PLA1 Activity Assay Condition | |
| --- | --- |
| Amount of yeast supernatant | 50 µl |
| Amount of PLA-lipid substrate | 50 µl |
| Substrate | PLA1 substrate from Kit |
| Buffer | 100 mM MOPS + 0.5 mM Zn |
| pH | 7.0 ± 0.05 |
| Incubation temperature | 22° C. (room Temperature) |
| Reaction time | 5 hrs |
| Wavelength | 505EX/515EM |

PLC (Phospholipase C) Activity Assay

PLC activity was detected by using EnzChek® PLC Kit from Invitrogen. The EnzChek® Phospholipase A Assay Kit measures phosphatidylcholine-specific phospholipase C (PC-PLC) activity by measuring the amount of starch degraded through enzymatic hydrolysis of starch. The assay uses a proprietary substrate (glycero-phosphoethanolamine with a dye-labeled sn-2 acyl chain) to detect PLC activity. Substrate cleavage by PLC releases the dye-labeled diacylglycerol, which produces a fluorescence signal that can be measure at 516 nm emission. Reaction conditions are described in Table 7.

Initial Preparation of Solutions for PLC Activity Assay:
1. Reaction Buffer: 100 mM NaAc+0.5 mM Zn pH 5
2. 200× stock of PLC substrate
   a. 100 ul DMSO (Comp B) added to one vial PLC sub
   b. Protected from light
   c. Sufficient volume for 125 rxns
3. 40 U/mL stock of positive control PC-PLC (Comp E)
   a. Dissolved Comp E vial in 200 uL of reaction buffer Final Secondary Preparation of Solutions and Samples for PLC Activity Assay
1. 1 U/mL positive control made by diluting 40 U/mL stock positive control 40-fold
   a. Example: added 25 ul of 40 U/mL positive control to 0.975 mL of Reaction buffer
2. Serial dilutions of positive control to obtain 8-point standard curve with initial concentration beginning at 0.125 U/ml
   a. Final positive control concentration two-fold lower (0.0625 U/ml) when substrate is added
3. When necessary, samples diluted in reaction buffer
4. PLC substrate: Added 40 ul of lecithin (Comp D) and 100 ul of PLC Substrate 200× stock solution (prepared in earlier step) to 9.86 mL of reaction buffer.

Assay Protocol for PLC Activity Assay:
1. 75 ul of 8-point standard curve to columns 10, 11, 12
   a. last row left blank for buffer
2. Added 75 ul of samples to remaining wells
3. Added 75 ul of PLC substrate to wells containing samples and controls. Mixed well without introducing bubbles.
4. Read a T0 at 509EX/516EM (490EX/520EM is ok as well)
5. Covered plate and incubate protected from light
6. Read after 5 hours

TABLE 7

| PLC Activity Assay Condition | |
| --- | --- |
| Amount of yeast supernatant | 75 µl |
| Amount of PLA-lipid substrate | 75 µl |
| Substrate | PLC substrate from Kit |
| Buffer | 100 mM NaAc + 0.5 mM Zn |
| pH | 5.0 ± 0.05 |
| Incubation temperature | 22° C. (room Temperature) |
| Reaction time | 5 hrs |
| Wavelength | 509EX/516EM |

Preparation of Yeast Culture for Microtiter Plate Fermentations

Simultaneous saccharification and fermentation (SSF) was performed via mini-scale fermentations using industrial corn mash (Avantec® Amp; Novozymes A/S). Yeast strains were cultivated overnight in YPD media with 6% glucose for 24 hours at 30° C. and 300 rpm. The corn mash was supplemented with 250 ppm of urea and dosed with 0.45 AGU/g-DS of an exogenous glucoamylase enzyme product (Spirizyme® Excel; Novozymes A/S). Approximately 0.6 mL of corn mash was dispensed per well to 96 well microtiter plates, followed by the addition of approximately 10^8 yeast cells/g of corn mash from the overnight culture. Plates were incubated at 32° C. without shaking. Fermentation was stopped by the addition of 100 µL of 8% $H_2SO_4$, followed by centrifugation at 3000 rpm for 10 min. The supernatant was analyzed for ethanol using HPLC. Fermentation reaction conditions are summarized in Table 8. SSF and activity assay results of yeast strains expressing a phospholipase are in Table 9.

TABLE 8

| Microtiter plate fermentation reaction conditions | |
| --- | --- |
| Substrate | Avantec ® Amp corn mash |
| Yeast pitch | 10^8 cells/g corn mash |
| Supplementary urea | 250 ppm |

TABLE 8-continued

Microtiter plate fermentation reaction conditions

| | |
|---|---|
| Exogenous glucoamylase product dose | 0.15 AGU/g-DS |
| pH | 5.0 ± 0.05 |
| Incubation temperature | 32° C. |
| Reaction time | 48 hours |

TABLE 9

Phospholipase yeast strains enzyme activity measurements and ethanol titers from SSF

| Strain ID | Promoter | SEQ ID NO: (mature polypeptide) | PLC activity units | PLA1 activity units | Mean Ethanol (g/L) |
|---|---|---|---|---|---|
| MHCT-484 | none | none | 99 | 0 | 107.31 |
| HP21-D04 | TEF2 | 236 | 776 | 23 | 110.67 |
| HP21-G06 | RPL18B | 236 | 793 | 0 | 110.6105 |
| HP21-B03 | ADH1v1 | 236 | 863 | 43 | 110.2833 |
| HP21-D05 | TDH3 | 236 | 688 | 29 | 110.0453 |
| HP21-C03 | ADH1v1 | 236 | 878 | 47 | 108.885 |
| HP21-E01 | PGK1 | 236 | 710 | 11 | 108.2008 |
| HP21-F01 | PGK1 | 236 | 680 | 0 | 106.1183 |
| HP21-F04 | TDH3 | 237 | 207 | 0 | 110.67 |
| HP21-F05 | RPL18B | 237 | 174 | 0 | 109.1528 |
| HP21-A02 | ADH1v1 | 237 | 273 | 0 | 109.0933 |
| HP21-B01 | PGK1 | 240 | 452 | 0 | 94.0695 |
| HP21-A04 | TEF2 | 240 | 451 | 0 | 83.27025 |
| HP21-G02 | ADH1v1 | 240 | 410 | 0 | 82.19925 |
| HP21-C05 | TDH3 | 240 | 426 | 0 | 81.36625 |
| HP21-C06 | RPL18B | 241 | 236 | 0 | 112.455 |
| HP21-B06 | RPL18B | 241 | 201 | 0 | 107.8735 |
| HP21-B05 | TDH3 | 241 | 356 | 0 | 100.436 |
| HP21-H03 | TEF2 | 241 | 275 | 0 | 99.3055 |
| HP21-F02 | ADH1v1 | 241 | 364 | 0 | 97.58 |
| HP21-G04 | TDH3 | 239 | 85 | 0 | 107.1893 |
| HP21-G05 | RPL18B | 239 | 251 | 0 | 84.7875 |
| HP21-H05 | RPL18B | 239 | 220 | 0 | 84.609 |
| HP21-E06 | RPL18B | 238 | 156 | 0 | 109.599 |
| HP21-B04 | TEF2 | 238 | 152 | 0 | 108.6768 |
| HP21-D01 | PGK1 | 238 | 99 | 0 | 108.0223 |
| HP21-C01 | PGK1 | 238 | 116 | 0 | 107.5463 |
| HP21-F06 | RPL18B | 238 | 142 | 0 | 105.077 |
| HP21-A03 | ADH1v1 | 238 | 99 | 0 | 104.5118 |
| HP21-H02 | ADH1v1 | 238 | 93 | 0 | 102.102 |
| HP21-C04 | TEF2 | 238 | 146 | 0 | 101.9235 |
| HP21-D06 | RPL18B | 238 | 141 | 0 | 82.25875 |
| HP21-E05 | TDH3 | 235 | 846 | 31 | 110.5808 |
| HP21-H06 | RPL18B | 235 | 685 | 56 | 109.0635 |
| HP21-E04 | TEF2 | 235 | 500 | 139 | 100.5253 |
| HP21-G01 | PGK1 | 235 | 428 | 123 | 96.06275 |
| HP21-D03 | ADH1v1 | 235 | 462 | 142 | 88.08975 |
| HP21-F03 | TEF2 | 242 | 115 | 0 | 108.171 |
| HP21-A05 | TDH3 | 242 | 126 | 0 | 108.0818 |
| HP21-A06 | RPL18B | 242 | 135 | 0 | 106.2373 |
| HP21-G03 | TEF2 | 242 | 113 | 0 | 105.791 |
| HP21-H04 | TDH3 | 242 | 102 | 0 | 104.6903 |
| HP21-A01 | PGK1 | 242 | 91 | 0 | 104.4523 |

Example 3: Fermentation of Yeast Strains Expressing Phospholipase

The purpose of this experiment was to determine if expressing phospholipase in yeast would enhance ethanol yields at the end of fermentation. Yeast strains (HP21-H06, HP21-D05, HP21-G12, HP21-A08, HP21-F05 and HP21-F04) were propagated overnight, and then used to dose a fermentation of industrially liquified mash. The fermented mash was sampled at the end of fermentation and the supernatant was filtered and analyzed by HPLC to determine the final ethanol titers and residual sugars.

Yeast Propagation

Yeast strains were received as glycerol stocks and were kept frozen at −80° C. until used. The yeast strains were propagated according to the following procedure:
1. Cryo-vials of yeast were removed from the −80° C. freezer.
2. For each sample, 2×50 mL sterile Erlenmeyer flasks were obtained and labeled.
3. The flasks were placed into a sterile hood along with 6% YPD media, pipettes and tips, and cryovials.
4. Using sterile technique, ~50 mL of 6% YPD media was poured into each bottle.
5. 150 uL of the appropriate yeast sample was added to each flask using a sterile 200 uL pipette and sterile tips.
6. The flasks were capped after each addition to maintain a sterile solution.
7. The flasks were placed into a 32° C. shaking incubator and mixed at ~150 rpm overnight.

Cell Counting

The propagation slurries described above were then tested to determine the number of yeast cells present for dosing, according to the following procedure:
1. The propagated yeast samples were removed from the incubator.
2. The 50 mL samples were poured into 50 mL flip top falcon tubes.
3. The samples were centrifuged 3,500 rpm for 7 min.
4. The supernatant was discarded into the old 50 mL flasks to be autoclaved.
5. 10 mL of deionized water was added to each tube.
6. The tubes were vortex mixed to suspend the pellet.
7. The replicate samples were combined into a single 50 mL falcon tube.
8. The samples were centrifuged 3,500 rpm for 7 min.
9. The supernatant was discarded into the original 50 mL flasks to be autoclaved.
10. 10 mL of deionized water was added to each remaining tube.
11. The tubes were vortex mixed to suspend the pellet.
    a. This slurry was saved and will be used to dose into the fermentations.
12. The yeast slurries were diluted 100× into 15 mL falcon tubes by adding 100 uL to 9.9 mL of deionized water.
13. The samples subjected to cell count using a Nucleo-Counter® YC-100 (Chemometec A/S) as follows:
    a. 50 uL of the 100× slurry dilution was added to 450 uL of Lysis buffer.
    b. The samples were vortexed and allowed to sit ~5 min for the cell lysis to occur.
    c. A nucleo-cassette was used to sample the lysed solution, then placed into the NucleoCounter® YC-100.
    d. The NucleoCounter® YC-100 analyzed the slurry and produced a cell count number.
    e. The resulting number is multiplied by 1000 to get the final cell counts for use in the spreadsheet.
14. The yeasts used in this experiment, and the yeast counts that were obtained according to the procedure above are displayed in the Table 10 below.

TABLE 10

| Strain ID | YCL-1 | YCL-2 | Average total cells |
|---|---|---|---|
| MHCT-484 | 1.26E+09 | 1.28E+09 | 1.27E+09 |
| HP21-H06 | 1.23E+09 | 1.16E+09 | 1.19E+09 |
| HP21-D05 | 1.38E+09 | 1.43E+09 | 1.40E+09 |

TABLE 10-continued

| Strain ID | YCL-1 | YCL-2 | Average total cells |
|---|---|---|---|
| HP21-G12 | 1.14E+09 | 1.12E+09 | 1.13E+09 |
| HP21-A08 | 1.38E+09 | 1.29E+09 | 1.33E+09 |
| HP21-F05 | 1.28E+09 | 1.28E+09 | 1.28E+09 |
| HP21-F04 | 1.41E+09 | 1.24E+09 | 1.33E+09 |

15. The calculation below was used to determine the number of mL of yeast slurry to add to each tube.

$$\frac{10{,}000{,}000 \text{ cells}}{\text{mL mash}} \times \frac{1 \text{ mL mash}}{1.15 \text{ g mash}} \times \text{g mash} \times \frac{\text{mL}}{X \text{ cells}} \times \frac{1000\ \mu\text{L}}{\text{mL}} =$$

μL yeast to add

Fermentation

Fermentations of industrially liquified mash were conducted according to the following procedure:

1. Industrially liquefied mash was acquired and stored frozen for future analysis. The mash used in this experiment was from a plant using Avantec® Amp and running a hydro-heater or jet cooker during liquefaction stage.
2. Two liters of the mash was thawed for approximately 2 hours prior to starting this study.
3. The mash was adjusted to 500 ppm urea and 3 ppm penicillin using stock solutions of 200 g/L urea and 1 g/L penicillin.
4. The mash was adjusted to pH 5 using 40% v/v $H_2SO_4$ and the dry solids content were measured on a Mettler-Toledo moisture balance.
5. 50.0+/−0.05 g of prepared mash was weighed into 250 mL media bottles.
6. The bottles were capped and stored in a refrigerator overnight.
7. The bottles were dosed with enzymes and yeast in the morning using a repeater pipette.
8. The conditions tested include Achieve® glucoamylase (0.42 AGU/gDS), trehalase (2 μg/gDS), and yeast dosed to approximately 7,000,000 cells per fermentation.
9. The bottles were capped with hole drilled caps. The holes were covered with labeling tape. A 0.24-gauge syringe needle was used to pierce a uniform vent hole to allow for $CO_2$ gas to escape during fermentation.
10. The bottles were placed into a 32° C. air shaker set to 150 rpm to begin fermentation.
11. Fermentation was run for 54 hours.

Sampling of Fermentations

1. After 52 hours of fermentation, 5 g of fermented mash were pipetted into a 15 mL conical falcon tube with 5 mL pipette equipped with a cut tip.
2. 50 uL of 40% $H_2SO_4$ were added to each of the tubes to stop fermentation and enzymatic hydrolysis.
3. The tubes were briefly mixed with a vortex mixer and centrifuged at 3,500 rpm for 7 minutes.
4. The supernatant was poured into a syringe equipped with a 0.45 um filter and the plunger of the syringe was used to push the sample through the filter into prenumbered HPLC vials.
5. The HPLC vials were capped and the samples were submitted to HPLC for analysis of the ethanol and sugars produced during fermentation. The HPLC setup was as shown in Table 11.

TABLE 11

| HPLC system | Agilent's 1100/1200 series with Chem station software |
| | Degasser |
| | Quaternary Pump |
| | Auto-Sampler |
| | Column Compartment/w Heater |
| | Refractive Index Detector (RI) |
| Column | Bio-Rad HPX- 87H Ion Exclusion Column 300 mm × 7.8 mm parts# 125-0140 |
| | Bio-Rad guard cartridge cation H parts# 125-0129, Holder parts# 125-0131 |
| Method | 0.005M $H_2SO_4$ mobile phase |
| | Flow rate of 0.6 ml/min |
| | Column temperature - 65° C. |
| | RI detector temperature - 55° C. |

The method quantifies analytes using calibration standards for dextrins (DP4+), maltotriose, maltose, glucose, fructose, acetic acid, lactic acid, glycerol and ethanol. A 4-point calibration including the origin was used.

Ethanol improvement for tested strains is shown in FIG. 1. Strains HP21-F05 and HP21-F04 show approximately 1.1% improvement in ethanol over control strain MHCT-484, while strain HP21-A08 showed approximately 0.5% improvement in ethanol titer of the control.

Example 4: Fermentation of Yeast Strains Expressing Phospholipase at Varying Urea Levels The purpose of this experiment was to examine the effect of nitrogen loading (urea level) on ethanol yields of phospholipase-expressing yeasts. Yeast strains (HP21-H08, HP21-F04 and HP21-F05) were propagated overnight, and then used to dose a fermentation of industrially liquified mash. The fermented mash was sampled at the end of fermentation and the supernatant was filtered and run on HPLC to determine the final ethanol titers and residual sugars.

Yeast Propagation

Yeast strains were propagated as described above in Example 3.

Cell Counting

The propagation slurries described above were then tested to determine the number of yeast cells present for dosing according to the procedure described above in Example 3. The yeasts used in this experiment, and the corresponding yeast counts are displayed in the Table 12.

TABLE 12

| Strain ID | YCL-1 | YCL-2 | Average total cells |
|---|---|---|---|
| MHCT-484 | 1.48E+09 | 1.44E+09 | 1.46E+09 |
| HP21-A08 | 1.24E+09 | 1.24E+09 | 1.24E+09 |
| HP21-F05 | 1.50E+09 | 1.48E+09 | 1.49E+09 |
| HP21-F04 | 1.37E+09 | 1.40E+09 | 1.38E+09 |

Fermentation

Fermentations of industrially liquified mash were conducted according to the following procedure:

1. Industrially liquefied mash was acquired and stored frozen for future analysis. The two mashes used in this experiment were from a plant using Avantec® Amp (Novozymes A/S) and a plant running another product Liquozyme® Pro (Novozymes A/S). Both mashes were from plants running a hydro-heater or jet cooker during liquefaction stage.

2. Two liters of each mash was thawed for approximately 2 hours prior to starting this study.
3. The mash was dosed with 3 ppm penicillin using a stock solution 1 g/L penicillin. Urea was added to the fermentation during enzyme dosing using stock solutions of 100 and 20 g/L.
4. The mash was adjusted to pH 5 using 40% v/v $H_2SO_4$ and the dry solids content were measured on a Mettler-Toledo moisture balance.
5. ~5 g of the prepared mash was added to preweighed 15 mL tubes
6. The tubes were reweighed and the weight of mash was used in calculating enzymes, yeast and urea dosing.
7. The tubes were capped and stored in a refrigerator overnight.
8. The tubes were dosed with enzymes, yeast and urea in the morning using a Biomek FX liquid handling robot.
9. The conditions tested in this experiment are displayed in Table 13 below. Yeast dose in this experiment was 7,000,000 cells per ferm.
10. The tubes were capped with holes to allow released $CO_2$ from fermentation.
11. Tubes were placed into a 32° C. incubator to begin fermentation.
12. Tubes were mixed with a vortex mixer twice a day for 52 hours.

TABLE 13

| Treatment | # | Yeast# | Glucoamylase | Dose | Units | Trehalase | Dose | Units | PLC | Dose | Units | Urea | Dose | Units |
|---|---|---|---|---|---|---|---|---|---|---|---|---|---|---|
| MHCT-484-Control | 1 | 1 | Achieve | 0.42 | AGU/gDS | Trehalase | 1 | ug/gDS | P. emersonii | 0 | µg/g DS | Urea | 0 | ppm |
| MHCT-484-5 ug PLC | 2 | 1 | Achieve | 0.42 | AGU/gDS | Trehalase | 1 | ug/gDS | P. emersonii | 5 | µg/g DS | Urea | 0 | ppm |
| MHCT-484-20 ug PLC | 3 | 1 | Achieve | 0.42 | AGU/gDS | Trehalase | 1 | ug/gDS | P. emersonii | 20 | µg/g DS | Urea | 0 | ppm |
| HP21-A08 | 4 | 2 | Achieve | 0.42 | AGU/gDS | Trehalase | 1 | ug/gDS | P. emersonii | 0 | µg/g DS | Urea | 0 | ppm |
| HP21-F05 | 5 | 3 | Achieve | 0.42 | AGU/gDS | Trehalase | 1 | ug/gDS | P. emersonii | 0 | µg/g DS | Urea | 0 | ppm |
| HP21-F04 | 6 | 4 | Achieve | 0.42 | AGU/gDS | Trehalase | 1 | ug/gDS | P. emersonii | 0 | µg/g DS | Urea | 0 | ppm |
| MHCT-484-Control | 7 | 1 | Achieve | 0.42 | AGU/gDS | Trehalase | 1 | ug/gDS | P. emersonii | 0 | µg/g DS | Urea | 150 | ppm |
| MHCT-484-5 ug PLC | 8 | 1 | Achieve | 0.42 | AGU/gDS | Trehalase | 1 | ug/gDS | P. emersonii | 5 | µg/g DS | Urea | 150 | ppm |
| MHCT-484-20 ug PLC | 9 | 1 | Achieve | 0.42 | AGU/gDS | Trehalase | 1 | ug/gDS | P. emersonii | 20 | µg/g DS | Urea | 150 | ppm |
| HP21-A08 | 10 | 2 | Achieve | 0.42 | AGU/gDS | Trehalase | 1 | ug/gDS | P. emersonii | 0 | µg/g DS | Urea | 150 | ppm |
| HP21-F05 | 11 | 3 | Achieve | 0.42 | AGU/gDS | Trehalase | 1 | ug/gDS | P. emersonii | 0 | µg/g DS | Urea | 150 | ppm |
| HP21-F04 | 12 | 4 | Achieve | 0.42 | AGU/gDS | Trehalase | 1 | ug/gDS | P. emersonii | 0 | µg/g DS | Urea | 150 | ppm |
| MHCT-484-Control | 13 | 1 | Achieve | 0.42 | AGU/gDS | Trehalase | 1 | ug/gDS | P. emersonii | 0 | µg/g DS | Urea | 500 | ppm |
| MHCT-484-5 ug PLC | 14 | 1 | Achieve | 0.42 | AGU/gDS | Trehalase | 1 | ug/gDS | P. emersonii | 5 | µg/g DS | Urea | 500 | ppm |
| MHCT-484-20 ug PLC | 15 | 1 | Achieve | 0.42 | AGU/gDS | Trehalase | 1 | ug/gDS | P. emersonii | 20 | µg/g DS | Urea | 500 | ppm |
| HP21-A08 | 16 | 2 | Achieve | 0.42 | AGU/gDS | Trehalase | 1 | ug/gDS | P. emersonii | 0 | µg/g DS | Urea | 500 | ppm |
| HP21-F05 | 17 | 3 | Achieve | 0.42 | AGU/gDS | Trehalase | 1 | ug/gDS | P. emersonii | 0 | µg/g DS | Urea | 500 | ppm |
| HP21-F04 | 18 | 4 | Achieve | 0.42 | AGU/gDS | Trehalase | 1 | ug/gDS | P. emersonii | 0 | µg/g DS | Urea | 500 | ppm |
| MHCT-484-Control | 19 | 1 | Achieve | 0.42 | AGU/gDS | Trehalase | 1 | ug/gDS | P. emersonii | 0 | µg/g DS | Urea | 0 | ppm |
| MHCT-484-5 ug PLC | 20 | 1 | Achieve | 0.42 | AGU/gDS | Trehalase | 1 | ug/gDS | P. emersonii | 5 | µg/g DS | Urea | 0 | ppm |
| MHCT-484-20 ug PLC | 21 | 1 | Achieve | 0.42 | AGU/gDS | Trehalase | 1 | ug/gDS | P. emersonii | 20 | µg/g DS | Urea | 0 | ppm |
| HP21-A08 | 22 | 2 | Achieve | 0.42 | AGU/gDS | Trehalase | 1 | ug/gDS | P. emersonii | 0 | µg/g DS | Urea | 0 | ppm |
| HP21-F05 | 23 | 3 | Achieve | 0.42 | AGU/gDS | Trehalase | 1 | ug/gDS | P. emersonii | 0 | µg/g DS | Urea | 0 | ppm |
| HP21-F04 | 24 | 4 | Achieve | 0.42 | AGU/gDS | Trehalase | 1 | ug/gDS | P. emersonii | 0 | µg/g DS | Urea | 0 | ppm |
| MHCT-484-Control | 25 | 1 | Achieve | 0.42 | AGU/gDS | Trehalase | 1 | ug/gDS | P. emersonii | 0 | µg/g DS | Urea | 300 | ppm |
| MHCT-484-5 ug PLC | 26 | 1 | Achieve | 0.42 | AGU/gDS | Trehalase | 1 | ug/gDS | P. emersonii | 5 | µg/g DS | Urea | 300 | ppm |
| MHCT-484-20 ug PLC | 27 | 1 | Achieve | 0.42 | AGU/gDS | Trehalase | 1 | ug/gDS | P. emersonii | 20 | µg/g DS | Urea | 300 | ppm |
| HP21-A08 | 28 | 2 | Achieve | 0.42 | AGU/gDS | Trehalase | 1 | ug/gDS | P. emersonii | 0 | µg/g DS | Urea | 300 | ppm |
| HP21-F05 | 29 | 3 | Achieve | 0.42 | AGU/gDS | Trehalase | 1 | ug/gDS | P. emersonii | 0 | µg/g DS | Urea | 300 | ppm |
| HP21-F04 | 30 | 4 | Achieve | 0.42 | AGU/gDS | Trehalase | 1 | ug/gDS | P. emersonii | 0 | µg/g DS | Urea | 300 | ppm |
| MHCT-484-Control | 31 | 1 | Achieve | 0.42 | AGU/gDS | Trehalase | 1 | ug/gDS | P. emersonii | 0 | µg/g DS | Urea | 1000 | ppm |
| MHCT-484-5 ug PLC | 32 | 1 | Achieve | 0.42 | AGU/gDS | Trehalase | 1 | ug/gDS | P. emersonii | 5 | µg/g DS | Urea | 1000 | ppm |
| MHCT-484-20 ug PLC | 33 | 1 | Achieve | 0.42 | AGU/gDS | Trehalase | 1 | ug/gDS | P. emersonii | 20 | µg/g DS | Urea | 1000 | ppm |
| HP21-A08 | 34 | 2 | Achieve | 0.42 | AGU/gDS | Trehalase | 1 | ug/gDS | P. emersonii | 0 | µg/g DS | Urea | 1000 | ppm |
| HP21-F05 | 35 | 3 | Achieve | 0.42 | AGU/gDS | Trehalase | 1 | ug/gDS | P. emersonii | 0 | µg/g DS | Urea | 1000 | ppm |
| HP21-F04 | 36 | 4 | Achieve | 0.42 | AGU/gDS | Trehalase | 1 | ug/gDS | P. emersonii | 0 | µg/g DS | Urea | 1000 | ppm |

Sampling of Fermentations
1. After 52 hours of fermentation, 50 uL of 40% $H_2SO_4$ were added to each of the tubes to stop fermentation and enzymatic hydrolysis.
2. The tubes were briefly mixed with a vortex mixer and centrifuged at 3,500 rpm for 7 minutes.
3. The tubes were placed onto a Biomek liquid handler which was used to pipette 200 uL of supernatant from the tubes into a 96 well 0.22 um filter plate.
4. The filter plate was placed on top of a round bottom 96 well polypropylene plate.
5. The filter and plate were placed into a floor centrifuge with bioseal caps on the buckets and spun at 3,500 rpm for 7 minutes or until liquid had passed through all the wells of the 96 well filter plate.
6. The plates were removed from the centrifuge and the round bottom plate with the filtered sample was heat sealed and submitted to HPLC for analysis of the ethanol and sugars produced during fermentation. The HPLC setup was as shown in Table 14.

TABLE 14

| | |
|---|---|
| HPLC system | Agilent's 1100/1200 series with Chem station software<br>Degasser<br>Quaternary Pump<br>Auto-Sampler<br>Column Compartment/w Heater<br>Refractive Index Detector (RI) |
| Column | Bio-Rad HPX- 87H Ion Exclusion Column<br>300 mm × 7.8 mm parts# 125-0140<br>Bio-Rad guard cartridge cation H parts# 125-0129, Holder parts# 125-0131 |
| Method | 0.005M $H_2SO_4$ mobile phase<br>Flow rate of 0.6 ml/min<br>Column temperature - 65° C.<br>RI detector temperature - 55° C. |

Figure 2:
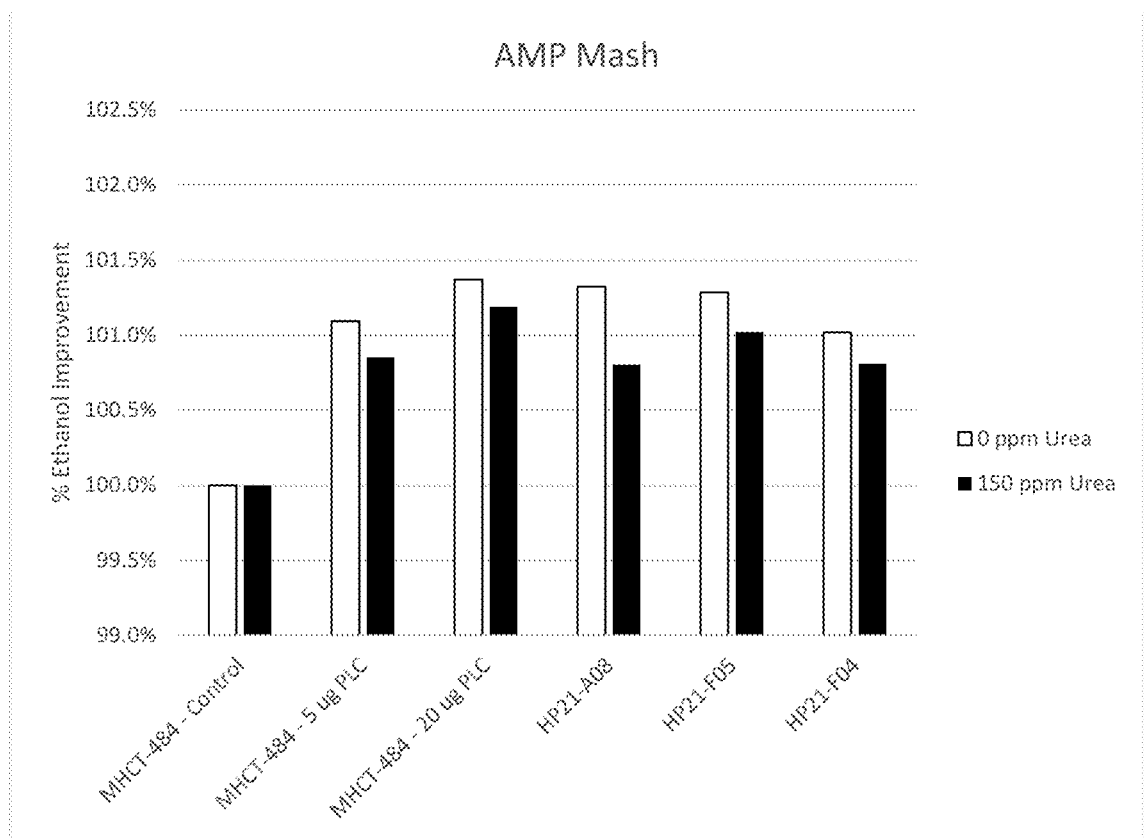
FIG. 2 shows normalized mean ethanol improvement after 54 hours of fermentation of AMP mash at 0 and 150 ppm urea as described in Example 4.

The method quantifies analytes using calibration standards for dextrins (DP4+), maltotriose, maltose, glucose, fructose, acetic acid, lactic acid, glycerol and ethanol. A 4-point calibration including the origin was used. Normalized mean ethanol values after 54 hours of fermentation of AMP mash at 0 and 150 ppm urea are shown in FIG. 2.

Figure 3:
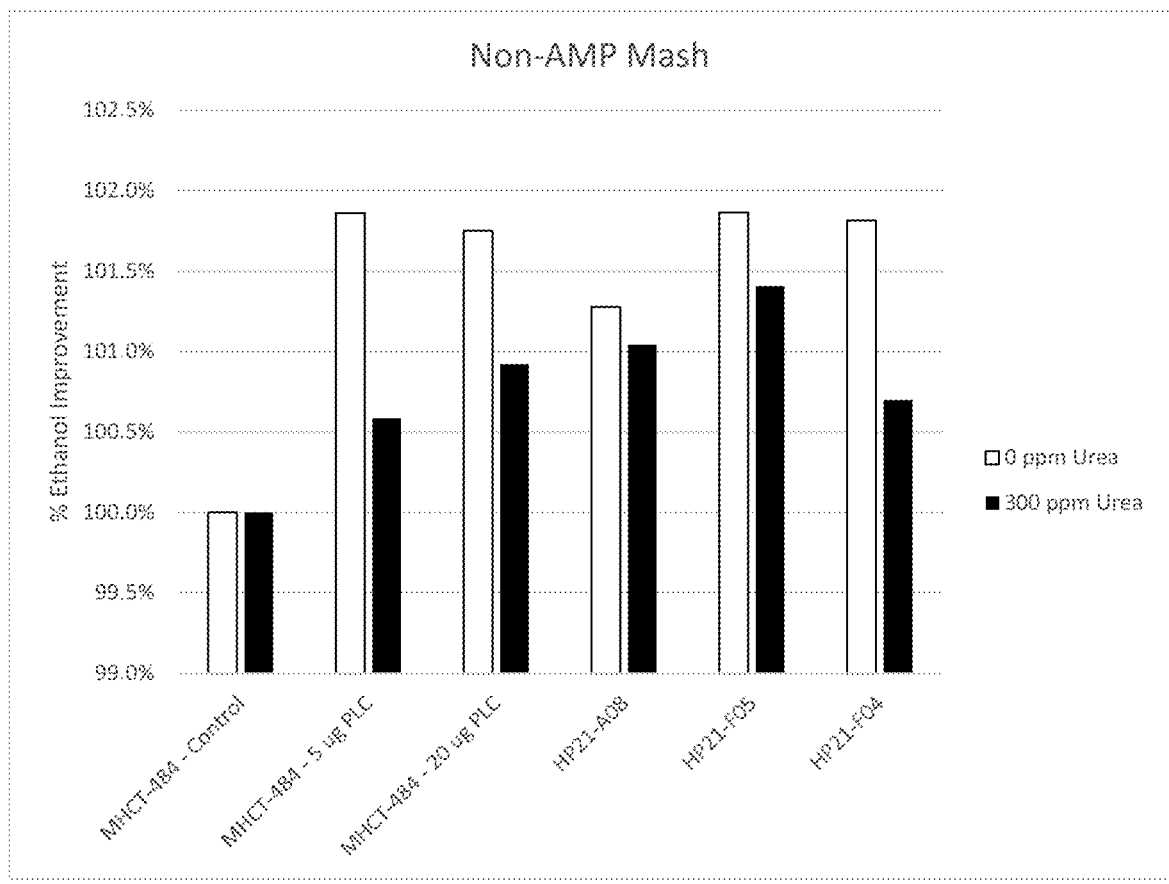
FIG. 3 shows normalized mean ethanol improvement after 54 hours of fermentation of the non-AMP mash at 0 and 300 ppm urea as described in Example 4.

All tested strains expressing phospholipase showed greater increases in ethanol titer with no urea loading. Normalized mean ethanol values after 54 hours of fermentation of non-AMP mash at 0 and 150 ppm urea are shown in FIG. 3. All tested strains expressing phospholipase showed greater increases in ethanol titer with no urea loading.

Example 5: Construction of Additional Yeast Strains Expressing a Heterologous Phospholipase This example describes the construction of yeast cells containing the remaining heterologous phospholipases of Table 1 under the control of an S. cerevisiae PGK1 promoter. Three pieces of DNA containing the promoter, gene and terminator were designed to allow for homologous recombination between the four DNA fragments and into the XII-2 locus of the strain MeJi797 (a derivative of MBG5012 expressing both alpha-amylase and glucoamylase; WO2019/161227). The resulting strain has one promoter-containing fragment (left fragment), one gene-containing fragment (middle fragment) and one PRM9 terminator fragment (right fragment) integrated into the S. cerevisiae genome at the XII-2 locus.

Construction of the Promoter-Containing Fragment (Left Fragment)

Linear DNA containing 500 bp homology to the XII-2 site and the S. cerevisiae pPGK1 promoter was PCR amplified from HP27 plasmid DNA with primers 1229945 (5'-TCTTT TCGCG CCCTG GAAAG G-3'; SEQ ID NO: 434) and 1227122 (5'-TGTTT TATAT TTGTT GTAAA AAGTA GATAA TTACT TCCTT GATGA TCTG-3'; SEQ ID NO: 435). Fifty pmoles each of forward and reverse primer was used in a PCR reaction containing 5 ng of plasmid DNA as template, 0.1 mM each dATP, dGTP, dCTP, dTTP, 1× Phusion HF Buffer (Thermo Fisher Scientific), and 2 units Phusion Hot Start DNA polymerase in a final volume of 50 μL. The PCR was performed in a T100™ Thermal Cycler (Bio-Rad Laboratories, Inc.) programmed for one cycle at 98° C. for 30 seconds followed by 32 cycles each at 98° C. for 10 seconds, 59° C. for 20 seconds, and 72° C. for 40 seconds with a final extension at 72° C. for 10 minutes. Following thermocycling, the PCR reaction products gel isolated and cleaned up using the NucleoSpin Gel and PCR clean-up kit (Machery-Nagel).

The linear DNA containing 243 bp homology to the S. cerevisiae pPGK1 promoter (SEQ ID NO: 4) and the MF1α signal peptide (SEQ ID NO: 7) was PCR amplified from DNA synthesized by GeneArt with primers 1229946 (5'-GTGAC AACAA CAGCC TGTTC TC-3'; SEQ ID NO: 436) and 1222995 (5'-AGCTA ATGCG GAGGA TGCTG C-3'; SEQ ID NO: 437). Fifty pmoles each of forward and reverse primer was used in a PCR reaction containing 5 ng of plasmid DNA as template, 0.1 mM each dATP, dGTP, dCTP, dTTP, 1× Phusion HF Buffer (Thermo Fisher Scientific), and 2 units Phusion Hot Start DNA polymerase in a final volume of 50 μL. The PCR was performed in a T100™ Thermal Cycler (Bio-Rad Laboratories, Inc.) programmed for one cycle at 98° C. for 30 seconds followed by 32 cycles each at 98° C. for 10 seconds, 59° C. for 20 seconds, and 72° C. for 20 seconds with a final extension at 72° C. for 5 minutes. Following thermocycling, the PCR reaction products gel isolated and cleaned up using the NucleoSpin Gel and PCR clean-up kit (Machery-Nagel).

Construction of the Terminator-Containing Fragment (Right Fragment)

The DNA containing 250 bp of the PRM9 terminator and 500 bp of the XII-2 3'-end homology was PCR amplified from TH12 plasmid DNA (GeneArt) with primers 1221473 (5'-ACAGA AGACG GGAGA CACTA GC-3'; SEQ ID NO: 438) and 1229949 (5'-GGGGT CGCAA CTTTT CCC-3'; SEQ ID NO: 439). Fifty pmoles each of forward and reverse primer was used in a PCR reaction containing 5 ng of plasmid DNA as template, 0.1 mM each dATP, dGTP, dCTP, dTTP, 1× Phusion HF Buffer (Thermo Fisher Scientific), and 2 units Phusion Hot Start DNA polymerase in a final volume of 50 μL. The PCR was performed in a T100™ Thermal Cycler (Bio-Rad Laboratories, Inc.) programmed for one cycle at 98° C. for 30 seconds followed by 32 cycles each at 98° C. for 10 seconds, 59° C. for 20 seconds, and 72° C. for 40 seconds with a final extension at 72° C. for 10 minutes. Following thermocycling, the PCR reaction products gel isolated and cleaned up using the NucleoSpin Gel and PCR clean-up kit (Machery-Nagel).

Construction of the Phospholipase-Containing Fragments (Middle Fragments)

Synthetic linear uncloned DNA containing the MF1α signal peptide, phospholipase gene and 50 bp of the PRM9 terminator were obtained from Geneart or Twist Bioscience.

Integration of the Left, Middle and Right-Hand Fragments to Generate Yeast Strains with a Heterologous Phospholipase The yeast MeJi797 was transformed with the left, middle and right integration fragments described above. In each transformation pool a fixed left fragment and right fragment with 100 ng of each fragment was used. The middle fragment consisted of a signal peptide and phospholipase gene with ~100 ng of each fragment (700 ng total). To aid homologous recombination of the left, middle and right fragments at the genomic XII-2 sites a plasmid containing MAD7 and guide RNA specific to XII-2 (pMIBa638) was also used in the transformation. These four components were transformed into the into *S. cerevisiae* strain MeJi797 following a yeast electroporation protocol. Transformants were selected on YPD+cloNAT to select for transformants that contain the Mad7 plasmid pMIBa638. Transformants were picked using a Q-pix Colony Picking System (Molecular Devices) to inoculate one well of 96-well plate containing YPD+cloNAT media. The plates were grown for two days then glycerol was added to 20% final concentration and the plates were stored at −80° C. until needed. Integration of specific phospholipase construct was verified by PCR with locus specific primers and subsequent sequencing. The strains generated were used in the following examples.

Example 6: Corn Mash Fermentations of Phospholipase-Expressing Yeast Strains

The strains described in Example 5 were tested for ethanol production and residual glucose using a 96-well corn mash fermentation described below. Propagation plates were prepared by inoculating 10 µL of each strain into a 96-well seed plate containing 150 uL YP+2% glucose medium per well. Plates were incubated at 30° C. and 300 RPM overnight. The following day, 10 µL of the seed culture was transferred to 96-deep well plates containing 500 µL of East Kansas Agri-Energy Liquefact Amp corn mash supplemented with 100 ppm urea and 0.42 AGU/g Spirizyme Excel. Plates were sealed with EnzyScreen plate covers and tightly clamped to limit oxygen transfer. Corn mash plates were incubated statically at 32° C. for 56 hours. After fermentation was completed, the plates were placed at −80 C for about 10 minutes before 100 µL of 8% $H_2SO_4$ was added to each well of the 96-deep well corn mash plates. Plates were sealed and mixed by inversion and centrifuged at 3000 rpm for 10 minutes. Supernatants were removed and diluted to 12× in sterile deionized water prior to HPLC analysis. The average ethanol and residual glucose per integrated heterologous phospholipase gene are shown in Table 15.

TABLE 15

| Donor Organism (catalytic domain) | SEQ ID NO: (coding) | SEQ ID NO: (mature polypeptide) | mean ethanol (g/L) | mean glucose (g/L) |
|---|---|---|---|---|
| N/A (MeJi797 control strain) | — | — | 128.84 | 4.82 |
| Penicillium cinnamopurpureum | 423 | 332 | 138.52 | 3.30 |
| Talaromyces rugulosus | 407 | 316 | 138.39 | 1.28 |
| Aspergillus turcosus | 384 | 293 | 136.06 | 1.42 |
| Aspergillus egyptiacus | 376 | 285 | 135.98 | 2.97 |
| Bacillus mycoides | 381 | 290 | 135.88 | 5.16 |
| Penicillium swiecickii | 392 | 301 | 134.40 | 5.30 |
| Lysinibacillus xylanilyticus | 388 | 297 | 134.23 | 1.94 |
| Listeria seeligeri | 391 | 300 | 133.80 | 3.99 |
| Penicillium spikei | 410 | 319 | 133.37 | 1.68 |
| Talaromyces leycettanus | 402 | 311 | 133.29 | 1.02 |
| Bacillus toyonensis | 404 | 313 | 133.10 | 2.35 |
| Bacillus mycoides | 373 | 282 | 132.84 | 5.32 |
| Bacillus mycoides | 397 | 306 | 132.72 | 5.88 |
| Rasamsonia argillacea | 356 | 265 | 132.72 | 0.96 |
| Bacillus toyonensis | 427 | 336 | 132.66 | 4.17 |
| Rasamsonia byssochlamydoides | 348 | 257 | 132.53 | 1.34 |
| Bacillus mycoides | 414 | 323 | 132.42 | 3.18 |
| Listeria innocua | 375 | 284 | 132.36 | 5.22 |
| Penicillium simplicissimum | 430 | 339 | 132.26 | 2.57 |
| Bacillus mycoides | 380 | 289 | 132.26 | 2.40 |
| Talaromyces boninensis | 393 | 302 | 132.05 | 1.08 |
| Hamigera paravellanea | 401 | 310 | 131.88 | 2.04 |
| Penicillium vasconiae | 416 | 325 | 131.76 | 1.08 |
| Rasamsonia brevistipitata | 352 | 261 | 131.76 | 2.52 |
| Bacillus mycoides | 422 | 331 | 131.68 | 4.36 |
| Bacillus pseudomycoides | 372 | 281 | 131.66 | 3.57 |
| Bacillus sp. | 428 | 337 | 131.60 | 2.88 |
| Bacillus acidiceler | 419 | 328 | 131.50 | 4.78 |
| Bacillus manliponensis | 429 | 338 | 131.36 | 2.44 |
| Hamigera avellanea | 409 | 318 | 131.23 | 1.49 |
| Penicillium flavescens | 358 | 267 | 131.22 | 4.68 |
| Bacillus sp. | 420 | 329 | 130.98 | 5.96 |
| Talaromyces bacillisporus | 367 | 276 | 130.86 | 3.80 |
| Talaromyces cellulolyticus | 425 | 334 | 130.74 | 0.84 |
| Rasamsonia eburnea | 349 | 258 | 130.61 | 2.07 |
| Bacillus acidiceler | 433 | 342 | 130.52 | 5.04 |
| Talaromyces rugulosus | 364 | 273 | 130.52 | 1.00 |
| Bacillus thuringiensis | 396 | 305 | 130.46 | 3.89 |
| Brevibacillus sp. | 415 | 324 | 130.44 | 18.72 |
| Bacillus drentensis | 383 | 292 | 130.41 | 6.75 |
| Talaromyces verruculosus | 424 | 333 | 129.78 | 3.18 |
| Penicillium piscarium | 366 | 275 | 129.74 | 4.37 |
| Penicillium sclerotiorum | 347 | 256 | 129.72 | 9.06 |
| Hamigera terricola | 365 | 274 | 129.68 | 10.32 |
| Penicillium arenicola | 431 | 340 | 129.65 | 1.34 |
| Aspergillus tamarii | 377 | 286 | 128.86 | 1.03 |
| Penicillium sp. | 408 | 317 | 128.04 | 1.92 |
| Bacillus sp. | 382 | 291 | 127.84 | 3.64 |
| Aspergillus tubingensis | 386 | 295 | 127.66 | 3.89 |
| Penicillium emersonii | 355 | 264 | 127.65 | 3.75 |
| Talaromyces subinflatus | 385 | 294 | 127.26 | 6.60 |
| Bacillus thuringiensis | 405 | 314 | 127.08 | 3.00 |
| Penicillium vasconiae | 361 | 270 | 126.96 | 12.44 |
| Talaromyces columbinus | 362 | 271 | 126.69 | 4.05 |
| Bacillus bingmayongensis | 413 | 322 | 126.67 | 6.86 |
| Bacillus luciferensis | 379 | 288 | 126.51 | 5.46 |
| Hamigera striata | 394 | 303 | 126.36 | 2.04 |
| Bacillus thuringiensis | 406 | 315 | 126.30 | 9.00 |
| Bacillus toyonensis | 389 | 298 | 126.30 | 11.82 |
| Bacillus mycoides | 412 | 321 | 126.15 | 13.95 |
| Bacillus acidiceler | 387 | 296 | 125.85 | 5.37 |
| Bacillus wiedmannii | 390 | 299 | 125.67 | 7.25 |
| Talaromyces variabilis | 363 | 272 | 125.33 | 5.78 |
| Bacillus thuringiensis | 374 | 283 | 125.32 | 4.08 |
| Penicillium simplicissimum | 360 | 269 | 125.04 | 10.32 |
| Aspergillus stramenius | 371 | 280 | 124.92 | 3.52 |
| Penicillium brefeldianum | 350 | 259 | 124.86 | 17.10 |
| Penicillium bialowiezense | 346 | 255 | 124.72 | 3.00 |
| Penicillium scabrosum | 353 | 262 | 124.56 | 14.67 |
| Penicillium megasporum | 369 | 278 | 124.44 | 2.10 |
| Penicillium donkii | 400 | 309 | 123.96 | 0.84 |
| Penicillium jensenii | 370 | 279 | 123.75 | 5.58 |
| Galactomyces candidus | 368 | 277 | 123.36 | 14.37 |
| Bacillus sp. | 395 | 304 | 123.18 | 8.82 |
| Aspergillus niger | 378 | 287 | 123.00 | 8.28 |
| Bacillus pseudomycoides | 421 | 330 | 122.22 | 4.86 |
| Penicillium hispanicum | 359 | 268 | 118.14 | 19.95 |
| Penicillium manginii | 354 | 263 | 117.96 | 13.15 |
| Penicillium meridianum | 345 | 254 | 117.72 | 14.92 |
| Paenibacillus sp. | 403 | 312 | 110.07 | 38.28 |
| Paenibacillus alginolyticus | 411 | 320 | 106.52 | 43.96 |

Example 7: Enhancement of Ethanol Yield with Phospholipase-Expressing Yeast Strains Commercial Amp corn mash was obtained from Trenton Agri at 35.9% (w/w) of dry solids content and was diluted with tape water to 32.0% (w/w). After dilution, the pH value of the mash was adjusted to 5.1 with 39% (w/v) NaOH solution. Urea and lactrol were added into the pH adjusted Amp mash to final concentration at 150 ppm and 3 ppm, respectively. The prepared corn mash was aliquoted into 250 mL flasks (100 g/flask).

To propagate yeast, 50 mL of 6% YPD and 100 µl of yeast-glycerol stock solution were mixed in a 125-mL flask and then incubated at 32° C. for overnight. After incubation, 45 mL of propagation was transferred to a 50 mL centrifuge tube and centrifuged at 3500 rpm for 10 minutes. The liquid fraction was decanted and deionized water was used to twice wash the cells. The cells were resuspended in 10 mL of deionized water and the total and dead cell accounts were measured using a NucleoCounter® YC-100.

The exogenous α-glucoamylase (Spirizyme Achieve-T™; Novozymes A/S) was added into the flasks containing corn mash per DOE and mixed well. Then the pre-determined amount of yeast suspension was added and mixed well. The fermentation was performed at 32° C. for 54 hours. After the fermentation, 5 g of slurry was taken out and the fermentation was stopped by adding 50 µL of 40% $H_2SO_4$. The liquid was separated from solid by centrifuging whole slurry at 900 g for 10 min. The ethanol concentration was measured using HPLC.

Compared with the control strain MHCT-484, both phospholipase-expressing yeast strains showed significantly increased final ethanol yield (13.30% for control strain MHCT-484, to 13.43% and to 13.42% for strains HP21-F04 and HP21-F05, respectively.

Example 8: Enhancement of Oil Extraction with Phospholipase-Expressing Yeast Strains Commercial Amp corn mash was obtained from Trenton Agri at 35.9% (w/w) of dry solids content and was diluted water to 32.0% (w/w). After dilution, the pH value of the mash was adjusted to 5.1 with 39% (w/v) NaOH solution. Urea and lactrol were added into the pH adjusted Amp mash to final concentration at 150 ppm and 3 ppm, respectively. The prepared corn mash was aliquoted into 250-mL flasks (100 g/flask).

To propagate yeast, 50 mL of 6% YPD and 100 µL of yeast-glycerol stock solution were mixed in a 125-mL flask and then incubated at 32° C. for overnight. After incubation, 45 mL of propagation was transferred to a 50-mL centrifuge tube and centrifuged at 3500 rpm for 10 minutes. The liquid fraction was decanted, and deionized water was used to twice wash the cells. The cells were resuspended in 10 mL of deionized water and the total and dead cell accounts were measured using a NucleoCounter® YC-100.

Exogenous α-glucoamylase (Spirizyme Achieve-T™; Novozymes A/S), was added into the flasks containing corn mash per DOE and mixed well. Then the pre-determined amount of yeast suspension was added and mixed well. The fermentation was performed at 32° C. for 54 hours. After fermentation, 10 mL of 95% hexane was added to 95 grams of whole slurry. The slurry-hexane mixture was mixed well and then centrifuged at 3000×g for 10 minutes. After centrifuge, the top layer was transferred into a 15-mL tube using positive displacement pipettes. The oil was extracted from the slurry again with the same method. The total weight of transferred liquor was measured. The oil content and density were measured on densiometer. The final extracted oil was calculated as:

Extracted oil (g/flask)=first extracted oil (g/flask)+ second extracted oil (g/flask)

Compared with the control strain MHCT-484, both lipase-expressing yeast strains HP21-F04 and HP21-F05 improved the final oil yield (0.518 g/flask and 0.966 g/flask for strains HP21-F04 and HP21-F05, respectively compared to 0.483 g/flask for control strain MHCT-484).

Example 9: Defoaming Capabilities with Phospholipase-Expressing Yeast Strains Commercial Amp corn mash was obtained from Trenton Agri at 35.9% (w/w) of dry solids content and was diluted with tape water to 32.0% (w/w). After dilution, the pH value of the mash was adjusted to 5.1 with 39% (w/v) NaOH solution. Urea and lactrol were added into the pH adjusted Amp mash to final concentration at 150 ppm and 3 ppm, respectively. The prepared corn mash was aliquoted into 250-mL flasks (100 g/flask).

To propagate yeast, 50 mL of 6% YPD and 100 µL of yeast-glycerol stock solution were mixed in a 125-mL flask and then incubated at 32° C. for overnight. After incubation, 45 mL of propagation was transferred to a 50-mL centrifuge tube and centrifuged at 3500 rpm for 10 minutes. The liquid fraction was decanted, and deionized water was used to twice wash the cells. The cells were resuspended in 10 mL of deionized water and the total and dead cell accounts were measured using a NucleoCounter® YC-100.

The exogenous α-glucoamylase, Spirizyme Achieve-T™ (Novozyems A/S), was added into the flasks containing corn mash per DOE and mixed well. Then the pre-determined amount of yeast suspension was added and mixed well. Also, the pre-determined exogenous lipase was added and used as control. The fermentation was performed at 32° C. for 54 hours.

Figure 4:
FIG. 4 shows improved defoaming capability during fermentation of a phospholipase-expressing yeast strain HP21-F04 (right) compared to control strain yMHCT48 (left) as described in Example 9.

The defoaming capability of control MHCT-484 and lipase-expressing yeast HP21-F04 was monitored using video camera after 12-hour fermentation. Compared with control yMHCT48, lipase-expressing yeast HP21-F04 showed significant defoaming capability (FIG. 4).

The invention claimed is:

1. A recombinant *Saccharomyces* yeast cell comprising a heterologous polynucleotide encoding a phospholipase and a heterologous polynucleotide encoding a glucoamylase,
wherein the phospholipase has a mature polypeptide sequence at least 90% sequence identity to the amino acid sequence of SEQ ID NO: 236, and
wherein the cell is capable of higher ethanol yield and/or reduced foam accumulation when compared to fermentation using the same process and an identical cell without the heterologous polynucleotide encoding the phospholipase under the same conditions.

2. The recombinant yeast cell of claim 1, wherein the fermenting organism comprises a heterologous polynucleotide encoding an alpha-amylase.

3. The recombinant yeast cell of claim 1, wherein the fermenting organism comprises a heterologous polynucleotide encoding a protease.

4. The recombinant yeast of claim 1, wherein the cell is a *Saccharomyces cerevisiae* cell.

5. The recombinant yeast of claim 1, wherein the phospholipase has a mature polypeptide sequence having at least 95% sequence identity to the amino acid sequence of SEQ ID NO: 236.

6. The recombinant yeast of claim 1, wherein the phospholipase has a mature polypeptide sequence having at least 97% sequence identity to the amino acid sequence of SEQ ID NO: 236.

7. The recombinant yeast of claim 1, wherein the phospholipase has a mature polypeptide sequence having at least 98% sequence identity to the amino acid sequence of SEQ ID NO: 236.

8. The recombinant yeast of claim 1, wherein the phospholipase has a mature polypeptide sequence having at least 99% sequence identity to the amino acid sequence of SEQ ID NO: 236.

9. The recombinant yeast of claim 1, wherein the phospholipase has a mature polypeptide sequence that comprises or consists of the amino acid sequence of SEQ ID NO: 236.

10. A method of producing a fermentation product from a starch-containing or cellulosic-containing material comprising:
(a) saccharifying the starch-containing or cellulosic-containing material; and
(b) fermenting the saccharified material of step (a) with the recombinant yeast of claim 1.

11. The method of claim 10, wherein saccharification of step (a) occurs on a starch-containing material, and wherein the starch-containing material is gelatinized.

12. The method of claim 10, wherein saccharification of step (a) occurs on a starch-containing material, and wherein the starch-containing material is ungelatinized.

13. The method of claim 10, wherein saccharification of step (a) occurs on a starch-containing material, and wherein the method comprises liquefying the starch-containing material by contacting the material with an alpha-amylase prior to saccharification.

14. The method of claim 10, wherein liquefying the starch-containing material and/or saccharifying the starch-containing material is conducted in presence of exogenously added protease.

15. The method of claim 10, wherein the recombinant yeast comprises a heterologous polynucleotide encoding an alpha-amylase.

16. The method of claim 10, wherein the recombinant yeast is a *Saccharomyces cerevisiae* cell.

17. The method of claim 10, wherein the method results in higher yield of fermentation product and/or reduced foam accumulation when compared to the same process using an identical cell without the heterologous polynucleotide encoding the phospholipase under the same conditions.

18. The method of claim 10, wherein the phospholipase of the recombinant yeast has a mature polypeptide sequence having at least 95% sequence identity to the amino acid sequence of SEQ ID NO: 236.

19. The method of claim 10, wherein the phospholipase of the recombinant yeast has a mature polypeptide sequence having at least 97% sequence identity to the amino acid sequence of SEQ ID NO: 236.

20. The method of claim 10, wherein the phospholipase of the recombinant yeast has a mature polypeptide sequence that comprises or consists of the amino acid sequence of SEQ ID NO: 236.

* * * * *

SEQUENCE LISTING

```
Sequence total quantity: 439
SEQ ID NO: 1             moltype = DNA   length = 621
FEATURE                  Location/Qualifiers
source                   1..621
                         mol_type = genomic DNA
                         organism = Saccharomyces cerevisiae
SEQUENCE: 1
```

```
cagttcgagt ttatcattat caatactgcc atttcaaaga atacgtaaat aattaatagt    60
agtgattttc ctaactttat ttagtcaaaa aattagcctt ttaattctgc tgtaacccgt   120
acatgcccaa aatagggggc gggttacaca gaatatataa catcgtaggt gtctggtga    180
acagtttatt cctggcatcc actaaatata atggagcccg cttttttaagc tggcatccag  240
aaaaaaaaag aatcccagca ccaaaatatt gttttcttca ccaaccatca gttcataggt   300
ccattctctt agcgcaacta cagagaacag gggcacaaac aggcaaaaaa cgggcacaac   360
ctcaatggag tgatgcaacc tgcctggagt aaatgatgac acaaggcaat tgacccacgc   420
atgtatctat ctcattttct tacaccttct attaccttct gctctctctg atttggaaaa   480
agctgaaaaa aaaggttgaa accagttccc tgaaattatt cccctacttg actaatagt    540
atataaagac ggtaggtatt gattgtaatt ctgtaaatct atttcttaaa cttcttaaat   600
tctactttta tagttagtct t                                             621

SEQ ID NO: 2           moltype = DNA   length = 644
FEATURE                Location/Qualifiers
source                 1..644
                       mol_type = genomic DNA
                       organism = Saccharomyces cerevisiae
SEQUENCE: 2
agctacctat attccaccat aatatcaatc atgcggttgc tggtgtattt accaataatg    60
tttaatgtat atatattagg ggccgtatac ttacatatag tagatgtcaa gcgtaggcgc   120
ttcccctgcc ggctgtgacg gcgccataac caaggtatct atagaccgcc aatcagcaaa   180
ctacctcgt acattcatgt tgcacccaca catgtacaca cccagaccgc aacaaattac    240
ccataaggtt gtttgtgacg gcgtcgtaca agagaacgtg ggaactttt aggctcacca    300
aaaaagaaag gaaaaatacg agttgctgac agaagcctca agaaaaaaa aattcttctt    360
cgactatgct ggaggcagag atgatcgagc cgtagttaa ctatatatag ctaaattggt    420
tccatcacct tcttttctgg tgtcgctcct tctagtgcta tttctggctt ttcctatttc   480
tttttttttcc attttctttt ctctcttttct aatatataaa ttctcttgca ttttctattt  540
ttctctctat ctattctact tgtttattcc cttcaaggtt tttttttaag gagtacttgt   600
ttttagaata tacggtcaac gaactataat taagctagaa caaa                    644

SEQ ID NO: 3           moltype = DNA   length = 457
FEATURE                Location/Qualifiers
source                 1..457
                       mol_type = genomic DNA
                       organism = Saccharomyces cerevisiae
SEQUENCE: 3
ctccagaaag gcaacgcaaa attttttttc cagggaataa actttctatg acccactact    60
tctcgtagga acaatttcgg gccctgcgt gttcttctga ggttcatctt ttacatttgc    120
ttctgctgga taattttcag aggcaacaag gaaaaattag atggcaaaaa gtcgtcttc    180
aaggaaaaat cccccaccatc cttcgagatc ccctgtaact tattggcaac tgaaagaatg   240
aaaaggagga aaatacaaaa tatactagaa ctgaaaaaaa aagtataaa tagagacgat    300
atatgccaat acttcacaat gttcgaatcc attcttcatt tgcagctatt gtaaaataat   360
aaaacatcaa gaacaaacaa gctcaacttg tcttttctaa gaacaaagaa taaacacaaa   420
aacaaaaagt ttttttaatt ttaatcgcta gaacaaa                           457

SEQ ID NO: 4           moltype = DNA   length = 700
FEATURE                Location/Qualifiers
source                 1..700
                       mol_type = genomic DNA
                       organism = Saccharomyces cerevisiae
SEQUENCE: 4
gtgagtaagg aaagagtgag gaactatcgc atacctgcat ttaaagatgc cgatttgggc    60
gcgaatcctt tattttggct tcaccctcat actattatca gggccagaaa aaggaagtgt   120
ttcccctcct cttgaattga tgttaccctc ataaagcacg tggcctctta tcgagaaaga   180
aattccgtc gctcgtgatt tgtttgcaaa aagaacaaa ctgaaaaaac ccagacacgc    240
tcgacttcct gtcatcctat tgattgcagc ttccaatttc gtcacacaac aaggtcctag   300
cgacggctca caggttttgt aacaagcaat cgaaggttct ggaatggcgg gaaagggttt   360
agtaccacat gctatgatgc ccactgtgat ctccagagca aagttcgttc gatcgtactg   420
ttactctctc tcttttcaaac agaattgtcc gaatcgtgtg acaacaacag cctgttctca   480
cacactcttt tcttctaacc aaggggggtgg tttagtttag tagaacctcg tgaaacttac   540
atttacatat atataaactt gcataaattg gtcaatgcaa gaaatacata tttggtcttt   600
tctaattcgt agttttcaa gttcttagat gctttctttt tctcttttt acagatcatc    660
aaggaagtaa ttatctactt tttacaacaa atataaaaca                         700

SEQ ID NO: 5           moltype = DNA   length = 705
FEATURE                Location/Qualifiers
source                 1..705
                       mol_type = genomic DNA
                       organism = Saccharomyces cerevisiae
SEQUENCE: 5
atcctttgt tgtttccggg tgtacaatat ggacttcctc ttttctgca accaaaccca     60
tacatcggga ttcctataat accttcgttg gtctccctaa catgtaggtg gcggagggga   120
gatatacaat agaacagata ccagacaaga cataatgggc taaacaagac tacaccaatt   180
acactgcctc attgatgtg gtacataacg aactaatact gtagcccta cttgatagc    240
catcatcata tcgaagtttc actaccctt ttccatttgc catctattga agtaataata   300
ggcgcatgca acttctttc ttttttttt ttttctctct ccccgttgt tgtctcacca   360
tatccgcaat gacaaaaaa tgatggaaga cactaaagga aaaattaac gacaaagaca   420
gcaccaacag atgtcgttgt tccagagctg atgagggta tctcgaagca cacgaaactt   480
tttccttcct tcattcacgc acactactct ctaatgagca acggtatacg gcctccttc   540
```

```
cagttacttg aatttgaaat aaaaaaaagt ttgctgtctt gctatcaagt ataaatagac    600
ctgcaattat taatcttttg tttcctcgtc attgttctcg ttcccttcct tccttgtttc    660
tttttctgca caatatttca agctatacca agcatacaat caact                   705

SEQ ID NO: 6              moltype = DNA  length = 700
FEATURE                   Location/Qualifiers
source                    1..700
                          mol_type = genomic DNA
                          organism = Saccharomyces cerevisiae
SEQUENCE: 6
aagaggatgt ccaatatttt ttttaaggaa taaggatact tcaagactag attcccccct     60
gcattcccat cagaaccgta aaccttggcg ctttccttgg gaagtattca agaagtgcct    120
tgtccggttt ctgtggctca caaaccagcg cgcccgatat ggctttcttt tcacttatga    180
atgtaccagt acgggacaat tagaacgctc ctgtaacaat ctctttgcaa atgtggggtt    240
acattctaac catgtcacac tgctgacgaa attcaaagta aaaaaaaatg ggaccacgtc    300
ttgagaacga tagattttct ttattttaca ttgaacagtc gttgtctcag cgcgctttat    360
gttttcattc atacttcata ttataaaata acaaagaaag aatttcatat tcacgcccaa    420
gaaatcaggc tgcttccaa atgcaattga cacttcatta gccatcacac aaaactcttt     480
cttgctggag cttcttttaa aaaagacctc agtacaccaa acacgttacc cgacctcgtt    540
attttacgac aactatgata aaattctgaa gaaaaaataa aaaaattttc atacttcttg    600
cttttattta aaccattgaa tgatttcttt tgaacaaaac tacctgtttc accaaaggaa    660
atagaaagaa aaatcaattt agaagaaaac aaaaaacaaa                          700

SEQ ID NO: 7              moltype = AA  length = 19
FEATURE                   Location/Qualifiers
source                    1..19
                          mol_type = protein
                          organism = Saccharomyces cerevisiae
SEQUENCE: 7
MRFPSIFTTV LFAASSALA                                                  19

SEQ ID NO: 8              moltype = AA  length = 556
FEATURE                   Location/Qualifiers
source                    1..556
                          mol_type = protein
                          organism = Gloeophyllum sepiarium
SEQUENCE: 8
QSVDSYVSSE GPIAKAGVLA NIGPNGSKAS GASAGVVVAS PSTSDPDYWY TWTRDSSLVF     60
KSLIDQYTTG IDGTSSLRTL IDDFVTAEAN LQQVSNPSGT LTTGGLGEPK FNVDETAFTG    120
AWGRPQRDGP ALRSTALITY GNWLLSNGNT SYVTSNLWPI IQNDLGYVVS YWNQSTYDLW    180
EEVDSSSFFT TAVQHRALRE GAAFATAIGQ TSQVSSYTTQ ADNLLCFLQS YWNPSGGYIT    240
ANTGGGRSGK DANTLLASIH TYDPSAGCDA ATFQPCSDKA LSNLKVYVDS FRSVYSINSG    300
IASNAAVATG RYPEDSYQGG NPWYLTTFAV AEQLYDALNV WESQGSLEVT STSLAFFQQF    360
SSGVTAGTYS SSSSTYSTLT SAIKSFADGF VAVNAKYTPS NGGLAEQYSK SDGSPLSAVD    420
LTWSYASALT AFEARNNTQF AGWGAAGLTV PSSCSGNSGG PTVAVTFNVN AETVWGENIY    480
LTGSVDALEN WSADNALLLS SANYPTWSIT VNLPASTAIE YKYIRKNNGA VTWESDPNNS    540
ITTPASGSTT ENDTWR                                                   556

SEQ ID NO: 9              moltype = AA  length = 374
FEATURE                   Location/Qualifiers
source                    1..374
                          mol_type = protein
                          organism = Aspergillus niger
SEQUENCE: 9
APAPTRKGFT INQIARPANK TRTINLPGMY ARSLAKFGGT VPQSVKEAAS KGSAVTTPQN     60
NDEEYLTPVT VGKSTLHLDF DTGSADLWVF SDELPSSEQT GHDLYTPSSS ATKLSGYTWD    120
ISYGDGSSAS GDVYRDTVTV GGVTTNKQAV EAASKISSEF VQNTANDGLL GLAFSSINTV    180
QPKAQTTFFD TVKSQLDSPL FAVQLKHDAP GVYDFGYIDD SKYTGSITYT DADSSQGYWG    240
FSTDGYSIGD GSSSSSGFSA IADTGTTLIL LDDEIVSAYY EQVSGAQESE EAGGYVFSCS    300
TNPPDFTVVI GDYKAVVPGK YINYAPISTG SSTCFGGIQS NSGLGLSILG DVFLKSQYVV    360
FNSEGPKLGF AAQA                                                     374

SEQ ID NO: 10             moltype = AA  length = 590
FEATURE                   Location/Qualifiers
source                    1..590
                          mol_type = protein
                          organism = Trichoderma reesei
SEQUENCE: 10
SVHLLESLEK LPHGWKAAET PSPSSQIVLQ VALTQQNIDQ LESRLAAVST PTSSTYGKYL     60
DVDEINSIFA PSDASSSAVE SWLQSHGVTS YTKQGSSIWF QTNISTANAM LSTNFHTYSD    120
LTGAKKVRTL KYSIPESLIG HVDLISPTTY FGTTKAMRKL KSSGVSPAAD ALAARQEPSS    180
CKGTLVFEGE TFNVFQPDCL RTEYSVDGYT PSVKSGSRIG FGSFLNESAS FADQALFEKH    240
FNIPSQNFSV VLINGGTDLP QPPSDANDGE ANLDAQTIIF IAHPLPITEF ITAGSPPYFP    300
DPVEPAGTPN ENEPYLQYYE FLLSKSNAEI PQVITNSYGD EEQTVPRSYA VRVCNLIGLL    360
GLRGISVLHS SGDEGVGASC VATNSTTPQF NPIFPATCPY VTSVGGTVSF NPEVAWAGSS    420
GGFSYYFSRP WYQQEAVGTY LEKYVSAETK KYYGPYVDFS GRGFPDVAAH SVSPDYPVFQ    480
GGELTPSGGT SAASPVVAAI VALLNDARLR EGKPTLGFLN PLIYLHASKG FTDITSGQSE    540
GCNGNNTQTG SPLPGAGFIA GAHWNATKGW DPTTGFGVPN LKKLLALVRF               590
```

```
SEQ ID NO: 11              moltype = AA  length = 511
FEATURE                    Location/Qualifiers
source                     1..511
                           mol_type = protein
                           organism = Thermoascus aurantiacus
SEQUENCE: 11
VPVEVAGSAQ GLDVTLSQVG NTRIKAVVKN TGSEDVTFVH LNFFKDAAPV QKVSLFRNAT    60
EVQFQGIKQR LITEGLSDDA LTTLAPGATI EDEFDIASTS DLSEGGTITI NSNGLVPITT   120
DNKVTGYIPF TSNELSIDVD AAEAASVTQA VKILERRTRI SSCSGSRQSA LTTALRNAAS   180
LANKAADAAQ SGSASKFSEY FKTTSSSTRQ TVAARLRAVA REASSSSGA TTYYCLDPFG   240
YCSGNVLAYT LPSYNIIANC PIFYTYLPPL TSTCHAQDQA TTVLHEFTHA PGVYSPGTLD   300
LAYGYQAAMG LSSSQAVMNA DTYALYANAI YLGCTRISSC SGSRQSALTT ALRNAASLAN   360
AADAAQSGS ASKFSEYFKT TSSSTRQTVA ARLRAVAREA SSSSSGATTY YCDDPYGYCS   420
SNVLAYTLPS YNIIANCDIF YTYLPALTST CHAQDQATTA LHEFTHAPGV YSPGTDDLAY   480
GYQAAMGLSS SQAVMNADTY ALYANAIYLG C                                   511

SEQ ID NO: 12              moltype = AA  length = 550
FEATURE                    Location/Qualifiers
source                     1..550
                           mol_type = protein
                           organism = Dichomitus squalens
SEQUENCE: 12
KPTARNLKLH ESRPSAPNGF SLVGSADSNR TLKLRLALAE SNFSELERKL YDVSTPKSAN    60
YGKHLSKAEV QQLVAPGQDS IDAVNAWLKE NDITAKTISS TGEWISFEVP VSKANDLFDA   120
DFSVFKHDDT GVEAIRTLSY SIPAELQGHL DLVHPTVTFP NPYSHLPVFQ SPVKKTAEIQ   180
NFTAGAIPSS CSSTITPACL QAIYNIPTTA ATESSNQLGV TGFIDQYANK KDLKTFLKKY   240
RTDISSSTTF TLQTDGGSN SQTGSKAGVE ANLDIQYTVG VATGVPTTFI SVGDDFQDGD   300
LEGFLDVINA LLDEDAPPSV LTTSYGQDES TISRALAVKL CNAYAQLGAR GVSILFASGD   360
GGVSGSQSAS CSKFVPTFPS GCPYMTSVGA TQGVNPETAA DFSSGGFSNY WGVPDYQSDA   420
VSTYLSALGK TNSGKYNASG RGFPDVSTQG VSFEVVVDGS VEAVDGTSCA SPTFASIISL   480
VNDKLVAAGK SPLGFLNPFL YSDGVAALND ITSGSNPGCN TNGFPAKKGW DPVTGLGTPD   540
FKKLLTAVGL                                                           550

SEQ ID NO: 13              moltype = AA  length = 353
FEATURE                    Location/Qualifiers
source                     1..353
                           mol_type = protein
                           organism = Nocardiopsis prasina
SEQUENCE: 13
ATGALPQSPT PEADAVSMQE ALQRDLDLTS AEAEELLAAQ DTAFEVDEAA AEAAGDAYGG    60
SVFDTESLEL TVLVTDAAAV EAVEATGAGT ELVSYGIDGL DEIVQELNAA DAVPGVVGWY   120
PDVAGDTVVL EVLEGSGADV SGLLADAGVD ASAVEVTTSD QPELYADIIG GLAYTMGGRC   180
SVGFAATNAA GQPGFVTAGH CGRVGTQVTI GNGRGVFEQS VFPGNDAAFV RGTSNFTLTN   240
LVSRYNTGGY ATVAGHNQAP IGSSVCRSGS TTGWHCGTIQ ARGQSVSYPE GTVTNMTRTT   300
VCAEPGDSGG SYISGTQAQG VTSGGSGNCR TGGTTFYQEV TPMVNSWGVR LRT           353

SEQ ID NO: 14              moltype = AA  length = 456
FEATURE                    Location/Qualifiers
source                     1..456
                           mol_type = protein
                           organism = Penicillium simplicissimum
SEQUENCE: 14
APASTAKDSV SSVVKNGVKY TVFEHAATGA KMEFVKNSGI CETTPGVNQY SGYLSVGSNM    60
NMWFWFFEAR NNPQQAPLAA WFNGGPGCSS MIGLFQENGP CHFVNGDSTP SLNEYSWNNY   120
ANMLYVDQPI GVGFSYGTDD VTSTVTAAPY VWKLLQAFYA QFPEYESRDF AIFTESYGGH   180
YGPEFASYIQ EQNSAIKTGS ISGENINLVA LGVNNGWIDS TIQEKAYIDF SYNNSYQQLI   240
DDSQRTSLLS AYNSQCLPAI QKCTKSGSNS DCQNADSVCY NKIEGPISSS GDWDVYDIRE   300
PSNDPYPPST YSTYLSNADV VKAIGAQSSY QECPNGPYNK FASTGDNPRS FLSTLSSVVK   360
SGINVLVWAG DADWICNWLG NYEVANAVDF SGHTEFSAKD LAPYTVNGTE KGMFKNVANF   420
SFLKVYGAGH EVPYYQPDTA LQVFEQVLQN KPIFST                              456

SEQ ID NO: 15              moltype = AA  length = 502
FEATURE                    Location/Qualifiers
source                     1..502
                           mol_type = protein
                           organism = Aspergillus niger
SEQUENCE: 15
LQNPHRRAVP PPLSHRSVAS RSVPVERRTT DFEYLTNKTA RFLVNGTSIP EVDFDVGESY    60
AGLLPNTPTG NSSLFFWFFP SQNPEASDEI TIWLNGGPGC SSLDGLLQEN GPFLWQPGTY   120
KPVPNPYSWT NLTNVVYIDQ PAGTGFSPGP STVNNEEDVA AQFNSWFKHF VDTFDLHGRK   180
VYITGESYAG MYVPYIADAM LNEEDTTYFN LKGIQINDPS INSDSVMMYS PAVRHLNHYN   240
NIFQLNSTFL SYINAKADKC GYNAFLDKAI TYPPPSPFPT APEITEDCQV WDEVVMAAYD   300
INPCFNYYHL IDFCPYLWDV LGFPSLASGP NNYFNRSDVQ KILHVPPTDY SVCSETVIFA   360
NGDGSDPSSW GPLPSVIERT NNTIIGHGWL DYLLFNGSL ATIQNMTWNG KQGFQRPPVE   420
PLFVPYHYGL AELYWGDEPD PYNLDAGAGY LGTAHTERGL TFSSVYLSGH EIPQYVPGAA   480
YRQLEFLLGR ISSLSAKGNY TS                                             502

SEQ ID NO: 16              moltype = AA  length = 547
FEATURE                    Location/Qualifiers
```

```
source                  1..547
                        mol_type = protein
                        organism = Meripilus giganteus
SEQUENCE: 16
TPTGRNLKLH EAREDLPAGF SLRGAASPDT TLKLRIALVQ NNFAELEDKL YDVSTPSSAN    60
YGNHLSKEEV EQYIAPAPES VKAVNAWLTE NGLDAHTISP AGDWLAFEVP VSKANELFDA   120
DFSVFTHDES GLEAIRTLAY SIPAELQGHL DLVHPTVTFP NPNAHLPVVR STQPIRNLTG   180
RAIPASCAST ITPACLQAIY GIPTTKATQS SNKLAVSGFI DQFANKADLK SFLAQFRKDI   240
SSSTTFSLQT LDGGENDQSP SEAGIEANLD IQYTVGLATG VPTTFISVGD DPQDGNLEGF   300
LDIINFLLGE SNPPQVLTTS YGQNENTISA KLANQLCNAY AQLGARGTSI LFASGDGGVS   360
GSQSAHCSNF VPTFPSGCPF MTSVGATQGV SPETAAAFSS GGFSNVFGIP SYQASAVSGY   420
LSALGSTNSG KFNRSGRGFP DVSTQGVDFQ IVSGGQTIGV DGTSCASPTF ASVISLVNDR   480
LIAAGKSPLG FLNPFLYSSA GKAALNDVTS GSNPGCSTNG FPAKAGWDPV TGLGTPNFAK   540
LLTAVGL                                                              547

SEQ ID NO: 17           moltype = AA  length = 541
FEATURE                 Location/Qualifiers
source                  1..541
                        mol_type = protein
                        organism = Lecanicillium sp.
SEQUENCE: 17
APAPHGPLVK FGEITKLPSK WIATGAADSD AVIKAQIGIK QNNIKGLQDK LADIADPNSP    60
NYGQWLSKEE VDKYSAPAAA DVAAVKAWLA SSGITDVTMP TNDWIEFSVP VSKMESLLGS   120
KYEWFVHLET GEKVPRTKQF SVPQNLHDLI DVVTPTTVLY HNMGPHAHAS PQAADASGLT   180
SPASIKSAYN VDYKGTGNTL VGTTGFLGVG ASHQDYANFA RQFSPGLTDF KDVSINGGSN   240
SGDGSALEGN LDTQYCGALA APNPSEYLAH APEGSDGSSF NDAMLAFGNY LNANSNPPSA   300
VSTSYGGEED GTDPNYMDRI CNEFMKAGSR GVSIFFSSGD NGVGGNGESS CYNGYYPLWP   360
ASCPYVTTVG GTEFDGSGRE VVANFEQYNK NVKSPGGGFS NHFPAPSYNK NVTTAYANSL   420
SAAQKQRLNP NGRGFPDIAL VSVKYQVNVN GQISQVLGTS ASSPSMAGLV GLLNDYRKTQ   480
GKPNLGFINP LLYSDKVKPA LRDVTSGANK GCDSSGLPAK TGWDAASGLG SFDFAKLRTL   540
V                                                                   541

SEQ ID NO: 18           moltype = AA  length = 633
FEATURE                 Location/Qualifiers
source                  1..633
                        mol_type = protein
                        organism = Talaromyces proteolyticus
SEQUENCE: 18
VPAPSKRHVV HERRDALPHS WSEPRRVDGR TQLPVRIGLT QSNIDESHDM LMDIASPSSP    60
NYRKYMTVHE VNELFAPAGE AVSAVRDWLE SAGIAAERVT QSANKQWLQF DGDAAEVESL   120
LGAEYYIYTH DTNGRSHMGC EKYHVPEHIS HHIDYIIPGV KSLEVREPQP AELEKRTFGF   180
RKPQPPLFKA LPESLETIIN SILGGLLDLC STVITPSCIK TLYNITEGTT ATKGNELGIF   240
EDLGDYYSQT DLDLFFTLFY SQIPAGTGPT LKGIDGAQAP TQTLTQAGPE SDLDFQVSYP   300
IIWPQNSILF QTDDANYEAN YTFNGFLNNF LDAIDGSYCT YSAFGIDGNT ADDPYPDPA    360
SNGYKGSLQC GVYEPTNVIS ISYGGDEAGL SVNYQKRQCN EYKKLGLQGV SVVVSSGDSG   420
VAGADGCLGG GKIFNPDFPA GCPYITTVGA TYLPSGASST SDSEVAVSRF PSGGGFSNIY   480
SQPSYQSDAV NTYLTQHTPP YPAYETSDNS SVGANGGIYN KAGRGYPDVA AVGDNIVIFN   540
AGAPTLIGGT SASAPIFASI LTRINEVLLA KKGTTVGFVN PTLYANPDAF HDITSGDNPG   600
CSTNGFSTAP GWDPVTGLGT PNYPALLKVF LGE                                 633

SEQ ID NO: 19           moltype = AA  length = 371
FEATURE                 Location/Qualifiers
source                  1..371
                        mol_type = protein
                        organism = Penicillium ranomafanaense
SEQUENCE: 19
VPTGGKKSFT VNQVAVSATK TQNFANNYAR ALAKYGAKVP THVQAAAQQS GSATTTPESD    60
DEEYLTPVNV GGTTLNLDFD TGSADLWVFS SELPASEQTG HSLYKPNNGT KLSGYTWSIS   120
YGDGSSASGD VYRDTVSVGG VKATGQAVEA ASTISQQFTQ DQNNDGLLGL AFSSINTVKP   180
KSQTTFFDTV KSTLASPLFA VSLKHNAPGS YDFGFIDKSK YTGSLTYTDV DSSQGFWGFT   240
ADSYKIGSTT GSSIKGIADT GTTLLLLDDE VVSAYYKQVS GAASDSSAGG YTFDCSSTLP   300
DFTVSISGYD AVVPGSLINY TPVSQGSSKC LGGIQSNSGL GFSIFGDIFL KSQYVVFDSN   360
GPRLGFAAQS S                                                         371

SEQ ID NO: 20           moltype = AA  length = 578
FEATURE                 Location/Qualifiers
source                  1..578
                        mol_type = protein
                        organism = Aspergillus oryzae
SEQUENCE: 20
EAFEKLSAVP KGWHYSSTPK GNTEVCLKIA LAQKDAAGFE KTVLEMSDPD HPSYGQHFTT    60
HDEMKRMLLP RDDTVDAVRQ WLENGGVTDF TQDADWINFC TTVDTANKLL NAQFKWYVSD   120
VKHIRRLRTL QYDVPESVTP HINTIQPTTR FGKISPKKAV THSKPSQLDV TALAAAVVAK   180
NISHCDSIIT PTCLKELYNI GDYQADANSG SKIAFASYLE EYARYADLEN FENYLAPWAK   240
GQNFSVTTFN GGLNDQNSSS DSGEANLDLQ YILGVSAPLP VTEFSTGRRG PLVPDLTQPD   300
PNSNSNEPYL EFFQNVLKLD QKDLPQVIST SYGENEQEIP EKYARTVCNL IAQLGSRGVS   360
VLFSSGDSGV GEGCMTNDGT NRTHFPPQFP AACPWVTSVG ATFKTTPERG TYFSSGGFSD   420
YWPRPEWQDE AVSSSYLETIG DTFKGLYNSS GRAFPDVAAQ GMNFAVYDKG TLGEFDGTSA   480
SAPAFSAVIA LLNDARLRAG KPTLGFLNPW LYKTGRQGLQ DITLGASIGC TGRARFGGAP   540
```

```
DGGPVVPYAS WNATQGWDPV TGLGTPDFAE LKKLALGN                              578

SEQ ID NO: 21              moltype = AA  length = 456
FEATURE                    Location/Qualifiers
source                     1..456
                           mol_type = protein
                           organism = Talaromyces liani
SEQUENCE: 21
APASTTKDNV SSVVKNGVTY TVFEHAATGA KMEFVKNSGI CETTPGVNQY SGYLSVGNNM       60
NMWFWFFEAR NNPQTAPLAA WFNGGPGCSS MIGLFQENGP CHFVNGASTP SLNEYSWNNY      120
ANMLYVDQPI GVGFSYGTDD VTSTVTAAPY VWKLLQAFYA QFPEYQSRDF AIFTESYGGH      180
YGPEFAAYIQ EQNSGIAAGS VSGENINLIA LGVNNGWIDP AIQEKAYIDF SYNNSYQQLI      240
DDSQRTNLLS DYNDQCLPAI QQCAQTGRNS DCQNADNVCY DTIEGPISSS GNWDVYDIRE      300
PSNDPYPPST YSSYLSNSRV VKAIGAQTSY QECPNGPYNK FASTGDNPRS FLSTLSSVVQ      360
SGIHVLVWAG DADWICNWLG NYRVANAVDF PGHAEFSAKA LAPYTVNGTE KGMFKNVDNF      420
SFLKVYGAGH EVPYYQPATA LQVFEQILQN KSITST                                456

SEQ ID NO: 22              moltype = AA  length = 589
FEATURE                    Location/Qualifiers
source                     1..589
                           mol_type = protein
                           organism = Thermoascus thermophilus
SEQUENCE: 22
EVFERLRAVP EGWRFSATPS DDQPIRLQIA LQQHDVEGFE RAVLDMSTPS SPNYGKHFQS       60
HDEMKRMLLP SDDAVDAVLD WLQSAGITDI EEDADWINFR TTVGVANELL DTQFQWFVSE      120
TSSHVRRLRA LEYSIPESVT PHIHMVQPTT RFGQIGRHHT TSREKPIVSG ADIHASIAGA      180
NNQTTGTDCN TEITPKCLQD LYKFGGYKAS ANSGSKVGFC SYLEEYARYD DLALFEEALA      240
PYAAGQNFSV ITYNGGLNDQ HSSSDSGEAN LDLQYIVGVS APLPVTEFST GGRGELVPDL      300
DQPNPADNSN EPYLDFLQNV LKLDQKDLPQ VISTSYGENE QSVPEKYARS VCNLFMQLGS      360
RGVSVIFSSG DSGVGSACLT NDGKNQTRFM PQFPASCPWV TSVGSTQHIA PEEATYFSSG      420
GFSDLWPMPD YQKSAVGEYL DRLGSKWAGL YNPQGRGFPD VAAQGVNFNV YDKGSLKRFD      480
GTSCSAPTFA GVIALLNDAR LRARQPPMGF LNPWLYGAGK GGLNDIVNGG STGCDGNARF      540
GGAPNGSPVV PFASWNATQG WDPVSGLGTP DFSRLLKLAV PSRVGGRLA                  589

SEQ ID NO: 23              moltype = AA  length = 413
FEATURE                    Location/Qualifiers
source                     1..413
                           mol_type = protein
                           organism = Pyrococcus furiosus
SEQUENCE: 23
AELEGLDESA AQVMATYVWN LGYDGSGITI GIIDTGIDAS HPDLQGKVIG WVDFVNGRSY       60
PYDDHGHGTH VASIAAGTGA ASNGKYKGMA PGAKLAGIKV LGADGSGSIS TIIKGVEWAV      120
DNKDKYGIKV INLSLGSSQS SDGTDALSQA VNAAWDAGLV VVVAAGNSGP NKYTIGSPAA      180
ASKVITVGAV DKYDVITSFS SRGPTADGRL KPEVVAPGNW IIAARASGTS MGQPINDYYT      240
AAPGTSMATP HVAGIAALLL QAHPSWTPDK VKTALIETAD IVKPDEIADI AYGAGRVNAY      300
KAINYDNYAK LVFTGYVANK GSQTHQFVIS GASFVTATLY WDNANSDLDL YLYDPNGNQV      360
DYSYTAYYDF EKVGYYNPTD GTWTIKVVSY SGSANYQVDS VSDGSLSQPG SSP             413

SEQ ID NO: 24              moltype = AA  length = 387
FEATURE                    Location/Qualifiers
source                     1..387
                           mol_type = protein
                           organism = Trichoderma reesei
SEQUENCE: 24
LPTEGQKTAS VEVQYNKNYV PHGPTALFKA KRKYGAPISD NLKSLVAARQ AKQALAKRQT       60
GSAPNHPSDS ADSEYITSVS IGTPAQVLPL DFDTGSSDLW VFSSETPKSS ATGHAIYTPS      120
KSSTSKKVSG ASWSISYGDG SSSSGDVYTD KVTIGGFSVN TQGVESATRV STEFVQDTVI      180
SGLVGLAFDS GNQVRPHPQK TWFSNAASSL AEPLFTADLR HGQNGSYNFG YIDTSVAKGP      240
VAYTPVDNSQ GFWEFTASGY SVGGGKLNRN SIDGIADTGT TLLLLLDDNVV DAYYANVQSA      300
QYDNQQEGVV FDCDEDLPSF SFGVGSSTIT IPGDLLNLTP LEEGSSTCFG GLQSSSGIGI      360
NIFGDVALKA ALVVFDLGNE RLGWAQK                                          387

SEQ ID NO: 25              moltype = AA  length = 408
FEATURE                    Location/Qualifiers
source                     1..408
                           mol_type = protein
                           organism = Rhizomucor miehei
SEQUENCE: 25
RPVSKQSESK DKLLALPLTS VSRKFSQTKF GQQQLAEKLA GLKPFSEAAA DGSVDTPGYY       60
DFDLEEYAIP VSIGTPGQDF LLLFDTGSSD TWVPHKGCTK SEGCVGSRFF DPSASSTFKA      120
TNYNLNITYG TGGANGLYFE DSIAIGDITV TKQILAYVDN VRGPTAEQSP NADIFLDGLF      180
GAAYPDNTAM EAEYGSTYNT VHVNLYKQGL ISSPLFSVYM NTNSGTGEVV FGGVNNTLLG      240
GDIAYTDVMS RYGGYYFWDA PVTGITVDGS AAVRFSRPQA FTIDTGTNFF IMPSSAASKI      300
VKAALPDATE TQQGWVVPCA SYQNSKSTIS IVMQKSGSSS DTIEISVPVS KMLLPVDQSN      360
ETCMFIILPD GGNQYIVGNL FLRFFVNVYD FGNNRIGFAP LASAYENE                   408

SEQ ID NO: 26              moltype = AA  length = 548
FEATURE                    Location/Qualifiers
source                     1..548
```

```
                        mol_type = protein
                        organism = Lenzites betulinus
SEQUENCE: 26
KPMGRNLKVH EAREEIPDGF SLQGSAAPDT TLKLRIALVQ SNFAELEQKL YDVSTPSSPN    60
YGAHLSKEEV EQLVAPSADS VDAVNAWLKE NDLSAQTISP AGDWLAFEVP VSKANELFDA   120
DFSVFTHDQT GLEAIRTMSY SIPAELQGHL DLVHPTVTFP NPYSHLPVVR SPIKASQNLT   180
SRATIPASCA STITPACLQD IYGIPTTKAT QSSNKLAVSG FIDQFANSAD LATFLKKFRT   240
DISSTTTFAL QTLDGGSNSQ SGSQAGVEAN LDIQYTVGLA SGVPVTFISV GDNFQDGDLE   300
GFLDIINFLL AESAPPQVLT TSYGQNENTI SVKLANQLCN AYAQLGARGT SILFASGDGG   360
VSGSQSSSCS KFVPTFPSGC PFMTSVGATQ GVNPETAADF SSGGFSNYFG IPSYQATAVK   420
TYLTALGTTN SGKFNTSGRA FPDVSTQGVD FEIVVDGRTE GVDGTSCASP TFAAIISLVN   480
DKLIAAGKSP LGFLNPFLYS TGASAFTDIT SGSNPGCNTK GFPAKAGWDP VTGLGTPNFA   540
KLLAAAGV                                                           548

SEQ ID NO: 27           moltype = AA  length = 547
FEATURE                 Location/Qualifiers
source                  1..547
                        mol_type = protein
                        organism = Neolentinus lepideus
SEQUENCE: 27
GPAPRNLVLH ESRDGVPEGF VKSSTASPDT TLKLRIALVQ GDMASLEKAL YDVSVPSSPL    60
YGQHLSKQEV EEYVKPTQES VDAVNQWLSS EGITANTISP AGDWLQFSVP VSKANEMFDA   120
DFSVFTHTES GQQAIRTLSY SIPKELVGHL DLVHPTITFP NPYSHLPVVS SPAPRNLTID   180
ASVPSSCGST ITPTCLQDLY GIPTTAATQS SNKLAVSGFI DQYANKADLK SFLTTYRKDI   240
SSSTTFTLET IDGGENPQDG SDAGVEANLD TQYTVGLATG VPTYFISVGD DYQDGDLEGF   300
LDIVNYLLSM DQPQQVLTTS YGQNENTMSR SLANNLCNAY MQLGARGTSI LFASGDGGVS   360
GSQSGSCGSK FVPTFPSGCP YLTSVGATTG INPEVAASFS SGGFSNYWGV PSYQQSVVSS   420
YISGLGSTNK GKYNSSGRGF PDVSAQGENV EIVVDGSTEG VDGTSCSSPI FASIVSLLND   480
ELIAAGKSPL GFLNPFLYSD GASAFNDITS GDNPGCNTNG FSAKSGWDPV TGLGTPNYAK   540
LRTAVGF                                                            547

SEQ ID NO: 28           moltype = AA  length = 399
FEATURE                 Location/Qualifiers
source                  1..399
                        mol_type = protein
                        organism = Thermococcus sp.
SEQUENCE: 28
VSAEKVRVII TIDKDFNENS VFALGGNVVA RGKVFPIVIA ELSPRAVERL KNAKGVVRVE    60
YDAEVQVLKG KSPGAGKPKP SQPAQTIPWG IERIKAPDVW SITDGSSSGV IEVAILDTGI   120
DYDHPDLAAN LAWGVSVLRG KVSTKPKDYK DQNGHGTHVA GTVAALNNDI GVVGAPAVE    180
IYAVRVLDAS GRGSYSDIIL GIEQALLGPD GVLDSDGDGI IVGDPDDDAA EVISMSLGGL   240
SDVQAFHDAI IEAYNYGVVI VAASGNEGAS SPSYPAAYPE VIAVGATDVN DQVPWWSNRG   300
VEVSAPGVDV LSTYPDDSYE TLSGTSMATP HVSGVVALIQ AAYYNKYGSV LPVGTFDDNT   360
MSTVRGILHI TADDLGSSGW DADYGYGIVR ADLAVQAVN                          399

SEQ ID NO: 29           moltype = AA  length = 396
FEATURE                 Location/Qualifiers
source                  1..396
                        mol_type = protein
                        organism = Thermococcus sp.
SEQUENCE: 29
EKVRVIITID KDFNENSVFA LGGNVVARGK VFPIVIAELS PRAVERLKNA KGVVRVEYDA    60
EVQVLKGKSP GAGKPKPSQP AQTIPWGIER IKAPDVWSIT DGSSSGVIEV AILDTGIDYD   120
HPDLAANLAW GVSVLRGKVS TKPKDYKDQN GHGTHVAGTV AALNNDIGVV GVAPAVEIYA   180
VRVLDASGRG SYSDIILGIE QALLGPDGVL DSDGDGIIVG DPDDDAAEVI SMSLGGLSDV   240
QAFHDAIIEA YNYGVVIVAA SGNEGASSPS YPAAYPEVIA VGATDVNDQV PWWSNRGVEV   300
SAPGVDVLST YPDDSYETLS GTSMATPHVS GVVALIQAAY YNKYGSVLPV GTFDDNTMST   360
VRGILHITAD DLGSSGWDAD YGYGIVRADL AVQAVN                             396

SEQ ID NO: 30           moltype = AA  length = 572
FEATURE                 Location/Qualifiers
source                  1..572
                        mol_type = protein
                        organism = Thermomyces lanuginosus
SEQUENCE: 30
APFQVVERLS APPDGWIKKE KAAPSAQIQF RLGLPQQNSE QLEQLALNIA TPGHELYRKH    60
LKRDEIKALV RPLASVSEKV LAWLRDEGVP EDRIHDDGAW IKFTVPVSTA EKLLNTEFFV   120
PHNERTGAEQ IRTLEYSVPQ DIHSLVKFIQ PTTHFSSLQP QVRRVVPLDV LPKLRITLED   180
CNKKITPDCL KQLYKIGDYV APEDPRNRIG ISGYLEQFAR YADFEEFLES YAPDRTDANF   240
TVVSINGGRN DQNSTLDSTE ASLDIDYAVT LSYKTQAVYY TTAGRGPLVP DESQPDPNEV   300
SNEPYMEQLQ FLLDLPDEEL PTVLTTSYGE NEQSLPGSYA DETCNMFRLL GMRGVSIFS    360
SGDWGTGIVC KANDGSERIK FDPVYPASCP YVTSVGGTTG VNPERAVEFS SGGFSDRFPR   420
PKYQDEAVRS YLTKLGDHWK GLYNESGRAF PDVAAQADNF VVRDQGQWVS VGGTSASAPV   480
FAAIIANVNA ELLKAGKPPL GFLNPWLYGL KGRGFTDVVH GGSTGCPGTV PWTGLPAGHV   540
PYASWNATEG WDPVTGLGTP LYDELVKAAL GK                                 572

SEQ ID NO: 31           moltype = AA  length = 397
FEATURE                 Location/Qualifiers
source                  1..397
```

```
                         mol_type = protein
                         organism = Thermococcus thioreducens
SEQUENCE: 31
EKPELVRVIV HVDRGHFNTA DVATIGGHVV YQFKLIDAVV VEVPSTAVGR LKKLPGVKMV    60
EFDHKARILA GPPSWLGGGQ PSQQIPWGIS RVRAPDVWGI TDGSGGVIEV AVLDTGVDYD   120
HPDLAGNIAW CVSTLRGRVT TNPAQCKDQN GHGTHVIGTI AALNNDIGVV GVAPGVEIYS   180
IRVLDASGSG SYSDIAIGIE QALLGPDGIL DKDGDGIIVG DPDDDAAEVI SMSLGGPTDD   240
QYLHDMIITA YNYGVVIVAA SGNEGASSPS YPAAYPEVIA VGASDVNDQI ASWSNRQPEV   300
SAPGVDILST YPDDTYETLS GTSMATPHVS GVVALIQAAY YNKYGKVLPV GTFDDMGTNT   360
VRGILHVTAD DLGDAGWDIY YGYGIVRADL AVQAAIG                            397

SEQ ID NO: 32            moltype = AA   length = 549
FEATURE                  Location/Qualifiers
source                   1..549
                         mol_type = protein
                         organism = Polyporus arcularius
SEQUENCE: 32
KPMARSMKLH ESREGIPEGF SLRGAAQPEQ TIKLRLALVQ SNFAELERKL MDVSTPSSAN    60
YGKHLSKAEV QQLVAPTQDS VDAVKSWLKE NDISAKTISA TGDWLSFEVP VSKANELFDA   120
DFSIYTHDET GTEAVRTLSY SIPAELQGHL DLVHPTVTFP NPRGLPPVFT APIKAEAQNL   180
TSRATIPSSC ARTITPACLQ AIYNIPSTPA TESSNKLAVT GFIEQFANKA DLKTFLTRFR   240
TDISSSTSFT LQTLDGGSNP QSSSEAGVEA NLDIQYTVGV ATGVPTVFIS VGEDFQDGDL   300
EGFLDVVNSL LDEDTPPFVM TTSYGQNENT ISRNLANNLC NAYAQLGARG VSILFASGDG   360
GVAGSQSASC SKFVPTFPSG CPFMTSVGAT QGFSPETAAD FSSGGFSNYF AIPDYQTSAV   420
SGYIKALGNT NSGKYNATGR GFPDIATQGV NFEVVGGQS GTVEGTSCSS PTLASIISLL    480
NDRLIAAGKS PLGFLNPFLY STGTSALNDI TSGSNPGCNT NGFPAKAGWD PVTGLGTPDF   540
NKLLSAVGL                                                           549

SEQ ID NO: 33            moltype = AA   length = 548
FEATURE                  Location/Qualifiers
source                   1..548
                         mol_type = protein
                         organism = Ganoderma lucidum
SEQUENCE: 33
KSTTRNLKLH ETRQGAPSGF SHTGSADPNQ TLKLRLALVQ GNTAELERKL YDVSTPSSAN    60
YGKHLSKEEV RQLVAPAQGS VDAVNAWLRE NGITAKSTSA AGDWLSFEVP VSKANELFDA   120
DFSVFKHDDT GVKAVRTLSY SIPAELQGHL DLVHPTVTFP NPNGHMPVFQ APVKDTDAVQ   180
NFSARAVPSS CSNTITPACL QALYNIPSDA ATQSSNKLAV TGFIEQYANQ VDLAVFLKQY   240
RADISSNTTF ALQTLDGGSN SQTNVPGVEA NLDIQYTVGI ATGVPTVFIS VGDQYQDGDL   300
EGFLDVINFL LDEDTPPYVV TTSYGQDEHT ISRKLAQNLC NAYAQLGARG VSILFASGDG   360
GVAGSRSNSC SKFVPTFPSG CPYMTSVGAT QGVPETAADF SSGGFSNYFG TPDYQASAVK   420
SYLSTLGSTN RGKFNASGRG FPDVATQGVN FEVIVDGEVE GVSGTSAASP MFAAIVALLN   480
DKLIAAGKSP LGFLNPFLYS KGVEALNDIT TGSNPGCGTI GFPAKEGWDP VTGLGTPDFQ   540
KLASAAGL                                                            548

SEQ ID NO: 34            moltype = AA   length = 548
FEATURE                  Location/Qualifiers
source                   1..548
                         mol_type = protein
                         organism = Ganoderma lucidum
SEQUENCE: 34
KTATRNLKLH ETSQGAPSGF SLTGSADPDQ TLKLRLALVQ GNVAELERRL YDVSTPSSPN    60
YGKHLSKSEV QQLVAPAQDS IDAINAWLKE NGISAKTTSA TGDWLSFEVP VSKANELFDA   120
DFSVYKHHDT GMEVVRTLSY SIPAELQAHL DLVHPTVTFP NPKGHPPVFQ APAMITNDVQ   180
NFSAGAVPSS CSSRITPACL QALYNIPSDP ATQPSNKLAV TGYIEQYANQ DDLAVFLKEY   240
RADMSSNTTF TLQTLDGGVN SQTDEAGIEA NLDVQYTVGI ATGVPTVFIS VGDQYQDGNL   300
EGFLDVVNFL LDEDTPPYVM TTSYGQDEHT MSRKLAQNLC NAYAQLGARG VSILFASGDG   360
GVAGSRSSSC SKFVPTFPSG CPYMTSVGAT QGVPETAADF SSGGFSNYFG IPDYQASAVS   420
GYLSALGHTN KGKYNASGRG FPDVSTQGVN FEVMVDGALE GVSGTSAASP TFAAVVALLN   480
DRLIAAGKSP LGFLNPFLYS KGVSALNDIT SGSNPGCRTN GFPAKEGWDP VTGLGTPDFQ   540
KLASAAGL                                                            548

SEQ ID NO: 35            moltype = AA   length = 541
FEATURE                  Location/Qualifiers
source                   1..541
                         mol_type = protein
                         organism = Ganoderma lucidum
SEQUENCE: 35
KPTARNLRLH ETRQGAPSGF SLTGSADPNQ TVRLRLALVQ GNTGELERKL YDVSTPSSAN    60
YGKHLSKAEV QQLVAPAQGS IDAVNAWLKE NDITAKTISA TGDWLSFEVP VNKANELFDA   120
DFSVFKHDDT GMEAVRTLSY SIPAELQGHL DLVHPTVTFP NPKGNLPLFQ TPIKSKRDVP   180
ADCSNNITPA CLQALYNIPS DAATQSSNTL AVTGYIEQYA NQQDLTSFLG QFRPDISSNT   240
TFALQTIDGG SNSQNGSDAG EANLDIQYT VGLATGVPTV FISVGEQYQD GDLGGLLDVI   300
NFVLAEDAPP NVITTSYGQN ENTISLKLAQ NLCNAYAQLG ARGVSILFAS GDGGVAGSQS   360
DNCTQFVPTF PSGCPYMTSV GATQGVPETA ADFSTGGFSN LFSVPDYQAA AVQSYLSALG   420
GTYQGLFNAS GRAFPDVSTQ GVNFETVVDG SVSGASGTSA ASPTFAAIVA LLNDRLVAAG   480
KSPLGFLNPF LYSTGASALN DIATGSNPGC GTNGFSAQKG WDPVTGLGTP DFQKLAAAAG   540
L                                                                   541
```

```
SEQ ID NO: 36           moltype = AA  length = 547
FEATURE                 Location/Qualifiers
source                  1..547
                        mol_type = protein
                        organism = Trametes sp.
SEQUENCE: 36
TPTGRNLKLH EAREDIPTGY SLRGAASPDT TLKLRLALVQ NNFAELEDKL YDVSTPSSAN    60
YGNHLSKEEV EQYIAPAPES VKAVNAWLTE NGLDAHTISP AGDWLAFEVP VSKANELFDA   120
DFSVFTHDES GLEAIRTLAY SIPAELQGHL DLVHPTVTFP NPNAHLPVVR STKPIQNLTG   180
RAIPASCAST ITPACLQAIY GIPTTKATQS SNKLAVSGFI DQFANSADLK SFLSTFRKDI   240
SSSTTFALQT LDGGQNNQSP SQAGIEANLD IQYTVGLATG VPVTFISVGD NFQDGDLEGF   300
LDIINFLLSE SNPPQVLTTS YGQNENTISA KLANQLCNAY AQLGARGTSI LFASGDGGVA   360
GSQSSSCRNF VPTFPSGCPF MTSVGATQGV SPETAADFSS GGFSNVFGIP SYQTSAVSGY   420
LSALGNTNSG KFNRSGRGFP DVATQGVNFQ IVSGGDTGGV DGTSCASPTF ASVISLINDR   480
LIAAGKSPLG FLNPFLYSAA GKAALNDVTS GSNPGCNTNG FPAKAGWDPV TGLGTPNFAK   540
LLTAVGL                                                            547

SEQ ID NO: 37           moltype = AA  length = 553
FEATURE                 Location/Qualifiers
source                  1..553
                        mol_type = protein
                        organism = Cinereomyces lindbladii
SEQUENCE: 37
KPTARNLLVH ESLDGVPTGF QLVGPASPDT VLSMRIALVQ SDPAGLEAAL YDVSTPSSAS    60
YGNHLSKAEV EKFVSPTSES VQAVNAWLTE NDLTATQLSP AGDWLGFEVP VSKAEDLFGT   120
QFSVFTHEAT GMQTVRTLSY SIPSELQGHL DLVFPTINPR DPNALPVFR HASKKREVTT    180
LNANLTSDAV PSSCADTITP ACLQALYGIP TTPATSSTNQ LGVSGFIDQF ANQADLKTFL   240
QNFRTDISSS TTFSLETLDG GSNSQNRGDA GVEANLDTQY TVGLATDVPT VFISVGEDNQ   300
DGSLGGFLDI INFLLDQDSP PQVLTTSYGQ NENTVSRAVA NNLCNAYAQL GARGTSILFA   360
SGDGGVSGSQ SASCRTFVPT FPSGCPFMTS VGATTGINPE TAATFSAGGF SNYFGTPSYQ   420
ASAVSSYLAA LGSTNSGKFN TSGRGYPDVS TQGENFEIVV SGEEEGVDGT SCASPTFASI   480
ISLVNDRLIA AGKPPLGFLN PFLYSTGASA FTDITTGDNP GCNTNGFPAK SGWDPVTGLG   540
TPNFSKLLTA VGL                                                    553

SEQ ID NO: 38           moltype = AA  length = 559
FEATURE                 Location/Qualifiers
source                  1..559
                        mol_type = protein
                        organism = Trametes versicolor
SEQUENCE: 38
AVASTLQLHE ARKGIPAGFS LHGAASPDTV LNLRMALVQS NFAGLEERLY DVSTPSSANY    60
GKHLSKAEVE QYVAPRQQSI TAVKAWLAAN GLSGTSISPA GDWIAAKVPV SKANKLLGAQ   120
FSVFNNDATG RQIIRTLAYS IPAELKGHLD LVHPTIFFAD IKPLVPVVSA RRESRVLVDS   180
DLVANTIPAS CNAAITPACL QDLYGIPSTP ATQSSNQLGV SGFIDQFANQ ADLATFLTEF   240
RPDVSNSTTF TLQTLDGGQN PQDPSDAGVE ANLDTQYTVG VATNVPTTFF SVGDDTKDGI   300
FGFLDLISFL LAAAAPPQVL TTSYGADEGG LSANLVRNLC QAYAQLGARG TSILFSSGDG   360
GVSGSQAEGC VDFVPTFPSG CPFLTSVGAT QLTTASGLTV ETAAGFSSGG FSNYFPTPPY   420
QQAVVDAYIK KTLVNGTVNE GLFNASGRAF PDVSAVGVDY LIVVGGGTDI VSGTSASSPL   480
FASVIALIND RRLAAGKPPL GFLNPFLYSQ AGASALNDVT VGSNPGCASP GFPAAQGWDP   540
VTGLGTPNFA KLLAAALAL                                              559

SEQ ID NO: 39           moltype = AA  length = 541
FEATURE                 Location/Qualifiers
source                  1..541
                        mol_type = protein
                        organism = Paecilomyces hepialid
SEQUENCE: 39
APAPHGPLVK FGEIRKLPSK WVATGAADAN AVIKGQIGIK QNNIQGLQAK LADIADPNSP    60
NYGQWLSKEE VDKYSAPAAA DVAAKAWLA SSGITDVTMP TNDWIEFSVP VSKMESLLGS    120
KYEWFVHLET GEKVPRTKEF SVPQNLHDLI DVVTPTTVLY HNINPHTHSS PQAAGAAGLT   180
SPASIKSAYN VDYKGTGNTL VGTTGFLGVG ASHTDYANFG QQFSPGLKDF QDVSNGGSN    240
SGDGSALEGN LDTQYCGALA APNPSEYLAH APEGSDNNSF NDAMLAFGNY LNSARNPPSA   300
VSTSYGGEED GVDASYLDRI CNEFMKAGSR GVSIFFSSGD NGVGGNGESS CQNGYYPLWP   360
ATCPYVTTVG GTEFDNSGRE VVANFEQYNK NIKSPGGGYS NHFAAPSYNK AVTTSYANGL   420
AAPQKQRLNP NGRGYPDISL VSVKYQVNVN NQISQVLGTS ASSPSIAGLV GLLNDYRKTQ   480
GKPNLGFINP LLYSDKVKPA LRDVTSGSNK GCDSVGLPAK TGWDAASGLG SFDFGKLRTL   540
V                                                                 541

SEQ ID NO: 40           moltype = AA  length = 541
FEATURE                 Location/Qualifiers
source                  1..541
                        mol_type = protein
                        organism = Isaria tenuipes
SEQUENCE: 40
APAPHGPLVK FGELKKLPSQ WVATGAANGD AVIKAQIGIK QNNIKGLQDK LAEISDPNSP    60
SYGQWLSKEE VAKYTAPADA DVAAKAWLS SAGITEVTMP TNDWLEFSVP VSKMESLLGS    120
KYEWFVHLET GEKAPRTKEF SVPQNLHGII DVVTPTTVLY HNINPNSHGN ELSASASGLT   180
SPASIKSAYN VDYKGTGNTL VATTGFLGVG ASHNDYLAFG HQFSPGLKDF QDVSNGGSN    240
SGDGSALEGN LDTQYCGALA SPNPSQYLAN SPEGSDNNSF NDAMTAFGNY LNSASNPPSA   300
```

```
VSTSYGGEED GVDAGYLDRI CNEFMKAGSR GISVFFSSGD NGVGGNGEPS CQNGYYPLWP   360
ATCPYVTTVG GTEFDDSGRE VVANFEQYNK NVKSPGGGYS NHFPAPDYNK NVTTAYANSL   420
SAAQQQRLNP NGRGFPDISL VSVKYQVSLN GQTKQVLGTS ASSPSVAGLV GLLNDYRKTQ   480
GKSNLGFLNP LLYSGKVNAA LRDVTSGSNK GCDSVGLPAK SGWDAASGLG SFDFAKLRSL   540
I                                                                  541

SEQ ID NO: 41            moltype = AA  length = 578
FEATURE                  Location/Qualifiers
source                   1..578
                         mol_type = protein
                         organism = Aspergillus tamarii
SEQUENCE: 41
EAFEKLSAVP KGWHYSSTPE GSTSVCLKIA LAQKDAAGFE KRVYEMSDPD HPNYGQHFTT   60
HEEMKRMLLP RDDTVDAVRQ WLENGGVTDV RQDSDWINFC TTVDTANKLL NAQFKWYVSD   120
VKHIRRLRTL QYDVPGSVAS HVNTIQPTTR FGKITPKKAV THSKPSQLDV TALAAAVVAK   180
NISHCDSIIT PTCLKELYNI GDYQADANSG SKIAFASYLE EYARYADLEN FENYLAPWAK   240
GQNFSVITYN GGLNDQNSSS DSGEANLDLQ YILGVSAPLP VTEFSTGGRG PLVPDLTQPD   300
PNANSNEPYL EFFQNVLKLD QEQLPQVIST SYGENEQEIP EKYARTVCNL IAQLGSRGVS   360
VLFSSGDSGV GEGCMTNDGT NRTHPPPQFP AACPWVTSVG ATYKTTPERA TYFSSGGFSD   420
YWARPEWQEE AVSSYLETIG DAFKGLYNAS GRAFPDVAAQ GMNFAVYDKG TLGEFDGTSA   480
SAPAFSAIIA LLNDARLRAG KPTLGFLNPW LYKTGRQGLQ DITLGASTGC TGRARFGGAP   540
DGGPVVPFAS WNATQGWDPV TGLGTPDFAE LKKLALAN                          578

SEQ ID NO: 42            moltype = AA  length = 587
FEATURE                  Location/Qualifiers
source                   1..587
                         mol_type = protein
                         organism = Aspergillus brasiliensis
SEQUENCE: 42
EIFEKLSGVP NGWRYANNPQ GNEVIRLQIA LQQHDVTGFE QAVMDMSTPG HADYGKHFRT   60
HEEMKRMLLP SDTAVDSVRD WLESAGVHNI QVDADWIKFH TTVTKANALL DADFKWYVSE   120
ARHIRRLRTL QYSIPDALVS HINMIQPTTR FGQIQPNRAT MRSKPKHADE TFLTAATLAQ   180
NTSHCDSIIT PSCLKQLYNI GDYQADPKSG SKIGFASYLE EYARYADLEK FEQHLAPNAI   240
GQNFTVVQFN GGLNDQLSTK DSGEANLDLQ YILGVSAPLP VTEYSTGGRG ELVPDLSSPD   300
PNDNSNEPYL DFLQNILKLN NSDLPQVIST SYGEDEQTIP VPYARAVCNL YAQLGSRGVS   360
VIFSSGDSGV GAACLTNDGT NRTHPPPQFP ASCPWVTSVG ATSKTSPEQA VSFSSGGFSD   420
LWPRPSYQHA AVQTYLTEHL GNKFSGLFNA SGRAFPDVSA QGVNYAVYDK GILGQFDGTS   480
CSAPTFSGVI ALLNDARLRA GLPVMGFLNP FLYGAGSKLG GLNDIVTGGS VGCDGRNRFG   540
GTPNGSPVVP FASWNATTGW DPVSGLGTPD FAKLKVVALG ESEGDEN                587

SEQ ID NO: 43            moltype = AA  length = 582
FEATURE                  Location/Qualifiers
source                   1..582
                         mol_type = protein
                         organism = Aspergillus iizukae
SEQUENCE: 43
EVFDTLAAVP KGWHYSHTPR ADQPISLKIA LKQHNVEGFE QAVLDMSTPG HEHYGKHFRE   60
HDEMKRMLLP SDATVDAVKD WLLAADVTDY EVDADWINLH TTVQQANELL DTEFAWYVSD   120
VRAVRRLRTL RYSVPDAVAP HINMVQPTTR FGQIHPDRAT FRAGSTHFGA HILSAMSAVG   180
DVSSANVTCD DVITPLCLKE LYKVDGYRAE AEHGSKIAFA SYLEEYARYD DMVRFQEKLA   240
PYAKGENFSV ILYNGGVDDQ QSTSDSGEAN LDLQTIMGLS APLPITEYIT GGRGKLIPDL   300
SQPDPNDNSN EPYLEWIQNV LKHSPEELPQ VISTSYGEDE QTIPRGYAES VCNLLAQLGS   360
RGVSVIFSSG DSGVGSACQT NDGTNTTHFP PQFPASCPWV TSVGATSKTH PEEAVYFSSG   420
GFSDLWARPA WQDDAVSTYI ESIGGKFAGL YNASGRAFPD VSAQGQNYAI FDKGRLGKMD   480
GTSCSAPAFA GIVSLLNDAR LRANRPVLGF LNPWLYGTAR EGLNDIVHGG SKGCDGRDRF   540
GGKPNGSPVV PYASWNATPG WDPVSGLGTP NFATLVQVAL HD                     582

SEQ ID NO: 44            moltype = AA  length = 456
FEATURE                  Location/Qualifiers
source                   1..456
                         mol_type = protein
                         organism = Penicillium sp.
SEQUENCE: 44
APASTAKDSV SSVVKNGVKY TVFEHAATGA KMEFVKNSGI CETTPGVNQY SGYLSVGSNM   60
NMWFWFFEAR NNPQQAPLAA WFNGGPGCSS MIGLFQENGP CHFVNGDSTP SLNEYSWNNY   120
ANMLYVDQPI GVGFSYGTDD VTSTVTAAPY VWKLLQAFYA QFPEYESRDF AIFTESYGGH   180
YGPEFASYIQ DQNAAIKAGS VSGENINLVA LGVNNGWIDS TIQEKAYIDF SYNNSYKQLI   240
DDSQRTSLLS AYNDQCLPAI QKCTSSGSNS DCKNADSVCY NQIEGPISSS GDWDVYDIRE   300
PSNDPYPPST YSTYLSNADV VKAIGAQSSY QECPNGPYNK FTSTGDNPRS FLSTLSSVVK   360
SGINVLVWAG DADWICNWLG NYEVANAVDF QSGHTDFSAKD LAPYTVNGTE KGLFKNVDNF   420
SFLRVYGAGH EVPYYQPDTA LQVFEQILQK KPIFST                             456

SEQ ID NO: 45            moltype = AA  length = 456
FEATURE                  Location/Qualifiers
source                   1..456
                         mol_type = protein
                         organism = Aspergillus denticulatus
SEQUENCE: 45
STASAAKDSV SSIVKNGVKY TVFEHAATGA KMEFVKNSGI CETTPGVNQY SGYLSVGDNM   60
```

```
NMWFWFFEAR NNPQQAPLAA WFNGGPGCSS MIGLFQEHGP CHFVNGEDTP SLNEYSWNNY    120
ANMLYVDQPI GVGFSYGTDD VTSTVTAAPY VWKLLQAFYA QFPEYESRDF AVFTESYGGH    180
YGPEFASYIQ QQNAAIKAGT VSGENINLIA LGVNNGWIDS AIQEKAYIDF SYNNTYKQLI    240
SSSDRTRLLS VYNSQCLPAI QKCTSTGTTA ACRNADSVCY NNIEGPISSS GDWDVYDIRE    300
PANDPYPPAT YSTYLADPDV VKAIGAQTSY QECPNGPYNK FASTGDNPRS FLSTLSNVVK    360
SGINVLVWAG DADWICNWLG NYEVANAVDY PGQSEFEAKD LAPYTVNGAE KGMFKNVDNF    420
SFLRVYGAGH EVPYYQPETA LQVFQQTLQK KPIFST                             456

SEQ ID NO: 46           moltype = AA  length = 456
FEATURE                 Location/Qualifiers
source                  1..456
                        mol_type = protein
                        organism = Hamigera sp.
SEQUENCE: 46
APASTAKDTL SSIVKNGVTY NVFEHADSGA KIEFVKNSGI CETTPGVNQY SGYLSVGDNM     60
NMWFWFFEAR NNPQKAPLAA WFNGGPGCSS MIGLFQENGP CHFVNGENTP SLNEYSWNNY    120
ANMLYVDQPI GVGFSYGTDD VDSTVTAAPY VWKLLQAFYA QFPEYESRDF AIFTESYGGH    180
YGPEFAHYIQ QQNAAIKSGS VKGENINLIG LGVNNGWIDS AIQEKAYIDF SYNNSYKQLI    240
DFSQRTSLMR AYKNQCLPAI QKCYQTGTNA DCTDASSVCY NNIEGPISSS GDWDVYDIRE    300
PSNDPYPPKT YSSYLSDPKV VKAIGARTNY KECPNGPYNK FSTTGDNPRS FLSTLSDVVK    360
SGINVILWAG DADWICNWLG GYGVANAVDY PGHAQFRAKA LAPYTVNGTE KGQFKTVDNF    420
QFLKVYGAGH EVPYYQPETA LQVFEQILQK KPIHST                             456

SEQ ID NO: 47           moltype = AA  length = 456
FEATURE                 Location/Qualifiers
source                  1..456
                        mol_type = protein
                        organism = Penicillium janthinellum
SEQUENCE: 47
APASTAKDTV SSVVKDGVTY TVFEHAATGA KMEFVKNSGI CETTPGVNQY SGYLSVGSNM     60
NMWFWFFEAR NNPQQAPLAA WFNGGPGCSS MIGLFQENGP CHFVNGESTP SLNENSWNNY    120
ANMIYIDQPI GVGFSYGTDR VTSTVTAAPY VWKLLQAFYA QFPEYESRDF AIFTESYGGH    180
YGPEFASYIE QQNAAIKAGS VTGQNVNIVA LGVNNGWIDA TIQEKAYIDF SYNNSYQQII    240
DSSTRDSLLD AYNNQCLPAL QQCAQSGSNS DCTNADSVCY QNIEGPISSS GDFDVYDIRE    300
PSNDPYPPKT YSTYLSDPTV VKAIGARTNY QECPNGPYNK FASTGDNPRS FLSTLSSVVQ    360
SGINVLVWAG DADWICNWLG NYAVANAVDF PGNAQFSAMD LAPYTVNGVE KGQFKTVDNF    420
SFLKVYGAGH EVPYYQPDTA LQVFKQILQK KPISST                             456

SEQ ID NO: 48           moltype = AA  length = 456
FEATURE                 Location/Qualifiers
source                  1..456
                        mol_type = protein
                        organism = Penicillium vasconiae
SEQUENCE: 48
APASTAKDSV SSVVKNGVKY TVFEHAATGA KMEFVKNSGI CETTPGVNQY SGYLSVGSNM     60
NMWFWFFEAR NNPQQAPLAA WFNGGPGCSS MIGLFQENGP CHFVNGDSTP SLNEYSWNNY    120
ANMLYVDQPI GVGFSYGTDD VTSTVTAAPY VWKLLQAFYA QFPEYESRDF AIFTESYGGH    180
YGPEFASYIQ EQNAAITAGS VSGQKINLIA LGVNNGWIDS TIQEKAYIDF SYNNSYQQLI    240
DDSQRTSLLS AYNKQCLPAI QKCTQTGSNS ACQNAANVCY NNIEGPISSS GDWDVYDIRE    300
PSNDPYPPST YSTYLANSDV VKAIGAQSSY QECPNGPYNK FASTGDNPRS FLSTLSSVVK    360
SGINVLVWAG DADWICNWLG NYEVANAVDF SGHAEFSAKD LAPYTVNGAE KGMFKNVDNF    420
SFLKVYGAGH EVPYYQPETA LQVFEQILQK KPISST                             456

SEQ ID NO: 49           moltype = AA  length = 454
FEATURE                 Location/Qualifiers
source                  1..454
                        mol_type = protein
                        organism = Hamigera paravellanea
SEQUENCE: 49
APSLRDKRSF VERDGVTYTV FEHAATGAKM EFVQNSGICE TTPGVNQYSG YLSVGDNMNM     60
WFWFFEARNN PTAAPLAAWF NGGPGCSSMI GLFQENGPCH FVNGESTPSL NEYSFNNYAN    120
VLYVDQPIGT GFSYGTDDVT STVTAAPYVW KLLQAFYAQF PEYESRDFGI FTESYGGHYG    180
PEFASYIQEQ NAAIKAGSVS GDNINLVALG INNGWFDAGI QEKAYIDFSY NNSYRQIISS    240
SQRSSYLDAY NHDCLPAIES CASSGTNSAC KNAESVCYNG IEGPISSAAD FDVYDVRQPS    300
NDPYPPATYS TYLQSASVRK AIGARTKYQE CPNGPYNKFE TTGDNSRSFL STLSDVVNTG    360
ITVLVWAGDA DWICNWVGGH AVADAVTFAR QKTFQAKPLE PYTVNGTEKG RFKTVDNFTF    420
LRVYEAGHEV PYYQPETALQ VFVQTMQKKA IFST                               454

SEQ ID NO: 50           moltype = AA  length = 453
FEATURE                 Location/Qualifiers
source                  1..453
                        mol_type = protein
                        organism = Talaromyces variabilis
SEQUENCE: 50
AAVPQDKRSI VKRDGVTYNV FEHAATGAKM EFVKNSGICE TTPGVNQYSG YLSVGDNMNM     60
WFWFFESRNN ASGAPLAAWF NGGPGCSSMI GLFQENGPCH FVNGEKKPSL NKYSFNEYAN    120
VLYVDQPIGV GFSYGTDDVT STESAAPYVW KLLQAFYAQF PQYESRDFGI FTESYGGHYG    180
PEFAHYLQQQ NEGVKNGSVD GENINLVALG INNGWFDTQL QEGAYIDAY SNNYKKIIDS     240
SQRSSLEDSL KSDCLPAVKQ CLSSGSDSDC ENASDTCGQI ESSIQQAADF DVYDVREPSN    300
```

```
DPYPPSTYSD YLADSSVVKA IGAKSTYKEC PNGPYYKFSS TGDNTRSFLS ELSSVVQSGI   360
QVLVWAGDAD WICNYMGVQR VADAVEFDGS SQFSNATLKP YTVNGTKKGE YKNVDNFSYL   420
RVYGAGHEVP YYQPAVALQV FKQTMQQQAI KST                               453

SEQ ID NO: 51           moltype = AA   length = 456
FEATURE                 Location/Qualifiers
source                  1..456
                        mol_type = protein
                        organism = Penicillium arenicola
SEQUENCE: 51
APATHLQDKR SIVERDGVNY TVFEHAATGA KLEFVTNSGI CETTSGVNQY SGYLSVGTNM    60
NMWFWFFESR NSPSTAPLAA WFNGGPGCSS MIGLFQENGP CQFYDGASTP SLNPYSFNEY   120
ANMIYIDQPI GVGFSYGTDD VTSTVTAAPY VWKLIQAFYA SFPAYESREF GLFTESYGGH   180
YGPEFAYYIQ QQNAAIASGT VTGDTIDIVA LGINNGWIDS ALQEKAYIEY SYNNSYKQII   240
TSSQRTSYLS TYTNDCLPAI NKCTTGGSNS ACSNAADVCY NDIESPIMSD ADFDVYDIRQ   300
PSNDAYPPET YVTYLQTSSV VKAIGASSTY QECPDAPYNK FATTGDNDRS FLATLSTVVQ   360
SGITVLLWAG DADWICNWVG NQYVADAVTW SGQSSFAAQT LTPYTVNGSE VGTFKTLDNL   420
SFLRVYEAGH EVPYYQPATA LQAFIQTMQK KALSST                            456

SEQ ID NO: 52           moltype = AA   length = 354
FEATURE                 Location/Qualifiers
source                  1..354
                        mol_type = protein
                        organism = Nocardiopsis kunsanensis
SEQUENCE: 52
APAPQNPTEP AEATTMAEAL ERDLGLNEAE ATDLIDAQES ALDVDAEATE AAGEHYGGSL    60
FDTETHDLTV LVTDSAAVPG VEAAGAEAAV VEHGVEGLDD LISDLDSAGA QEGVVGWYPE   120
VENDTVVIET LEGADADVDA LLSSAGVDPA DVRVETTDEA PEVYANIVGG DAYTIGGSSR   180
CSVGFPASDS YGQPGFVTAG HCGTTGSSVS IGNGSGVFSQ SVFPGNDAAF VRGTSNFSLT   240
NLVNRYNSGS DVAVSGSTQA PIGSQVCRSG STTGWHCGTI QARGQTVSYP QGTVRDLTRT   300
SVCAEPGDSG GSFISGSQAQ GVTSGGSGNC SWGGTTYYQE VNPMLNSWNL NLST         354

SEQ ID NO: 53           moltype = AA   length = 425
FEATURE                 Location/Qualifiers
source                  1..425
                        mol_type = protein
                        organism = Streptomyces parvulus
SEQUENCE: 53
GTAPSPAAPT AAESLRADAA PPALLRAMER DLGLGREQAE RRLGNEAEAG AVAGRLRADL    60
GGDFAGAWVR GAESGTLTVA TTDAADVPAI EARGAVAEVV RHSLADLGAA KSRLDRAAAH   120
RDTAEAPVRY VDVRTNTVTV QAVRPSAARA LLAAAGVDAG LARVETSAER PRPLYDLRGG   180
EAYYINNSGR CSVGFPVTKG TQQGFATAGH CGRAGASTSG ANRVAQGTFQ GSVFPGRDMA   240
WVAANSQWTA TPYVSGAGGQ NVQVAGSTQA PVGASVCRSG STTGWHCGTI QQHDTSVTYP   300
EGTITGVTRT TVCAEPGDSG GSYISGSQAQ GVTSGGSGNC GSGGTTFFQP INPLLQNYGL   360
TLKTTGGGGE DPGEPGEPGG TWAAGTVYRP GDTVTYGGAT YRCLQGHQAQ RGWEPANVPA   420
LWQRV                                                              425

SEQ ID NO: 54           moltype = AA   length = 350
FEATURE                 Location/Qualifiers
source                  1..350
                        mol_type = protein
                        organism = Saccharopolyspora endophytica
SEQUENCE: 54
LTATIADPAG PPVSPELVTA MQRDLGLTAD QAVARLGQEA VAARADSALR DALAGSYGGS    60
YFDANLGKLV VGTTDAAKSD EVRAAGAEPR QVDASERQLD GIVEALNGRG AQVPAAVTGV   120
YADVRENAVV VTTQPGTAEQ ATGFVRDAQV PQESVRVWES PAQPETYADV VGGYAYYTAS   180
GARCSMGFAV QGGFVTAGHC GAPGESTTQP TGYFAGSSFP GNDYAFVNTG TDDTGYPLVY   240
NYSSGYVRVS GSAEAPLGSS ICRSGSTTGW HCGTVLAKNQ SVRYQEGTVS GLTRTNVCAE   300
PGDSGGSFIS GNQAQGMTSG GWDCRTGGE TYYQPVREAL SAYGLTLLTQ              350

SEQ ID NO: 55           moltype = AA   length = 355
FEATURE                 Location/Qualifiers
source                  1..355
                        mol_type = protein
                        organism = Luteus cellwall
SEQUENCE: 55
ASGPLPQSPS PDSDVATTMA EALERDLNLT STEAQELLTA QEAAFEADEA AAQAAGDAYG    60
GSVFDTETLD LTVMVTDAAA VQAVEATGAK ADVVSYGIDG LDTIIDDLNE ADAPEGVVGW   120
YPDIDSDTVV LEVLEGSGAD VDALLAEAGV DASAVKVEST TEQPELYADI IGGLAYYMGG   180
RCSVGFAATN ASGQPGFVTA GHCGRVGTQV TIGNGRGVFE RSVFPGNDAA FVRGTSNFTL   240
TNLVSRYNSG GYATVSGSSV APIGSSVCRS GSTTGWRCGT IQARGQTVTY PQGTIYNMTR   300
TSACAEPGDS GGSFISGTQA QGVTSGGSGN CSWGGTTFYQ EVNPMLNSWN LRLRT        355

SEQ ID NO: 56           moltype = AA   length = 406
FEATURE                 Location/Qualifiers
source                  1..406
                        mol_type = protein
                        organism = Saccharothrix australiensis
SEQUENCE: 56
```

```
GPPTTHQEES GLIAAMARDF KITPDQARAR LVREAKAATT EQSLKSRLGG HYAGAWLNEG   60
ATELVVAVTD AAQAKVVEDA GATPKVVQRS QIQLDELKAK LDANKNAPKD VPAWYVDVKT  120
NSVVVLARNT ASAKAFARAS GLSEADVRIE QSTEDPRPLI DVIGGNAYYM GSGGRCSVGF  180
SVNGGFVTAG HCGRVGTTTT QPSGTFAGST FPGRDYAWVR VSSGNTMRGL VNRYPGTVPV  240
KGSNESSVGA SVCRSGSTTG WHCGTIQQKN TSVTYPEGTI SGVTRTNACA EPGDSGGSWL  300
TGDQAQGVTS GGSGNCSSGG TTYFQPVNPI LQAYGLQLVI EGGPTGTTGP TTTSSNPGGT  360
TWQPGVAYTA GTTVTYEGVG YECLQGHTSQ IGWEPSAVPA LWERVG                406

SEQ ID NO: 57              moltype = AA   length = 346
FEATURE                    Location/Qualifiers
source                     1..346
                           mol_type = protein
                           organism = Nocardiopsis baichengensis
SEQUENCE: 57
DAFPEGTEPL AEAIERDLGV ASGQADELLT AEESARSLEK EAEKAAGEAF AGAVFDTETH   60
ELTVSVADPS AVEAVEATGA ETRVVEASQD ELDAAMADLD AASEDGVSEE VTGWHVDLES  120
NTVVVEALEG SEDAAEDLIA DAGLDSAPVV VEKADAQPET FGAIVGGDAY YPGNSRCSIG  180
FSVRGGFVTA GHCGSTGTSV SGSAGESGRV AGSVFPGRDM GYVRANSGWT PSPYVNNYRG  240
GRVAVRGSNE ASVGASVCRS GSTTGWHCGT IQAKNQTVNY PQGTVRGLTR TTACAEPGDS  300
GGSWLSGNQA QGVTSGGSGN CSWGGTTFFQ PVNPILSQWG LSLTTT                 346

SEQ ID NO: 58              moltype = AA   length = 353
FEATURE                    Location/Qualifiers
source                     1..353
                           mol_type = protein
                           organism = Streptomyces sp.
SEQUENCE: 58
NDTLTERADA AVAELPAGVL DAMERDLGLS EQEAGLQLVA QYDASLLGET LSADLDAYAG   60
SWLADGTDLV VATTDRAEAA QITEAGAKVE IVDHTLTELE SVKAALDEAA ESYDTTDAPV  120
WYVDITTNDV VLLTSDTAEA KGFVEAAGVD AGAVSIQTDD EQPQAFYDLV GGDAYYMGGS  180
RCSVGFSVTQ GSTPGFATAG HCGTVGTSTT GFNQAAQGTF EESSFPGDDM AWVSVNSNWN  240
TTPTVNDGAV TVSGSTQGAV GASICRSGST TGWHCGTIEQ HNTSVTYPEG TITGVTRTSV  300
CAEPGDSGGS YISGSQAQGV TSGGSGNCTS GGTTYHQPIN PLLSAYGLDL VTG         353

SEQ ID NO: 59              moltype = AA   length = 353
FEATURE                    Location/Qualifiers
source                     1..353
                           mol_type = protein
                           organism = Actinoalloteichus spitiensis
SEQUENCE: 59
DTPSPDGADA TVASPEMLSA MQRDLGLTEQ EALTRVAVEA TAVETEDELR ASLGPAFGGA   60
HFDGDTNTLV VGVTSAAKAD EVRAAGATPE VVAFSADTLG GVVSTLNETS EVPDGVTGWY  120
VDTADNTVVV TTALGSGEAA ADFVAESGVN ADAVTVVEST EQPRTLYDII GGDAYYFGGS  180
RCSVGFSVSV GYVTAGHCGG VGTATQGYNR VSSGQVAGSV FPGSDMGYVR TNANWTPRPL  240
VNRYSGGATV TVSGSNEAAV GASICRSGST TGWRCGTVQA KNQTVFYAQG AVSGLTRTNA  300
CAEGGDSGGS WLSGSQAQGV TSGGSGNCTW GGTTYFQPLN PILSRWGLSL TRG         353

SEQ ID NO: 60              moltype = AA   length = 338
FEATURE                    Location/Qualifiers
source                     1..338
                           mol_type = protein
                           organism = Byssochlamys verrucosa
SEQUENCE: 60
FPAAVDVKRA PSSLGITLSQ VSNTLIKAVV QNTGRGEVSF IHLNFFKDDA PVKKVAVYRN   60
GSEVQFEGIQ RRYKSTGLTR DAFTTLAPGK TAEDVFDIAS TCDLISGGPV TIRSEGVVPY  120
ATANGIDIAG YIPYSSNELT IDVDGAIAST VSKAIAPLNR RTNISSCSGS EQSTLTMALK  180
NAASLAHAAA DAAESGSASK FSEYFKTTAS STRKTVAARL RAVAQEASSS SSGSTTYYCN  240
DAYGYCTTNV LAYTLPSHNT IATCDLYYTN LSALTRTCHA QDQATTSLHE FTHAPGVYSP  300
GTDDLAYGYA SSTSLSSSQA VMNADSYALY ANAIYVGC                         338

SEQ ID NO: 61              moltype = AA   length = 339
FEATURE                    Location/Qualifiers
source                     1..339
                           mol_type = protein
                           organism = Hamigera terricola
SEQUENCE: 61
SPVNVNVGRE ELPALDVTLS QIGNTQIKAV VKNTGSEDVT FMHLNFFTDS APVKKVSVFQ   60
NNTEVEFQGI LRRVKYTDVS TDSVTTLAPG ASIEDVFDIA TTTDLASGGA VTVKTDGFVP  120
ILASAENKVT GYARYTSNEL HLDVDGPSAA TVSKAIAPLD RRTRLSSCSG SRSSSALQTAL  180
RNTVSLANAA ANAARSGSAS KFSEYFKTTS SSVRSTVAAR LSAVASEASS TSSGSTTYYC  240
NDPYGYCSTD VLAYTLPSYN IIANCDIYYS YLPALTGSCH AQDQATTTLH EFTHAPGVYS  300
PGTEDYGYGY NAATSLSSSQ AVLNADSYAL YANAIYLGC                        339

SEQ ID NO: 62              moltype = AA   length = 334
FEATURE                    Location/Qualifiers
source                     1..334
                           mol_type = protein
                           organism = Aspergillus tamarii
SEQUENCE: 62
```

```
IPVEVPASAP GLDVTLSQVG NTRIKAVVKN TGSEEVTFVH LNFFKDAAPV QKVSLFRNAT      60
EVQFQGIKQR LITEGLSDEA LTTLAPGATI EDEFDIASTS DLSEGGTITI NSNGLVPITT     120
ENKVTGYIPF ASNELSIDVD AAEAATVSQA VKILDRRTKV TSCSGSRSSA LQTALRNTVS     180
LARAAASAAQ SGSSSRFQEY FKTTSSSTRS TVAARLNAVA NEAASTASGS TTYYCSDVYG     240
YCSSNVLAYT LPAYNIIANC DLYYSYLPAL TSTCHAQDQA TTTLHEFTHA PGVYSPGTDD     300
LGYGYSAATA LSASQALLNA DTYALFANAV NLNC                                 334

SEQ ID NO: 63              moltype = AA  length = 334
FEATURE                    Location/Qualifiers
source                     1..334
                           mol_type = protein
                           organism = Aspergillus niveus
SEQUENCE: 63
LPAKTGEQLQ KLDVALSQVD NTLIKAVVKN TGSEDITFVH LNFFRDTAPV KKVSLFRNTT      60
EVPFHGIKQR LRSDGLSADA LTVLAPGESI EDEFDIAATS DLSEGGSITI SADGFVPIAS     120
GNKITGYVPF SSNELSVEVD AAQAASVASA VKPLDRRTKV ASCSGSRSSA LTQALRNTVS     180
LANAAASAAQ SGSSTRFQEY FKTTSSSVRS SVAARFRAVA SEASSTSAGS TTYYCTDVYG     240
YCSSNVLAYT LPAYNIIANC DIYYTYLPAL TSTCHAQDQA TTTLHEFTHA PGVYSPGTDD     300
LGYGYDAATA LSSSQALNNA DSYALFANAV NLNC                                 334

SEQ ID NO: 64              moltype = AA  length = 372
FEATURE                    Location/Qualifiers
source                     1..372
                           mol_type = protein
                           organism = Penicillium sclerotiorum
SEQUENCE: 64
IPTGGKKSSF SVDQVAIPAT KTKNFADTYA RAISKFGGNV PSHVRAAAQQ SGAATTTPEA      60
NDEEYLTPVN VGGTTLNLDF DTGSADLWVF SEQLPSSEQS GHSVYKPNNG TKLSGATWSI     120
SYGDGSSASG DVYKDTVSVG PVKATGQAVE AASKISAQFT RDSNNDGLLG LAFSSINTVK     180
PKAQTTFFDT VKSSLASPLF AVTLKHNAPG TYDFGFVDSS KYTGSLAYTD VDNSQGFWEF     240
TADSYKVGSQ SGSSIKGIAD TGTTLLLLDD EVVSAYYKQV SGASDSQSAG GYTFDCSADL     300
PDFTVTISGY DAVVPGSLIN YAPVSDGSST CLGGIQSNSG IGFSIFGDIF LKSQYVVFDS     360
NGPRLGFAAQ SS                                                         372

SEQ ID NO: 65              moltype = AA  length = 371
FEATURE                    Location/Qualifiers
source                     1..371
                           mol_type = protein
                           organism = Penicillium bilaiae
SEQUENCE: 65
VPTGGKKSFS INQVAIPATK TKNFAGNYAH AIAKYGGNVP SHVEAAAQQS GAATTTPESN      60
DEEYLTPVNV GGTTLNLDFD TGSADLWVFS AELPSAEQSG HALYKPSNGT KLSGASWSIS     120
YGDGSSASGD VYKDTVSGS VKATGQAVEA ASKISAQFTK DKNNDGLLGL AFSSINTVKP     180
KAQTTFFDTV KSSLASPLFA VTLKHNAPGT YDFGFIDSKT KYTGSLAYADV DNSQGFWEFT     240
ADSYSVGSSK GSSIKGIADT GTTLLLLDDE VVSAYYKQVQ GAQQDSSAGG YTFDCSSKLP     300
DFTVTISGYD AVVPGDLINF APASEGSSTC LGGIQSNSGI GFSIFGDIFL KSQYVVFDSN     360
GPRLGFAAQS S                                                          371

SEQ ID NO: 66              moltype = AA  length = 373
FEATURE                    Location/Qualifiers
source                     1..373
                           mol_type = protein
                           organism = Penicillium antarticum
SEQUENCE: 66
SPLVTPRKGF TINQETRAVT KSKTVNLPGV YAQALSKYGA TVPQHVAAAA VSGSAVTTPE      60
ESDVEYLTPV NVGGTTLNLD FDTGSADLWV FSSELTSSQQ SGHSIYKPSS SATKLSGSSW     120
SISYGDGSSA SGDVYKDTVT VGGVKATGQA VEAASKISSA FLQDVNNDGL LGLAFSSINT     180
VSPRAQTTFF DTVKSQLDSP LFAVTLKHNA PGSYDFGYID KSKYTGSLTY ANVDDSQGFW     240
SFTASSYKIG TTTGGSITGI ADTGTTLLLL PDSVVSAYYK KVSGSQNSNY YGGYVFPCSA     300
TLPDFTVTIN GYNAVVPGNL INFAQATTGS STCYGGIQSN SGIGFSIFGD IFLKSQYVVF     360
DSEGPRLGFA AQA                                                        373

SEQ ID NO: 67              moltype = AA  length = 370
FEATURE                    Location/Qualifiers
source                     1..370
                           mol_type = protein
                           organism = Penicillium sumatrense
SEQUENCE: 67
VPTNNVASKF SVNQVSRPAT KTTNFAANYG RALSKYGAGV PSHVEAAAAA SGSAVTTPES      60
NDVEYLTPVS IGGTTLNLDF DTGSADLWVF STELSSSEQS GHSVYNPSKS GKKISGASWD     120
ISYGDGSGAS GDVYTDTVTV GGVTASKQAV EAAKQISSQF QQDTNDGLL GLAFSSINTV     180
SPTPQKTFFD NVKSSLSQPL FAVALKHNAP GVYDFGFIDS SKHTGSIAYT SVDSSQGFWS     240
FTVDGYKVGS KSGAGFDGIA DTGTTLLLLD DSVVSAYYSQ VSGAKNDNNA GGYVFDCSAD     300
LPDFSVTIGS YTATVPGSLI NYGDSGDNSC IGGIQSNSGI GFSIFGDIFL KSQYVVFNAN     360
GPKLGFAPQA                                                            370

SEQ ID NO: 68              moltype = AA  length = 384
FEATURE                    Location/Qualifiers
source                     1..384
```

```
                          mol_type = protein
                          organism = Trichoderma lixii
SEQUENCE: 68
LPTEGQKTAS IEVTYNKNYV AHGPTALFKA KRKYGAPISD NLRAAVAAKH SLTKRQTGSA   60
NTNPSDSADD EYITSVSIGT PAQVLPLDFD TGSSDLWVFS SETPKSSASG HVTYSPSKSS  120
TAKKLSGSTW SITYGDHSSS SGDVYTDVVS IGGFSVKTQA IESATKVSTQ FVQDTVISGL  180
VGLGFDVGNT VKPRAQKTWF SNAASSLAEP LFTADLRHQE TGSYNFGFID NSLAKGTIGY  240
TPADGSEGYW GFTATGYSVG GAKLGRSSIT GIADTGTTLL LLPDNVVDAY YNNVESAQYD  300
DSQEGVVFDC SEDLPSFSFG VGGQTITISG DLLNLTPIEE GSSTCFGGLQ SSADIGINIF  360
GDVALKAALV VFDLGNERLG FAQK                                        384

SEQ ID NO: 69             moltype = AA   length = 384
FEATURE                   Location/Qualifiers
source                    1..384
                          mol_type = protein
                          organism = Trichoderma brevicompactum
SEQUENCE: 69
LPTEGQKTAS VEVTYNQNYA AHGPTQLYKA KRKYGAPISD NLKAIVANRK ALIKRQTGSA   60
PNHPSDSADD EYITNVSIGT PAQVLPLDFD TGSSDLWVFS SETPKSSASG HTIYTPSKSS  120
TSKKLSGATW SIEYGDKSTS SGDVYTDKVT VGGFSVSTQA VESATKVSAQ FVQDTANSGL  180
LGLAFDSINT VSPRQQKTWF SNAANSLAQP LFTANLNHQA TGSYNFGFID TSLASGPINY  240
VPVDNSQGFW GFTASGYSVG GGKLNRSSLS GIADTGTTLL LLPDAVVNAY YANVESAEYD  300
DEQEGVVFDC SEDLPTFSFG VGSGTITIPG DLLNLTPIDS SGQTCYGGLQ SSSDIGINIF  360
GDVALKAALV VFDLGNERLG WAQK                                        384

SEQ ID NO: 70             moltype = AA   length = 379
FEATURE                   Location/Qualifiers
source                    1..379
                          mol_type = protein
                          organism = Penicillium cinnamopurpureum
SEQUENCE: 70
IPTGVPNRKG FTVNQQVRPV TNGTKSKTLN LPAIYANALS KYGVAVPANI KAAAESGTAT   60
TTPEDNDIEY LTPVDVGGTT LNLDFDTGSA DLWVFSSELP SSESSGHSIY KPSQSGKKLD  120
GYSWKISYGD SSSASGDVYT DTVTVGGVTA DGQAVEAAKS ISQQFVQDKN NDGLLGLAFS  180
SINTVQPKAQ TTFFDTVKDQ LDSPLFAVTL KHNAPGSYDF GFIDKSKYTG SLTYADVDKS  240
DGFWAFTADG YSVGSGSSSS SRIKGIADTG TTLLLIDDEI VSAYYKQVDG AQESYSVGGY  300
TFDCSTKLPD FNIKIGDYTA VIPGDVINYA PVQQGSSTCF GGIQSNSGLP FSIFGDIFLK  360
SQYVVFDANG PRLGFAAQA                                              379

SEQ ID NO: 71             moltype = AA   length = 350
FEATURE                   Location/Qualifiers
source                    1..350
                          mol_type = protein
                          organism = Bacillus lichenformis
SEQUENCE: 71
AQPAKNVEKD YIVGFKSGVK TASVKKDIIK ESGGKVDKQF RIINAAKAKL DKEALKEVKN   60
DPDVAYVEED HVAHALAQTV PYGIPLIKAD KVQAQGFKGA NVKVAVLDTG IQASHPDLNV  120
VGGASFVAGE AYNTDGNGHG THVAGTVAAL DNTTGVLGVA PSVSLYAVKV LNSSGSGSYS  180
GIVSGIEWAT TNGMDVINMS LGGASGSTAM KQAVDNAYAR GVVVVAAAGN SGSSGNTNTI  240
GYPAKYDSVI AVGAVDSNSN RASFSSVGAE LEVMAPGAGV YSTYPTNTYA TLNGTSMASP  300
HVAGAAALIL SKHPNLSASQ VRNRLSSTAT YLGSSFYYGK GLINVEAAAQ             350

SEQ ID NO: 72             moltype = AA   length = 360
FEATURE                   Location/Qualifiers
source                    1..360
                          mol_type = protein
                          organism = Bacillus subtilis
SEQUENCE: 72
FSNMSAQAAG KSSTEKKYIV GFKQTMSAMS SAKKKDVISE KGGKVQKQFK YVNAAAATLD   60
EKAVKELKKD PSVAYVEEDH IAHEYAQSVP YGISQIKAPA LHSQGYTGSN VKVAVIDSGI  120
DSSHPDLNVR GGASFVPSET NPYQDGSSHG THVAGTIAAL NNSIGVLGVA PSASLYAVKV  180
LDSTGSGQYS WIINGIEWAI SNNMDVINMS LGGPTGSTAL KTVVDKAVSS GIVVAAAAGN  240
EGSSGSTSTV GYPAKYPSTI AVGAVNSSNQ RASFSSAGSE LDVMAPGVSI QSTLPGGTYG  300
AYNGTSMATP HVAGAAALIL SKHPTWTNAQ VRDRLESTAT YLGSSFYYGK GLINVQAAAQ  360

SEQ ID NO: 73             moltype = AA   length = 548
FEATURE                   Location/Qualifiers
source                    1..548
                          mol_type = protein
                          organism = Trametes cf versicol
SEQUENCE: 73
TPTARNLKLH ESREEIPAGF SLSGAASPDT TLKLRLALVQ SNFAELEDKL YDVSTPSSAN   60
YGQHLSKEEV EQLVAPSAES VNAVNAWLTE NGLTAQTISP AGDWLAFEVP VSKANELFDA  120
DFSVFTHDES GLKAVRTLAY SIPAELQGHL DLVHPTITFP NPNSHLPVVR SPVKPVQNLT  180
SRAVPASCAS TITPACLQAL YGIPTTKATQ SSNKLAVSGF IDQFANSADL KTFLGKFRTD  240
ISSSTTFTLQ TLDGGSNSQS SSQAGVEANL DIQYTVGLAS AVPTIFISVG DDFQDGDLEG  300
FLDIINFLLN ESAPPQVLTT SYGQNENTIS AKLANQLCNA YAQLGARGTS ILFASGDGGV  360
SGSSQSSSCSK FVPTFPSGCP FMTSVGATQG INPETAADFS SGGFSNVFAR PSYQSTAVSS  420
YLTALGSTNS GKFNTSGRAF PDIATQGVDF EIVVSGRTEG VDGTSCASPT LAAIISLLND  480
```

```
RLIAAGKSPL GFLNPFLYSA AGTAALTDIT SGSNPGCNTN GFPAKAGWDP VTGLGTPNFA    540
KLLTAVGL                                                             548

SEQ ID NO: 74           moltype = AA  length = 439
FEATURE                 Location/Qualifiers
source                  1..439
                        mol_type = protein
                        organism = Bos taurus
SEQUENCE: 74
MAKEYFPFTG KIPFEGKDSK NVMAFHYYEP EKVVMGKKMK DWLKFAMAWW HTLGGASADQ    60
FGGQTRSYEW DKAECPVQRA KDKMDAGFEI MDKLGIEYFC FHDVDLVEEA PTIAEYEERM    120
KAITDYAQEK MKQFPNIKLL WGTANVFGNK RYANGASTNP DFDVVARAIV QIKNSIDATI    180
KLGGTNYVFW GGREGYMSLL NTDQKREKEH MATMLGMARD YARAKGFKGT FLIEPKPMEP    240
SKHQYDVDTE TVIGFLKAHG LDKDFKVNIE VNHATLAGHT FEHELACAVD AGMLGSIDAN    300
RGDAQNGWDT DQFPIDNFEL TQAMLEIIRN GGLGNGGTNF DAKIRRNSTD LEDLFIAHIS    360
GMDAMARALM NAADILENSE LPAMKKARYA SFDSGIGKDF EDGKLTFEQV YEYGKKVEEP    420
KQTSGKQEKY ETIVALHCK                                                 439

SEQ ID NO: 75           moltype = AA  length = 591
FEATURE                 Location/Qualifiers
source                  1..591
                        mol_type = protein
                        organism = Saccharomyces cerevisiae
SEQUENCE: 75
MLCSVIQRQT REVSNTMSLD SYYLGFDLST QQLKCLAINQ DLKIVHSETV EFEKDLPHYH    60
TKKGVYIHGD TIECPVAMWL GALDLVLSKY REAKFPLNKV MAVSGSCQQH GSVYWSSQAE    120
SLLEQLNKKP EKDLLHYVSS VAFARQTAPN WQDHSTAKQC QEFEECIGGP EKMAQLTGSR    180
AHFRFTGPQI LKIAQLEPEA YEKTKTISLV SNFLTSILVG HLVELEEADA CGMNLYDIRE    240
RKFMYELLHL IDSSSKDKTI RQKLMRAPMK NLIAGTICKY FIEKYGFNTN CKVSPMTGDN    300
LATICSLPLR KNDVLVSLGT STTVLLVTDK YHPSPNYHLF IHPTLPNHYM GMICYCNGSL    360
ARERIRDELN KERENNYEKT NDWTLFNQAV LDDSESSENE LGVYFPLGEI VPSVKAINKR    420
VIFNPKTGMI EREVAKFKDK RHDAKNIVES QALSCRVRIS PLLSDSNASS QQRLNEDTIV    480
KFDYDESPLR DYLNKRPERT FFVGGASKND AIVKKFAQVI GATKGNFRLE TPNSCALGGC    540
YKAMWSLLYD SNKIAVPFDK FLNDNFPWHV MESISDVDNE NWIAIIPRLS P             591

SEQ ID NO: 76           moltype = AA  length = 444
FEATURE                 Location/Qualifiers
source                  1..444
                        mol_type = protein
                        organism = Bacillus subtilis
SEQUENCE: 76
ETANKSNELT APSIKSGTIL HAWNWSFNTL KHNMKDIHDA GYTAIQTSPI NQVKEGNQGD    60
KSMSNWYWLY QPTSYQIGNR YLGTEQEFKE MCAAAEEYGI KVIVDAVINH TTFDYAAISN    120
EVKSIPNWTH GNTQIKNWSD RWDVTQNSLL GLYDWNTQNT QVQSYLKRFL ERALNDGADG    180
FRFDAAKHIE LPDDGSYGSQ FWPNITNTSA EFQYGEILQD SASRDAAYAN YMDVTASNYG    240
HSIRSALKNR NLGVSNISHY AYDVSADKLV TWVESHDTYA NDDEESTWMS DDDIRLGWAV    300
IASRSGSTPL FFSRPEGGGN GVRFPGKSQI GDRGSALFED QSITAVNRFH NVMAGQPEEL    360
SNPNGNNQIF MNQRGSHGVV LANAGSSSVS INTPTKLPDG RYDNKAGAGS FQVNDGKLTG    420
TINARSVAVL YPDDIEIRCN TFFQ                                           444

SEQ ID NO: 77           moltype = AA  length = 476
FEATURE                 Location/Qualifiers
source                  1..476
                        mol_type = protein
                        organism = Saccharomycopsis fibuligera
SEQUENCE: 77
QPVTLFKRET NADKWRSQSI YQIVTDRFAR TDGDTSASCN TEDRLYCGGS FQGIIKKLDY    60
IKDMGFTAIW ISPVVENIPD NTAYGYAYHG YWMKNIYKIN ENFGTADDLK SLAQELHDRD    120
MLLMVDIVTN HYGSDGSGDS IDYSEYTPFN DQKYFHNYCL ISNYDDQAQV QSCWEGDSSV    180
ALPDLRTEDS DVASVFNSWV KDFVGNYSID GLRIDSAKHV DQGFFPDFVS ASGVYSVGEV    240
FQGDPAYTCP YQNYIPGVSN YPLYYPTTRF FKTTDSSSSE LTQMISSVAS SCSDPTLLTN    300
FVENHDNERF ASMTSDQSLI SNAIAFVLLG DGIPVIYYGQ EQGLSGKSDP NNREALWLSG    360
YNKESDYYKL IAKANAARNA AVYQDSSYAT SQLVIFSND HVIATKRGSV VSVFNNLGSS    420
GSSDVTISNT GYSSGEDLVE VLTCSTVSGS SDLQVSIQGG QPQIFVPAKY ASDICS        476

SEQ ID NO: 78           moltype = AA  length = 487
FEATURE                 Location/Qualifiers
source                  1..487
                        mol_type = protein
                        organism = Debaryomyces occidentalis
SEQUENCE: 78
QPIIFDKRDV GSSADKWKDQ SIYQIVTDRF ARSDGSTTAD CLVSDRKYCG GSYKGIIDKL    60
DYIQGMGFTA IWISPVVEQI PDNTAYGYAY HGYWMKNIDE LNTNFGTADE LKQLASELHS    120
RSMLLMVDVV YNHYAWNGDG SSVDYSSFTP FNQQSYFHDY CLITNYNDQT NVEDCWEGDT    180
EVSLPDLSTE DNEVIGVFQT WVSDFVQNYS IDGLRIDSAK HVDTASLTKF EDASGVYNLG    240
EVYQGDPTYT CPYQSYMKGV TNYPLYYPVY RFFSDTSATS SELTSMISTL QSSCSDVSLL    300
GNFIENHDQV RFPSVTSDTS LIKNAMAFII LGDGIPIIYY GQEQGLNGGS DPANREALWL    360
SGYNTDSEYY ELISKLNQIR NQAIKKDSAY STYKSSVVSS SDHYIATRKG SDANQLISIF    420
NNLGSNGSQD ITVSNTGYSS GDKVIDIISC NSVSAGDFGS LSVSISGGMP QVYAPSSVLS    480
```

```
GSGICNQ                                                                      487

SEQ ID NO: 79           moltype = AA  length = 487
FEATURE                 Location/Qualifiers
source                  1..487
                        mol_type = protein
                        organism = Debaryomyces occidentalis
SEQUENCE: 79
KPIFLSKRDA GSSAAAAWRS ESIYQLVTDR FARTDGSTSA TCNTGDRVYC GGTFQGIIDK      60
LDYIQGMGFT AIWISPVVEQ IPDDTGYGYA YHGYWMKDIY AINSNFGTAD DLKNLSNELH     120
KRNMKLMVDI VTNHYAWNGA GSSVAYSNYN PFNQQSYPHD YCLITNYDDQ TNVEDCWEGD     180
NTVSLPDLRT EDSDVSSIFN LWVAELVSNY SIDGLRIDSA KHVDESFYPS FQSAAGVYLL     240
GEVYDGDPAY TCPYQNYMSG VTNYPLYYPM LRFFQGTSNS VDELNAMISS LESDCKDITL     300
LGNFIENHDQ PRLPSYTSDS ALIKNAIAFN LMSDGIPIIY YGQEQGYSGS SDPNNREALW     360
LSGYSTSNGY YKLISSVNQI RNQAIYKDSK YTTYWSDVLY ASGHVIALQR GADDQRIVSV     420
FNNLGSSGSQ TVTFSTKYSG GEKVVDVLTC QTSYANSDST LTVSISGGAP RIYAPASLIA     480
NSGICNF                                                                     487

SEQ ID NO: 80           moltype = AA  length = 570
FEATURE                 Location/Qualifiers
source                  1..570
                        mol_type = protein
                        organism = Lipomyces kononenkoae
SEQUENCE: 80
MCGSTLSASL YVYNDDYDKI VTLYYLTSSG TTGSTLALIL PVWSNNWELW TLSAIAAGAV      60
EITGASYVDS DTSVTYTTSL DLPLTTTSAS VPTGTAANWR GRSIYQVVTD RFARTDGSIT     120
YSCDVTDRVY CGGSYRGIIN MLDYIQGMGF TAIWISPIVE NIPDDTGYGY AYHGYWMKDI     180
FALNTNFGGA DDLIALATEL HNRGMYLMVD IVVNHFAFSG NHADVDYSEY FPPYSSQDYFH     240
SFCWITDYSN QTNVEECWLG DDSVPLVDVN TQLDTVKSEY QSWVKQLIAN YSIDGLRIDT     300
VKHVQMDFWA PFQEAAGIYT VGEVPDGDPS YTCPYQENLD GVLNYPVYYP VVSAFQRVGG     360
SISSLVDMID TLKSECIDTT LLGSFLENQD NPRFPSYTSD ESLIKNAIAF TILSDGIPII     420
YYGQEQGLNG GNDPYNREAL WPTGYSTTST FYEYIASLNQ IRNHAIYIDD TYLTYQNWVI     480
YSDSTTIAMR KGFTGNQIIT VLSNLGSSGS SYTLTLSNTG YTASSVVYEI LTCTAVTVDL     540
SGNLAVPMSG GLPRVFYPES QLVGSGICSM                                            570

SEQ ID NO: 81           moltype = AA  length = 476
FEATURE                 Location/Qualifiers
source                  1..476
                        mol_type = protein
                        organism = Lipomyces kononenkoae
SEQUENCE: 81
KTAAEWKELS IYQVITDRFA TTNLTAPDCW IRAYCGGTWK GLERKLDYIQ NMGFDAVWIS      60
PVIHNIEVNT TWGFAHGYW GDDPYRLNEH FGTAADLKSL SDSLHARGMS LMVDVVINHL     120
ASYTLPQDVD YSLYPAPFNT SSAFHQPCPI DFSNQSSIED CWLVTEPAPA LVDLKNEDQV     180
ILDALINSVV DLVETYDIDG IRLDTARHVP KPSLAKFQEK VGVFVTGEAL NQSVPYVAQY     240
QGPLNSAINY PLWYALVDSF MGRTTFDYLE SVVKSEQATF SDAHALTNFL DNQDQPRFAS     300
YLGDGNGDDV LRDENAATFL FFVSGIPVIY YGFEQRFDGG FDPVNREPMW TSGYNTSTPL     360
YNYLARLNAI RKYAASITGT QVFYSDDTVF LGSGVSHMAM QRGPLVIVLT NVGQHIIDNT     420
GYTVTGSQFS AGDSLTDLVS CTKVKVVGAN GTFTSPSNGG KARIWIKSKY AGKFCS             476

SEQ ID NO: 82           moltype = AA  length = 626
FEATURE                 Location/Qualifiers
source                  1..626
                        mol_type = protein
                        organism = Bacillus subtilis
SEQUENCE: 82
ETANKSNELT APSIKSGTIL HAWNWSFNTL KHNMKDIHDA GYTAIQTSPI NQVKEGNQGD      60
KSMSNWYWLY QPTSYQIGNR YLGTEQEFKE MCAAAEEYGI KVIVDAVINH TTSDYAAISN     120
EVKSIPNWTH GNTQIKNWSD RWDVTQNSLL GLYDWNTQNT QVQVSYLKRFL DRALNDGADG     180
FRFDAAKHIE LPDDGSYGSQ FWPNITNTSA EFQYGEILQD SASRDAAYAN YMDVTASNYG     240
HSIRSALKNR NLGVSNISHY ASDVSADKLV TWVESHDTYA NDDEESTWMS DDDIRLGWAV     300
IASRSGSTPL FFSRPEGGGN GVRFPGKSQI GDRGSALFED QAITAVNRFH NVMAGQPEEL     360
SNPNGNNQIF MNQRGSHGVV LANAGSSSVS INTATKLPDG RYDNKAGAGS FQVNDGKLTG     420
TINARSVAVL YPDDIAKAPH VFLENYKTGV THSFNDQLTI TLRADANTTK AVYQINNGPE     480
TAFKDGDQFT IGKGDPFGKT YTIMLKGTNS DGVTRTEKYS FVKRDPASAK TIGYQNPNHW     540
SQVNAYIYKH DGSRVIELTG SWPGKPMTKN ADGIYTLTLP ADTDTTNAKV IFNNGSAQVP     600
GQNQPGFDYV LNGLYNDSGL SGSLPH                                                626

SEQ ID NO: 83           moltype = AA  length = 483
FEATURE                 Location/Qualifiers
source                  1..483
                        mol_type = protein
                        organism = Bacillus subtilis
SEQUENCE: 83
VNGTLMQYFE WYTPNDGQHW KRLQNDAEHL SDIGITAVWI PPAYKGLSQS DNGYGPYDLY      60
DLGEFQQKGT VRTKYGTKSE LQDAIGSLHS RNVQVYGDVV LNHKAGADAT EDVTAVEVNP     120
ANRNQETSEE YQIKAWTDFR FPGRGNTYSD FKWHWYHFDG ADWDESRKIS RIFKFRGEGK     180
AWDWEVSSEN GNYDYLMYAD VDYDNPDVVA ETKKWGNWYA NELSLDGFRI DAAKHIKFSF     240
LRDWVQAVRQ ATGKEMFTVA EYWQNNAGKL ENYLNKTSFN QSVFDVPLHF NLQAASSQGG     300
```

```
GYDMRRLLDG TVVSRHPEKA VTFVENHDTQ PGQSLESTVQ TWFKPLAYAF ILTRESGYPQ    360
VFYGDMYGTK GTSPKEIPSL KDNIEPILKA RKEYAYGPQH DYIDHPDVIG WTREGDSSAA    420
KSGLAALITD GPGGSKRMYA GLKNAGETWY DITGNRSDTV KIGSDGWGEF HVNDGSVSIY    480
VQK                                                                 483

SEQ ID NO: 84              moltype = AA   length = 589
FEATURE                    Location/Qualifiers
source                     1..589
                           mol_type = protein
                           organism = Bacillus subtilis
SEQUENCE: 84
MMEYAAIHHQ PFSTDAYSYD GRTVHIKIRT KKGDADHIRF IWGDPYEYND GKWSANEQPM     60
RKIAATEMHD YWFAEVVPPF RRLQYAFVVT DDHEDIFFGS SGVCPYNEKT LETIHYYFKF    120
PFVHEADTFQ APEWVKSTVW YQIFPERFAN GREDLSPKNA LPWGSKDPGV NDFFGGDLQG    180
IVDKLDYLED LGVNGIYLTP IFSAPSNHKY DTLDYFSIDP HFGDPEIFRT LVSQLHQRGM    240
RIMLDAVFNH IGSASPQWQD VVKNGDQSRY KDWFHIHSFP VTDDNYDRFA FTADMPKLNT    300
ANPEVQKYLL DIALYWIREF DIDGWRLDVA NEVDHVFWKT FRQAVSTEKP DVYILGEIWH    360
SAEPWLRGDE FHAAMNYPFT EPMIEYFADQ TISASRMAHR VNAHLMNGMK QANEVMFNLL    420
DSHDTKRLLT RCRNDEKKAR ALLAFMFAQT GSPCIYYGTE IGLDGENDPL CRKCMVWEKE    480
KQNQDMLQFM KRLIALRKQE NTLLTEGHLE WNLLDDKNDF ISFSRTLDEK ILIYFFNQGN    540
VVQHISLREL NIDRNNKICD AWTEQPLHYH DVIAVQPGEF LILSAAAPV                589

SEQ ID NO: 85              moltype = AA   length = 483
FEATURE                    Location/Qualifiers
source                     1..483
                           mol_type = protein
                           organism = Bacillus lichenformis
SEQUENCE: 85
ANLNGTLMQY FEWYMPNDGQ HWKRLQNDSA YLAEHGITAV WIPPAYKGTS QADVGYGAYD     60
LYDLGEFHQK GTVRTKYGTK GELQSAIKSL HSRDINVYGD VVINHKGGAD ATEDVTAVEV    120
DPADRNRVIS GEHLIKAWTH FHFPGRGSTY SDFKWHWYHF DGTDWDESRK LNRIYKFQGK    180
AWDWEVSNEN GNYDYLMYAD IDYDHPDVAA EIKRWGTWYA NELQLDGPRL DAVKHIKFSF    240
LRDWVNHVRE KTGKEMFTVA EYWQNDLGAL ENYLNKTNFN HSVFDVPLHY QFHAASTQGG    300
GYDMRRLLNG TVVSKHPLKS VTFVNDHDTQ PGQSLESTVQ TWFKPLAYAF ILTRESGYPQ    360
VFYGDMYGTK GDSQREIPAL KHKIEPILKA RKQYAYGAQH DYFDHHDIVG WTREGDSSVA    420
NSGLAALITD GPGGAKRMYV GRQNAGETWH DITGNRSEPV VINSEGWGEF HVNGGSVSIY    480
VQR                                                                 483

SEQ ID NO: 86              moltype = AA   length = 478
FEATURE                    Location/Qualifiers
source                     1..478
                           mol_type = protein
                           organism = Aspergillus niger
SEQUENCE: 86
ATPADWRSQS IYFLLTDRFA RTDGSTTATC NTADQKYCGG TWQGIIDKLD YIQGMGFTAI     60
WITPVTAQLP QTTAYGDAYH GYWQQDIYSL NENYGTADDL KALSSALHER GMYLMVDVVA    120
NHMGYDGAGS SVDYSVFKPF SSQDYFHPFC FIQNYEDQTQ VEDCWLGDNT VSLPDLDTTK    180
DVVKNEWYDW VGSLVSNYSI DGLRIDTVKH VQKDFWPGYN KAAGVYCIGE VLDGDPAYTC    240
PYQNVMDGVL NYPIYYPLLN AFKSTSGSMD DLYNMINTVK SDCPDSTLLG TFVENHDNPR    300
FASYTNDIAL AKNVAAFIIL NDGIPIIYAG QEQHYAGGND PANREATWLS GYPTDSELYK    360
LIASRNAIRN YAISKDTGFV TYKNWPIYKD DTTIPMRKGT DGSQIVTILS NKGASGDSYT    420
LSLSGAGYTA GQQLTEVIGC TTVTVGSDGN VPVPMAGGLP RVLYPTEKLA GSKICSSS     478

SEQ ID NO: 87              moltype = AA   length = 477
FEATURE                    Location/Qualifiers
source                     1..477
                           mol_type = protein
                           organism = Aspergillus niger
SEQUENCE: 87
ATPADWRSQS IYFLLTDRFA RTDGSTTATC NTADQKYCGG TWQGIIDKLD YIQGMGFTAI     60
WITPVTAQLP QTTAYGDAYH GYWQQDIYSL NENYGTADDL KALSSALHER GMYLMVDVVA    120
NHMGYDGAGS SVDYSVFKPF SSQDYFHPFC FIQNYEDQTQ VEDCWLGDNT VSLPDLDTTK    180
DVVKNEWYDW VGSLVSNYSI DGLRIDTVKH VQKDFWPGYN KAAGVYCIGE VLDGDPAYTC    240
PYQNVMDGVL NYPIYYPLLN AFKSTSGSMD DLYNMINTVK SDCPDSTLLG TFVENHDNPR    300
FASYTNDIAL AKNVAAFIIL NDGIPIIYAG QEQHYAGGND PANREATWLS GYPTDSELYK    360
LIASRNAIRN YAISKDTGFV TYKNWPIYKD DTTIPMRKGT DGSQIVTILS NKGASGDSYT    420
LSLSGAGYTA GQQLTEVIGC TTVTVGSDGN VPVPMAGGLP RVLYPTEKLA GSKICYG      477

SEQ ID NO: 88              moltype = AA   length = 431
FEATURE                    Location/Qualifiers
source                     1..431
                           mol_type = protein
                           organism = Streptomyces avermitilis
SEQUENCE: 88
SPPGTKDVTA VLFEWKFDSV ARECTNTLGP AGYGYVQVSP PAEHQGSQW WTSYQPVSYK      60
IAGRLGDATA FQNMINTCHT AGVKVVVDTV VNHMSAGSGT GTGGSAYTKY NYPGLYSSYD    120
MDDCTATITD YTNRANVQNC ELVGLADLDT GEEYVRKTIA GYMNTLLGYG ADGFRVDAVK    180
HIPAADLANI KSRLTNPSVY WKQEIVIYAS EAVQPTEYTG NGDVQEFRYA YDLKRVFNNE    240
NLAYLKNYGE GWGYLNSSVA GVFVDNHDTE RNGSTLNYKD GANYTLANVF MLAYPYGAPD    300
```

```
INSGYEWSDA DAGPPGGGTV NACWQDGWKC QHAWPEIKAM VAFRNATRGE SVTNWWDNGG    360
DAIAFGRGAK GYVAINHESG SLTRTYQTSL TAGTYCNVQN NTGVTVDSSG RFTATLGANT    420
ALALYSGKST C                                                        431

SEQ ID NO: 89           moltype = AA  length = 643
FEATURE                 Location/Qualifiers
source                  1..643
                        mol_type = protein
                        organism = Clostridium phytofermentans
SEQUENCE: 89
MYTLKSKLRD LYRHPVGYDV INKILLQAGL SKGLIENPVI GALPLSFLNR IAGKKLGNGF     60
FDALLALLNQ SNDRLDPYSS KDKKITPTWW KEAVFYQIYP RSFMDGNGDG VGDLPGIISK    120
LDYLKELGVD ALWLSPIYDS PGDDNGYDIR DYQKIDSQFG TMEDFDLLLT ELHARNMRLV    180
MDLVVNHTSD EHHWFKEALK SSESTYRDYY FLRKEPNNWT SFFSGSAWNH YPEEDLWGLH    240
LFSKKQMDLN WENPKLRQDI YQMIRWWLEK GVDGFRLDVI NYISKETGLP DGDSFIGNLM    300
GFTGIEHYFY GPKLHNHLQE IQKEAFTPYQ AFSVGETPGI GMKMGKLLTD DSRGELNMMF    360
SFDHLETSGH ARFDQYEYDL NYYKSYIMDW MENFADTSWM SLFYDNHDNP RMLSKVDHTH    420
THRQELAKML AMIQMTLKGT PFLYQGQELG MINKDFHEIS NFRDVESINK YKELCEKMPK    480
EEAFLQILAG SRDHARTPMQ WSAKPGCGFS NAVPWIDSDG DELVCNAEIQ MQDSESVLSF    540
YRDLIALRRK TPALIYGDIE FTHKKRKDIL IYTRYLEGET YLIICNLSND EQKLPGNVPV    600
SESLEGLESL SASADERKGL VLCNYPAKVM KSLRAYEGRV YRI                      643

SEQ ID NO: 90           moltype = AA  length = 1016
FEATURE                 Location/Qualifiers
source                  1..1016
                        mol_type = protein
                        organism = Clostridium phytofermentans
SEQUENCE: 90
ATDTITIHYH RDDGDYEKWN LWLWAEGKDG AAYYFDGEDA FGPYVSVSLD KSADRIGFIV     60
RTDSWEKDVS EDRFIDTSLG DEIWISSGES TFSYEAPEGY EKEVSIESFQ LKLNYLRYDE    120
EYTDISFRLT FEDGTTDFLT KEHMRIENGI LKAEKEVKYG KKITLDVLKN GLEEDYQGVS    180
FSTAKIDEES KLEMYWMQGT GTISPKADFI KRSKEIESAL ITSMKEITVK LSVPCRVDDI    240
KQDGFKLSPK LAVSKVEATS TRDSEYKTIK EGYADTFIIT MEEPLDMSKK YALSKTDYGS    300
RNLTLDSGLY TSEEFEAAYT YEGNDLGATY SKEKTVFKVW SPSAESISVL FYPHGEAKDG    360
EKPEITYPMK QTGAGVWQAE IEGDLKNKYY VYQVTVDGKT KLVVDPYAKA AGVNGERGMV    420
IDLSETDPDG FREHSSPEFK NPVDAVIYEI HVRDLSMNEN SGIENKGKFL GFTETGTTNS    480
AGLSTGLDHM KELGVTHVHL LPSFDYKTID ESKLGENKFN WGYDPQNYNL PEGSYTTDPY    540
QGEVRVREYK EMVQALHENG LHVVMDVVYN HTYTAGDSNF TSLVPGYYYR TDINGNFTNG    600
SGCGNETASE RAMVRKFIVD SVVYWATEYK VDGFRFDLMG LHDIETMNMV REALDKIDPS    660
ILLYGEGWTG GSTPLPDSKQ AIKNNAVELN ERIACFSDDI RDAIKGSVFD ASDTGFINSG    720
KRNVSNRDES IKFGIVASVS HPQVNLSGVP YSSRFWANEP SQTINYASAH DNLTLWDKLL    780
ETNKMASKEE LVQMNKLSAA IVLTSQGIPF FQAGEEMART KKGNDNSYQS PDSINMLNWD    840
NKTEYKDLFE YYKGLIALRK TYDAFRMQTA EEIQQKLEFV DSDSSVIAYR IHDAVKDGRE    900
IALIFNGTLE EKEVVLSANA WDVLVNQDTA GTDVIETITG GTIKVPAKST LVLLENKDAV    960
IKGDKDAVKG DEIQELPTNM QEVAEKESGN AWLWVGIATV CVLAGGVLFW ILKRKR      1016

SEQ ID NO: 91           moltype = AA  length = 554
FEATURE                 Location/Qualifiers
source                  1..554
                        mol_type = protein
                        organism = Clostridium phytofermentans
SEQUENCE: 91
MKNTNTLHPW WESAAAYQIY PRSFMDSNGD GVGDLQGIIS RLPYLSELGF DLIWICPIYP     60
SPNDDNGYDI SDYQNIQKEY GTMEDFEELL HKAHERGIRV IMDLVVNHTS SSHPWFIESR    120
SSKDNPKRDW YIWKDGKDNV EPNNWESIFG GSTWEYDEKS GQYFLHVFGK TMPDINWENT    180
QVKKAIFDMI CWWLDKGIDG FRVDAISHIK KPDFNDMPNP KNERYVSSFD KHMNQSGILD    240
LLNELKENAF SKYDIFTVAE ANGVRIEEIE EWVSSEKGIF NSLFQFDHLN LWNVGSEEGK    300
ISIKKLKNAL TKWQKAAPMD GNVALVMENH DLVRSISRFG SEDKYWKESA KCLALMYYMQ    360
KGVPFIYQGQ EIGMLNADYE SHLDFRDDPT LFAYQDRINN GMSPAESLQV LKKSSRDNSR    420
TPMQWDASPH AGFTTGTPWM KVNQNYHWLN AEVQKEDEDS ILNFYKKLIK IKKETTGLIY    480
GDYKLLMEES ESIYAYTREY EEKNYLVVCN LSEELSELQI DLDITKGEIL ISNYEDRNSK    540
EMLLKPYECR LYSL                                                     554

SEQ ID NO: 92           moltype = AA  length = 538
FEATURE                 Location/Qualifiers
source                  1..538
                        mol_type = protein
                        organism = Clostridium phytofermentans
SEQUENCE: 92
MVKKWWHSSV VYQIYPRSFN DSNGDGIGDL KGIIEKLDYL KNLGIDVIWL SPVFKSPNDD     60
NGYDISDYED IMDEFGTLED MELLLKEANN RGIKILMDLV ANHTSDEHKW FIESRKSKDN    120
AYRDYYIWRD PVDGHEPNDL GSTFSGSAWE WDEATGQYYL HLFSKKQPDL NWENPIVREE    180
VWKSMNFWID KGIGGFRMDV IELLGKIPDE KIISNGPMLH EYIREMNRNS FGDKDLLTVG    240
ECWGATPEIA KMYSNPDGSE LSMVFQFEHI GLDQIPGKDK WDLQPLNLID LKNVFHKWQT    300
CFHDDGWNSL FWNNHDTPRI VSRWGNDKVY KIESAKMLAT LLHGLKGTPY IYQGEELGMA    360
NIKFKDINQY KDIETLNMYK DRLNKGYKHE DIMESIYAKG RDNARTPMQW SDEIDGGFTT    420
GTPWIEVNPN FTEINAKEQV SNPNSIYNYY KKLIEIRKNN EVIVYGDFEM LLPEDKNIFA    480
YVRTLKDSKI VVVCNFYENE VEYNIPKEYE EKKEVLISNY GLSLTGRLRP FEAIMYRV     538
```

```
SEQ ID NO: 93            moltype = AA  length = 555
FEATURE                  Location/Qualifiers
source                   1..555
                         mol_type = protein
                         organism = Clostridium phytofermentans
SEQUENCE: 93
CKKADVNQNP SELNQDESQK EKEENDDEGT PEVSQDETKA VIPYDYVQNL NIIDDNYRNF    60
YEIFVYSFYD SNGDGIGDIN GVISKLDYIN DGNDATDSDL GFNGIWLMPI MPSTTYHKYD   120
VTDYYNIDPQ YGTLEDFKNL VSECHKRGIH LIIDFVFNHT SAKHPWFLEA VSYLESLKEG   180
EEPDLEKCPY VGYYHFTKDY NGSKTYYKAG TSNWYYEGVF WDQMPDLALE NENVRKEIED   240
IAKYWLDLGV DGFRLDAAKE YFSGEKERNI EVLKWFSDYV KSVKEDADIV AEVWDEEGTI   300
AAYYESGIPS LFNFPLSQHN GLITNTARKL GTSSGKNFAK TLLRLDEKYK EGNPKYIDAP   360
FISNHDTTRI SAQCVNDEDQ MKMSAGMLLT MNGSPYVYYG EEIGMNSKGT KDENKRLPMQ   420
WSATDTTGIT TPPANADSVE QKFPPVDEQM KDPLSLYNYY KRAVRIRNEN PEIARGDMSV   480
IEELCTKDIS AIKKVYQGSE IVILYNINTE SANILLKDAG LTELNIRGYL SVDGNAVTMS   540
DGVVSMPKYS IVILK                                                    555

SEQ ID NO: 94            moltype = AA  length = 583
FEATURE                  Location/Qualifiers
source                   1..583
                         mol_type = protein
                         organism = Clostridium phytofermentans
SEQUENCE: 94
MKFEAIYHRT SDNYCYPLNE EDLIINIKTG HDIERVFIYY GDPFEGGILG GNWTWNGVEE    60
ELIYKKNLTH HIWWTTTVKP KFKRCKYYFK LVANDTSYYY FEDGFYTEAE MNHQDKNLVY   120
FTFPWMNSID INKTPDWVND TVWYQIFPER FNNGDKENDP KNVKAWGFHT VSNDEFYGGD   180
LQGIINRLDY LADIGISGIY LTPIFEANTS HKYDTKDYMK IDPHFGDEKV FKNLVDTAHE   240
KGIRIMLDGV FNHCGNQFAP WLDVLKNGPD SKYFNWFMIN KWPFNKEDHN TNDGSFYSFA   300
FTSRMPKLNT NNPEVIKYLL DVVEYWVKNF DIDGIRLDVA NEISHRFCKD LRKLTKELKP   360
DFYILGELWH DAITWLHGDE FDGVMNYPLA TSLADYWVPF EKTNYDFECA INHNFTMYMQ   420
QTNDVLFNLL DSHDTNRLID KVKDIDIFYQ QLAVLFTMPG SPCIYYGTEI AMEGSYDPDC   480
RRCMPWEDID AGLFKDRIEI IKALIHLRKT NNAFKSRHYH FIEDKNNNRV IHYIKTDEDH   540
KQVEVILNCS KDSIVVQRKG NELFSLLNED TILKPKGVFI QQI                     583

SEQ ID NO: 95            moltype = AA  length = 575
FEATURE                  Location/Qualifiers
source                   1..575
                         mol_type = protein
                         organism = Clostridium thermocellum
SEQUENCE: 95
MKLEAIYHKP YSEFAFPVAP DTLVIRLRTA KNDVNTCILI YHEKYDTSQR GKVKMDKVAS    60
DGMFDYYEVE LNVGIKRIKY MFYLEDNYSI KWYSSDGFFD YMPQWGHFTY SYICKDDIFH   120
EVEWFRNSTI YQIFPDRFAK FPPDTENSGK RTIHGGNIKG IIDRFDHLVK LGVDVVYLNP   180
IFKSESYHRY DVVDYYEIDP MFGSKEELRE LMDLCHKNGI KVIFDGVFNH SGDKFFAFRD   240
VVEKGEKSKY ANWYFINSFP VQGYPRPNYE CFSFYGGMPK LNTGNPETAK YFLDVVKYWT   300
VEFGVDGWRL DAADEVDRKF WRKLRDMLKD LNKDVVLIGE IFDEASSWLW GDQFDSVINY   360
PLKAMINDLF AYRSIDVETF RNRISGYIMK FNKKVLSSLV NIISTHDTPR PLTLCNGDEK   420
RFEMAVVFQF TFPGVPLIYY GDEIGMEGEG DPDCRRPMIW DEAKWNKKTL ELYKFLIGLR   480
KRFDALRTGE YGELPVTGCN GILAYRRGRG ENGIIVAMNT LDRKENVVVE TGDSFDTVKA   540
FESLKDEERL NVDKKRINIC LNPFEWRIYK ACGEL                              575

SEQ ID NO: 96            moltype = AA  length = 655
FEATURE                  Location/Qualifiers
source                   1..655
                         mol_type = protein
                         organism = Thermobifida fusca
SEQUENCE: 96
MIGRFPILDV SPVVDIGTAK AVVGETFPVR ATVFREGHEA LGAGVVLYTP EGQRQPLVPL    60
REIAPGTDRY EAEVTVTSEG LWHFAIEAWS DPYATWCHDA RIKIPAGQDV ELMLEEGARL   120
LERAARRVPR RPALAEIAAA MRDGSRSAHE RLDLALSDLV RDELAERPLR ELVTRSQRFP   180
VMVSRRRALF GSWYEFFPRS EGAVLDTEDG EPRSGTFATA ARRLPAIADM GFDVVYIPPI   240
HPVGYSFRKG RNNSTVAQPG DPGSVWAIGS HEGGHDAIHP DLGTIDDFDA FVARARELGL   300
EIAMDLALQA SPDHPWVKEH PEWFTVRADG SIAYAENPPK KYQDIYPINF DKDPEGIFTE   360
VRRIVRYWMS HGVRIFRVDN PHTKPVAFWE RLLADIAATD PDVIFLSEAF TRPAMMHTLA   420
KIGFHQSYTY FTWRNTKQEL EEYLTELTGE AAAYMRPNFF VNTPDILHAY LQHGGRPAFE   480
VRAILAATLS PTWGMYSGYE LCENRALKPG SEEYLDSEKY QYKPRDWEAA EAAGITITPL   540
IRKLNSLRRS HPALQELRNL RFHYADQOPEI ICYSKRLAGA NHGADDTILV VANLDPHHTR   600
EATVWLDMPA LGFAPGDHIT VTDQLSGHSY HWVEANYVRL DPHVQTAHIF TVAPA        655

SEQ ID NO: 97            moltype = AA  length = 572
FEATURE                  Location/Qualifiers
source                   1..572
                         mol_type = protein
                         organism = Thermobifida fusca
SEQUENCE: 97
APSGNRDVIV HLFQWRWKSI ADECRTTLGP HGFGAVQVSP PQEHVVLPAE DYPWWQDYQP    60
VSYKLDQTRR GSRADFIDMV NTCREAGVKI YVDAVINHMT GTGSAGAGPG SAGSSYSKYD   120
YPGIYQSQDF NDCRRDITNW NDKWEVQHCE LVGLADLKTS SPVQDRIAA YLNELIDLGV   180
AGFRIDAAKH IPEGDLQAIL SRLKNVHPAW GGGKPYIFQE VIADSTISTG SYTHLGSVTE   240
```

```
FQYHRDISHA FANGNIAHLT GLGSGLTPSD KAVVFVVNHD TQRYEPILTH TDGARYDLAQ    300
KFMLAHPYGT PKVMSSYTWS GDDKAGPPMH SDGTTRPTDC SADRWLCEHR AVAGMVGFHN    360
AVAGQGIGSA VTDGNGRLAF ARGSAGYAAF NATNTAWTRT FTTSLPDGVY CDVANGTFVD    420
GVCDGPSYQV SGGKFTATVP ANGAVALHVE APGSCGPDGC GTPPGGGDDC TTVTARFHAT    480
VTTWYGQEVA VVGSIPELGS WQPAQGVRLR TDSGTYPVWS GAVDLPAGVG FEYKYVKLNP    540
DGTVEWEQGG NRIATVDDSG GGCSQNFYDS WR                                 572

SEQ ID NO: 98           moltype = AA   length = 825
FEATURE                 Location/Qualifiers
source                  1..825
                        mol_type = protein
                        organism = Anaerocellum thermophilum
SEQUENCE: 98
MLVRAYIDDF NEIVVVLSQM VHSVKKEDFK VFLNEEEIDI EKIDKIIPHS DNPAEAETRG     60
YEICEQKGKI RFVLKEGHFD YHRKPYKKPV FVIGEMNDWQ ISPEWEMTYS KLRGRYELIK    120
DLKEIKIGQK FKFAEGASQK LWYPPGFGND IVITEYFDRE TAFTNMIRII PSNRLLPNLK    180
YKVVYKSEHI WARPREILTR PEFFYPGELG IKYEPYGTYF KLWAPTAYKV KVKVFDESEN    240
FRFEKEMARS ENGTWNIYLT GDLKNHYYLY EVWHYNYDED EGFIVYEVPD PYSKASSSNS    300
QKSFIFDPAD TLIEGWQQDE FVKTIEKQQD AIIYEMHVRD FTIDKNSGVD EKFRGKFLGL    360
CQKSFYKEKF STGLLHLKEL GITHIHLLPI SDFGSVDDKN PDKKYNWGYD PVLYQCPEYW    420
YSTKSGGIEA LKELKTMIKT LHQNGIGVVM DVVFNHTYHT KGGKFSIFDK IVPGYFYRID    480
DYGDYSNATG CGNEIATEKP MVRKFILDTI IYWTEDFHID GFRFDLMGLI DTLTMRMIAK    540
EVRKRNPYAL IYGEGWVMGD SMCLLEERAT IESTAHHGYS IGLFNDRIRD SIRGDLDGFK    600
TGYMHGNLSD IERLKQGIRA AIDDDFAKEPD ECVNYVSCHD NLTLFDKAQK TMVGEDIFWI    660
DRVCRLANAI ILTSQGIPFL HGGVEFNRSK GGHPNTYNAG DNINKIDWSL KEKFYDTFKF    720
YCDLIKLRKE HVAFRMRSSG EIRKYLKFLP APDGIVAFLI SYPYDAWKKI IVAYNPFKEK    780
KVITLPEGVW KIKANDGIIF SEENELEAIG SFEISPVSLF IAYQK                    825

SEQ ID NO: 99           moltype = AA   length = 1104
FEATURE                 Location/Qualifiers
source                  1..1104
                        mol_type = protein
                        organism = Anaerocellum thermophilum
SEQUENCE: 99
DEKTTLIIHY YRYNEDYQGW NLWIWPVEPV GAEGKAYEFT SKDDFGVKAV VELPGKVTKV     60
GIIVRKGNWE AKDVAVDRFI SGISGSKEVW LIEGEEQIYT SQPQKTKPMT AFIDGLNTIV    120
VKLAKKADIL SNNRTQGFKV TAFYEEVPIK KVEPVLPKIN KNFKPEEAGY ELIDGGTKVK    180
FILKPGAGDF KFTDTSGKLD VYVSGTMNDW GGTASSEGKY KPLPAWKMTW NAEKGYYELV    240
KELGKDGVVI GAKFKFTSWD GTSAKWYPDG MGNDKVIEEL YTGNEKITKV DTFKITTEDE    300
LEPQVPYVVS KDSFKPTVAQ ARNILDNPKY YYKGNDLGCT YTKAYSAFRL WAPTAIGVIL    360
RLYDDYKTTK YKEYEMQQSF NGTWYLKING DLKGKYYQYE VWHASNSITD DTIRKYVVPD    420
PYSRATSANS ERTLIFDPKD TNPVGWEKDT FVTLKNQEDA IIYETHVRDF TIDASSGVRP    480
EFRGKYLGFT QTGAKGPNGV KTGIDHLKEL GITHVHLLPT YDFGSIDETN PDKGYNWGYD    540
PVLYQNVEGS YATNPNTIVR IKEYKQMVMA LHKAGIGIIQ DVVFNHTYQI GDAKFSIFDK    600
IVPGYFYRKD KDGNYSNASG CGNEIATEKP MVRKFIIDTL TYLTKEYHID GFRFDLMAAI    660
DRVTMAKAQE EVRKINPSAV IYGEGWLAGS TPLDSSLRME IGSFNQAGLH IGLFNDRIRE    720
AIRGNLDNES KGFMQGNYSF RLEDLKRGIQ GGLGDFAADP DECINYVSAH DNLTLWDKLQ    780
KSVPNEPDYI KDKMGRLANA IVLTAQGVPF LHGGVEFNRT KYMNHNSYNA GDKINKYNWN    840
LKVKWYNTFK YYQGLIALRK AHPAFRMTTA EDIQKYLTFI QTPKGTLGFR LTYPKDTWND    900
IIVVYNSTKK VQEEVTLPEGN WVVVANGDEV GTTPIKNLTN FVAGKALVAP ISMFVAYKSN    960
EFPQGFTKVT GKDPVSLESS STVTVPKVYG NGNIEVTFKV KVPHGTDDDV IYLAGSFGKA   1020
GLSDWNPGDK DGAIELVRLQ DGTYTVTVKL NAGETFYEKY TRGSWTTVEK GANKEEIENR   1080
KLTVKDEGGG KMIVSDTVLN WADK                                         1104

SEQ ID NO: 100          moltype = AA   length = 611
FEATURE                 Location/Qualifiers
source                  1..611
                        mol_type = protein
                        organism = Anaerocellum thermophilum
SEQUENCE: 100
MRKPHIIEAI IGNTKVLGQL DSNGILQRFY WPAVDYYQQL KLFLAAVFLD GLVFFEDENF     60
KIKSGFVDDF VYFFEYKIAD KTIFQLDFVD FETDSLVRLW ETGFEDFYVF LEPMINSSSL    120
FNAAKVDKEN EIVYAYFKGT YIGLAFENKI KSFTVKNGID DANDNQLEGW NEATNPQIAV    180
KLKNTGKVVC FLAFGNSKDE IYQKLSYLKQ KGYDEVYRQN KAFWEKKFSK VKLICTQDPK    240
DMQLQKRSAY VFYVLQNSKT GGILAASEVD EKFFHCGGYG FVWGRDAAFI VSAMDELGLS    300
REVEKFFGFK FSCQEKEGFW DQRYYTDGSL APSWGIQIDE TASVVWGFLE HCEKQNSLHL    360
IDLHKEQLKK ALLFLIAAVD SEKGVIFRSF DLWEEREGIH LYSNASIYAA LKKAKKYFPE    420
LESEIEKKLK AIKNQMATRF YSPKLSRYVR STDVRIPHEE FLKLPEENRY MQKDERYEIT    480
YYFKKQDEVV DISMLGIYYP FEMVDSSDKA FKATILAIER ECQNSIVGGY KRYSDDRYIG    540
GNPWILTTLW LAIYYKKTGQ IDRAEKLFEW AKAHSLPNGL FPEQVDRITG KPAWVVPLAW    600
SHAMYVLYLY E                                                         611

SEQ ID NO: 101          moltype = AA   length = 529
FEATURE                 Location/Qualifiers
source                  1..529
                        mol_type = protein
                        organism = Streptomyces avermitilis
SEQUENCE: 101
MTSFRPAPAW LADAVFYQIY PQSFADSDGD GIGDFNGIVQ RLDHLVWLGV TAVWLNPCFV     60
```

```
SPFRDAGYDV SDYLNVAPRY GSADDLAELV DEAGRRGIRV LLDLVAGHTS DEHPWFTASA   120
NDPDDHRYIW APEGRPDGFV TSPGTRPGAY LPNFFDTQPA LNFGYGRKNP AEPWRQPVDA   180
AGPRANREAL RTIMDHWLGL GLAGFRVDMA ASLVKDDPGR TETARIWTEL RHWLDTAHPD   240
AVLLSEWGEP EVSVPAGFHT DFFLQFGGAT DGLPLRSLWS NGDGTVNEAW DPLDCFFDAS   300
GKGSPRPFVE AWRKASDAVG ATGFVSLPTA NHDFSRLNCG PRTAEQLPAA FAFQLTWPTL   360
PAIYYGDEIG MRYVGGLPDK EGSVLGPRYN RAGSRTPMQW DDGPGAGFST APADRLYLPL   420
DPSPDRPTVA AQRADDGSLL HLVRRLVALR ASTPALGSSG SVEVLHTGYP FVYVRGGRYL   480
VVVNPQRNEV RCPYDATREA RALEASGVRV GNGTIEAEGF SYGVFDLGR              529

SEQ ID NO: 102          moltype = AA  length = 431
FEATURE                 Location/Qualifiers
source                  1..431
                        mol_type = protein
                        organism = Streptomyces avermitilis
SEQUENCE: 102
SPPGTKDVTA VLFEWKFDSV ARECTNTLGP AGYGYVQVSP PAEHIQGSQW WTSYQPVSYK   60
IAGRLGDATA FQNMINTCHT AGVKVVVDTV VNHMSAGSGT GTGGSAYTKY NYPGLYSSYD   120
MDDCTATITD YTNRANVQNC ELVGLADLDT GEEYVRKTIA GYMNTLLGYG ADGFRVDAVK   180
HIPAADLANI KSRLTNPSVY WKQEVIYASG EAVQPTEYTG NGDVQEFRYA YDLKRVFNNE   240
NLAYLKNYGE GWGYLNSSVA GVFVDNHDTE RNGSTLNYKD GANYTLANVF MLAYPYGAPD   300
INSGYEWSDA DAGPPGGGTV NACWQDGWKC QHAWPEIKAM VAFRNATRGE SVTNWWDNGG   360
DAIAFGRGAK GYVAINHESG SLTRTYQTSL TAGTYCNVQN NTGVTVDSSG RFTATLGANT   420
ALALYSGKST C                                                       431

SEQ ID NO: 103          moltype = AA  length = 503
FEATURE                 Location/Qualifiers
source                  1..503
                        mol_type = protein
                        organism = Saccharomycopsis fibuligera
SEQUENCE: 103
LPLQEGPLNK RAYPSFEAYS NYKVDRTDLE TFLDKQKDVS LYYLLQNIAY PEGQFNDGVP   60
GTVIASPSTS NPDYYYQWTR DSAITFLTVL SELEDNNFNT TLAKAVEYYI NTSYNLQRTS   120
NPSGSFDDEN HKGLGEPKFN TDGSAYTGAW GRPQNDGPAL RAYAISRYLN DVNSLNKGKL   180
VLTDSGDINF SSTEDIYKNI IKPDLEYVIG YWDSTGFDLW EENQGRHFFT SLVQQKALAY   240
AVDIAKSFDD GDFANTLSST ASTLESYLSG SDDGGFVNTDV NHIVENPDLL QQNSRQGLDS   300
ATYIGPLLTH DIGESSSTPF DVDNEYVLQS YYLLLEDNKD RYSVNSAYSA GAAIGRYPED   360
VYNGDGSSEG NPWFLATAYA AQVPYKLVYD AKSASNDITI NKINYDFFNK YIVDLSTINS   420
GYQSSDSVTI KSGSDEFNTV ADNLVTFGDS FLQVILDHIN DDGSLNEQLN RNTGYSTSAY   480
SLTWSSGALL EAIRLRNKVK ALA                                          503

SEQ ID NO: 104          moltype = AA  length = 497
FEATURE                 Location/Qualifiers
source                  1..497
                        mol_type = protein
                        organism = Saccharomycopsis fibuligera
SEQUENCE: 104
VPVELDKRNT GHFQAYSGYT VARSNFTQWI HEQPAVSWYY LLQNIDYPEG QFKSAKPGVV   60
VASPSTSEPD YFYQWTRDTA ITFLSLIAEV EDHSFSNTTL AKVVEYYISN TYTLQRVSNP   120
SGNFDSPNHD GLGEPKFNVD DTAYTASWGR PQNDGPALRA YAISRYLNAV AKHNNGKLLL   180
AGQNGIPYSS ASDIYWKIIK PDLQHVSTHW STSGFDLWEE NQGTHFFTAL VQLKALSYGI   240
PLSKTYNDPG FTSWLEKQKD ALNSYINSSG FVNSGKKHVS ESPQLSSRGG LDSATYIAAL   300
ITHDIGDDDT YTPFNVDNSY VLNSLYYLLV DNKNRYKING NYKAGAAVGR YPEDVYNGVG   360
TSEGNPWQLA TAYAGQTFYT LAYNSLKNKK NLVIEKLNYD LYNSFIADLS KIDSSYASKD   420
SLTLTYGSDN YKNVIKSLLQ FGDSFLKVLL DHIDDNGQLT EEINRYTGFQ AGAVSLTWSS   480
GSLLSANRAR NKLIELL                                                 497

SEQ ID NO: 105          moltype = AA  length = 747
FEATURE                 Location/Qualifiers
source                  1..747
                        mol_type = protein
                        organism = Saccharomyces cerevisiae
SEQUENCE: 105
FPTALVPRGS SSSNITSSGP SSTPFSSATE SFSTGTTVTP SSSKYPGSKT ETSVSSTTET   60
TIVPTTTTTS VITPSTTTIT TTVCSTGTNS AGETTSGCSP KTITTTVPCS TSPSETASES   120
TTTSPTTPVT TVVSTTVVTT EYASTSTKQG GEITTTFVTK NIPTTYLTTI APTSSVTTVT   180
NFTPTTITTT VCSTGTNSAG ETTSGCSPKT VTTTVPCSTG TGEYTTEATA PVTTAVTTTV   240
VTTESSTGTN SAGKTTTSYT TKSVPTTYVF DFGKGILDQS CGGVFSNNGS SQVQLRDVVL   300
MNGTVVYDSN GAWDSSPLEE WLQRQKKVSI ERIFENIGPS AVYPSILPGV VIASPSQTHP   360
DYFYQWIRDS ALTINSIVSH SADPAIETLL QYLNVSFHLQ RTNNTLGAGI GYTNDTVALG   420
DPKWNVDNTA FTEPWGRPQN DGPALRSIAI LKIIDYIKQS GTDLGAKYPF QSTADIFDDI   480
VRWDLRFIID HWNSSGFDLW EEVNGMHFFT LLVQLSAVDR SLSYFNASER SSPFVEELRQ   540
TRRDISKFLV DPANGFINGK YNYIVETPMI ADTLRSGLDI STLLAANTVH DAPSASHLPF   600
DIDDPAVLNT LHHLMLHMRS IYPINDSSKN ATGIALGRYP EDVYDGYGVG EGNPWVLATC   660
AASTTLYQLI YRHISEQHDL VVPMNNDCSN AFWSELVFSN LTTLGNDEGY LILEFNTPAF   720
NQTIQKIFQL ADSFLVKLKA TWEQTGN                                      747

SEQ ID NO: 106          moltype = AA  length = 621
FEATURE                 Location/Qualifiers
source                  1..621
```

```
                            mol_type = protein
                            organism = Aspergillus niger
SEQUENCE: 106
NVISKRATWD SWLSNEATVA RTAILNNIGA DGAWVSGADS GIVVASPSTD NPDYFYTWTR     60
DSGLVLKTLV DLFRNGDTSL LSTIENYISA QAIVQGISNP SGDLSSGAGL GEPKFNVDET    120
AYTGSWGRPQ RDGPALRATA MIGFGQWLLD NGYTSTATDI VWPLVRNDLS YVAQYWNQTG    180
YDLWEVNGSS FFTIAVQHRA LVEGSAFATA VGSSCSWCDS QAPEILCYLQ SFWTGSFILA    240
NFDSSRSAKD ANTLLLGSIH TFDPEAACDD STFQPCSPRA LANHKEVVDS FRSIYTLNDG    300
LSDSEAVAVG RYPEDTYYNG NPWFLCTLAA AEQLYDALYQ WDKQGSLEVT DVSLDFFKAL    360
YSDATGTYSS SSSTYSSIVD AVKTFADGFV SIVETHAASN GSMSEQYDKS DGEQLSARDL    420
TWSYAALLTA NNRRNVVPSA SWGETSASSV PGTCAATSAI GTYSSVTVTS WPSIVATGGT    480
TTTATPTGSG SVTSTSKTTA TASKTSTSTS STSCTTPTAV AVTFDLTATT TYGENIYLVG    540
SISQLGDWET SDGIALSADK YTSSDPLWYV TVTLPAGESF EYKFIRIESD DSVEWESDPN    600
REYTVPQACG TSTATVTDTW R                                             621

SEQ ID NO: 107          moltype = AA  length = 593
FEATURE                 Location/Qualifiers
source                  1..593
                        mol_type = protein
                        organism = Aspergillus oryzae
SEQUENCE: 107
VQPVLRQATG LDTWLSTEAN FSRQAILNNI GADGQSAQGA SPGVVIASPS KSDPDYFYTW     60
TRDSGLVMKT LVDLFRGGDA DLLPIIEEFI SSQARIQGIS NPSGALSSGG LGEPKFNVDE    120
TAFTGAWGRP QRDGPALRAT AMISFGEWLV ENSHTSIATD LVWPVVRNDL SYVAQYWSQS    180
GFDLWEEVQG TSFFTVAVSH RALVEGSSFA KTVGSSCPYC DSQAPQVRCY LQSFWTGSYI    240
QANFGGGRSG KDINTVLGSI HTFDPQATCD DATFQPCSAR ALANHKVVTD SFRSIYAINS    300
GRAENQAVAV GRYPEDSYYN GNPWFLTTLA AAEQLYDALY QWDKIGSLAI TDVSLPFFKA    360
LYSSAATGTY ASSTTVYKDI VSAVKAYADG YVQIVQTYAA STGSMAEQYT KTDGSQTSAR    420
DLTWSYAALL TANNRRNAVV PAPWGETAAT SIPSACSTTS ASGTYSSVVI TSWPTISGYP    480
GAPDSPCQVP TTVSVTFAVK ATTVYGESIK IVGSISQLGS WNPSSATALN ADSYTTDNPL    540
WTGTINLPAG QSFEYKFIRV QNGAVTWESD PNRKYTVPST CGVKSAVQSD VWR           593

SEQ ID NO: 108          moltype = AA  length = 579
FEATURE                 Location/Qualifiers
source                  1..579
                        mol_type = protein
                        organism = Rhizopus oryzae
SEQUENCE: 108
ASIPSSASVQ LDSYNYDGST FSGKIYVKNI AYSKKVTVIY ADGSDNWNNN GNTIAASYSA     60
PISGSNYEYW TFSASINGIK EFYIKYEVSG KTYYDNNNSA NYQVSTSKPT TTTATATTTT    120
APSTSTTTPP SRSEPATFPT GNSTISSWIK KQEGISRFAM LRNINPPGSA TGFIAASLST    180
AGPFDYYAWT RDAALTSNVI VYEYNTTLSG NKTILNVLKD YVTFSVKTQS TSTVCNCLGE    240
PKFNPDASGY TGAWGRPQND GPAERATTFI LFADSYLTQT KPAIFKDLDY    300
VVNVWSNGCF DLWEEVNGVH FYTLMVMRKG LLLGADFAKR NGDSTRASTY SSTASTIANK    360
ISSFWVSSNN WIQVSQSVTG GVSKKGLDVS TLLAANLGSV DDGFFTPGSE KILATAVAVE    420
DSFASLYPIN KNLPSYLGNS IGRYPEDTYN GNGNSQGNSW FLAVTGYAEL YYRAIKEWIG    480
NGGVTVSSIS LPFFKKFDSS ATSGKKYTVG TSDFNNLAQN IALAADRFLS TVQLHAHNNG    540
SLAEEFDRTT GLSTGARDLT WSHASLITAS YAKAGAPAA                           579

SEQ ID NO: 109          moltype = AA  length = 644
FEATURE                 Location/Qualifiers
source                  1..644
                        mol_type = protein
                        organism = Clostridium thermocellum
SEQUENCE: 109
MANTYFNDAI IGNSGMLVCL TRNGELTRLF WPNIDYPQHF EKMATGIFYT GQKNSTSWFY     60
EDNWHHTQYY VEDTNILKTI CEDGGRGLRV EQTDFVLKDR DVMVRRYVIE NIGPNEVDLG    120
FVQYSSTVST TPELRSTLFD FNVDALIHYR HNYYISISSD SEVVQFQLGN NAFDCARYTE    180
LYGYDSIGMM KDGAMSFNIG KIEPGGKKTF NLFICASHTL KGVKELVRWC RKMNVDEEYE    240
KTRKYWLDFL KNARLIVTGD KNIDNLYKRS ILVFKLMSDE RTGGLLASAE IDEGFTRCGR    300
YAYCWGRDAA FITGALDTAG LTEAVDKFYQ WAVMTQDDDG SWQQRYHMDG NLAPSWGLQI    360
DETGTLIWGM LKHYEVTKNI DFLKSMWESI KKGVEFLTRF IDSDTGLPAP SYDLWEERVG    420
EHTYSSAAVY AGIKAGAEAA RILGASEELI EKWEKAASDM KASIEKNFWR DEAGRFIRSV    480
RTKLNPWGSE HSPYTTVIKV NEKGYFRDVT LEDWTIDVSL LGVSIPFGVF DVHDERVKKT    540
VEAIERALTS HPVGGIKRYE NDNYIGGNPW VLATLWVALY YIEIKEYEKA KDYLRWATKS    600
CTALGLLPEQ VSKDNGEPCW VIPLTWSHAM YVLVLAGLKE AGVL                    644

SEQ ID NO: 110          moltype = AA  length = 644
FEATURE                 Location/Qualifiers
source                  1..644
                        mol_type = protein
                        organism = Clostridium thermocellum
SEQUENCE: 110
MQKSYYNNAI TGNSSMLACF SERAELLRLF WPDIDYIQNL DKMFLGLFEK NKTGSTVWLN     60
DIRCEHHQEY LPDSNIIKNM VTNFFDGYKV VLYDFVHPEM DVLVRRFEIE NLRGESRELG    120
LMSFSAATSS DSEVACSLFD FMNEALVHYK PDSYIAVTSD IPVYQFQIGN NANDAAVNTY    180
LYGKDDIGMM KDAAISWDLG VFQPHAVKTT NVYLCAADTL KSCKALVRRV KTVGGLTAFR    240
ETGRYWKDYL EKTTKLKSGN TLLDDLYKRS LLVFRLMYSK KSGGLMAAPE VDEYFTKCGK    300
YAYCWGRDAA FITGALDIGG LCESVDHFYK WAVNVQDEDG SWQQRYHMNG NLGPCWGLQV    360
```

```
DETGTIIWGM LNHYNYTKNT DFLKSVWDSV KAAADFLVRF IDSETGLPRP SFDLWEERYG   420
EHAYSSASVC AGLKSASEMA RILGKPSQEY IQWETTADSI KKAIVKYFWK EDYRRFIRSI   480
RVKLNGFGQE PSSDTMLIKV NPKGYVRDVT KEDWIVDVSL VGLGIPFEIF ELNDPMLRDT   540
VSLIEQVLTA QGVGGIKRYE NDTYIGGNPW ILTTLWIALY HAKSGNYKKA KEYLIWAASG   600
KTELGLLPEQ INRDTGKPEW IIPLTWSHAM YVHVYSELIN AGVL                   644

SEQ ID NO: 111           moltype = AA  length = 608
FEATURE                  Location/Qualifiers
source                   1..608
                         mol_type = protein
                         organism = Arxula adeninivorans
SEQUENCE: 111
DSCHTFTLAN SPPDDKAVAL SSYSYCGGYL SASAFVKNLS YDKLVTLYWT NADNKSTPLN    60
AGSLDYVKAA SDDQSWELWS LNVTTVPDGV DALLNITYVA ASIGKTNSQQ LNVQVEATGD   120
PIPTPQIPTI YKPYASPSDF SDDITNWLKP SNDSQTGIAK SFLFNNINIP GAAPGTVIAA   180
QSYSEPDYAY TWVRDASLVM DVVNRLYSSA KSEEKRQLYE KILFQYAKAG AQEQNDPTAI   240
SGMGEPKFYL NNTAFTGSWG RPQNDGPATR AITLIEFANA YLANGGSQDT VREQLYDSDK   300
YPQVAPIKKD LQFVASNMES PSFDLWEEEE SAHFYTRLVQ RKALLLGADF ANDMGDHELS   360
DKLKTQASKL SDTLPEFWDS ARQLILYEYG PVLRGKYSYK DISVVLGVMH GYANDNVFSY   420
TNDQILATAY QVSTSFLDVY KVANTTSDES GKPLGIPVGR YPEDVYDGVG TSQGNPWYLT   480
TMAMAEFLYR SVQEFEDAGS IIISDTSLPF WKYFASSVDH KAGAKYNKND QSFKTSLKSL   540
TGWGDAFMRR AKYHTPSSGH MSEEFNRTTG EPRGAKDLTW SYASLLSAAF AREELRNQKN   600
YLTNVADL                                                           608

SEQ ID NO: 112           moltype = AA  length = 595
FEATURE                  Location/Qualifiers
source                   1..595
                         mol_type = protein
                         organism = Hormoconis resinae
SEQUENCE: 112
APTELKARDL SSFIASERAI ALQGALNNIG PDGSAVPGAG AGFVVASPSK ANPDFYTWS     60
RDSALTKMI IDEFILGNTT LQTIIEQYIH AQAVLQTVSN PSGTFLPDGV GLGEPKFMVD   120
GTRFNGPWGR PQRDGPALRA IALMTYSNWL IKNGQFAEAK TKIWPIIAND LSYVGQYWNQ   180
SGFDLWEETY ASSFFTIQNQ HRALVEGAQL AHDLGVCTG CDQAPEVLCF LQSFWNGKYI   240
VSNINVNNGR TGLDGNSILG AISTFDIDAY CDSPTLQPCH SQSLANFKVL TDTFRNLYTI   300
NAGIPEGQGV AVGRYAEDVY MGGNPWYLIT TAAAEFLYDA VAQWKARHVL TVDETSLAFF   360
KDIYPEVTVR EYKSGNANSP FAQIMDAVTA YADSYVAIAE KYIPSNGSLS EQFNRDTGTP   420
LSAIDLTWSY AAFITMSQRR AGQYPSSWGS RNALPPPTTC SASSTPGIYT PATAAGAPNL   480
TSSCQVSITF NINATTYYGE NLYVIGNSSD LGAWNIADAY PLSASAYTQD RPLWSAAIPL   540
NAGEVISYQY VRQEDCDQPY IYETVNRTLT VPACGGAAVT TDDAWMGPVG SSGNC         595

SEQ ID NO: 113           moltype = AA  length = 601
FEATURE                  Location/Qualifiers
source                   1..601
                         mol_type = protein
                         organism = Aureobasidium pullulans
SEQUENCE: 113
LPSPESIQER ATGSLSSWLS SENTVALQGV LNNIGASGSK ASGASAGVVV ASPSKSNPDY    60
FYTWTRDSAL VFKALVDQLI AGNKSLEPLI QQYISAQAKL QTVNNPSGGL CSGGLAEPKF   120
EVDLTPFTGA WGRPQRDGPA LRATAMIAYS RYLIANGNTT TVNNIIWPIV QNDLSYVTQY   180
WNQTTFDLWE EINSSSFFTT AVQYRALVEG NNLATQLSKS CPNCVSQAPL VLCFLQSYWT   240
GSYALSNTGG GRSGKDANSI LTSIHIFDPA ASCDSTTFQP CSDKALANHK VVTDSFRSIY   300
SINQGIAQGS GVAVGRYPED SYYNGNPWYL NTFAAAEQLY DAVYQWKKIG SISITSISLP   360
FFKDVYSSAA VGTYSSSTVT FTSIVNAVQT YADSYMSIAQ KYTPSNGALS EQYNRADGTP   420
LSAVDLTWSY AAFLTAYNAR ANVLPASWGA SSAKLPNSCS SGSATGPCAA ATNTNWGNPG   480
SPSTGTPTTT TGGSCTTPTS IAVTFNEQKT TSYGENIYIV GSIPALGNWN TANAVALSAS   540
KYTSSNPLWT VTINFATGTS FNYKYIKKAQ DGSVTWESDP NRSYTVTGNC AGTATENDSW   600
R                                                                  601

SEQ ID NO: 114           moltype = AA  length = 718
FEATURE                  Location/Qualifiers
source                   1..718
                         mol_type = protein
                         organism = Bacillus subtilis
SEQUENCE: 114
MVSIRRSFEA YVDDMNIITV LIPAEQKEIM TPPFRLETEI TDFPLAVREE YSLEAKYKYV    60
CVSDHPVTFG KIHCVRASSG HKTDLQIGAV IRTAAFDDEF YYDGELGAVY TADHTVFKVW   120
APAATSAAVK LSHPNKSGRT FQMTRLEKGV YAVTVTGDLH GYEYLFCICN NSEWMETVDQ   180
YAKAVTVNGE KGVVLRPDQM KWTAPLKPFS HPVDAVIYET HLRDFSIHEN SGMINKGKYL   240
ALTETDTQTA NGSSSGLAYV KELGVTHVEL LPVNDFAGVD EEKPLDAYNW GYNPLHFFAP   300
EGSYASNPHD PQTRKTELKQ MINTLHQHGL RVILDVVFNH VYKRENSPFE KTVPGYFFRH   360
DECGMPSNGT GVGNDIASER RMARKFIADC VVYWLEEYNV DGFRFDLLGI LDIDTVLYMK   420
EKATKAKPGI LLFGEGWDLA TPLPHEQKAA LANAPRMPGI GFFNDMFRDA VKGNTFHLKA   480
TGFALGNGES AQAVMHGIAG SSGWKALAPI VPEPSQSINY VESHDNHTFW DKMSFALPQE   540
NDSRKRSRQR LAAAIILLAQ GVPFIHSGQE FFRTKQGVEN SYQSSDSINQ LDWDRRETFK   600
EDVHYIRRLI SLRKAHPAFR LRSAADIQRH LECLTLKEHL IAYRLYDLDE VDEWKDIIVI   660
HHASPDSVEW RLPNDIPYRL LCDPSGFQED PTEIKKTVAV NGIGTVILYL ASDLKSFA     718

SEQ ID NO: 115           moltype = AA  length = 710
```

```
FEATURE                 Location/Qualifiers
source                  1..710
                        mol_type = protein
                        organism = Bacillus licheniformis
SEQUENCE: 115
MPGISRPFEA YLDEMRTITV LVPKSRASSC SPPFLLEDDQ GERIELSVKA QVELEEQFKY    60
VLESSCTVPF GRVHKVCCEE SVWTDLQIGS VTRSAAFDKA FFYDGRLGAF YSKGSTLFKV   120
WAPTASAAAI KLEDPDSLQT NTFQMMRRKK GVFEVTVEGD LNGWSYLYEL YVNGKPLLTV   180
DPYAKAVTAN GEKGVVLDPE EVKVEKHRAP RLHSPCDAVI YEVHIRDFSI HEDSGMRHKG   240
KYVAFTEDGT ETSGGFSTGI AYLKELGVTH IEVLPFHDFA GVDELSPDQS YNWGYNPLHF   300
NAPEGSYSLD PQNPKCRITE LKTMIQSLHK HGFSVIMDAV YNHVYKRETS PFEKTVPGYF   360
FRHNEYGFPS DGTGVGNDIA SERLMVRKYI LDSVRYWLEE YDVDGIRFDL MGILDIETVR   420
QISTLAENVK PGVPLFGEGW DLNTPLDSGQ KATLQNAGKV PAVGFFNDRF RNAVKGSTFE   480
LSDRGYALGD TGKKAALQHG IAGSPGFLQP AQSINYVECH DNHTFWDKMA LCFEEDADTK   540
RLRQRLAVSI VLLSQGVPFL HAGQEFCRTK NGDSNSYRSG DDINKLDWEK RAELCEDVEY   600
VRQLIRLRRS HPAFRLQKEE EVKEHLSFMD GTGEVTAYKL KNIAAIDPWN EIIVVHCPFA   660
KKETLKLPDQ KQYLLHCDPF TFFNGKVQAE KRLRLNGIGT YVLYEPKGIF             710

SEQ ID NO: 116          moltype = AA  length = 918
FEATURE                 Location/Qualifiers
source                  1..918
                        mol_type = protein
                        organism = Oryza sativa
SEQUENCE: 116
MAVGEECAAA VASQGFVSDA RAYWVTRSLI AWNVNDQDTS LFLYASRDAT MHVSDGAIHG    60
YDSKIELEPE HASLPDNVAE KFPFIRSYRT FRVPSSVDVT SLVKCQLAVA SYDAHGRHQD   120
VTGLQLPGVL DDMFAYTGPL GAVFSDKDVD LYLWAPTAQD VRVCFYDGPA GPLLQTVQLK   180
ELNGVWSVTV PRYRENQYYL YEVKVYHPST SQVEKCLADD PYARGLSANG TRTWLVDINS   240
ETLKPASWDE LSDEKPNLES FSDISIYELH IRDFSAHDST VDCNSRGGFR AFTFQDSAGI   300
RHLRKLSAAG LTHVHLLPSF HFASVDDNKS NWKFVDEAQL AKLPPGSDEQ QAAIVSIQQE   360
DPYNWGYDPV LWGVPKGSYA SNPDGPSRII EYRQMVQALN RIGLRVVMDV VYNHLDSSGP   420
FGVSSVLDKI VPGYYLRRNV NGQIENSAAM NNTASEHFMV DRLIVDDLLN WAINYKVDGF   480
RFDLMGHIMK STMFTVMSIC TISTIIKIKD VFADTLIRAK SAIRSLTRDV HGVDGSKIYL   540
YGEGWDFGEV AQNKRGINAS QINMSGTGIG SFNDRIRDSV NGGNPFGNPL QQGFSTGLFL   600
EPNGYYQGNE ADTRRELATY ADHIQIGLAG NLKDYVLRTH TGEAKKGSDI YTFDGSPVGY   660
TSSPVETINY VSAHDNETLF DIVSIKTPIG LSIDEKCRIN HLASSMIALS QGIPFFHAGD   720
EILRSKSLDR DSYNSGDWFN KLDFTYETNN WGVGLPPRDK NEENWHLIKP RLENPSFRPL   780
KNHILSVFDN FVDILKIRYS SPLFRLSTAS DIEQRVRFHN TGPSMVPGVI VMSIKDAQNE   840
KCKMAQLDKN FSYVVTIFNV CPHEVSIEIH DLASLGLELH PIQVNSSDAL VRQSAYEASK   900
GRFTVPRRTT AVFVQPRC                                                918

SEQ ID NO: 117          moltype = AA  length = 963
FEATURE                 Location/Qualifiers
source                  1..963
                        mol_type = protein
                        organism = Triticum aestivum
SEQUENCE: 117
MPMPMRTMLL RHLSPAPALP NPRRSSASSP QRRPARARPP PLHSARATAL RARRTPMAAG    60
ETGASVSVSA AEAEAEATQA FMPDARAYWV TSDLIAWNVS EQEAASVYLY ASRTAAMGLS   120
PSNGGIQGYD SKVELQPESA GLPETVTQKF PFISSYRAFR VPSSVDVASL VKCQLVIASF   180
GADGKHVDVT GLQLPGVLDD IFAYTGPLGA VFREDSVSLH LWAPTAQDVS VCFFDGPAGP   240
VLETVQLKES NGVWSVTGPR EWENRYYLYE VDVYHPTKAQ VLKCLAGDPY ARGLSANGAR   300
TWLVDINNET LKPASWDELA DEKPLDSFS DITIYELHIR DFSAHDGTVD SDSCGGFRAF   360
AYQASAGMQH LRKLSDAGLT HVHLLPSFHF AGVDDIKSNW KFVDECKLAT FPPGSDMQQE   420
AVVAIQEEDP YNWGYNPVLW GVPKGSYASD PDGPSRIIEY RQMVQALNRI GLRVVMDVVY   480
NHLDSSGPCG ISSVLDKIVP GYYVRRDTNG QIENSAAMNN TASEHFMVDR LIVDDLLNWA   540
VNYKIDGFRF DLMGHIMKHT MMRAKAALQS LTRDAHGVDG SKIYLYGEGW DPAEVARNQR   600
GINGSQLNMS GTGIGSFNDR IRDAVNGGNP FGNPLQQGFN TGLFLEPNGF YQGNEADTRR   660
SLATYADQIQ IGLAGNLRDY VLITHTGETK KGSEIHTFDG LPVGYTSSPI EIINYVSAHD   720
NETLFDVISV KTPMNLSVDE RCRINHLASS MMALSQGIPF FHAGDEILRS KSIDRDSYNS   780
GDWFNKLDFT YETNNWGVGL PPSEKNEDNW PLMKPRLENP SFKPAKGHIL AALDSFVDIL   840
KIRYSSPLFR LSTASDIKQR VHFHNTGPSS VPGVIVMGIE DARDEKPEMA QLDANFSYVV   900
TVFNVCPHEV SMDIPALASM RLELHPVQVN SSDALVGKSV YEAATGRFTV PRRTVSVFVE   960
PRC                                                                963

SEQ ID NO: 118          moltype = AA  length = 647
FEATURE                 Location/Qualifiers
source                  1..647
                        mol_type = protein
                        organism = Clostridium phytofermentans
SEQUENCE: 118
MDEFWNSIDG EKQYYYDGND LGCTYTNRST KLKVWAPTAS MVVVNLYQNG NAGKPYITEI    60
MKKEESGIWS VCLLGDEGV YYTYLVTVDG QTKEAVDPYA RTTGLNGKRA MILDLEKTNP   120
TGFLEDTKPK FDSFLDAVIY ELHIRDLSME SDSGIKEKGK LLGLTELNTR NSDGLTTGLS   180
HILDLGVTHI HLLPCFDYAS VDEENSSIFN WGYDPENYNV VEGSYSTNPY DGAVRVKEFK   240
TLVQSLHENG LRVIMDVVYN HTMKTEESNF NKIVPDYYYR KVGDKFSDAS ACGNETASER   300
LMVRKFIVDS IIYWAKEYHI DGFRFDLMGI HDIETMNEVR KVLDQIDPSI ILYGEGWVGG   360
DSPLPAGQRA MKANMSMLPG IAAFSDDFRD LGKGSVFLAE EKGFATGDSD KKESVKFGVV   420
ASTLHPQIDY KKVNYSDSPW ALEPAQCINY VSAHDNYTLW DKIACSCKED TYEIRVKKNK   480
```

```
LCAAIVFTSQ GIPFLQAGEE MLRNKPSSEI AGEFVENSYN SSDSVNCIKW SNKANVIDVV    540
SYYEGLIRFR KEHKALRMQS AKEISKRLTF LPEEREDVIS YLIQGDLVDK TLCVIYNSSE    600
EKVTIRLPES DWTVYIDGNN SGVEPLYEVK GTTVEVEPIS CMVLVKD                 647

SEQ ID NO: 119          moltype = AA   length = 1764
FEATURE                 Location/Qualifiers
source                  1..1764
                        mol_type = protein
                        organism = Streptomyces avermitilis
SEQUENCE: 119
ATPPAPPSDA KLAAEPARHD ATREQFYFVM PDRFANGDTS NDKGGLTGSR LSTGYDPTDK     60
GFYQGGDLKG LTRKLDYIKG LGTTSIWLAP IFKNQPVQGT GKDASAGYHG YWITDFTKVD    120
PHFGTNKDLE TLISKAHAKG MKVFFDVITN HTADVVDYEE KSYGYLSKGA FPYLTKDGRP    180
FDDAGYTDGP RKFPAVDGDS FPRTPAVAAR KKNAKVPSWL NDPTMYHNRG DSTFAGESST    240
HGDFSGLDDL WTERPEVVRG MEKIYEKWVR DFGIDGFRID TVKHVNTEFW TQWATALDAY    300
AKKRGKDDFF MFGEVYSADT SVTSPYVTQG RLDSTLDFPF QDAARSYASQ GGSAKKLASV    360
FGDDYKYTTD KANAYEQVTF LGNHDMGRIG YFLNQDNPKA TDAELLRKDR LANELMFLSR    420
GNPVVYYGDE QGFTGSGGDK DARQTMFASK VADYLDDDEI GTDRGHASDA YDTSAPLYKE    480
IAALSKLRKD NPALADGIQT ERYAADGAGV YAFSRTDART GTEYVVAVNN ADKASAATFA    540
TGSADTAFKG IHGTDDVLKS DADKKITVTV PAGAAVVLKA AGRPGTPAAK PSLTLKAPDA    600
GATGTVELSA DVDGGRLNRV VFAAQVGNAK WRTLGSADHA PYRVTQTIGK DVPAGTALRY    660
KAVVIDAAGR TASATAASTT GTPPAAETPT ASSRDYAIVH YKRPDGDYTD WRLYAWGDLA    720
DGESTTWPAG HDFVGRDAYG AFAYVKLKPG ASTVNFLVID KDGDKDVSAD RTIDVTKAGE    780
VWVEQGKETV RTERPDYPAQ DKTKAVIHYH RADGDLTGWG LHVWTGAATP TDWSKPLEPV    840
RTDAYGAVFE VPLTDGATSL SYIIHKGDEK DLSADRSLDL TADGHEVWLL NGQENHLLPQ    900
PAGSAAALDL TTSAKAVWIDR NTVAWNGSDA AASTQLLSSR DGSIAVKDGS LTSDDERWLR    960
LSKTSLTDAQ KAAFPHLKSY TAWSVDPRDR DRVREALAGQ VVASQRAANG AVLAATGVQL   1020
AGVLDDLYDA TKADLGPTFR GGHPTLAVWA PTAQSVSLEL DGAHVRMKRN NATGVWSVTG   1080
PASWKGKPYR YVVKVWAPTV RKVVTNKVTD PYSVALTTDS ERSLVVDLDD RSLAPSGWSS   1140
LKKPKAVPLR DAEIQELHIR DFSVADRTVP AKDRGTYLAF TDKNSDGSRH LRQLAESGTS   1200
YVHLLPAFDI ATIAEKKSGQ QATDCDLASY AADSEKQQEC LTAVAAKDAY NWGYDPYHYT   1260
VPEGSYATDA NGTRRTVEFR RMVKSLNQDG LRVVMDVVYN HTAAAGQAGT SVLDRIVPGY   1320
YQRLLADGSV ATSTCCANTA TENAMMGKLV VDSLVTWAKE YKVDGFRFDL MGHQPKANIL   1380
AVRKALDALT VAKDGVDGKK IILYGEGWNF GEVADDARFV QATQKNMAGT GIATFSDRAR   1440
DAVRGGGPFD ADPGVQGFGS GLYTDPNSSD ANGTPAEQKA RLLHYQDLIK VGLSGNLAKY   1500
RFTDSSGKEV TGSEVDYNGT GAGYADAPGD ALAYADAHDN ESLYDALTYK LPKGTPAGDR   1560
ARMQVLAMAT AALAQGPSLS QAGSDLLRSK SLDRNSYDSG DWFNAIHWNC QDGNGFGRGL   1620
PMAADNKSKW PYATPLLTSV KVGCDQIEGT SAGYQDLLRI RTTEPDFSLS TAGQVQSKLT   1680
FPLSGKDETP GVITMKLGDL VVVFNATPDQ QEQTVAALAG KDYALHPVQA AGADPIVKSA   1740
SYTAKSGMFA VPGRTVAIFS QVAR                                          1764

SEQ ID NO: 120          moltype = AA   length = 1079
FEATURE                 Location/Qualifiers
source                  1..1079
                        mol_type = protein
                        organism = Klebsiella pneumoniae
SEQUENCE: 120
SSSSPSGSPG SPGNPGNPGT PGTPDPQDVV VRLPDVAVPG EAAQASANQA VIHLVDIAGI     60
TSSTPADYAT KNLYLWNNET CDALSAPVAD WNDVSTTPTG SDKYGPYWVI PLTKESGCIN    120
VIVRDGTNKL IDSDLRVSFG DFTDRTVSVI AGNSAVYDSR ADAFRAAFGV ALADAHWVDK    180
TTLLWPGGEN KPIVRLYYSH SSKVAADSNG EFTDKYVKLT PTTVSQQVSM RFPHLASYVA    240
FKLPDDVNVD ELLQGETVAI SAESDGILSS ATQVQTAGVL DDTYAAAAEA LSYGAQLTDS    300
GVTFRVWAPT AQQVELVVYS ADKKVVASHP MTRDSASGAW SWQGGSDLKG AFYRYAMTVY    360
HPQSRKVEQY EVTDPYAHSL STNSEYSQVV DLNDSALKPE GWDGLTMPHA QKTKADLAKM    420
TIHESHIRDL SAWDQTVPAE LRGKYLALTA QESNMVQHLK QLSASGVTHI ELLPVFDLAT    480
VNEFSDKVAD IQQPFSRLCE INSAVKSSEF AGYCDSGSTV EEVLTQLKQN DSKDNPQVQA    540
LNTLVAQTDS YNWGYDPFHY TVPEGSYATD PEGTARIKEF RTMIQAIKQD LGMNVIMDVV    600
YNHTNAAGPT DRTSVLDKIV PWYYQRLNET TGSVESATCC SDSAPEHRMF AKLIADSLAV    660
WTTDYKIDGF RFDLMGYHPK AQILSAWERI KALNPDIYFF GEGWDSNQSD RFEIASQINL    720
KGTGIGTFSD RLRDAVRGGG PFDSGDALRQ NQGVGSGAGV LPNELTSMTD DQARHLADLT    780
RLGMAGNLAD FVLIDKDGAV KKGSEIDYNG APGGYAADPT EVVNYVSKHD NQTLWDMISY    840
KAAQEADLDT RVRMQAVSLA TVMLGQGIAF DQQGSELLRS KSFTRDSYDS GDWFNRVDYS    900
LQDNNYNVGM PRSSDDGSNY DIIARVKDAV ATPGETELKQ MTAFYQELTA LRKKSSPLFTL   960
GDGATVMQRV DFRNTGADQQ TGLLVMTIDD GMQAGASLDS RVDGIVVAIN AAPESRTLQD   1020
FAGTSLQLSA IQQAAGDRSL ASGVQVAADG SVTLPAWSVA VLELPQGESQ GAGLPVSSK    1079

SEQ ID NO: 121          moltype = AA   length = 546
FEATURE                 Location/Qualifiers
source                  1..546
                        mol_type = protein
                        organism = Rhizomucor pusillus
SEQUENCE: 121
ATSDDWKGKA IYQLLTDRFG RADDSTSNCS NLSNYCGGTY EGITKHLDYI SGMGFDAIWI     60
SPIPKNSDGG YHGYWATDFY QLNSNFGDES QLKALIQAAH ERDMYVMLDV VANHAGPTSN    120
GYSGYTFDDA SLYHPKCTID YNNQTSIEQC WVADELPDID TENSDNVAIL NDIVSGWVGN    180
YSFDGIRIDT VKHIRKDFWT GYAEAAGVFA TGEVFNGDPA YVGPYQKYLP SLINYPMYYA    240
LNDVFVSKSK GFSRISEMLG SNRNAFEDTS VLTTFVDNHD NPRFLNSQSD KALFKNALTY    300
VLLGEGIPIV YYGSEQGFSG GADPANREVL WTTNYDTSSD LYQFIKTVNS VRMKSNKAVY    360
MDIYVGDNAY AFKHGDALVV LNNYGSGSTN QVSFSVSGKF DSGASLMDIV SNITTTVSSD    420
```

```
GTVTFNLKDG LPAIFTSAGA TSPGGSSGSV EVTFDVYATT VYGQNIYITG DVSELGNWTP    480
ANGVALSSAN YPTWSATIAL PADTTIQYKY VNIDGSTVIW EDAISNREIT TPASGTYTEK    540
DTWDES                                                               546

SEQ ID NO: 122          moltype = AA   length = 481
FEATURE                 Location/Qualifiers
source                  1..481
                        mol_type = protein
                        organism = Bacillus licheniformis
SEQUENCE: 122
VNGTLMQYFE WYTPNDGQHW KRLQNDAEHL SDIGITAVWI PPAYKGTSQA DVGYGAYDLY    60
DLGEFHQKGT VRTKYGTKGE LQSAIKSLHS RDINVYGDVV INHKGGADAT EDVTAVEVDP    120
ADRNRVISGE HLIKAWTHFH FPGRGSTYSD FKWYWYHFDG TDWDESRKLN RIYKFQGKTW    180
DWEVSNEFGN YDYLMYADID YDHPDVVAEI KRWGTWYANE LQLDGFRLDA VKHIKFSFLR    240
DWVNHVREKT GKEMFTVAEY WSNDLGALEN YLNKTNFNHS VFDVPLHYQF HAASTQGGGY    300
DMRKLLNGTV VSKHPLKSVT FVDNHDTQPG QSLESTVQTW FKPLAYAFIL TRESGYPQVF    360
YGDMYGTKGD SQREIPALKH KIEPILKARK QYAYGAQHDY FDHHDIVGWT REGDSSVANS    420
GLAALITDGP GGAKRMYVGR QNAGETWHDI TGNRSEPVVI NSEGWGEFHV NGGSVSIYVQ    480
R                                                                    481

SEQ ID NO: 123          moltype = AA   length = 484
FEATURE                 Location/Qualifiers
source                  1..484
                        mol_type = protein
                        organism = Aspergillus niger
SEQUENCE: 123
LSAAEWRTQS IYFLLTDRFG RTDNSTTATC DTGDQIYCGG SWQGIINHLD YIQGMGFTAI    60
WISPITEQLP QDTADGEAYH GYWQQKIYDV NSNFGTADDL KSLSDALHAR GMYLMVDVVP    120
NHMGYAGNGN DVDYSVFDPF DSSSYFHPYC LITDWDNLTM VQDCWEGDTI VSLPDLNTTE    180
TAVRTIWYDW VADLVSNYSV DGLRIDSVLE VEPDFFPGYQ EAAGVYCVGE VDNGNPALDC    240
PYQKVLDGVL NYPIYWQLLY AFESSSGSIS NLYNMIKSVA SDCSDPTLLG NFIENHDNPR    300
FASYTSDYSQ AKNVLSYIFL SDGIPIVYAG EEQHYSGGKV PYNREATWLS GYDTSAELYT    360
WIATTNAIRK LAISADSAYI TYANDAFYTD SNTIAMRKGT SGSQVITVLS NKGSSGSSYT    420
LTLSGSGYTS GTKLIEAYTC TSVTVDSSGD IPVPMASGLP RVLLPASVVD SSSLCGGSGR    480
LYVE                                                                 484

SEQ ID NO: 124          moltype = AA   length = 586
FEATURE                 Location/Qualifiers
source                  1..586
                        mol_type = protein
                        organism = Aspergillus tamarii
SEQUENCE: 124
ATPADWRSQS IYFLLTDRFA RTDGSTTAAC NTEDRKYCGG TWQGIIDKLD YIQGMGFTAI    60
WITPVTGQLP QHTAYGDAYH GYWQQDIYSL NENYGTADDL KALSSALHER GMYLMVDVVA    120
NHMGYDGAGA SVDYSVFKPF NSQEYFHSFC LIQNYEDQTQ VENCWLGDNT VSLPDLDTTK    180
DEVKNEWYDW VGTLVSNYSI DGLRVDTVKH VQKDFWPGYN KAAGVYCIGE VLDGDPAYTC    240
PYQDVLDGVL NYPIYYPLLN AFKSTSGSMN DLYNMINTVK SDCPDSTLLG TFVENHDNPR    300
FASYTNDIAL AKNVAAFIIL NDGIPIIYAG QEQHYAGGND PANREATWLS GYATDSELYK    360
LIASANAIRS HAISKDTGFV TYKNWPIYKD DTTIAMRKGT DGSQVVTILS NKGASGDSYT    420
LSLGDTGYKA GQQLTEVIGC TTVTVGSDGK VPVPMAGGLP RVLYPTEKLA DSKICSSSGA    480
TSPGGSSGSV EVTFDVYATT VYGQNIYITG DVSELGNWTP ANGVALSSAN YPTWSATIAL    540
PADTTIQYKY VNIDGSTVIW EDAISNREIT TPASGTYTEK DTWDES                   586

SEQ ID NO: 125          moltype = AA   length = 603
FEATURE                 Location/Qualifiers
source                  1..603
                        mol_type = protein
                        organism = Acidomyces richmondensis
SEQUENCE: 125
LTPAEWRAQS IYQVLTDRFA LTNGSTTAPC NLNEYCGGTW QGIINKLDYI QGMGFTAIWI    60
SPVVENIPAS DNTADGESYH GYWAQRIYEV NPNFGSAADL EALSEAIHAR GMYLMVDIVT    120
NHMGYDGCGT CVDYSVFDPF DNQSYFHPFC LINYNNATSI QVCWEGDNIV SLPDLRTEDS    180
DVLGMWETWI TQLVANYSID GLRVDSMQQV DQAFWQPFMS AAGDLYAVGE VFNGDPTYTC    240
PYQQYLPGVL NYPAYYWITQ AFESTSGSIG NLVVGINEMK NDCLDTTLLG SFLENHDNPR    300
FPSYTSDYSL DKNAIAFAML QDGIPIVYEG QEQHYSGGSV PNNREDIWSS GYSTTSELYT    360
FIKIINAIRT QALTKDSSYL TYKAYPVYSD SQTIAMRKGE TYPIISVFTN SGASGSAYSI    420
TLSSSDTGFS ENQSITELLT CTVSTTDSGG NLVVNISSGL PRVYYPTSAI SGSTVCAEST    480
STLTISSPIS TSTSDCTTAS SVAVTFDETV TTTYGETIKL SGSISQLGDW NTQDAILLSA    540
ADYKSTDNVW FVTINLPAGI VFQYKYINVD SDGDVTWEAD PNHTYTVSAT CATAATIHDT    600
WQN                                                                  603

SEQ ID NO: 126          moltype = AA   length = 588
FEATURE                 Location/Qualifiers
source                  1..588
                        mol_type = protein
                        organism = Aspergillus bombycis
SEQUENCE: 126
ATPADWRSQS IYFLLTDRFA RTDGSTTATC NTEDRKYCGG TWQGIIDKLD YIQGMGFTAI    60
WITPVTGQLP QDTAYGEAYH GYWQQDIYAL NENHGTADDL KALSSALHER GMYLMVDVVA    120
```

```
NHMGYDGAGA  SVDYSVFNPF  SSQDYFHSFC  LIENYDDQTQ  SENCWLGDNS  VSLPDLDTTK  180
DEVKNEWYEW  VGNLVSNYSI  DGLRVDTVKH  VQKDFWPGYN  EAAGVYCIGE  VLNGDPAYTC  240
PYQDVMDGVL  NYPIYYPLLN  AFKSTSGSMN  DLYNMINTVK  SDCPDSTLLG  TFVENHDNPR  300
FASYTNDIAL  AKNVAAFIIL  NDGIPIIYAG  QEQHYAGGND  PANREATWLS  GYSTDSEIYK  360
LIASANAIRN  HAVSTDTGFV  TYKNWPIYKD  DTTIAMRKGT  DGSGIVTILS  NKGASGDAYT  420
LSLGNTGYTA  GQQLTEVIGC  TTLTVGSDGN  VPVPMAGGLP  RVLYPTEKLG  DSKICSSSGR  480
GATSPGGSSG  SVEVTFDVYA  TTVYGQNIYI  TGDVSELGNW  TPANGVALSS  ANYPTWSATI  540
ALPADTTIQY  KYVNIDGSTV  IWEDAISNRE  ITTPASGTYT  EKDTWDES                588

SEQ ID NO: 127          moltype = AA  length = 570
FEATURE                 Location/Qualifiers
source                  1..570
                        mol_type = protein
                        organism = Alternaria sp.
SEQUENCE: 127
ADTSAWKSRS  IYFVLTDRIA  RSSSDTGGGS  CSNLGNYCGG  TFKGLESKLD  YIKNLGFDAI   60
WITPVVANSA  GGYHGYWAQD  LYAVNSNYGT  AADLKSLVNT  AHSKGIYVMV  DVVANHMGQG  120
AISGNRPEPL  NQDSSYHSAC  DINYSSQTSI  EQCRIANLPD  LNTQSSQIRS  LLNTWISWLV  180
NEYSFDGVRI  DTVKHVEKDF  WPGFASAAGV  YSIGEVWDGN  PTYLAEYARL  MPGLLNYATY  240
YPMNNFYQQK  GSSQALVDMM  NTVRDTFPDP  SALGTFLDNH  DNNRWLNQKN  DVTLLKNALA  300
FVILSRGIPI  VYYGTEQGYA  GGADPANRED  LWRSSFNTNA  DLYQAIKKLN  AARTSAGGLA  360
GNDHTHLYVS  SNAYAWSRAN  GNLVVLTTNA  GSGSNAQHCF  NTQKANGRWT  NVYGNGATVT  420
ADGSGNICVN  VANGEPVVLL  VSTATPTSAT  PTSNPSPTTL  LTTSTACPTS  VSVSFTHRVT  480
TVFGDTIKIT  GNTAQLGNWN  PSNGVALSAA  SYTSSNPIWT  LTLPLPAGSA  IQYKFVKVSS  540
GGTVTWESDP  NRSYSVPGCQ  ASASVSSQWQ                                     570

SEQ ID NO: 128          moltype = AA  length = 551
FEATURE                 Location/Qualifiers
source                  1..551
                        mol_type = protein
                        organism = Rhizopus microsporus
SEQUENCE: 128
SPITIRSQNS  NDWSSRVIYQ  LLTDRFAKTV  DDQSPCSDLG  NYCGGSFQGI  INHLDYIAGM   60
GFDAIWISPI  PQNAQGGYHG  YWATNFSAIN  SNFGSSNDLK  KLVQAAHAKN  MYVMLDVVAN  120
HVGTPSTPNN  YNGYTFNQGS  YYHSYCDINY  NDQTSVEQCW  LSGLPDLNTE  NDYVVNTLYS  180
TVSNWISEYG  FDGIRIDTVK  HVRKDFWDGY  VKAAGVFATG  EVLHGSVSYV  APYQSHVPSL  240
INYPLYYPIY  DVFTKAATMT  RLKSGYNDIQ  SGGFSNLNLL  LNFIDNHDNP  RLLSKADQSL  300
VKNALTYSML  IQGIPVVYYG  TEQSYKGGND  PNNREPLWTS  GYSSSSEMYQ  FIKQVIQIRK  360
GSNATVTMDI  DQADNVYVFQ  RGNYLAVVNN  YGQGSTNSVT  VKSGSFADGT  VLKDVFSGAT  420
ATVKNKSITF  QLQNGNPAVF  SPQGATSPGG  SSGSVEVTFD  VYATTVYGQN  IYITGDVSEL  480
GNWTPANGVA  LSSANYPTWS  ATIALPADTT  IQYKYVNIDG  STVIWEDAIS  NREITTPASG  540
TYTEKDTWDE  S                                                          551

SEQ ID NO: 129          moltype = AA  length = 565
FEATURE                 Location/Qualifiers
source                  1..565
                        mol_type = protein
                        organism = Syncephalastrum racemosum
SEQUENCE: 129
VPLSIIDKRA  GVTTLSKRAA  ADDWKSRSIY  QIVTDRFARS  DGSTSGCGDL  SNYCGGDYKG   60
IQNQLDYIAG  MGFDAIWISP  IPENTDGGYH  GYWAKNFEAL  NTNFGSADDL  KALVTAAHGK  120
GMYVMLDVVA  NHAGPTSGGD  YSGFTFDSAS  NYHAQCDIDY  ENQTSIEQCW  VADNLPDINT  180
EDDTIVSKLH  SIVSDVVTTY  DFDGIRIDTV  KHIRKDFWSG  YEEAAGVFAT  GEVFDGAAYV  240
VGPYQDQLSS  LINYPLYYAI  RDVFTAGSGF  SRISDMLSSI  NSNFKDPSVL  TTFVDNQDNA  300
RFLSVKSDTS  LYKNALAFTI  LTEGIPVVYY  GTEQGFRGSN  DPNNREVLWT  SNDYTSSDLY  360
KFIKIVNDQV  RQKSNKTVKL  NVDVGTNTYA  FTHGKNLIVV  NNYGSGSTAS  VTVKVGDSIA  420
DGTKLVDAVS  NITATVSGGS  ITFSLNNGLP  ALFVPSSGAT  SPGGSSGSVE  VTFDVYATTV  480
YGQNIYITGD  VSELGNWTPA  NGVALSSANY  PTWSATIALP  ADTTIQYKYV  NIDGSTVIWE  540
DAISNREITT  PASGTYTEKD  TWDES                                          565

SEQ ID NO: 130          moltype = AA  length = 583
FEATURE                 Location/Qualifiers
source                  1..583
                        mol_type = protein
                        organism = Rhizomucor pusillus
SEQUENCE: 130
ATSDDWKGKA  IYQLLTDRFG  RADDSTSNCS  NLSNYCGGTY  EGITKHLDYI  SGMGFDAIWI   60
SPIPKNSDGG  YHGYWATDFY  QLNSNFGDES  QLKALIQAAH  ERDMYVMLDV  VANHAGPTSN  120
GYSGYTFDDA  SLYHPKCTID  YNNQTSIEQC  WVADELPDID  TENSDNVAIL  NDIVSGWVGN  180
YSFDGIRIDT  VKHIRKDFWT  GYAEAAGVFA  TGEVFNGDPA  YVGPYQKYLP  SLINYPMYYA  240
LNDVFVSKSK  GFSRISEMLG  SNRNAFEDTS  VLTTFVDNHD  NPRFLNSQSD  KALFKNALTY  300
VLLGEGIPIV  YYGSEQGFSG  GADPANREVL  WTTNYDTSSD  LYQFIKTVNS  VRMKSNKAVY  360
MDIYVGDNAY  AFKHGDALVV  LNNYGSGSTN  QVSFSVSGKF  DSGASLMDIV  SNITTTVSSD  420
GTVTFNLKDG  LPAIFTSATG  GTTTTATPTG  SGSVTSTSKT  TATASKTSTS  TSSTSCTTPT  480
AVAVTFDLTA  TTTTYGENIYL  VGSISQLGDW  ETSDGIALSA  DKYTSSDPLW  YVTVTLPAGE  540
SFEYKFIRIE  SDDSVEWESD  PNREYTVPQA  CGTSTATVTD  TWR                    583

SEQ ID NO: 131          moltype = AA  length = 553
FEATURE                 Location/Qualifiers
```

```
source                    1..553
                          mol_type = protein
                          organism = Dichotomocladium hesseltinei
SEQUENCE: 131
QPVNITKRAS AADWRSRAIY QVLTDRFART DGSTSGCSNL SNYCGGTFKG ITNKLDYIAN    60
LGFDAIWISP IPTNSPGGYH GYWATDFYGI NSNFGSSNDL KELVNAAHAK GMYVMLDVVA   120
NHAGPTSNGD YSGYTFGSSG LYHNRCSINY NDQRSIEQCW VADDLPDINT ENNDNVNKPN   180
NIVSTWVKTY GFDAIRIDTV KHVRKDFWPG YTSAAGVFAT GEVFDGNPSY VADYQNYMES   240
LINYPLYYAL NDVFASGYSF SRLSNQRVAN YHAFKDVSVL PIFIDNHDNP RFLNKKNDIA   300
QFKNALTYVL LGEGIPVVYY GSEQAYAGGA DPANREALWS SGFSTNSDMY QFIAKLNRVR   360
QKSNKSVYMD LDVQNNVYAF MHGKSLVVLN NFGNGASRQV TVNVGAQVAS NTRLTDVVSG   420
TSVTVSGSSV TFTINNGLPA VFTVSGATSP GGSSGSVEVT FDVYATTVYG QNIYITGDVS   480
ELGNWTPANG VALSSANYPT WSATIALPAD TTIQYKYVNI DGSTVIWEDA ISNREITTPA   540
SGTYTEKDTW DES                                                     553

SEQ ID NO: 132            moltype = AA  length = 552
FEATURE                   Location/Qualifiers
source                    1..552
                          mol_type = protein
                          organism = Lichtheimia ramosa
SEQUENCE: 132
RPFVKRATAD DWRDRAIYQI LTDRFARSDG STDNCSDLSN YCGGNYQGII QQLDYIEGMG    60
FDAIWISPIP ANADGGYHGY WATDFESLND HFGSQDDLKA LVDAAHERGM YVMLDVVANH   120
AGPTNNGDYS GYTFGSSDLY HPQCSIDYSN QNSIEQCWVA DNLPDIDTEN DSNVNKLHDI   180
VSTWVSTYGF DGIRIDTVKH VRKDFWPGYA SAAGVFATGE VYDGDQTYVG AYQDYLDSLL   240
NYPLYYALND VFASGQGFQR LSNQRNAIMS AFKDVSVLTS DNHDVARF LSTKNDQALF    300
KNALAFVLLG ETIPVVYYGS EQFAGGADP ANREALWSSG YDTSSDLYQF IATINNNVRQ   360
KSGKKVYMDL DVQDNVYAFM HGDALVVLNN YGSGASNQVS VNVGAQVAES TSFTDAISGT   420
SITVSSGSVT FTLDNGNPAI FVPAGATSPG GSSGSVEVTF DVYATTVYGQ NIYITGDVSE   480
LGNWTPANGV ALSSANYPTW SATIALPADT TIQYKYVNID GSTVIWEDAI SNREITTPAS   540
GTYTEKDTWD ES                                                      552

SEQ ID NO: 133            moltype = AA  length = 587
FEATURE                   Location/Qualifiers
source                    1..587
                          mol_type = protein
                          organism = Penicillium aethiopicum
SEQUENCE: 133
ARTADWKPRS IYQTMTDRFA RTDGSTTSPC NTKAGLYCGG TWRGTIDHLD YIQGMGFDAV    60
MISPIIENIE GRVDYGEAYH GYWPLNLDNL NSHFGTHQDL LDLSDALHSR GMYFMMDTVI   120
NNMAYITNGS DPATDIDYSV FTPFNNADYF HPYCTMNWSV PAIAQRCNTG DDTVALPDLF   180
TEHEDVQQLL IKWANKAIKT YSIDGLRIDA AKHVNPDFLR KFSDGVDIFM TGEVLEGSVS   240
IMEDYQSNYI NSLPNYPIYF EILSAFTNGN TSQLAIAVEN MRVAIPDVNA MASFSENHDK   300
PRIASYNDDM SIAKNVLVFT MLFDGIPMIY QGQEQHLKGD GVPHNREAIW LSKYDTEAEL   360
YKLIAKLNRI RNHAGYLGSD YFEDATHPIY QGSSELAFTK GVQGRQVVMV LSNQPSTSGR   420
YALDLAVSYN AGTELMDVLN CNNYTVDNQG VLRVDMDKGE PRVFFPRKYM EGSGLCGYSG   480
ATSPGGSSGS VEVTFDVYAT TVYGQNIYIT GDVSELGNWT PANGVALSSA NYPTWSATIA   540
LPADTTIQYK YVNIDGSTVI WEDAISNREI TTPASGTYTE KDTWDES                587

SEQ ID NO: 134            moltype = AA  length = 597
FEATURE                   Location/Qualifiers
source                    1..597
                          mol_type = protein
                          organism = Subulispora sp.
SEQUENCE: 134
LTPAEWGSQS IYQVLTDRFA LTDGSTTASC DLNTYCGGTW LGIQNHLDYI QGMGFTAIWI    60
SPIVTNIAGD SVDGDSYHGY WAQDITTVNS AFGTEQDLIN LSAALHERGM YLMVDVVNNH   120
MGYLGCGTCV DYSEYTPFNE ESYYHPYCPT DYSNLTSIQV CWEGDNIVSL PDLRTEDSDV   180
RSMWYDWITP LVAKYSIDGL RMDSAEHVEK SFWPGWVSAS GVYNVGEVDE GDPTIFPDWL   240
NYIDGTLNYP AYYWITQAFQ STSGSISNLV TGVNQLKASM KTSTFGSFLE NHDQPRFPSL   300
TSDTDLAKNA IAFAMLADGV PIVYYGQEQG YSGGGVPNDR EPLWTSGYST TSAGYTFIKT   360
INAVRHLAVT QDTAYVAYQA YPIYSDSRVI AMKKSSVLAV FSNIGSSGSG YSITLPAGAF   420
AASQALTDAV SCQTYTADAS GGLTFTFGQA PSVFYATASL AGSGLCGTTG TGGSTGTTTA   480
SETGGSSPTS TACASVPVTF NEKVTTVVGE TIKISGSVAA LGDWATGSAV ALSAASYTSS   540
NPQWDVTISF APGTVIEYKY INVASSGAVT WEADPNHTYT VPASCATAAV VSDTWQT     597

SEQ ID NO: 135            moltype = AA  length = 601
FEATURE                   Location/Qualifiers
source                    1..601
                          mol_type = protein
                          organism = Trichoderma paraviridescens
SEQUENCE: 135
LTAAQWRSQS IYQVLTDRFS QTNGATNSAC NAGNQVYCGG TWQGIIKNLD YIKSMGFTAI    60
WISPVVENLA GNSADGEAYH GYWAQDIYQV NTNFGSAADL RALSEALHNA GMYLMVDIVT   120
NHMGYLGCGT CVQYNTFNPF NSQSYYHPFC LINFNSSNMT QIQNCWEGDN TVSLPDLATE   180
NANVLSMWQT WITQLVANYT IDGLRMDSCF ELNYGYFEPF QSSANVYIVG EVDNGDPAIV   240
CPYQKNYGLN TLNYPAYYWI TQAFQSTSGS ISNLVNGLNT MKSECSDTTL LGSFMENHDN   300
PRFPSLTSDI SLAKNAIAFT MLADGIPIIY EGQEQHLNGG GVPNNREAIW LSGYSTSAVL   360
YTHIKALNQI RSQAIKQNSA YVTTQAAVTY SDSSTIVTRK GSTGSQIVGV FSNKGANGNS   420
```

```
YTLTLPSADT GFTSNEQVVE ILSCTAYTTD SSGNLAVAMA GGLPRVFYAR SSLSGSGICP    480
NLGSGGGTPT STPPTSCTAI PVTFDEKVTT TFGQTIKIAG DISALGNWNT ANAVTLSAAN    540
YTSSNPLWAI TLNLAPGQVV EYKYINVAQN GGVTWEADPN HTYTVPSACT AQPTVANTWQ    600
G                                                                   601

SEQ ID NO: 136           moltype = AA  length = 598
FEATURE                  Location/Qualifiers
source                   1..598
                         mol_type = protein
                         organism = Byssoascus striatosporus
SEQUENCE: 136
LSADDWRAQS IYQLLTDRFA LTNGSTTAPC DTEEQIYCGG SWQGIIDKLD YIQGMGFTAI    60
WISPVVENLS GDSADGEAYH GYWAQNVYEV NPNFGATSDL VALSQVVHDK GMYLMLDVVT    120
NHMGYLGCGT CVDYSVFNPF NEESYYHPFC LIDYDNTTSI EVCWEGDNIV SLPDLRTEDS    180
DVLSTWESWV TELVSNYTVD GIRLDSTEEL DQAFLPPFES AAGVYIVGEV DNGDPAVVCP    240
YQEYVSGVLN YPAYYWITQA FESTSGSIGN LVNGINTMKS DCSDTSLLGS FLENHDQPRF    300
ASLTSDISLA KNAIAFSMLQ DGIPIVYAGE EQHYSGGAVP NDREALWLSG YPTSSTLYTW    360
ITSLNQIRSH AIATNSSYLT YNAYPVYSDD STIVMRKGFA DNQIVSVYTN QGADATAYTL    420
DLPSTDTGFT ASQSLVEIGG CTTTATDDSG NLAVAMASGL PRIYYPAAGL SGSGVCGQLG    480
SGGGTPTSTP PTSCTAIPVT FDEKVTTTFG QTIKIAGDIS ALGNWNTANA VTLSAANYTS    540
SNPLWAITLN LAPGQVVEYK YINVAQNGGV TWEADPNHTY TVPSACTAQP TVANTWG      598

SEQ ID NO: 137           moltype = AA  length = 615
FEATURE                  Location/Qualifiers
source                   1..615
                         mol_type = protein
                         organism = Aspergillus brasiliensis
SEQUENCE: 137
LSAAEWRTQS IYFLLTDRFG RTDNSTTATC NTGDQIYCGG SWQGIINHLD YIQGMGFTAI    60
WISPITEQLP QDTSDGEAYH GYWQQKIYDV NSNFGTADDL KSLSDALHAR GMYLMLDVVT    120
NHMGYAGSGN DVDYSVFDPF DSSSYFHPYC LITDWDNLTM VQDCWEGDTI VSLPDLNTTE    180
TVVRTIWYDW VADLVSNYSV DGLRIDSVLE VEPDFFPGYQ EAAGVYCVGE VDNGNPALDC    240
PYQDYLDGVL NYPIYWQLLY AFESSSGSIS DLYNMIKSVA SDCSDPTLLG NFIENHDNPR    300
FAYYTSDYSQ AKNVLSYIFL SDGIPIVYAG EEQHYSGGDV PYNREATWLS GYDTSAELYT    360
WIATTNAIRK LAIAADSSYI TYANDPIYTD SNTIAMRKGT SGSQVITVLS NKGSSGSSYT    420
LTLSGSGYTS GTKLIEAYTC TSVTVDSNGD IPVPMASGLP RVLLPASVVD DSSLCGGSGS    480
STSTTTSTAT ATTTSKTSTT SSSSSSSSCT ASATAIPITF EELVTTTYGE EIYLSGSISQ    540
LGDWDTSDAV KLSADDYTSS NPEWSVTVTL PVGTTFEYKF IKVESGGSVT WESDPNREYT    600
VPECGSGETV VDTWR                                                    615

SEQ ID NO: 138           moltype = AA  length = 604
FEATURE                  Location/Qualifiers
source                   1..604
                         mol_type = protein
                         organism = Penicillium subspinulosum
SEQUENCE: 138
ALSAEWRTQS IYFLLTDRFG RTDNSTTATC DTGDQIYCGG SWQGVINHLD YIQGMGFTAI    60
WISPITEQLS GDTSDGEAYH GYWQQKIYNV NSNFGTADDL VALSDALHAR DMYLMLDVVP    120
NHMGYDGDGD DVDYSVFDPF DSSSYFHPYC LITDYDDIEM VQDCWEGDTI VSLPDLNTTE    180
TVVQDIWYAW VADLVANYSV DGLRIDSVLE VQPAFFPAYQ SAAGVYCVGE VDNGDPTLDC    240
PYQDYLDGIL NYPIYYQLLY AFESSSGSIS DLYDMINSVA SDCSDPTLLG NFIENHDNPR    300
FAYYTSDYSQ AKNVASFIFL SDGIPIVYAG QEQHYSGGDV PYDREATWLS GYSTTAELYT    360
WIATTNSIRK LAISLDDDYI TYVNDPFYTD ENTIAMRKGT SGLQVITVLS NLGADGSAYT    420
LTLSGSGYDS GTDLIEVYTC TSVTVDSSGD IAVPMESGLP RVFLPESSIK DSDLCSGTTT    480
TTTSTAATAT ATSTSTCTAA TEVSIIFEEL VTTTYGEEIY LSGSISELGS WDTSDALELS    540
AANYTSSNPE WYLEVTLPVG TSFEYKFIMI ESDGTVVWES DPNRSYTVPS ACSGAVETVV    600
DTWR                                                                604

SEQ ID NO: 139           moltype = AA  length = 606
FEATURE                  Location/Qualifiers
source                   1..606
                         mol_type = protein
                         organism = Penicillium antarcticum
SEQUENCE: 139
LTPAEWRSQS IYFMLTDRFG RSDNSTTAAC NVSDRTYCGG TWQGIINHLD YIQGMGFTAI    60
WITPVTEQLP QDTGDGEAYH GYWQQNIYEV DSNLGTAADL LALSEALHAR GMYLMVDVVA    120
NHMGYAGAGS SVEYSVFHPF SSSSYFHSYC LISNYDDQSN VEDCWLGDTI VSLPDVDTTQ    180
TAVQTLWYDW IGDLVSNYSI DGLRIDTVKH VQKSFWPGYN DAAGVYCVGE IPDGDPAYTC    240
DYQNYMDGVL NYPIYYQLLY AFQSSSGSIS DLYDMINSVK SDCADPTLLG NFIENHDNPR    300
FASYTSDYSQ AKNVISFLFL SDGIPIIYSG QEQHYSGGAD PANREATWLS GYSTTAELYK    360
YIATTNRIRK AAVSADSSYI TTKNVPFYQD SHTLAMKKGS SASPVITVLS NYGSSGSSYT    420
LSLSGSGYSS GTNLMEMYTC TSVTVDSSGN IAVPMESGLP RVLMLASSAS SICASSTTTS    480
TATVATQTTT LTTTGTSCTQ ATVLPVLFKE LVTTTYGQNV YISGSISQLG SWDTSSAIAL    540
SASSYNSSNP LWQVAITLPV GTSFQYKFLE KTTGSTTIQW ESDPNRSYTV PTGCVGTTAT    600
AIATWR                                                              606

SEQ ID NO: 140           moltype = AA  length = 609
FEATURE                  Location/Qualifiers
source                   1..609
```

```
                           mol_type = protein
                           organism = Penicillium coprophilum
SEQUENCE: 140
LTPAEWRSQS IYFLLTDRFG RTDNSVTANC NVNDRVYCGG TWQGIINQLD YIQGMGFTAI    60
WITPVTKQLS QNTGDGTSYH GYWQQDIYNV NPNHGTSDDL LALSKALHAR GMYLMVDVVA   120
NHMGYAGAGN NVDYSVFTPF NSASYFHSYC LISNYNDQSN VENCWLGDTT VSLPDLDTTQ   180
SSVQTLWNNW ISDLVSKYSI DGLRVDTVKH VQKSFWPAFN RAAGVYSVGE VFDGSPSYTC   240
DYQKYMDGVL NYPMYYPLLR AFQSTSGSIS DLYNMIGTLS STCADSTLLG NFIENHDNPR   300
FPSYTSDYSQ AKNVLSFLFL SDGIPIVYSG QEQHYSGGSD PANREALWLS KYSTTAELYK   360
YIATTNKIRK AAVAADSSYI TSKNVAFYQD SHTLAMKKGS GSSPVITVLS NAGSSGSSYT   420
LYLSGSGYSS GTQLMELYTC TSVTVDSSNK IAVPMASGLP RVFVLASSVS NSGLCGSSTP   480
TTTATTATTA TQTTTATTTA GGCTQATALP VLFKELVTTS YGQDIYISGS ISQLGTWDTS   540
KAVALSADSY TSSNPLWQAT ITLPVGTTFQ YKFIKKANGA ITWESDPNRS YTVPTGCSGS   600
TATVTASWK                                                           609

SEQ ID NO: 141         moltype = AA  length = 602
FEATURE                Location/Qualifiers
source                 1..602
                       mol_type = protein
                       organism = Penicillium olsonii
SEQUENCE: 141
LTPAEWRSQS IYFLLTDRFG RDDNSTTATC NTGDRTYCGG TWQGIINQLD YIQGMGFTAI    60
WITPVTEQLS ANTGYGTAYH GYWQQDIYEV NPNHGSSADL KALSAALHAR GMYLMVDVVA   120
NHMGYNGIGS SVDYSVFNPF SSSSYFHSYC LISNYNDQSN VENCWLGDTT VSLPDLDTTQ   180
TAVQTIWNEW ITDLVSNYSI DGLRIDTVKH VQKSFWPGFN DAAGVYSVGE IFDGNPSYTC   240
DYQNYLDGVL NYPIYYPLLY AFQSTSGSIS DLYNMINTVA SDCADSTLLG NFIENHDNPR   300
FPSYTGDYSQ AKNVISYLFL SDGIPIIYSG QEQHYSGASD PANREALWLS GYSTTAELYK   360
WIATTNKIRK LAVSADSSYI TSKNSPFYQD SHTLGMKKGS VITILSNNGA SGSSYTLSLS   420
GSGYSSGTKL MELYTCTSIT VDSSGNIPVP MVSGLPRALI PASSIGSNGL CGSTTSPTTT   480
AATQTTTATT TGTCTQATAL PVLFKELVTT SYGQNVYISG SISQLGNWDA SSAIALSASS   540
YTSSNPLWQV TITLPVGTKF EYKFIEKSSG SATATWESDN NRSYTVPTGC AGTTATVTAT   600
WR                                                                  602

SEQ ID NO: 142         moltype = AA  length = 621
FEATURE                Location/Qualifiers
source                 1..621
                       mol_type = protein
                       organism = Penicillium vasconiae
SEQUENCE: 142
LTAAEWRTQS IYFLLTDRFG RTDNSTTATC SVSDRIYCGG SWQGIINHLD YIQGMGFTAI    60
WITPVTEQLS QDTGDGEAYH GYWQQEIYNV NTNYGTAADL LALSKALHSR GMYLMVDVVA   120
NHMGYDGAGN TVDYSVFNPF DSSSYFHSYC EISDYSNQTN VEDCWLGDTT VSLPDLDTTL   180
SSVQTIWYNW VTELVSNYSI DGLRIDTVKH VQKSFWPGYN SAAGVYCVGE VFDGDPAYTC   240
PYQSYLDGVL NYPIYYQLLY AFESTSGSIS SLYNMINSVA SDCSDPTLLG NFIENHDNPR   300
FASYTSDYSQ AKNVISFIFF SDGIPIVYAG QEQHYSGGSD PANREATWLS GYDTTATLYK   360
YITSTNKIRS LAISKDTAYI TSKNNAFYTD SNTIAMKKGS SGSQVITVLS NRGSSGSSYT   420
LTLSGSGYSS GTQLMEMYTC TAVTVDSSGN IAVPMASGLP RIYMLASSAC SICSSSCSTT   480
TTTSTTSTST TTASTLKTTT STTSATSTTS TSCTQATALP VLFKEIVTTS YGQNIYISGS   540
ISQLGSWDTS NAVALSADQY TSSNNLWYVV VTIPVGTSFE YKFIEETSGS STITWESDPN   600
RSYTVPTGCA GSTATVTATW R                                             621

SEQ ID NO: 143         moltype = AA  length = 615
FEATURE                Location/Qualifiers
source                 1..615
                       mol_type = protein
                       organism = Penicillium sp.
SEQUENCE: 143
LTAAEWRSQS IYFLLTDRFG RTDNSTTATC NVSDRIYCGG SWQGIINHLD YIQGMGFTAI    60
WITPVTEQLS QDTGDGEAYH GYWQQEIYNV NTNYGTAADL LALSKALHSR GMYLMVDVVA   120
NHMGYDGAGN TVDYSVFNPF DSSSYFHSYC EITDYSNQTN VEDCWLGDTT VSLPDLNTTL   180
SSVQTIWYDW VAALVSNYSI DGLRIDTVKH VQESFWPEYN SAAGVYCVGE VFDGDPAYTC   240
PYQNYLDGVL NYPIYYQLLY AFESTSGSIS DLYNMINSVA SDCSDPTLLG NFIENHDNPR   300
FASYTSDYSQ AKNVLSFIFF SDGIPIVYAG QEQHYSGGSD PANREATWLS GYDTSAELYT   360
WITSTNKIRS LAVSKDTAYI TSKNDAFYTD SNTIAMKKGS GGSQVVTVLS NRGSSGSSYT   420
LTLSGSGYSS GTKLMEMYTC TAVTVDSSGN IAVPMASGLP RVYMLASSAC SICSSACSTT   480
TTSSTTSTAT TTSTTLKTTT TTTSTSCTQA TALPVLFKEI VTTSYGQNIY ISGSISELGD   540
WDTSNAVALS ADQYTSSNNL WYVVVTIPVG TSFEYKFIEE TSGSSSITWE SDPNRSYTVP   600
TGCAGSTATV TATWR                                                    615

SEQ ID NO: 144         moltype = AA  length = 606
FEATURE                Location/Qualifiers
source                 1..606
                       mol_type = protein
                       organism = Heterocephalum aurantiacum
SEQUENCE: 144
LTAAEWRQQS IYFLLTDRFA RTDGSTTAAC NLSQRAYCGG SWQGIINHLD YIQGMGFTAI    60
WITPVTKQIE ASTSDGTAYH GYWQQDIYNI NSHYGTADDL RALSSALHSR GMYLMIDVVA   120
NHMGYPGAGT SVDYSIFTPF GSSSYFHSYC QITDYDNQSN VENCWLGDNV VSLPDLNTQN   180
SNVRNLWYDW VEELVANYSV DGLRVDTVKH VEKDFWPSYN AAAGVYCVGE VFHGDPAYTC   240
```

```
PYQNYMDGVL NYPIYYQLLY AFQSSSGSIT DLYNMINSVA SDCKDPTTLG NFIENHDNPR    300
FPSYTSDMSQ AKSVIAFLFL SDGIPIIYAG QEQHYSGGAD PNNREAIWLS GYSTSSTLYQ    360
FISSTNSIRK LAISKDSSYL TSRNNPFYTD SNTIAMRKGS SGSQVITVLS NKGSSGNSYT    420
LTLTNHGYSS GAQLTELYTC SSIQVASSGG LAVPMASGLP RVLVPSSWIQ GSGLCGGGST    480
TTTTTATTTT TTTTSTSSCA AATSLAVVFN ELVTTYYGEN IFIAGSISQL GSWDTGKSVA    540
LSASQYTSSN PLWTATVSLP VGTSFQYKFI KKEPDGQVVW ESDPNRSYTV PAGCAGTTQT    600
VNTSWR                                                              606

SEQ ID NO: 145         moltype = AA   length = 602
FEATURE                Location/Qualifiers
source                 1..602
                       mol_type = protein
                       organism = Neosartorya massa
SEQUENCE: 145
LTPAEWRSQS IYFLLTDRFG REDNSTTAAC DVTQRLYCGG SWQGIINHLD YIQGMGFTAI    60
WITPVTEQFY EDTGDGTSYH GYWQQNIYEV NYNYGTAQDL KNLADALHAR GMYLMVDVVA    120
NHMGYDGAGN TVDYSVFTPF DSSSYFHPYC LISDYSNQTN VEDCWLGDTT VSLPDLDTTD    180
TTVRTIWYDW VKGLVANYSI DGLRIDTVKH VEKDFWPGYN DAAGVYCVGE VFSGDPTYTC    240
PYQNYLDGVL NYPIYYQLLY AFESTSGSIS NLYDMINSVA SDCADPTLLG NFIENHDNPR    300
FASYTSDYSQ AKNVISFIFF SDGIPIVYAG QEQHYSGGAD PANREAVWLS GYSTSATLYS    360
WIASTNRIRK LAISKDAAYI TSKNNPFYYD SNTLAMRKGS IAGAQVITVL SNKGSSGSSY    420
TLSLSGTGYS AGASLVEMYT CTTLTVDSSG NLPVPMASGL PRVLVPSSWV SGSGLCGSGS    480
TTTTTTTATA TTTACTSATA LPIVFEEVVT TTYGENVYLT GSISQLGNWD TSSAIALSAS    540
KYTSSNPEWY VTVTLPVGTS FQYKFFKKES DGSIVWESDP NRSYTVPTGC AGTTVTSDT    600
WR                                                                  602

SEQ ID NO: 146         moltype = AA   length = 588
FEATURE                Location/Qualifiers
source                 1..588
                       mol_type = protein
                       organism = Penicillium janthinellum
SEQUENCE: 146
ATPAQWRSQS IYFMLTDRFA RTDGSTTAPC DTSQRAYCGG TWQGIIDKLD YIQGMGFTAI    60
WITPVTGQLD GDTGDGTAYH GYWQQDIYSL NSNYGTASDL KALASALHAR GMYLMVDVVA    120
NHMGYNGAGN TVDYSVFDAF NSNQYFHSYC EVTNYSNQTN VEDCWLGDTT VSLPDLNTEL    180
SSVQSIWYNW VGSLVSNYSI DGLRVDTVKH VQKDFWPGYN KAAGVYCVGE VFDGDASYTC    240
PYQEVMDGVL NYPMYYPLLR AFQSTSGSMS DLYNMINTVK STCSDSTLLG TFVENHDNPR    300
FASYTNDMSL AKNVAAFTIM ADGIPIIYAG QEQHYSGGGD PANREAVWLG GYNTDSALYK    360
LIAKVNAIRS YAISQSASYV TYKNYPIYQD ASTLAMRKGS SGTQTITVLS NRGASGSQYT    420
LSLGNTGYST GTTLTEIITC AKITVDSSGN VPVPMASGEP RILYPSSSIK GSAICASSGR    480
GATSPGGSSG SVEVTFDVYA TTVYGQNIYI TGDVSELGNW TPANGVALSS ANYPTWSATI    540
ALPADTTIQY KYVNIDGSTV IWEDAISNRE ITTPASGTYT EKDTWDES                588

SEQ ID NO: 147         moltype = AA   length = 589
FEATURE                Location/Qualifiers
source                 1..589
                       mol_type = protein
                       organism = Aspergillus brasiliensis
SEQUENCE: 147
ATPAEWRSQS IYFLLTDRFA RTDNSTTASC DLSARQYCGG SWQGIINQLD YIQGMGFTAI    60
WVTPVTAQIP QDTGYGQAYH GYWQQDAYAL NSHYGTADDL KALATALHSR GMYLMVDVVA    120
NHMGHNGTGS SVEYSVYNPF NAKKYFHNLC WISNYDNQTN VEDCWLGDNT VALPDLTTR    180
TDVKNMWYDW VKSLVSNYSV DGLRVDTVKN VQKNFWPGYN NASGVYCIGE VFDGDASYTC    240
PYQDDLDGVL NYPMYYPLLR AFKSTTGSIS DLYNMINTVK STCKDSTLLG TFIENHDNPR    300
FANYTSDMSL AKNVATFTIL ADGIPIIYAG QEQHYSGGGD PYNREATWLS GYKTTSELYT    360
HIAASNKIRT HAIKQDSGYL TYKNYPIYQD TSTLAMRKGY NGTQTITVLS NLGASGSSYT    420
LSLPGTGYTA GQKITEIYTC TNLTVNSNGS VPVPMKSGLP RILYPTDKLV NGSSFCSSSG    480
RGATSPGGSS GSVEVTFDVY ATTVYGQNIY ITGDVSELGN WTPANGVALS SANYPTWSAT    540
IALPADTTIQ YKYVNIDGST VIWEDAISNR EITTPASGTY TEKDTWDES               589

SEQ ID NO: 148         moltype = AA   length = 588
FEATURE                Location/Qualifiers
source                 1..588
                       mol_type = protein
                       organism = Aspergillus westerdijkiae
SEQUENCE: 148
ATPAQWRSQS IYFLLTDRFA RDDGSTTATC NTEDRKYCGG TWQGIIDQLD YIQGMGFTAI    60
WITPVTAQLT EDTKYGDAYH GYWQQDIYSL NENYGTADDL KALADALHER DMYLMVDVVA    120
NHMGYAGAGD SVDYSVFNPF NSQDYFHSFC LIQDYNDQTQ SEDCWLGDNS VSLPDLDTTK    180
SEVQDIWYDW VGGLVSNYSI DGLRIDTVKH VQKEFWPGYN DAAGVYCIGE ILDGDASYTC    240
PYQEVLDGVL NYPIYYPLLN AFKSTSGSIS DLYNMINTVK SDCPDSTLMG TFIENHDNPR    300
FASYTDDIAL AKNVAAFTIL ADGIPIVYAG QEQHYAGGED PANREATWLG KYNTDSELYK    360
LIAASNAIRN HAISTDKEYV NYKNYPIYKD DSTIAMRKGF DGAQIITVLS NQGSSGSYT    420
LSLGDTGFSS GDKLTEIYTC TAVTVDSDGK VPVPMDGGAP RALFPTEKLS GSSLCSGSGR    480
GATSPGSSG SVEVTFDVYA TTVYGQNIYI TGDVSELGNW TPANGVALSS ANYPTWSATI    540
ALPADTTIQY KYVNIDGSTV IWEDAISNRE ITTPASGTYT EKDTWDES                588

SEQ ID NO: 149         moltype = AA   length = 476
FEATURE                Location/Qualifiers
```

```
source                  1..476
                        mol_type = protein
                        organism = Hamigera avellanea
SEQUENCE: 149
ATPADWRSRS IYFILTDRFA RTDGSTTAEC DTSARAYCGG TWRGIINKLD YIQNMGFTAI    60
WITPVTAQLP GSTGHGSAYH GYWQQDIYSL EPNYGTADDL RALASALHER NMYLMVDVVA   120
NHMGWAGSGD SVDYSVFNPF DSADYFHPYC LISNYEDQTE VENCWLGDTN VALVDLDTTR   180
SDVQNIWYEW VDSLVGNYSI DGLRIDTVRH VQKDFWPGFN DAAGVYSVGE VFSGDTAYTC   240
PYQEVLDGVL NYPIYYPLLR AFQSTSGSIN DLYNMINTVK SDCADSTLMG TFLENHDNPR   300
FASYTSDVAL AKNAIAFTIL SDGIPIIYAG QEQHYSGGND PANREAVWLS GYSTDSELYS   360
FVAVTNQIRN YAISQDGYV TWKNVPIYQD TSTLAMRKGT DGSQVITVLS NLGASGSSYT   420
LTLGGSGYSS GQQLTEIFSC ATVTVDSSGN IPVPMGSGQP KVFYPTAGLG GSGICQ      476

SEQ ID NO: 150          moltype = AA   length = 586
FEATURE                 Location/Qualifiers
source                  1..586
                        mol_type = protein
                        organism = Hamigera avellanea
SEQUENCE: 150
ATPADWRSRS IYFILTDRFA RTDGSTTAEC DTSARAYCGG TWRGIINKLD YIQNMGFTAI    60
WITPVTAQLP GSTGHGSAYH GYWQQDIYSL EPNYGTADDL RALASALHER NMYLMVDVVA   120
NHMGWAGSGD SVDYSVFNPF DSADYFHPYC LISNYEDQTE VENCWLGDTN VALVDLDTTR   180
SDVQNIWYEW VDSLVGNYSI DGLRIDTVRH VQKDFWPGFN DAAGVYSVGE VFSGDTAYTC   240
PYQEVLDGVL NYPIYYPLLR AFQSTSGSIN DLYNMINTVK SDCADSTLMG TFLENHDNPR   300
FASYTSDVAL AKNAIAFTIL SDGIPIIYAG QEQHYSGGND PANREAVWLS GYSTDSELYS   360
FVAVTNQIRN YAISQDGYV TWKNVPIYQD TSTLAMRKGT DGSQVITVLS NLGASGSSYT   420
LTLGGSGYSS GQQLTEIFSC ATVTVDSSGN IPVPMGSGQP KVFYPTAGLG GSGICQSSGA   480
TSPGGSSGSV EVTFDVYATT VYGQNIYITG DVSELGNWTP ANGVALSSAN YPTWSATIAL   540
PADTTIQYKY VNIDGSTVIW EDAISNREIT TPASGTYTEK DTWDES                 586

SEQ ID NO: 151          moltype = AA   length = 576
FEATURE                 Location/Qualifiers
source                  1..576
                        mol_type = protein
                        organism = Meripilus giganteus
SEQUENCE: 151
RPTVFDAGAD AHSLHARAPS GSKDVIIQMF EWNWDSVAAE CTNFIGPAGY GFVQVSPPQE    60
TIQGAQWWTD YQPVSYTLTG KRGDRSQFAN MITTCHAAGV GVIVDTIWNH MAGVDSGTGT   120
AGSSFTHYNY PGIYQNQDFH HCGLEPGDDI VNYDNAVEVQ TCELVNLADL ATDTEYVRGR   180
LAQYGNDLLS LGADGLRLDA SKHIPVGDIA NILSRLSRSV YITQEVIFGA GEPITPNQYT   240
GNGDVQEFRY TSALKDAFLS SGISNLQDFE NRGWVPGSGA NVFVVNHDTE RNGASLNNNS   300
PSNTYVTATI FSLAHPYGTP TILSSYDGFT NTDAGAPNNN VGTCSTSGGA NGWLCQHRWT   360
AIAGMVGFRN NVGSAALNNW QAPQSQQIAF GRGALGFVAI NNADSAWSTT FTTSLPDGSY   420
CDVISGKASG SSCTGSSFTV SGGKLTATVP ARSAIAVHTG QKGSGGATPT SAPSTTPTSG   480
TVSMTFAEQA TTTFGENIFL VGSISQLGNW NPASAIALSS AAYPTWSVSV NIPAGTTFQY   540
KFIRKETDGS VVWESDPNRQ ATAPASGTTT LTSSWR                             576

SEQ ID NO: 152          moltype = AA   length = 575
FEATURE                 Location/Qualifiers
source                  1..575
                        mol_type = protein
                        organism = Cerrena unicolor
SEQUENCE: 152
RPLNASNALD ARAPSGAKSV IIQMFEWTWD SVAAECTNFI GPAGYGFVQV SPPQETIQGD    60
QWWTDYQPVS YILTSKRGTR DQFAAMIDTC HDAGVKVIVD TIWNHMAGVE SGTGVAGSSF   120
THYNYPGIYQ NQDFHHCGLE SGDDIVNYDN AQEVQTCELV NLADLATETD YVRGRLAEYG   180
NDLLSLGADG LRLDAAKHIA VGDLANIIGR LNSTPYITQE VIFGSGEPIT PNQYTGNGDV   240
QKFRYTSALK DAFLNGDISS LQDFENRGWV AGSGANVFVT NHDTERNGNS LNNNSPNNAY   300
TLAMIFSLAH PYGTPSILSS YSGFTDTDAG APNGGAGTCS SGGGSNGWLC QHRWTAVAGM   360
VGFRNTVGSA ALNNWVSPQS SQIAFGRGAL GFVAINNGDS TWSTTFTTSL PDGTYCDVIT   420
GTSSSGSCTG SSFTVSGGTF TANVAARDAV AIHTGATGTG SGSGNTSTGS GGTTSDTVSV   480
SFAETATTTF GENIFLVGSI SQLGAWDPAS AIALSSASYP TWTVTVTLPA GTTFEYKFIR   540
KETDGSVVWE SDPNRQATTP SSSDAATTTL STSWR                              575

SEQ ID NO: 153          moltype = AA   length = 562
FEATURE                 Location/Qualifiers
source                  1..562
                        mol_type = protein
                        organism = Physalacria cryptomeriae
SEQUENCE: 153
APFLELQVRA PSSTKQVIIQ MFEWTWDSVA AECTDFIGPA GYGYVQVSPP AEHITGDQWW    60
TDYQPVSYIL TSKRGNRSQF ANMVTTCHTA GVLVIADALF NHMAGIESGT GTAGSSFTHY   120
DYPGIYQTQD FHHCGLTSGD DISDYSSQAQ VQTCELVNLA DLATDTEYVR AKLASYANDL   180
ISLGVGLRL DAAKHIATDD IKNILSRLSS TVYITQEVIF SGGEPVTLSM YTQNGDVQEF   240
RYTSTLQSAF SGGDISQLQN LDSKGWIAGT SANVFVANHD TERGGSSLNY KSSSNTYVTA   300
TIFSLAHPYG TPTILSSYEF SDTDAGSPNG GAGTCSTTGG ANGWLCQHRW VAFSGMVGFH   360
NNVGTASLTN WVSPQSNQIA FERSGKGFVA INNADSAWTA TFTTSLAAGS YCDVITGTSN   420
GSACSGTSYT VSGGSFSATV AARSAVAIHT GATGSGSGGG GGSTGSVAIT FQETATTTLG   480
ENIFLVGSIS QLRTWAPASA IALSSASYPT WSVTVSIPAG TTFEYKFIRK ESDGSVVWES   540
```

```
DPNRSATASS SASTQTILTS WR                                              562

SEQ ID NO: 154          moltype = AA  length = 578
FEATURE                 Location/Qualifiers
source                  1..578
                        mol_type = protein
                        organism = Lenzites betulinus
SEQUENCE: 154
RPASTVFHGA ETRSLDARAP SGSKDVIIQM FEWTWDSVAA ECTNFIGPAG YGFVQGSPPQ     60
EHIQGAQWWT DYQPVSYTLT SKRGDRTSFA NMIQTCHTAG VGVIVDTLFN HMAGVDSGTG    120
VAGSSFTHYN YPGIYQNQDF HHCGLEPGDD IVNYDNAVEV QTCELDNLAD LATETEYVRG    180
RLAQYGNDLL SLGADGMRLD AAKHIAVGDI ANILSRLNRT VYITQEVIFG AGEPITPNQY    240
TGNGDVQEFR YTSALQDAFL NSGIANLQVL ENRGWVPGSG ANVFVTNHDT ERNGASLNNN    300
SPSNTYVTAM IFSLAHPFGT PSILSSYSGF TDTDAGAPNG GVGTCSGSGG TNGWLCQHRW    360
TAVAGMVGFR NQVGSAALGN WQSPQSQQIA FGRGALGFVA INNADSAWSA TFTTSLPDGS    420
YCDVISGQTS GSTCTGSSFT VSGGGSLSATV PARSAIAVHT GQKGTGSGSG TGTGGGGSTG   480
SGNVAVNFAE TATTTFGENI FVVGSISQLG TWNTANAIAL SSPSYPTWTV SISIPAGTTF    540
QYKFIRKETD GSVVWESDPN RQATAPASGS TTLSTSWR                            578

SEQ ID NO: 155          moltype = AA  length = 571
FEATURE                 Location/Qualifiers
source                  1..571
                        mol_type = protein
                        organism = Trametes ljubarskyi
SEQUENCE: 155
RPATFDAADA RSVQPRAPSG SKDVIIQMFE WTWDSVAAEC TNFIGPAGYG FVQGNPPQEH     60
IQGDQWWTDY QPVSYILTSK RGDRTAFANM ISTCHAAGVG VIVDTIFNHM SGVDSGTGVA    120
GSSFTHYNYP GIYQNQDFHH CGLEPGDDIV NYDNAVEVQT CELENLADLA TDTEYVRGRL    180
AQYANDLLSL GADGLRLDAA KHIPTGDIAN ILSRLNRSVY ITQEVIYGDG EPITPNQYTG    240
NGDVQEFRYT TALKNAFLGG GISSLQSFDN LGWVPGTGAN VFVTNHDTER NGNSLNNNSP    300
SNTYVTAMIF SLAHPYGTPT ILSSYSGFTN TDAGAPNGGT GTCSGSGGAN GWLCQHRWTA    360
VAGMVGFRNN VGSAALTNWQ SPQSQQIAFG RGALGFVAIN NADSAWSTTF TTSLPDGSYC    420
DVVSGTSSNG GCTGSSFSVS GGSLTATVPA RSAIAIHTGE TGSGSNSGGG SGGSGTVTIN    480
FAETATTTFG ENIFVVGSIP QLGSWNPANA IALSSASYPT WTVSVSVPAG TTFEYKFIRK    540
ETDGSVVWES DPNRSDTAPA SGTQTITTSW R                                   571

SEQ ID NO: 156          moltype = AA  length = 451
FEATURE                 Location/Qualifiers
source                  1..451
                        mol_type = protein
                        organism = Bacillus subtilis
SEQUENCE: 156
GPAAASAETA NKSNELTAPS IKSGTILHAW NWSFNTLKHN MKDIHDAGYT AIQTSPINQV     60
KEGNQGDKSM SNWYWLYQPT SYQIGNRYLG TEQEFKEMCA AAEEYGIKVI VDAVINHTTS    120
DYAAISNEVK SIPNWTHGNT QIKNWSDRWD VTQNSLLGLY DWNTQNTQVQ SYLKRFLERA    180
LNDGADGFRF DAAKHIELPD DGSYGSQFWP NITNTSAEFQ YGEILQDSAS RDAAYANYMD    240
VTASNYGHSI RSALKNRNLG VSNISHYAYD VSADKLVTWV ESHDTYANDD EESTWMSDDD    300
IRLGWAVIAS RSGSTPLFFS RPEGGGNGVR FPGKSQIGDR GSALFEDQSI TAVNRFHNVM    360
AGQPEELSNP NGNNQIFMNQ RGSHGVVLAN AGSSSVSINT PTKLPDGRYD NKAGAGSFQV    420
NDGKLTGTIN ARSVAVLYPD DIEIRCNTFF Q                                   451

SEQ ID NO: 157          moltype = AA  length = 633
FEATURE                 Location/Qualifiers
source                  1..633
                        mol_type = protein
                        organism = Bacillus subtilis
SEQUENCE: 157
GPAAASAETA NKSNELTAPS IKSGTILHAW NWSFNTLKHN MKDIHDAGYT AIQTSPINQV     60
KEGNQGDKSM SNWYWLYQPT SYQIGNRYLG TEQEFKEMCA AAEEYGIKVI VDAVINHTTF    120
DYAAISNEVK SIPNWTHGNT QIKNWSDRWD VTQNSLLGLY DWNTQNTQVQ SYLKRFLDRA    180
LNDGADGFRF DAAKHIELPD DGSYGSQFWP NITNTSAEFQ YGEILQDSAS RDAAYANYMD    240
VTASNYGHSI RSALKNRNLG VSNISHYASD VSADKLVTWV ESHDTYANDD EESTWMSDDD    300
IRLGWAVIAS RSGSTPLFFS RPEGGGNGVR FPGKSQIGDR GSALFEDQAI TAVNRFHNVM    360
AGQPEELSNP NGNNQIFMNQ RGSHGVVLAN AGSSSVSINT ATKLPDGRYD NKAGAGSFQV    420
NDGKLTGTIN ARSVAVLYPD DIAKAPHVFL ENYKTGVTHS FNDQLTITLR ADANTTKAVY    480
QINNGPETAF KDGDQFTIGK GDPFGKTYTI MLKGTNSDGV TRTEKYSFVK RDPASAKTIG    540
YQNPNHWSQV NAYIYKHDGS RVIELTGSWP GKPMTKNADG IYTLTLPADT DTTNAKVIFN    600
NGSAQVPGQN QPGFDYVLNG LYNDSGLSGS LPH                                 633

SEQ ID NO: 158          moltype = AA  length = 487
FEATURE                 Location/Qualifiers
source                  1..487
                        mol_type = protein
                        organism = Schwanniomyces occidentalis
SEQUENCE: 158
KPIFLSKRDA GSSAAAAWRS ESIYQLVTDR FARTDGSTSA TCNTGDRVYC GGTFQGIIDK     60
LDYIQGMGFT AIWISPVVEQ IPDDTGYGYA YHGYWMKDIY AINSNFGTAD DLKNLSNELH    120
KRNMKLMVDI VTNHYAWNGA GSSVAYSNYN PFNQQSYFHD YCLITNYDDQ TNVEDCWEGD    180
NTVSLPDLRT EDSDVSSIFN LWVAELVSNY SIDGLRIDSA KHVDESFYPS FQSAAGVYLL    240
```

```
GEVYDGDPAY TCPYQNYMSG VTNYPLYYPM LRFFQGTSNS VDELNAMISS LESDCKDITL   300
LGNFIENHDQ PRLPSYTSDS ALIKNAIAFN LMSDGIPIIY YGQEQGYSGS SDPNNREALW   360
LSGYSTSNGY YKLISSVNQI RNQAIYKDSK YTTYWSDVLY ASGHVIALQR GADDQRIVSV   420
FNNLGSSGSQ TVTFSTKYSG GEKVVDVLTC QTSYANSDST LTVSISGGAP RIYAPASLIA   480
NSGICNF                                                            487

SEQ ID NO: 159          moltype = AA  length = 583
FEATURE                 Location/Qualifiers
source                  1..583
                        mol_type = protein
                        organism = Rhizomucor pusillus
SEQUENCE: 159
ATSDDWKGKA IYQLLTDRFG RADDSTSNCS NLSNYCGGTY EGITKHLDYI SGMGFDAIWI    60
SPIPKNSDGG YHGYWATDFY QLNSNFGDES QLKALIQAAH ERDMYVMLDV VANHAGPTSN   120
GYSGYTFGDA SLYHPKCTID YNDQTSIEQC WVADELPDID TENSDNVAIL NDIVSGWVGN   180
YSFDGIRIDT VKHIRKDFWT GYAEAAGVFA TGEVFNGDPA YVGPYQKYLP SLINYPMYYA   240
LNDVFVSKSK GFSRISEMLG SNRNAFEDTS VLTTFVDNHD NPRFLNSQSD KALFKNALTY   300
VLLGEGIPIV YYGSEQGFSG GADPANREVL WTTNYDTSSD LYQFIKTVNS VRMKSNKAVY   360
MDIYVGDNAY AFKHGDALVV LNNYGSGSTN QVSFSVSGKF DSGASLMDIV SNITTTVSSD   420
GTVTFNLKDG LPAIFTSATG GTTTTATPTG SGSVTSTSKT TATASKTSTS TSSTSCTTPT   480
AVAVTFDLTA TTTYGENIYL VGSISQLGDW ETSDGIALSA DKYTSSDPLW YVTVTLPAGE   540
SFEYKFIRIE SDDSVEWESD PNREYTVPQA CGTSTATVTD TWR                    583

SEQ ID NO: 160          moltype = AA  length = 616
FEATURE                 Location/Qualifiers
source                  1..616
                        mol_type = protein
                        organism = Aspergillus niger
SEQUENCE: 160
AEWRTQSIYF LLTDRFGRTD NSTTATCDTG DQIYCGGSWQ GIINHLDYIQ GMGFTAIWIS    60
PITEQLPQDT ADGEAYHGYW QQKIYDVNSN FGTADDLKSL SDALHARGMY LMVDVVPNHM   120
GYAGNGNDVD YSVFDPFDSS SYFHPYCLIT DWDNLTMVQD CWEGDTIVSL PDLNTTETAV   180
RTIWYDWVAD LVSNYSVDGL RIDSVLEVEP DFFPGYQEAA GVYCVGEVDN GNPALDCPYQ   240
KVLDGVLNYP IYWQLLYAFE SSSGSISNLY NMIKSVASDC SDPTLLGNFI ENHDNPRFAS   300
YTSDYSQAKN VLSYIFLSDG IPIVYAGEEQ HYSGGKVPYN REATWLSGYD TSAELYTWIA   360
TTNAIRKLAI SADSAYITYA NDAFYTDSNT IAMRKGTSGS QVITVLSNKG SSGSSYTLTL   420
SGSGYTSGTK LIEAYTCTSV TVDSSGDIPV PMASGLPRVL LPASVVDSSS LCGGSGRTTT   480
TTTAATSTSK ATTSSSSSSA AATTSSSCTA TSTTLPITFE ELVTTTYGEE VYLSGSISQL   540
GEWDTSDAVK LSADDYTSSN PEWSVTVSLP VGTTFEYKFI KVDEGGSVTW ESDPNREYTV   600
PECGNGSGET VVDTWR                                                  616

SEQ ID NO: 161          moltype = AA  length = 512
FEATURE                 Location/Qualifiers
source                  1..512
                        mol_type = protein
                        organism = Bacillus stearothermophilus
SEQUENCE: 161
APFNGTMMQY FEWYLPDDGT LWTKVANEAN NLSSLGITAL WLPPAYKGTS RSDVGYGVYD    60
LYDLGEFNQK GTVRTKYGTK AQYLQAIQAA HAAGMQVYAD VVFDHKGGAD GTEWDAVEV   120
NPSDRNQEIS GTYQIQAWTK FDFPGRGNTY SSFKWRWYHF DGVDWDESRK LSRIYKFRGK   180
AWDWEVDTEF GNYDYLMYAD LDMDHPEVVT ELKNWGKYV NTTNIDGFRL DAVKHIKFSF   240
FPDWLSYVRS QTGKPLFTVG EYWSYDINKL HNYITKTDGT MSLFDAPLHN KFYTASKSGG   300
AFDMRTLMTN TLMKDQPTLA VTFVDNHDTE PGQALQSWVD PWFKPLAYAF ILTRQEGYPC   360
VFYGDYYGIP QYNIPSLKSK IDPLLIARRD YAYGTQHDYL DHSDIIGWTR EGGTEKPGSG   420
LAALITDGPG GSKWMYVGKQ HAGKVFYDLT GNRSDTVTIN SDGWGEFKVN GGSVSVWVPR   480
KTTVSTIARP ITTRPWTGEF VRWTEPRLVA WP                                512

SEQ ID NO: 162          moltype = AA  length = 483
FEATURE                 Location/Qualifiers
source                  1..483
                        mol_type = protein
                        organism = Bacillus halmapalus
SEQUENCE: 162
HHNGTNGTMM QYFEWHLPND GNHWNRLRDD ASNLRNRGIT AIWIPPAWKG TSQNDVGYGA    60
YDLYDLGEFN QKGTVRTKYG TRSQLESAIH ALKNNGVQVY GDVVMNHKGG ADATENVLAV   120
EVNPNNRNQE ISGDYTIEAW TKFDFPGRGN TYSDFKWRWY HFDGVDWDQS RQFQNRIYKF   180
RGKAWDWEVD SENGNYDYLM YADVDMDHPE VVNELRRWGE WYTNTLNLDG FRIDAVKHIK   240
YSFTRDWLTH VRNATGKEMF AVAEFWKNDL GALENYLNKT NWNHSVFDVP LHYNLYNASN   300
SGGNYDMAKL LNGTVVQKHP MHAVTFVDNH DSQPGESLES FVQEWFKPLA YALILTREQG   360
YPSVFYGDYY GIPTHSVPAM KAKIDPILEA RQNFAYGTQH DYFDHHNIIG WTREGNTTHP   420
NSGLATIMSD GPGGEKWMYV GQNKAGOVWH DITGNKPGTV TINADGWANF SVNGGSVSIW   480
VKR                                                                483

SEQ ID NO: 163          moltype = AA  length = 478
FEATURE                 Location/Qualifiers
source                  1..478
                        mol_type = protein
                        organism = Aspergillus oryzae
SEQUENCE: 163
```

```
ATPADWRSQS IYFLLTDRFA RTDGSTTATC NTADQKYCGG TWQGIIDKLD YIQGMGFTAI    60
WITPVTAQLP QTTAYGDAYH GYWQQDIYSL NENYGTADDL KALSSALHER GMYLMVDVVA   120
NHMGYDGAGS SVDYSVFKPF SSQDYFHPFC FIQNYEDQTQ VEDCWLGDNT VSLPDLDTTK   180
DVVKNEWYDW VGSLVSNYSI DGLRIDTVKH VQKDFWPGYN KAAGVYCIGE VLDGDPAYTC   240
PYQNVMDGVL NYPIYYPLLN AFKSTSGSMD DLYNMINTVK SDCPDSTLLG TFVENHDNPR   300
FASYTNDIAL AKNVAAFIIL NDGIPIIYAG QEQHYAGGND PANREATWLS GYPTDSELYK   360
LIASANAIRN YAISKDTGFV TYKNWPIYKD DTTIAMRKGT DGSQIVTILS NKGASGDSYT   420
LSLSGAGYTA GQQLTEVIGC TTVTVGSDGN VPVPMAGGLP RVLYPTEKLA GSKICSSS    478

SEQ ID NO: 164           moltype = AA   length = 483
FEATURE                  Location/Qualifiers
source                   1..483
                         mol_type = protein
                         organism = Bacillus amyloliquefaciens
SEQUENCE: 164
VNGTLMQYFE WYTPNDGQHW KRLQNDAEHL SDIGITAVWI PPAYKGLSQS DNGYGPYDLY    60
DLGEFQQKGT VRTKYGTKSE LQDAIGSLHS RNVQVYGDVV LNHKAGADAT EDVTAVEVNP   120
ANRNQETSEE YQIKAWTDFR FPGRGNTYSD FKWHWYHFDG ADWDESRKIS RIFKFRGEGK   180
AWDWEVSSEN GNYDYLMYAD VDYDHPDVVA ETKKWGIWYA NELSLDGFRI DAAKHIKFSF   240
LRDWVQAVRQ ATGKEMFTVA EYWQNNAGKL ENYLNKTSFN QSVFDVPLHF NLQAASSQGG   300
GYDMRRLLDG TVVSRHPEKA VTFVENHDTQ PGQSLESTVQ TWFKPLAYAF ILTRESGYPQ   360
VFYGDMYGTK GTSPKEIPSL KDNIEPILKA RKEYAYGPQH DYIDHPDVIG WTREGDSSAA   420
KSGLAALITD GPGGSKRMYA GLKNAGETWY DITGNRSDTV KIGSDGWGEF HVNDGSVSIY   480
VQK                                                                 483

SEQ ID NO: 165           moltype = AA   length = 583
FEATURE                  Location/Qualifiers
source                   1..583
                         mol_type = protein
                         organism = Rhizomucor pusillus
SEQUENCE: 165
ATSDDWKGKA IYQLLTDRFG RADDSTSNCS NLSNYCGGTY EGITKHLDYI SGMGFDAIWI    60
SPIPKNSDGG YHGYWATDFY QLNSNFGDES QLKALIQAAH ERDMYVMLDV VANHAGPTSN   120
GYSGYTFDDA SLYHPKCTID YNNQTSIEQC WVADELPDID TENSDNVAIL NDIVSGWVGN   180
YSFDGIRIDT VKHIRKDFWT GYAEAAGVFA TGEVFNGDPA YVGPYQKYLP SLINYPMYYA   240
LNDVFVSKSK GFSRISEMLG SNRNAFEDTS VLTTFVDNHD NPRFLNSQSD KALFKNALTY   300
VLLGEGIPIV YYGSEQGFSG GADPANREVL WTTNYDTSSD LYQFIKTVNS VRMKSNKAVY   360
MDIYVGDNAY AFKHGDALVV LNNYGSGSTN QVSFSVSGKF DSGASLMDIV SNITTTVSSD   420
GTVTFNLKDG LPAIFTSATG GTTTTATPTG SGSVTSTSKT TATASKTSTS TSSTSCTTPT   480
AVAVTFDLTA TTTYGENIYL VGSISQLGDW ETSDGIALSA DKYTSSDPLW YVTVTLPAGE   540
SFEYKFIRIE SDDSVEWESD PNREYTVPQA CGTSTATVTD TWR                     583

SEQ ID NO: 166           moltype = AA   length = 623
FEATURE                  Location/Qualifiers
source                   1..623
                         mol_type = protein
                         organism = Kionochaeta ivoriensis
SEQUENCE: 166
LSPAGWRQQS IYQVMTDRFA RTDGSTIASC DTSQQAYCGG TWQGLINKLD YIQGMGFTAV    60
WISPMVHQMA GATSDGESYH GYWAQDINTV NSAFGTAADL KALSSAALHAR GMYLMLDVVT   120
NHFAYDGCGT CVDYSIFNPF NSESYFHPFC LIDYSNTTHI QVCWEGDNTV SLPDLRTEDS   180
DVRSIWNSWI SSVISTYGVD GLRVDSAQQV ETSFWAGFEA AAGVYMVGEV FNGDPTYVTP   240
FQDYMDGVLN YPAYYWITQA FESTSGSISN LANGMNTMKS LAKNTSLLGS FLENHDNPRF   300
PSLTSDMSLA QNAIAFTMLM DGIPIIYQGQ EQHFSGGGVP SDREAVLSG YPNDTTLYAW    360
ITKLNAVRSW AIAKDSSYLA YMAYPVYTDT HTIAMRKGDT GYQVISVYTN VGASGSSYSV   420
TLTSADTGFT ASQSVVDLVG CKTYTADSTG SLSLSLTGGI PIILYPAASL TGNTICTSTG   480
GTTTTATPTG SGSVTSTSKT TATASKTSTS TSSTSCTTPT AVAVTFDLTA TTTYGENIYL   540
VGSISQLGDW ETSDGIALSA DKYTSSDPLW YVTVTLPAGE SFEYKFIRIE SDDSVEWESD   600
PNREYTVPQA CGTSTATVTD TWR                                           623

SEQ ID NO: 167           moltype = AA   length = 588
FEATURE                  Location/Qualifiers
source                   1..588
                         mol_type = protein
                         organism = Aspergillus niger
SEQUENCE: 167
LSAAEWRTQS IYFLLTDRFG RTDNSTTATC DTGDQIYCGG SWQGIINHLD YIQGMGFTAI    60
WISPITEQLP QDTADGEAYH GYWQQKIYDV NSNFGTADDL KSLSDALHAR GMYLMVDVVP   120
NHMGYAGNGN DVDYSVFDPF DSSSYFHPYC LITDWDNLTM VQDCWEGDTI VSLPDLNTTE   180
TAVRTIWYDW VADLVSNYSV DGLRIDSVLE VEPDFFPGYQ EAAGVYCGE VDNGNPALDC    240
PYQKVLDGVL NYPIYWQLLY AFESSSGSIS NLYNMIKSVA SDCSDPTLLG NFIENHDNPR   300
FASYTSDYSQ AKNVLSYIFL SDGIPIVYAG EEQHYSGGKV PYNREATWLS GYDTSAELYT   360
WIATTNAIRK LAISADSAYI TYANDAFYTD SNTIAMRKGT SGSGQVITVLS NKGSSGSSYT  420
LTLSGSGYTS GTKLIEAYTC TSVTVDSSGG IPVPMASGDN RVLPASVVD SSSLCGGSGR   480
GATSPGGSSG SVEVTFDVYA TTVYGQNIYI TGDVSELGNW TPANGVALSS ANYPTWSATI   540
ALPADTTIQY KYVNIDGSTV IWEDAISNRE ITTPASGTYT EKDTWDES               588

SEQ ID NO: 168           moltype = AA   length = 588
FEATURE                  Location/Qualifiers
```

```
source                          1..588
                                mol_type = protein
                                organism = Aspergillus oryzae
SEQUENCE: 168
ATPADWRSQS IYFLLTDRFA RTDGSTTATC NTADQKYCGG TWQGIIDKLD YIQGMGFTAI   60
WITPVTAQLP QTTAYGDAYH GYWQQDIYSL NENYGTADDL KALSSALHER GMYLMVDVVA  120
NHMGYDGPGS SVDYSVFVPF NSASYFHPFC FIQNWDNQTQ VEDCWLGDNT VSLPDLDTTK  180
DVVKNEWYDW VGSLVSNYSI DGLRIDTVKH VQKDFWPGYN KAAGVYCIGE VLDGDPAYTC  240
PYQEVLDGVL NYPIYYPLLN AFKSTSGSMD DLYNMINTVK SDCPDSTLLG TFVENHDNPR  300
FASYTNDIAL AKNVAAFIIL NDGIPIIYAG QEQHYAGGND PANREATWLS GYPTDSELYK  360
LIASANAIRN YAISKDTGFV TYKNWPIYKD DTTIAMRKGT DGSQIVTILS NKGASGDSYT  420
LSLSGAGYTA GQQLTEVIGC TTVTVDSSGD VPVPMAGGLP RVLYPTEKLA GSKICSSSGR  480
GATSPGGSSG SVEVTFDVYA TTVYGQNIYI TGDVSELGNW TPANGVALSS ANYPTWSATI  540
ALPADTTIQY KYVNIDGSTV IWEDAISNRE ITTPASGTYT EKDTWDES              588

SEQ ID NO: 169                  moltype = AA  length = 583
FEATURE                         Location/Qualifiers
source                          1..583
                                mol_type = protein
                                organism = Penicillium canescens
SEQUENCE: 169
LTPAEWRSQS IYFMLTDRFG RSDNSTTAAC NVSDRTYCGG TWQGIINHLD YIQGMGFTAI   60
WITPVTEQLP QDTGDGEAYH GYWQQNIYEI DSKLGTAADL LALSKALHAR GMYLMVDVVA  120
NHMGYAGSGN SVDYSVFNPF SSSSYFHSYC LISNYDDQSN VENCWLGDTI VSLPDLDTTQ  180
TAVQTIWYDW IADLVSNYSI DGLRIDTVKH VQKSFWPGYN DAAGVYCGE IFDGDPAYTC  240
DYQNYMDGVL NYPIYYQLLY AFQSSSGSIS DLYNMINSVK CDCADSTLLG NFIENHDNPR  300
FASYTSDYSQ AKNVISFLFL SDGIPIIYSG QEQHYSGGAD PANREATWLS GYSTTAELYK  360
YIATTNKIRK LAVSDSSYLT TKNVPFYQDS HTLAMKKGSS ASPVITVLSN YGSSGSSYTL  420
SLSGSGYSSG TKLMEMYTCT SVTVDSSGNI AVPMASGLPR VLMLASSANS LCGSSGATSP  480
GGSSGSVEVT FDVYATTVYG QNIYITGDVS ELGNWTPANG VALSSANYPT WSATIALPAD  540
TTIQYKYVNI DGSTVIWEDA ISNREITTPA SGTYTEKDTW DES                   583

SEQ ID NO: 170                  moltype = AA  length = 583
FEATURE                         Location/Qualifiers
source                          1..583
                                mol_type = protein
                                organism = Acidomyces acidothermus
SEQUENCE: 170
LTPAQWRGQS IYQVLTDRFG RTDDSTTAAC DVNDYCGGSW QGIINHLDYI QDMGFSAIWI   60
SPVVENLVGD TQDGSAYHGY WAQNIYALNP NFGTVSDLVA LSAALHQRGM YLMVDVVTNH  120
MGYDGCGDCV DYSVFTPFNS QSYFHPFCLI DYNNSTIKV CWEGDNIVSL PDMRTEDSDV  180
ATEWNTWISE LVSNYSIDGL RIDSAQQVDN AFFPPFQAAA GGIHVLGEVF NGDPNYVCPY  240
QDFMSGVLNY PAYYITQAF QSTSGSISNL VNGINQMKST CTDTTLLGSF LENHDNPRF  300
SYTSDLSLDK NAITFTILQD GIPIIYEGQE QHYSGGTVPN NREAIWLSGY DKSAPLYTWI  360
ASVNQIRNQA IFKDSNYLTY MAWPIYSDAS TIAMRKGFDG LQIISVYSNK GASAASYTIS  420
LESSTTGFTA NEALVEVMSC TTYTTDGSGN LAVTISGGLP AVFYPKAQLA GSGICGATSP  480
GGSSGSVEVT FDVYATTVYG QNIYITGDVS ELGNWTPANG VALSSANYPT WSATIALPAD  540
TTIQYKYVNI DGSTVIWEDA ISNREITTPA SGTYTEKDTW DES                   583

SEQ ID NO: 171                  moltype = AA  length = 586
FEATURE                         Location/Qualifiers
source                          1..586
                                mol_type = protein
                                organism = Kinochaeta ivoriensis
SEQUENCE: 171
LSPAGWRQQS IYQVMTDRFA RTDGSTIASC DTSQQAYCGG TWQGLINKLD YIQGMGFTAV   60
WISPMVHQMA GATSDGESYH GYWAQDINTV NSAFGTAADL KALSAALHAR GMYLMLDVVT  120
NHFAYDGCGT CVDYSIFNPF NSESYFHPFC LIDYSNTTSI QVCWEGDNTV SLPDLRTEDS  180
DVRSIWNSWI SSVISTYGVD GLRVDSAQQV ETSFWAGFEA AAGVYMVGEV FNGDPTYVTP  240
FQDYMDGVLN YPAYYWITQA FESTSGSISN LANGMNTMKS LAKNTSLLGS FLENHDNPRF  300
PSLTSDMSLA QNAIAFTMLM DGIPIIYQGQ EQHFSGGGVP SDREAVWLSG YPNDTTLYAW  360
ITKLNAVRSW AIAKDSSYLA YMAYPVYTDT HTIAMRKGDT GYQVISVYTN VGASGSSYSV  420
TLTSADTGFT ASQSVVDLVG CKTYTADSTG SLSLSLTGSP PIILYPAASL TGNTICTSGA  480
TSPGGSSGSV EVTFDVYATT VYGQNIYITG DVSELGNWTP ANGVALSSAN YPTWSATIAL  540
PADTTIQYKY VNIDGSTVIW EDAISNREIT TPASGTYTEK DTWDES                586

SEQ ID NO: 172                  moltype = AA  length = 585
FEATURE                         Location/Qualifiers
source                          1..585
                                mol_type = protein
                                organism = Aspergillus terreus
SEQUENCE: 172
LTPAEWRSQS IYFLLTDRFG RTDNSTTAAC DTSDRVYCGG SWQGIINQLD YIQGMGFTAI   60
WITPVTGQFY ENTGDGTSYH GYWQQDIYDL NYNYGTAQDL KNLANALHER GMYLMVDVVA  120
NHMGYDGAGN TVDYSVFNPF SSSSYFHPYC LISNYDNQTN VEDCWLGDTT VSLPDLDTTS  180
TAVRNIWYDW VADLVANYSI DGLRVDTVKH VEKDFWPGYN SAAGVYCGE VYSGDPAYTC  240
PYQNYMDGVL NYPIYYQLLY AFESSSGSIS DLYNMISSVA SSCKDPTLLG NFIENHDNPR  300
FASYTSDYSQ AKNVITFIFL SDGIPIVYAG QEQHYSGGSD PANREATWLS GYSTSATLYT  360
WIATTNQIRS LAISKDAGYV QAKNNPFYSD SNTIAMRKGT TAGAQVITVL SNKGASGSSY  420
```

```
TLSLSGTGYS AGVTLVETYT CTTVTVDSSG NLPVPMTSGL PRVFVPSSWV NGSALCNGAT    480
SPGGSSGSVE VTFDVYATTV YGQNIYITGD VSELGNWTPA NGVALSSANY PTWSATIALP    540
ADTTIQYKYV NIDGSTVIWE DAISNREITT PASGTYTEKD TWDES                    585

SEQ ID NO: 173          moltype = AA   length = 565
FEATURE                 Location/Qualifiers
source                  1..565
                        mol_type = protein
                        organism = Thamnidium elegans
SEQUENCE: 173
VPLSVLDKRN GVTTLSKRAA AADWKSRSIY QLVTDRFGRS DGSTSACGDL SNYCGGDYKG     60
IQNQLDYIAG MGFDAIWISP IPENTDGGYH GYWAKDFEKL NTNFGSADDL KALVTAAHGK    120
GMYVMLDVVA NHAGPASGGD YSGFTFSSAS NYHPQCTIDY DNQTSVEQCW VADDLPDINT    180
EDDTIVSKLH SIVSDWVTTY DFDGIRIDTV KHIRKDFWSG YEEAAGVFAT GEVFDGDAAY    240
VGPYQDQLSS LINYPLYYAI RDVFSAGSGF SRISDMLSTI KSNFKDPSVL TTFVDNQDNA    300
RFLSVKSDMS LYKNALAFTI LTEGIPVVYY GTEQGFKGGD DPKNREVLWT SNYDTSSDLY    360
KFIKIVNNDV RQKSDKTVTL DVDVGTNTYA FTHGKNLIVV NNYGSGSTES VTVKVGDSVA    420
DGTKLVDAVS NITATVSGGS ITFSLKDGLP ALFVPSSGAT SPGGSSGSVE VTFDVYATTV    480
YGQNIYITGD VSELGNWTPA NGVALSSANY PTWSATIALP ADTTIQYKYV NIDGSTVIWE    540
DAISNREITT PASGTYTEKD TWDES                                          565

SEQ ID NO: 174          moltype = AA   length = 574
FEATURE                 Location/Qualifiers
source                  1..574
                        mol_type = protein
                        organism = Meripilus giganteus
SEQUENCE: 174
RPTVFDAGAD AHSLHARAPS GSKDVIIQMF EWNWDSVAAE CTNFIGPAGY GFVQVSPPQE     60
TIQGAQWWTD YQPVSYTLTG KRGDRSQFAN MITTCHAAGV GVIVDTIWNH MAGVDSGTGT    120
AGSSFTHYNY PGIYQNQDFH HCGLEPGDDI VNYDNAVEVQ TCELVNLADL ATDTEYVRGR    180
LAQYGNDLLS LGADGLRLDA SKHIPVGDIA NILSRLSRSV YITQEVIFGA GEPITPNQYT    240
GNGDVQEFRY TSALKDAFLS SGISNLQDFE NRGWVPGSGA NVPVVNHDTE RNGASLNNNS    300
PSNTYVTATI FSLAHPYGTP TILSSYDGFT NTDAGAPNNN VGTCSTSGGA NGWLCQHRWT    360
AIAGMVGFRN NVGSAALNNW QAPQSQQIAF GRGALGFVAN NNADSAWSTT FTTSLPDGSY    420
CDVISGKASG SSCTGSSFTV SGGKLTATVP ARSAIAVHTG QKGSGGGATS PGGSSGSVEV    480
TFDVYATTVY GQNIYITGDV SELGNWTPAN GVALSSANYP TWSATIALPA DTTIQYKYVN    540
IDGSTVIWED AISNREITTP ASGTYTEKDT WDES                                574

SEQ ID NO: 175          moltype = AA   length = 671
FEATURE                 Location/Qualifiers
source                  1..671
                        mol_type = protein
                        organism = Chaetomium megalocarpum
SEQUENCE: 175
LYINGSVTAP CDSPIYCQGE ILKAIELARP FSDSKTFVDM PTIKPVDEVI AAFSRLSQPL     60
SNNSELTAFL AENFAPAGGE LEEVPISELE TDPSFLNKLE DVDIKEFVGK VIDIWPDLTR    120
RYAGPGNCSQ CANSFIPVNR TFVVAGGRFR EPYYWDSYWI LEGLLRTGGA FTQISKNMIE    180
NFLDFVETIG FVPNGARIYY LNRSQPPLLT LMVKTYVDYT NDTSILERAL PLLVKEYEFW    240
TNNRTVSITA TDGKEYTLNR YSVNNNQPRP ESYREDYVTA NNASYYAQSG IIYPVKTPLN    300
ETEKAELYSN LASGAESGWD YTARWLKTPD DAARDVYFPL RSLNVRSIVS VDLNSILYQN    360
EVIISEYLEQ AGNSSEAKRF ADAAEQRSEA MYALMWNATH WSYFDYNLTD NSQRVFVPAD    420
ADTAPSDQTA APPGQQVLFD IAQLYPFWTG AAPASLKANP LAVQNAYARV ARMLDTKAGA    480
IAATNLRTGQ QWDQPNVWPP LQHILMKGLL NTPATFGTED PAYAHTQDLA LRLAQRYLDS    540
TFCTWYATGG STSATPQLQG AAPGATGTMF EKYADDATNV AGGGGEYEVV EGFGWTNGVL    600
IWAADVFGDR LVRPDCGNIT AAHTSSEKRT VAGASRPDA GASGVRRERR AVELDPWDAA    660
WTKMFGRSKL R                                                         671

SEQ ID NO: 176          moltype = AA   length = 662
FEATURE                 Location/Qualifiers
source                  1..662
                        mol_type = protein
                        organism = Lecanicillium psalliotae
SEQUENCE: 176
LYQNGSVIAP CDSPIYCHGD ILKEVELARP FTDSKTFVDM PAKKPLAEIQ AAFDKLEKPL     60
SNNTALNEFL STYFEDAGGE LKAVSKDKLK TDAKFVDKLN DTVIKEFVNK VIDIWPDLTR    120
EYAGSATNCT NCPNSFIPVN RTFVVAGGRF REPYYWDSYW IVEGLLRTGG AFVDITKNTI    180
ENFLDLIEQF GFIPNGARLY YLNRSQPPLL SQMVKNYISY TNDTDILKRA LPILVKEHEF    240
FMNNRSVEIT VENKTYTLNR YAVNSNTQPRP ESFREDYNTV NNNSYYAASG IIYPVKTPLN    300
ESEQATLYAN LASGAESGLD YTTAKWSTNP RDSMEDIYFP LRSLNIMNIV PVDLNSILYG    360
NEKAISEFYN ITGNSSEADS WSKKAAERQE AIQAVFWNET LYSYFDYNRT SSSQHIYIPS    420
DDDTQSFENA TAPAGMQEVF TVTQFYPFWM GAAPDYIRNN PHAVKTAYSR IAKYLELKPG    480
GIPSSNLRSG QQWDQPSVWP PLMHVLMKGL VNTPATFGKE DPAYKDVHKL ALTLGQRYLD    540
STFCTWYATG GSTSETPQLS GLSDSDVGIM FEKYDDTSIN HAGGGGEYEV VEGFGWSNGV    600
LMWVADTFGN ELKRPDCGNI TAANVHPGKR SVSAVELSSR DAQRVKKFGR RAEGRMKVPG    660
VL                                                                   662

SEQ ID NO: 177          moltype = AA   length = 637
FEATURE                 Location/Qualifiers
source                  1..637
```

```
                        mol_type = protein
                        organism = Doratomyces sp.
SEQUENCE: 177
LYTNGSIIAP CDSPIYCHGD ILHQVQLAHP FPDSKTFVDM PAIKSVDEIQ AAFDKLDKPL    60
KNDTALQNFL AENFAEAGHE LAEVDPSELS TDPRFLDKVS DTVIHEFTQK VIDIWPDLTR   120
SYSPSGAGSD CPDCPNSFLP VNRTFVVAGG RFREPYYWDS YWIVEGLLRT GGDFLGVSRN   180
IIENFLDFVD DFGFVPNGAR RYYLNRSQPP LLSLMVKSYV EQTNDTEILD RAVPLLIKEY   240
EFWTKNRTVE VPFGNETITL NQYNVDNTQP RPESYREDYI TATNASYYSA SGEVYEEVEK   300
LNETQRATVY RNLATGAESG WDYTSRWMAR PRDAVEDVYF PLRSLNIIEI VPVDLNSILY   360
ANELAIAEFV RLAGADDCEE EAAAWEALAE KRSADMHRLM WNDTLHSYFD YNLTSSSQNV   420
YVPADNDTAP FERPGGTPEG SQVFFSAAQF YPFWTGAAPS SLRDDPAAVQ LAYSRVASYL   480
DLRAGGIPAT NLRTGQQWDQ PSVWPPLMHI LTSGLLNTSP ASASDDDDPS YAPTRDLALS   540
LAQRYLDSTF CTWYATGGST SETPQLDGFT DEDKGAMFEK YDDSATNVAG GGGEYEVVEG   600
FGWTNGVLIW MVDTFGDELS RPDCGDIEAA NAHPARK                            637

SEQ ID NO: 178          moltype = AA   length = 601
FEATURE                 Location/Qualifiers
source                  1..601
                        mol_type = protein
                        organism = Mucor moelleri
SEQUENCE: 178
IQNHTSFSCD SPIYCEGDIL HTVQLAKIFS DSKTFVDMPT SKSESQVIEA FKAIGGRNAT    60
IAQVQQFLNE NFLTAGTEVK RLTNITIPEL NWIDNITDPD YRGWISKLNQ AWSNLTFTFD   120
TSVLCQDCAT STLPVSRPFV VPGGRFREFY YWDSFFVIKG LLLSDQVELA KNMILNFFDF   180
IDTYGFIPNG ARIYYLNRSQ PPFLTQMVEA FWEKTSDKEF MTNALPFLDK EYNFWMTNNS   240
ISVPDPKNPS KKYKMNHYVT LNTSPRPESY VEDYNTVNNG TDYSQAVKLQ LYADIAAGAE   300
TGWDYSSRWT RQKHPAPNQT EGYEMLRSIN TANIVPIDLN SLLWNTETML AEWHDRFGEK   360
SKSKKKSAYY QTQAKKRLDA MEKLMWNPTD YTYYDYNLTS SSQNLEFTPA NLFPIWLGAL   420
PNKVMKNKTE LARVFDETEN ALRKYPGILT TSYYNTTMQW DWPNGWPPLS YVAMEGMNKV   480
EESLNGKKGS KQDGKTYTTS RGTSLARLSF TLAERYAASA YCGWYKTGGS IPGILNKIDG   540
VADDGHMFEK FDVNTIGISG SQGEYVSQTG FGWTNGIALW IFDTYANLTA PDCNQTITLN   600
I                                                                  601

SEQ ID NO: 179          moltype = AA   length = 650
FEATURE                 Location/Qualifiers
source                  1..650
                        mol_type = protein
                        organism = Phialophora cyclaminis
SEQUENCE: 179
LYINGSVIAP CDSPIYCHGE LLKAIELARP FSDSKTFVDM PTRKPVDEVV AAFEKLSKPV    60
VNDTKLGEFL QANFLPAGGD LSDFPPGSLE TDPKFLDNIN DTVIREFTEA VIDIWPDLTR   120
RYVGASNCTG CANSFIPVNR TFVVAGGRFR EPYYWDSYWI IEGLLRTGGN FVQISKNIIE   180
NFLDFVETIG FVPNGARIYY LNRSQPPLLT AMVKAYLEHT NDTKILDRAV PLLIKEYNFW   240
ITNRSVTLTG PDGNEYTLQR YSVNNNQPRP ESYREDYNTA NNKSYYSTSG IIYPENVSLN   300
DSEKKELYAN LATGAESGWD YGTRWLSRPA DALRRDVYFPL RYVKTRDLVP VDLNAILYQN   360
EASISSFLYI QGNDTGAAHF AKLAAARQKA MTAVLWNATL FSYFDYNMTS SSHFSFIPVD   420
DDATSIETAT APRGFQQIFH VAQLYPFWTG AAPASLREPY LAVQRAFSRV SQMLEEKAGS   480
IPATNFYTGQ QWDEPNVWPP LQHIIMEGLR NTPATFGEDD PIYQGVQDLA LRVAQRYLDS   540
TFCTWYATGG STSLTPKLAG LTDNAKGIMF EKYGDNSTNV AGGGGEYEVV EGFGWTNGVL   600
IWAVDTFGNK LKRPDCGDIQ PAHVEARGLQ RRAVELDKWD AQWVKRFGAK              650

SEQ ID NO: 180          moltype = AA   length = 654
FEATURE                 Location/Qualifiers
source                  1..654
                        mol_type = protein
                        organism = Thielavia arenaria
SEQUENCE: 180
LYINGSVIAP CDSPLYCHGD ILKAIELARP FQDSKTFVDM PTIRPVEEVI AAFNRLSQPL    60
SNNSELNAFL QANFAPAGGE LEEVPESELS TNPVFLDKLN DTVIKEFVAK VIDIWPDLTR   120
RYAGPGNCSE CADSFIPVNR TFVIAGGRFR EPYYWDSFWI LEGLLRTGGA FTEISKNMIE   180
NFLDFVETIG HIPNGARIYY LNRSQPPLLA GMVKNYVDYT NDTSILERAL PLLIKEYEFW   240
TNNRTVQVTA SDGKTYTLHR YNVNNNQPRP ESYREDWITA NNASYYAASG IIYPVKTPLN   300
ESEKKAALYSN LASGAESGWD YGTRPFMRPE DAARDIYFPL RHLNVRDMVT VDLNAILYQN   360
EVIISEYLEQ AGNNTEAERF ASAARQRSEA MYALMWNETL WSYFDYNLTS NSQYTFIPAD   420
VNATAAEKAN APEGQKVIFH IAQLYPFWTG AAPDQLKNNP LAVQKAYSRV AEMLDIKPGA   480
IPATNFITGQ QWDQPNVWPP LMHVLMAGLL NTPPTFGEDD PAYQAVQALA LRLGQRYLDS   540
TFCTWYATGG ETSQTPRLQG VSPDATGTMF EKYADNAINV AGGGGEYEVV EGFGWTNGVL   600
IWAADVFANG LKRPDCGNIT AAHTHNGAKR AVELHPRDAA WTKKFGKRAL KKRA         654

SEQ ID NO: 181          moltype = AA   length = 661
FEATURE                 Location/Qualifiers
source                  1..661
                        mol_type = protein
                        organism = Thielavia antarctica
SEQUENCE: 181
LYVNGSVTAP CDSPLYCQGE ILKAIELARP FADSKTFVDM PTLRPLDDVI AAFRKLSQPL    60
SNSSELNAFL AANFAPAGGE LEEVPKSELR TKPAFLDKVE DVVIKEFVGK VIDIWPDLTR   120
RYAGPGNCTE CANSFIPVNR TFVVAGGRFR EPYYWDSYWI LEGLLRTGGD FTKISRNIIE   180
NFLDFVDTIG FVPNGARIYY LNRSQPPVLT LMVKTYVDYT NDTSILERAL PLLIKEHEFW   240
```

```
TTNRSVSVEV DGKTHTLNRY FVNNNQPRPE SYREDWITAN NASYYAASGI IYPVKTPLNG    300
TQQAELYANL ASGAESGWDY TSRWLKTPSD AARDVYFPLR SLNVINTIPV DLNSILYQNE    360
VIISEYLEQA GNKSGAEKFS DAARQRSEAM YALMWNATNW SYFDYNLTSS GQNTHFPADA    420
DATAAETTSS PAGTQLLFSV SQLYPFWTGA APQQLKSNPL AVTQAYARVA AMLDAKAGAI    480
PATNLLTGQQ WDEPNVWPPL QHVLMQGLLN TPATFGADDP AYQATQALAL RLAQRYLDST    540
FCTWYATGGS TSATPRLAGV SAGAEGSMFE KYGDDSTNVA GGGGEYEVVE GFGWTNGVLI    600
WAADVFAGKL QRPECGDIEA AQTHGGAARR GLGMERRAIE LDPWDARWTK AFGKRALRRR    660
A                                                                   661

SEQ ID NO: 182         moltype = AA   length = 667
FEATURE                Location/Qualifiers
source                 1..667
                       mol_type = protein
                       organism = Chaetomium sp.
SEQUENCE: 182
LYINGSVTAP CDSPLYCQGE ILKAIELARP FSDSKTFVDM PTIKPVDDVI AAFSRLSQPL     60
SNNSELNAFL AENFAPAGGE LEEVPESELE TDPAFLDKLE DTTIKEFVTK VIDIWPDLTR    120
RYAGPGNCSK CANSFIPVNR TFVVAGGRFR EPYYWDSYWI LEGLLRTGGA FTEISKNIIE    180
NFLDFVDTIG FIPNGARIYY LNRSQPPLLT LMVKTYVDYT NDTSILERAL PLLIKEHEFW    240
TNNRSVAITA ADGKKYTLQR YVVNNNQPRP ESFREDYITA NNASYYAASG IIYPVKTPLN    300
ETEKAELYSN LASGAEAGWD YTARWLKTPN DAARDVYFPL RSLNVIGMVP VDLNSILYQN    360
EVIIAEYLQQ AGNSSEARRF ATAAEKRSEA MYALMWNSTH WSYFDYNLTS NSQRIFVPTD    420
ADADPVDQTN APPGHQVLFD IAQLYPFWTG AAPASLKNNP LAVQLAYARV AHMLDTKAGA    480
IPGTNFRTGQ QWDQPNVWPP LQHVLMKGLL NTPPTFGEAD PAYQEVQRLA LRLAQRYLDS    540
TFCTWYATGG STSDMPQLQG VNPGATGTMF EKYADNATNV AGGGGEYEVV EGFGWTNGVL    600
IWAADVFGEG LTRPDCGNIT AAHTSGAKR GLDGGEGGAG GLWGRRAVEL DPWDARWTKM     660
FGRRKRE                                                             667

SEQ ID NO: 183         moltype = AA   length = 671
FEATURE                Location/Qualifiers
source                 1..671
                       mol_type = protein
                       organism = Chaetomium nigricolor
SEQUENCE: 183
LYINGSVTAP CDSPLYCQGE ILRAIELARP FSDSKTFVDM PTIKPLEEVI AAFNQLTQPL     60
SNNSELNTFL AENFAPAGGE LEEVPKDELN TDPGFLDKLN DTTIREFVAK VIDIWPDLTR    120
RYAGGGNCSE CANSFIPVNR TFVVAGGRFR EPYYWDSYWI LEGLLRTGGA FIEISKNIIE    180
NFLDFVETIG FIPNGARIYY LNRSQPPLLT LMVKTYVDYT NDTSILERAL PLLIKEHEFW    240
VNNRSVEITA ANGQTYTLNR YHVNNNQPRP ESYREDYITA NNGSYYAASG IIYPVRTPLN    300
ETEKAELYAN LASGAESGWD YTARWLKTPN DAANDVYFPL RSLNVRGLVP VDLNSILYQN    360
EVIIAEYLQQ AGNLSLAQRF AEAAEQRSEA MYALMWNATY WSYFDYNLTS NSQRIFVPLD    420
ADSRTIETVG APPGHQVLFD IAQLYPFWTG AAPANLKNNP LAVQQAYSRV ASMLDAKAGA    480
IPATNFRTGQ QWDQPNVWPP LQHILMQGLL NTPPTFGDSD PAYQHVRDLA LRLAQRYLDS    540
TFCTWYATGG STSDMPQLQG VSPDATGTMF EKYADNATNV AGGGGEYEVV EGFGWTNGVL    600
IWAADVFGDA LKRPDCGDIE AAHTQAKKR DVEGLERRAV ELDPWDAAWT KMFGRSKLRK     660
RGAGGQKRWV S                                                        671

SEQ ID NO: 184         moltype = AA   length = 666
FEATURE                Location/Qualifiers
source                 1..666
                       mol_type = protein
                       organism = Chaetomium jodhpurense
SEQUENCE: 184
LYFNGSVIAP CDSPLYCQGE ILKAIELARP FSDSKTFVDM PTIKPVDEVI AAFNRLSQPL     60
TNNSELNAFL AENFAPAGGE LEEVPKDELN TDPKFLDKLE DATIKEFVAK VIDIWPDLTR    120
RYAGASNCSE CANSFIPVNR TFVIAGGRFR EPYYWDSYWI LEGLLRTGGA YTQISRNMLE    180
NFLDFVETIG FIPNGARIYY LNRSQPPLLA MMIKNYVDYT NDTSILDRAL PLLIKEHEFW    240
INNRSVSITA ADGKQYTLHR YVNNNQPRP ESYREDYITA NNASYYAASG IIYPVKTPLN     300
ESEKAELYAN LATGAESGWD YTARWLKTPN DAAKDVYFPL RSLNVRGMVS VDLNSILYQN    360
EVIIAEYLER AGNISEAERF AAMAQQRSEA MYALMWNSTH WSYFDYNLTS NSQRIFVPLD    420
DDSSTAEQAN SPPGHQVLFD IAQLYPFWTG AAPESLKSNP LAVQLAYSRV ARMLDTKAGA    480
IPATNFRTGQ QWDQPNVWPP LQHVLMAGLL NTPPTFGESD PAYQNVRALA LRLAQRYLDS    540
TFCTWYATGG ETSQTPRLQG VSPDATGTMF EKYADNATNV AGGGGEYEVV EGFGWTNGVL    600
IWAADVFADG LKKPDCGNIT AAHTSAKRG LERRAVELDP WDAAWTKMFG RSKLRKREEG     660
RKRWLS                                                              666

SEQ ID NO: 185         moltype = AA   length = 670
FEATURE                Location/Qualifiers
source                 1..670
                       mol_type = protein
                       organism = Chaetomium piluliferum
SEQUENCE: 185
LYINGSVIAP CDSPLYCHGE ILKAIELARP FSDSKTFVDM PTIKPLDEVI AAFSQLSQPL     60
SNNSELNAFL AENFAPAGGE LEEVSKDELQ TDPTFLDKLD DTTIKEFVSK VIDIWPELTR    120
RYVGSSDCSG CANSFIPINR TFVVAGGRFR EPYYWDSYWI LEGLLRTGGA FVDISRNIIE    180
NFLDFVETIG FVPNGARIYY LNRSQPPLLT LMVKTYVDYT NDTSILERAL PLLVKEHEFW    240
TTNRSVSITA NGKEYTLNRY SVNNNQPRPE SYREDYITAS NESYYAESGI IYPVRTPLNE    300
TEKAELYSNL ASGAESGWDY TSRWLKTPND AANDVYFPLR SLNVLGLPV DLNSILYQNE     360
VILAEYFEQA GNSSEAERFA AAAEQRSEAM YDLMWNATHW SYFDYNLTSS SQRIFVPLDD    420
```

```
GASTQEQSTS PPGYQVLFDV AQLYPFWTGA APAALKSNPL AVQHAYSRVA DMLNTKAGAI   480
PATNFRTGQQ WDQPNVWPPL QHIIMQGLLN TPPTFGESDP AYENTQSLAL RLAQRYLDST   540
FCTWYATGGS TSDMPPLQGV SAGATGTMFE KYADDATNVA GGGGEYEVVE GFGWTNGVLI   600
WAADVFGDAL KRPDCGNITA ASTHEGATKR DLRGLGRRAV ELDPWDAAWT KMFGRAKLRK   660
REQGRETWVN                                                         670

SEQ ID NO: 186           moltype = AA  length = 674
FEATURE                  Location/Qualifiers
source                   1..674
                         mol_type = protein
                         organism = Myceliophthora hinnulea
SEQUENCE: 186
LYINGSVTAP CDSPIYCHGE LLKGVELAHP FVDSKTFVDM PTLKPVDEVL AAFSKLRQPL    60
SNNSELNNFL AEYFAPAGHE LEEVPDSELQ TDPKFLDKLE DRTIKEFVSK VIDIWPDLTR   120
RYAGPGDCSD CANSFIPVNR TFVVAGGRFR EPYYWDSYWI LEGLLRTGGA FTQISKNIIE   180
NFLDFIDTIG FIPNGARIYY LNRSQPPLLT RMVKSYVDYT NDTSILERAL PLLIKEHDFF   240
TNNRSVSVTA SNGKTYTLHR YHVENNQPRP ESYREDYITA NNGSYYAASG IIYPVKTPLN   300
ETEKAVLYSN LASGAESGWD YTARWLRVPD DAARDVYFPL RSLNVREIVP VDLNSILYEN   360
EVIIAGYLEK AGNSSEAKRF ASAAKQRSEA MYNLMWNATH WSYFDYNLTS NAQNIFIPAD   420
EDTAPFDRTA APPGKQVLFH IAQLYPFWTG AAPAHLKSNP LAVQKAYARV SRMLDSKKGA   480
IAATNYRTGQ QWDQPNVWPP LQHVLMQGLL NTPATFGESD PAYQGVQKLA LRLAQRYLDS   540
TFCTWYATGG STSDFPQLQG VSPDATGIMF EKYADSAINV AGSGGEYEVV EGFGWTNGVL   600
IWAADVFGNK LKRPDCGNIT AAHTHSEAKR SLGDGGLARR AVELDPWDAA WTKMFGRSKL   660
RRREAEDVRK RWSS                                                    674

SEQ ID NO: 187           moltype = AA  length = 659
FEATURE                  Location/Qualifiers
source                   1..659
                         mol_type = protein
                         organism = Chloridium virescens
SEQUENCE: 187
LYINGSVIAP CDSPLYCQGD ILKAIQLAQP FSDSKTFVDM PTTQPVDQVI AAFNQLPQPV    60
SNNSGLQNFL STYFAPAGGE LTEVPKDQLQ TNPMFLNKLN DTVIREFVTA VIDIWPDLTR   120
TYTGASNCTG CSDSFIPVNR TFVVAGGRFR EPYYWDSFWI LQGLLRTGGA FTQISKNIIE   180
NFLDLVDQFG FVPNGARVYY LNRSQPPVLS EMVRTYVAYT NDTSILARAI PTLIKEHNFW   240
MQNRTVNITG ADGNTYTLNQ YHVENTQPRP ESYTEDYITA NNHSYYATSG IIYPETKPLN   300
DSEIANLYAN LASGAESGWD YGSRYLARPN DAAQDVYFPL RSLNVLNIVP LDLNSLLYQS   360
EQNIALFLQA TGNSSEAEQW TSLAAQRQTA IHALMWNETL WSYFDYNLTS NGQNIYVPAD   420
KDATPADTAS APPGYQVLFD VAQFYPFWTG AATDELRRPN LAVRQAFTRV DAYLTAKAGG   480
IPATNLMTGQ QWDQPNVWPP LMHVLMQSLL DTPATFGAAD PSYAALQGLA LRLAQRYLDM   540
TFCTWYATGS TSTSQTPKLQG LGPDAVGTMF EKYADNATNI AGSGGEYTVV EGFGWTNGVL   600
IWAADTFGAQ LTRPNCGNIT AAHVTPGKRS VGLGRRAVEL HESDARWVKM FGSRAWRNA    659

SEQ ID NO: 188           moltype = AA  length = 662
FEATURE                  Location/Qualifiers
source                   1..662
                         mol_type = protein
                         organism = Gelasinospora cratophora
SEQUENCE: 188
LYVNGSVTAP CDSPIYCYGE LLHQVELARP FSDSKTFVDM PTIKPVDEVL EAFSKLTLPL    60
SNNSELHEFL NTYFGPAGGE LEAVPTDQLH VSPTFLDNVS DDVVKQFVNS VINIWPDLTR   120
KYVGAGEICT GCANSFIPVN RTFVVAGGRF REPYYWDSFW ILEGLLRTGG AFTEISKNTI   180
ENFLDLVEQI GFVPNGARLY YLNRSQPPLL TQMVRIYVEH TNDTSILERA VPILKKEWEW   240
WITNRTVEVT ADGKTYSLQR YHVDNNQPRP ESYSEDYITA NNNSYYATSG IIYPETTPLN   300
DTQKAQLYAN LASGAESGWD YSTRWLKNPN DAARDVYFPL RSLNVLEIVP VDLNSILYQN   360
EVTIGKFLAQ QGNKDEAEEW AKKAEQRSEA MYKLMWNSTL WSYFDYNLTS SSQNIYVPAD   420
PQVFPPEKPS GTPEGYQVLF SINQMFPFWT GAAPDQLKAN PLAVKLTFDR VKNYLDNKAG   480
GIPATNFVTG QQWDEPNVWP PLMHVLMDGL LNTPATFGED DPAYQETQNL ALRLAQRYVD   540
STFCTWWATG GSTSETPKLQ GLGSDAKGIM FEKYADNSTN VAGGGGEYEV VEGFGWTNGV   600
LIWAADKFGD KLKRPNCGDL TPANVGKRAV ELDAFDAKFT KKFARKGKLE KLKAKFKRRA   660
AI                                                                 662

SEQ ID NO: 189           moltype = AA  length = 543
FEATURE                  Location/Qualifiers
source                   1..543
                         mol_type = protein
                         organism = Acidobacteriaceae bacterium
SEQUENCE: 189
QTTTTSAGLH DTLAYIKRTW HTLERSNKTL LKSADDVKVG QAGTLTLYVS QDVKPQAVNA    60
SLRRELPPAD KKRIVVRQLP EHPEAVEPAG LLYLPYPYVV PGGRFNEMYG WDSYFILLGL   120
VHDDELALAK NMTDNFIYEI EHYGMILNAN RTYYLTRSQP PFLTQMILEV YRRTGDGKWL   180
ASTLPAIEKY YAYWMREPHL TPETGLSRYW GGADTPAPEV VHGEKDAAGH NQYDRVREYY   240
RTHNVTAYDV SQYYDKATDR LKPLFYIADR AMRESGFDPS SRYGPFSADI IHYDPVCLNS   300
LLYRMESDTA TILKQLNRTS EARVWEKRAT QRAELVNRLM WNEEKGLYFD YDFITRRQSN   360
YHFVTTFYPL WAGIASRQQA DRVRKNLSIF ERAGGLQTSD YISGSQWDAP FGWAPLQIMT   420
VEGLRRYGFN EDADRISRKF INMVVRDFEE HGTIKEKYDV VIGKSDLAAG LKFGYTSNEA   480
GFGWTNAAVV LFIEELAGER PLAASLDRES MPMLRQRHLS PQPSVWPPFS PQAPQYRRRD   540
PYR                                                                543
```

```
SEQ ID NO: 190            moltype = AA   length = 532
FEATURE                   Location/Qualifiers
source                    1..532
                          mol_type = protein
                          organism = Acidobacterium capsulatum
SEQUENCE: 190
GARSSLSPHA VAGPQPIDAY IHTAWSTLTR SMSDCKSVAD PKLKSTPVLY LPRDLAVPAN     60
VAAMQKQCHV RVLRLPIVIT HFDQIRESQI ATPGLLYLPH PYVVPGGRFN EMYGWDSFFI    120
LKGLLDDHHI ALARGIVENF FFEIAHYGGI LNANRTYYFT RSQPPFLSSM IRAIYAEAVA    180
EGHTQAAHAW LVEAYPYAVR DHALWMSPIH QAGNTGLARY FDTGQGPVPE MADDSTYYQD    240
VIRWLLAHPG LHTGYLMHGS PHLDAAARER LAQLSCDPTL SKVCARAHVH GYWLTRSFYK    300
GDRAMRESGF DTTFRFGPFS GSTQHFAPVG LNALLYKYER DLAWMAAQLG KPGEAAKWNS    360
EAETRRAEMN HYLWNAQKKM YFDYNFETHR QSSYAFITTF YPLWAGAADK AQQQGVIASL    420
PLFEHPGGLA ISNHDSGVQW DLPYGWAPTE WMAVQGLLRA DDQHDARRIA SEFNRTVRTT    480
YQHDHAIYEK YDVVNRSNDF RVTAGYTQNV VGFGWTNAVY LEFQSLLAHP GQ            532

SEQ ID NO: 191            moltype = AA   length = 568
FEATURE                   Location/Qualifiers
source                    1..568
                          mol_type = protein
                          organism = Acidovorax wautersii
SEQUENCE: 191
AAAVSSGLRI SERHPAYSTN PARVQVPGAP GAPPSDHCTP ADRYQELFVA VQSQQIFEDS     60
KTFVDCGPIG EPEDILAAYR AEHAQPDFDL ARFVAQHFTA PQVAANDYVG APGMALAEHI    120
DALWPVLTRK PEDHPVRGSA LPLAHPYVVP GGRFAELYYW DSYFTMLGLA ATGRSELVQC    180
MTDNFARLID AFGFVPNGTR TYYLSRSQPP LFAAMAELGA LVGGPPVSHY LPQLLQBHAW    240
WMDGLHVLHP GEARRVVAL PGGEILNRYW DDRDTPREES WREDIETASA VDRPSADVYR     300
DLRAAAESGW DFSTRWLRAP DAANPASLHL SQICTTDLLP VDLNAFLYRM EVSIAKASQS    360
AGDRATATHF HDLAAHRREA VNRLMWNEAE GAYFDYDWRR GELRGCLTAA TVVPLYAGMA    420
TEAQAAAVAR AVRTHLLAAG GLATTVCSSD QQWDRPNGWA PLQWMAVRGL ERYGHKDLAL    480
EVRQRWIETV RSVYQREGKL VEKYAVGNGD GAPLCGGGGG EYPLQDGFGW TNGVVQCWLD    540
PRYDTYAAAQ TVYYGPTDDG TADSLPEA                                      568

SEQ ID NO: 192            moltype = AA   length = 529
FEATURE                   Location/Qualifiers
source                    1..529
                          mol_type = protein
                          organism = Xanthomonas arboricola
SEQUENCE: 192
APMDTPVVNA PAATPPTPDL AYPELFQAVQ SGELFDDQKH FVDFLPLRDP ALINADYLAQ     60
HDHPGFDLRK FVDANFEESP PVQTDAIRQD TALREHIDEL WPKLVRSQTH VPPYSSLLAL    120
PHPYVVPGGR FREVYYWDSY FTMLGLVKSG ETTLSRQMLD NFAYLIDTYG HIPNGNRSYY    180
LSRSQPPFFS YMVELQAGVE GEAVYQRYLP QLRKEYAYWM QGSEDLQPGQ AARHVVRLAD    240
GSLLNRYWDE RDTPRPEAWL HDTRTAAEAG DRPAAEVYRD LRAGAESGWD YTSRWLADGQ    300
NLRTIRTTAI VPIDLNSLLY HLERTLAQAC AQPGAECAQD YAALALRRKQ AIDAHLWNAA    360
GYYADYDWQT RKLSDQVTAA ALYPLFTGLA TDAHAKRTAS TVRARLLLRPG GLATTAVKTG   420
QQWDEPNGWA PLQWVAVDGL RRYGEDALAR TIGERFLTQV QALFAREHKL VEKYGLEADA    480
AGGGGGEYAL QDGFGWTNGV TLMLLNLYPD TATKPAPAKR ARKPEAAAR                529

SEQ ID NO: 193            moltype = AA   length = 540
FEATURE                   Location/Qualifiers
source                    1..540
                          mol_type = protein
                          organism = Kosakonia sacchari
SEQUENCE: 193
AEAQNTPQPP DILLGPLFSD VQTAKLFPDQ KTFADAVPKG DPLMILADYR MQRMQTSFDL     60
RHFVDVNFTL PKEGEKYVPP EGQNLREHID GLWPVLTRTT DSAGKWDSLL PLPKPYVVPG    120
GRFREVYYWD SYFTMLGLAE SGHWDKIEDM VTNFAHEIDT WGHIPNGNRS YYLSRSQPPF    180
FSLMVELLAT HDGDEALKTW LPQMEKEYQY WMEGADTLQP GQANKRVVKL SDGSVLNRYW    240
DDRDTPRPES WLDDVTTAKN NPNRPATEIY RDLRSAAASG WDFSSRWMDD PNQLGTIRTT    300
SIVPVDLNAL MFKMEKMLAR GYQAAGDSAK ASQYDALANA RQKGIEANLW NEKEGWYADY    360
DLKTKKVRNQ LTAAALYPLF VNAAAKDRAD KVASAAKERL LKPGGIATTT VNSGQQWDAP    420
NGWAPLQWVA TAGLQNYDQQ KLAMEVSWRF LTNVQHTYDR EKKLVEKYDV STTGTGGGG     480
EYPLQDGFGW TNGVTLKMLD QICPKEKPCD SVPQTQPAQQ PAAKVEPTSQ PSKQQQAVAQ    540

SEQ ID NO: 194            moltype = AA   length = 532
FEATURE                   Location/Qualifiers
source                    1..532
                          mol_type = protein
                          organism = Enterobacter sp.
SEQUENCE: 194
DEQPAFQKNS PDILLGPLFN DVQSAKLFPD QKTFADAVPK SDPLMILADY RMQHTQSSFD     60
LRHFVEMNFT LPAEGEKYVP PAGQSLREHI DDLWPVLTRT TDKASNKWDS LLPLPKPYVV    120
PGGRFREVYY WDSYFTMLGL AESGHWDKIS DMVDNFAWEI DTFGHIPNGN RSYYLSRSQP    180
PFFSMMVELL ATHDSDALKK YRPQMEKEYA YWMEGVDSLQ PGQANQRVVK LDDGSVLNRY    240
WDDRDTPRPE SWLDDVNTAK NNPNRPATEI YRDLRSAAAS GWDFSSRWMD DPQKLGTIRT    300
TSIVPVDLNA LMFKMEKLLA RASQEAGDSA AASKYEALAT ARQKAIENHL WNDKEGWYAD    360
YDLKSKKVRN QLTAAALFPL YVKAASQERA DKVAAATSAR LLKPGGITTT TINSGQQWDA    420
PNGWAPLQWV ATEGLQNYGQ NKVAMDVTWR FLKNVQHTYD REKKLVEKYD VSTTGTGGGG    480
```

```
GEYPLQDGFG WSNGVTLKML DLVCPKEKPC DSVPENQPAA NDEAAPVKAS AQ            532

SEQ ID NO: 195              moltype = AA  length = 720
FEATURE                     Location/Qualifiers
source                      1..720
                            mol_type = protein
                            organism = Saitozyma flava
SEQUENCE: 195
QNPASSSSFS PTPVTTMVPS PTAALNATVP GQGVYPPLQA WCNNGGNDTF CPGVLLQDVQ     60
LSGIFPDSKT FVDKPTRGTL NETLRTFASL GNNLTVGQIE GFVNNSFKGE GLELSQVALE    120
GFNPNPAFLD TISDPIYQGW MSVVNSYWTL LIRETNRSAL CNGDCESSLI PLNNTIVVPG    180
GRYREIYYWD SYWILIGLLE SELTAYATDL ISNFMDFIQT YGFIPNGGRK YYLNRSQPPV    240
FTQMLNTYVQ RTGNTSILAR GLPLAHQELV WWENNRVISV TSPYSNITRR VAHFAVNNTA    300
PRPEGYVEDY ETAFGASPAL NETARGQLYS DLAAGAESGW DYSSRWCKQP VINLTDNFPA    360
LRTINTAKII PVDLNSLLAG DHTLLANLYE LYGNSSNANT SVTSNSSQLV PYHRQLAKNY    420
SDAVLDLHWD AQKAWFYDFN LTANARADIY HPGGTFALWQ NITPPAVASN ETYALEVVSG    480
ARFLLGKYTS IPSVSTLIET GLNWDFPNSW PPHVYSSIKA FETLGRAFPN ASVLSNISIP    540
FSDVQKNQLG LDESAIPAQP ASTIGNSTSQ IAEAQGKPWP QALSIEYANR YMQAAFCSWY    600
STGGSIDGLL TQLPLSELNM TGTFQAGTTG VMFEKFNVTD LDAAGGGGEY KVQIGFGWTN    660
GVALWLGANF GQYLPQPTCP LIPIIEVQNG MNSSVYQNGT MTNSTKTQSY IFQGHRIPRK    720

SEQ ID NO: 196              moltype = AA  length = 723
FEATURE                     Location/Qualifiers
source                      1..723
                            mol_type = protein
                            organism = Phaeotremella skinneri
SEQUENCE: 196
QTPTSSSSSS FSATPVSTSV PSPTVPLNSS VIGQGLYPPA QAWCNGGMND TFCPGVLLQD     60
VELSGIFADS KTFPDKPTVG TLNSTLQAFA ALPANVTVGE IETFVNQYFK GEGLELEQVA    120
IEGFVANPAI LNNITDPVFK GWVSTVNGYW QLLIRQTNES SLCNETSCAS SLIPLNHTIV    180
VPGGRYREIY YWDSFWILQG LLKSELYTYS WDLLQNFMDL IETYGFLPNG GRKYYLNRSQ    240
PPVFIQMLDA YIKVTGNSSI LARALPIATT ELAWWSSNRT IPVTSPYTGI THLVAHYAVT    300
NSAPRPEGYV EDFTTAMGAS PALNDSARAE LYSELASGAE TGWDYSSRWC RQPLLNLTDN    360
NPALRTLNVK AIIPVDLNSL LAGDHALLAN LYDLYSNSSS SNSTSNSSSI SNSSSQAAYH    420
RQAAQNLTAA ILDLHWSPSK SFFYDFNTSS NSQSDIYTPA SLFPLWQNIT PPALVGNETA    480
ALQLVSGVRY LLGKYAGIPS VATLLATGLN WDFPNSWPPH VYTSIKAFQT LYRVNPNATV    540
LSNLTLSFAQ VQAGQLGLSE TGFQIQPAST VGNTSLETAE AKGKPWPVAL GIEYANRYMQ    600
SAFCSWYSTG GEISGVLTQL PLSDLNSTGT FTAGQTGVMF EKFNVTDPDA AGGGGEYTVQ    660
TGFGWTNGVV LWVAGEFGSL LPAPTCPLIP IIEISGSSNS SIYANGTVTN STALYRGYKI    720
PRK                                                                  723

SEQ ID NO: 197              moltype = AA  length = 663
FEATURE                     Location/Qualifiers
source                      1..663
                            mol_type = protein
                            organism = Trichoderma asperellum
SEQUENCE: 197
LYTNGSVIAP CDSPIYCHGD ILQDIQLAHP FSDSKTFVDM PAKRPLREIQ SAFNNLSKPL     60
TNDSSLQVFL ETYFADAGGE LVEVPRSSLT TNPAFLNKIN DTVIREFVTK VIDIWPDLTR    120
RYSGAVGNCS TCPNSFIPVN RTFVVAGGRF REPYYWDSYW IIEGLLRTGG AFVGIAKNTI    180
ENFLDFIDRF GFIPNGARLY YLNRSQPPLL SQMVRIYIEH TNDTSILKRA LPLLVKEHDF    240
WIRNRTISVN IANKTYTLQQ YAVQNTQPRP ESFLEDYVTA NNRSYYATSG IIYPENKHLN    300
STEMADLYAN LATGAESGND YTSRWLANPS DAINDVYFPL RSLNNKEIVP VDLNSILYGN    360
ELTISQFYNR TGDATAARAW AERAANRSAA IQAVFWNETL FSYFDYNLTS SSQYVYVPAD    420
KDTISLDRQT APSGKQVFFH VGQFYPFPWTG AAPDYVKNNP YAVTRAYDRV TGYLDAQPGG    480
IPASNVQTGQ QWDQPNVWPP HMHILMQGLN NVPATFTAQD PSYQDIQNLS LRLGQRYLDF    540
TFCTWLATGG STSEPKLHG LSDQDVGIMF EKYDDNSTNA AGGGGEYEVV EGFGWTNGVL    600
LWTADTFGNK LKRPQCGNIT AGHPAPASSS SKRSAVQLDA WDARRVKKFG KRTEGRVKRP    660
FLF                                                                  663

SEQ ID NO: 198              moltype = AA  length = 674
FEATURE                     Location/Qualifiers
source                      1..674
                            mol_type = protein
                            organism = Corynascus sepedonium
SEQUENCE: 198
LYINGSVTAP CDSPIYCQGE LLKAVELARP FVDSKTFVDM PTIKPVDEVL AAFSKLSLPL     60
SNNSELNAFL YENFAQAGHE LEEVPDSELE TDAKFLDKLE DRTIKEFVGK VIDIWPDLTR    120
RYAGPSNCTE CANSFIPVNR TFVVAGGRFR EGYYWDSYWI VEGLLRTGGA FTHISKNIIE    180
NFLDFVDTIG FIPNGARIYY LNRSQPPLLT LMVKSYVDYT NDTSILDRAL PLLIKEHEFF    240
MNNRTVSITG SNGKEYTLNR YHVENNQPRP ESFREDYITA NNGSYYASSG IIYPVKTPLN    300
ETEKAALYSN LATGAESGWD YTSRWLGVPS DAARDVYFPL RSLNVRDIVP VDLNSILYQN    360
EVIIAEYLEK AGNSSAAKRF ATAAEQRSEA MYSLMWNATH WSYFDYNLTD NTQHIFVPAD    420
EDTAPQGDRIE APPGGQVFFH IAQLYPFWTG AAPASLKANP LAVQQAYARV ARMLDIKKGA    480
IPATNYRTGQ QWDQPNVWPP LQHILMKGLL NTPATFGKSD PAYQSVQNLA LRLAQRYLDS    540
TFCTWYATGG STSDFPQLEG VTPGATGVMF EKYADNATNV AGTGGEYEVV EGFGWTNGVL    600
IWAADVFGNK LKRPDCGNIT AAHTSSAKR GLEENKLPRR AVELDPWDAA WTKMFGRSKL    660
RRREAEDVRK RWMS                                                      674
```

```
SEQ ID NO: 199         moltype = AA  length = 674
FEATURE                Location/Qualifiers
source                 1..674
                       mol_type = protein
                       organism = Myceliophthora thermophila
SEQUENCE: 199
LYINGSVTAP CDSPIYCHGE LLKGVELAHP FVDSKTFVDM PTLKPVDEVL AAFSKLRQPL   60
SNNSELNNFL AEYFAPAGHE LEEVPKGELQ IDPKFLNKLE DRTIKEFVSK VIDIWPDLTR  120
RYAGPGDCSG CANSFIPVNR TFVVAGGRFR EPYYWDSYWI LEGLLRTGGA FTQISKNIIE  180
NFLDFIDTIG FIPNGARIYY LNRSQPPLLT RMVKSYVDYT NDTSILERAL PLLIKEHDFF  240
TNNRSVSVTA SNGKTYTLHR YHVENNQPRP ESYREDYIITA NNGSYYAASG IIYPVKTPLN  300
ETEKAVLYSN LASGAESGWD YTARWLRVPD DAARDVYFPL RSLNVREMVP VDLNSILYEN  360
EVIIAEYLEK AGNSSEAKRF ASAAKQRSEA MYNLMWNATH WSYFDYNLTS NAQNIFVPAD  420
EDTASFDRYA APPGQQVLFH VAQLYPFWTG AAPAHLKSNP LAVQKAYARV SRRLDTKKGA  480
IAATNYRTGQ QWDQPNVWPP LQHVLMQGLL NTPATFGESD PAYQGVQKLA LRLAQRYLDS  540
TFCTWYATGG STSDFPQLQG VSPDATGIMF EKYADSATNV AGGGGEYEVV EGFGWTNGVL  600
IWAADVFGNK LKRPDCGNIT AAHTSEAKR SLGDGGLARR AVELDPWDAA WTKMFGRSKL  660
RRREAEDVRK RWSS                                                   674

SEQ ID NO: 200         moltype = AA  length = 661
FEATURE                Location/Qualifiers
source                 1..661
                       mol_type = protein
                       organism = reesei GH37
SEQUENCE: 200
LYINGSVIAP CDSPIYCHGD ILREIELAHP FSDSKTFVDM PAKRPLSEIQ TAFANLPKPL   60
RNDSSLQTFL ASYFADAGGE LIQVPRANLT TNPTFLSKIN DTVIEQFVTQ VIDIWPDLTR  120
RYAGDAAVKN CSSCPNSFIP VNRTFVVAGG RFREPYYWDS YWIVEGLLRT GGAFVGIARN  180
TIDNFLDFIE RFGFVPNGAR LYYLNRSQPP LLSRMVKVYI DHTNDTAILR RALPLLVKEH  240
EFWTRNRTVD VRVNNKTYVL NQYAVQNTQP RPESFREDFQ TANNRSYYAA SGIIYPATKP  300
LNESQIEELY ANLASGAESG NDYTARWLAD PSDAMRDVYF PLRSLNNKDI VPVDLNSILY  360
GNELAIAQFY NQTGNTTAAR EWSSLAANRS ASIQAVFWNE TLFSYFDYNL TSSSQNIYVP  420
LDKDAVALDR QTAPPGKQVL FHVGQFYPFW TGAAPEYLRN NPFAVTRIFD RVKSYLDTRP  480
GGIPASNVNT GQQWDQPNVW PPHMHILMES LNSVPATFSE ADYAAYQDVRN LSLRLGQRYL  540
DFTFCTWRAT GGSTSETPKL QGLTDQDVGI MFEKYNDNST NAAGGGGEYQ VVEGFGWTNG  600
VLLWTADTFG SQLKRPQCGN IMAGHPAPSK RSAVQLDMWD ASRVKKFGRR AEGRMGTLHA  660
W                                                                 661

SEQ ID NO: 201         moltype = AA  length = 670
FEATURE                Location/Qualifiers
source                 1..670
                       mol_type = protein
                       organism = Chaetomium virescens
SEQUENCE: 201
LYINGSVTAP CDSPLYCQGE ILKAIELARP FSDSKTFVDM PTIKPLEEVI AAFGRLKQPL   60
SNNSELTAFL AENFAPAGGE LEEVPKSELH TDPVFLNKLD DAVVKEFVGK VIDIWPDLTR  120
RYAGPGNCSN CENSFIPVNR TFVVAGGRFR EPYYWDSYWI VEGLLRTGGA FVGITKNILE  180
NFLDFIETIG FVPNGARIYY LNRSQPPLLT KMIKIYVDHT KDTSILQRAL PLLIKEHEWW  240
TNNRSVTVTG PNGKTYTLNR YHVNNNQPRP ESFREDYIITA NNGSYYATSG IIYPVKSPLN  300
ETEKDETYAN LATGAESGWD YTARWLRTPN DAAKDVYFPL RSLNVRNMIP VDLNSILYQN  360
EVIIGEYLEQ AGNKSEAQRW FQAANQRSEA MYALMWNATH WSYFEDYNLTS NSQYIFIAND  420
EDATTAEQAN SPPGQQVLFS ISQLYPFWTG AAPDQLKKNP LAVQQAYYRI ERMLNEKAGA  480
IPSTNFRTGQ QWDEPNVWPP LQHILMQGLL NTPATFGTAD PAYAAVQNLA LRLAQRYLDS  540
TFCTWYATGG STSQTPQLQG VSPGATGIMF EKYADNATNV AGSGGEYEVV EGFGWTNGVL  600
IWAAETFGNK LKRPDCGDIQ AAHTDKKK RWSVDGEVRA RERMAVELDP WDAKWTKMFG  660
QAKGRVGRRS                                                        670

SEQ ID NO: 202         moltype = AA  length = 508
FEATURE                Location/Qualifiers
source                 1..508
                       mol_type = protein
                       organism = Rhodothermus marinus
SEQUENCE: 202
QDRVACQVPL PSVERIEAVR AYIRQSWDVL TRSHRDLLAA VQDPKIEHEP GTPWPLYIAA   60
TEDSVAVWHR LQQELPDSVL QQIVLRVLPE DPVAHLDEIH PHGLLYLPEP YVVPGGRFNE  120
MYGWDSYFIV VGLLRDGRVD LAKAMTDNHL YQVRHYGKVL NANRTYYLTR SQPPFLSAMV  180
LAVYAHTQDR DWLAAAVPLI ERYYAYWTTP PHLAGETGLS RYYDLGEGPA PEVVAGERDA  240
QGRTHYDRVR EYYRMHEVTA YDESLYYVAE ADSLTPLFYK GDRSMRESGF DPSNRFGPFS  300
VDIIHYAPVG LNALLYRMET DLARIHEILG DTAAAAAWRA RAEARRERVD RYLWDSERGL  360
YFDYNFRTGR RSDYVFATTF YPLWVGMASP EQAARVAANL YLLEAPGGLL TSTHISGSQW  420
DAPYGWAPLY LIAVEGLRRY GYDEAADRLT AKFVSMIVED FERTGVILEK YDVVQRRSDV  480
ALRYGYTSNE IGFGWTNAVF AELLAQMD                                    508

SEQ ID NO: 203         moltype = AA  length = 674
FEATURE                Location/Qualifiers
source                 1..674
                       mol_type = protein
                       organism = Myceliophthora sepedonium
SEQUENCE: 203
```

```
LYINGSVTAP CDSPIYCQGE LLKAVELARP FVDSKTFVDM PTIKPVDEVL AAFSKLSLPL    60
SNNSELNAFL YENFAQAGHE LEEVPDSELE TDAKFLDKLE DRTIKEFVGK VIDIWPDLTR   120
RYAGPSNCTE CANSFIPVNR TFVVAGGRFR EPYYWDSYWI VEGLLRTGGA FTHISKNIIE   180
NFLDFVDTIG FIPNGARIYY LNRSQPPLLT LMVKSYVDYT NDTSILDRAL PLLIKEHEFF   240
MNNRTVSITG SNGKEYTLNR YHVENNQPRP ESFREDYITA NNGSYYASSG IIYPVKTPLN   300
ETEKAALYSN LATGAESGWD YTSRWLGVPS DAARDVYFPL RSLNVRDIVP VDLNSILYQN   360
EVIIAEYLEK AGNSSAAKRF ATAAEQRSEA MYSLMWNATH WSYFDYNLTD NTQHIFVPAD   420
EDTAPQDRIE APPGQQVFFH IAQLYPFWTG AAPASLKANP LAVQQAYARV ARMLDIKKGA   480
IPATNYRTGQ QWDQPNVWPP LQHILMKGLL NTPATFGKSD PAYQSVQNLA LRLAQRYLDS   540
TFCTWYATGG STSDFPQLEG VTPGATGVMF EKYADNATNV AGGGGEYEVV EGFGWTNGVL   600
IWAADVFGNK LKRPDCGNIT AAHTSSSAKR GLEENKLPRR AVELDPWDAA WTKMFGRSKL   660
RRREAEDVRK RWMS                                                    674

SEQ ID NO: 204          moltype = AA   length = 657
FEATURE                 Location/Qualifiers
source                  1..657
                        mol_type = protein
                        organism = Moelleriella libera
SEQUENCE: 204
LHTNGSLIAP CDSPIYCYGD ILKQVELARP FADSKTFVDM PGVKPLAEIQ AAFDKLEKPL    60
RNNTALQDFL KTYFADAGQE LQEVPKSELK TDPQFLKTLN DTVIREFVTK VIDIWPDLTR   120
SYKGSNTNCT DCPNSFIPIN RTFVIAGGRF REPYYWDSYN ILEGLLRTRG SFTQIAKNTL   180
ENFLDFVEQF GFVPNGARIY FLNRSQPPML SQMVKLYIDH TNDTAILQRA LPLLVKEHAW   240
WMNNRTVDVQ VGGKTYKLNR YAVSNTEPRP ESYREDFETA SNSSYYAQSG IIYPETKKLN   300
DSQRAVLYAN MATGGENGWD FSSRWIANPS DSVRDVYFPL RTNNAQNVVP VCLNSILYGN   360
EMTIGGFFNS TGNTTAGQEW AAKAKARSEA MHATMWNETH FSYFDYNLTS SAQDVYTLAD   420
DDTSIYDNGT LTGAPPGYQV AFNGAQFYPF WQGAAPTYLK ENPQAVKTAY ARVAQYLKVR   480
KGGIPATNLK AREQWDQPNV WPPLMHILMQ GLLNTPPTFG SSDPSYKSVR SMALTLAQRY   540
LDSTFCTWYA TGGSTSETPK RPGLPEKDKG IMFEKYADNS IDIAGSGGEY EVVEGFGWTN   600
GVLIWAADTF ANELKRPDCG NGSSSSSTSS AAKRGLSAVE LHPADASRIK RFGSSKG      657

SEQ ID NO: 205          moltype = AA   length = 660
FEATURE                 Location/Qualifiers
source                  1..660
                        mol_type = protein
                        organism = Acremonium dichromosporum
SEQUENCE: 205
IYVDGNITAP CDSPVYCYGE MLHQIQLAKP FDDSKTFVDM PALKPLSQIQ AAFDRLDKPL    60
SNNSALNNFL DEFFADAGGE LSEVDKADLE TDPVFLDKID DEVVKEFTNK VIDIWPDLTR   120
RYSGAAASNC TNCPSSFIPL NRTFVVAGGR FREPYYWDTY WIIEGLLRTG GSFTDISRDI   180
IENFLDFVDQ FGFVPNGARI YYLNRSQPPV LSRMVQAYIE HTNDTDILDR ALPLLMKEHE   240
FFSENRTIDI EGPNGTTYTL NRYDVRNNQP RPESYSEDYE TATNTSYYSH DSGIIYPETE   300
PLNDTERANL YSALASGAES GWDYSSRWIA RPRDAAEDVY FPLRSLNTNN IVPVDLNSIM   360
YANEMAIAGF LNQTGNASAA AEWEELAYNR SEAIHALMWN ETYMSYFDYN LTSAAQHIYV   420
PADDDVSTLE SSTAPEGHMV LFSVSQFYPF WTGAAPSYIK NNPFAIAQIY KRVETLLDTR   480
KGGIPATNFR TGQQWDQPSV WPPLMHILMA GLQNTPATFG EDDPAYQHVH EIALRIGQRY   540
LDSTFCTWRA TGGATSETPQ LEGFTDRDVG IMFEKYADNS TNIAGGGGEY EVVEGFGWTN   600
GVLIWTVDEF GNELKRPDCG DLEAADTTER RKRSALQLAP RDAQRTKKFG KRAVERQPWF   660

SEQ ID NO: 206          moltype = AA   length = 667
FEATURE                 Location/Qualifiers
source                  1..667
                        mol_type = protein
                        organism = Fusarium sambucinum
SEQUENCE: 206
LYVNGTVVAP CDSPIYCHGD ILEQVELARP FSDSKTFVDM PAIRPLSEIQ KAFDELDKPL    60
RNNSALADFL SENFADAGNE LEEVPEDELK TDPKFLDNIN DTVIREFTEK VIDIWPDLTR   120
RYDQDSKNCS DCPNSFIPVN RSFVVAGGRF REPYYWDSYW IIEGLLRTGG SFVNIAKNTI   180
ENFLDFIEEY GFVPNGARIY YLNRSQPPLL SQMVKIYIDH TNDTDILERA LPLLVKEHEF   240
FMKNRSVPVY INDETYMLNT YNVSNTQPRP ESYREDYITA TNKSYYSTSG EVYSGGEELS   300
FKQKETLYGN LASGAESGLD YTSKWIARPE NAIRDNYFPL RYLNTRNIIP VDLNSILYGN   360
EIAIADFYEQ TGNSSASEQW REVAANRSYA MHAFMWNETL WSYFDYNLTS KAQQIYFPAD   420
NNTVSVDTED APKGQQVFFS PTQFYPFWLG AAPDYLKNNP YAVLSAYKRV ATYLDKREGG   480
IPASNIETGQ QWDQPNVWPP MMHILMAGLE KVPATFGIMD PSFIEIRKLA LRLGQRYLDS   540
TFCTWYATGG STSETPKLES VSDKEDGIMF EKYADNATNT AGGGGEYEVV EGFGWTNGVL   600
IWAVEEFGNR LTRPKCKNLE TAHSSDKRDT SAVMLHARDA KHVKKFGRRK RAEEKAAKKR   660
SSRLFHF                                                            667

SEQ ID NO: 207          moltype = AA   length = 660
FEATURE                 Location/Qualifiers
source                  1..660
                        mol_type = protein
                        organism = Phoma sp.
SEQUENCE: 207
LYQNGSIIAP CDSPIYCYGD LLREIELAQP FSDSKTFVDL PTIRPLDEVL RAFNNLTKPI    60
QNNTELNNFL TTYFGEAGSE LDALPKDQLE TQPDFLDNVN SSVIVNFTSQ VIDIWPDLTR   120
RYVGAGNCTG CVSSFIPVNR TFVVAGGRFR EPYYWDSFWI IEGLLRTKGS FTQIAENIIE   180
NFMDLVEELG FVPNGARRYY ENRSQPPLLT QMVRVYVEYT QNYTLLERAL PVLEQEYEFW   240
VNNRSVTLER GGKNYTLHHY NVSNTQPRPE SYREDYITAN NLTYYNENGE QFNASHPLND   300
```

```
TQKALLYAEL ASGAETGWDY SSRWLANPSD AVNDDFFPLR SLNVINTIPV DLNSILYYNE    360
ITIAEFHRRE GNYCAARQWA ELARNRSEAM TALLWNAEYY SYFDYNLTSS AQNIYTLADN    420
TSTPLSLAGA PAGYQVGFQL SQLYPFWTGA APDSIKGDPT AIRRAFARVE EALDTEAGAV    480
SATNLFTGQQ WDEPNVWPPL QYIAIQGLLN TPLEVSEDDD EQTAEDYVWT QNLALRLAQR    540
YTDSLFCTWR STGGATEEEP QLPGATGNGT IFEKYSDEAI NARGGGGEYT VVEGFGWSNG    600
VLIWAVDNFG QKLTTPDCGN ITAAAPPSTA SKRKRSAVEI HQRDAAWIKG TKENKMFGKK    660

SEQ ID NO: 208           moltype = AA  length = 737
FEATURE                  Location/Qualifiers
source                   1..737
                         mol_type = protein
                         organism = Lentinus similis
SEQUENCE: 208
LPQAVTPSST SVSSQTVSTA VPSPTASLTS TLPSQIPLPP KQDWCPSEIF CAGELLQTVN     60
VAQLYPDPKT FVDKPTARKS QQVVSNFQNI GGNSSNVTVG AIEDFVNSNF KGEGLELEPI    120
AFANFNPTPA FLNNVSDPLV KAWSQIVHGY WTQLTRSTND SALCPEGTES GSCESSLIPL    180
NHTFVVPGGR FREQYYWDSY WIVQGLLVSE LYDIVNDTLQ NFMDELEHIG FIPNGGRIYY    240
LNRSQPPLFI HMLTSYVQAS GDTSILKRAL PLAEKELAWW SANRSVQVKS PYTNATHNVY    300
RYHVTNTAPR PESYYTDYIT ANDPTLQTPL TEQQRADLYA ELATGAESGW DYSSRWLKEP    360
LAGGSNNTSP ALRSLNIRSL VPVDLNSILY KAHLNLAALY NNESHSAAAS NHTQAAIALR    420
EAILDLHWDA NKRAFYDFNI TSNARNDIFS AATFYPLWSG IIPDEILSDG SGATAFGAFA    480
AVNMVLNRYN GTFPVTFLET GLQWDAPNAW PPHQFIIIEA LRNLPSNITN TPLPSAPSGN    540
STYALIPAGQ VGIAEGDLPG QILSPGQNAT KTGPAADINT LNGTVVNGGN ATSGEGWAAV    600
LQRELANRYI ASALCSWHAT GGEVPNLLPR LSDSQLQITQ SQNNTGNMFE KFSINDIDSA    660
GRGGEYTVQA GFGWTNGVVL YLTHVFGDKL VAPSCPNLVA LSSNTATTSG AVAQMTLPSS    720
LAVTVGAVVL GFVGLVL                                                  737

SEQ ID NO: 209           moltype = AA  length = 683
FEATURE                  Location/Qualifiers
source                   1..683
                         mol_type = protein
                         organism = Diaporthe nobilis
SEQUENCE: 209
QTLDGIYYDG DNIAPCSSAL YCYGDILDSI QRAKPFADSK TFVDMPTRVP LEEVRAAYDQ     60
LTKPLQNNTE LLDFLSNNFG PAGQEVVPVD PGSLGVNASF LGGIANAVNR EFTEAVIDLW    120
PNLTRWVNES AVCAECDNSL LSIKRPFIVA GGRFREPYYW DSYWILHGLL RSGGNFTRIA    180
RNQIENFLDF VEDGYFVPNG ARVYYLNRSQ PPLLAQMVRI YIEQTGDATI LDRAIPLLIR    240
EHDFFMSNRT VHVSVGSRNY TLNRYNVANT EPPRESYYED YTQVNNASYY ANDGRVFPTR    300
NTTQAEKDLQ YKNLASGAES GWDFSTRFMR DPTIAANDTY FPLASYNIIN IIPVELNSIL    360
YWNEVTIAAF LRQQQQQVPN ATAEADADAW DARAASRSEA MYSVMWNETL GGYFDFNLTS    420
GSQDVFWARD ADSLPTEQAG TEPGQQVVFN IGQLSPFWTG AAPRSLAGDP AAVRRAFSRV    480
DEYLGSRKGG IAPTNFVSGQ QWDQPSVWPP HMHILMEALL RTAEAGGESE GGSEDWAWAQ    540
DLALRLGQRY FDSAYCTWRA TGGGTPSSPP LANPPQDLGG QMFEKYSDQS LNEAGSGGEY    600
VVVVGFGWSN GVLIWVADTF RDRLQTPACG DLTTRGEAGK MREKRMSENG RHGDGSNAIS    660
AVKLDYFDAA WTSENVGGLH GVR                                           683

SEQ ID NO: 210           moltype = AA  length = 763
FEATURE                  Location/Qualifiers
source                   1..763
                         mol_type = protein
                         organism = Solicoccozyma terricola
SEQUENCE: 210
QGNSSMSASN ATSSSTGTGT SSSAAAVMTA VPMPTAPLSS PVEMLPLPPV QPWCNGGENA     60
TYCPGSLMQL VQLSGIYNDS KTFPDKPTQY NASVTYQAFD ALPVNATVGD VETFVEKYFK    120
GEGQELETVQ IQNFTQNPTF LNVIDDELYK GFVSTVNGYW SLLVRQTNES ALCTNGACES    180
SLIPLNRSFI VPGGRYREIY YWDSFWILEG LLKSELYLYA YNLLENFMDL IEKFGFLPNG    240
GRSYYLNRSQ PPVFVQMLNA YIQVTGNVSI LTRALPIAET ELQWWRTNRT ISVTSPYTGT    300
NYSVARYFVT NSAPRPEGYV EDITTAFGGN PALNESARSA LYAELASGAE TGWDYSSRWC    360
KQPLLNLTDN DPALRTLNVR QQIPVDLNSL LCGDHVLLAN LYEFYMNSTI GGGSGISSGG    420
GNSTIGMGAW ANSTSGSNMT SNSTSSSNMT GLVQSHRMIA KEFEAAINDL MWDKQKLWWY    480
DFNMTANARA DVYHPGGLFP LWQNITPSDI VGNDTAAFGV FAGVRYMVGM YPGPPAPASL    540
IQTGLNWDAP NVWPPHVYTG IKALETVLRI NPNSSVVPNI TLTDFTRIPT GQLGLNQSQL    600
PPQPASALGN GTADLLDQAIA QMQKGKPWPT ALAIEFANRY LQSAFCSWYS TGGSIPGLLQ    660
QLSPQELNLT GSLTTGSQAM GNIFEKFNLT NVDAAGGGGE YTVQIGFGWS NGVILHTAGE    720
YGQYLVQPSC PLIAIHETAN ATSTNATKSN NTMVFSGYRL PHD                     763

SEQ ID NO: 211           moltype = AA  length = 734
FEATURE                  Location/Qualifiers
source                   1..734
                         mol_type = protein
                         organism = Dioszegia cryoxerica
SEQUENCE: 211
QSSSSSSFSP TPVTTAVPSA TAALNQTVSG QGVYPPLQPW CNAGENATYC PGVILQDVQL     60
SGLFPDSKTF VDKPTNGTQN ATQQAFQQLG NNITLGQLAQ FVNTSFRGEG LELSQVPING    120
FVANPAAVNK VSNPLYRGWV STVNSYWSLL IRETNQSAVC TTQCESSLIP LNYTIVVPGG    180
RYREIYYWDT FWILEGLLKS ELYTYAWDVL QNFMDFVDVY GFIPNGGRKY YLNRSQPPVF    240
IQMLDAYVKA TGNVTILERA LPLASEEMRW WINNRTTQVT SPFTGITRRV YVFNVTNSAP    300
RPEGYVEDYE AAFGAQPPLT EAQRGALYAE LATGAESGWD YSSRWCKQPV INVTDNLPAL    360
RTLNGRSIVP VDLNSLQAGN HALLARLYEV YINASTTSNT TAAQTIRANA TQEIALHKTL    420
```

```
ANDYSQAVLD LHWDPARAWF YDFNLTSNSR ESLYTPAGTF ALWQNITPPG LEGNDTAALR    480
IASGARYLLG RYGGIQGVSS LLVTGLNWDF PNSWPPHTYT SIKAFQTLGR LVGNASIVGN    540
ATIPFSQVAT NQLGLNETQL PPQDPALQGN ASLTVPSARN VSWPLALEIE YASRYMGAF     600
CSWYSTGGSI SGLLTQLPVS QLNATGTYQA GQTGQMFEKF NATDIDAAGG GGEYTVQIGF    660
GWTNGVVLWL ADNFGQYLPQ PTCPLVVLSL TNLNSTTAGN STNGTSPAAP GNATSLVAVS    720
ELQGIWEGQR VSRD                                                      734

SEQ ID NO: 212              moltype = AA   length = 1020
FEATURE                     Location/Qualifiers
source                      1..1020
                            mol_type = protein
                            organism = Talaromyces funiculosus
SEQUENCE: 212
LPFNERVDQV LRSYEVTSKL DSRSTKPSKH GHTYQTQFLG VTWDQRNWRL QSTVLDQGHY     60
ESRGSIANGY IGLNVAGAGP LFELDSPVDG DVINGWPLFS RRQTFAGLAG FYDLQPRTNG    120
TNFPWLSQYG DDSAISGVPH WGGMVLDLGD GEYLDATVDN STISDYTTTY DYKAGVLSWD    180
YKWTPKNANG SFGISYKIFA NKLDVNQAVV QLSITPSTNG SASVVNVIDG YAAVRTDFVS    240
SGNESDVVYT AVKPNGVTNV TAWIYTALDG DDAFDISSAA LVNDKPYVHQ NDSSIAQSVN    300
VTFTAGTTIT INKFVGAAST DAFPDPQSTA REAALSARRR GFDDLFRSHI SEWAQVMPDD    360
SVDDFTLANG TLPNDTFIIE SAVMAVVNPY YLLQNTVGPN ALRRVNNAPV NDWSIPVGGL    420
TSDSYAGQIF WDADVWMQPG LVAAFPESAK RITNYRAAKY SQALENAKTA YTSSQNOTWF    480
SPDAAIYSWT SGRVGNCTAT GPCWDYEYHL NGDIGISLVN EWVVSGDNET FKNKHFPIYN    540
SIATLYGDLL KKNGSYYTLT NMTDPDEYAN NVDAGGYTMT LISQTLSNAN AFRKQFGMNE    600
NTTWTEMADN ILLIRENDVT LEYTTMNNSV AVKQADVILS TFPLDYTKNY TTSAALNDLD    660
YYALKQSPDG PGMTYAIFSI VANDVSPSGC SAYTYAQYSY DPYIRGPFFQ FSEQLLDDYT    720
INGGTHPAFP FLTGHGGANQ VVLYGYLGLR LLPDDMLHID PNLPPQIPSI KYRTFYWRGW    780
PIQAASNYTH TTIQRATTVA PLSTADPTYA NKSIHVSVGH NTVNSTTYSL SANGSALVVP    840
NRQIGSINTV AGNVVQCKSV LSTDAYQKGQ YPISAVDGAA STKWQPEFAA NISSLTVDLT    900
GSNVSSVSGF YFDWAQAPPT NITVLLHNSS SAALASSGDK PGSSAVTLNI TISNPYNAST    960
YNANIIALPS SNSTNYTFPA PVPKPRYATL FVQGNQALDE TDTKSGNGTG ATVAEWAILS   1020

SEQ ID NO: 213              moltype = AA   length = 1063
FEATURE                     Location/Qualifiers
source                      1..1063
                            mol_type = protein
                            organism = Hamigera avellanea
SEQUENCE: 213
ASPKSRINQC LKKHAGQGSH DDETSSNVYQ TRFPGVTWDE DNWSLTTSVL DQGHYQSRGS     60
VANGYLGINV ASVGPFFELD IPLNGDVING WPLYSRRQTF ATISGFFDSQ PETNGTNFGW    120
LNQYGGESVI SGVPHWSGLI LDLGDGTYLD STVDNATLSG FTSSYDFKAG VLSWSYQWTP    180
EGKHGSYDIT YRLFTNKLYV NQAVVDMEIV PTVAGKASVV NVIEGSSAVR TDFVESGEDD    240
GAIFSAVRPW GISNVTAYFY ANLTVSDNVD LSSRTLVSNK PYVSTNESSI AQSVDVQFIP    300
GKSVRITKFV GAASTDAFAN PQETAKRAAS TAQTNGYLKS LNSHIAEWAS VMPDDSVEDF    360
SLPETGKLPA DEHIIESAII SVTNTYYLLQ NTVGKNAIKA SSDAALNMDS ISVGGLTSDS    420
YAGLIFWDAD IWMQPGLVAS HPEAAEVFTN YRVAKYPQAV KNIETAFASS KNQTNFSPSA    480
AAYPWTSGRY GNCTGTGPCF DYQYHLNGDI GLSMINQWVV SGDTQTFREK HFPIYDSAAT    540
FFSNLVERNG STWTLTNMTD PDEYANHIDA GGYTMPLIAE TLLYANSFRK QFGVEPNETW    600
NEIAENVLVL RTNGVTLEFT SMNGSAPVKQ ADVVLVTYPL DYNNNYSPED SLNDLDYYAN    660
KQSEDGPAMT WAIFSVVANE ASPSGCSAYT YAQYAYYPYA RAPFFQLSEQ MIDDASINGG    720
THPAYPFLTG HGGANQVNLM GYLGLRLLPD NVIHVDPNLP PQIPHLKYRT FYWRGWPMSA    780
ASNYTHTTIQ RAVNVPALST ADQKFANVSI PVHVGMECTNA TVYRLPVNGT LTIPNRQIAS    840
KNTVAGNLIQ CRPVESQNDF QPGQFPISVV DGASSTRWQP KHADNVSAVT VTFADEEVGS    900
LVSGFYFDWA QAPPVDAAVI FHNSSLENPA SAFSFASNSS SSEYSVITTL KNVEQSDPYD    960
PESDKLDIIA IPTGNTTKVT LPSAVPAARY ATLFITGNQA LGPEDIAAKN GTGATVAEWA   1020
IVGQTSSATS KRSIQTRKLQ VRSGAALSGL GFAQRRRQSA EMY                     1063

SEQ ID NO: 214              moltype = AA   length = 1020
FEATURE                     Location/Qualifiers
source                      1..1020
                            mol_type = protein
                            organism = Talaromyces ruber
SEQUENCE: 214
LPFNERVDHV LRSHDLTSRL HSRSAKPSNH GGTYQTQFTG VTWDQRNWRL QSNVLDQGHY     60
ESRGSIANGY IGLNVAGAGP FFELDTAVDG DVINGWPLFS RRQTFAGLAG FYDLQPTTNG    120
SNFPWLDQYG DDSVISGVPH WGGLVLDLGN GEYLDATVDN STISDYSTTY DYKAGVLSWH    180
YKWTPKNANG SFEIKYKIFA NKLDVNQAVV QLSITPSANG SASVANVIDG YSAVRTEFVA    240
SGNESDAIFT AVKPVGVSNV TAWIYAALDG DDAFDFSSAT LVNDKPYVHQ NDSSIAQSVN    300
VTFTAGTTIT INKFVGAAST DAFPDPQSTA REAALKARRR GFDDLFRSHI SEWAQVMPDD    360
SVDDFTLANG TLPNDPFIIE SAVMAVVNPY YLLQNTVGPN ALRRVNNAPV NDWSIPVGGL    420
TSDSYAGQVF WDADVWMQPG LVAAFPESAK RITNYRTAIY SQALENAKTA YTSSQNQTSF    480
SSDAAIYSWT SGRYGNCTAT GPCWDYEYHL NGDIGISLVN QWVVSGDNDT FKNTHFPIYN    540
SIATLYGDLL KKNGSYYTLT NMTDPDEYAN NVDAGGYTMT LISQTLSNAN AFRKQFGMDE    600
NTTWTDMADN VLLIRENDVT LEYTTMNNSV AVKQADVILS TYPLDYTKNY TTSAALNDLD    660
YYALKQSPDG PGMTYAIFSI VANDVSPSGC SAYTYAQYSY DPYIRGPFFQ FSEQLLDDYT    720
ANGGTHPAFP FLTGHGGANQ VVLYGYLGLR LLPDNVLHID PNLPPQIPSV KYRTFYWRGW    780
PIQAASNYTH TTIQRATSVA PLSTADQTYA NRSISVQVGQ NTVNSTTYSL PANGSAIVVP    840
NRQIGSINTV AGNIAQCKSV LSTDAYQPGQ YPISAVDGAA STKWQPEFAA NISSLTVDLT    900
SSNASTVSGF YFDWAQAPPT NITVLLHNSS NAPLTSSNSN GGNSTVSLNV TISNPYDASA    960
YNANVITLSS SNTTNYTFPA PVSKPRYATL FVQGNQALDE TDLKAGNGTG ATVAEWAVLS   1020
```

```
SEQ ID NO: 215              moltype = AA  length = 1055
FEATURE                     Location/Qualifiers
source                      1..1055
                            mol_type = protein
                            organism = Trichoderma lixii
SEQUENCE: 215
ATSNNRVSEC LGRNGGSSTG VHFSKNVYKT DFAGVTWDED NWLLSTTELK QGAFESRGSI    60
ANGYLGINVA SVGPFFELDT EENGDVISGW PLFSRRQSFA TIAGFWDSQP VMNGTNFPWI   120
SQYGSDTAIS GIPHWSGLIL DLGGNTYLDA TVDNRTISNF RSTYDYKAGV LSWSYKWTPK   180
GNKGSFDISY RIFANKLYVN QAVVDLQVTA SKNVEASIVN VIDGFAAVRT DFVESGEDGN   240
AIFSAVRPNG VANVTAYVYA DITGSGGVDL SSRKIVHNKP YVHANASSIA QAVPVKFSAG   300
RAVRVTKFVG GASSDAFKNP KQIAKSAAAT ALKNGYSKSL NSHVTEWAAV MPESSVDSFA   360
DPKTGKLPND NYIIDSAIIA VVNTYYLLQN TVGKNGSKAA NGAPVNVDSI SVGGLTSDSY   420
AGQVFWDADL WMQPGLLAAH PEAAERIINY RLARYGQAKE NVKTSYAGSQ NETFFSASAA   480
VFPWTSGRYG NCTATGPCWD YEYHLNGDIG LALVNQWVN GDTKDFEKNL FPVYDSIAQL   540
YGNLLKPNGT AWTLTNMTDP DEYANHVDAG GYTMPFIAET LQNANTFRKQ FGIEQNKTWN   600
DMASNALVLR ENGVTLEFTT MNGSAVVKQA DVIMVTFPLS YTTNYTTEDA LNDLDYYANK   660
QSPDGPAMTY AFFSIVANEI SPSGCSAYTY AQYAFKPYVR APFYQLSEQI IDDSSINGGT   720
HPAYPFLTGH GGANQVVLFG YLGLRLVPDD FIHIEPNLPP QIPYLRYRTF YWRGWPISAW   780
SNYTHTTISR ASGVAALDGA DQRFAGKTIT IHSGPEESPK AYHLPVKGSV VVPNKQIGSQ   840
QTYAGNLVQC HAASSPSDYV PGQFPIAAVD GATSTKWQPA SADKLSSITV SLDQEDVGSL   900
VSGFHFDWAQ APPVNATIIF HNEAINDPAT VLKSQKHNSN YKVVSSLTNI KQSNPYIKTT   960
DLDIIAIPIG NTTNVTLSQP VAASRYASLV IVGNQGLDHA DVVGKNGTGA TVAEWAIIGH  1020
SKGHTGAPGH HGKRKLNLRA AAAMSDPDSF ARRRQ                             1055

SEQ ID NO: 216              moltype = AA  length = 1056
FEATURE                     Location/Qualifiers
source                      1..1056
                            mol_type = protein
                            organism = Aspergillus cervinus
SEQUENCE: 216
STFSHKNDRI LKGLKRHGDH YSRKSNTNST DVYQTKFDGV TWDDDNWLLT TTALDQGDFR    60
SRGSIANGYL GINVASVGPF FELDTAENGD VISGWPLFSR RQTFATIAGF FDSQPTTNGS   120
NFPWLYQYGG DSVISGVPHW SGLVLDLGND TYLDSTVDNQ TIENFTSMYD YKSGVLSWSY   180
TWVPAGNKGS FDIVYRLFAH KLNVNQAVVD MEITPSLSFN ATVVNILDGY SAVRTDFVES   240
GNDNGAIFTA VRPWGISNVT AYVYANLTGT PNVDLSSRTI VANKPYVHTN ASSIAQAVNV   300
SCSPNETVRI TKFVGAASSD AFENPQETAR QAVSAAIGAG YLRSLGTHIA EWASIFPDDS   360
VDRFTDPATG KLPANKHIIN SAIIAVTNTY YLLQNTVGKN AIQAVSGAPV NIDSISVGGL   420
TSDSYAGQVF WDADVWMQPG LAASHPEAAQ RITNFRAAKY PQALANIETA FTSSKNQTSF   480
SPSAAAFPWT SGRFGNCTAT GPCWDYEYHL NGDIGLSLMY QWIASGDTQT FRETHFPIYD   540
SIATMYSNIV ERNGSYWTLK NMTDPDEYAN QIDAGGFTMP LISQTLNYAN AFRQQFGLDV   600
NQTWSEIANN VLVLNDNGVT LEYTTMNGST VVKQADVVLD TYPLVYSNNY TSQNSLDDLD   660
YYANQQSPDG PAMTWAIFSI VANDVSPSGC SAFTYHQYSY DPYARAPPFQ LSEQLIDDAS   720
TNGGTHPAFP FLTGHGGANQ VVIFGYLGLR LLPDEAIHID PNLPPQIPHV AYRTFYWRGW   780
PISAQSNSTH TTISRAMNAS PLDTADSRFA NVSIPIYVGT ESNATVFQLP PTGPLTILNR   840
QNGFNNTIPG NVAQCRPVYS PDDYAPGQFP IAAVDGASTS KWQPSSANTS SVTVTLPDTQ   900
INSPVSGFYF NWWQLPPVNA TVIFHDDLLE NPAATISSSG NSSSYRVVMT LTNIQQSSPY   960
NAQIAALDEI TIPTGNTTTV QLTNHAQTSR YATLLISGNQ GLGDTQDGVG ATVAEWVILG  1020
QGQGSSSSNS NGKRKLGARS AAALSNGWTE RRRRLI                            1056

SEQ ID NO: 217              moltype = AA  length = 1053
FEATURE                     Location/Qualifiers
source                      1..1053
                            mol_type = protein
                            organism = Rasamsonia brevistipitata
SEQUENCE: 217
LRSEARVAQV VRAYSSSTGV EAGHGNATQY ETRFPGVTWD QRHWRLKSTV LDQGHFQSRG    60
SIANGYVGIN VASAGPFFEL DTPVDGDVIN GWPLFSRRQT FATIAGFYDE QPRTNGSNFD   120
WLYQDGGESV ISGVPHWSGL ILDLGDGTYL DATVDDSTIS DYSTVYDYKA GILSWSYKWT   180
PKSSKGSFKI SYRLFAHKLN INQAVVRMEI TPSADTDATV VNVLDGYSAV RTDFVGSGKD   240
GDAVYSAVSP WEVQNVTAYV YAVLDGSDGV DLSTLSLVNG KPYVHTNESS IAQSVNVRFR   300
AGKTVTVTKF VGAASTDAFP DPQQTAREAA LAAKEEGYDA LLRSHVAEWA AVMPEESVDS   360
FTYHNGTLPG DDFIVESAIM AVVNPYYLLQ NTVGENALRE VSHAPVNEWS ISVGGLTSDS   420
YAGLIFWDAD LWMHPGLAVA FPQAATRITN YRVAKYEQAR QNAKTSFTGS KNQTWFSDSA   480
AVYPWTSGRY GNCTGTGPCW DYEYHLNGDI GLSLINEWVA SGDTKTFQES YFPIYDSIAT   540
LYADLLQQNG SHWTLTNMTD PDEYANAVDA GGYTMPLIAQ TLLYANSFRQ QFGAQPNSTW   600
TEMASNILFL RENDITLEYT TMNNSVQVKQ ADVVLVTYPL EYTTNYNAGN ALTDLDYYAL   660
KQSPDGPAMT YAIFSIVANE VSPSGCSVYT YAQYSYDPYV RPPFFQLSEQ LVDDYTLNGG   720
THPAYPFLTG HGGANQVVIF GYLGLRLLPD NVIHIDPNLP PQIPVKYRT FYWRGWPIQA    780
YSNYTHTTIG RAADVLALDT ADQRFANTTI PVQVGSGSNA TVYQLPIDGV LTVANRQVAS   840
TNTVAGNLAQ CQPVDSSDSY VPGQYPLAAV DGAASTKWQP SFAANVSSVT VSLPESESGT   900
LVSGFYFDWA QAPPVNATVV FHNNTVENPT RYMSSPTFVT HIDNITLSSP YNAEANPAAT   960
VTLPSSNTTN VTLAHPMPVP RYATLFITGN QALSESEVQA QNGTGATVAE WAILASNPET  1020
GSSKRNLQLR GVGRSALAGL PRRANRKERR TDV                               1053

SEQ ID NO: 218              moltype = AA  length = 1034
FEATURE                     Location/Qualifiers
source                      1..1034
```

```
                            mol_type = protein
                            organism = Acremonium curvulum
SEQUENCE: 218
LEERVSQTLN RHGVRSSYNR RADNGDQNRI SNTSHPYIYQ TSFEGVTWDS RNWRLQGTVL    60
DQGHYQSRGS IANGYFGINV ASAGPFFELD TPVDGDVING WPLFSRRQTF AGLAGFWATQ   120
PTTNGTNFPW LYQYGDESPI SGIPHWGGLV LDLGDDVYLD ATVDNKTIKN YRTTFDYKAG   180
VLTWDYTWSP KKRGSGSFDI TYSLFANKLD INQAAVRLSI RPSRDTKAKV VNVLEGYAAV   240
RTDFVDSGKD GDAIYSAVRP VGVNNVTAYV YAVLDADSAV DLSSAKVIDD APYLYTNKST   300
IAQSVNVEFK ANQNVTITKF VGIASTDAFP KPRDVAKQAA FAGKRRGYDD ALRSHVSEWA   360
QVMPDDSVDD FSSDNGTLPD DGFIIESSIM AVVNPFYLLQ NTVGANALRR VNNAAVNDYS   420
ISVGGLTSDS YAGLVFWDAD IWMQPGLAAA FPEAAQRITN YRVALYPQAK RNIKTAFQSS   480
KNKTRFSDDA ALYPWTSGRW GNCTASGPCF DYEYHLNGDI GIAFVNEWIT SGDEKAFEEK   540
YPPIYDSIAT AFANLLQKNG TQWTLTNMTD PDEYANHVDA GGFTMPLISQ TLTYANLFRK   600
KFGKEENDTW ADMAENVLIL RENDVTLEYT AMNNSVEVKQ ADVVLNTFPL DYTRDYAPSA   660
ALNDLDYYAL KQSPDGPAMT YAIFSIVANE VSPSGCSAYT YAQYSYSPYL RGPFHQLSEQ   720
LTDDFTTNGG THPAYPFLTG HGGANQVVLF GYLGLRIVPD DKIHVDPNLP PQIPQVKYRT   780
FYWHGWPIAA KSNYTHTTIS RATTIKELDT ANKKYANASI QVVVGSGKSA KTYKLPANGS   840
SIVVANRKIG TVNTLEGNMI QCQPAQSFDT FVPGQFPISI NDGAASTKWQ PEFANNISAV   900
TVTVPASKSK KISGFYFDWA QAPPTNATVV LHDEKMDNPT MVLLPVSKDD DKKGSVARVN   960
VTISEPWSAK DKSNFVIGLQ GGNTTNFTFS EPVAAKRYAT LFIQGNQALD KVDIKYKNGT  1020
GATVAEWGIL SDDA                                                   1034

SEQ ID NO: 219          moltype = AA  length = 1015
FEATURE                 Location/Qualifiers
source                  1..1015
                        mol_type = protein
                        organism = Talaromyces piceae
SEQUENCE: 219
ARVDQVLQAR DTHHPSLHSS SSYQTRFDGV TWDQRNWRLQ SRVLDQGHYQ SRGSVANGYL    60
GINVASAGPF FELDTPVGDG VINGWPLFSR RQTFAGLAGF YDRQPTTNST NYGWLNQYGD   120
ESVISGIPHW SGLVLDLGDG HYLDATVDSS TISDYTTTYD FKAGVLSWDY NWAPRQHGGG   180
NSSFHISYQL FAHKLDINQA VVKLSITPSA SGNASVVNVI DGYSAVRTEF VKSGTDGDAV   240
YSAVSPVGVS NVTAWVYTVL DGDEAFNLSS AQLVTGKPYV YQNDSSIAQS VNVEFRAGET   300
VTITKFVGAA STDAFADPRQ TARDAALLAK KKGFDDLLRS HVSEWAQVMP DGSVDDFTRE   360
DGTLPDDEFI IESAVTAVVN PFYLLQNTVG KNALQRVSNA PVNDWSIPVG GLSSDSYAGL   420
IFWDADVWMQ PGLVAAFPES AQRITNYRAA MYRQARANIQ SAFASSQNKT VFSPDGAIYP   480
WTSGRYGNCT GTGPCFDYEY HLNGDIAISL VNQWVVSGDT ETFKNEHFPI YDSIATMYAD   540
VLKKNGSFYT LTNMTDPDEY ANNKDAGGFT MPLIAKTLLN ADFRKQFNM EENSTWNEKA   600
ASVQILREND VTLEYTTMNN SVAVKQADVV LMTFPLDYTA NYSSSSALND LDYYALKQSP   660
DGPGMTYAIF SIVANQVSPS GCSAYTYAQY SYYPYARAPF FQLSEQLLDD YTANGGTHPA   720
YPFLTGHGGA NQVVLYGYLG LRLVPDETLY IDPNLPPQIP QVKYRTFYWR GWPIQAASNY   780
THTTIRRATT VAPLDTADEK YTDEAITLHV GQQSDGNKYQ LPADGTPVTV ANRRVSSVNT   840
VKGNMIQCQP VQSTASIQPG QFPIAAVDGA ASTKWQPEFA ANASSLTVEI PSSGKKRKTV   900
SGFFFDWAEA PPTNATVVLH NNPVSEPTLS SFEAGKDGVV LRAFDIEISS PYNASTYADE   960
IIIPQGNSTN YTFSHPVPAP RFATLFVQGN QALDKVDVEN KNGTGPMVAE WVILE       1015

SEQ ID NO: 220          moltype = AA  length = 1022
FEATURE                 Location/Qualifiers
source                  1..1022
                        mol_type = protein
                        organism = Penicillium sp.
SEQUENCE: 220
LPLEERVDRV LRSYSVGSGL EARHSKYTYQ TQFDGVTWDQ QNWRLESTVL DQGHYSSRGS    60
IANGYIGLNV AGAGPFFELD APVDGDVING WPLFSRRQTF AGLSGFYDVQ PTTNGSNYPW   120
LDQYGDSVI SGIPHWGGLV LDLGNGDYLD ATVDNSTISD YTTTFDYKAG VLSWDYNWTP   180
KNTSFGISYK IFSSKLDINQ AVVQLSITPS ANGTASVANV IDGYAAVRTE FVTSGNDSDA   240
LFTAVKPTGI NNVTAWIYAV LDGDDAFDFS SATLVNNKPY INQNDSSIAQ AVDVEFTADS   300
TVTITKFVGA ASTDAFADPQ KTAKDAALAA RIKGFEDLLR SHVSEWAQVM PDDSVDDFSL   360
ADGTLPDDIF IIESSVMAVV NPYYLLQNTV GENALRRVNG APVNIWSIPV GGLTSDSYAG   420
QIFWDADLWM QPGLVAAFPE SAKRISNYRV AKYPEALANT NTSFAGSQNH TTFSSDAAIY   480
SWTSGRYGNC TATGPCWDYE YHLNGDIGIS LVNQWVTSGD TETFQNDLFP IYNSVATLYA   540
DLLKLNGSYT TLTNMTDPDE YANNVDAGGY TMTLISKTLS NANAFRKHFG LDQNSTWTEM   600
AENVLVIREN DVTLEYTTMN NSVAVKQADV VLSTFPLDYT MNYTTRRDAVN DLDYYALKQA   660
SDGPGMTYAI FSIVADKVSK SGCSAYTYAQ YSFDPYIRSP FFQFSEQLDD DYTTNGGTHP   720
AFPFLTGHGG ANQVVLYGYL GLRLLPDNVL HIDPNLPPQI PSVKYRTFYW HGWPIQANSN   780
YTHTTIRRAT TTAPLSTADQ TYSNTSITVQ VGTSNGTTYS LRVDGTPLTI KNRRIGSVQT   840
ISGNIAQCQP VQSPDSYEPG QYPLSVVDGA SSTKWQPESA ANISSVTVTL GSSYSPGNSS   900
NATASSILGF YFNWAQAPPD NITVVLHNAS IPYLNASLSS LSNTTTTTSL NITVSNPYDS   960
SADEKIIVLP SSNTTNYTFP SPVPVPRFAT LFIQGNQGLD QTDLEYGNGT GATVAEWAIL  1020
SA                                                                 1022

SEQ ID NO: 221          moltype = AA  length = 1020
FEATURE                 Location/Qualifiers
source                  1..1020
                        mol_type = protein
                        organism = Talaromyces aurantiacus
SEQUENCE: 221
LPFQDRVDQV LRSYSAKTLD IRSAKSSSKH GNTYETQFPG VTWDQRNWRL QSTVLDQGHY    60
ESRGSIANGY IGLNVAGAGP FFELDTPVDG DVINGWPLFS RRQTFAGLAG FYDLQPTTNG   120
```

```
SNFPWLDQYG DDSAISGVPH WGGLVLDLGD GQYLDATVDN STVSDYKTTY DFKAGVLSWD    180
YKWTPKSSNV SFGISYKVFA NKLDVNQAVV QLSITPSANG SASVVNVIDG YSAVRTDFVS    240
SGNESDAIYT AVKPLGVSNV TAWIYATLDG DDAFDFSSAT IVNNKPYVHQ NDSSIAQSVN    300
VTFTAGTTVT INKFVGAAST DAFPDPRSTA KEAALAGRRR GYDDSFRAHI SEWAQVMPDD    360
SVDDFTLANG TLPNDTFIIE SAVMAVVNPY YLLQNTVGPN ALRRVNNAPV NDWSISVGGL    420
TSDSYAGQVF WDADVWMQPG LVAAFPESAK RITNYRAAIY SQALANAKTA YTSSQNQTSF    480
SSDAAIYSWT SGRYGNCTAT GPCWDYEYHL NGDIGISLVN QWVASGDNET FKNTHFPIYN    540
SIATLYGDLL KKNGSYYTLT NMTDPDEYAN NVDAGGYTMT LISQTLSNAN AFRKQFGMDE    600
NTTWTEMADN VLLIRENDIT LEYTTMNNSV AVKQADVILS TYPLDYTKNY TTSAALNDLD    660
YYALKQSPDG PGMTYAIFSI VANDVSPSGC SAYTYAQYSY DPYIRGPFFQ FSEQLLDDYT    720
ANGGTHPAFP FLTGHGGANQ VVLYGYLGLR LVPDDKLHID PNLPPQIPSV KYRTFYWRGW    780
PIQAASNYTH TTIQRATRVA PLSTADMTYA NKSISVQVGQ NTANSTTYSL PVNGSALVIS    840
NRQIGSINTV QGNIAQCKSV QSMNGYQPGQ YPISAVDGAA STKWQPEFAA NVSSLTVDLT    900
SSNASSVSGF YFDWAQAPPV NVTVVLHNST SASLTSSAAQ NGSSTVSLNI TISNPYNASS    960
YDANVIELSS SNTTNYRFPA PVPKPRYATL FVQGSQALDE TDMKAGNGTG ATVAEWAILS   1020

SEQ ID NO: 222          moltype = AA  length = 1016
FEATURE                 Location/Qualifiers
source                  1..1016
                        mol_type = protein
                        organism = Talaromyces pinophilus
SEQUENCE: 222
LPFNERVDQV LRSYSPKNLE SRSTKHGNSY QTQFSGVTWD QRNWRLQSTV LDQGHYESRG     60
SIANGYIGLN VAGAGPFFEL DTAVDGDVIN GWPLFSRRQT FAGLAGFYDL QPTTNGSNFP    120
WLSQYGDDSA ISGVPHWGGL ILDLGDGEYL DATVDNSTIS DYTTTYDYKA GVLSWDYKWT    180
PKNSKASFGI NYKIFANKLD VNQAVVQLSI TPSANGSGSV VNVIDGYSAV RTDFVSSGNE    240
SDVIYTAVKP VGVNNVTAWI YAALDGDEAF DFSSAELVND KPYVHQNDSS IAQSVNVAFT    300
AGTTITINKF VGAASTDAFP DPQSTAREEA MTARRRGFDD LFRSHVSEWA QVMPDDSVDD    360
FTLANGTLPN DTFIIESAVM AVVNPYYLLQ NTVGANALRR VNNAPVNDWS IPVGGLTSDS    420
YAGQIFWDAD VWMQPGLVAA FPESAKRITN YRTAKYSQAL ENAKTAYTSS QNQTSFSSDA    480
AIYSWTSGRY GNCTATGPCW DYEYHLNGDI GISLVNQWVV SGDNETFKNT HFPIYNSIAT    540
LYGDLLKKNG SYYTLTNMTD PDEYANNVDA GGYTMTLISQ TLSNANAFRK QFGMDENTTW    600
TEMADNILLI RENDVTLEYT TMNNSVAVKQ ADVILSTFPL DYTKNYTTSA ALNDLDYYAL    660
KQSPDGPGMT YAIFSIVAND VSPSGCSAYT YAQYSYDPYI RGPFFQFSEQ LLDDYTANGG    720
THPAFPFLTG HGGANQVVLY GYLGLRLLPD DMLHIDPNLP PQIPSVKYRT FYWRGWPIQA    780
ASNYTHTTIQ RATSVAPLST ADPAYANTSI SVSVGQNTAN STTYSLPVNG SAIVVPNRQI    840
GSINTVAGNI AQCVSVLSTD AYQPGQYPIS AVDGAASTKW QPEFAANVSS LTVDLTSSNA    900
SSVSGFYFDW AQAPPTNITV LLHNSSSAAL TSSSTHGGSS SVSLNITISN PYDASSYDAN    960
VIALSSSNTT NYTFSAPVAK PRYATLFVQG NQALDETDTK AGNGTGATVA EWAILS       1016

SEQ ID NO: 223          moltype = AA  length = 1069
FEATURE                 Location/Qualifiers
source                  1..1069
                        mol_type = protein
                        organism = Talaromyces leycettanus
SEQUENCE: 223
TSANARINRC VKKHAGGKTP SGPSNNTYQT RFPGVTWDQD NWCLSTTTLD QGHYESRGSV     60
ANGYLGINVA SVGPFFEFDT PVDGDVINGW PLFDRRMSFA TISGFWDQQP TTNGSNFPWL    120
YQYGGESVIS GVPHWSGLIL DLGDNTYLDA TVDSRTISGF STTYDFKSGV LSWSYQWTPA    180
GNMGSYNITY RLFAHKLYVN QAVVDMEVVS STEAKATVVN VIDGASAVRT DFVESGQDDG    240
AIYTAVRPWG IANVTAYIYA NITGSNDVDM RSRALVTNKP YVNGNASSIT QAVNVHFTPG    300
KSVRITKFVG GASSDAFSNP QQIAKQACST AQANGYVKSL RSHVAEWSAV MPDDSVDDFT    360
FPSNGTLPAD EYIIESQIIS VANTYYLLQN TVGKNAINAS SSTELNKDSI AVGGLTSESY    420
AGMIFWDADV WMQPGLVASH PEAAQRITNY RVAKYPQAKA NVATAYQSSK NQTNFSPDAA    480
VYSWTSARYG NCTATGPCWD YEYHLNGDIG LSIINQYVSA GDTQTFKEKL FPVFDSVATL    540
YSNIVQKNGS SWTLTNMTDP DEYANQVDAG GYTMPLIAQT LLYANSFRQQ FGLETNDTWN    600
EIAQDVLVIR ENGVTLEFTT MNGSAVVKQA DVVLDTYPLG YTHNYGPTDA LNDLDYYANR    660
QSPDGPAMTW AIFSVVANQI SPSGCSAYTY AQYAFSPYAR APFYQLSEQL IDDASLNGGT    720
HPAYPPLTGH GGALQVNLFG YLGFRYLPDN VIHIDPNLPP QIPHITYRTF YWRGWPITAA    780
STYTHTTLSR AWNVSSLDSA DPKFANASIP VHVGLESNVT VYRLPVNGTL TVPNRMVGSK    840
NTLAGNMVQC RPVQSMDGYQ PGQPPISVVD GASSTKWQPL YSANVSSVTV TLSSSAVGKS    900
VNGFYFDWAQ NPPVNAAVVF HNSSFAQNPA TTFSFDNPSA SGNLYSVVSV LKDIQLSDPY    960
DPATTDLDVI AIPKGNTTNV TLSSPVPAAR YATLFIQGNQ ANSPAEVAAK NGTGATVAEW   1020
AILGQEVQNN GYGDQIEARR LDVRGAAALS GMGSFTQRRK RKMILPRFD              1069

SEQ ID NO: 224          moltype = AA  length = 1016
FEATURE                 Location/Qualifiers
source                  1..1016
                        mol_type = protein
                        organism = Talaromyces variabilis
SEQUENCE: 224
ALSPGARVNQ VLRAHNSLPP SLTDNSTGSS YKTRFDGVTW DQRNWRLQSR VLDQGHYEAR     60
GSVANGYIGI NVASAGPFFE LDTPVDGDVI NGWPLFSRRQ TFAGLAGFYD LQPTTNSTNY    120
GWLNQYGDES VISGIPHWAG LVLDLGNGDY LDATVDNSTI SDYTTTYDYK AGILSWDYKW    180
TPRQNSSSFR ISYQLFANKL DINQAVVKLS ITPSKSGNAS VVNVIDGYSA VRTDFVKSGS    240
DGNAIYTAVS PVGVSNVTAW VYAVLDGDKA FDLSSPSRVT GKPYIHQNES SIAQAVNVEF    300
SAGKTVTIAK FVGAASTDAF SNPQKKAKTA ALDGKKKGFE DLLRSHVSEW AQVMPDDSVD    360
DFTLANGTLP DDSFIIEQAV TAVVNPYYLL QNTVGKNALQ RVNNAPVNDW SIPVGGLSSD    420
SYAGMIFWDA DVWMQPGLVA AFPESAKRIT NYRAAKYQQA IANVKTAYSS QNETVFSPN     480
```

```
                                          -continued

AAIFPWTSGR YGNCTGTGPC WDYEYHLNGD IAISLVNQWV VSGDTETFQN EHFPIYNSIA   540
TVYGDLLKKN GSYYTLTNMT DPDEYANNKD AGGYTMPLIA NTLIKANEFR RQFGMAENAT   600
WNEMAENVLI IRENDVTLEY TTMNNSVAVK QADVVLRTFP LDYTTNYSSS AALNDLDYYA   660
LKQSPDGPGM TYAIFSIVAN EVSPSGCSAY TYAQYSYDPY ARAPFFQLSE QLIDDYTTNG   720
GTHPAYPFLT GHGGANQVVL YGYLGLRLVA DEILHIDPNL PPQIPQVTYR TFYWRGWPIQ   780
AASNYTHTTI HRATTVAPLD SAEKKYAKSA ISVQVGQQAN STTYKLPADG TPLTVANRKV   840
GSTNTIKGNI AQCQSVQSVD SYQPGQYALA AVDGAASTKW QPEFAANVSS LTVSIPSGKT   900
SVSGFYFDWA QAPPSNATVV FHNNSVSNPT FSSFGSRKGA RITHIDVKLS NPYNASSNAD   960
AIVIPSGNTT NFTFSNPVPA PRFATLFVQG NQGLDKVDVQ NGNGTGATVA EWAILE     1016

SEQ ID NO: 225           moltype = AA  length = 1050
FEATURE                  Location/Qualifiers
source                   1..1050
                         mol_type = protein
                         organism = Aspergillus niger
SEQUENCE: 225
LPGKNARISA SLKRHAGRDV PQTALNSTNV YQTKFSGVTW DEDHWLLTTT TPDQGHYQSR    60
GSVANGYLGI NVANIGPFFE LDEPVNGDVI NGWPLYSRRQ SFATISGFWD RQAHTNGSNF   120
PWLSQYGDDS VISGVPHWSG LILDLGDDTY LDATVDNRTI SNFKSTYDFK SGVLSWSYTW   180
TPQGNKGSYA ITYRLFAHKL YVNRAVVDME ITPLTNGNAT VVNVLDGYAA VRTDFVASGQ   240
EEGAIFSAVR PWGVNNVTAY VYATLDGSDS VDLSSRRIVT DKPYVSTNSS SVAQAVDVMF   300
TANETVRITK FVGGATTDYF LATQETAKAA CLAGLADGYV KSLQSHVGEW ATIMHDHSVD   360
RFTDPATGKL PEDSHIVDSA IIAVTNTYYL LQNTAGTNAI VAAGGIPVNV DSCAPGGLTS   420
DSYGGQIFWD ADLWMQPGLV ASHPESAQRF TNYRIALHYQ AQANIETAFT GSKNQTSFSS   480
SAAIYPWTSG RFGNCTATGP CWDYQYHLNG DIGLAMINQW VASGDTAWFK NYLFPIYDAA   540
ATLYSELVER NGSSWTLTNM TDPDEYANSI NAGGYTMPLI AETLQNANKL RKQFGLEPNE   600
TWDEIAEDVL ILRENGVTLE YTSMNGSAVV KQADIVLNTF PLTYESDNYT ATNSLTDLDY   660
YANKQSADGP AMTYAIFAIV ASDVSPSGCS AFTYHQYSYA PYARGPWYQL SEQMIDDASI   720
NGGTHPAPFF LTGHGGANQV ALYGYLGLRL HPDDTIYIDP NLPPQIPHIT YRTFYWHGWP   780
ISAWSNYTHT TIQRDSSLAP LASADLLFSN VSIKVQVGQS TASADEATIY YLPLSGALTV   840
PNRMIGSVNT TPGNQVQCHP VYSPDAYEPG QFPISAVDGA TSTKWQPSTS DLTSLTVTLS   900
TTAEAGAEEV SGFYFDWSQA PPENLTVIPH DSPIGNPSTV FAAAGSNSTG YRVITSMSNI   960
VQSKPYNAIS AEELNVVSIP TANTTTITLD APVQKARYAT LLIAGNQANE TAGATVAEWV  1020
ILGQNSTSSS SAQAKRKMSA RSKATLAQLS                                 1050

SEQ ID NO: 226           moltype = AA  length = 1056
FEATURE                  Location/Qualifiers
source                   1..1056
                         mol_type = protein
                         organism = Trichoderma reesei
SEQUENCE: 226
TTLVDRVTKC LSRHDGSDAE SHFSKNVYKT DFAGVTWDED NWLLSTTQLK QGAFEARGSV    60
ANGYLGINVA SVGPFFEVDT EEDGDVISGW PLFSRRQSFA TVAGFWDAQP QMNGTNFPWL   120
SQYGSDTAIS GIPHWSGLVL DLGGGTYLDA TVSNKTISHF RSTYDKAGV LSWSYKWTPK    180
GNKGSFDISY RLFANKLHVN QAVVDMQVTA SKNVQASIVN VLDGFAAVRT DFVESGEDGS   240
AIFAAVRPNG VANVTAYVYA DITGSGGVNL SSRKIVHNKP YVHANASSIA QAVPVKFAAG   300
RTVRVTKFVG AASSDAFKNP KQVAKKAAAA GLSNGYTKSL KAHVEEWATV MPESSVDSFA   360
DPKTGKLPAD SHIVDSAIIA VTNTYYLLQN TVGKNGIKAV DGAPVNVDSI SVGGLTSDSY   420
AGQIFWDADL WMQPGLVAAH PEAAERITNY RLARYGQAKE NVKTAYAGSQ NETFFSASAA   480
VFPWTSGRYG NCTATGPCWD YEYHLNGDIG ISLVNQWVVN GDTKDFEKNL FPVYDSVAQL   540
YGNLLRPNKT SWTLTNMTDP DEYANHVDAG GYTMPLIAET LQKANSFRQQ FGIEQNKTWN   600
DMASNVLVLR ENGVTLEFTA MNGTAVVKQA DVIMLTYPLS YGTNYSAQDA LNDLDYYANK   660
QSPDGPAMTY AFFSIVANEI SPSGCSAYTY AQNAFKPYVR APFYQISEQL IDDASVNGGT   720
HPAYPFLTGH GGAHQVVLFG YLGLRLVPDD VIHIEPNLPP QIPYLRYRTF YWRGWPISAW   780
SNYTHTTLSR AAGVAALEGA DQRFARKPIT IHAGPEQDPT AYRLPVKGSV VIPNKQIGSQ   840
QTYAGNLVQC HAASSPNDYV PGQFPIAAVD GATSTKWQPA SADKVSSITV SLDKEDVGSL   900
VSGFHPDWAQ APPVNATVIF HDEALADPAT ALASAHKHNS KYTTVTSLTN IELSDPYVST   960
KDLNAIAIPI GNTTNVTLSH PVAASRYASL LIVGNQGLDP VDVKAKNGTG ATVAEWAIFG  1020
HGKEHSGKPS SHSKRRLNVR TAATLSNPRS FMRRRL                          1056

SEQ ID NO: 227           moltype = AA  length = 19
FEATURE                  Location/Qualifiers
source                   1..19
                         mol_type = protein
                         organism = Saccharomyces cerevisiae
SEQUENCE: 227
MLSLKTLLCT LLTVSSVLA                                               19

SEQ ID NO: 228           moltype = DNA  length = 185
FEATURE                  Location/Qualifiers
source                   1..185
                         mol_type = genomic DNA
                         organism = Saccharomyces cerevisiae
SEQUENCE: 228
agtgcttta actaagaatt attagtcttt tctgcttatt ttttcatcat agtttagaac    60
actttatatt aacgaatagt ttatgaatct atttaggttt aaaaattgat acagttttat   120
aagttacttt tcaaagact cgtgctgtct attgcataat gcactggaag gggaaaaaaa   180
aggtg                                                              185
```

-continued

```
SEQ ID NO: 229           moltype = AA  length = 555
FEATURE                  Location/Qualifiers
source                   1..555
                         mol_type = protein
                         organism = Pycnoporus sanguineus glucoamylase
SEQUENCE: 229
QSSAVDAYVA SESPIAKQGV LNNIGPNGSK AHGAKAGIVV ASPSTENPDY LYTWTRDSSL    60
VFKLLIDQFT SGDDTSLRGL IDDFTSAEAI LQQVSNPSGT VSTGGLGEPK FNIDETAFTG   120
AWGRPQRDGP ALRATSIIRY ANWLLDNGNT TYVSNTLWPV IQLDLDYVAD NWNQSTFDLW   180
EEVDSSSFFT TAVQHRALRE GATFASRIGQ SSVVSGYTTQ ADNLLCFLQS YWNPSGGYVT   240
ANTGGGRSGK DSNTVLTSIH TFDPAAGCDA ATFQPCSDKA LSNLKVYVDA FRSIYTINNG   300
IASNAAVATG RYPEDSYMGG NPWYLTTSAV AEQLYDALYV WDQLGGLNVT STSLAFFQQF   360
ASGLSTGTYS ASSSTYATLT SAIRSFADGF LAINAKYTPA DGGLAEQYSR NDGTPLSAVD   420
LTWSYAAALT AFAAREGKTY GSWGAAGLTV PASCSGGGGA TVAVTFNVQA TTVFGENIYI   480
TGSVAALQNW SPDNALILSA ANYPTWSITV NLPANTVVQY KYIRKFNGQV TWESDPNNQI   540
TTPSGGSFTQ NDVWR                                                   555

SEQ ID NO: 230           moltype = AA  length = 599
FEATURE                  Location/Qualifiers
source                   1..599
                         mol_type = protein
                         organism = Trichoderma reesei
SEQUENCE: 230
SVDDFISTET PIALNNLLCN VGPDGCRAFG TSAGAVIASP STIDPDYYYM WTRDSALVFK    60
NLIDRFTETY DAGLQRRIEQ YITAQVTLQG LSNPSGSLAD GSGLGEPKFE LTLKPFTGNW   120
GRPQRDGPAL RAIALIGYSK WLINNNYQST VSNVIWPIVR NDLNYVAQYW NQTGFDLWEE   180
VNGSSFFTVA NQHRALVEGA TLAATLGQSG SAYSSVAPQV LCFLQRFWVS SGGYVDSNIN   240
TNEGRTGKDV NSVLTSIHTF DPNLGCDAGT FQPCSDKALS NLKVVVDSFR SIYGVNKGIP   300
AGAAVAIGRY AEDVYYNGNP WYLATFAAAE QLYDAIYVWK KTGSITVTAT SLAFFQELVP   360
GVTAGTYSSS SSTFTNIINA VSTYADGFLS EAAKYVPADG SLAEQFDRNS GTPLSAVHLT   420
WSYASFLTAA ARRAGIVPPS WANSSASTIP STCSGASVVG SYSRPTATSF PPSQTPKPGV   480
PSGTPYTPLP CATPTSVAVT FHELVSTQFG HTVKVAGNAA ALGNWSTSAA VALDAVNYRD   540
NHPLWIGTVN LEAGDVVEYK YIIVGQDGSV TWESDPNHTY TVPAVACVTQ VVKEDTWQS    599

SEQ ID NO: 231           moltype = AA  length = 633
FEATURE                  Location/Qualifiers
source                   1..633
                         mol_type = protein
                         organism = Bacillus amyloliquefaciens
SEQUENCE: 231
GPAAANAETA NKSNKVTASS VKNGTILHAW NWSFNTLTQN MKDIRDAGYA AIQTSPINQV    60
KEGNQGDKSM RNWYWLYQPT SYQIGNRYLG TEQEFKDMCA AAEKYGVKVI VDAVINHTTS   120
DYGAISDEIK RIPNWTHGNT QIKNWSDRWD VTQNSLLGLY DWNTQNTEVQ VYLKRFLERA   180
LNDGADGFRY DAAKHIELPD DGNYGSQFWP NITNTSAEFQ YGEILQDSAS RDTAYANYMN   240
VTASNYGHSI RSALKNRNLS VSNISHYASD VSADKLVTWV ESHDTYANDD EESTWMSDDD   300
IRLGWAVIGS RSGSTPLFFS RPEGGGNGVR FPGKSQIGDR GSALFKDQAI TAVNTFHNVM   360
AGQPEELSNP NGNNQVFMNQ RGSKGVVLAN AGSSSVTINT SAKLPDGRYD NRAGAGSFQV   420
ANGKLTGTIN ARSAAVLYPD DIGNAPHVFL ENYQTGAVHS FNDQLTVTLR ANAKTTKAVY   480
QINNGQTAF KDGDRLTIGK GDPIGTTYNI KLTGTNGEGA ARTQEYTFVK KDPSQTNIIG   540
YQNPDHWGQV NAYIYKHDGG RAIELTGSWP GKAMTKNANG MYTLTLPENT DTANAKVIFN   600
NGSAQVPGQN QPGFDYVQNG LYNNSGLNGY LPH                                633

SEQ ID NO: 232           moltype = DNA  length = 700
FEATURE                  Location/Qualifiers
source                   1..700
                         mol_type = genomic DNA
                         organism = Saccharomyces cerevisiae
SEQUENCE: 232
cacccatgaa ccacacggtt agtccaaaag gggcagttca gattccagat gcgggaatta    60
gcttgctgcc accctcacct cactaacgct gcggtgtgcg gatacttcat gctatttata   120
gacgcgcgtg tcggaatcag cacgcgcaag aaccaaatgg gaaatcgga atgggtccag    180
aactgctttg agtgctggct attggcgtct gatttccgtt ttgggaatcc tttgccgcgc   240
gcccctctca aaactccgca caagtcccag aaagcgggaa agaaataaaa cgccaccaaa   300
aaaaaaaaaa taaagccaa tcctcgaagc gtgggtggta ggccctggat tatcccgtac   360
aagtatttct caggagtaaa aaaccgttt gttttggaat ttcccattc gcggccacct    420
acgccgctat ctttgcaaca actatctgcg ataactcagc aaattttgca tattcgtgtt   480
gcagtattgc gataatggga gtcttacttc aacataacg gcagaaagaa atgtgagaaa   540
attttgcatc ctttgcctcc gttcaagtat ataaagtcgg catgcttgat aatctttctt   600
tccatcctac attgttctaa ttattcttat tctcctttat tctttcctaa cataccaaga   660
aattaatctt ctgtcattcg cttaaacact atatcaataa                         700

SEQ ID NO: 233           moltype = DNA  length = 240
FEATURE                  Location/Qualifiers
source                   1..240
                         mol_type = genomic DNA
                         organism = Saccharomyces cerevisiae
SEQUENCE: 233
tcagtactga caataaaaag attcttgttt tcaagaactt gtcatttgta tagtttttt     60
atattgtagt tgttctattt taatcaaatg ttagcgtgat ttatattttt tttcgcctcg   120
```

```
acatcatctg cccagatgcg aagttaagtg cgcagaaagt aatatcatgc gtcaatcgta    180
tgtgaatgct ggtcgctata ctgctgtcga ttcgatacta acgccgccat ccagtgtcga    240

SEQ ID NO: 234          moltype = AA  length = 18
FEATURE                 Location/Qualifiers
source                  1..18
                        mol_type = protein
                        organism = Saccharomyces cerevisiae
SEQUENCE: 234
MQLLRCFSIF SVIASVLA                                                   18

SEQ ID NO: 235          moltype = AA  length = 274
FEATURE                 Location/Qualifiers
source                  1..274
                        mol_type = protein
                        organism = Thermomyces lanuginosus
SEQUENCE: 235
EVSQDLFNQF NLFAQYSAAA YCGKNNDAPA GTNITCTGNA CPEVEKADAT FLYSFEDSGV     60
GDVTGFLALD NTNKLIVLSF RGSRSIENWI ANLNFWLKKI NDICSGCRGH DGFTSSWRSV    120
ADTLRQKVED AVREHPDYRV VFTGHSLGGA LATVAGADLR GNGYDIDVFS YGAPRVGNRA    180
FAEFLTVQTG GTLYRITHTN DIVPRLPPRE FGYSHSSPEY WIKSGTLVPV TRNDIVKIEG    240
IDATGGNNQP NIPDIPAHLW YFQATDACNA GGFS                                274

SEQ ID NO: 236          moltype = AA  length = 277
FEATURE                 Location/Qualifiers
source                  1..277
                        mol_type = protein
                        organism = Thermomyces lanuginosus
SEQUENCE: 236
APAPVLRRDV SSSVLSELDL FAQYSAAAYC SSNIGSPGTK LTCSVGNCPR VEAADTETLI     60
EFNESSSFGD VTGYIAVDRT NSLLVLAFRG SSTVSNWEAD LDFPLTDASS LCSGCEIHSG    120
FWAAWQTVQA SITSTLESAI ASYPGYTLVF TGHSYGAALA AIAATTLRNA GYTIQLYDYG    180
QPRLGNLALA QYITAQTQGA NYRVTHTDDI VPKLPPELFG YHHFSPEYWI TSGDNVTVTT    240
SDVQVVTGID STAGNDGTLL DSTSAHDWYI VYIDGCD                             277

SEQ ID NO: 237          moltype = AA  length = 594
FEATURE                 Location/Qualifiers
source                  1..594
                        mol_type = protein
                        organism = Penicillium emersonii
SEQUENCE: 237
SAPYDKRDLA QEIWDDIKNA VDCAGCQVVL TALKGVADLG TTALVDVLTE VCNISGKEDS     60
DVCSGIISRE GPVLDYVLQH LDIGSHTSQV ICASAFGLCQ YPEVRPYNLT FPKPKPNTTR    120
PEPSGESPIQ VVHFSDTHVD LSYETGSNYN CTKPICCRPY TAEDAPGNTT TPCGPYGNTK    180
CDAPLSLEES MFAAIKALNP QPAFSIYTGD VVAHDIWLVD QNEVIEDLNA TYDRMAGLGL    240
VYAAIGNHDT APVNDLPTSN IPSEYSANWT YEALSYDFTM LTQSASAQTA ANYGSYSAIY    300
PGSYGTDLRV ISYNSIFYYV DNFWAYQDPM EFDPDGQLAW LINELQEAET AGQRVWIIAH    360
VPTGTSDHFH DYSHYFDQIV QRYEATIAAL FYGHTHIDQF QISYSNYSNR AFDTATAIGY    420
IMPSLTPTSG PPTFRVYDVD PKTFAVLDFT NYIANISDPA FQSGPSWQKY YSAKETYGSL    480
LSPPVTDPTA ELTPAFWHNV TVAFEQDNAT FQEYWARQTR GYDVSSCTGS CITQAICGLR    540
AGDAQYNCVT PTPGFNFAKR DTSNPKQALS HVEKCEGSGL LGLLRRMVAD SKSS          594

SEQ ID NO: 238          moltype = AA  length = 259
FEATURE                 Location/Qualifiers
source                  1..259
                        mol_type = protein
                        organism = Bacillus thuringiensis
SEQUENCE: 238
HENDGGSKIK IIHRWSAEDK HKEGVNSHLW IVNRAIDIMS RNTTLVKQDR VAQLNEWRTE     60
LENGIYAADY ENPYYDNSTF ASHFYDPDNG KTYIPFAKQA KETGAKYFKL AGESYKNKDM    120
KQAFFYLGLS LHYLGDVNQP MHAANFTNLS YPQGFHSKYE NFVDTIKDNY KVTDGNGYWN    180
WKGTNPEDWI HGAAVVAKQD YSGIVNDNTK DWFVKAAVSQ EYADKWRAEV TPMTGKRLMD    240
AQRVTAGYIQ LWFDTYGDR                                                 259

SEQ ID NO: 239          moltype = AA  length = 297
FEATURE                 Location/Qualifiers
source                  1..297
                        mol_type = protein
                        organism = Pseudomonas sp.
SEQUENCE: 239
QESPAFIDPA SWNTPFNGIA QVACHNCYEK QYANTFSSVL DSVRTLELDF WDQRDAVSGG     60
SPHHWFVRHN PGTLFQSGND NNCTGDGTGK NDLEACLNDV KNWSDKHPGH FPITLILDKK    120
QGWSKESSGR TPKDFDELVA RVFQGKLFTP QDLATHIGGS AGALQGNLKG KSWPTANDLQ    180
GKVLLVLNHS ENQKLSQYAE ARTSKAKVFI SPVTNGQNDI SGKVSGMSSQ SSGYVAMNNM    240
GKGDKSWAKQ AFAYSHIGRV WGDDEVSFAQ HINQKINLSA YYRFAAQSAG GYRIRPF       297

SEQ ID NO: 240          moltype = AA  length = 625
FEATURE                 Location/Qualifiers
source                  1..625
```

```
                        mol_type = protein
                        organism = Kionochaeta sp.
SEQUENCE: 240
AVNPADVLSV VEKRVDPASG LEVRSIWDTI WNDIKSAADC TACEAVLTLL KGVAAFGDNF   60
FVEVLTEICD LSGAEDDDVC SGVLSLEGPI IANDIRKMSI GSKTSELFCI TFLGLCSYPA  120
VDAFTVPFPT AKSAATRPVS SGKDPIYVVH YSDIHIDPFY VAGSASNCTK PICCRDYTSA  180
SSPGNNNSPA GPYGDHNCDV PISLEDSMYA AIKKLVPDAA FGIFTGDIVD HAVWNTSESQ  240
NIIDMNDAYT RMKNSGMLPT IFATAGNHEA SPVNSFPPPA IGNESQWVYD TLASDWSQWI  300
GTSGASSVES IGAYSVQYGS TKLRVISLNT NMYYIENFYL YEPTMEQDPA GQFAWLVSEL  360
SAAEEAAGERV WIIGHMPLGL SDAFHDPSNY FDQIVNRYEA TIAAMFFGHT HEDHFQISYS  420
DYNARTAANA RAVSYIMPSL TPTSGHPTFR VYTVDPETFG VLDATTYYAD MSQPTYQTAG  480
PAWSVYYSAK AAYGGLVDPP VAADDAAAEL TPAFWHNVTA ALAADPASFD AYYARKTRGW  540
DVAACAGACA AAEVCALRAA RAQDNCVVPT PGVHFSKRAD EGTLAHHRDE CGVSVARNSL  600
SSLVVQREAL EHLEGRLSEK RRMAV                                       625

SEQ ID NO: 241          moltype = AA  length = 613
FEATURE                 Location/Qualifiers
source                  1..613
                        mol_type = protein
                        organism = Mariannaea pinicola
SEQUENCE: 241
QEVTHDLAGI KRSLESRDWV EDLWDKFESD ATCAGCESLV LVLKGLAAIS DQAFIDVLQE   60
ICKISGAEDD DVCDGSIQLE GPVIASGLRS MAIGSRTSKE FCTTFLGLCA YPAVQQWSVP  120
FSSSKSSKTR PSSSGKDPIK VVHYSDIHID PLYVGGSNSN CTKPICCRSY TKADQPGNNK  180
YPAGPNGDHN CDSPVSLEKS MYNAIKEIVP DAAFTIFTGD IVDHAWWNTS QSYNTEQITN  240
AYGLMSDNLG TIYGTAGNHE AHPANAFQPN SVGNVSQWVY DLLSGLWSQW ISTEAKADSE  300
KLGAYSTKYP GGNLRIISLN TNMYYRENYW LYRKTMIQDP SNQISWLVNE LEAAETAGER  360
VYIIGHMPLG DSNSFHDQSN YLDQVINRYS ATISAMFFGH THDDQFQISY SNWSNRNFSN  420
ALVTSYIGPS LTPTAGMPAF RVYDVDPVTF GILDSTTYIA DMTDSAFQTT GPVWKKYYSA  480
KEVYGSLLSP AVTDSSAELT AAFWHNVTTL FEADNTAFEA FLSRKSRGWK SESCTGTCKA  540
NEICQLRAAR SENNCYTPSL GISFNKRSLN PVEERDECGI SVTRATVSAM GVRKDVLRLL  600
KKRFIEKAGE VRG                                                    613

SEQ ID NO: 242          moltype = AA  length = 259
FEATURE                 Location/Qualifiers
source                  1..259
                        mol_type = protein
                        organism = Fictibacillus macauensis
SEQUENCE: 242
HENEGGNKVR VIQYWSAEDP HHEDTNTHLW IVRHAMEIMA NNKDVVKPGE VEQLKQWQSD   60
LEQGIYDADH ANPYYDNATF ASHFYDPDTG KSYIPLAAHA KTTSVKYFKR AGEAYQKGDH  120
KQAFYNLGLA LHYIGDLNQP MHAANFTNLS YPQGFHSKYE NYVDSFKEDY AVKDGEGYWH  180
WKGTNPEDWL HGTAVAAKKD YPDIVNDTTK AWFVKAAVSN SYAAKWRAAV VPATGKRLTE  240
AQRILAGYMQ LWFDTYVNK                                              259

SEQ ID NO: 243          moltype = DNA  length = 250
FEATURE                 Location/Qualifiers
source                  1..250
                        mol_type = genomic DNA
                        organism = Saccharomyces cerevisiae
SEQUENCE: 243
acagaagacg ggagacacta gcacacaact ttaccaggca aggtatttga cgctagcatg   60
tgtccaattc agtgtcattt atgattttt gtagtaggat ataaatatat acagcgctcc  120
aaatagtgcg gttgcccaa aaacaccacg gaacctcatc tgttctcgta ctttgttgtg  180
acaaagtagc tcactgcctt attatcacat tttcattatg caacgcttcg gaaaatacga  240
tgttgaaaat                                                        250

SEQ ID NO: 244          moltype = DNA  length = 822
FEATURE                 Location/Qualifiers
misc_feature            1..822
                        note = ARTIFICIAL SYNTHETIC DNA
source                  1..822
                        mol_type = other DNA
                        organism = synthetic construct
SEQUENCE: 244
gaggtttctc aggatctttt caatcagttc aatttgtttg ctcagtactc cgcagcagct   60
tactgtggca agaataacga tgccccagcc ggaaccaaca tcacgtgtac aggtaacgct  120
tgtcctgagg ttgaaaaggc agacgctacc ttcttataca gttttgaaga tagtggggtt  180
ggagacgtga ctggattcct ggcactagac aatacgaaca aattgattgt tttgtctttt  240
agaggctctc gttctatcga aaactggatt gcaaacctga acttttggtt gaagaagatt  300
aacgatatct gttctggttg tagaggacac gatggtttta catcttcttg gagatccgtg  360
gccgacacct tgagacaaaa ggttgaagat gccgttcgtg aacatccaga ttacagggtc  420
gtgtttacgg gtcatagttt aggtggtgct ttggccacag ttgctggtgc agaccttaga  480
ggtaatggtt acgatatcga tgtcttttcc tatggagcac caagggttgg taatagagct  540
ttcgctgagt tcttgacagt ccaaactggt gggaccttgt atagaatcac tcacaccaat  600
gatattgtgc ctagactacc cccaagagaa tttgggtatt ctcattcctc tcccgagtat  660
tggattaaga gtgaacatt agtaccgtt accaggaacg acattgtcaa gattgaaggg  720
attgacgcaa ctggtggcaa caatcaaccg aatatcccag atatcccagc acatctttgg  780
tactttcaag ctacagacgc ttgtaacgct ggtggattta gc                    822
```

```
SEQ ID NO: 245           moltype = DNA  length = 831
FEATURE                  Location/Qualifiers
misc_feature             1..831
                         note = ARTIFICIAL SYNTHETIC DNA
source                   1..831
                         mol_type = other DNA
                         organism = synthetic construct
SEQUENCE: 245
gctccagctc cagttcttag gagagatgta tcttcctctg tattgtctga gctggactta    60
ttcgctcagt actctgccgc tgcatattgc tcttccaata tcggttctcc gggtacgaag   120
cttacttgta gtgtcggtaa ttgtccccgt gttgaagctg ccgatacaga gacgttgata   180
gagtttaacg aatcatcttc ttttggtgat gtgactggct atatcgctgt ggataggacc   240
aattcactac tggtgttggc atttaggggc tcttccacag tgtcaaattg ggaagcagat   300
ctagattttc cattaacaga tgcttctagt ctgtgcagtg gctgtgaaat tcactctggt   360
ttttgggctg cctggcaaac cgtacaggca tccatcacta gcacattgga gtcagctatt   420
gcttcttacc ctggttatac tttggtcttc acaggtcatt catacggtgc cgcttttggca  480
gcaatagcag caactacatt gagaaatgct ggttacacaa tccagtttgta cgactatggc   540
cagccgaggt taggtaatct tgctctggcc cagtacatta cggcacaaac acagggtgcc   600
aactatcgtg ttactcatac cgatgacatc gtacccaaac taccccctga gttgtttggc   660
tatcaccact tctccccaga gtattggata acgtcaggcg ataatgttac agttacaact   720
agcgatgtgc aagtagtcac tggaattgac agtacagctg gaaatgatgg gactttgctt   780
gattctacaa gtgcccatga ttggtacatt gtctacattg atgggtgcga t             831

SEQ ID NO: 246           moltype = DNA  length = 1782
FEATURE                  Location/Qualifiers
misc_feature             1..1782
                         note = ARTIFICIAL SYNTHETIC DNA
source                   1..1782
                         mol_type = other DNA
                         organism = synthetic construct
SEQUENCE: 246
tctgctccgt atgacaaaag agacttggct caggagattt gggacgacat taagaatgcc    60
gttgactgcg ctggctgtca agttgttttg acagctttga aaggtgttgc cgatctgggc   120
acaacagctt tagttgatgt cttaactgag gtgtgcaata tctctggtaa gaggattca    180
gatgtctgct ctggtatcat tagtagagag ggtcctgttc tagactacgt gcttcaacat   240
ctagacatcg ggtctcatac atcacaagtc atttgtgctt cagcatttgg tttatgccaa   300
tatcccgaag tgagaccta taacttgact tttcctaagc ccaaaccaaa cacaaccaga   360
cctgaacctt ccggtgaatc tccaattcaa gtagtgcact ctccgatac gcacgttgaa   420
ttaagttacg agactggttc caattacaat tgcactaagc caatttgttg tagaccttac   480
actgccgaag atgcacctgg gaacactact actccatgtg gtccgtacgg taataccaag   540
tgtgatgccc cattatcctt ggaagagtct atgtttgctg ccatcaaagc cttaaaccct   600
caaccagcat tttctatcta cacaggagat gttgtagcac atttggttagtgat         660
caaaacgagg ttatcgaaga tttgaacgca acgtacgata gaatggctgg tctgggttta  720
gtctatgccg ctattggtaa tcatgataca gcaccggtta acgacctgcc gacgtcaaac   780
attccatccg agtattcagc aaattggact tatgaagctt tgtcttacga ctttacaatg   840
ttgactcaaa gcgccagtgc tcaaactgct gcaaactatg gttcctattc agccatttac   900
cctggatctt acgtacagac cctaagagtc atttcataca actctatctt ctattacgtt   960
gacaactttt gggcttatca agatccaatg gaatttgacc cagatggcca gctagcatgg  1020
ttgataaacg agttgcaaga agctgaaact gctggcaaaa gagtctggat catagcacat  1080
gttcctacgg gtacttccga tcacttccat gactattctc actactttga ccaaatagtc  1140
caaagatatg aagccacgat tgctgccttg ttctatggtc ataccacat agaccagttt  1200
cagattagtt actcaaacta ttcaaacaga gcatttgata ccgcaactgc catcggctac  1260
attatgcctt ctttaacacc cactagcggt ccacctacct ttagagtttta cgacgttgat  1320
ccaaagacgt tcgcagtgtt agatttcacc aattacattg ccaacatttc cgatcctgca  1380
tttcaatcag gtccatcatg gcagaaatac tattccgcca aggagaccta cggctcacta  1440
ttgtctccac ctgtaaccga ccctactgct gaattgacgc ctgcattctg gcataatgtc  1500
accgtggcat ttgagcaaga caacgcaaca tttcaagagt attgggctcg tcaaaccagg  1560
ggatacggta tctcatcatg tacaggtagt tgcataaccc aagcaatatg cggattgcgt  1620
gctggcgacg cacaatacaa ttgtgttact cctactcccg gtttcaactt gcgcaaagcgt  1680
gacactagta accccaaaca agccttgtca catgttgaga aatgtgaagg atccggtctt  1740
ctaggcttgt taaggcgtat ggttgcagac tctaaatctt ct                        1782

SEQ ID NO: 247           moltype = DNA  length = 777
FEATURE                  Location/Qualifiers
misc_feature             1..777
                         note = ARTIFICIAL SYNTHETIC DNA
source                   1..777
                         mol_type = other DNA
                         organism = synthetic construct
SEQUENCE: 247
catgagaatg atgggggttc caagattaag atcatacata gatggtctgc cgaagataaa    60
cataaagaag gggttaactc tcacttatgg atagtcaaca gagcaatcga cattatgtca   120
agaaatacaa ctttagtgaa acaagacaga gtcgcccaac taaatgaatg gagaactgag   180
ctagaaaatg gcatttacgc tgcagattat gagaacccgt attacgataa ctccacgttc   240
gcttccccatt tctatgatcc agacaatggt aagacataca tccccttttgc aaagcaggca  300
aaagaaactg tgccaaaata cttcaagtta gctggggaat cctacaaaaa caaagatatg   360
aaacaagcct ttttctatct tggtctgtct ctgcattacc taggtgatgt caaccagcca   420
atgcatgcag ccaatttcac aaactatctc tatcctcaag gattccattc caagtatgag   480
```

```
aactttgttg atacgatcaa ggacaactac aaagtcacag atggaaacgg ttactggaat    540
tggaagggga ccaacccgga agactggatt cacggtgctg ctgttgttgc caaacaagac    600
tattcaggaa tcgtaaatga caataccaaa gactggtttg taaaagcagc agtctctcaa    660
gaatatgcag acaaatggag agccgaggtt acacccatga cgggcaagag gttaatggat    720
gcccaacgtg tcactgctgg ttacatacaa ctatggtttg atacttatgg ggataga      777

SEQ ID NO: 248           moltype = DNA   length = 891
FEATURE                  Location/Qualifiers
misc_feature             1..891
                         note = ARTIFICIAL SYNTHETIC DNA
source                   1..891
                         mol_type = other DNA
                         organism = synthetic construct
SEQUENCE: 248
caggaaagcc cagccttcat tgatccagct agctggaaca ctccgtttaa cggtatagca    60
caagtagcat gccacaattg ttatgagaag caatacgcaa acactttttc ttcagtatta    120
gactctgtta gaacattgga attggacttt tgggaccaaa gggatgctgt tagtggtggt    180
tctccgcatc actggtttgt cagacacaat ccagggactc ttttcaaag tggtaatgac     240
aacaattgca caggtgatgg tactggaaag aatgatttgg aagcctgtct gaatgatgtc    300
aagaattggt ccgataagca tccaggtcat tttcccatta cgcttattct agacaaaaag    360
caggggtggt caaaagaaag ttcagggagg actccaaaag acttcgatga acttgttgca    420
agagttttcc aaggtaaact attcactccc caagacttag caacccacat aggatcaggc    480
gctggcgcac tacagggcaa cttgaaagga aagtcatggc ctactgcaaa tgatttacaa    540
gggaaagtgt tgttagtctt gaatcatagt gaaaatcaga agttatccca gtatgctgag    600
gctagaacat ccaaggctaa agtgttcatt tcaccagtta caaacgggca aaacgacatt    660
tccggtaaag tgtctggtat gtcatcccaa agttccggt atgttgcat gaacaatatg       720
ggtaagggag ataagagttg ggcaaagcaa gcttttgcat actctcacat tgggagagtc    780
tggggtgatg acgaagtgtc atttgcccaa cacatcaatc aaaagatcaa tcttagtgcc    840
tactacagat ttgccgctca gtccgcaggt ggttaccgta tacgtccatt t             891

SEQ ID NO: 249           moltype = DNA   length = 1875
FEATURE                  Location/Qualifiers
misc_feature             1..1875
                         note = ARTIFICIAL SYNTHETIC DNA
source                   1..1875
                         mol_type = other DNA
                         organism = synthetic construct
SEQUENCE: 249
gcagtcaatc cagcagacgt tttgagtgtt gtggagaaaa gagtggatcc agcatccgga    60
cttgaagtac gttccatctg ggatactata tggaatgaca tcaaatctgc tgcagactgc    120
accgcatgtg aggccgtttt gactttactt aagggtgttg ctgctttcgg tgacaatttc    180
tttgttgaag tattgacaga aatctgcgat ttgtcaggag ccgaagatga tgatgtttgt    240
tctggggtgt tatcactaga aggaccaatc attgcaaacg acattaggaa aatgtcaatc    300
ggatccaaga cctccgagtt gttttgtata acttttctgg ggttatgttc ttatcctgca    360
gttgatgctt ttactgttcc atttccgacc gctaagtcag ctgctaccag accggtctcc    420
tcaggaaaag atccgatcta tgtcgtacac tattcagata ttcatattga tcctttctat    480
gtcgcaggga gcgcctcaaa ctgtactaag ccaatttgtt gtagagacta tacttcagct    540
tcttctcctg gcaacaacaa tagcccagca ggtcccctacg tgatcacaa ttgtgacgtt     600
ccaatctcat tagaagattc catgtacgct gccatcaaaa agctagttcc agatgctgca    660
ttcggtatct tcactggcga tatcgtggat cacgctgtat ggaatacttc tgaatcacag    720
aacatcatag acattgaacga tgcctatacc cgtatgcagg atttctggtat gttacctacc   780
atttccgcca ctgcaggaaa tcatgaagcc tcaccagtga atagtttccc tccccctgct    840
atcggtaatg agtcacaatg ggtttatgat acactggcct cagattggtc tcagtggatt    900
ggaaccagtg gtgccagctc tgtcgaatcc ataggtgcct attctgtgca atacggttca    960
accaaattgc gctgtgattc tttgaatacc aatatgtatt acattgagaa cttttaccta    1020
tatgaaccaa ccatggaaca agatccagcc ggacaattcg catggttagt ttcagaattg    1080
agcgcagctg aggctgcagg agaaaagagtt tggatcattg acatatgcc gttgggcctg     1140
tccgacgcct tccacgatcc ttccaactac tttgatcaga tcgtcaatag atatgaagct    1200
accatagccg ctatgtttt cggccacaca catgaggatc acttccagat ttcttactca    1260
gactataacg ccagaactgc cgcaaacgct agggcgtgtt cctacattat gccttccctt    1320
actcctacca gcggacatcc gactttccgt gtctacacgg ttgatccaga aacattcggc    1380
gtactagacg caacaaccta ctacgcagat atgagtcaac caacgtatca aactgctggg    1440
ccagcttggt ccgtctatta cagtgctaaa gcagcatatg ggggtttggt cgatccacca    1500
gttgcagcg atgatgcagc cgcagagttg acaccagcct tttggcataa cgttactgca    1560
gcattagctc ccgatcccgc ttctttcgat gcctactatg ctagaaagac cagaggttgg    1620
gatgttgctg cctgcgcagg cgcttgtgct gctgctgaag tgtgcgcctt gagggctgcc    1680
cgtgcacaag acaattgtgt ggttccaact cctggtgtgc atttcagtaa gcgtgcagat    1740
gaaggcactt tagcccacca cagggatgaa tgcggtgtat ctgtagccag gaattccactt    1800
tcctctttgg ttgtacagag ggaagcatta gaacacttag aaggcaggct ttctgagaaa    1860
agaagaatgg cagtt                                                     1875

SEQ ID NO: 250           moltype = DNA   length = 1839
FEATURE                  Location/Qualifiers
misc_feature             1..1839
                         note = ARTIFICIAL SYNTHETIC DNA
source                   1..1839
                         mol_type = other DNA
                         organism = synthetic construct
SEQUENCE: 250
```

```
caggaagtaa cacatgactt ggctggcatt aagagaagtt tggaatctag ggactgggtg    60
gaggacttat gggacaagtt cgaatcagat gcaacttgtg ctggatgtga agtttagtt   120
ttagtcttga aaggcttagc cgcaatatca gaccaagcct tcatagacgt cttgcaagag   180
atatgcaaga tatctggagc cgaagatgat gatgtttgtg atgggagtat acagttagaa   240
ggcccagtta ttgcaagtgg cttgagatct atggcaattg gctctcgtac ttctaaagaa   300
ttctgtacaa cgttcttggg tttatgcgcc tacccagctg ttcaacaatg gagcgtgcct   360
ttttcctcct ccaaaagttc taaaaccaga ccaagctctt ctggtaagga tcctatcaag   420
gtagtgcact attcagatat tcatatcgac cctctatatg ttggtggatc aaattcaaat   480
tgtactaaac caatcctgctg tcgttcatat actaaggcag accaacctgg caacaacaga   540
tacccagctg gcccaaacgg tgatcacaat tgtgattcac ctgtgtctct agagaagagc   600
atgtataacg ccattaagga aattgtacca gatgctgctt ttaccatctt tactggagat   660
attgtagatc acgctgtatg gaacacctca caatcctata acaccgaaca aatcacaaat   720
gcatatggat tgatgtcaga caacttagga accatctatg gtacagcagg caatcacgag   780
gctcacccag ccaacgcatt ccaaccaaac tcagttgcta atgtaagcca atgggtctac   840
gacttgttaa gtggactatg gtctcaatgg atttctactg aagcaaaggc agacagtgaa   900
aagttaggtg cttatagcac caaataccca ggcggaaacc ttaggattat ctcattgaac   960
acaaacatgt actatagaga aaactactgg ttatacagaa agactatgat tcaggaccct  1020
agcaaccaga tatcttggct agttaacgaa ttggaggcag cagaaactgc aggtgaacgt  1080
gtgtacatca ttggtcatat gcctttaggc gatagcaatt cttttccacga tcaatcaaac  1140
tacttggatc aagtgatcaa cagatactca gcaacaattt cagcaatgtt cttcggtcac  1200
actcacgatg atcaatttca gatttcatat tcaaattggt caaccgtaa cttcagtaac  1260
gccttagtca cttcctacat tggacctagt ttaactccaa ctgctgggat gcctgccttt  1320
agagtttacg acgtggatcc agtgactttc ggcatcttag attccactac ctatatcgcc  1380
gatatgaccg atagtgcttt ccaaacaaca ggtccagtat ggaagaagta ttacagtgcc  1440
aaagaagtgt atgcagcct actaagccca gctgttacag atagtagtgc tgaattgaca  1500
gcagccttct ggcataatgt cactacctta ttcgaagcag acaatacggc ttttgaagca  1560
ttcttaagta ggaaatccag aggctgaaag tctgaatcct gtacaggtac ttgcaaggca  1620
aatgagatct gccagttgag ggctgccaga tctgaaaaca attgttacac cccttctctt  1680
ggcatctcct ttaacaaaag atccttgaat ccagtggagg aaagagatga atgtgggatc  1740
tccgtaacca gagcaactgt ttctgcaatg ggggtcagaa aggatgtcct taggttgttg  1800
aagaaaaggt tcattgaaaa ggctggggaa gtcaggggc                         1839

SEQ ID NO: 251        moltype = DNA  length = 777
FEATURE               Location/Qualifiers
misc_feature          1..777
                      note = ARTIFICIAL SYNTHETIC DNA
source                1..777
                      mol_type = other DNA
                      organism = synthetic construct
SEQUENCE: 251
catgagaatg aaggggtaa caaagttagg gtaatacagt attggtctgc cgaagatcca      60
catcatgaag acacaaacac tcacttatgg atagtccgtc atgcaatgga gattatggcc   120
aacaacagaa atgttgtgaa accaggcgaa gtcgagcaac taaaacaatg gcaatcagac   180
ctagaacaag gcatttacga tgcagatcat gccaacccgt attacgataa cgcaacgttc   240
gcttcccatt tctatgatcc agacactggt aagtcataca tccccttggc agcacacgca   300
aaaacaacca gcgtcaaata cttcaaagaa gctgggaag cataccaaaa gggtgatcat   360
aaacaagcct tttacaatct tggtctggct ctgcattaca taggtgatct aaaccagcca   420
atgcatgcag ccaatttcac aaaacttatct tatcctcaag gattccatta caagtatgag   480
aactatgttg atagcttcaa ggaggattat gctgtcaaag atggagaggg ttactggcat   540
tggaaaggga ccaaccccgga agactggttg acggtacag ctgttgctgc caagaaaagat   600
tatccagaca tcgtaaatga tacaaccaaa gcctggtttg taaaagcagc agtctccaaa   660
tcttatgcag ctaaatggag agctgccgtt gttcccgcaa cgggcaagag gttaacagaa   720
gcccaacgta tcttggctgg ttacatgcaa ctatgcgtttg atacttatgt gaacaaa     777

SEQ ID NO: 252        moltype = AA  length = 585
FEATURE               Location/Qualifiers
source                1..585
                      mol_type = protein
                      organism = Aspergillus wentii
SEQUENCE: 252
NWAESIWDDV KHAVNCAGCE TVLFALKGVA DLGEHAFQTV LTDVCDISGT EDKDVCSGLI    60
AAESPALYYN IKNLGVKSHT SKVLCAQLFG LCQFPAVRPY NLTFPSPKPT TSRPPPSGQS   120
PIRVAHISDT HVDLSYETGS NYECSKPICC RVYTDEDAPG NTSFPCGPYG NTNCDPPLRL   180
EESMMAAIKS LNPAFSIYTG DVVAHDLWMV DKTEVLDDFN ATYSMLDQLD LVYAAVGNHD   240
TTPVNLFPST QLPDKDNQWA YDALTAEWKS LTNSSIQTTE YGSYSAIYEN LRIISYNSIF   300
YYQDNFYAYT DPMAHDPSNQ LTWLIDQLHE AESANQRVWL ISHIPTGVD HLHDYSHYID   360
EIVQRYEATI SALFFGHTHT DLFQIAYSDY KNRAWDTASA IGYVAPSLTP TSGPPAFRIY   420
DIDPVTFAVL DYTVYIANIS NPSYQSNPKW EKYYSAKEAY GSLLSPPVTD SSSELTPSFW   480
HNVTALMEKD DSVFQDWWSR TTRGYNVTTC TGDCAKKEIC ALRGADAQYN CVTATPGFHF   540
DKREESEQKP RPECEDGLGR VLGDMIHKKD FVDLLHERTA QYQHR                   585

SEQ ID NO: 253        moltype = AA  length = 588
FEATURE               Location/Qualifiers
source                1..588
                      mol_type = protein
                      organism = Penicillium cylindrosporum
SEQUENCE: 253
TYDKRDLAQD LWNDIKNAVD CGGCQVILTA LKGLSDLGTT VFVDVLTEVC EIGKLEDSDV    60
CSGTISREGP VLDYILQHLD IGSHTSQVLC ASAFGLCQYP AVRPYNLPFP SPKPNTTRPA   120
```

```
PSGELPIQVV HISDTHVDLS YETGSSYNCT KPICCRPYTA ADAPGNTTTP CGPYGNTNCD   180
APIGLEESMF AAIKALQPAF SIYTGDVVAH DLWLVDQNEV LQDFNATFNR MAELGVVYAA   240
IGNHDTAPVN DLPASNIPSQ YSANWTYDAL AYDFSTLTNS ASAQTAEDYG SYSSVYRGSH   300
GTDLRVISYN SIFYYVDNFW VYQDPMLYDP DGQLAWLISE LQEAETGGQR VWLIAHVPSG   360
ISDHFHDYSH YFDQIVQRYE ATIAALFYGH THRDQFQISY SDYTNRTWNT ATAMGYITPS   420
LTPTSGPPTY RVYKVDPKTF GVLDFTNYIA NISDPAYQSG PTWQKYYSAK ETYGSLLSPP   480
VTDPTAELTP AFWHNVTVLF ENDNATFQQY IARQTRGWDP SSCTGSCIDQ TICGLRAGDA   540
QYNCVTPTPG FNFAKRDAST GGQPETHVEK CEGSGLLALL GRMVATKS               588

SEQ ID NO: 254            moltype = AA  length = 588
FEATURE                   Location/Qualifiers
source                    1..588
                          mol_type = protein
                          organism = Penicillium meridianum
SEQUENCE: 254
SADSWITIIW DDFKEAVDCA SCQALLGGLK YVAGFGESFM EDVLTGVCDI SGAEDSDVCS   60
GIIANEGPAV YYSLKNLELG SHTAKTFCSN LVGLCDYPAV RPYDLSFPSP KPSISRPPPS   120
GKPPLKVVHF SDTHVDLSYE PGSSFDCTKP ICCRVYSEDD APGNTSSPCG PWGNAKCDPP   180
HQLQQSMMDA IASLNPAFSI YTGDVVAHDV WLVNKTEVLQ DFNATYSTME STLGLVYAAL   240
GNHDTAPLNL FPSTNIPSSY NPQWAYDALS TSWLTLTSDN PAISTAKEYG SYSARHKDTK   300
LRIISYNSIF YYKYNFFSYE EPMPFDPDGQ LSWLISELSA AEEAASERVWL ISHIPSGNSD   360
HFRDHSHYFD QIVQRYEATI AGLFFGHTHT DEFQVSYSDY AHRSWDTATA MGYVAPSMTP   420
TSGPPSFRVY EIDPVTFGVL DFTQYIADIS DSSEPKWMPY YSAKKDYGSR LDVPVGEDME   480
LTPAFWHNVT VGMEKDPSLF RDFWARRTRG FEVPGCEGDC VSKEICALRG ADAQYSCVEA   540
TPGFSFEKRG ERTVLLEKRF QPECNHAGMA PLLAKIAHRA SLAREMEA               588

SEQ ID NO: 255            moltype = AA  length = 590
FEATURE                   Location/Qualifiers
source                    1..590
                          mol_type = protein
                          organism = Penicillium bialowiezense
SEQUENCE: 255
EVLLENSIAS LWDDFKNAVD CASCQALLGG LKLVSGFGED FMIDVLTGIC DISKAEDSDV   60
CEGIIKKEGP ALHDAFQALH IGSNSTQTMC ASLIGLCQYP EVRAHSLSFP SPKPNKVKPP   120
PSGKPPIKVV HFSDTHVDLY YETGSSYECS KPICCRVFED KYAPGITKTP CGPFGNPRCD   180
PPLKLQESMN AAIADINPEF SIYTGDVVAH DVWLVNQAEA LESFNSTYSQ MEKSLGMVYA   240
AIGNHDTAPL NLFPSSIVPD GDNQWAYNAL AEYWLTLTSI SSVQSADEYG SYSAIHPDSN   300
LRIISYNSIF YYKFNFYMYQ EPMEKDPNGQ FEWLIKELQA AEDAGQRAWL ISHIPPGVAD   360
HFHDYSHYFD QIVQRYEATI AGLFYGHTHM DEFQIAYSNY KNRNHETATA MGYIAPAMTP   420
TEGPPSFRVY EIDPETFGVL DYTQYIANIS DPTYQEKPQW LPYYSAKADY GSKLSPPVTD   480
PKIELTPAFW HNVTVAMENE PSIFQEFWAR RVRGYKVTDC NGDCMKTEIC ALRAADAQFN   540
CVKPKPGFNF SKRDGKDTLA EQPHHCDHAG LAPLLGKIAY RARIAREMEA             590

SEQ ID NO: 256            moltype = AA  length = 590
FEATURE                   Location/Qualifiers
source                    1..590
                          mol_type = protein
                          organism = Penicillium sclerotiorum
SEQUENCE: 256
SADSWISSIW DDFKEAVDCG SCQALLGGLK VVAAFGESFM EDVLIGVCDI SGAEDSDVCA   60
GVIANEGPAV HYSLTNLEIG SHTAKTFCAT LVGLCKYPEV RPYNLTFPSP KPPTSRPPPS   120
GKTPIKVVHF SDTHVDLSYE TGSNYDCSKP ICCRAYTEDD APGNTSSPCG PWGNTNCDPP   180
HRLQKSMNAA IADLKPAFSI YTGDVVAHDV WLVNKSEALQ DFNATYGAME DSLGRVYAAL   240
GNHDAAPLNL FPSNQIPSEY NPQWAYDALA ADWMALTDIP SVETANEHGS YSAIHPDSNL   300
RIISYNSIFY YKYNFFSYTE PMEYDPNGQL EWLINELHAA ETANQRVWLI SHIPSGNSDH   360
FHDHSHYFDE IIQRYEATIA GLFFGHTHTD EFQISYSNYS NRNWDTATAM GYVAPSMTPT   420
SGPPSFRVYE IDPVTFGVLD FMQYIANISD PSYQQKPEWV PYYSAKSDYG SRLSPPVTDA   480
DVELTPAFWH NVTVLMEEDS SVFDEFWARR TRGFQVPACT GDCVSNEICA LRGADGQYNC   540
FIEKPGFSFE KRDGTVDEVS WKKRFQPECN HAGMAPLLAK IAHRASLARE             590

SEQ ID NO: 257            moltype = AA  length = 592
FEATURE                   Location/Qualifiers
source                    1..592
                          mol_type = protein
                          organism = Rasamsonia byssochlamydoides
SEQUENCE: 257
SYNKRGLAQE IWDDIVNAVD CSGCQVILTA LQGAAELGTS AFVDILTEVC DISGKEDSDV   60
CSGIISREGP VLDYILQNLD IGSHTSDVIC ASAFGLCQYP AVRSYNLTFP TPKPDTTRPA   120
PSGESPIQVV HFSDTHVDLS YETGSSYNCT KPICCRPYTA ADAPGNTTTP CGPYGNTNCD   180
APLSLEESMF NAIKALSPQP AFSIYTGDVV AHDIWLVDQN EVIQDLNTTY DMAELGLVY   240
AAIGNHDTAP VNDLPTTNIP SEYSTNWTYE ALAYDFTMLT SSSSAQTAAN YGSYSSIYKG   300
SYGTDLRIIS YNSIFYYIDN FWAYQDPMPY DPDGQLAWLI NELQEAETAG QRVWIIAHVP   360
TGTSDHFHDY SHYFDQIVQR YEATIAALFY GHTHIDQFQI SYSDYSNQAW DTATAIGYIM   420
PSLTPTSGPP TFRVYVDPVK TFAVLDFTNY IANISDPAYQ SGPTWQKYYS AKETYGALLS   480
PPLTDPTAEL TPAFWHNVTV AFENDNAAFQ EYWARQTRGW DVSSCTGSCI TQAICGLRAA   540
DAQYNCVTPT PGFNFAKRDA SSATQAMAHV EKCEGSGLLA LLGRMVADKK SA           592

SEQ ID NO: 258            moltype = AA  length = 593
FEATURE                   Location/Qualifiers
```

```
                          source          1..593
                                          mol_type = protein
                                          organism = Rasamsonia eburnea
   SEQUENCE: 258
   TYDKRGLAQD IWNDIKNAVD CAGCQGILTA LKGLSYLGTT AFVDVLTEVC DISGVEDSDV    60
   CSGIISSEGP ALVYILKHLD IGSHTSQVIC ASVFGLCQYP AVRAYNLTFP SPKPDKTCPE   120
   PSGESPVQIV HFSDTHADLS YETGSNYNCT KPICCRSYTA EDAPGNTTTP CGPYGNPKCD   180
   APMSLEESMF AAIKALSPQP AFSIYTGDVV AHDIWLVDQN EVVEDLNATY DRMAGLGLVY   240
   AAIGNHDTAP VNNLPTSNIP SQYSANWTYE ALEYHFSLLT KSASAQTAEN YGSYSSVYRG   300
   RYGTDLRVIS YNSIFYYIAD FWAYQDPMLY DPDGQLAWLI NELQEAETAG QRVWLIAHVP   360
   SGTADHFHDY SHYFDQIVQR YEATIAALFY GHTHIDQFQI SYSDYSNRAF DTATAIGYIM   420
   PSMTPTSGPP TFRVYDVDPK TFAVLDFTNY IANISDPAYQ SGPTWQKYYS AKEAYGSLLS   480
   PPVTDATAEL TPAFWHNVTV AFENDDTAFQ EYWARQTRGY AVSSCTGDCI TQAICGLRAG   540
   ESQHNCVTPT PGFNFAKRDV STDGQALPHI EKCEGSGLMA LLAKMVASNR QSS           593

SEQ ID NO: 259            moltype = AA   length = 593
   FEATURE                   Location/Qualifiers
   source                    1..593
                             mol_type = protein
                             organism = Penicillium brefeldianum
   SEQUENCE: 259
   GAIENWAATI WEDFKEAVDC GSCQVLLGGL KLVADFGEGF LGDVLTGVCD ISKAEDRDVC    60
   AGVVASEVPA LHYALKNMKV GSHTAKTLCS ALVGLCDFPD VRPFDLTFPS PKPATSRPPP   120
   SGKPPIKVVH FSDTHVDLSY ETGSNYDCSK PICCRVYTDK DAPGTTDKPC GPWGHPKCDP   180
   PHQLQESMMT AIANLNPAFS IYTGDVVAHD VWLVNKDEVL QDLNATYGAM ENHLGLVYAA   240
   LGNHDAAPLN LFPSNKVPSK YNPQWAYDAL TADWMTLTGL DSVQNANKYG SYSAVHPNSK   300
   LRIISYNSIF YYKYNFFSYT EPMEYDPNGQ LTWIINELQA AETAGQRVWL ISHIPSGDVD   360
   HFRDHSHYFD QIVQRYEATI AGLFFGHTHT DEFQIAYSDY NNRNWDTATA MGYVAPSMTP   420
   TSGPPSFRVY DIDPETFGVM DYTQYIANIS DPSFQTKQEW VPYYTAKKDY GAKLSPPPAP   480
   TGELTPAFWH NVTVAMEKDS SVFEAFWARR TRGFSIPACT GDCVKNEICA LRGADAQYSC   540
   VKRTPGFSFS KRDEIESDPL LSKRFQPECN HAGMAPLLAK IAHKANVAKW NGE           593

SEQ ID NO: 260            moltype = AA   length = 593
   FEATURE                   Location/Qualifiers
   source                    1..593
                             mol_type = protein
                             organism = Penicillium adametzii
   SEQUENCE: 260
   SVDSWITTIW DDFKEAVDCA SCQALLGGLK LVAVFGESFM EDVITGVCSI SGAEDSDVCA    60
   GVIANEGPAV YHSLSNLKIG SHTAKTFCAS LVGLCDYPAV RPYSLTFPSP KPPTTRPPPS   120
   GKSPIKVVHF SDTHVDLSYE TGSNYDCSKP ICCRAYTEND APGNTSSPCG PWGNSKCDPP   180
   HRLQESMNEA IADLNPAFSI YTGDVVAHDV WLVDKSEALQ DFNATFSAME TLGRVYAALG   240
   NHDAAPLNLF PSNQIPSQYN PQWAYDTLAS DWMGLTGIQS VETANEYGSY SAIHPNSNLR   300
   IISYNSIFYY KYNFFSYTEP MEYDPNSQLQ WLINELHEAE LANQRVWLIS HIPSGDPDHF   360
   HDHSHYFDQI VQRYDATIAA LFFGHTHTDQ FQISYSSYQN RTWDKATAMG YVAPSMTPTS   420
   GPPSFRVYEI DPVTFGVLDF TQYIANISDP TQTKPKWVPY YSAKKDYGSH LDPPVTDAHA   480
   ELTPAFWHNV TVSMENDNSV FQDFWARRTR GFQVPDCTGD CSSSEICALR GADAYNCFV    540
   EKPGFSFEKR DVQESDEEMW KKRFQPECNH AGMAPLLAKI AYRASLEREQ KGK           593

SEQ ID NO: 261            moltype = AA   length = 594
   FEATURE                   Location/Qualifiers
   source                    1..594
                             mol_type = protein
                             organism = Rasamsonia brevistipitata
   SEQUENCE: 261
   TSLTHDKRDL AQEIWNDIKN AATCAGCQVI LTALKGVSDL GTSIFVDVLT EVCDISGLED    60
   PDVCSGIISR EGPVLDYILQ HLDIGSHTSD VLCASAFGLC QYPAVRPYNL TFPSPKPDTT   120
   RPAPSGESPI QVVHISDTHV DLSYETGSSW NCTKPICCRP YTAEDAPGNT TTPCGPYGDT   180
   HCDAPMSLQE SMIAAIQALR PQPAFSIYTG DVVAHDIWLV DQNEVIEDFN ATYNRMAELG   240
   LVYAAIGNHD SAPVNDLPAS NIPSQYSVNW TYEALAYDFS MLTGSASAQE AENYGSYSSI   300
   YKGSNGTDLR VISYNSIFYY VTNFWAFQDP MPYDPDGQLA WLINELQEAE TAGQRAWLIA   360
   HVPTGTGDHF HDYSHYFDQI VQRYEATIAA LFFGHTHQDE FQIAYSNYSN QNFDTATAIG   420
   YIMPSLTPTS GPPSFRVYDI DPKTFGVLDF TNYIANISDP AYQSGPTWQK YYSAKEAYGT   480
   LLSPAVTDPT AELTPAFWHN LTVVFENDNA TFQEYWTRKT RGHAVSNCTG SCITQSICGM   540
   RAADAQYNCV TPTPGLSFAK RDAETSTPEP HIEPCEGSGL MSLLGRMVAQ GKSS          594

SEQ ID NO: 262            moltype = AA   length = 594
   FEATURE                   Location/Qualifiers
   source                    1..594
                             mol_type = protein
                             organism = Penicillium scabrosum
   SEQUENCE: 262
   ETTLEKSISS IWEDFKNAVD CGSCQVLLGG LKFVSGFGEN FMIDVLTGLC DISKAEDSDV    60
   CEGIIKKEGP ALHDAFQALK IGSHSTKTMC ANLIGLCQYP EVRPNTLSFP SPKPKDVRPT   120
   TSGKPPIKVV HFSDTHVDLL YETGSNYECT KPICCRVFED KDAPGITKNP CGPFGNPKCD   180
   PPQALQESMN AAIAEINPAF SIYTGDVVSH DVWLVNQEEA LESFNSTYSQ IEKSLGMVYA   240
   AIGNHDTAPL NLFPSKNQPD GNNQWAYDAL AEDWLAITGI PSVQSADEYG SYSAIHPNSN   300
   LRIISYNSIF YYKFNFYMYQ EPIEKDPNGQ FEWLIKELQA AEDAGQRAWL ISHIPSGVAD   360
   HFHDHSQYFD QIVQRYEATI AGMFYGHTHM DEFQIAYSDY KNRNWETATA MGYIAPAMTP   420
```

```
TEGPPSFRVY EIDPDTFGVL DFTQYIANIS DPAYQKKPEW VPYYSAKADY GSKLSPPVTD    480
PKVELSPAFW HNVTVSMERD ESVFQDFWAR RSRGYNVTAC TGDCMKMELC TLRAADAQYN    540
CVKPKPGFNF SKRDGELGGL LEQESHSNCD HAGLATLLGK IAHRARVARK IEEA          594

SEQ ID NO: 263            moltype = AA   length = 594
FEATURE                   Location/Qualifiers
source                    1..594
                          mol_type = protein
                          organism = Penicillium manginii
SEQUENCE: 263
SADDWITTIW DDFKNAVDCF SCQALLGGLK LVSGLGESFM EDVITGVCSI SGAEDNDVCA     60
GVIANEGPAV YYSLKNLKLG SHTAKTFCAT LTGLCEFPKV RPYDISFPSP KPSTTRPPPS    120
GEAPIKVVHF SDTHVDLSYE EGSNYECSKP ICCRAYTEKD APGNTTSPCG PWGNSKCDPP    180
HRLQESMMSA IADINPAFSI YTGDVVAHDV WLVNKTEVLQ DLNATYSSIE NHLGLVYAAL    240
GNHDAAPLNL FPSDKIPSQY NPQWAYDALA EDWLTLTGIP SVQKASEYGS YSAVHPGSKL    300
RIISYNSIFY YKYNFFSYTE PMEFDPNKQL DWLIAQLQEA EDAKQRVWLI SHIPTGNSDH    360
FRDHSHYFDQ IIQRYDATIA ALFFGHTHTD EFQISYSNYK NRNWDTATAM GYVAPSMTPT    420
SGPPSFRVYE IDPVTFGVMD FTQYIANITD PSLQTEPEWK PYYSAKADYG SKLSPAIKDP    480
GIELTPGFWH NVTVAMEKDA TVFQDFWSRR TRGFNVPGCT GDCISNEICA LRGADAQYSC    540
YKQAPGFSFE KRDGSGVPYL SEESFQQPEC NHAGMAPLFA KISHRAKLAR ERGE          594

SEQ ID NO: 264            moltype = AA   length = 594
FEATURE                   Location/Qualifiers
source                    1..594
                          mol_type = protein
                          organism = Penicillium emersonii
SEQUENCE: 264
SAPYDKRDLA QEIWDDIKNA VDCAGCQVVL TALKGVADLG TTALVDVLTE VCNISGKEDS     60
DVCSGIISRE GPVLDYVLQH LDIGSHTSQV ICASAFGLCQ YPEVRPYNLT FPKPKPNTTR    120
PEPSGESPIQ VVHFSDTHVD LSYETGSNYN CTKPICCRPY TAEDAPGNTT TPCGPYGNTK    180
CDAPLSLEES MFAAIKALNP QPAFSIYTGD VVAHDIWLVD QNEVIEDLNA TYDRMAGLGL    240
VYAAIGNHDT APVNDLPTSN IPSEYSANWT YEALSYDFTM LTQSASAQTA ANYGSYSAIY    300
PGSYGTDLRV ISYNSIFYYV DNFWAYQDPM EFDPDGQLAW LINELQEAET AGQRVWIIAH    360
VPTGTSDHFH DYSHYFDQIV QRYEATIAAL FYGHTHIDQF QISYSNYSNR APDTATAIGY    420
IMPSLTPTSG PPTFRVYDVD PKTFAVLDFT NYIANISDPA FQSGPSWQKY YSAKETYGSL    480
LSPPVTDPTA ELTPAFWHNV TVAFEQDNAT FQEYWARQTR GYDVSSCTGS CITQAICGLR    540
AGDAQYNCVT PTPGFNFAKR DTSNPKQALS HVEKCEGSGL LGLLRRMVAD SKSS          594

SEQ ID NO: 265            moltype = AA   length = 595
FEATURE                   Location/Qualifiers
source                    1..595
                          mol_type = protein
                          organism = Rasamsonia argillacea
SEQUENCE: 265
GVTYDKRDLA QDIWNDIKNA VDCAGCQGIL TALKGLSYLG TTAFVDVLTE VCDISGMEDS     60
DVCSGIISSE GPVLDYILKQ LDIGSHTSQV ICASAFGLCQ YPAVRAYNLT FPSPKPDKTR    120
PEPSGESPMQ IVHFSDTHVD LSYETGSNYN CTKPICCRPY TADDAPGNTT TPCGPYGNTK    180
CDAPMTLEES MFAAIKALSP QPAFSIYTGD VVAHDIWLVD QNEVVEDLNA TYDRMAGLGL    240
VYAAIGNHDT APVNDLPTSN IPSQYSANWT YEALEYHFSL LTNSASAQTA ENYGSYSSVY    300
PGKYGTDLRV ISYNSIFYYV DNFWAYQDPM LYDPDGQLAW LINELQEAET AGQRVWLIAH    360
VPSGTADHFH DYSHYFDQIV QRYETTIAAL FYGHTHMDQF QISYSDYSNR APDTATAIGY    420
IMPSMTPTSG PPTFRVYDVD PKTFAVLDFT NYIANISDPA YQSGPTWQKY YSAKEAYGPL    480
LSPPVTDATA ELTPAFWHNV TVAFENDDTA FQEYWARQTR GYAVSNCTGN CVTQAICGLR    540
AGESQYNCVT PTPGFNFAKR DVSSDGQALP HIEKCEGSGL LSLLAKMVAS NGQSS         595

SEQ ID NO: 266            moltype = AA   length = 595
FEATURE                   Location/Qualifiers
source                    1..595
                          mol_type = protein
                          organism = Penicillium parviverrucosum
SEQUENCE: 266
HIESADNWIT TIWDLSKQAV DCAGCQALLG GLKLAADLGE TFMEDVLIGV CNIAGVEDHD     60
VCSGIIQNEG PAVHYSLLNL HIGSHTATTL CASLFGLCQY PAVRPYNLSF PVPKPTKSRP    120
EPSGQSPIRI VHFSDTHVDL SYETGSNYDC SKPICCRPYT EEDAPGNTST PCGPWGNPMC    180
DPPNRLQESM MTAIADLNPA FSIYTGDVPA HDIWSATKAE ALRDFNATYG SMEKRLGMVF    240
AALGNHDAAP LNLFPSNKIP SEYSPQWAYD ALAADWLGLS AMASVHSAIH HGSYSAVHSE    300
DKLRVISYNS IFYYKDNFFM YEEPMEHDPN GQFAWLISEL QSAESTSQRV WLIAHIPSGN    360
ADHFRDFSHY FDEIVQRYDT TIAALYFGHT HTDTFQIAYS NYSNRSWDTA SAMGYVAPSM    420
TPTSGSPSFR VYEVDPVTFG IIDFTQYIAN ISDPSYQINP KWEPYYSAKK AYGSKLSPPA    480
QDPGAEMTPA FWHNVTIAME QDASIFQAFW ARRTRGNKVT SCTGNCMANE ICALRGADAQ    540
YNCATPTVGF RFRKRDMTSD LSLQKEEFRP ECNHAGMGPL LAKIVHQAAL ENERG         595

SEQ ID NO: 267            moltype = AA   length = 595
FEATURE                   Location/Qualifiers
source                    1..595
                          mol_type = protein
                          organism = Penicillium flavescens
SEQUENCE: 267
HSESAESWIS DIWDHFKEAV DCTSCQVLLG SLKLVAAFGD TFMVDVLTGV CAISGAEDHD     60
```

```
VCAGVIAGEG PSVQYSLKNL KIGSHTAKTF CASLVGLCQY PKVREYDLAF PAPKPPNGRP   120
PPSGEPPIKV VHFSDTHVDL AYEPGSNYAC SKPICCRTYK ENDAPGNTSS ACGPWGNPRC   180
DSPHRLQESM NAAIADLNPA FSIYTGDVVA HDVWLDNKFE VLQNFNATYG AMETTLGQVY   240
AALGNHDTAP LNLFPSSKIP SIYNPQWAYD ALTENWLALT GIPSIESADQ YGSYSVLHPD   300
SNLRIISYNS IFYYKYNFFA YTEPMEYDPN SQLKWLINEL QAAEKASERV WLISHIPSGN   360
SDHFHDHSHY FDQIIQRYDA TIAALFFGHT HLDEFQISYS DYKSRTWDTA TAMGYIAPSM   420
TPTSGPPSFR VYDIDPVTFG VLDFTQYIAN INAPDQESLE WVPYHSAKEA YGSKLVSPIT   480
DPSAELSPAF WHNVTLAMEN DSAIFGDFWA RRTRGYQVPS CTGDCISGEI CTLRGADAQY   540
NCFVQKVGFS FEKRDHQGDS TREERILPEC NHAGMAPLLA KIARLAAIAR DMEKR        595

SEQ ID NO: 268              moltype = AA   length = 596
FEATURE                     Location/Qualifiers
source                      1..596
                            mol_type = protein
                            organism = Penicillium hispanicum
SEQUENCE: 268
ESAESWVASI WDDFKVAVDC ASCQALLGGL KLVAEFGESF MEDVLIGVCD VSGVEDSDVC   60
AGVIANEGPA VHYTLKNLEI GSHAANTLCA SLVGLCEYPA VRPYNLSFPS LKPATSRPPP   120
SGKPAIKVVH FSDTHVDLSY ETGSNFDCSK PICCRVYTEE DAPGNTSSPC GPWGNPKCDP   180
PHRLQESMVE AIAVLDPAFS IYTGDVVAHD VWLVNKSEAL QDFNATYGAM ENRFGPVYAA   240
LGNHDTAPLN LFPSNKISRE YNPQWAYDAL AADWAALTGI PSVASAREYG SYSAIHPNSN   300
LRIISYNSIF YYRFNFFAYE EPMEYDPDSQ LAWLITELDA AETAGQRVWL ISHIPSGKPD   360
HFRDHSHYFD QIVQRYDATI AALFFGHTHK DEFQISYSTY TNRAWDTATA MGYIAPSMTP   420
TSGPPSFRVY EIDPVTFGVM DYTQYIAKIS DSSAQIDTTP EWVPYYSAKA DYGAKLAPPV   480
EGAGVELTPA FWHNVTVAME ADSSLFQAFW GRRTRGYNVS SCTGECMATE ICALRGADAQ   540
YSCVGAKPGL SFSKRGGKDV DVLWQRRLQP ECNHAGMAPL LGKIWTRAAL VWRSEA       596

SEQ ID NO: 269              moltype = AA   length = 598
FEATURE                     Location/Qualifiers
source                      1..598
                            mol_type = protein
                            organism = Penicillium simplicissimum
SEQUENCE: 269
GATENWISTI WNDFKEAVDC GSCQVLLGGL KLVADFGEGF MEDVLTGVCD ISGAEDRDVC   60
AGVIASEVPA LHYAIKNMHV GSHTAKTLCS ALVGLCDFPD VRPFDLAFPS PKPANSRPPP   120
SGKPPIKVVH FSDTHVDLSY ETGSNYDCSK PICCRVYTDA DAPGTTDKPC GPFGNTKCDP   180
PHQLQESMMT AIAELNPAFS IYTGDVVAHD VWLVTKEEVL QDLNATYGAM ENHLGLVYAA   240
LGNHDAAPLN LFPSHNVPSK YNPQWAYDAL TADWMALTGI ENVQNANEYG SYSAIHPNSK   300
LRIISYNSIF YYKYNFFSYT EPMEYDPNGQ LTWLTEELQA AENAGQRVWL ISHIPSGDVD   360
HFRDHSHYFD QIIQRYEATI AGLFFGHTHT DEFQVSYSDY KNRNWDTATA MGYVAPSMTP   420
TSGSPSFRVY DIDPVTFGVL DFTQYIANIS DASFQTKPTW IPYYTAKKDY GSKLPTIPDD   480
TAELTPAFWH NVTVAMEKDS AVFDEFWARR TRGYNVPACT GDCAKNEICA LRGADAQYSC   540
VQRTPGFSFS KRDGVDGEME EVAPLLSKRF QPECNHAGMA PLLAKIAHNA NLAKMNGE     598

SEQ ID NO: 270              moltype = AA   length = 599
FEATURE                     Location/Qualifiers
source                      1..599
                            mol_type = protein
                            organism = Penicillium vasconiae
SEQUENCE: 270
GAVESWISTI WNDFKEAVDC GSCQVLLGGL KLVADFGEGF LEDVLTGVCD ISGAEDRDVC   60
AGVIASEVPA LHYALKNMHV GSHTAKTLCS ALVGLCDFPD VRPFGLTFPS PKPAKSRPPP   120
SGKSPIKVVH FSDTHVDLSY ETGSNYDCSK PICCRVYSDE DAPGKTDKPC GPFGNTKCDP   180
PHQLQESMMT AIADLNPAFS IYTGDVVAHD VWLVNKDEVL QDFNSTYGAM ENHLGLVYAA   240
LGNHDAAPLN LFPSKNVPSK YNPQWAYDTL TANWMTLTGI ESVQNANEYG SYSAIHPNSK   300
LRIISYNSIF YYKYNFFSYT EPMEYDPNGQ LTWLISELQS AENAGQRVWL ISHIPSGNVD   360
HFRDHSHYFD QIIQRYEATI AGLFFGHTHT DEFQIAYSDY KNRNWNTATA MGYVAPSMTP   420
TSGPPSFRVY DIDPVTFAVI DFTQYIANIS DPTFQKKPDW VPYYSAKKDY GGKLSPRPAD   480
TAELTPAFWH NVTVAMEKDS SVFNEFWARR TRGYNVPACT GDCVKNEICA LRGADAQYSC   540
VQRTPGFSFS KRDDENVDGD VGNYPLLSKR FQPECNHAGM APLLAKIAHK ASLAKANGE    599

SEQ ID NO: 271              moltype = AA   length = 600
FEATURE                     Location/Qualifiers
source                      1..600
                            mol_type = protein
                            organism = Talaromyces columbinus
SEQUENCE: 271
YDSALVDHNL VSDIWEDIKE AVTCAGCQVI LAALKGVSDL GTTALVDTLT GVCKLSGAAD   60
DNVCEGIISR EGAVLHYVLS ESLGSETSN  ALCASAFGLC LYPDVRNYTL NFPSAKPKNI   120
TRPAPSGKPP IQVAHFSDTH VDLSYEVGSN WNCTKPICCR SFEASDAPGN TTTPCGPFGN   180
TKCDTPLTLE ENMLDSIKKS DPTPAFSIYT GDVVAHDIWL VDKDEVLTDL NATYSLMAEI   240
GTVYAAIGNH DTAPLNDLPT TQVPESYSAN WTYQALATNF TTLTRDSSVI SVAKNYGSYS   300
SVFTGSYGTD LKIISYNSMF YYVDNFYAFL DPMPYDPDGQ LAWLIDELQS AETAGQRVWL   360
IAHVPTGSSD HFHDYSHYFD QIVQRYDATI AALFFGHTHT DQFQIAYSDY ANQNADTATA   420
IGYIMPSLTP TSGPPAYRIY DIDPVTFSVL DYTVYITNIS HPDFQKGPKW EKYYSAKDTY   480
GSLLSPPVTD PSAEMTPAFW HNVTAVFESD DVAFQGYWAR QTRGYDVSDC TDESCKNQTI   540
CALRAADAQY NCVVPSIGFN FAKRDDTDQA HVRAQKEKCD DTGLVSSLGK ILAKSKETTN   600

SEQ ID NO: 272              moltype = AA   length = 600
```

```
FEATURE                 Location/Qualifiers
source                  1..600
                        mol_type = protein
                        organism = Talaromyces variabilis
SEQUENCE: 272
SSSALIDRDL ASEIWDDIKE AATCAGCQVI LAALKGVSDL GTTALIDTLT EVCKISGAED    60
DDVCEGIISR EGPVLHYILS QLSLGSETSD ALCTTAFGLC AYPDVRNYTL TFPSAKPENS   120
TRPSSSGESP IQVVHFSDTH VDLSYETGSN WNCTKPICCR SFDSSDAPGN TKTPCGPYGN   180
TKCDAPISLE KSMVDSIKGL SPAPAFSIYT GDVVAHDIWL VDEDEVLTDL SSTYGLVQDV   240
GTVFAAIGNH DTAPVNDLPT TQVPSTYSAN WTYEALAGNC TTLTGDSSVM SVAENYGSYS   300
SVFTGSHGTD LKVISYNSIF YYADNFYAPL DPMPYDPDGQ LAWLIDELQA SETAGQRVWL   360
IAHVPTGSSD HFHDYSHYLD QIVQRYDATI AALFFGHTHT DQFQIAYSNY SNQNADTATA   420
IGYIAPSLTP TSGPPAYRVY DIDPVTFGVL DFTVYIANIS DPDYQNGPTW AKYYSAKETY   480
GSLLSPPVTD SSAELTPAFW HNVTAVFETD DAAFQGYWAR QTRGYDVSNC TDSSCKNQNI   540
CALRAADAQY NCVVPSIGFN FAKRDETDQA HVKAQKEKCD DAGLVSLLGK IISKSRDVSN   600

SEQ ID NO: 273          moltype = AA  length = 600
FEATURE                 Location/Qualifiers
source                  1..600
                        mol_type = protein
                        organism = Talaromyces rugulosus
SEQUENCE: 273
SSSALVDRDL ASEIWDDIKE AATCTGCQVI LAALKGVSDL GTTVLVDTLT EVCKLSGAED    60
DDVCEGIISR EGPVLQYILS QLSLGSETSD ALCASAFGLC SYPDVRSYTL TFPSTKPENS   120
TRPSSSGQAP IQVVHFSDTH VDLSYETGSN WNCTKPICCR SFDSSDAPGN TSTPCGPYGN   180
TKCDAPLSLE ESMFDSIKSL SPAPAFSIYT GDVVAHDKVL VDKEVLTDL NATYSLMAEV   240
GTVYAAIGNH DTAPLNDLPT SQVPSTYSAN WTYQALATNF TTLSGDSSIM SVAENYGSYS   300
SVFAGSHGTD LKVISYNSIF YYVDNFYAPL DPMPYDPDGQ LAWLIDELQA AESAGQRVWL   360
IAHVPTGSSD HFHDYSHYFD QIVQRYDATI AALFFGHTHT DQFQIAYSDY SNQNSDTATA   420
IGYIMPSLTP TSGPPAYRVY DIDPVTFGVL DFTVYIANIS DPDYQNGPTW AKYYSAKETY   480
GTLLSPAVTD SSAELTPAFW HNVTAVFETD DTSFQGYWAR QTRGYDVSNC TDSSCKNQTI   540
CALRAADAQY NCVVPTIGFN FAKRDETDQA HVKAQKEKCD DTGLVSLLGK IISSSRNVSS   600

SEQ ID NO: 274          moltype = AA  length = 601
FEATURE                 Location/Qualifiers
source                  1..601
                        mol_type = protein
                        organism = Hamigera terricola
SEQUENCE: 274
QMQTSERSWG STIWKDVEEA VDCAGCEVIL GALKLVADLG KGTLETAMID VCDLSGAEDS    60
DVCSGLITAE IDALYYALNN VHVGSHTSKV LCAHLFGLCS YPDVRSYHLI FPSSKPATSR   120
PSPSGQKPIK VAHISDTHVD LSYEPGSNYE CSKPICCRAY TKEDSPGNTP HPCGPYGNTN   180
CDAPYRLEES MFAAIEALDP AFSIYTGDVV AHDIWLVNET EVLDDLDATY SLMKSLGLVY   240
AAVGNHDAAP VNLFPSNRIP STYSPQWAYD ALAEDWLALT NDSSVDSARE YGSYSAVYPG   300
SNLRIISYNS VFYYKDNFWM YEDPMEYDPN GQLAWLINEL QAAESAGERV WLISHIPSGN   360
SDHLYDYSHY FDAIVQRYEA TIAALFFGHT HTDLFQIAYS DYDNRNWDTA TAIGYIAPSM   420
TPTSGSPAFR IYEVDPVTFG ILDYTVYIAN ISHPSYQTQP TWEKYYSAKE AYGSLLTPPV   480
TNPSIELTPA FWHNVTVLME DDESVFKDFW ARTTRGFNVS TCVGSCMTEE ICALRSADAK   540
YNCATAKPGL NFLKRDDVEA QSKPVKPQCE DSGLAAVLVK MMENTDDFAG LLKEKALAHG   600
K                                                                  601

SEQ ID NO: 275          moltype = AA  length = 601
FEATURE                 Location/Qualifiers
source                  1..601
                        mol_type = protein
                        organism = Penicillium piscarium
SEQUENCE: 275
RTEAADSWIS NIWNEFKEAV DCGSCQVLLG GLKLVADFGE GFLEDVLTGV CDVSGAEDRD    60
VCAGVIANEV PALHYALKNM HVGSHTAKTL CSALVGLCDF PNVRPFDLTF PSPKPAKSRP   120
PPSGKPPIKV VHFSDTHVDL SYETGSNYDC SKPICCRVYS DKDAPGKTDK PCGPFGNTKC   180
DPPERLQDSM MAAIADLNPA FSIYTGDVVA HDVWLVNKDE VLQDFNSTYG AMENHLGLVY   240
AALGNHDAAP LNLFPSNNIP SKYNPRWAYE ALTANWITLT GIQSVQNANE YGSYSAIHPN   300
SKLRIISYNS IFYYKYNFFS YTEPMEYDPN GQLTWLIEEL QAAENAGQRV WLISHIPSGN   360
VDHFRDHSHY FDQIIQRYEA TIAGLFFGHT HTDEFQISYS DYKNRNWDTA TAMGYVAPSM   420
TPTSGPPSFR IYDIDPETFA VMDFTQYIAN ISEASFQTKP NWIPYYSAKK DYGGRLTPPT   480
PNTAELTPAF WHNVTVAMEK DSSVFNEFWA RRTRGYSVPA CTGDCVKNEI CALRGADAQY   540
SCVQRTPGFS FSKRDDGEVE VDLENAPLLS KRFQPECNHA GMAPLLAKIA HKASIAKMNG   600
E                                                                  601

SEQ ID NO: 276          moltype = AA  length = 602
FEATURE                 Location/Qualifiers
source                  1..602
                        mol_type = protein
                        organism = Talaromyces bacillisporus
SEQUENCE: 276
GQTPTSSLVA RDLASEIWND IKEAATCAGC KVILAALKGV ADLGTTVLID VLTEVCKISG    60
EEDDDVCEGI ISREGPVLEY ILSQLSLSSE TSDVLCASAF GLCSYPAVRD YTLTFPSPKP   120
ANITRPSPSG KSPIQVVHFS DTHVDLSYET GSNWNCTKPI CCRAYEASDA PGNTTTPCGP   180
YGNTKCDAPL SLEQSMIDSI KALDPAPAFS IYTGDVVAHD IWIVDEDEVL TDLNASYSLM   240
```

```
AETGKVFAAI GNHDSAPVND LPTTQVPSKY NANWTYQALA NNFSTLTGDS AVLSVAEQYG   300
SYSSVFTGSY GTDLKVISYN SIFYYIDNFY AFLDPMPYDP DGQLAWLIEE LQASETAGQR   360
VWLIAHVPTS SSDHFHDYSH YFDQIVQRYE ATIAALFFGH THTDQFQISY SNYSNQNADT   420
ASAIGYIMPS LTPTSGPPAY RVYDIDPVTF GVLDFTVYIS NISDPAFQNG PTWSKYYSAK   480
ETYGSLLSPP VTDSTAELTP AFWHNVTAVF ETDDDAFQGY WARQTRGYDV SNCTDTCKNQ   540
TICGIRGADA QYNCVVPKIG FNFAKRDETD QAHVKTQKEK CDDAGLASLF GRMVANSKNA   600
SN                                                                 602

SEQ ID NO: 277          moltype = AA   length = 604
FEATURE                 Location/Qualifiers
source                  1..604
                        mol_type = protein
                        organism = Galactomyces candidus
SEQUENCE: 277
APPTTKRSLA SDIWDDIVDA VDCGACDTIL EALKGLADLG NTVFVDVLTD VCDISGAEDS    60
DVCSGTISEE GPILRTIIKG LSVGSATSDL FCGTLLGLCQ NPAIASWSVP FPKPKPNTVR   120
PPPSGQSPIS VAHISDVHVD LSYTTGANYD CSKPICCRPY TSDDAPGNTD YPAGPYGNTN   180
CDAPLDLESS AMAAIKKLNP AFSIFTGDVA AHDVWLVNQA EVELDLNTTY NTQFTTLGTV   240
FPALGNHDVA PVNGFAPSGV SSNPNIQWAY DTNAEDWTKW IGSTAANAEE SFGAYSIVHG   300
NLRVISFNSI FYYRLNFYMY QDPLQRDPSS QFSWLVNQLQ AAEDAGQRAW LISHVPSGSG   360
DYFPQYSNYF NQIVNRYEAT IAALFYGHTH VDQFEISYSD YSNQNSNTAV AMSYITPSLT   420
PTSGSPSFRI YSIDPVTYGV LDYTNYIANI SSPTYQNGPQ WVEYYSAKAA YGPYVSPPLT   480
SAAAELTPAF WHNVTAFQN NNDLFQEYIS RKSRGFDVSS CTGSCQTDEI CQLRAAESQY   540
NCVTISPGIN FNKRDQQSNL GAQEKHRDGC EGSPIRDIFA TLMQDRRGLV SAINEGIAKR   600
SIRA                                                               604

SEQ ID NO: 278          moltype = AA   length = 607
FEATURE                 Location/Qualifiers
source                  1..607
                        mol_type = protein
                        organism = Penicillium megasporum
SEQUENCE: 278
NIIESWASEI WDDIKNAVDC AGCETIIGAL KVVADLGKGT LNGTLIDVCD LSGVEDPDVC    60
TGLISSEIDA LYYSLKNMAV DSHTSKVLCA GLFSLCPFPA ARPYNLSFPT PKPATSRPAP   120
SGQQPIKVAH ISDTHVDLDY EAGSNYQCSK PICCRPYTAE DAPGNTSHPC GPWGNTKCDP   180
PPRLEESMVA AVNALNPSFS IYTGDVVAHD IWLVNESEVL TDLNATYSLF QNLNSLVYAA   240
VGNHDVAPVN LFPSNKIDSA YNPQWAYDAL TADWLALTNG DSSVASAKAD GSYSAIYPGT   300
NLRIISYNSI FYYKDNFWMY SDPMEYDPNG QFAWLIDELQ AAETAGQRVW LISHIPSGNS   360
DHLYDYSHYF DQIVQRYEAT IAALFFGHTH TDLFQVAYSD YGNRNSDTAS AIGYVTPSMT   420
PTSGPPAFRI YEIDPVTFGV LDYTVYIANI SDPAYQTGPS WQKYYSAKEV YGSLLSPPLT   480
DPAAELTPAF WHNVTVLMEE DDSVFQDWWA RTTRGFNVST CTGSCATNEI CALRGADAQY   540
NCVTASPGIQ FAKRGGAVDF DPNAQPVAKP HCDEGSGLAP VLVKMMRNTD DFAGLLKERA   600
ALQDSQQ                                                            607

SEQ ID NO: 279          moltype = AA   length = 610
FEATURE                 Location/Qualifiers
source                  1..610
                        mol_type = protein
                        organism = Penicillium jensenii
SEQUENCE: 279
ETSKASTESF ISSIWDDFKQ AVDCGSCQAL LGGLKLVSGF GEGFMIDVFI GLCNLSGVED    60
PDVCRGIIEK EGPALHDAFQ NLHIGSHATR TMCASLIGLC QYPEVRPHTL QFPSSKPDTT   120
RPPPSGKSPI KVVHFSDTHV DLFYETGASY ECSKPICCRV YEDKDAPGIT KTPCGPFGNT   180
KCDPPHILQE SMNAAIAKID PDFSIYTGDV VAHDIWLVGQ DEALQVFNDT YGQMEKDLGM   240
VYAAIGNHDT APVNLFPPND IKGKDSAQFA YNALAEDWVA LTGIPSVKSA DEFGSYSAIH   300
PNSNLRIISY NSIFYYNFNF YMYQDPMEKD PNGQFEWLIK ELQAAEDAGQ RAWLISHIPS   360
GVTDHFRDYS QYFDQIVQRY EATIAGLFYG HTHMDEFQIA YSDYNNRKWD TATAMGYIAP   420
SMTPTSGPPS FRVYEIDPVT YGVLDFTQYI ANISDPSYQT KPEWVPYYSA KAAYGSKLSP   480
PLTDSTAELT PAFWHNVTVT MEKDPSIFQD FWARRNRGWN IAACTGDCMK KELCTLRAAD   540
AQHNCHEPTP GLNISINKRD QGSGDVPLEG EKVSGPECDH AGMATLLGKI AYRARLVREA   600
EERDPVRAEA                                                         610

SEQ ID NO: 280          moltype = AA   length = 610
FEATURE                 Location/Qualifiers
source                  1..610
                        mol_type = protein
                        organism = Aspergillus stramenius
SEQUENCE: 280
ENWVNTIWDE IKETISCAGC EGLLGTLKLV AGLGPDVLTN VLTDVCKLAK VEDPDVCAGI    60
IEAEGPAAYY VLKQLKVGSH TSKSFCSQMV GLCDYPEVRP YNISFPIPKP STHRPPPSGQ   120
PPIRVAHISD THVDRAYETG ANYECSKPIC CRVYTEDDAP GKTSFPCGPY GHPKCDPPLR   180
LEESMMAAIA AMDPAFSIYT GDVVPHDVWS VNRTEVLHDL NATYSLLDRL GLVYAALGNH   240
DTAPVNLFPS ERIPVSHNPQ WAYDALAEDW TNLVDGPLSA PVVHATDQFG SYSALHPGGK   300
LRIISYNSVF YYTYNFYAYQ EPMEYDPNGQ LAWLVAELQA AETAGQRVWL IAHIPTGAAD   360
TLRDYSHYLD QIIQRYDATI AALFFGHTHT DLFQVSYANP AHPSADSASA VGYITPSLTP   420
TSGPPAFRIY DIDPVTFAVL DYTVYTANIS TGATPKWNKY YSAKQTYGSL LTPPLTDPTA   480
ELTPAFWHNV TALMETDDNTV FQAWWARTTR GFNVPECNAQ CARDQICSLR AADAQYGCVR   540
GTLSITKRAG DGDGLDLGGA GAGGPPGRRR HVQSARPQCE EAGLARVLAA VIRETDDLQG   600
LLLQRAQLYI                                                         610
```

```
SEQ ID NO: 281          moltype = AA  length = 258
FEATURE                 Location/Qualifiers
source                  1..258
                        mol_type = protein
                        organism = Bacillus pseudomycoides
SEQUENCE: 281
HTNDCGNEAP ILRWSAEDRH KEGVNSHLWI VNRAIDIMSR NNTIVKPNET ALLNEWRNEL    60
ENGIYSADYE NPYYDNSTFA SHFYDPDTQK TYIPLAKQAK ETGSKYFKLA GEAYQNKDMK   120
QAFFYLGLSL HYLGDVNQPM HAANFTNLSY PMGFHSKYEN FVDTIKDNYK VADGNGYWNW   180
KGTNPEEWIH GAAAAAKQDY PGIVNDSTKS GFVKAATSQE YANKWRAEVT PATGKRLTEA   240
QRVTAGYIHL WFDTYVNR                                                 258

SEQ ID NO: 282          moltype = AA  length = 259
FEATURE                 Location/Qualifiers
source                  1..259
                        mol_type = protein
                        organism = Bacillus mycoides
SEQUENCE: 282
QENDGGNRVN IIQYWSAEDK HTEGVNSHLW IVNRAIDIMS RNMTLVKQDQ VALLNEWRTD    60
LENGIYSADY ENPYYDNSTF ASHFYDPDDG STYIPFAKQA KETGAKYFKL AGESYKNKDM   120
KQAFFYLGLS LHYLGDVNQP MHAANFTNIS YPQGFHSKYE NFVDTIKDNY KVTDGNGYWN   180
WKGANPEDWI HGAAVAAKQD FPGIVNSNTK SWFVKAAVSQ SYADKWRAEV TPMTGKRLIE   240
AQRVTAGYIQ LWFDTYVNR                                                259

SEQ ID NO: 283          moltype = AA  length = 259
FEATURE                 Location/Qualifiers
source                  1..259
                        mol_type = protein
                        organism = Bacillus thuringiensis
SEQUENCE: 283
HEKTEGHNVN IIQYWSAEDK HSEGVNSHLW IVNRAIDIMS RNTTRVKQDQ VVLLNEWRTD    60
VENGIYSADH ENPYYDNSTF ASHFYDPDDG STYIPFAKQA KETGAKYFKL AGESYKNKDM   120
KQAFFYLGVS LHYLGDVNQP MHAANFTNLS YPQGFHSKYE NFVDTIKDNY KVMDGNGYWN   180
WKGIHPEDWI HGAAVAAKQD FSGIVNRNTK SWFVQAAVSQ SYADKWRAEV TPMTGKRLIE   240
AQRVTAGYIQ LWFDTYGNR                                                259

SEQ ID NO: 284          moltype = AA  length = 262
FEATURE                 Location/Qualifiers
source                  1..262
                        mol_type = protein
                        organism = Listeria innocua
SEQUENCE: 284
CCDEYLQAPA APHDIDSKLP HKLSWSADNP TNTDVNTHYW LFKQAEKILA KDVNHIRANL    60
MNELKNFDKQ IAQGIYDADH KNPYYDTSTF LSHFYNPDRD NTYLPGFANA KITGAKYFNQ   120
SVADYREGKF DTAFYKLGLA IHYYTDISQP MHANNFTAIS YPPGYHCAYE NYVDTIKHNY   180
QATEDMVVKR FCSDDVKVWL YENAKRAKAD YPKIVNAKTK KSYLVGNSKW KKDTVEPTGA   240
RLRDSQQTLA GFLEFWSKKT NE                                            262

SEQ ID NO: 285          moltype = AA  length = 275
FEATURE                 Location/Qualifiers
source                  1..275
                        mol_type = protein
                        organism = Aspergillus egyptiacus
SEQUENCE: 285
APAPLTRRDV SSEVLEQLTL FAEYSAASYC PSNLDPGTK LTCSTGNCPT VEAADTETLA     60
EFYHADEYGD VAGYLAVDTT NQLLVVAFRG SRALDTWIAN LNFGKDSVDD LCSGCEVHGG   120
FWQSWQVVAD SVASGVESAL QTYPDYTIVF TGHSFGGAVA TLGAVELRNA GYDIELYPYG   180
APRVGNEALA QYITDQGSNY RVTHTNDIVP RLPPMSFGFS HSSPEYWITS DDEVTPTTAD   240
VEVIEGVGST EGNAGEFPQS TAAHSHYIID ISACE                              275

SEQ ID NO: 286          moltype = AA  length = 276
FEATURE                 Location/Qualifiers
source                  1..276
                        mol_type = protein
                        organism = Aspergillus tamarii
SEQUENCE: 286
TPAPLRRDVS SSLLNNLDLF AQYSAAAYCS ENLNSTGTKL TCSVGNCPLV ELASTNTLDE    60
FDESSSYGNP AGYLAADETN KLLVLSFRGS SDLANWVANL NFGLEDASDL CSGCEVHSGF   120
WKAWSEIADT ITSKVESALS DHSDYSLVLT GHSYGAALAA LAATALRNAG HSVQLYNYGQ   180
PRLGNEALAT YITDQNKGAN YRVTHTNDIV PKLPPTLLGY HHFSPEYYIS SADEATVTTA   240
DVTEVTGIDA TGGNDGTDGT SIDAHRWYFI YISQCS                             276

SEQ ID NO: 287          moltype = AA  length = 277
FEATURE                 Location/Qualifiers
source                  1..277
                        mol_type = protein
                        organism = Aspergillus niger
SEQUENCE: 287
```

```
APAPMQRRDI SSTVLDNIDL FAQYSAAAYC SSNIESTGTT LTCDVGNCPL VEAAGATTID    60
EFDDTSSYGD PTGFIAVDPT NELIVLSFRG SSDLSNWIAD LDFGLTSVSS ICDGCEMHKG   120
FYEAWEVIAD TITSKVEAAV SSYPDYTLVF TGHSYGAALA AVAATVLRNA GYTLDLYNFG   180
QPRIGNLALA DYITGQNMGS NYRVTHTDDI VPKLPPELLG YHHFSPEYWI TSGNDVTVTT   240
SDVTEVVGVD STAGNDGTLL DSTTAHRWYT IYISECS                           277

SEQ ID NO: 288         moltype = AA   length = 349
FEATURE                Location/Qualifiers
source                 1..349
                       mol_type = protein
                       organism = Bacillus luciferensis
SEQUENCE: 288
ITSFFGNYQK AFAWSDEDVH NQDHSTHHFI VNGSVKLIAD NANPAINKPT TLLNQFRDRW    60
EQGLYDADHI NPFYDTGTFM SHFYDPDTQT NYTGASYPTA RQSGAKYFNL ASDYYKKGDF   120
NNAFYYLGVS LHYFTDVTQP LHASNISNLD HHAPGYHSKF ETYAESIQNE MTVPDSGLYN   180
WIGSTDPEAW IHQAAVQAKS VLPQVWNDTI INWFWQAAYS NYYSAMWKNE VKNPTLVQLN   240
QAERETAGFI DMFFRVNGVE MPVTVYKENA FGGVSELLGS GNYDYDQLVK GIGNDTISSI   300
HIAPGYQVTL FSDANYKGAS IVLTNDVHDL GNFSHQVSSI KIAKISALK              349

SEQ ID NO: 289         moltype = AA   length = 258
FEATURE                Location/Qualifiers
source                 1..258
                       mol_type = protein
                       organism = Bacillus mycoides
SEQUENCE: 289
QTNNSENPTP VLRWSAEDKH NEGVSTHLWI VNRAIDIMSR NTAIVKPNET ALLNEWRTDL    60
ENGIYSADYE NPYYDNGTYA SHFYDPDTGG TYIPFAKQAK ETGTKYFKLA GEAYQNQDMK   120
QAFFYLGLSL HYLGDVNQPM HAANFTNLSY PMGFHSKYEN FVDTVKDNYI VSDSNGYWNW   180
KGTNPEDWIQ GSAVAAKQDY PGIVNDTTKD WFVKAAVSQE YADKWRAEVT PVTGKRLMEA   240
QRVTAGYIHL WFDTYVNR                                                258

SEQ ID NO: 290         moltype = AA   length = 259
FEATURE                Location/Qualifiers
source                 1..259
                       mol_type = protein
                       organism = Bacillus mycoides
SEQUENCE: 290
HENEGGNKVR VIQYWSAEDK HAEGVNSHLW IVNRAIDIMS RNTTVVKQDQ VALLNEWRTE    60
LENGIYAADY ENPYYDNSTF ASHFYDPDTG KTYIPFAKQA KETGAKYFKL AGEAYQKQEI   120
KQAFFYLGLS LHYLGDVNQP MHAANFTNLS YPQGFHSKYE NFVDTIKNNY KVADGNGYWN   180
WKGVNPEDWI HGAAVAAKQD YAGIVNGTTK DWFVRAAVSQ EYADKWRAEV TLTTGKRLVE   240
AQRVTAGYIQ LWFDTYVNR                                               259

SEQ ID NO: 291         moltype = AA   length = 259
FEATURE                Location/Qualifiers
source                 1..259
                       mol_type = protein
                       organism = Bacillus sp.
SEQUENCE: 291
HENDGGHGVG VIPRWSAEDR HKEGVNSHLW IVNRGIDIMS HNTTVVKQDE VALLNEWRTD    60
LENGIYSADY ENPYYDNSTF ASHFYDPDNG TTYIPFAKQA KETGAKYFKL AGESYQNKDM   120
KQAFFYLGLS LHYLGDVNQP MHAANFTNLS YPQGFHSKYE NFVDTIKDNY KVNDGNGYWN   180
WKGTNPEDWI HASAVAAKQD FPSIVNDNTK DWFVKAAVSQ DYANKWRAEV TPMTGKRLME   240
AQRVTAGYIQ LWFDTYVNR                                               259

SEQ ID NO: 292         moltype = AA   length = 263
FEATURE                Location/Qualifiers
source                 1..263
                       mol_type = protein
                       organism = Bacillus drentensis
SEQUENCE: 292
ARVNHDSSYD SGIIISPYWS AEEMHTEGKN THLWIVNRAI DIMARDNTVV KENEVALLNE    60
WRTDLEDGIY TADYENPYYD NGTFASHFYD PDTDDTYIPF AKNAKVTGVK YFKLAGEAYQ   120
QQAMNQAFFY LGLSLHYFGD INQPMHASNF TNISHPFGFH SKYENFVDTI KAPYSVTDGN   180
GYWNFAGETP EEWLHTAAVA AKQDAPGIVN ETTISWFLQA AFSQEYADMW RAEVTPETGA   240
RLIEAQRAMA GYIHLWFDTY VNL                                          263

SEQ ID NO: 293         moltype = AA   length = 275
FEATURE                Location/Qualifiers
source                 1..275
                       mol_type = protein
                       organism = Aspergillus turcosus
SEQUENCE: 293
APAGLAERDV SASVLQELSL FAQYSAAAYC TNNINSTGTK LTCSAGNCPL VEAANTKTLA    60
EFYDSDSFGD TAGFLVADTT NKLLVVSFRG SRTLDNWIAN LDFVLDSISD ICSGCAAHGG   120
FWKSWEVVAN SLTTELNSAV NTYPGYTIVP TGHSLGAALA TLGATTLRKA GIPVQLYNYG   180
SPRVGNKALA TYITAQGPNY RVTHTNDIVP RLPPQSFGFS HLSPEYWITS GDNVPVTTSD   240
ITVIQGIDSN AGNSGEDITS IEAHNWYIGN IDACP                             275
```

```
SEQ ID NO: 294              moltype = AA  length = 276
FEATURE                     Location/Qualifiers
source                      1..276
                            mol_type = protein
                            organism = Talaromyces subinflatus
SEQUENCE: 294
VLSPIGRRTV TTTQLDDMNL FAQYSAAAYC SANLNSTGSA LACNVGNCPL VEGADTTILY    60
DFDESAGFGD ATGYIAVDET HKSIILAFRG SSDLDNWIAD LDIPLVASSI CLGCEVHQGF   120
WDTWQTVASD VTSQVEYALS AYAGYTFVVT GHSMGAALAA IAATVFRDSG YTVELYNYGQ   180
PRIGNLILAY YITNQNHGSN YRVTHTDDIV PKLPPELLGY DHFSPEYWIT SGDNVTVTDS   240
DIDVIVGIDS ADGNDGTIDD SVEAHHWYFV YISECS                            276

SEQ ID NO: 295              moltype = AA  length = 277
FEATURE                     Location/Qualifiers
source                      1..277
                            mol_type = protein
                            organism = Aspergillus tubingensis
SEQUENCE: 295
APAPMQRRDI SSTVLDNIDL FAQYSAAAYC SSNIESTGTT LTCDVGNCPL VEAAGATTID    60
EFDDSSSYGD PTGFIAVDPT NELIVLALRG SSDISNWIAD LDFGLTSVSD ICDGCEMHKG   120
FYEAWEVIAD TITSKVEAAV SSYPDYSIVF TGHSYGAALA AIAATVLRNA GYTLDLYNFG   180
QPRIGNLALA DYITDQNMGS NYRVTHTDDI VPKLPPKLLG YHHFSPEYWI TSGNDVTVTT   240
SDVTEVVGVD STDGNDGTLL DSTTAHRWYT IYISECS                           277

SEQ ID NO: 296              moltype = AA  length = 350
FEATURE                     Location/Qualifiers
source                      1..350
                            mol_type = protein
                            organism = Bacillus acidiceler
SEQUENCE: 296
ITSLFSNDQK AFAWSDEDVH NQDHSTHHFI VNGSVKLIAD NTNPAINKPT TLLNQFRDRW    60
EQGLYDADHI NPFYDTGTFM SHFYDPDTQT NYTGVSYPTA RQSGGKYFNL ASDYYKKGDF   120
YNAFYYLGVS LHYFTDVTQP LHASNISNLD HNAPGYHSKF ENYAESIQNQ MAIPDSGLYN   180
WISSTDPEAW IHQAAVQAKS VLPQVWNDTI INFFWQAAYS NYYSSMWKNE VKNPTLVQLN   240
QAERETAGFI DMFFRVNGVE MPVKVYKENA FGGASEILGL GNYDYDQFVK GIGNDTISSI   300
HIAPGYQVTL FSDANYKGTS TVLTGDVNDL GNFNHQVSSL KIVKISAISK              350

SEQ ID NO: 297              moltype = AA  length = 259
FEATURE                     Location/Qualifiers
source                      1..259
                            mol_type = protein
                            organism = Lysinibacillus xylanilyticus
SEQUENCE: 297
HENCYQDPPI PLKWSAESIH NEGVSSHLWI VNRAIDIMSQ NTTIVKQHET DLLNEWRTDL    60
EEGIYSADYQ NPYYDNSTFA SHFYDPDSGK TYIPFAKQAK QTGAKYFKLA GEAYQNKDLK   120
NAFFYLGLSL HYLGDVNQPM HAANFTNISH PFGFHSKYEN FVDTVKDNYR VTDGNGYWNW   180
KSANPEEWVH ASAVAAKADF LLIVNDNTES GFLKAAVSQD SADKWRAEVT PVTGKRLMEA   240
QRITAGYIHL WFDTYVNNK                                                259

SEQ ID NO: 298              moltype = AA  length = 259
FEATURE                     Location/Qualifiers
source                      1..259
                            mol_type = protein
                            organism = Bacillus toyonensis
SEQUENCE: 298
HENEDVNYNA PILRWSAEDK HKEGVNSHLW IVNRSIDMMS RNTTIVKKNQ VALLNEWRTE    60
LENGIYNADH ENPYFDNFTF ASHFYDPETG STYIPLVSTQ AKEAGSYKFK LAGESYKKND   120
MKQAFFYLGL SLHYLGDVNQ PMHAANFTNL SYPQGFHSKY ENFVDTIKDN YKVNDGNGYW   180
NWKGSNPGDW IHGAAVAAKK DYTGIVNDTT KDWFVKAAIS SEYADKWRAE VTPATGKRLM   240
EAQRITAGYI QLWFDTYAN                                                259

SEQ ID NO: 299              moltype = AA  length = 259
FEATURE                     Location/Qualifiers
source                      1..259
                            mol_type = protein
                            organism = Bacillus wiedmannii
SEQUENCE: 299
HENDGGSKIK IVHRWSAEDK HKEGVNSHLW IVNRAIDIMS RNTTLVKQDR VTQLNEWRTE    60
LENGIYAADY ENPYYDNSTF ASHFYDPDNG KTYIPLAKQA KETGAKYFKL AGESYKNKDM   120
KQAFFYLGLS LHYLGDVNQP MHAANFTNLS YPQGFHSKYE NFVDTIKDNY KVTDGNGYWN   180
WKGTNPEEWI HGAAVVAKQD YSGIVNDNTK DWFVKAAVSQ EYADKWRAEV TPMTGKRLMD   240
AQRVTAGYIQ LWFDTYGDR                                                259

SEQ ID NO: 300              moltype = AA  length = 268
FEATURE                     Location/Qualifiers
source                      1..268
                            mol_type = protein
                            organism = Listeria seeligeri
SEQUENCE: 300
```

```
CGDESIKDQI APHAIQNKLP SKLGWSAEHP SKDEINTHLW LFNQAEKILA KDVTGAQLDL    60
VRELKNYNKE IAQGIFDADH KNPYYDKNTF LSHFYNPKTH KTYIPGFPNA KDTGTKYFNI   120
SVEEYQDGNF EKAFYNLGLA IHYYTDVSQP MHANNFTALS HPVGYHCAYE NYVDTFKQIF   180
QASAESEAKW FCTDDISEWY HENAKRAQAD YPKIVNAIIK KSYIQGLSDS QKDRTWKKAV   240
RAATGKRLRD SQETLAGFLE FWYAKTNE                                     268

SEQ ID NO: 301            moltype = AA  length = 275
FEATURE                   Location/Qualifiers
source                    1..275
                          mol_type = protein
                          organism = Penicillium swiecickii
SEQUENCE: 301
APSRPVPRDV STSVLSQLSL FAEYSAASYC SNNINSTGNA LSCEAGNCPS VQSADTTTLW    60
EFDRTCSYGN VAGFLAVDKT NKLLVVSFRG SRSISNWIAN INFGLTDAPS LCSGCEAHSG   120
FLESWETVAD DLTTNIKSAQ STYSGYTLVL TGHSFGGAVA ALGGTALRNG GSTLNVYTYG   180
QPRVGNGALA SYITNQGSLW RVTHTDDIVP KLPPSSFGFS HPSPEYWITS ENEVTVTSSD   240
VEVIEGVGSK SGNAGTLNPD VEAHNWYLGY IDGCQ                             275

SEQ ID NO: 302            moltype = AA  length = 276
FEATURE                   Location/Qualifiers
source                    1..276
                          mol_type = protein
                          organism = Talaromyces boninensis
SEQUENCE: 302
VPTPVTRRTV STALLDTLDL FAQYSAAAYC PANFNSSSTS LACSAGNCPT VQAADTTILY    60
SFDKSASFGD ATGYVAVDNT NQLIVIAFRG SSDLSNWIAN LDVPFTDAGN ICSGCEVHSG   120
FYDTWQTVAS DITATVDSAL STYPGYTVVA TGHSLGGALA AIGATVLRSS GQVVQLYDYG   180
QPRIGNLALA DFITSETAGS NYRVTHSDDI VPKLPPEFLG YAHFSPEYWI TSGDNVAVTD   240
ADIVEVIGVD STAGNDGTFG DSINAHLWYF EAISAC                             276

SEQ ID NO: 303            moltype = AA  length = 277
FEATURE                   Location/Qualifiers
source                    1..277
                          mol_type = protein
                          organism = Hamigera striata
SEQUENCE: 303
APAPILRRDV SASVLNELDL FAQYSAAAYC SSNIGSTGNK LMCNVGNCPR VEASDTVTID    60
EFNESASYGD VAGYIAVDNT NQLLVLSFRG SSSLSNWIAN IDVDLTDASS LCSGCEVHSG   120
FWSAWQTVQG TITSKLESAR ASYPGYTLVF TGHSYGAALA GLAATTLRDA GWTIQLYNYG   180
QPRLGNLALA QYITSQTQGS NYRVTHTDDI VPKLPPEFLG YDHYSPEYWI TSGDNVTVTT   240
SDVQVIEGID SVAGNDGTSD DSTEAHQWYF IYISECS                            277

SEQ ID NO: 304            moltype = AA  length = 351
FEATURE                   Location/Qualifiers
source                    1..351
                          mol_type = protein
                          organism = Bacillus sp.
SEQUENCE: 304
ITSLFGSFQK AFAWSCDDPH NQDQSTHLFI VNNGVKLISG NADPAINKPS TLLEQFRDRW    60
EQGLYDADHI NPFYDTSTFM SHFYDPDTQT NYAGRSYPTA RQSGAKYFNL ASDYYKNGDF   120
YNAFYYLGVS LHYFTDATMP LHASNISNLD HQAPGYHSKL ESYSESIQDQ VTVPDSGLFN   180
WVSSTDPELW IHQAAVQAKS VLPQVWNDSI ISWFWQAAYS NYYSDMWKSA VKAPILNQLN   240
QAERETAGFI DMFFRLNGVE MPVTVYSETA FGGASELLGS GNYDYDQLVK GIGNDAISSI   300
HIAPGYQVTL FADSNYSGAS KVLTADASDL DNFNKTISSL KIEKIQPVNV H            351

SEQ ID NO: 305            moltype = AA  length = 259
FEATURE                   Location/Qualifiers
source                    1..259
                          mol_type = protein
                          organism = Bacillus thuringiensis
SEQUENCE: 305
HENAGGQRVG VIPRWSAEDK HKEGVNSHLW IVNRAIDIMS RNTTIVKQDQ VALLNEWRTD    60
LENGIYSADF ENPYYDNSTF ASHFYDPDSE KTYIPLAKQA KETGAKYFKL AGESYQNNDM   120
KQAFFYLGLS LHYLGDVNQP MHAANFTNLS YPQGFHSKYE NFVDTIKDNY KVTDGTGYWN   180
WKGTNPEDWI HGAAVVAKQD YSGIVNNNTK EWFVKAAVSQ EYADKWRAEV TPMTGKRLID   240
AQRITAGYIQ LWFDTYVNR                                                259

SEQ ID NO: 306            moltype = AA  length = 259
FEATURE                   Location/Qualifiers
source                    1..259
                          mol_type = protein
                          organism = Bacillus mycoides
SEQUENCE: 306
HENCHQDPPI ALKWSAESIH NEGVSSHLWI VNKAIDIMSQ NTTVVKQNET ALLNEWRTDL    60
EKGIYSADYQ NPYYDNSTFA SHFYDPDSGK TYIPFAKQAK QTGAKYFKLA GEAYQNKDMK   120
NAFFYLGLSL HYLGDVNQPM HAANFTNISH PFGFHSKYEN FVDTVKDNYR VTDGNGYWNW   180
QSTNPEDWVH ASASAAKADF PSIVNDNTKN WFLKAAVSQD SADKWRAEVT PVTGKRLIEA   240
QRITAGYIHL WFDTYVNNK                                                259
```

```
SEQ ID NO: 307            moltype = AA  length = 259
FEATURE                   Location/Qualifiers
source                    1..259
                          mol_type = protein
                          organism = Fictibacillus macauensis
SEQUENCE: 307
HENEGGNKVR VIQYWSAEDP HHEDTNTHLW IVRHAMEIMA NNKDVVKPGE VEQLKQWQSD   60
LEQGIYDADH ANPYYDNATF ASHFYDPDTG KSYIPLAAHA KTTSVKYFKR AGEAYQKGDH  120
KQAFYNLGLA LHYIGDLNQP MHAANFTNLS YPQGFHSKYE NYVDSFKEDY AVKDGEGYWH  180
WKGTNPEDWL HGTAVAAKKD YPDIVNDTTK AWFVKAAVSN SYAAKWRAAV VPATGKRLTE  240
AQRILAGYMQ LWFDTYVNK                                               259

SEQ ID NO: 308            moltype = AA  length = 268
FEATURE                   Location/Qualifiers
source                    1..268
                          mol_type = protein
                          organism = Listeria seeligeri
SEQUENCE: 308
CGDESVKDQI APHDIQNKLP SKLGWSAEHP SKNEINTHLW LFNQAEKILA KDVTGAQLDL   60
VRELKNYNKE IAQGIFDADH KNPYYDKNTF LSHFYNPKTH KTYIAGFPNA KDTGTKYFNI  120
SIEEYQDGNF EKAFYNLGLA IHYYTDISQP MHANNFTALS HPVGYHCAYE NYVDTFKQIF  180
QASAESEAKW FCTDDVSEWF HENAKRAQAD YPKIVNTIIK KSYIQGLSDS QKDRTWKKAV  240
RAATGKRLRD SQETLAGLLE FWYTKTNE                                     268

SEQ ID NO: 309            moltype = AA  length = 275
FEATURE                   Location/Qualifiers
source                    1..275
                          mol_type = protein
                          organism = Penicillium donkii
SEQUENCE: 309
APARPVPRDI SSSLLDELTL FAEYAAASYC SNNIDSTGDA VTCSGDYCPL VQSAGAKTLY   60
EFNDSTEWGD VAGFLAVDTT NKLIVLSFRG SRSISTWIAN LDFGLTDTSS LCDDCEAHSG  120
FWKSWETVAD DMTAQIESAQ SSYPSYTLVL TGHSFGAAVA ALGATALRNA GYTLDLYTYG  180
QPRVGNEALA TYMTSQGSLW RVTHEDDIVP KLPPMSWGFS HASPEYWVTS DSDVTVTTSD  240
VEEVVGVDST AGNAGTSGES ISAHNWYFVE IDGCD                             275

SEQ ID NO: 310            moltype = AA  length = 276
FEATURE                   Location/Qualifiers
source                    1..276
                          mol_type = protein
                          organism = Hamigera paravellanea
SEQUENCE: 310
APAAVRRDVS AGVLANLDLF AQYSAAAYCD SNLNSDGTKL TCQAGNCPLV EAADTETLDE   60
FDMTATYGNV AGYIAVDRTN RLLVLAFRGS ASISNWIANL NLGLTDASAL CAGCRVHSGF  120
WEAWQTAEAT MSDIIASAAQ TYPGYTLVAT GHSYGAALAA IAATKFRNEG YAVELYDYGQ  180
PRIGNLALAQ YITNQSSGGN FRVTHTNDIV PKLPPDWLGY SHFGPEYWIT SGDGIPVTTA  240
DVEVISGVDA TGGNDGAEGT SVDAHRWYFV YISQCE                            276

SEQ ID NO: 311            moltype = AA  length = 277
FEATURE                   Location/Qualifiers
source                    1..277
                          mol_type = protein
                          organism = Talaromyces lecycettanus
SEQUENCE: 311
APAPVLRRDV SSSVLSELDL FAQYSAAAYC SSNIGSPGTK LTCSVGNCPR VEAADTETLI   60
EFNESSSFGD VTGYIAVDRT NSLLVLAFRG SSTVSNWEAD LDFPLTDASS LCSGCEIHSG  120
FWAAWQTVQA SITSTLESAI ASYPGYTLVF TGHSYGAALA AIAATTLRNA GYTIQLYDYG  180
QPRLGNLALA QYITAQTQGA NYRVTHTDDI VPKLPPELFG YHHFSPEYWI TSGDNVTVTT  240
SDVQVVTGID STAGNDGTLL DSTSAHDWYI VYIDGCD                           277

SEQ ID NO: 312            moltype = AA  length = 449
FEATURE                   Location/Qualifiers
source                    1..449
                          mol_type = protein
                          organism = Paenibacillus sp.
SEQUENCE: 312
ITSIFGNSQD AYAWSADDPH SQDFSTHLFI VNGGVKLISG NVDSAINKSS TLLEQFRGRW   60
EQGLYDADHL NPFYDSSTFM SHFYDPDTQT NYAGLSYPTA RQSGSKYFKV ASNYYKNGDF  120
SNAFYYLGVS LHYFTDSTMP LHASDISNLD HRAPGYHAKL EEYATSIQNQ INVPDSGLFN  180
WISSTDPELW IHQAAVQAKS VMPEVFNDTI TDWFWKAAFS YYYSDMWKSA VKIPILNQLN  240
QAERETAGYI DLFFRLNGVD MPVAVYKGTA FGGALQLLGF GNYDYDQLVK GIGNDTVSSI  300
RIAPGYQVTL FADSNYSGVS KVLTADASDL GNFNKTTSSL KIEKIQPVTV YTDASFSGSS  360
QSFSVGNHDY NEIVNRKLND TISSIRIAPG YQVTLFRDSN YSGVSTVVTG DVYGLSNLND  420
QTSSLKVEVI PTNPAPSQTK QSIFSNPLN                                    449

SEQ ID NO: 313            moltype = AA  length = 259
FEATURE                   Location/Qualifiers
source                    1..259
                          mol_type = protein
```

```
                         organism = Bacillus toyonensis
SEQUENCE: 313
HENDGGQRVG VIPRWSAEDK HKEGVNSHLW IVNRAMDIMS RNTTLVKQDR VALLNEWRTE      60
LENGIYAADY ENLYYDNSTF ASHFYDPDNG KTYIPYAKQA KETGAKYFKL AGESYKNKDM     120
KQAFFYLGLS LHYLGDVNQP MHAANFTNLS YLQGFHSKYE NFVDTIKDNY KVTDGNGYWN     180
WKGTNPEDWI HGAAVVAKQD YAGIVNDNTK DWFVRAAVSQ EYADKWRVEV TPMTGKRLMD     240
AQRVTAGYIQ LWFDTYGNR                                                  259

SEQ ID NO: 314           moltype = AA  length = 259
FEATURE                  Location/Qualifiers
source                   1..259
                         mol_type = protein
                         organism = Bacillus thuringiensis
SEQUENCE: 314
DEHTTNNKID IFQPWSNEEN HKEGKNSHLW IVNGAIDIMS RNTTIVKQEN LALLQQWRTH      60
LENGLYVADY ENPYYDSGTF ASHFYNPDTD STYLPFAKHA KETGATYFTL AGEAYQHKNI     120
QQAFFYLGVS LHYLGDINQP MHAANFTNLS YPFGFHSKYE HFVDTIKQNY EIMDGEGYWN     180
WKGRDPEDWI HQAAVAANQD FSDIVNSDTK NWFVKAAVSQ TYADRWRAAV TPITGKRLIE     240
AQRITAGYIQ LWFDTYIHQ                                                  259

SEQ ID NO: 315           moltype = AA  length = 259
FEATURE                  Location/Qualifiers
source                   1..259
                         mol_type = protein
                         organism = Bacillus thuringiensis
SEQUENCE: 315
HENDGGSKIK IIHRWSAEDK HKEGVNSHLW IVNRAIDIMS RNTTLVKQDR VAQLNEWRTE      60
LENGIYAADY ENPYYDNSTF ASHFYDPDNG KTYIPFAKQA KETGAKYFKL AGESYKNKDM     120
KQAFFYLGLS LHYLGDVNQP MHAANFTNLS YPQGFHSKYE NFVDTIKDNY KVTDGNGYWN     180
WKGTNPEDWI HGAAVVAKQD YSGIVNDNTK DWFVKAAVSQ EYADKWRAEV TPMTGKRLMD     240
AQRVTAGYIQ LWFDTYGDR                                                  259

SEQ ID NO: 316           moltype = AA  length = 269
FEATURE                  Location/Qualifiers
source                   1..269
                         mol_type = protein
                         organism = Talaromyces rugulosus
SEQUENCE: 316
DVTTAVLDDL TLFSQYSAAA YCSTNLNSTG VAVTCSVGNC PLVEAADTQI LYDFDESCKF      60
GDASGFIAVD NTNNLIVLSF RGSHDLSNWI ANLDFFLVET ASICEGCYMH GGFWETWQTV     120
AANVTEQLEA AITANPGYTL VMTGHSLGAA LAAIVATEFR NEGIDVEMYN YGQPRLGNLA     180
LAQYMTNQTQ TSNYRVTHSD DIVPKLPPRV LDFDHYSPEY WITSANNVSV SDADVVQVVG     240
IDSTDGNDGT ILDDIEAHRW YLGYISECS                                       269

SEQ ID NO: 317           moltype = AA  length = 275
FEATURE                  Location/Qualifiers
source                   1..275
                         mol_type = protein
                         organism = Penicillium sp.
SEQUENCE: 317
APARPVPRDV SSATLSELTL FAEYAAAAYC SNNIDSTGDA LSCSGGYCPE VQSAGATTLY      60
EFEDSTDFGD VTGFFAVDNT NKLLVLSFRG SSSISNWIAN LDFGLTDASS LCSGCEAHSG     120
FYKSWGVVAD TLTAQVASAV STYPSYTLVV TGHSLGGALA ALGGTALRNA GYTLDIYTYG     180
QPRVGNTALA DYMTNQGSLW RVTHSNDIVP KLPPASWGFT HASPEYWITS GNDVTVTTSD     240
VTEVTGVGSS DGNAGSSGDS VSAHNWYIVD IDGCS                                275

SEQ ID NO: 318           moltype = AA  length = 276
FEATURE                  Location/Qualifiers
source                   1..276
                         mol_type = protein
                         organism = Hamigera avellanea
SEQUENCE: 318
APAPVRRDVS AGVLANLDLF AQYSAAAYCD SNLNSDGTKL TCAAGNCPLV EAADTETLDE      60
FDMTATYGNV AGYIAVDRTN RLLVLAFRGS ASISNWIANL NLGLTDASAL CAGCEVHSGF     120
WEAWQTAEAT ISDIIASAAQ TYPGYTLVVT GHSYGAALAA IAATRFRNEG YAVELYDYGQ     180
PRIGNLALAQ YITNQSGGGN FRVTHTNDIV PKLPPDWLGY SHFGPEYWIT SGDGVPVTTA     240
DVEVISGVDA TGGNDGAEGT SVDAHRWYFV YISQCE                               276

SEQ ID NO: 319           moltype = AA  length = 278
FEATURE                  Location/Qualifiers
source                   1..278
                         mol_type = protein
                         organism = Penicillium spikei
SEQUENCE: 319
APTRLLIPRD ISSDVLAELT LFAEYSAAAY CSANIDSASA GSALTCESGN CPEVQSADTS      60
TLYEFPDETTD YGDVAGFFAV DKTNELLVLS FRGSRTISNW VANLDFDLTD ASSLCSDCEA    120
HSGFWKSWET VADELTTQIE SAQNSYPDYQ LVLTGHSLGA ALAALAGTAL RNAGYTLDLY    180
TFGQPRVGNL ALADYMTDQG SLWRVTHTDD IVPRVPPESF GYAHASPEYW ITSGNDVTVT    240
TSDVEEIVGV NSSAGNAGEA DLSIDAHNWY IVYIDECE                             278
```

```
SEQ ID NO: 320            moltype = AA  length = 480
FEATURE                   Location/Qualifiers
source                    1..480
                          mol_type = protein
                          organism = Paenibacillus alginolyticus
SEQUENCE: 320
ITSVFGNYQN AYAWSADDVH NQDYSTHLFI VNGGVKLISG NADSAINKSS TLLEQFRDRW   60
EQGLYDADHL NPFYDSSTFM SHFYDPDTQT NYAGLSYPTA RQSGSKYFKV ASDYYKNGDF  120
SNAFYYLGIS LHYFTDSTMP LHASDISNLD HRAPGYHAKL EEYTTSIQNQ ITVPDSGLFN  180
WISSTDPELW IHQAAVQAKS VMPQVFNDSI TDWFWKAAVS YYYSDMWKNT VKTQILNQLN  240
QAERETAGYI DLFFRLNGVD MPVTVYNGTA FGGASQLLGF GNYDYNQLVK GIGNDTISSI  300
RIAPGYQVTL FADSNYSGVS TVVTGNVYGL SNLNDQTSSL KVGVIPTNPA PSPTIQAESF  360
SGSQGILTHS AGSGTVVGNI NSGSWLSYDN VDFGTGKTKF VASVGMDPAF AAIGKQLELR  420
LDSPTGTLIG TFTISSSGGW DAYTTQNCYV TSASGTHKLY IITKGNGSGF GNIDWFTFSS  480

SEQ ID NO: 321            moltype = AA  length = 259
FEATURE                   Location/Qualifiers
source                    1..259
                          mol_type = protein
                          organism = Bacillus mycoides
SEQUENCE: 321
HENDGGSRIN IVHRWSAEDK HKEGVNSHLW IVNRAMDIMS RNTTLVKQDQ VALLNEWRTE   60
LENGIYAADY ENPYDNSTF ASHFYDPDNG KTYIPFAKQA KETGAKYFKL AGESYKNKDM  120
KQAFFYLGLS LHYLGDVNQP MHAANFTNLS YPQGFHSKYE NFVDTIKDNY KVTDGNGYWN  180
WKGTNPEDWI HGAAVAAKQD YSGIVNDNTK DWFVKAAVSQ EYADKWRAEV TPMTGTRLMD  240
AQRVTAGYIQ LWFDTYGNR                                              259

SEQ ID NO: 322            moltype = AA  length = 259
FEATURE                   Location/Qualifiers
source                    1..259
                          mol_type = protein
                          organism = Bacillus bingmayongensis
SEQUENCE: 322
HENEGGNKIR VIQYWSAEDK HAEGVNSHLW IVNRAIDIMS RNTTIVKQDE VALLNEWRTE   60
LENGIYAADY ENPYDNSTF ASHFYDPDSG KTYIPFAKQA KETGAKYFKL AGESYQKQEM  120
KQAFFYLGLS LHYLGDVNQP MHVANFTNLS YPQGFHSKYE NFVDTIKDNY KAIDGNGYWN  180
WKGTNPEDWI HGAAVAAKQE YAGIVNDTTK DWFVWAAVSQ EYADKWRAEV TPATGKRLVE  240
AQRVTAGYIQ LWFDTYGNR                                              259

SEQ ID NO: 323            moltype = AA  length = 260
FEATURE                   Location/Qualifiers
source                    1..260
                          mol_type = protein
                          organism = Bacillus mycoides
SEQUENCE: 323
HENSHQNGIS FGHKWSAEAI HDEGVSTHLW IVNRSIEVMA QNKTVVQPNE ISLLNEWRAD   60
LEKGIYSADY DNPYFDNGTF ASHFYDPDTG GTYLPLAKHA KETGAKYFKL AGEAYQNNDL  120
KNAFFYLGLS LHYLGDVNQP MHAANFTNVS LPVALHSKYE NFVDTIKDNY KVKDGNGYWN  180
WKSVNPEDWV HASAVGAKAD FPLIVNDKTK KWFLDAAISQ DAADKWRAEV TPVTGKRLME  240
AQRITAGYIH LWFDTYVNYK                                              260

SEQ ID NO: 324            moltype = AA  length = 269
FEATURE                   Location/Qualifiers
source                    1..269
                          mol_type = protein
                          organism = Brevibacillus sp.
SEQUENCE: 324
KKEYKVKYHG KTITSPYKID PRWSEESPHE EGHATHLWIV NRAIDILSRT SNKDVNSKET   60
EMLNAWRSSW EQGLYDADHT NPYYNFGTFA SHFYDPDTKS NWLDTSGTAL TEGSRYFALA  120
GKYYQNGDKE KAFYYLGLSL HYLTDVTQPM HAANFTWLNW PTSFHGKFED YTDDIQGNYA  180
VTDGEGYWDF QDSNPEHWIH QAAVDAKAEF PNIHTSDITK WFLAAAVSDY YSDKWHKAVQ  240
PTIEHRLTEA QRITAGYLHL WFKTYVDNQ                                   269

SEQ ID NO: 325            moltype = AA  length = 275
FEATURE                   Location/Qualifiers
source                    1..275
                          mol_type = protein
                          organism = Penicilliumvasconiae
SEQUENCE: 325
APARPVPRDV SSATLSELTL FSQYAAAAYC TNNVNSAGDA VSCSGGYCPE VQSAGATTLY   60
EFDDSTDFGD VAGFFAVDAT NKLLVLSFRG SRTISNWIAN LDFGQTDASS LCSGCEAHSG  120
FFKAWEAVAD TLTAQIASAV ATYPSYTVL TGHSFGGAVA ALGGTALRNA GYTLDLYTYG  180
QPRVGNTALA DYMTNQGSLW RVTHSDDIVP KLPPTSWGFT HASPEYWITS GDDVTVTTSD  240
VTEVTGVGSS GGNAGTSGDS VSAHNWYIVD IDGCQ                            275

SEQ ID NO: 326            moltype = AA  length = 277
FEATURE                   Location/Qualifiers
source                    1..277
```

```
                             mol_type = protein
                             organism = Talaromyces diversus
SEQUENCE: 326
AIDPLNRRTI SESLLDELDL FAQYSAAAYC SANLDSTGSA LACDVGNCPL VEAASTTILY       60
DFDETNDFGD ATGYIAVDTT NEYIILSFRG TDDLENWIAN LDFPLIDASD ICSGCEIHEG       120
WWDSWETVAS DITAQIESAV STYPDYTLVA TGHSLGAALA AIAATVLRLD GYTVQLYNYG       180
EPRIGNLALA DYITTETMGS NYRVTHTDDI VPKLPPELLG YDHFSPEYWI TSGDDVTVLD       240
TDVTEVVGVD STAGNDGTLL DSIDAHRWYF VYISECS                                277

SEQ ID NO: 327           moltype = AA  length = 280
FEATURE                  Location/Qualifiers
source                   1..280
                         mol_type = protein
                         organism = Aspergillus wentii
SEQUENCE: 327
APSPVRRDVD SSVLNNLDLF AQYSAASYCL ENLNSSNTKL ECSVGNCPLV EAASTVTLDE       60
FDESSSFGDV TGFIAADETN KLLVLSFRGS SDIANWIADL DFGLTDGSDL CSGCKVHSGF       120
WEAWGTVSDN ITSIIESATA KYPNYELAFT GHSYGAALAA VAAVVFRNSG YTVQLYNYGQ       180
PRIGNLALAD YITNVTDKGD NYRVTHTDDI VPKLPPKLLG YHHASPEYWI TSGNNVTVTT       240
ADVDVVTGVD STDGNDGTTA DSRTAHRWYF GYISECSTLY                              280

SEQ ID NO: 328           moltype = AA  length = 480
FEATURE                  Location/Qualifiers
source                   1..480
                         mol_type = protein
                         organism = Bacillus acidiceler
SEQUENCE: 328
ITSLFGNYQR AFAWSDEDVH NQDHSTHHFI VNGGVKLIAD NTDPAINKPT TLLNQFRDRW       60
EQGLYDADHI NPFYDTGTFM SHFYDPDTQT NYSGLSYPTA RQSGGKYFNL ASDYYKKGDF       120
NNAFYYLGVS LHYFTDVTQP LHASNISNLD HNAPGYHSKY ETYAESIQSQ IIVPDSGLYN       180
WTDSTDPEAW IHKAAIQAKS VLPLVWNDTI INWFWQAAYS NYYSAMWKNE VKNPTLAQLN       240
QAERETAGFI DMFFRLNGVE MPVTVYNENA FGGASELLGS GNYDYDQLIK CIGNDTISSI       300
HIAPGYQVTL FADANYKGAS IVLTGDVNDL GNFNHQVSSL KIEKISTNPA SSPTIQAESF       360
ISSKGILTHN VGSGTVVGNI NSGSWIGYDN VDFGTGKTKF IARVGMDPSY AIFDKQLELR       420
LDSPTGTIIG TFTINNTGGW DTYATQTSIL SGATGTHKLY IVSKGSGDGF GNIDWITFSP       480

SEQ ID NO: 329           moltype = AA  length = 259
FEATURE                  Location/Qualifiers
source                   1..259
                         mol_type = protein
                         organism = Bacillus luti
SEQUENCE: 329
HEKNEGNVPI ITQYWSAEDT HSEGVNSHLW IVNRAIDIMS RNTTLVRQDE VALLNAWRTD       60
LEKGIYAADY ENPYDNSTF TSHFYDPDTG KTYVGLAKQA KETGNKYFKL AGESYKNKDM       120
KQAFFYLGLS LHYLGDVNQP MHAANFTNLS YPQGFHSKYE NFVDTIKDNY KVTDGNGYWN       180
WKGMNPEEWI HGAAVAAKQD YSGIVNSNTK SWFVKAAVSQ SYADKWRAEV TPTTGKRLME       240
AQRVTAGYIQ LWFDTYGNR                                                    259

SEQ ID NO: 330           moltype = AA  length = 259
FEATURE                  Location/Qualifiers
source                   1..259
                         mol_type = protein
                         organism = Bacillus pseudomycoides
SEQUENCE: 330
HTNDCGNEAP VLKWSAEDKH NEGRNSHLWI VNRAIDIMSR DKTVVKPNET ALLNEWRDDL       60
ENGIYSADYE NPYFDNGTFA SHFYDPDTQK SYIPFAKHAK ETGAKYFKLA GEAYQNKDMK       120
QAFFYLGLSL HYLGDVNQPM HAANFTNIST EAPIFHSKYE NFVDTIKDNY KVADGNGYWN       180
WKGTNSEDWI HGAAVASKQD YSSIVNDTTT SWFLKAATSQ EYANKWRAEV TPTSGKRLIE       240
AQRVTAGYIH LWFDTYVNR                                                    259

SEQ ID NO: 331           moltype = AA  length = 260
FEATURE                  Location/Qualifiers
source                   1..260
                         mol_type = protein
                         organism = Bacillus mycoides
SEQUENCE: 331
HENDGQFDPP IAQRWSAESI HNEGVSSHLW IVNRAIDIMS QNTTVVKQNE TALLNEWRTN       60
LEEGIYSADY KNPYYDHSTF ASHFYDPDSG KTYIPFAKQA KQTGAKYFKL AGEAYQNKDM       120
KNAFFYLGLS LHYLGDVNQP MHAANFTNIS HPFGFHSKYE NFVDTVKDNY RVTDGDGYWN       180
WKSANPEEWV HASASAAKAD FPSIVNDNTK NWFLKATVSQ DSADKWRAEV TPVTGKRLME       240
AQRITAGYIH LWFDTYVNNK                                                   260

SEQ ID NO: 332           moltype = AA  length = 272
FEATURE                  Location/Qualifiers
source                   1..272
                         mol_type = protein
                         organism = Penicillium cinnamopurpureum
SEQUENCE: 332
VPLRRDVSSD DLKQLTLFAE YASASYCTNN INSTGDALSC AEGNCPAVQS ATTKTLYEFN       60
```

```
DSTEFGDVAG FLAADETNEL LVLSFRGSRT ISTWVANLDF GLTDTSDLCS GCEAHGGFWK    120
SWQTVTDDIT SKIDAGLKSH PGYTVVLTGH SFGAAMATLG GTALRNAGYK IKLYTYGEPR    180
VGNEALAKYI TKQGDLYRVT HADDVVPKVP PASFGFSHAS PEYWITSGNN KTVSTSDIKV    240
IQGVGSKDGN AGTINPDIEA HNWYIVHIDG CQ                                 272

SEQ ID NO: 333         moltype = AA   length = 275
FEATURE                Location/Qualifiers
source                 1..275
                       mol_type = protein
                       organism = Talaromyces verruculosus
SEQUENCE: 333
EPIYRRKIAT SLLDSLDLFA QYSAAAYCSA NLDTTGTALA CNVGNCPAVE AADTTILYSF     60
DSSSSFGDAT GYIAVDESHG YIILSFRGTS NLENFIATLD MQLIDASSIC SGCKVHKGFW    120
NTWETVASDV TSQIKAALSA YPDYTLVATG HSLGAALAAI AATVFRASGY TVQLYNYGEP    180
RIGNLALADF ITSETSGTNY RVTHSNDIIP KLPPGLLGYH HFSPEYWITS KDNVTVTDSD    240
VVEIKGVDST DGNDGTAGAS IEAHTWYFVY ISECL                              275

SEQ ID NO: 334         moltype = AA   length = 277
FEATURE                Location/Qualifiers
source                 1..277
                       mol_type = protein
                       organism = Talaromyces cellulolyticus
SEQUENCE: 334
APKPIHRRTI PTSLLDNLDL FAQYSAAAYC SANLETTGTA LACNVGNCPA VEAADTTILY     60
SFDSSSSFGD ATGYVAVDES NEYIILSFRG SSNLENWIAN LDIPLIDASS ICSGCTVHEG    120
FWDTWETVAS DVTSQIESAL STYPNYTLVA TGHSLGGALA AIAATVFRAS GYTVQLYNYG    180
QPRIGNLALA DFITSETSGT NYRVTHSDDI VPKLPPELLG YHHFSPEYWI TSNDNVTVTD    240
SDVVEIQGVD STAGNDGTSG DSIDAHSWYF VSISECS                            277

SEQ ID NO: 335         moltype = AA   length = 280
FEATURE                Location/Qualifiers
source                 1..280
                       mol_type = protein
                       organism = Penicillium megasporum
SEQUENCE: 335
GPVSVLRRDE DVSASVLSEL DFFSQYSAAA YCSTNINSAG TKLTCSEGIC PLVENADTET     60
LDEFDESASY GDVAGFIAVD RTNELLVLSF RGSASFSNWL ANIDLFLDDA SSVCSGCEVH    120
SGFWDAWQTV EGQITTALGS AMETYPGYTL VFTGHSYGAA LAAIAATIFR NSGYTVELYN    180
YGQPRIGNLA LAEYITNQNK GGNYRVTHTD DIVPKVPPKI TGYHHASPEY WITSGNNVTV    240
TTSDVQLITG VDSTSGNDGT SDDSVEAHRW YFVHISMCTI                         280

SEQ ID NO: 336         moltype = AA   length = 259
FEATURE                Location/Qualifiers
source                 1..259
                       mol_type = protein
                       organism = Bacillus toyonensis
SEQUENCE: 336
HEKTEGHNVN IIQYWSAEDK HSEGVNSHLW IVNRAIDIMS RNTKLVKQDQ IILLNEWRTD     60
LENGIYSADH ENPYYDNSTL VSHFYDPDDG STYIPFAKQA KETGAKYFKL AGESYKNKDM    120
KQAFFYLGVS LHYLGDVNQP MHAANFTNLS YPQGFHSKYE NFVDTIKDNY KVTDGNGYWN    180
WKGIHPEDWI HGAAVGAKQD FSGIVNSNTK SWFVKAAVSQ SYADKWRAEV TPMTGKRLIE    240
AQRVTAGYIQ LWFDTYVNR                                                259

SEQ ID NO: 337         moltype = AA   length = 259
FEATURE                Location/Qualifiers
source                 1..259
                       mol_type = protein
                       organism = Bacillus sp.
SEQUENCE: 337
HEDTHQDPPI ALKWSAESVH NEGVSSHLWI VNRAIDIMSQ NTTVVKQNET ALLNDWRTNL     60
EEGIYSADYK NPYYDNSTFA SHFYDPDSEK TYIPFAKQAK QTGAKYFKLA GEAYQNKDMK    120
NAFFYLGLSL HYLGDVNQPM HAANFTNISH PFGFHSKYEN FVDTVKDNYR VTDGNGYWNW    180
KSANPEEWVH ESAAAAKADF PSIVNDNTKS WFLKAAVSQD SADKWRAEVT PVTGKRLIEA    240
QRITAGYIHL WFDTYVNNK                                                259

SEQ ID NO: 338         moltype = AA   length = 262
FEATURE                Location/Qualifiers
source                 1..262
                       mol_type = protein
                       organism = Bacillus manliponensis
SEQUENCE: 338
HGNHDASNDS GISISPRWSA EEMHAEGKNS HLWIVNRAID IMARDTTVVK ENEVALLNEW     60
RTDLEDGIYT ADYENPYYDN STFASHFYDP DTDDTYIPFA KNAKVTGAKY FKLAGEAYEQ    120
QDMQQAFFYL GLSLHYFGDI NQPMHASNFT NISHPFGFHS KYENFVDTIK APYAVTDSKG    180
YWNFAGGTPE EWLHTAAVAA KKDAPGIVNE TTKSWFLKAS VSQEYANMWR AEVTPETGAR    240
LMEAQRAMAG YIHLWFDTYV NR                                            262

SEQ ID NO: 339         moltype = AA   length = 274
FEATURE                Location/Qualifiers
```

```
                         -continued source                   1..274
                         mol_type = protein
                         organism = Penicillium simplicissimum
SEQUENCE: 339
APARSVPRDV SASVLEQFTL YAQWAAAAYC SNNLDSTGDA ITCAGGYCPE VESSTTISLS      60
EFNDTNDFGD TAGFVAVDKT NKQIVVAFRG SKSISNWIAD LDFGLTDASN LCSGCEAHTG     120
FLEAWETVAD SITSQIGAAM KTYSGYTLVV TGHSLGGAIA AIGATVLRNA GYTLDLYTFG     180
QPRVGNLALA TFLTKQGNNR MTHLNDIVPR LPPTSFGFSH SSPEYWITSA DDVTVTTSDI     240
EVIEGIDSTA GNAGELIESV AAHAWYIIDI DGCE                                 274

SEQ ID NO: 340           moltype = AA  length = 276
FEATURE                  Location/Qualifiers
source                   1..276
                         mol_type = protein
                         organism = Penicillium arenicola
SEQUENCE: 340
APFQLWSRAV TPSVLSKLDL YGQYAIAAYC DDNIASAGTE VTCSAGNCPL VQAATTNTLS      60
EFNESNEFGD VAGFFAVDTT NQALVLSFRG SHTIDNWIAN LDFGLTSVST LCSGCKAHTG     120
FWKAWNTVAS DIAAAVDAAQ DTYPSYPIIF TGHSYGAALA ALAATTMRNA GYSIELYTYG     180
QPRIGNTALA TYITNQNKGG NYRVTHTNDI VPRLVPRLLG YSHFSPEYWI TSGNNVTVTA     240
SDITLVTGID SNGGNAGELL QSVEPHYWYF VEVEDC                               276

SEQ ID NO: 341           moltype = AA  length = 277
FEATURE                  Location/Qualifiers
source                   1..277
                         mol_type = protein
                         organism = Aspergillus aculeatus
SEQUENCE: 341
APAPIERRSV STTLLDQMDL FAQYSAAAYC STNIDSASTA LSCSADNCPL VVAAAPTVLD      60
EFNETAEFGD TAGFVAVDST NKAIVVAFRG SSDLSNWIAN IDFGLTDASS ICTGCEIHSG     120
FWKAWETVAS TIASKVEAAV TTYSDYDVVF TGHSLGAALA AIGATVLRND GYTVDLYNFG     180
QPRIGNLALA DYITDQNKGS NYRVTHTDDI VPKVPPELLG YHHFSPEYWI TSDNDVTVTT     240
SDITEVTGVD STAGNDGTLL DSVSAHKFYF EYISACD                              277

SEQ ID NO: 342           moltype = AA  length = 349
FEATURE                  Location/Qualifiers
source                   1..349
                         mol_type = protein
                         organism = Bacillus acidiceler
SEQUENCE: 342
ITSFFGNYQK AFAWSDEDVH NQDHSTHHFI VNGSVKLIAD NTNPAINKPT TLLNQFRDRW      60
EQGLYDADHI NPFYDTGTFM SHFYDPDTQT NYTGASYPTA RQSGAKYFNL ASDYYKKGDF     120
NNAFYYLGVS LHYFTDVTQP LHASNISNLD HHAPGYHSKY ETYAESIQNE MTMPDSGLYN     180
WIASTDPEAW IHQAAVQAKS VLPQVWNDTI INYFWQAAYS NYYSAMWKSE VKNPTLDQLN     240
QAERETAGFI DMFFRVNGVE MPVTVYKENA FSGASELLGS GNYDYDQLVK GIGNDTISSI     300
HIAPGYQVTL FSDANYKGAS TVLTNDVHDL GNFSHQVSSI KVAKISALK                 349

SEQ ID NO: 343           moltype = DNA  length = 1815
FEATURE                  Location/Qualifiers
source                   1..1815
                         mol_type = genomic DNA
                         organism = Aspergillus wentii
SEQUENCE: 343
atgagatttc cttcaattt tactacagtt ttattcgcag catcctccgc attagctaac      60
tgggcagaaa gtatctggga cgatgtaaaa catgccgtga attgcgctgg ttgtgaaaca    120
gttttgtttg ctctaaaagg tgtggcagat ctgggtgagc atgcatttca aacggtctta    180
accgatgtgt gtgacattag cgggacggaa gacaaagacg tttgttctgg tttgatcgca    240
gctgaatcac ctgctttgta ctacaacatc aagaatttgg gtgtcaaatc tcatacatct    300
aaagttttgt gtgcccaact gttttggttta tgccaatttc cagcagttg gccttacaac    360
ttgacctttc cttcccctaa accaactact tctaggcctc ctccctctgg gcaatcaccc    420
atcagagttg ctcacatctc cgatactcac gttgatttgt catatgagac tggtagcaac    480
tatgaatgta gtaaacctat ctgttgtaga gtgtacacag acgaggatgc tccaggaaat    540
acgtcatttc cctgtgggcc atacggaaac acaaactgtg acccacctttt gaggctggag    600
gaaagtatga tggcagctat caaatccca aatcccgctt tttcaatcta cactggggat    660
gtcgtcgctc atgacttgtg gatggtcgac aaaactgaag tattggatga cttcaatgcc    720
acttattcaa tgtggatca attggatcta gtttatgctg ctgtggggaa ccatgacact    780
accccctgtta atctatttcc atctacacaa ttgccagata aggataatca atgggcatat    840
gatgctttaa ctgcagaatg gaaatcccttt accaattctt caatccaaac tacggagtat    900
ggctcatata gcgccatata cgaaaacctg aggatcataa gctacaacag catcttctac    960
tatcaagaca acttctacgc atacacagac ccgatggcac atgatccttc aaatcagtta   1020
acatggttga tagatcaact gcacgaagct gaatctgcaa atcaaagggt tggttgata    1080
agtcacattc caactggcgg tgtggatcat ttgcacgatt acagtcatta catagatgaa   1140
atagtccaac gttacgaagc aactatctcc gctttgttct ttggtcacac acatacagac   1200
ttgtttcaaa tcgcttacag cgactacaaa aacagagctt gggacgccttt ctccgccatt   1260
ggttacgtag ctcccagttt aactccaact tctggcccac cagcttttag gatctacgat   1320
attgatcctg ttaccttttgc cgtccttgac tatacggtct atatcgcaaa catatcaaac   1380
ccctcatacc aaagcaatcc gaaatgggag aagtactatt cagccaagga ggcctatggt   1440
agtttgttga gtcctccagt caccgattca tcttctgagt tgacgccttc tttctggcat   1500
aatgtgacag cattgatgga aaaggacgac tcagtttttc aagactggtg gtcccgtacg   1560
```

```
accagaggtt acaatgtcac aacatgcact ggggattgcg ccaaaaagga gatatgtgct 1620
ttgagaggtg cagatgctca gtacaattgt gtgacggcta cacctgggtt tcattttgac 1680
aaaagagagg agtccgaaca aaaacccaga cctgaatgcg aggatggctt gggcagagtg 1740
ttaggtgata tgatccacaa gaaagatttt gtggatttgt tgcatgaaag aaccgcacaa 1800
taccaacata gataa                                                  1815

SEQ ID NO: 344          moltype = DNA  length = 1824
FEATURE                 Location/Qualifiers
source                  1..1824
                        mol_type = genomic DNA
                        organism = Penicillium cylindrosporum
SEQUENCE: 344
atgagatttc cttcaatttt tactacagtt ttattcgcag catcctccgc attagctaca  60
tacgataaga gagatcttgc ccaagacttg tggaatgaca tcaagaatgc tgttgattgt 120
ggtggctgcc aagtgattct tactgcattg aaagggttat cagacttggg gacaacagtt 180
ttcgtggacg ttttgacaga ggtttgtgaa attggtaagt tagaagattc agatgtttgc 240
tctggtacta tttctagaga aggtccagtt ttggattaca tttgcaaca tctagacata  300
gggtctcata caagtcaagt attgtgtgct agtgcatttg ggttgtgcca ataccctgca 360
gtaagaccct acaatctacc tttccccctcc ccgaaaccaa acaccactag accagctccg 420
tccggtgaac tgccaattca agtagttcac atttcagaca ctcatgtaga tctttcatac 480
gagactggat ccagctacaa ttgcacgaaa ccaatttgtt gtcgtcctta taccgctgcc 540
gatgcacctg gaaataccac aaccccatgt ggtccttacg gcaataccaa ctgtgatgct 600
cccattggac tagaagagtc aatgtttgct gccattaagg ctctacagcc tgctttctcc 660
atctataccg gtgatgttgt cgcacatgac ttatggttag tggatcaaaa tgaagtttta 720
caagacttta acgctacctt caatcgtatg gccgaacttg gtgtcgtcta tgctgcaatt 780
ggtaatcatg acactgctcc agtgaatgat ttacctgcca ccaacattcc ttcacagtat 840
agcgcaaact ggaccctatga tgcacttgct tatgacttct ctaccttaac aaactctgca 900
agtgctcaga cggcagaaga ttacgggagc tacagcagtg tctatagagg aagtcacggc 960
acagacttac gtgtgatatc ctataactcc atctttttact atgtagacaa cttttgggta 1020
taccaggatc caatgttgta cgatccagac ggtcaattag catggttgat ttctgaacta 1080
caagaggcag aaactggggg tcagcgtgtt tggttgattg ctcatgtccc aagcggcatt 1140
tccgatcact ttcatgacta ttctccattac ttcgatcaaa tagtacaaag atacgaagcc 1200
acgattgcag ctctgttcta tggtcacaca cacagagacc aatttcagat ttcatacagt 1260
gactatacaa atagaacctg gaatactgct acagccatgg gctacataac accatccttg 1320
acgcccacct ctggtccgcc tacatacagg gtgtacaaag tcgacccaaa gacattcggt 1380
gtgttggatt tcaccaacta catagccaac atcagtgatc cagcctatca aagtggacca 1440
acctggcaga agtactatag tgccaaggaa acttacggat ctttactgtc cctcctgta 1500
acagatccga cggcagaatt gacacctgct ttttggcaca acgtcactgt tctatttgag 1560
aatgataacg ccacgtttca gcagtacata gccaggcaaa caagaggttg ggatccttct 1620
tcttgtacag gaagttgcat tgatcaaacg atttgtggtt tgagagctgg cgacgcacag 1680
tacaattgcg ttaccccctac tcccggtttc aatttcgcta agagagatgc ttctactggc 1740
ggtcaaccag aaacgcatgt tgaaaagtgt gaaggctccg gtctgttggc tttgttggga 1800
agaatggtcg caactaaatc ataa                                        1824

SEQ ID NO: 345          moltype = DNA  length = 1824
FEATURE                 Location/Qualifiers
source                  1..1824
                        mol_type = genomic DNA
                        organism = Penicillium meridianum
SEQUENCE: 345
atgagatttc cttcaatttt tactacagtt ttattcgcag catcctccgc attagcttca  60
gccgatagtt ggattaccat catatgggat gacttcaaag aagctgttga ttgtgcatca 120
tgtcaggcac tactgggtgg cttgaagtat gttgccggtt ttggagaaag ctttatggaa 180
gacgtgttga caggggtatg cgacatttct ggtgctgagg attcagatgt atgttctggc 240
atcattgcaa atgaaggtcc agctgtctca tattctttga agaacttaga actagggagt 300
cacactgcta aaacctttg ttccaatttg tcggattat gcgattaccc agcagtaaga 360
ccatatgatt tgtcttttcc tagtcccaag ccgtcaattt cccgtcctcc accaagcggg 420
aagcctccac tgaaagttgt tcactttttcc gatactcacg ttgacttatc atacgaacct 480
ggctcagtt ttgactgtac aaagccgatt tgttgtagag tttactcaga agacgatgcc 540
ccaggcaata cctcatcccc atgcggtcct tggggaaacg ccaaatgcga tccacctcat 600
cagttgcaac aatctatgat ggatgcaatc gcctctctga atccagcctt ttctatctat 660
actggtgacg ttgttgctca cgatgtttgg ttagtcaata agactgaagt attgcaagat 720
ttcaatgcaa cctattctac tatggagagc acgttaggct tggtctacgc tgctctaggt 780
aatcatgata ccgctccatt gaacttgttt ccttcaacca acattccaag ttcatacaat 840
ccgcaatggg cctacgatgc tttatccaca tcttggttga ctcttacatc agacaatcct 900
gccatttcca cggcaaaaga tacgggagc tacagcgcca gacataaaga caccaagcta 960
agaatcattt cctacaattc cattttctac tacaaatata cttttttcag ctatgaagaa 1020
ccgatgccat ttgacccaga cggtcaactt tcatggttga tatccgagtt gtctgctcca 1080
gaagccgcat ctgaacgtgt ttggttgatt tcccatatte caagtggaaa tagcgaccat 1140
ttcagagacc attcacacta ctttgatcaa atagttcaaa ggtatgaagc taccattgct 1200
gggttgttct tggggcatac tcataccgat gagtttcagg tttcttactc agattacgcc 1260
catagatctt gggataccgc tactgctatg ggatacgtag caccatcaat gactcctact 1320
tctggtcccc catcattcag agtatacgaa atcgatccag tcacctttgg ggtcctggat 1380
ttcactcaat acattgcaga caattccgac tcctccgaac caaagtggat gccctactat 1440
tccgccaaga aagattatgg cagccgtcta gatgtgcctg ttgagaggga tatggagtta 1500
acacctgcct tctggcataa cgtaaccgtt ggtatggaga aggacccatc tttgtttagg 1560
gactttgggg ctcgtagaac gagagggtttc gaggtaccag gttgtgaagg tgattgtgtt 1620
tctaaagaga tatgcgcctt gagaggagcc gatgcacagt attcatgtgt ggaggcaaca 1680
ccaggttttct ctttcgaaaa gagggtgag agaaccgttc tgttagagaa aagattccag 1740
```

```
ccagaatgta atcacgctgg tatggcacca ttgcttgcca aaatcgctca tagagcttca   1800
ttggctaggg aaatggaagc ataa                                          1824

SEQ ID NO: 346          moltype = DNA  length = 1830
FEATURE                 Location/Qualifiers
source                  1..1830
                        mol_type = genomic DNA
                        organism = Penicillium bialowiezense
SEQUENCE: 346
atgagatttc cttcaatttt tactacagtt ttattcgcag catcctccgc attagctgaa    60
gttcttcttg aaaactctat tgcttcctta tgggatgact ttaagaatgc tgtggactgt   120
gcctcttgcc aagcattgtt aggtggctta aagttggtgt caggatttgg ggaggacttt   180
atgattgacg ttttgactgg tatttgcgac atttccaaag cagaagactc agatgtttgt   240
gaaggcatca tcaagaaaga aggtcctgct ttgcatgatg cattccaagc cttgcatatt   300
ggctcaaatt ctacacaaac catgtgtgcc tcttttgattg gattatgtca atatccagaa   360
gttagggcac acagtctaag cttttccaagt cccaaaccca ataaggtgaa gcctccaccg   420
tctggtaaac ctcccatcaa agttgtgcac ttttccgata cgcatgtcga cttgtactat   480
gagacaggta gcagctatga atgttccaaa ccgatttgtt gcagagtgtt tgaggataag   540
tatgcaccag gcattacaaa aacaccgtgc ggtcccttcg gtaatccaag gtgtgaccct   600
ccattgaagt tacaagagag tatgaacgct gcaatcgcag atatcaatcc agaattctcc   660
atctataccg gagatgttgt agctcatgac gtttggttag ttaatcaagc agaagcacta   720
gaatccttca atagcacgta ctcccagatg gagaagtctt tgggaatggt ttatgcagca   780
attggtaatc acgatactgc acccttgaat ttgtttcctt catccatagt gccagatggc   840
gacaatcaat gggcctacaa tgccctggct gagtattggt tgactttgac ctctatcagc   900
tccgtacaat ctgccgacga gtacggctca tattcagcaa tccacccaga tagtaatctt   960
aggatcattt cttacaactc cattttctat tacaagttca ttctatat gtaccaagaa   1020
cctatggaga aagatcccaa tggtcaattt gagtggttga tcaaagagtt gcaggcagct   1080
gaagacgctg gcagagagc ctggttgatt cccacattc cgcctggtgt cgcagaccat   1140
tttcatgact attctcacta cttttgatcaa attgttcaaa ggtatgaggc cacaatagct   1200
gggttgttct attggccatac gcatatggat gaattccaaa ttgcctactc caactacaag   1260
aataggaatc atgaaactgc aaccgcaatg ggctacatag ctcctgctat gaccccact   1320
gaagggcctc ctagtttccg tgtatatgaa atcgatccgg aaacgtttgg ggttttagac   1380
tatacacagt atatcgcaaa catctcagat cccacttatc aggaaaaacc ccagtggtta   1440
ccctattaca gcgccaaggc agactacggt tccaagttat caccctcctgt aacagaccg   1500
aagattgagt taaccccagc tttttggcac aacgttactg tcgcaatgga aaatgagccg   1560
agcattttcc aagaattctg ggcaagaaga gttagaggct ataaggttac agattgtaat   1620
ggcgactgta tgaaaacgga gatatgtgct ttaagagccg cagatgcaca gtttaactgt   1680
gtcaagccca agcaggcttt taactttagc aaaagagatg gtaaggacac tttggctgaa   1740
cagccacatc attgtgatca tgccggatta gctccttat gggcaagat tgcttacagg   1800
gctagaatag caagagagat ggaagcttaa                                    1830

SEQ ID NO: 347          moltype = DNA  length = 1830
FEATURE                 Location/Qualifiers
source                  1..1830
                        mol_type = genomic DNA
                        organism = Penicillium sclerotiorum
SEQUENCE: 347
atgagatttc cttcaatttt tactacagtt ttattcgcag catcctccgc attagcttct    60
gcagactcct ggatctcttc tatttgggat gacttcaaag aagcagtaga ttgcggcagt   120
tgccaagcct tgttaggtgg tctgaaagta gtcgctgcct ttggagaaag cttcatggaa   180
gacgtattga ttggtgtttg tgatatctca ggtgcagaag attcagacgt ttgtgctgtc   240
gttattgcaa atgaaggtcc agctgtccca tattcattga caaacctaga gattggttca   300
cacacagcaa aaacatttg cgcaacactg gttggcttgt gcaagtatcc agaagttaga   360
ccatacaatt tgaccttccc gtcaccaaaa cccccaactt ctcgtccgcc tccatctggg   420
aaaactccca tcaaagtcgt tcatttctca gatacacatg tggatctatc ctatgaaaca   480
ggctccaatt acgactgttc taaacctatt tgctgtagag cctatacgag agacgatgca   540
cctgcaata cctcttcacc atgtggtccc tggggcaaca caaattgtga ccacctcac   600
agacttcaga aatcaatgaa cgctgccatt gcagacttga aaccggcttt ttccatctat   660
actggtgacg tagttgctca tgatgtatgg ttggtcaaca aatctgaagc attgcaagac   720
ttcaatgcta cttatggtgc catggaggat tccctaggta gagtctatgc tgctttagga   780
aatcatgatg ccgctccctt gaacttgttt ccatcaaatc aaatacctag cgaatacaac   840
ccccaatggg catacgatgc tcttgccgca gactggatgg ccttgacaga cattccagc   900
gtagaaacag ccaacgagca cgggtcctat tcagctatac acccgacag taacttacgt   960
atcatatcct ataactccat cttttactac aaataacct tcttttcata cacggaaca   1020
atggaatacg atccaaacgg tcaattagaa tggttgatca atgaactaca tgccgcagaa   1080
actgccaatc agcgtgtttg gttgattct catataccaa gcggcaatag tgatcacttt   1140
catgatcatt ctcattactt cgatgagatc attcaaagat acgaagccac gattgcaggt   1200
ctgttcttt g gtcacacaca cacagacgaa tttcagattt catactccaa ctattcaaat   1260
agaaactgg atactgctac agccatggga tatgtagcac caagtatgac gcccacctct   1320
ggtccgcctt cattcagggt gtacgaaata gacccagtga cattcggtgt gttggatttc   1380
atgcagtaca tagccaacat ctccgatcca tcctatcaac agaagccaga gtgggttccc   1440
tactattccg ccaagagtga ttacggatct aggctgagtc ctcctgtaac agatgccgac   1500
gtagaattga cacctgcttt ttggcacaac gtcactgttt tgatggagga agattccagc   1560
gtgtttgcag agttttttggc caggagaaca agaggttttc aagtaccagc ttgtacagga   1620
gactgcgttt caaatgagat ttgtgctttg agaggtgccg acggacagta caattgcttc   1680
atagaaaaac ccgttctctc tttcgaaaag agagatggta ctgtcgacga gtttcttgg   1740
aagaaaagat tcaaccagaa atgcaaccat gccggtatgg ctcccttatt ggctaagata   1800
gctcatagag catcactggc aagagaataa                                    1830
```

| SEQ ID NO: 348 | moltype = DNA   length = 1836 |
|---|---|
| FEATURE | Location/Qualifiers |
| source | 1..1836 |
| | mol_type = genomic DNA |
| | organism = Rasamsonia byssochlamydoides |

SEQUENCE: 348

```
atgagatttc cttcaattttt tactacagtt ttattcgcag catcctccgc attagcttcc   60
tacaacaaaa gaggattagc tcaagagatt tgggatgata tcgtcaacgc cgttgactgt  120
tcaggttgtc aggtcatttt gactgcctta caaggtgctg ccgagttagg gacaagcgct  180
tttgttgata ttcttacaga agtatgtgac attagtggta aagaagattc agatgtttgt  240
tcaggcatca tttccagaga aggtccagtc ctggattaca ttttgcaaaa cttagatatt  300
ggatctcaca catccgacgt catatgtgca tccgcatttg gtttatgtca ataccctgca  360
gtcaggagct acaatttgac cttcaact ccgaagccag atactacgag accagctcct  420
tctggcgaat ctccgattca agtagtacac ttttccgaca ctcatgaa cctatcatac  480
gagactggtt catcctataa ctgtacaaag ccaatctgtt gcagaccta taccgctgcc  540
gatgcaccag aaacaccac tacccttgt ggaccatacg gtaacaccaa ttgcgatgct  600
cctctgagtt tggaggaaag tatgttcaat gccatcaaag ctctatctcc acaacctgca  660
ttttccatct atacaggcga tgttgtagct catgacatat ggttagtcga tcaaaatgaa  720
gtgatccagg atttgaatac tacctatgat ttgatggctg aattaggatt ggtttatgcc  780
gctattggaa atcatgatac tgctcctgtt aatgatctgc caacaaccaa cattccatca  840
gagtattcta cgaactggac ctatgaagcc ttggcatacg atttcacgat gttaacaagc  900
agcagctctg cccagacagc tgcaaactac ggatcctcaa gttcaatcta caaaggttcc  960
tacggcacag atcttaggat cataagctac aattcaatct tctactacat agataacttt 1020
tgggcctatc aagatcctat gcctatgat ccagacggtc agttagcttg gttgattaac 1080
gagttgcagg aagctgaaac agcaggtcag agggtatgga ttatcgcaca tgtccctact 1140
ggtacctccg atcatttcca tgactatagt cattacttcg atcaaattgt gcaaagatat 1200
gaggctacga tagccgcttt gttctatggt cacacccata ttgatcaatt tcagatttct 1260
tattcagatt actccaatca agcatgggat accgctacgg ccatcggcta tatcatgcct 1320
agtttgacgc ctacttctgg cccaccgaca ttcagagtgt atgatgtgga tccaaaaaca 1380
ttcgcagtgc ttgactttac caactatatc gccaatatca gtgatcctgc ttatcagtct 1440
gggcctactt ggcagaaata ctactccgca aaggaaacat atggtgcctt attgagccct 1500
cctttgacag atcccactgc cgaattgaca cctgccttt ggcacaacgt gactgtggct 1560
tttgaaaacg ataatgctgc ttttcaagaa tactgggcta gacaaacacg tgggtgggat 1620
gtaagctcat gtactggttc atgtatcacc caagcaattc gtggcttgag ggcagccgac 1680
gctcagtata actgtgtgac accaactcca ggcttcaact ttgctaaacg tgatgcttct 1740
tccgctactc aggcaatggc ccatgttgag aaatgtgaag gttccggatt gttggccttg 1800
ttagggagga tggttgcaga caagaaatcc gcttaa                            1836
```

| SEQ ID NO: 349 | moltype = DNA   length = 1839 |
|---|---|
| FEATURE | Location/Qualifiers |
| source | 1..1839 |
| | mol_type = genomic DNA |
| | organism = Rasamsonia eburnea |

SEQUENCE: 349

```
atgagatttc cttcaattttt tactacagtt ttattcgcag catcctccgc attagctact   60
tatgacaaaa gaggtttggc tcaagacatt tggaacgaca taagaatgc cgttgattgt  120
gctggtgtc aaggcatttt gacagcattg aagggcttgt catacttagg gactactgct  180
tttgttgacg tcttaacaga agtatgtgac atttcaggtg tagaagattc agatgttttgt  240
tctggcatca tttcttcaga aggaccggca ctggtctaca ttcttaaaca tttggatatt  300
ggcagtcata cgtctcaggt catatgtgca tcagtttttg gtttgtgcca atatcccgca  360
gtgagagctt acaacttgac ttttccgagc cctaaaccag acaaaacttg tcctgaacct  420
tctggtgagt ctccagtaca aatcgtacac ttctcagata cacacgcaga tcttagctat  480
gaaacaggat caaactacaa ttgcacaaag ccaatatgtt gcagatccta taccgctgaa  540
gatgcaccag gcaataccac aactccttgt ggcccatacg gaaatcccaa atgtgatgct  600
cccatgagct tagaggagtc aatgttcgct gccattaagg ctttgtctcc tcaaccagct  660
ttttccatat acactggtga tgttgttgct catgacatat ggttagttga tcaaaacgag  720
gtggtagagg atcttaacgc tacttacgat agaatggcag gattgggttt ggtgtatgct  780
gcaataggta atcatgatac agctcctgta aacaatctac ccacctccaa catccctca  840
caatacagcg caaactggac ttacgaagca cttgaatacc acttctcctt attgacgaag  900
agcgcctccg cacaaacagc agagaactac ggatcctatt ccagcgtcta tagaggaagg  960
tatggtaccg acttaagggt gatatcctat aacagcatct tttactatat cgcagatttc 1020
tgggcttatc aagaccccat gttgtatgac ccagacggtc aattggcctg gttgatcaat 1080
gagttacaag aagcagaaac agctggccaa aggggtttggt tgattgcaca tgttccaagt 1140
ggaactgcag accatttca tgactattcc cactacttcga atcagatagt tcaaagtgat 1200
gaggcaacca ttgctgcctt gttttacggc catactcata ttgatcagtt tcagatttca 1260
tactccgact attcaaatag ggcttttgat acggctaccg ctattgggta cataatgcct 1320
agcatgactc ctacctcagg gcctccgact ttcagagtat acgatgtaga tcctaagacc 1380
ttcgccgttt tagacttttac aaactacatt gccaacattt cagatccagc ctaccagagt 1440
ggtccgacat ggcaaaagta ctatagtgca aaagaagcct acggttctct gttaagtcca 1500
ccagtaacgg acgccactgc tgagttaacc ccagcattct ggcacaatgt gactgttgca 1560
ttcgaaaatg atgatactgc ttttcaagag tattgggcta gacagacgag aggttatgcc 1620
gtttcatctt gtacaggtga ctgcataaca caagctatct gtggactaag agccggtgag 1680
tctcagcata actgtgttac tccaactcca ggcttcaact tgccaaaag atgtgtctct 1740
acagacggac aagcctgcc acatattgag aaatgtgaag gatctggctt aatggcactg 1800
ctagccaaaa tggtcgcctc aaacagacaa agttcataa                        1839
```

| SEQ ID NO: 350 | moltype = DNA   length = 1839 |
|---|---|
| FEATURE | Location/Qualifiers |
| source | 1..1839 |

```
                        mol_type = genomic DNA
                        organism = Penicillium brefeldianum
SEQUENCE: 350
atgagatttc cttcaatttt tactacagtt ttattcgcag catcctccgc attagctggt    60
gctattgaga attgggctgc tactatatgg gaagacttca aggaggctgt ggattgtggt   120
tcttgccaag tactattagg tggcttgaaa ctggtggccg atttcggtga gggcttttg   180
ggtgatgtct taacaggagt atgtgatatc tctaaagctg aagatagaga tgtttgtgct   240
ggtgttgtcg cttctgaagt tcctgcccta cactatgcct taaagaatat gaaagtaggt   300
agtcatacag ccaaaacctt gtgctccgca ttagttggtt tgtgtgactt tccagacgtc   360
cgtccatttg accttacttt tccaagcccg aagccagcta cgtctcgtcc acctccaagt   420
ggtaaacctc ccatcaaagt agtgcatttc agtgatacac atgtggactt aagctacgaa   480
actggttcca attacgattg tagtaaaccg atttgctgta gggtatacac agacaaagat   540
gctcctggga ccacagacaa gccatgtggt ccctggggac acccaaagtg tgatcctccg   600
caccaactgc aagagagtat gatgacggct attgcaaact tgaatccagc attttccatc   660
tatactggag acgttgttgc acatgatgtt tggttggtaa acaaagatga agttctgcag   720
gacttaaacg ctacctacgg tgctatgaaa aatcatttag gattggttta tgccgctttg   780
ggaaatcatg atgctgctcc cttgaactta ttcccatcca acaaggtacc atcaaagtac   840
aatcccagt gggcctatga tgccttgaca gccgattgga tgacattaac agggctggac   900
agcgtgcaga atgccaataa gtacggatcc tacagtgctg tgcacccaaa ttctaagcta   960
aggattatct catacaacag catcttctat tacaagtaca atttctttag ttatactgag  1020
ccaatggaat acgaccccaa tggtcaattg acttggatca tcaatgagtt gcaagccgct  1080
gagacagctg gtcaaagggt ttggttgatt tcccatatcc cttcaggaga tgttgatcac  1140
ttcagagatc actcacacta tttcgatcag atcgtacaaa gatacgaagc tactatagct  1200
gggttattct ttggtcacac acataccgac gaatttcaaa ttgcttactc agactacaat  1260
aacaggaatt gggatacagc aactgcaatg gggtacgtcg ctccaagcat gacacccaca  1320
agcggtccac ctagttttcg tgtctacgat atcgatcctg agacttttgt tgtaatggac  1380
tacacccagt atatcgccaa tatctccgat cccagttttc aaactaaaca ggagtgggtc  1440
ccatactaca ctgcaaagaa ggattacgga gctaagctga gccctccacc ggcacctact  1500
ggtgaactta ctcccgcttt ttggcataac gttacagtgg ccatgaaaa ggattcttcc  1560
gtgttcgaag cttttttggc tagaaggact agaggttttt ccattccggc ttgtacaggg  1620
gattgtgtca agaatgaaat ctgcgcacta agaggtgccg atgcacaata cagttgtgtc  1680
aaaaggactc cgggatttc ttttagtaag agagatgaaa ttgagtcaga tccactattg  1740
tctaagaggt ttcagccaga atgtaatcat gctggtatgg caccattgtt agccaaaatc  1800
gcacataaag caaacgtcgc taagtggaat ggagaataa                          1839

SEQ ID NO: 351           moltype = DNA   length = 1839
FEATURE                  Location/Qualifiers
source                   1..1839
                         mol_type = genomic DNA
                         organism = Penicillium adametzii
SEQUENCE: 351
atgagatttc cttcaatttt tactacagtt ttattcgcag catcctccgc attagcttct    60
gttgattcct ggattactac aatttgggat gatttcaagg aagccgttga ctgtgcatct   120
tgtcaggctt tactaggtgg gttaaagttg gtggccgtgt ttggggaaag ctttatggaa   180
gatgttatca caggtgtatg ttccattagt ggtgctgaag attcagatgt ttgtgctggt   240
gttattgcaa atgaaggtcc agcagtgtac cactctttgt caaacttgaa gattggatct   300
cacacagcaa agacttttctg tgcatcctta gtaggtttat gtgattaccc tgcagtcagg   360
ccgtattcat tgacctttcc atctccgaag cctccaacta cgcgtcctcc accttctggc   420
aaatctccga tcaaagtagt acactttttcc gacactcatg tagaccatc atacgagact   480
ggttccaact atgactgttc aaagccaatc tgttgcagag catataccga aaacgatgca   540
ccaggaaaca cctctagtcc ttgtggacca tgggtaact ccaaatgcga tccacctcac   600
aggttgcagg aaagtatgaa tgaagccatt gcagatctaa atccagcttt ctccatctat   660
acaggtgatg tggttgctca tgatgtttgg ctagttgata agtcagaagc tttgcaggac   720
ttcaatgcca ctttcagtgc tatggaaaca ttgggtagag tctatgctgc tctgggtaat   780
catgatgcag ctccattgaa cttgtttcct agcaatcaaa tcccctcaca gtataaccca   840
caatgggcct atgacacatt agcctcagat tggatgggct tgacaggaat acagagcgtg   900
gagacggcca atgaatatgg aagttactcc gcaatccatc ccaactccaa tttgaggatc   960
atttcttaca attccatatt ctactacaaa tacaacttct tttcctatac cgaaccaatg  1020
gaatatgatc caaacagtca attgcaatgg ttgatcaatg aattgcacga agccgagttg  1080
gccaatcaaa gagtctggtt aatcagtcat ataccaagcg gagatccaga tcattttcac  1140
gatcattccc actactttga tcagattgtg cagagatatg atgccacaat tgctgcctta  1200
ttctttggcc atactcacac agatcagttc cagattctt attctagtta tcagaataga  1260
acatgggata aagctacagc aatgggatat gttgctccct ctatgacgcc tacaagtgga  1320
ccgccttctt tcaggttta cgaaatcgat ccggttacat tcggtgtatt ggattcaacc  1380
cagtacattg caaacatttc agaccctact cagaccaaac taaatgggt gccgtactac  1440
tctgccaaga aagattacgg atcacactta gatcctccgg tgacagatgc ccatgcagag  1500
ttaacaccag ccttctggca taacgtaacc gtttccatgg agaacgataa ctctgttttc  1560
caggacttt gggctagaag aacaaggggt tttcaagttc cagctgcac tggtgattgc  1620
tcatcatctg agatttgtgc cctaagagga gcagatgccc aatacaactg cttcgttgag  1680
aaacctggtt tctcttttga gaaaggggac gttcaagaat cagacgaaga aatgtggaag  1740
aaacgtttcc aaccggaatg taatcatgca ggtatggcac ctttgttggc caagatagcc  1800
tacagagctt ctctagagag agaacaaaaa ggaaaataa                          1839

SEQ ID NO: 352           moltype = DNA   length = 1842
FEATURE                  Location/Qualifiers
source                   1..1842
                         mol_type = genomic DNA
                         organism = Rasamsonia brevistipitata
SEQUENCE: 352
```

```
atgagatttc cttcaattt tactacagtt ttattcgcag catcctccgc attagctact    60
agtttaacac atgacaaaag ggatttggcc caggaaatct ggaacgacat caagaatgcc   120
gctacatgcg ctgggtgtca agttatcttg acggctctga aaggggtttc agatttgggt   180
acctccattt tcgtagatgt tcttactgaa gtttgtgaca tttctggttt agaagatcca   240
gatgtttgtt caggcataat cagtcgtgaa ggtcctgtct tagactacat attgcagcat   300
ttagacattg gctctcatac atcagatgtc ttatgtgcta gtgcattcgg cctatgccaa   360
tatccagccg ttagaccata caacttaact tttccgtctc caaaaccaga taccactaga   420
ccggctccaa gtggtgagtc acctatccaa gtagtacaca tatcagacac gcatgttgac   480
ttatcttacg aaacaggctc aagctggaac tgtaccaaac ctatttgctg tagaccatac   540
actgccgaag acgcaccagg aaataccact accccttgtg gcccatatgg tgacacccat   600
tgcgatgcac ccatgtctct gcaagaatcc atgattgctg ctatacaagc tttgagacca   660
caacccgctt tttccatcta tactggagat gtagtcgctc atgacatttg gctggtggat   720
cagaatgagg tcattgaaga cttcaatgct acatacaata gaatggccga attgggatta   780
gtatatgctg ctataggtaa tcatgactct gcacccgtca atgatttacc cgcttcaaac   840
atcccatccc agtatagcgt taactggact tacgaggcat tagcatacga cttcagcatg   900
cttacaggtt cagcatccgc acaggaagcc gaaaactacg gatcatatag ttccatctat   960
aagggtagta acgggacaga tttacgtgtg atttcttaca attccatctt ttactatgtt  1020
accaatttct gggcttttca agaccccaatg ccttatgatc cggatgggca gttggcctgg  1080
ttgattaacg aattacagga ggcagaaact gccggacaaa gggcatggtt gatagcacat  1140
gtccctacag gtacaggcga tcacttccat gactatagcc actactttga ccaaatcgta  1200
cagagatatg aggcaacaat tgccgcattg ttctttggtc acactcatca agatgaattc  1260
caaatagctt attccaatta ctcaaaccag aactttgata cggcaacagc cataagggtac  1320
attatgccct cattgacacc gactagcggt cctccctctt ttagagtata cgacatcgac  1380
ccaaaaacct tggtgtgct agatttcacc aactacattg caaacatcag cgatccagcc  1440
taccaaagtg ggcctacatg gcagaaatac tacagcgcaa aagaggcata cggtacttta  1500
ctttctcccg ctgttacaga tcccacagca gagttgacgc cagcctttg gcacaactta  1560
actgttgttt ttgaaaatga taatgctaca tttcaagagt actggacaag aaagactaga  1620
ggtcatgcag tttccaactg tacaggttct tgcattaccc aatccatctg tggcatgagg  1680
gctgccgatg ctcagtataa ctgcgttact ccaactccgg gtttgtcttt cgctaaacgt  1740
gatgcagaga cttcaactcc agaaccacat atagaaccat gtgaaggatc agggttgatg  1800
tctttgctag gcagaatggt tgctcaaggt aaatcttcat aa                    1842

SEQ ID NO: 353          moltype = DNA   length = 1842
FEATURE                 Location/Qualifiers
source                  1..1842
                        mol_type = genomic DNA
                        organism = Penicillium scabrosum
SEQUENCE: 353
atgagatttc cttcaattt tactacagtt ttattcgcag catcctccgc attagctgaa    60
acaacattag agaatctat atcatctatc tgggaagact ttaagaatgc agttgattgc   120
ggttcatgcc aagtgttgtt aggtgggctg aagtttgtgt cagggtttgg tgagaacttt   180
atgattgatg tcttaacagg tctttgtgac atttcaaaag ctgaagattc agatgtttgt   240
gaaggcatca tcaaaaagga gggaccggct ttgcatgacg catttcaagc attgaagata   300
ggaagccatt ccactaagac aatgtgtgcc aatttgattg gcttatgcca gtacccggaa   360
gttaggccca atactttgag cttcccttca ccaaagccaa aagatgtaag acctactact   420
agcggtaaac ctcctatcaa agtcgtgcat ttcagtgaca cacatgtgga cttgttgtat   480
gaaactgggt ccaattacga atgcactaag cctatatgtt gcagagtgtt tgaagataag   540
gatgccccag gcataaccaa gaatccctgt ggacctttg gcaatccaaa atgcgaccca   600
ccgcaagcac ttcaagaaag catgaatgct gcaattgctg agatcaatcc agctttttcc   660
atatacactg tgatgttgt ttcacatgat gtatggttag ttaatcaaga ggaggcctta   720
gagtctttca actctactta ctcacaaatt gaaaagtctt taggtatggt ttatgcagca   780
attggtaatc atgatactgc acctctgaat ctattcccct ccaagaatca gccagatggc   840
aacaatcagt gggcttacga tgcacttgct gaggactggt tagcaatcac ggggatcccg   900
tccgtacaat cagcagacga atacggatcc tattccgcca tacatccaaa ctccaatttg   960
aggatcatat cctacaattc catttctac tacaaattca atttctatat gtaccaagaa  1020
ccaatagaga aggatccaaa tggccaattc gaatggttga tcaaagagct tcaagccgca  1080
gaagatgcag gacaacgtgc atggttgatt agccatattc ctagtggtgt tgcagatcat  1140
ttccacgatc attcacagta tttcgaccaa atagttcaga gatatgaagc aacaatcgca  1200
ggcatgtttt acggtcatac ccacatggat gaatttcaaa tagcttattc agattacaag  1260
aatagaaatt gggaaactgc aactgccatg ggctacattg ccctgcaat gacaccgaca  1320
gaaggacccc caagcttccg tgtttacgaa atagacccag atactttggg cgtccttgac  1380
tttacacagt acattgccaa catttccgac ccagcatatc aaaagaagcc ggaatgggtg  1440
ccctattaca gcgcaaaagc agattatgga agcaagttat ctccgcctgt cacagatcct  1500
aaggtggagt tgtctcctgc attctggcat aacgtgcaga ttagcatgga aagggacgaa  1560
tctgtttttc aagactttg ggctagaaga tcaagaggct acaatgtaac agcctgtaca  1620
ggtgattgta tgaagatgga actatgtact cttagcagca gacgccca atacaattgc  1680
gttaagccta aaccaggttt caactttct aaaagagacg tgaattggg aggttttgctt  1740
gaacaagagt ctcattcaaa ttgtgatcat gcaggattgg ctaccttgtt agggaagatt  1800
gctcataggg ccagagtcgc taggaagatt gaagaagcat aa                    1842

SEQ ID NO: 354          moltype = DNA   length = 1842
FEATURE                 Location/Qualifiers
source                  1..1842
                        mol_type = genomic DNA
                        organism = Penicillium manginii
SEQUENCE: 354
atgagatttc cttcaattt tactacagtt ttattcgcag catcctccgc attagcttct    60
gcagatgatt ggattactac aatttgggac gacttcaaga atgccgttga ttgttttagc   120
tgtcaagcat tgctgggagg attgaagctg gtgtcagggt taggggaatc ctttatgaa   180
```

```
gacgtcatta caggtgtatg ttccatttca ggtgctgaag ataatgatgt ttgtgctggt    240
gtcattgcaa atgaaggacc ggcagtgtac tattcattga agaatttgaa attgggcagt    300
catacggcta agactttctg tgcaacattg actggtttgt gcgaattccc caaggtgaga    360
ccatacgaca tttcttttcc gagccctaaa ccaagcacta ctagacctcc accttctggt    420
gaggctccca tcaaagtggt acacttctca gatacacacg tcgatcttag ctatgaagaa    480
ggatcaaact atgaatgctc aaagccaata tgttgcagag catataccga aaaagatgca    540
ccaggcaata ccacatctcc ttgtggccca tggggaaatt ccaaatgtga tccaccccat    600
cgtttacagg agtcaatgat gtctgctatt gcagatatca atcctgcatt ttccatctat    660
acaggcgatg ttgtagctca tgatgtctgg ttagtcaaca aaactgaagt gctgcaggat    720
cttaatgcta cctattctag tattgaaaat catctcaggtt tagtttacgc tgctttagga    780
aatcatgatg ctgcacccct gaatctgttt ccttccgaca agattccttc ccagtataac    840
ccgcaatggg cttatgacgc tctagccgaa gactggttga cattaacggg gatcccgagc    900
gtgcaaaaag ctagtgagta cggcagttac tcagccgtgc atcctggtag taagttaaga    960
atcattagtt acaactccat cttttactac aagtataact ttttctctta taccgaacca   1020
atggaattcg accccaacaa acagttggac tggttgattg cccaactgca ggaagccgaa   1080
gatgctaagc aaagagtgtg gttgatatct cacataccta caggaaattc agaccacttt   1140
agggaccatt cacattactt tgaccagatc atacaacgtt atgatgctac cattgccgca   1200
ttgttctttg ggcatacaca caccgatgaa tttcagattt cctattccaa ctataagaac   1260
agaaattggg atacagctac cgctatgggc tacgttgctc cgagtatgac gcctacgagt   1320
ggtcctccct cattcagggt gtatgagatt gatcccgtta catttggagt gatggacttc   1380
actcaataca ttgcaaacat aacagacccc tcttttacaaa ctgagccgga gtggaaaccg   1440
tactatagtg ccaaggcaga ctatggtagt aagctgtac cagccattaa ggatccagga   1500
atcgagctta ctccaggatt ttggcataat gtgacggtgg ctatgaaaaa agatgccaca   1560
gtttttcaag acttttggag tagaagaaca agaggattca acgttcctgg atgcactgga   1620
gattgtattt caaacgagat atgtgctttg agggtgcag acgcccagta ttcctgttac   1680
aaacaggcac caggtttttc cttcgagaaa agagatgggt ctggtgttcc ctatttgtcc   1740
gaagaaagct ttcaacaacc agaatgtaat catgcaggta tggcacccct attcgccaag   1800
atttctcaca gggctaagtt ggctagagaa agaggtgaat aa                      1842

SEQ ID NO: 355         moltype = DNA  length = 1842
FEATURE                Location/Qualifiers
source                 1..1842
                       mol_type = genomic DNA
                       organism = Penicillium emersonii
SEQUENCE: 355
atgagatttc cttcaattttt tactacagtt ttattcgcag catcctccgc attagcttct     60
gctccgtatg acaaaagaga cttggctcag gagatttggg acgacattaa gaatgccgtt    120
gactgcgctg gctgtcaagt tgttttgaca gctttgaaag tgttgccga tctgggcaca    180
acagctttag ttgatgtctt aactgaggtg tgcaatatct ctggtaagga ggattcagat    240
gtctgctctg gtatcattag tagagagggt cctgttctag actacgtgct tcaacatcta    300
gacatcgggt ctcatacatc acaagtcatt tgtgcttcag catttggttt atgccaatat    360
cccgaagtga gaccctataa cttgactttt cctaagccca aaccaaacac aaccagacct    420
gaaccttccg gtgaatctcc aattcaagta gtgcacttct ccgatacgca cgttgactta    480
agttacgaga ctggttccaa ttacaattgc actaagccaa tttgttgtag accttacact    540
gccgaagatg cacctgggaa cactactact ccatgtggtc cgtacggtaa taccaagtgt    600
gatgccccat tatccttgga agagtctatg tttgctgcca tcaaagcctt aaaccctcaa    660
ccagcatttt ctatctacac aggagatgtt gtagcacatg acgtttgatcaa    720
aacgaggtta tcgaagattt gaacgcaacg tacgatagaa tggctggtct gggtttagtc    780
tatgccgcta ttggtaatca tgatacagca ccggttaacg acctgccgac gtcaaacatt    840
ccatccgagt attcagcaaa ttggacttat gaagctttgt cttacgactt tacaatgttg    900
actcaaagcg ccagtgctca aactgctgca aactatggtt cctattcagc catttacct    960
ggatcttacg gtacagacct aagagtcatt tcataccaact ctatcttcta ttacgttgac   1020
aactttgtgg cttatcaaga tccaatgaaa tttgacccag atggccagct agcatgttg   1080
ataaacgagt tgcaagaagc tgaaactgct ggccaaagag tctggatcat agcacatgtt   1140
cctacgggta cttccgatca cttccatgac tattctcact actttgacca aatagtccaa   1200
agatatgaag ccacgattgc tgccttgttc tatggtcata cccacataga ccagtttcag   1260
attagttact caaactattc aaacagagca tttgataccg caactgccat cggctacatt   1320
atgccttctt taacacccac tagcggtcca cctaccttta gagttacga cgttgatcca   1380
aagacgttcg cagtgttaga tttcaccaat tacattgcca acatttccga tcctgcattt   1440
caatcaggtc catcatggca gaaatactat tccgccaagg agacctacgg ctcactattg   1500
tctccacctg taaccgaccc tactgctgaa ttgacgcctg cattctggca taatgtcacc   1560
gtggcatttg agcaagacaa cgcaacattt caagagtatt gggctcgtca aaccagggga   1620
tacgatgtct catcatgtac aggtagttgc ataacccaag caatatgcgg attcgtgct   1680
ggcgacgcac aatacaattg tgttactcct actcccggtt tcaacttcgc aaagcgtgac   1740
actagtaacc ccaaacaagc cttgtcacat gttgagaaat gtgaaggatc cggtcttcta   1800
ggcttgttaa ggcgtatggt tgcagactct aaatcttctt aa                      1842

SEQ ID NO: 356         moltype = DNA  length = 1845
FEATURE                Location/Qualifiers
source                 1..1845
                       mol_type = genomic DNA
                       organism = Rasamsonia argillacea
SEQUENCE: 356
atgagatttc cttcaattttt tactacagtt ttattcgcag catcctccgc attagctggt     60
gtcacctacg ataagcgtga tttagcacaa gacatatgga acgacataaa gaatgctgta    120
gattgtgctg gttgtcaagg tatcttgacc gctctaaaag gtctttcata tcttggcact    180
acggcctttg ttgatgtttt gaccgaagtc tgtgacatct ccggaatgga ggactcagac    240
gtttgttccg gcatcataag cagcgaaggc ccagtgcttg actatatcct gaagcaatta    300
gatatcgggt ctcatacttc tcaagtgatc tgcgcctcag ctttttggtct gtgccagtat    360
```

```
cctgctgttc gtgcttacaa ccttacattt ccttcaccaa agccagataa gactcgtcct    420
gaaccgagtg gagaatcacc aatgcaaatt gttcacttta gcgatacaca tgtggactta    480
tcatatgaaa caggtagcaa ctacaattgc actaagccta tttgctgcag accgtatacg    540
gcagacgatg cacctggtaa caccactact ccatgtggac cctacggaaa tacaaaatgt    600
gacgcaccta tgaccttaga ggaatcaatg ttcgcagcca tcaaagcact ttcacctcaa    660
cccgctttca gcatctatac cggtgatgta gtagcccacg acatatggtt agtagaccaa    720
aacgaagtcg ttgaagactt gaatgcaaca tacgatagaa tggcaggttt gggcttggtt    780
tacgctgcca ttggcaacca cgatactgct cccgttaatg atcttcctac ttccaacatt    840
ccctctcagt attcagcaaa ttggacgtat gaagccttag aataccattt ctctttgtta    900
acaaactcag cctctgccca aactgccgag aactatggtt cttactcatc cgtctatcct    960
ggcaagtatg gcacggattt gagagtgatt tcatacaatt ccatattcta ctatgtcgac   1020
aacttctggg catatcaaga tccgatgttg tacgatccag acggccaact ggcctggttg   1080
atcaatgaat tacaagaggc cgaaactgct ggtcaaagag tctggttgat agctcatgtt   1140
ccgagtggga ctgccgacca tttccacgat tactcccact actttgacca aattgttcag   1200
aggtatgaaa ccacgattgc tgccttgttt tacggtcata cccatatgga tcaatttcag   1260
atttcttatt cagactattc caataggcgc tttgatacag caaccgctat aggttacatt   1320
atgccttcca tgacgcctac atctggtccg cctacattca gagtttatga tgttgaccca   1380
aaaacattcg ctgtcttgga cttcaccaac tacatagcca acattagtga tcccgcataa   1440
cagagtggtc caacctggca aaagtactat agtgcaaaag aagcttatgg tccacttctg   1500
tctcctccag tcacagacgc tactgcagag ttaactccag cattttggca taatgttacc   1560
gtggctttcg aaaatgacga tacggctttc caagagtact gggctagaca gacgaggggt   1620
tacgcagttt caaattgcac cggtaattgc gttacccagc ctatctgtgg cctgagggca   1680
ggtgaaagtc aatacaattg tgtcactcca acaccaggct tcaactttgc aaaaagagat   1740
gtctcttcag atggtcaagc acttccccac atagagaagt gtgaaggttc tggcctacta   1800
tccttattgg ccaaaatggt agcctcaaac ggtcagtcaa gttaa              1845

SEQ ID NO: 357          moltype = DNA  length = 1845
FEATURE                 Location/Qualifiers
source                  1..1845
                        mol_type = genomic DNA
                        organism = Penicillium parviverrucosum
SEQUENCE: 357
atgagatttc cttcaatttt tactacagtt ttattcgcag catcctccgc attagctcat     60
attgaatcag cagacaattg gatcaccaca atctgggact tgtcaaaaca agccgtagat    120
tgcgctgggt gtcaagctct gttaggggct ctgaaactgg ctgcagattt gggtgagacc    180
tttatggaag atgttcttat tggtgtttgc aacattgctg gtgttgaaga tcatgatgtt    240
tgttcaggca taatccaaaa cgaaggtcct gccgtacact attcattgct taacttacac    300
attggctctc atacagcaac aactttatgt gcttccttat tcggcctatg ccaatatcca    360
gccgttagac catacaactt atcatttccg gttccaatac ctactaagtc tagaccggaa    420
ccatccggtc agtcacctat cagaatagta cacttctcag acacgcatgt tgacttatct    480
tacgaaacag gctcaaacta tgactgttcc aaacctattt gctgtagacc atacacggag    540
gaagacgcac caggaaatac ctctacccct tgtggcccat ggggtaaccc catgtgtgat    600
ccacccaata gactgcaaga atctatgatg actgctatag cagatttgaa tccagcattc    660
tccatctata ctggtgatgt cccagcacac gacatttggt ctgccacgaa ggcagaggct    720
cttagggact ttaacgctac ttatggatcc atggaaaaac gtttgggtat ggtatttgct    780
gctttgggaa atcatgatgc cgctcctctt aacttgtttc cttccaacaa aatcccgtct    840
gagtattcac cgcaatgggc ctatgacgcc ctagcagcag actggctggg gctgagtgca    900
atggcttccg tgcactccgc aatccatcac gggtcctatt ctgcagtcca ttctgaggat    960
aaactacgtg tcatttcata caactccatt ttctattaca aagataactt ctttatgtac   1020
gaggagccaa tggaacacga tccgaatggt caattcgctt ggttgattag tgaattgcaa   1080
tccgcagaaa gcacctcaca aagagtgtgg ttgatagcaa atattccttc cggtaacgca   1140
gatcacttta gggatttcag ccactacttt gacgaaattg ttcagagata cgataccact   1200
attgctgcct tatacttcgg acatactcat acagacactt tcaaattgca atactccaac   1260
tattcaaata gatcctggga caccgcctct gctatgggat atgtggcacc gtccatgaca   1320
cccactagcg gaagcccaag ctttagggtg tatgaagttg atcccgtcac cttcggcatt   1380
atcgactttta cccagtatat cgccaacatt tcagatccca gctaccagat taaccctaaa   1440
tgggagccct attactcagc taagaaggcc tatggtagca aactatctcc acctgcccag   1500
gacccaggtc cagaaatgac acctgccttc tggcataacg ttactatagc catggaacaa   1560
gatgcttcca tattcaaagc ttttttgggca cgtcgtacta gaggaaacaa agtaacttct   1620
tgtactggca actgtatggc aaattgagatt tgcgcactta ggggtgccga tgcacaatac   1680
aattgtgcta ctcccaccgt tggttttaga ttcagaaaaa gagatatgac tagtgactta   1740
agcttgcaaa aagaagagtt tagacctgaa tgtaatcatg caggaatggg tccattgttg   1800
gcaaagattg tccatcaagc agctttggaa aatgaacgtg ggtaa              1845

SEQ ID NO: 358          moltype = DNA  length = 1845
FEATURE                 Location/Qualifiers
source                  1..1845
                        mol_type = genomic DNA
                        organism = Penicillium flavescens
SEQUENCE: 358
atgagatttc cttcaatttt tactacagtt ttattcgcag catcctccgc attagctcat     60
agtgaatccg ctgagagctg gattagtgac atatgggacc acttcaaaga agctgttgat    120
tgtacttctt gtcaagtttt acttggttcc ttaaagttag tagccgcatt tggcgacact    180
ttcatgtaag atgtattgac tggcgtatgt gctatcagtg ggcagaagaa ccacgatgtg    240
tgtgctggcg ttattgcagg ggagggtcct tctgtgcagt attcactgaa gaacttgaag    300
attggcagcc atactgctaa aactttctgc gccagtttga ttggtttgtg ccagtaccca    360
aaggttagag agtatgacct ggccttccct gcaccaaaaac cgccaaatgg aagaccgcct    420
cctagcggag aacctcccat caaagtagtt catttctcag acacacatgt agacttgca    480
tatgaaccag gttcaaacta tgcatgtagc aaaccctat gttgcaggac ttacaaagag    540
```

```
aatgacgctc ctggcaatac cagttctgct tgtggtcctt ggggcaatcc tagatgtgat   600
agccctcata gactacaaga gtctatgaat gccgcaatcg cagacttaaa cccagcattt   660
tccatttaca ctggcgatgt ggttgctcat gatgtgtggc tagacaacaa gtttgaagtt   720
ctacaaaact tcaatgcaac atatggagct atggaaacta ccctaggtca agtctatgct   780
gccttaggca atcacgatac ggcacctctt aacttgtttc caagttccaa gattccatca   840
atctataacc cacaatgggc ttatgacgct ttgaccgaga attggttagc attgaccgga   900
ataccttcaa tcgaaagcgc agaccagtac ggatcttatt ctgtcttaca cccagattcc   960
aatttgagaa tcatctccta caattccatc ttttactaca aatacaactt ctttgcctac  1020
accgaaccta tggaatatga tccgaattct cagttgaaat ggttgataaa cgagttgcaa  1080
gctgctgaaa aagctagtga gagagtttgg ttgatttcac acataccttc cggtaactca  1140
gaccacttcc acgaccactc tcactactte gaccagatca tccaaaggta tgatgctacc  1200
atagctgctc tattctttgg tcatactcat ctggatgaat tccaaatctc ctattcagac  1260
tacaaatcta gaacttggga cactgccact gctatgggtt acatcgctcc ttcaatgaca  1320
cctaccagtg gtccgccttc atttagagtg tacgatatcg atccagttac ttttggcgtt  1380
ttagatttca ctcagtacat agccaacatc aatgcaccag atcaagaaag tcttgagtgg  1440
gtgccttatc atagtgctaa agaagcttat ggcagtaaac tagtttctcc aattaccgac  1500
ccatcagctg aattgagccc agcttctgg cataatgtta cattagctat ggaaaatgac  1560
agcgctatct tcggagactt ttgggctagg agaaccaggg gttatcaagt gccgagttgt  1620
accggagatt gtattagtgg cgagatttgc acacttaggg gtgccgacgc ccagtacaac  1680
tgtttcgtcc aaaaggttgg tttctctttt gaaaagagag atcatcaagg agattctact  1740
agggaagaaa ggatcttacc tgagtgcaac catgctggca tggctccatt gcttgcaaag  1800
attgcaagat tagctgctat agccagagac atggagaaaa ggtaa              1845

SEQ ID NO: 359           moltype = DNA   length = 1848
FEATURE                  Location/Qualifiers
source                   1..1848
                         mol_type = genomic DNA
                         organism = Penicillium hispanicum
SEQUENCE: 359
atgagatttc cttcaatttt tactacagtt ttattcgcag catcctccgc attagctgaa    60
tcagctgaat catgggtggc atccatctgg gacgacttca aagttgccgt agattgcgct   120
agctgtcaag ctctgttagg gggtctgaaa ctggttgctg aatttggtga gtcctttatg   180
gaagatgttc ttattggtgt ttgtgatgta tctggtgttg aagattcaga tgtttgtgct   240
ggtgtcatcg caaacgaagg tcctgccgta cactatacat tgaagaactt agagattggc   300
tctcatgcag caaatacttt atgtgcttcc ttagtcggcc tatgcgaata tccagcctgt   360
agaccataca acttatcatt tccgtctttg aaacctgcta cctctagacc tccaccatcc   420
ggtaagcctg caatcaaagt agtacacttc tcagacacgc atgttgactt atcttacgaa   480
acaggctcaa actttgactg ttccaaacct atttgctgta gagtttacac ggaggaagac   540
gcaccaggaa atacctcttc ccccttgtggc ccatgggata accccaaatg cgatccaccc   600
catagactgc aagaatctat ggttgaagct atagcagttt tggatccagc attctccatc   660
tatactggtg atgtcgttgc cacgatgtt tggttggtga acaagtccga ggctcttcag   720
gactttaacg ctactatgg agcaatggaa atcgttttg tcctgtata tgctgctttg   780
ggaaatcatg atacggctcc tcttaacttg tttccttcca acaaaatcag cagagagttac  840
aatccgcaat gggcctatga cgccctagca gcagactggg ctgccttgac cggaattcca   900
tccgtggcat ccgcaaggga atacgggtcc tattctgcaa tacatccaaa ctcaaatcta   960
aggatcattt catacaactc cattttctat tacaggttta acttctttgc ttacgaggag  1020
ccaatggaat acgatccgga ttctcaactg gcttggttga ttaccgaatt ggatgcagca  1080
gaaacggcag gtcaaagagt gtggttgata tcccatattc cttccggtaa gccagatcac  1140
tttagggatc acagccacta cttttgaccaa attgttcaga gatacgatgc cactattgct  1200
gccttattct tcggacatac tcataaagac gaatttcaga tttcctactc cacatataca  1260
aatagagcat gggacaccgc cactgctatg ggctatatcg caccgtccat gacacccact  1320
agcggaccgc caagctttag ggtgtatgaa attgatcccg tcaccttcgg tgtaatggac  1380
tatacccagt atatcgccaa gatttcagat agttctgccc aaattgacac aactcctgag  1440
tgggtaccct actattccgc caaggcagat tacggtgcca agttagctcc accggtcgaa  1500
ggtgcaggag tcgagttaac tccagccttt tggcataatg tcacggtagc tatggaagca  1560
gattcatcct tgtttcaagc tttttgggg agaagaacac gtggctacaa tgtttcatct  1620
tgcaccggag aatgtatggc cactgagata tgcgccttga ggggtgcaga tgcccagtat  1680
tcttgtgttg gcgctaaacc aggtctgtct ttttctaaga gaggtggcaa ggatgtggat  1740
gttttgtggc aaagaagact acaaccagaa tgtaatcatg ctggcatggc tccactcttt  1800
ggtaagattt ggacaagagc tgctttagtt tggcgttcag aagcttaa              1848

SEQ ID NO: 360           moltype = DNA   length = 1854
FEATURE                  Location/Qualifiers
source                   1..1854
                         mol_type = genomic DNA
                         organism = Penicillium simplicissimum
SEQUENCE: 360
atgagatttc cttcaatttt tactacagtt ttattcgcag catcctccgc attagctggt    60
gctaccgaga actggattag tactatatgg aatgacttca agaagctgt ggattgtgat   120
agctgccagg ttctgttagg gggttttgaaa ttggttgccg attttggaga aggctttatg   180
gaagatgtct taactggtgt ttgtgacatt tctggtgcag aagatagaga tgtctgcgca   240
ggggttattg caagtgaagt accagcattg cactacgcaa tcaaaaacat gcatgtaggt   300
tcacatactg ctaaaacctt atgcagtgca ctggttggtc tatgcgattt tccagactgt   360
aggccatttg acttggtttt tcctttctcct aaaccagcca attctagacc tccccctcc   420
ggcaaacctc ctatcaaggt tgtgcacttt tcagatacac atgtggactt aagttatgag   480
actggctcaa actatgactg tagtaaacct atttgttgca gggttacac agatgatgag   540
gccccaggaa ccacagacaa accatgtggt cccttgggaa taccaagtg tgatccgcca   600
catcaactac aagaatctat gatgactgct attgctgaac ttaatccagc attttccatt   660
tacactggag acgttgttgc tcatgacgtg tggttagtga ctaaggagga agttctacaa   720
```

```
gatttgaatg caacttatgg tgccatggaa aatcatttag gtttggttta tgctgcatta    780
gggaatcacg atgccgcacc cttaaacttg tttcccagcc ataacgttcc aagcaaatac    840
aacccacagt gggcatatga tgccttgact gccgactgga tggctttaac cggcatagaa    900
aatgtgcaaa acgccaatga atatggatcc tattctgcca ttcatccaaa ctccaagtta    960
cgtatcattt cttacaattc catctttac tacaagtaca atttcttctc ttatactgag   1020
ccaatggaat atgatccgaa tgggcagttg acctggttga ctgaagaatt acaggcagca   1080
gaaaatgccg acaaagggt atggttgata tcccatatac cttcaggtga tgtcgatcac   1140
ttcagagatc atagccacta ctttgaccaa atcatacaga gatatgaggc aacaattgcc   1200
ggattgttct ttggtcacac tcatacagat gaattccaag tatcttattc cgattacaag   1260
aacaggaact gggatacggc aacagccatg gggtacgttg cacctcaat gacaccgact    1320
agcggttccc cctctttag agtatacgac atcgacccag taacctttgg tgtgctagat   1380
ttcacccagt acattgcaaa catcagcgat gctagcttcc aaacaaagcc tacatggata   1440
ccatactaca cggccaaaaa ggattacggt tcaaagcttc cgaccattcc agatgatacc   1500
gctgaactta ctccggcttt ctggcataac gtgacagttg ctatgaaaa agattccgca   1560
gttttgatg aattctgggc tagaagaacg agaggctaca atgtaccagc ctgcacagga   1620
gattgtgcca aaaacgaaat ctgcgctctt agaggcgcag acgcacagta ttcttgcgtg   1680
caaagaactc caggggttttc tttttccaaa agagacggag tagacggtga aatggaagaa   1740
gttgctcctc tattgtctaa aagatttcag cctgaatgta atcatgccgg tatggctccc   1800
ttgttagcca agatagctca caacgccaat ttggctaaga tgaatggcga ataa          1854

SEQ ID NO: 361         moltype = DNA  length = 1857
FEATURE                Location/Qualifiers
source                 1..1857
                       mol_type = genomic DNA
                       organism = Penicillium vasconiae
SEQUENCE: 361
atgagatttc cttcaattt tactacagtt ttattcgcag catcctccgc attagctggc      60
gcagtcgagt cttggatttc aactatttgg aatgatttca aagaggcagt agattgcggg    120
agctgtcagg tactgttggg tggtttgaaa cttgtagcag attttggaga aggcttttg     180
gaagatgtct taactggtgt ttgtgacatt agtggtgctg aagatagga cgtctgcgct    240
ggtgtaatcg caagtgaagt accagcccta cattacgctt tgaaaaacat gcatgtaggt    300
tcacatactg caaaaaccct ttgtagcgct ttggtcggct tgtgtgattt cccggatgtt    360
agaccgtttg gtttgacatt tccttctcca aagccagcta aatcacgtcc tcctccctct    420
ggaaaaagcc ccattaaggt ggttcacttt agtgatacgc atgtagactt aagctatgag    480
acaggatcaa actatgactg ttcaaaacct atctgctgtc gtgtctatag tgatgaggat    540
gcacctggta agacagataa accgtgcggt ccgttggca acacaaaatg cgatccacca    600
caccaattgc aagaaagtat gatgacagct atagccgatt gaatccagc ttttccatc     660
tataccggtg atgttgttgc ccacgacgta tggttggtca acaaagatga agtattgcaa    720
gattcaatt caacttacgg tgctatggaa aatcatttgg gtttagttta cgcagccttg    780
ggaaaccacg atgctgcacc cttgaatctt ttcccatcca agaatgtgcc aagtaagtat    840
aacccgcaat gggcatacga cacgttgacg gccaattgga tgcccttac cggcatagag    900
tcagtgcaga atgcaaatga atacggttct tactcagcaa tacacccaaa ttcaaagctt    960
aggatcatat cttacaattc tatcttctac tacaaatcca acttcttttc atacactgag   1020
cctatggaat acgatccgaa cggtcagtta acttggttga tatcagagct acaaagtgct   1080
gagaatgctg gacaaagagt ttggttgatt agtcacattc catcaggcaa tgtggaccac   1140
tttagagacc attctcatta ctttgaccaa atcattcaac gttatgaagc taccatagct   1200
ggtttgtttt tcggtcatac tcatacagac gaatttcaaa tagcatatag tgattacaag   1260
aacagaaatt ggaatacagc cacagccatg ggttacgtcg ctccgagtat gactccgact   1320
agtggcccac catcttttcg tgtctacgac attgatcccg ttactttcgc agttatcgac   1380
tttacacagt atatcgccaa catatcagac cctactttc agaagaaacc agattgggtc   1440
ccgtactatt ctgccaaaaa ggattatgga ggcaagcttt ctccaaggcc tgccgataca   1500
gccgagttga ctccggcttt ttggcacaac gttacagttg ctatggaaaa ggattcttca   1560
gtctttaacg agttttggc acgtagaaca agaggctaca atgtgcctgc atgtactggt   1620
gactgtgtca agaacgagat ttgcgctcta agagggcag atgctcaata ctcctgtgtt   1680
caaagaaacg caggttttag tttttctaag agggatgag aaaatgttga tggagatgtt   1740
ggaaactatc ccttgttatc aaagagtgtttt caaccagaat gcaatcatgc tggtatggct   1800
ccattgttag ctaagatcgc tcataaagct tccttggcta aggcaaatgg tgaataa       1857

SEQ ID NO: 362         moltype = DNA  length = 1860
FEATURE                Location/Qualifiers
source                 1..1860
                       mol_type = genomic DNA
                       organism = Talaromyces columbinus
SEQUENCE: 362
atgagatttc cttcaattt tactacagtt ttattcgcag catcctccgc attagcttac      60
gactctgcct tggtagatca taacttagta tccgatatct gggaagatat caaggaggct    120
gtgacatgcg ctggttgtca agttatctta gctgccttga aggtgtctc agatttgggt     180
actacagctt tggttgatac tttgacaggt gttgtaaac taagcggagc cgcagatgat    240
aacgtatgtg aaggcattat ctccaggag ggtgcagttc tacattatgt attgtcagaa     300
ttgtccttag gaagtgaaac gtcaaatgca ctttgtgctt ctgccttcgg attatgtctg    360
tatccagatg taagaaacta tactctgaac tttccttcag ccaaacctaa gaacataaca    420
cgtcctgctc cgagcggtaa acctccatt caggtagctc actttagcga tacccatgtc    480
gatctatcat acgaagtagg ttccaactgg aattgcaaca aactatttg ctgtaggtcc    540
tttgaggctt cagatgctcc cggtaacaca actacccctt gggccatt tggtaacact    600
aaatgtgaca caccattgac attggaagag aatatgttag attccattaa gaaatcagac    660
ccaactccag ctttcagcat ctatacgggt gacgtcgttg ctcacgacat tggttagtc     720
gataaagatg aggttttgac agacttgaat gctacttatt cctaatggc cgaaatagcc    780
accgtatatg cagccattgg taaccacgat accgctccac tgaatgatct tccaaccacg    840
caagtaccctg agagctacag cgccaactgg acatatcaag ccctagcaac aaactttacc    900
```

```
acgttaacaa gagattcctc agttatctca gtagcaaaga actatggtag ctactcttct   960
gtctttaccg gttcttacgg tacagactta aagatcattt cctataactc tatgttctac  1020
tatgtggata acttctatgc cttttggat cctatgccat acgacccaga tggtcagtta  1080
gcttggttga ttgatgaact acaatccgca gaaacagctg ccaacgtgt gtggttgatt  1140
gcccatgttc caaccggtag ctccgaccat tttcacgact atagtcacta ctttgatcaa  1200
attgtccaaa gatatgatgc aaccatagca gccttgttct ttggacatac gcacaccgat  1260
caattccaaa tagcctacag cgattatgca aaccaaaacg cagacactgc cactgcaatc  1320
ggctacatta tgcccagtct taccccaaca agtggtccac ccgcatatag gatctatgat  1380
attgatcccg tgacgttctc tgtgctagat tacacggtct acataaccaa catatctcac  1440
ccagatttcc aaaagggtcc aaagtgggag aagtactatt ccgcaaagga tacatacggg  1500
agcttgctgt ctccacctgt gacagatcca tctgctgaaa tgacaccagc ttttggcat  1560
aacgtgactg cagtattcga atcagatgat gtagctttcc agggatactg ggctaggcaa  1620
accaggggct acgatgtctc agactgtacg gatgaatctt gtaagaacca aactatttgt  1680
gccttgagag ctgcagatgc tcagtacaat tgcgttgttc catctatagg ctttaacttc  1740
gctaaaagag atgatacgga ccaagctcat gtcagggctc aaaaagagaa atgtgatgat  1800
acaggtcttg tgtccttatt gggtaagatt ttggcaaaat caaagaaaac tacaaactaa  1860

SEQ ID NO: 363        moltype = DNA  length = 1860
FEATURE               Location/Qualifiers
source                1..1860
                      mol_type = genomic DNA
                      organism = Talaromyces variabilis
SEQUENCE: 363
atgagatttc cttcaattt tactacagtt ttattcgcag catcctccgc attagcttcc    60
agctctgcct tgatagatag agacttagca tccgaaatct gggatgatat caaggaggct  120
gccacatgcg ctggttgtca agttatctta gctgccttga aaggtgtctc agatttgggt  180
actacagctt tgattgatac tttgacagaa gtttgcaaga taagcggagc cgaagatgat  240
gacgtatgtg aaggcattat ctccagggag ggtcctgttc tacactacat tttgtcacaa  300
ttgtccttag gaagtgaaac gtcagatgca ctttgtacta ctgccttcgg attatgtgcc  360
tatccagatg taagaaacta tactttgact tttccttcag ccaaacctga gaattccaca  420
cgtccttcaa gcagcggtga atcacctatt caggtagtac actttagcga tacccatgtc  480
gatctatcat acgaaacagg ttccaactgg aattgcacaa aacctatttg ctgtaggtcc  540
tttgactcat cagatgctcc cggtaacaca aagacccctt gtgggccata tggtaacact  600
aaatgtgacg caccaatttc attggaaaag tctatggtag attccattaa gggtttaagt  660
ccagctccac ctttcagcat ctatacgggt gacgtcgttg ctcacgacat ttggttagtc  720
gatgaagatg aggttttgac agactttatct tctacttatg gttagtaca ggatgtcggc  780
accgtatttg cagccattgg taaccacgat accgctccag tgaatgatct tccaaccacg  840
caagtaccta gcacgtacag cgccaactgg acatatgaag ccctagcagg aaactgtacc  900
acgttaacag gtgattcctc agttatgtca gtagcagaa actatggtag ctactcttcc  960
gtctttaccg gttctcacgg tacagactta aaggtgattt cctataactc tatcttctac  1020
tatgccgata acttctatgc cttttggat cctatgccat acgacccaga tggtcagtta  1080
gcttggttga ttgatgaact acaagcatcc gaaacagctg ccaacgtgt gtggttgatt  1140
gcccatgttc caaccggtag ctccgaccat tttcacgact atagtcacta tttggatcaa  1200
attgtccaaa gatatgatgc aaccatagca gccttgttct ttggacatac gcacaccgat  1260
caattccaaa tagcctacag caactattcc aaccaaaacg cagacactgc cactgcaatc  1320
ggctacattg cacccagtct taccccaaca agtggtccac ccgcatatag ggtgtatgat  1380
attgatcccg tgacgttcgg tgtgctagac tttacggtct acatagccaa cataagcgac  1440
ccagattacc aaaacggtcc aacatgggcc aagtactatt ccgcaaagga aacatacggg  1500
agcttgctgt ctccacctgt gacagattca tctgctgagt taacaccagc ttttggcat  1560
aacgtgactg cagtattcga aacagatgat gcagctttcc agggatactg ggctaggcaa  1620
accaggggct acgatgtctc aaactgtacg gattcatctt gtaagaacca gaacatttgt  1680
gccttgagag ctgcagatgc tcagtacaat tgcgttgttc catctatagg ctttaacttc  1740
gctaaaagag atgaaacgga ccaagctcat gtcaaggctc aaaaagagaa atgtgatgat  1800
gcaggtcttg tgtccttatt gggtaagatc attagtaaat caagagacgt ttcaaactaa  1860

SEQ ID NO: 364        moltype = DNA  length = 1860
FEATURE               Location/Qualifiers
source                1..1860
                      mol_type = genomic DNA
                      organism = Talaromyces rugulosus
SEQUENCE: 364
atgagatttc cttcaattt tactacagtt ttattcgcag catcctccgc attagcttct    60
tccagtgcat tggtcgacag agatctagca agtgagatat gggatgacat caagaaagct  120
gctacttgta ctggatgtca agtgattctt gctgccttga aaggcgtatc agacctttggt  180
acgaccgtat tggtagatac tcttacagaa gtttgcaagc ttagtggagc cgaggatgac  240
gatgtatgcg aaggcataat cagcagagag ggtccggtct tgcaatacat ccttttcacag  300
ttatccctgg gttctgaaac ttcagacgcc ctgtgcgcat cagcttttgg gctttgctca  360
tacccagatg tgagaagcta caccttgaca tttccatcta cgaaacctga gaatagcaca  420
aggccgagta gttcaggaca agctccctatt caagtcgttc acttttcaga taccccatga  480
gatttgtctt atgaaacggg tagtaattgg aattgcacaa aaccgatctg ttgcagatcc  540
tttgactcta gtgacgctcc aggcaatact tcaactcctt gtggccctta tggaaataca  600
aagtgtgatg cacctttaag cttggaagag tccatgttcg attccataaa gtcattatct  660
cccgctccac ccttctcaat ctatactgga gatgtggtcg cacatgatgt ttggatagtt  720
gacaaagatg aagtccttac agacttgaat gccacttatt ccttgatggc tgaggttggt  780
acggtatacg ctgccatagg gaatcacgac accgctcct taaacgattt gccaacttca  840
caggttcctt ctacatattc agcaaactgg acttaccaag ctttagctac caatttcaca  900
acactatcag gcgatagctc tatcatgtcc gtagctgaga attacggttc ctactcatcc  960
gttttgctg gctcccatgg tacagacttg aaagtgatta gttacaactc cattttctac  1020
tacgtcgaca acttctatgc attcttagat cctatgccat acgacccaga cggccaatta  1080
```

-continued

```
gcttggttga tagatgagct gcaagctgct gaatctgctg gccagagagt ctggttgatt   1140
gcccacgtgc cgaccgggtc tagcgaccat ttccacgact actctcacta ctttgatcag   1200
atagttcaaa ggtacgatgc tactattgca gccttgtttt tcggtcacac acatacagat   1260
caatttcaaa tagcttattc cgattactca aatcagaata gtgacactgc aacagcaatt   1320
ggatacatca tgccgtcatt aactccaacg agtggactcc cagcttatag agtttacgat   1380
attgatccgg ttacctttgg cgtgttagac tttacagtct acattgcaaa catctccgac   1440
ccggattatc aaaacggtcc aacctgggct aagtactata gtgctaaaga aacttacggg   1500
accttattga gtccagccgt tacagactct agtgctgagt aacaccagc ttttttggcac   1560
aacgttaccg cagtattcga aacggatgat acttccttcc aaggttattg ggccaggcaa   1620
accaggggtt atgatgtgtc caattgtacc gattcctcct gtaagaacca gacgatctgc   1680
gcactaaggg ctgccgatgc tcagtacaat tgtgtcgtac ctactattgg cttcaacttt   1740
gccaaaagag atgaaacaga tcaggcacac gtaaaggccc aaaaagagaa atgcgacgat   1800
actggtttgg tatccttgtt agggaaaatc atttcctcaa gtcgtaatgt ttcctcttaa   1860
```

SEQ ID NO: 365          moltype = DNA   length = 1860
FEATURE                 Location/Qualifiers
source                  1..1860
                        mol_type = genomic DNA
                        organism = Hamigera terricola SEQUENCE: 365
```
atgagatttc cttcaatttt tactacagtt ttattcgcag catcctccgc attagctcaa     60
atgcaaacat ctgaacgttc atggggatct acgatatgga aagacgtgga ggaagccgta   120
gactgtgctg gttgtgaagt catcttagga gccttgaaac ttgttgcaga tttaggtaaa   180
ggtactttag aaactgctat gattgatgtt tgtgatctgt ctggggctga agatagtgat   240
gtatgttcag gtttgataac agccgaaata gatgccttgt actatgcctt gaacaatgtc   300
catgtcggct cccacacatc aaaggtgttg tgtgctcacc tgtttggttt gtgctcttat   360
ccagatgtta ggtcttatca cttgatcttt cctagttcaa aacccgctac atcccgtcct   420
tcaccgagcg gtcaaaaacc cattaaggta gctcacatta gcgataccca tgtcgatcta   480
tcatacgaac ctggttccaa ctacgaatgc tccaaaccta tttgctgtag ggcatatacc   540
aaagaagatt ctcccggtaa cacaccccac ccttgtgggc catatggtaa cacaaattgt   600
gacgcaccat atagattgga agagtctatg tttgctgcta ttgaagcttt agacccagct   660
tttctatct acacgggaga cgttgtcgca catgacatat ggttggttaa tgaaactgaa   720
gttctggatg atttagatgc aacttattcc ttaatgaaat ccctgggtct agtctacgca   780
gctgtaggca atcatgatgc cgctcccgtt aatctgtttc ctagtaatcg tatccctttca   840
acatactctc cgcagtgggc ctatgatgct ctagccgaag actggcttgc tcttacgaat   900
gattcttccg tcgattctgc cagagaatac gggtcatatt cagccgtgta tcaggatca    960
aacttgagaa tcatttccta caatagtgtg ttctactata aggataactt ttggatgtac   1020
gaagacccca tggagtatga tccaaacgga caactggcat ggttgattaa cgaattacaa   1080
gcagctgaat ccgcaggtga aagggtatgg ttaatctctc acatcccttc aggtaactca   1140
gatcatctat atgactatag tcactatttc gatgctatcg tgcaaagata tgaagctacc   1200
attgctgcct tattcttcgg acatactcat acagatctat ttcagatcgc ctattcagac   1260
tatgataaca ggaactggga tacagccact gccatagggt atatcgctcc tagtatgaca   1320
ccaacaagtg gcagtcccgc ttttaggatc tatgaggtcg atcccgtgac ttttggtatt   1380
cttgactaca cagtttacat agccaatatc tcccatcctt catatcaaac gcagcctact   1440
tgggaaaagt actattccgc caaggaggct tatggatcct tgttaactcc accggtgaca   1500
aacccatcta tagagttaac tccagctttt tggcataacg ttactgtctt aatggaggac   1560
gatgaatcag tgttcaaaga cttttgggct cgtaccacaa ggggctttaa cgttttccacc   1620
tgcgtcggta gttgtatgac tgaggagatt tgtgctctta ggtctgcaga tgctaagtac   1680
aattgtgcaa ctgctaagcc tggtctgaac ttttttgaaaa gagatgatgt cgaagctcaa   1740
tcaaaacctg tgaagccaca atgtgaagac tctggattgg ctgcagtttt ggtcaaaatg   1800
atggagaata cagatgattt cgctggtttg ttgaaagaaa aggctttagc acatggctaa   1860
```

SEQ ID NO: 366          moltype = DNA   length = 1860
FEATURE                 Location/Qualifiers
source                  1..1860
                        mol_type = genomic DNA
                        organism = Penicillium piscarium SEQUENCE: 366
```
atgagatttc cttcaatttt tactacagtt ttattcgcag catcctccgc attagctaga     60
accgaagcag cagacagctg gatttccaac atatggaacg agttcaaaga agctgttgat   120
tgtggttctt gtcaagtttt acttggtggc ttaaagttag tagccgattt tggcgagggt   180
ttccttgaag atgtattgac tggcgtatgt gatgtgtctg gcgcagaaga cagggatgtg   240
tgtgctggcg ttattgcaaa cgaggtacct gctctgcact atgcactgaa gaacatgcat   300
gtaggcagcc atactgctaa aactctgtgc agcgccttag ttggtttgtg cgacttccca   360
aacgttagac cgtttgactt gaccttccct tcaccaaaac cggctaaaag tagaccgcct   420
cctagcggaa aacctcccat caagtagtt catttctcag acacacatgt agacttgtca   480
tatgaaactg gttcaaacta tgattgtagc aaacccatat gttgcagggt ttactcagac   540
aaagacgctc ctggcaaaac cgacaaacca tgtggtcctt tcggcaatac aaaatgtgat   600
ccgcctgaaa gactacaaga ctctatgatg gctgcaatcg cagacttaaa cccagcttgt   660
tccatttaca ctggcgatgt ggttgctcat gatgtgtggc tagtcaacaa agatgaagtt   720
ctacaagact tcaatagtac atatggagct atggaaaatc acctaggttt ggtctatgct   780
gccttaggca atcacgatgc cgcacctctt aacttgtttc catccaacaa cattccatca   840
aagtataacc aagatgggc ttatgaggct tgaccgcaa attggattac cttgaccgga   900
atacagcag tccaaaacgc aaacgagtac ggatcttatt ctgcaattca cccaaattcc   960
aaattgagaa tcatctccta caattccatc ttttactaca aatacaactt cttttcctac  1020
accgaaccta tggaatatga tccgaatggt cagttaactt ggcttataga gagttgcaa   1080
gctgctgaaa atgctggcca gagagtttgg ttgatttcac acatacctag tggtaacgtt  1140
gaccacttcc gtgaccactc tcactactc gaccagatca tccaaaggta tgaagctacc  1200
atagctggtc tattctttgg tcatactcat acggatgaat tccaaatcag ttattcagac   1260
```

```
tacaagaata gaaattggga cactgccact gctatgggtt acgtggctcc ttcaatgaca   1320
cctacctccg gtccgccttc atttagaatc tacgatatag atccagaaac ttttgccgtt   1380
atggatttca ctcagtacat agccaacatt tctgaagctt cttttcaaac caagccaaac   1440
tggatacccct attactctgc taagaaagat tatggcggta ggttgactcc accaccccg    1500
aatacagctg aattgacgcc agcttttctgg cataatgtta cagtagctat ggaaaaagac   1560
agctctgtct tcaatgagtt ttgggctagg agaaccaggg gttattctgt tccagcctgt    1620
accggagatt gtgtaaagaa cgagatttgc gctcttaggg gtgccgacgc ccagtacagt    1680
tgtgtccaaa gaacgccagg tttctctttt tcaaagagag atgatggtga agttgaagtt    1740
gacttggaaa atgctccttt actttccaag agattccagc cagaatgtaa tcacgcagga    1800
atggcaccct tgttagccaa aatcgctcac aaagcctcaa tagccaaaat gaacggttaa    1860
```

SEQ ID NO: 367          moltype = DNA   length = 1866
FEATURE                 Location/Qualifiers
source                  1..1866
                        mol_type = genomic DNA
                        organism = Talaromyces bacillisporus
SEQUENCE: 367
```
atgagatttc cttcattttt tactacagtt ttattcgcag catcctccgc attagctggt   60
caaactccaa cgtcatcact agttgccaga gatttggcca gcgagatttg gaatgacatc   120
aaagaagctg ctacctgtgc tggatgtaaa gttatcttgg ctgccttgaa aggtgttgca   180
gatttgggta ctacagtttt gattgatgtc ttgacagagg tttgcaaaat ctcaggagaa   240
gaagatgacg atgtatgcga aggcatcata agtagagagg gtccagtttt ggagtacata   300
cttagtcagt tatcactatc ctctgaaact agcgacgtct tatgtgcctc tgcttttgga   360
ttgtgctctt atccggctgt tagagattac acattgacct ttcctagtcc caagccagcc   420
aacattacta gaccttctcc gtcaggtaag tcaccgattc aggtagtcca tttctcagac   480
actcatgttg atctgtccta tgagacaggt agtaattgaa attgcaccaa acccatttgt   540
tgtcgtgcct atgaggcttc cgacgctcca gggaatacta ctacccccatg tggtcccttac   600
ggtaatacaa aatgtgacgc tccattatct ttggaacaat ctatgatcga ttccatcaaa   660
gccctggacc ctgccccagc cttctccatt tacacaggtg atgtagtcgc tcatgatatc   720
tggattgtag atgaaagtga agtcttaaca gacttaaacg ctagttactc cttaatgaca   780
gagacaggta aggtgtttgc cgctattggg aatcatgact ctgctccggt aaatgatctg   840
ccgacgacgc aggtgccttc caaatacaac gcaaactgga cctatcaggc cttagccaat   900
aacttctcaa ctcttacagg agacagcgca gtcttaagcg tggctgaaca atatggctct   960
tattcctcag tcttacagg ctcctatggt acagacttga aggtcattttc ttacaatagc   1020
atctttctact acattgataa cttctatgcc ttcttagatc caatgcctta tgatccagat   1080
ggtcaactag cttggttgat tgaagaactt caagccagcg aaacagctgg gcaaagagtt   1140
tggttaatcg cacacgttcc aacgtcatca tccgaccatt tcatgactct ttcccactac   1200
tttgatcaaa tcgtacaaag atatgaagct accattgctg ccttgttctt tgggcataca   1260
cacacagacc aatttcaaat ctcatacagt aactatagca atcaaaacgc agatactgca   1320
tccgcaatcg gctacattat gccatctctt accccaacct ccggtcctcc agcttaccgt   1380
gtgtacgata tcgatccagt aacgtttgga gtcttagatt tcacggtgta cattagcaac   1440
atatcagatc ctgccttcca gaatggtcct acatggtcaa agtactacag cgctaaggaa   1500
acttacggga gtttgttatc tccaccagta acagattcca gctgtgaact tacgccagca   1560
ttttggcata atgttactgc agttttcgag acagatgatg atgcctttca aggctactgg   1620
gctaggcaaa ccagagggta tgatgtttca aactgcacag atacttgtaa gaatcaaact   1680
atatgtggta tcaggggtgc cgatgctcag tacaattgtg ttgtcccaa gattggcttc    1740
aatttcgcaa aaagagatga aaccgatcaa gctcatgtca aaactcaaaa agaaaagtgc    1800
gatgatgctg gtctagcttc tctatttggt agaatggttc caaactcaaa gaatgcctcc    1860
aattaa                                                              1866
```

SEQ ID NO: 368          moltype = DNA   length = 1872
FEATURE                 Location/Qualifiers
source                  1..1872
                        mol_type = genomic DNA
                        organism = Galactomyces candidus
SEQUENCE: 368
```
atgagatttc cttcattttt tactacagtt ttattcgcag catcctccgc attagctgcc   60
ccacctacca ctaagagatc cttggccagc gacatttggg atgacattgt tgatgctgtt   120
gactgtggtg catgtgatac tatcttggaa gccttgaaag gtttggcaga tttgggtaat   180
acagttttg ttgatgtctt gacagacgtt tgtgatatct caggagctga agatagtgat    240
gtatgctctg gcactatatc cgaagaaggt cccatttttga ggaccataat caaggggtta   300
tcagtcggct ctgctactag cgacttgttt tgtgggactt tgttgggatt gtgccaaaat   360
ccggctattg catcatggtc agtccccttt cctaaaccca agccaaacac ggttcgtcca   420
cctccaagcg gtcaaagtcc aatctctgtc gcacacatca gtgatgtgca tgtagatcta   480
agctacacta ccggagccaa ctatgactgt tccaagccaa tctgttgtag accgtacact   540
agcgatgatg ccctggtaa cacagattat cctgctggtc catacggaaa tacaaattgt    600
gatgccccat tggatttgga atcatccgct atggcagcca tcagaaaact gaatccggca   660
ttctctatct tcactggtga cgtagctgct catgacgttt ggttggtgaa tcaagcagaa   720
gtagaattgg acttgaatac aacatacaat acacagttca caactttagg cacagttttt   780
ccggctcttg gtaatcacga tgttgcccca gtgaacggat tgcaccgtc tggggtgagc    840
agtaatccca acatacagtg ggcatacgac acaaacgccg aagattggac aaagtggatt   900
ggctcaacag cagccaatgc tgaagagagc tttggtgcat agtattgt tcacggcaac    960
ttaagagtca tctccttcaa ttccattttc tactatagac tgaatttcta catgtaccaa   1020
gatccactac aaagagaccc ttcatcccaa ttctcctggc tagtaaatca actacaagct   1080
gcagaagatg ctggtcagag agcctggttg atatcacacg taccatctgg ctcaggggat   1140
tactttccac agtattcaaa ctacttcaat caaattgtta acagatatga agctacaatc   1200
gcagcattgt tttacggtca cactcacgtc gaccaatttg agatatcata ctccgactac   1260
tcaaaccaga atagcaacac ggctgtggct atgtcctaca ttactcctag tttgacccc    1320
acttcaggct ctccaagttt cagaatctac tctattgatc cagtgacgta cggagttctg   1380
```

```
gactatacaa actacatagc caacatttcc agcccgacat atcagaatgg accacaatgg    1440
gtggagtact attctgcaaa agccgcttat ggtccgtacg ttagcccacc attgacgtcc    1500
gctgctgctg agttaacacc tgcttttggg cataatgtga cggttgcatt tcagaacaac    1560
aatgacttgt tcaggagta catatcaaga aagtctaggg gcttcgacgt tagttcttgc     1620
actggtcat gtcaaacaga cgagatttgt caattgcgtc ctgctgaatc ccagtataac     1680
tgtgtaacga tttcaccagg catcaacttt aacaagagag atcaacaatc aaacctaggt    1740
gctcaagaaa agcataggga tggttgtgaa ggttctccta ttcgtgacat ctttgctact    1800
ttgatgcaag acagaagagg tctagtttca gccattaacg aagggatcgc taagagatct    1860
attagagcct aa                                                        1872

SEQ ID NO: 369           moltype = DNA  length = 1881
FEATURE                  Location/Qualifiers
source                   1..1881
                         mol_type = genomic DNA
                         organism = Penicillium megasporum
SEQUENCE: 369
atgagatttc cttcaatttt tactacagtt ttattcgcag catcctccgc attagctaat    60
atcatagaat cttgggcctc agagatatgg gatgacataa agaatgcagt cgattgtgct    120
ggttgtgaaa ccatcattgg tgccttgaag gtagtcgcag atcttggtaa aggcaccttg    180
aacggcacat tgatagatgt ttgcgatcta tcagggggtgg aggatccaga cgtctgtacc    240
ggcttaatct cttcagaaat cgacgcattg tattactcct tgaaaaacat ggcagtagat    300
tcacacacgt ctaaagtttt gtgtgctggc ctgttctcat tatgtccatt tccagccgct    360
aggccctata acttgagctt ccccacacct aaaccagcta cgtcaagacc tgctccgagt    420
ggacagcaac ccatcaaagt agctcacatt tcagacactc acgttgattt agactatgaa    480
gctggttcca actatcagtg tagtaaaccg atttgctgta gaccgtacac tgccgaagac    540
gctcccggta atacctctca cccttgtggt ccatgggaaa acaccaaatg tgatccacct    600
ttcagattag aagaatcaat ggttgcagcc gtgaatgcct tgaatccttc ctttttcatt    660
tacactgggg acgtcgttgc ccatgacata tggctggtca acgaatctga agtattgaca    720
gacttgaacg ctacttactc cttgtttcaa aacttgaatt cccctagttta tgccgctgtt    780
gggaatcaag atgtcgcacc ggtaaaacctt tccccatcca ataagataga ttctgcctat    840
aacccacaat gggcttatga tgcttttgaca gcagactggt tggcattaac caatgggcgat   900
agtagtgtag cctctgccaa agccgacggc tcatattctg ccatctatcc tggaacaaac    960
ttgaggatta tctcctacaa tagtatcttc tattacaaag ataacttctg gatgtacagc    1020
gaccctatgg aatatgatcc aaacggtcaa ttcgcttggt tgatcgatga gcttcaagca   1080
gctgaaactg caggtcagcg tgtttggttg atttctcata tccccagtgg aaatagtgat   1140
cacctatacg actacagcca ttacttcgat cagatcgtgc agagatacga agctactatc    1200
gcagctttgt tcttcggtca tactcataca gacttgtttc aggtagccta ttcagattat    1260
ggtaataaga attcagatac cgcttccgct attggatatg tcaccccaag tatgaccccct  1320
acctctggcc caccggcatt taggatttac gaaatagaac cagttacttt tggtgtcttg    1380
gactatacgg tttacattgc aaacatttca gatcctgctt atcaaacagg tccctcctgg    1440
cagaagtact attccgctaa agaagtttat ggctccttgc tatctccacc attgaccgac    1500
ccagcagctg aattgacgcc agctttctgg cataatgtta cagtattgat ggaagaagac    1560
gactcgtcct tccaagactg gtgggctagg actaccaggg gcttcaatgt gagcacctgt    1620
accggatctt gtgctacgaa cgagatttgc gctcttaggg gtgccgacgc ccagtacaac    1680
tgtgtcaccg ctagcccagg tatccaatttt gctaagagag aggtgctgt agattttgat    1740
cccaatgcac aaccagtagc aaagccccac tgtgacgagg gttctggttt agccctgtc    1800
ttggtcaaaa tgatgagaaa tacgatgac tttgccggtc tactgaaaga acgtgctgca    1860
ttgcaagatt ctcaacagta a                                              1881

SEQ ID NO: 370           moltype = DNA  length = 1890
FEATURE                  Location/Qualifiers
source                   1..1890
                         mol_type = genomic DNA
                         organism = Penicillium jensenii
SEQUENCE: 370
atgagatttc cttcaatttt tactacagtt ttattcgcag catcctccgc attagctgaa    60
acctccaagg ctagtacgga atcattcata tcctccatat gggatgattt caaacaagct    120
gttgattgtg gttcctgtca agccttgctt ggtggcttga acttgtatc aggcttcggt    180
gagggcttta tgatagatgt tttcattgga ttatgcaacc tttccggagt cgaggatccc    240
gatgtatgca gaggcataat cgagaaagag ggtccagcct tgcatgacgc cttccagaac    300
ttacacatcg gttctcatgc tactcgtacc atgtgcgcat cattgattgg gctttgccaa    360
tacccagaag tgagaccgca caccctacaa tttccatcta gcaaaccaga tactacgagg    420
cctccgcctt ccggtaaaatc ccccatcaaa gttgtccatt tctcagatac acacgttgac    480
ttgttctatg aaactggggc ttcctatgag tgtagtaagc caatctgctg tcgtgtttac    540
gaagacaaag atgcaccagg cataactaaa acaccatgtg gcccttttgg taatactaaa    600
tgcgatcctc ctcacattct gcaagaaagt atgaatgccg ctattgcaaa gattgatcca    660
gactttagca tctacactgg cgatgttgta gcacacgaca tatggttggt tggacaagat    720
gaggctctac aagtcttcaa tgatacatat ggccaaatgg agaaggattt gggcatggtt    780
tacgctgcca ttggcaacca tgatcctgct ccgtcaact tattccctcc aaatgacatt    840
aagggtaagg attcagctca atttgcctac aatgccttag ctgaagattg gtatgcctta    900
acaggaatac cctctgtgaa atctgccgac gaatttggtt cttactcagc aatacatcca    960
aattcaaatc ttaggatcat ttcctacaat tcaatcttct attacaactt caatttctac    1020
atgtaccaag atcctatgga aaaggatcca aacggtcaat tcgagtggtt gatcaaagaa    1080
ttgcaagctg cagaagatgc cggtcaaaga gcttggttaa tcagtcatat accatccggt    1140
gtgaccgacc acttccgtga ttacagtcaa tacttcgacc agattgtcca aagatatgag    1200
gcaactattg caggctgtt ctatggtcat acgcatatgg acgaattcca aattgcttat    1260
tcagactaca acaatagaaa gtgggacact gctacgacta tgggctacat agctcccctca  1320
atgaccccca caagcggtcc tccatctttc agagtctacg aaattgatcc agttacctat    1380
ggtgtactgg atttcactca gtacattgcc aacatatcag atccatccta ccagaccaag    1440
```

```
ccggaatggg ttccctacta ttccgctaaa gcagcatatg gatccaaatt gtctccaccg    1500
ttgacagatt ccactgccga attgacccca gcattttggc ataatgttac tgttactatg    1560
gagaaagacc cttccatctt tcaggatttc tgggcaagga gaaatagagg gtggaacatt    1620
gcagcatgta ctggtgactg catgaaaaag gaactttgca ctcttcgtgc tgccgacgca    1680
caacacaact gtcacgaacc aaccccaggc ttaaacatat ccatcaataa gagagatcaa    1740
ggctctggtg atgttccttt agagggcgag aaagtgagtg gtccagaatg tgaccacgca    1800
ggtatggcta ccttgttagg aaagattgcc tatagggcaa ggctggttag agaggctgaa    1860
gaaagagatc cagtcagggc tgaagcataa                                     1890

SEQ ID NO: 371          moltype = DNA   length = 1890
FEATURE                 Location/Qualifiers
source                  1..1890
                        mol_type = genomic DNA
                        organism = Aspergillus stramenius
SEQUENCE: 371
atgagatttc cttcaatttt tactacagtt ttattcgcag catcctccgc attagctgaa    60
aactgggtca ataccatctg ggatgagata aaggaaacca tctcttgtgc aggttgtgaa    120
ggtttgttgg gtaccttgaa acttgttgcc ggtctaggac cagacgtctt aaccaacgtt    180
ttgaccgatg tttgcaaatt ggccaaagtc gaagaccccg acgtctgtgc tggcattatc    240
gaagctgagg gtcctgcagc ctactatgtc ttgaagcagt tgaaagtggg gtcccataca    300
tcaaagagct tttgttctca aatggtgggc ctgtgcgatt atccagaagt gcgtccctat    360
aacatttcat tcccaatccc gaagccttca acacatagcc atccacctag tggtcagcgt    420
cctatcaggg tagctcacat ttcagatact catgtcgatc gtgcttatga aaccggtgcc    480
aactatgaat gttctaagcc aatatgttgc agagtctaca cagaggacga tgccccaggc    540
aaaacctctt ttccttgtgg cccttatggt catccaaaat gcgaccctcc tttaagatta    600
gaggaaagta tgatgctgc cattgcagct atggatccgg cttttagtat ctatacaggt    660
gacgttgtgc cgcacgatgt gtggtctgta aatcgtaccg aggtcttgca tgatctaaat    720
gcaacttact ctttgttaga tagattaggt cttgtttatg ccgcattggg taaccatgat    780
acggctcccg ttaacctatt ccctagtgag aggattcctg tttcccataa tccacaatgg    840
gcctatgatg ctttagctga agattggaca aatcttgtag tggaccact atctgcccct    900
gtagtccatg ccacagacca attcggctcc tattctgctt tgcaccctgg cggaaaacta    960
aggatcattt cctacaactc tgtattctac tatacgtaca atttctacgc ctatcaggag    1020
cctatggaat atgatccaaa cgggcaattg gcatggttgg tggccgaact gcaggctgca    1080
gaaacagctg gacaaagggt gtggttgatt gctcatattc ccaccggagc agcagatact    1140
ctgagggact actcccacta tctggaccaa atcatccaga ggtatgacgc tactattgcc    1200
gcattgtttt tcggccatac tcatacagat ctgtttcaag tctcatacgc aaatccagca    1260
catccatctg cagattcagc ctctgccgtt ggctacatta cccctcttt aacacccaca    1320
agtggtcccc cagcctttag gatctatgac atagaccctg ttacatttgc tgttcttgac    1380
tatacagtgt ataccgcaaa catctcaaca ggtgcaactc caaaatggaa caagtactac    1440
agcgcaaaac aaacctatgg tagtttgttg accctccat tgacagatcc aactgccgag    1500
ttgacaccag catttggca taatgtcact gcattgatgg aaacagacaa tactgttttc    1560
caggcttggt gggcaaggac tacgagaggc tttaacgtcc cagaatgtaa cgcccagtgt    1620
gcaaggcatc agatttgctc cttaagagcc gcagacgcc aatacgggtg cgtgagggga    1680
acactaagta ttacgaaaag agccggtgat ggtgacggtt tagatttggg aggtgctggt    1740
gccggtggtc ctcaggaag acgtaggcac gtacagtccg ctagaccaca atgcgaagaa    1800
gctggttttgc aagagtttt agccgctgtg attagggaaa cagacgattt gcagggctta    1860
ttgttgcaaa gagcacagtt gtacatataa                                    1890

SEQ ID NO: 372          moltype = DNA   length = 834
FEATURE                 Location/Qualifiers
source                  1..834
                        mol_type = genomic DNA
                        organism = Bacillus pseudomycoides
SEQUENCE: 372
atgagatttc cttcaatttt tactacagtt ttattcgcag catcctccgc attagctcat    60
accaacgact gtggcaacga agctcctata ctaaggtgga gtgctgaaga cagacataaa    120
gaaggtgtca attcccactt atggattgtc aatagggcaa ttgacattat gagtaggaat    180
aacaccattg ttaagccaaa tgagacagca ttactgaacg agtggagaaa cgagttagag    240
aatgtatct attcagcaga ctacgaaaac ccatactacg acaatagcac gttcgcatca    300
catttctacg atccagatac tcaaaagacc tacatccctt tagctaaaca ggccaaggaa    360
acaggttcaa agtatttcaa gcttgcaggt gaagcttatc agaacaaaga tatgaagcaa    420
gcattcttct acttaggatt atctttacat tatcttggtg acgttaatca acccatgcat    480
gctgccaact ttacaaactt gtcctatccg atgggctttc atagcaagta tgagaatttc    540
gttgacacca taaggataa ctacaaagtt gcagatgaa acggctattg gaattggaaa    600
gggacaaatc ctgaagaatg gattcatggt gccgcagccg ctgctaaaca ggattaccca    660
ggcattgtga acgactcaac caatctggca tttgtgaagg cagcaacttc acaagaatat    720
gccaataagt ggagagcaga agttacacca gccactggta gaggttgac tgaggctcaa    780
cgtgtaaccg ctggctacat ccatctatgg ttcgatacat atgtcaacag ataa          834

SEQ ID NO: 373          moltype = DNA   length = 837
FEATURE                 Location/Qualifiers
source                  1..837
                        mol_type = genomic DNA
                        organism = Bacillus mycoides
SEQUENCE: 373
atgagatttc cttcaatttt tactacagtt ttattcgcag catcctccgc attagctcag    60
gagaatgacg gaggtaatag agtgaacatc attcagtatt ggagtgctga ggacaagcac    120
accgaaggtg tcaactctca cttatggatc gtcaatagac aatagacat tatgtccagg    180
aatatgacct tggtaaagca agatcaagtg gcactgttaa acgagtggag aacagatctt    240
```

```
gaaaacggca tctattcagc agattatgag aatccgtatt acgataacag cacttttgcc  300
tctcacttct atgatccaga cgacggttct acctatatcc catttgccaa acaagcaaag  360
gaaactgggg ctaagtactt taagcttgct ggagaatctt acaagaataa ggatatgaag  420
caagccttct tctatcttgg cctatcttta cattatctgg gtgatgtaaa ccaacctatg  480
catgcagcca actttaccaa catatcttat ccccaaggct tccactccaa atacgagaac  540
tttgttgata ccatcaagga caattacaaa gttacagatg gtaatggcta ttggaactgg  600
aaaggcgcaa atcctgaaga ttggatacat ggcgctgctg tcgcagccaa gcaagatttt  660
cctggtattg tcaatagcaa cacaaagtct tggttcgtca aggctgctgt ttcccaatca  720
tatgcagata agtggagagc agaagtaacc ccaatgaccg gaaaaaggtt gattgaagca  780
caaagagtta cagcaggata catacagtta tggttcgata cctatgtgaa cagataa     837

SEQ ID NO: 374         moltype = DNA  length = 837
FEATURE                Location/Qualifiers
source                 1..837
                       mol_type = genomic DNA
                       organism = Bacillus thuringiensis
SEQUENCE: 374
atgagatttc cttcaatttt tactacagtt ttattcgcag catcctccgc attagctcac  60
gagaaaaccg aaggtcataa tgtgaacatc attcagtatt ggtccgctga ggacaagcac  120
tccgaaggtg tcaactctca cttatggatc gtcaatagag caatagacat tatgagtaga  180
aatactacca gagtaaagca agatcaagtg gtcctgttaa acgagtggag aacagatgtg  240
gaaaacggca tctattcagc agatcatgag aatccgtatt acgataacag cacttttgcc  300
tctcacttct atgatccaga cgacggttct acctatatcc catttgccaa acaagcaaag  360
gaaactgggg ctaagtactt taagcttgct ggagaatctt acaagaataa ggatatgaag  420
caagccttct tctatcttgg cgtctcttta cattatctgg gtgatgtaaa ccaacctatg  480
catgcagcca actttacaaa tctatcttat ccccaaggct tccactccaa atacgagaac  540
tttgttgata ccatcaagga caattacaaa gttatggatg gtaatggcta ttggaactgg  600
aaaggcattc atcctgaaga ttggatacat ggcgctgctg tcgcagccaa gcaagacttt  660
tcaggtattg ttaatcgtaa cacaaagtct tggttcgtcc aggctgctgt tagtcaatca  720
tatgcagata agtggagagc agaagtaacc ccaatgaccg gaaaaaggtt gattgaagca  780
caaagagtta cagcaggata catacagtta tggttcgata cctatgggaa cagataa     837

SEQ ID NO: 375         moltype = DNA  length = 846
FEATURE                Location/Qualifiers
source                 1..846
                       mol_type = genomic DNA
                       organism = Listeria innocua
SEQUENCE: 375
atgagatttc cttcaatttt tactacagtt ttattcgcag catcctccgc attagcttgt  60
tgtgacgagt atttgcaggc tccagccgct ccccacgaca tcgacagtaa actacctcat  120
aagttatcat ggtctgcaga taaccctaca aatacagatg tcaatactca ctattggttg  180
ttcaaacaag ccgagaagat acttgccaaa gatgttaatc acataagggc caatttgatg  240
aatgagttaa agaatttcga taagcaaata gcccaaggta tctatgatgc agatcacaaa  300
aacccctact atgatacttc cacatttctg tctcactttt acaacccaga cagagacaat  360
acataccttc caggatttgc aaacgccaag ataactggtg ccaaatactt caatcaatcc  420
gtcgcagact atagagaagg gaagtttgat acagcattct acaaactagg tttagctatt  480
cattactata cagacatttc ccagcctatg catgccaaca actttactgc tatatcctac  540
cctccagggt atcattgtgc atatgaaaac tatgttgaca ccattaagca caactatcaa  600
gctacggaag acatggttgt taagaggttc tgctcagatg atgtaaaagt ttggttgtac  660
gagaatgcaa aaagagcaaa ggccgattat ccaaagattg ttaatgctaa gaccaagaaa  720
tcctacttag tcggtaacag taaatggaag aaagatacag tagaaccaac tggagcaagg  780
ctgagagatt cacagcagac acttgcaggg ttcttggaat tctggagcaa gaaaaccaat  840
gaataa                                                             846

SEQ ID NO: 376         moltype = DNA  length = 885
FEATURE                Location/Qualifiers
source                 1..885
                       mol_type = genomic DNA
                       organism = Aspergillus egyptiacus
SEQUENCE: 376
atgagatttc cttcaatttt tactacagtt ttattcgcag catcctccgc attagctgct  60
cctgcacctt taactagaag ggatgtttct agtgaagtat tagaacagtt aacgctattc  120
gcagagtact ctgctgcttc ttactgccct tccaatttgg attcaccagg aacgaaattg  180
acttgctcaa cagggaattg tcccactgta gaagctgcag ataccgagac tttggcagaa  240
ttctatcatg ccgatgaata tggagacgtt gccggttact tggcagtcga cactacaaat  300
caactattag tagtcgcttt tcgtggaagc cgtgctttgg acacctggat tgccaatttg  360
aactttggta aagattccgt cgatgatcta tgttcaggtt gtgaagtcca tggtggcttt  420
tggcagtcct ggcaagtcgt agcagattct gttgcaagtg gagtcgaaag cgctttgcaa  480
acatatccag actatactat agtctttacc ggtcattcat ttggtggggc agtggccact  540
ttaggcgcag tcgagttaag aaatgctggt tatgatattg agctatatcc ttatggagca  600
cctagggttg gtaatgaagc attagctcaa tacataacag atcaaggatc aaactatcgt  660
gtcacacata caaatgatat tgtacctaga ttacctccta tgagctttgg atttagtcac  720
tccagtcctg agtactggat tacctccgac gacgaagtca caccaaccac agcagatgtt  780
gaggtaatcg aaggtgttgg ttctacagag ggtaacgctg gtgaatttcc tcagagtaca  840
gcagcccatt ctcactacat cattgacatt tcagcctgtg aataa                  885

SEQ ID NO: 377         moltype = DNA  length = 888
FEATURE                Location/Qualifiers
source                 1..888
```

```
                        mol_type = genomic DNA
                        organism = Aspergillus tamarii
SEQUENCE: 377
atgagatttc cttcaatttt tactacagtt ttattcgcag catcctccgc attagctact    60
cccgcacctt tgaggcgtga tgtatccagt agtctactaa acaacttaga cttgtttgct   120
cagtattctg ctgcagctta ttgctctgag aatttgaatt caaccggtac aaagcttact   180
tgctccgtag gtaattgtcc acttgtagaa ttagcctcca ccaacacact tgacgaattc   240
gatgaatcct cttcatacgg gaaccctgca ggttaccttg ctgcagacga gaccaacaag   300
ttacttgtgt tgtcttttag aggtagctcc gaccttgcaa attgggttgc caacttgaat   360
ttcggtttag aggatgccag cgacctatgt tcaggttgtg aggttcatag tggtttctgg   420
aaggcctgga gtgaaatagc agatacaatt acatccaaag tggaatcagc actttcagat   480
cattcagact attctctggt cttaactggg cattcctacg gtgctgcctt agccgctctt   540
gctgccactg cactaagaaa cgcaggtcat tcagttcaac tttacaacta tggacaacct   600
cgtttaggaa atgaagctct ggctacatac atcacagacc agaacaaagg tgccaactat   660
cgtgttacgc acaccaatga cattgttccc aagttacccc ctacattgtt aggataccat   720
cactttagtc cagaatacta catttcatca gccgatgaag ccacagttac taccgcagat   780
gtgacagagg ttaccggaat cgatgcaact ggcggtaatg atggcacaga tggtacttca   840
atcgatgcac atagatggta ctttatctac atttcccaat gtagttaa               888

SEQ ID NO: 378          moltype = DNA   length = 891
FEATURE                 Location/Qualifiers
source                  1..891
                        mol_type = genomic DNA
                        organism = Aspergillus niger
SEQUENCE: 378
atgagatttc cttcaatttt tactacagtt ttattcgcag catcctccgc attagctgca    60
ccagctccta tgcaaagaag ggacataagt tctacagtac ttgacaacat agaccttttt   120
gctcagtatt ccgcagcagc ttattgttca tccaacatag agtctacggg taccacattg   180
acgtgtgatg tgggtaattg tccattggtt gaagccgctg gtgcaactac cattgatgag   240
tttgatgata ccagttctta cggtgaccca acaggatgca ttgcagttga tcctacaaat   300
gagttgattg tgttaagctt cagaggttcc tccgacttgt caaattggat cgcagattta   360
gatttcggct tgactagtgt ttcatcaatt tgtgacggtt gtgagatgca caagggcttc   420
tatgaggctt gggaagttat tgcagacaca ataactagca aagttgaagc agctgtttcc   480
tcatatccag actataccct tagtctttact ggtcacagtt atggcgctgc tcttgcagcc   540
gtggcagcta cagtattgag aaatgctggg tacacactag acttatacaa cttcggtcaa   600
ccaaggattg gcaacttagc actagcagac tacataacag gccaaaacat gggatccaac   660
tatagagtta cacatacaga tgatatagtc ccgaagcttc cacccgagtt acttggttat   720
caccactttt cccctgagta ctggatcaca tcaggcaatg atgttactgt gacaacctca   780
gatgttactg aagttgtggg tgtggattca actgctggca acgacggtac cctgttagat   840
tcaacaactg ctcatagatg gtacaccatt tacatttccg agtgtagtta a             891

SEQ ID NO: 379          moltype = DNA   length = 1107
FEATURE                 Location/Qualifiers
source                  1..1107
                        mol_type = genomic DNA
                        organism = Bacillus luciferensis
SEQUENCE: 379
atgagatttc cttcaatttt tactacagtt ttattcgcag catcctccgc attagctatt    60
acctccttct ttggcaacta tcaaaaggca ttccatggga gtgatgaaga cgttcataat   120
caagatcatt ctacacatca tttcattgtc aatggctcag taaagttgat agccgacaat   180
gccaacccag ccatcaacaa acccacaaca ttactgaacc agttcagaga caggtgggag   240
caaggtcttt atgatgcaga ccacattaac ccattctacg atacagggac gttcatgtca   300
catttctacg atccagatac tcaaacgaac tacaccggtg cttcttatcc gaccgccaga   360
caatctggtg ccaaatactt caacctgcag tcagactatt acaagaaagg agatttcaac   420
aacgccttct actacttagg tgtttcattg cattacttta cggatgtaac acagccatta   480
catgcttcca acattagcaa cttagatcac catgcacctg gttaccactc taagtttgag   540
acttacgctg aaagtattca gaacgaaatg acagttccag acagtggctt atacaattgg   600
atcggatcca cagacccaga ggcttggatc caccaagccg ctgttcaagc caaatccgtt   660
cttccacagg tgtggaatga caccatcatc aattggttct ggcaagctgc ttattccaat   720
tactattccg ctatgtggaa gaatgaagtt aagaatccaa ccctagttca acttaatcaa   780
gccgaacgtg aaaccgcagg gttcatagac atgttcttta gagtcaacgg tgttgaaatg   840
cccgttacag tctacaaaga aaatgccttt ggtggcgtat ctgaattact aggtagtggc   900
aattacgatt acgatcagtt ggtgaagggc ataggtaatg atacaattag ttccattcac   960
attgctccag gctaccaagt tacattgttt tcagacgcca attacaaagg cgctagtatc  1020
gtcttgacaa atgatgttca tgacttaggt aacttttctc accaggtaag ctccatcaag  1080
attgccaaga tatctgcact gaaataa                                      1107

SEQ ID NO: 380          moltype = DNA   length = 834
FEATURE                 Location/Qualifiers
source                  1..834
                        mol_type = genomic DNA
                        organism = Bacillus mycoides
SEQUENCE: 380
atgagatttc cttcaatttt tactacagtt ttattcgcag catcctccgc attagctcaa    60
acgaacaact ctgaaaaccc aactcctgtg ctaagatggt ccgctgagga caaacacaac   120
gagggggtca gtacacacct atggatcgtc aatagggcta ttgacataat gtcaagaaat   180
acagctattg ttaagccaaa tgaaactgca ttacttaacg agtggaggac cgatttggaa   240
aatggcatat actctgcaga ttatgaaaat ccttactatg acaatggcac atacgcctct   300
catttctatg atccagatac tggtgaacc tacattcctt ttgccaaaca agccaaagaa   360
```

```
acaggaacca aatactttaa gttggcagga gaggcttacc aaaatcaaga tatgaagcaa   420
gctttctttt acctgggttt gtccctacac tacttaggtg atgtgaatca acctatgcat   480
gcagccaatt tcaccaactt atcatacact atgggtttcc attccaagta cgagaatttc   540
gtagatacag ttaaagacaa ctacatagtt agcgattcaa atggatattg gaactggaaa   600
ggcacaaatc ccgaagattg gattcaaggg agtgccgtcc ctgctaagca agactaccct   660
ggtatagtaa atgatactac taaggactgg ttcgttaaag cagcagtctc tcaagaatac   720
gcagacaaat ggagggcaga agttacacct gtaaccggta agaggttaat ggaagcacaa   780
agagtaacag ctggttacat acacctgtgg tttgatacct acgtaaacag ataa          834

SEQ ID NO: 381          moltype = DNA   length = 837
FEATURE                 Location/Qualifiers
source                  1..837
                        mol_type = genomic DNA
                        organism = Bacillus mycoides
SEQUENCE: 381
atgagatttc cttcaatttt tactacagtt ttattcgcag catcctccgc attagctcac    60
gagaatgaag gaggcaacaa agtgagggta attcagtatt ggagtgctga ggacaagcac   120
gcagaaggtg tcaactctca cttatggatc gtcaataaga caatagacat tatgtccaga   180
aatactaccg ttgtaaagca agatcaagtg gcactgttaa acgagtggag aactgaactt   240
gaaaacggca tctatgcagc agattatgag aatccgtatt acgataacag cactttgcc    300
tctcacttct atgatccaga caccggtaaa acctatatcc catttgccaa acaagcaaag   360
gaaactgggg ctaagtactt taagcttgct ggagaagctt accaaaaaca ggagattaag   420
caagccttct tctatcttgg cctatcttta cattatctgg gtgatgtaaa ccaacctatg   480
catgcagcca actttacaaa tctatcttat ccccaaggct tccactccaa atacgagaac   540
tttgttgata ccatcaagaa caattacaaa gttgcagatg gtaatggcta ttggaactgg   600
aaaggcgtaa atcctgaaga ttggatacat ggcgctgtcg tcgcagccaa gcaagattat   660
gctggtattg ttaatgggac cacaaaggat tggttcgtca gggctgctgt ttcccaagaa   720
tatgcagata agtggagagc agaagtaacc ttgacgaccg gaaaaagatt agttgaagca   780
caaagagtta cagcaggata catacagtta tggttcgata cctatgtgaa cagataa      837

SEQ ID NO: 382          moltype = DNA   length = 837
FEATURE                 Location/Qualifiers
source                  1..837
                        mol_type = genomic DNA
                        organism = Bacillus sp.
SEQUENCE: 382
atgagatttc cttcaatttt tactacagtt ttattcgcag catcctccgc attagctcac    60
gagaatgacg gaggtcatgg tgtgggcgta attcccagat ggtccgctga ggacaggcac   120
aaggaaggtg tcaactctca cttatggatc gtcaataagc gcatagacat tatgagtcac   180
aatactaccg ttgtaaagca agatgaagtg gcactgttaa acgagtggag aacagatctt   240
gaaaacggca tctattcagc agattatgag aatccgtatt acgataacag cactttgcc    300
tctcacttct atgatccaga caacggtact acctatatcc catttgccaa acaagcaaag   360
gaaactgggg ctaagtactt taagcttgct ggagaatctt accagaataa ggatatgaag   420
caagccttct tctatcttgg cctatcttta cattatctgg gtgatgtaaa ccaacctatg   480
catgcagcca actttacaaa tctatcttat ccccaaggct tccactccaa atacgagaac   540
tttgttgata ccatcaagga caattacaaa gttaatgatg gtaatggcta ttggaactgg   600
aaaggcacaa atcctgaaga ttggatacac gcctctgctc tcgcagccaa gcaagattac   660
ccttctattg ttaatgacaa cacaaaggat tggttcgtca aggctgctgt tagtcaagat   720
tatgcaaaca agtggagagc agaagtaacc ccaatgaccg gaaaaaggtt aatgaaagca   780
caaagagtta cagcaggata catacagtta tggttcgata cctatgtgaa cagataa      837

SEQ ID NO: 383          moltype = DNA   length = 849
FEATURE                 Location/Qualifiers
source                  1..849
                        mol_type = genomic DNA
                        organism = Bacillus drentensis
SEQUENCE: 383
atgagatttc cttcaatttt tactacagtt ttattcgcag catcctccgc attagctgcc    60
agggtaaatc acgatagtag ttatgacagc ggcatcatca tatcaccta ctggagcgct    120
gaagagatgc atacagaggg caagaatact catttgtgga ttgtcaatag agcaattgac   180
attatggcac gtgataacac cgttgttaaa gaaaacgaag tcgccttatt gaatgaatgg   240
agaacggatc tggaagacgg catatacact gcagactatg aaaatcccta ctatgacaac   300
ggtacttttg ctagtcactt ttacgatcca gatccgacg atacgtatat cccatttgca    360
aagaatgcaa aagttacagg tgtaaagtac tttaagttag ctggggaagc ttaccagcag   420
caagcaatga atcaggcctt cttttaccta ggcttgtctc tacactactt tggtgacatc   480
aatcaaccca tgcacgcatc caactttacc aacatttcac atccattcgg cttccactct   540
aagtatgaga actttgttga taccatcaaa gcaccatata gtgtaacaga tggtaatggg   600
tattggaact tgctggcga aactccggaa gaatggttac atactgctgc tgtggcagca   660
aagcaagatg cacctggcat tgttaatgaa acaacaattt catggttctt acaagcagca   720
tttagtcaag agtacgcaga tatgtggaga gctgaagtaa ctccagaaac aggagccagg   780
ttgattgagg cacaaagggc aatggctggc tacatacatc tgtggtttga cacatatgtc   840
aacttataa                                                             849

SEQ ID NO: 384          moltype = DNA   length = 885
FEATURE                 Location/Qualifiers
source                  1..885
                        mol_type = genomic DNA
                        organism = Aspergillus turcosus
SEQUENCE: 384
```

```
atgagatttc cttcaattt tactacagtt ttattcgcag catcctccgc attagctgct    60
cccgcaggat tggcagagag agatgtcagt gcaagtgtcc ttcaagaact atctttgttt   120
gctcagtatt ctgcagctgc ttactgtacc aataacatca attccacagg aaccaagttg   180
acgtgctcag ctgaaattg tcccttagtc gaagctgcca acacaaaaac ccttgctgag    240
ttctatgact cagatagttt cggggatacc gctgggttc tggtagccga cactaccaac    300
aaacttctgg ttgtttcttt tagagggtcc cgtaccttag acaattggat cgccaactta   360
gattttgttc tggatagcat ctccgacatt tgttcaggtt gcgctgcaca cggtgggttc   420
tggaagagtt gggaagtagt agcaaattct ttaaccactg agttgaattc agccgtcaat   480
acttatccag gttatacgat tgtctttacg ggtcacagtt caggtgccgc tctggctacg   540
ttaggcgcta caaccttgag gaaggctggt attccagtac agttgtacaa ttacggtagt   600
ccgagagtag gtaacaaagc cttggcaacc tacataacgg ctcaaggacc caattacaga   660
gtgactcaca cgaacgatat cgttccaaga cttccacccc agagttttgg ttttagtcat   720
ctatctcctg agtattggat tacatcaggt gacaatgttc ccgtcactac ttccgacatt   780
acggtaatcc aaggcataga ctcaaatgct ggcaatagtg gtgaggacat tacttctatt   840
gaggctcaca attggtacat tggtaacatt gatgcctgtc cataa              885

SEQ ID NO: 385          moltype = DNA  length = 888
FEATURE                 Location/Qualifiers
source                  1..888
                        mol_type = genomic DNA
                        organism = Talaromyces subinflatus
SEQUENCE: 385
atgagatttc cttcaattt tactacagtt ttattcgcag catcctccgc attagctgtc    60
ttatcaccaa ttggaagaag aactgtcact acaacacaat tagatgacat gaacttattc   120
gcccagtatt ctgctgccgc atactgttca gccaacttga attcaacggg tagcgctctt   180
gcatgtaacg ttggtaactg tcctttggtt gaaggtgcaa acattaccat cttatacgat   240
tttgacgaat ctgcaggatt cggtgacgct accggctaca tagccgttga tgaaactcac   300
aaatccatca ttttggcctt tcgtgggtct tcagacctag acaattggat tgcagacttg   360
gatataccct agtcgcttc tagtatttgt ttaggttgtg aagttcatca gggtttctgg   420
gacacctggc agacagttgc atcagatgtc accagtacaa ttgagtatgc tttaagtgct   480
tatgcaggtt atacctttgt tgtcacaggt cattctatgg gtgcagccct tgctgctatc   540
gcagccacgg tctttagaga ttctggttat actgtggagt tatacaacta tggccaaccc   600
agaattggta acttgatttt ggcttactac ataacaaatc aaaatcacgg tagcaactat   660
agagttacac atacagatga tattgttcct aaactaccgc ctgaattact tggctacgac   720
catttctccc cagaatactg gatcacgtca ggcgataatg tcacagtaac agattccgat   780
atcgatgtta tgtttggtat tgactctgcc gatgataatg atggcaccat cgatgacagc   840
gtagaagctc atcattggta ctttgtttac atttctgaat gttcctaa             888

SEQ ID NO: 386          moltype = DNA  length = 891
FEATURE                 Location/Qualifiers
source                  1..891
                        mol_type = genomic DNA
                        organism = Aspergillus tubingensis
SEQUENCE: 386
atgagatttc cttcaattt tactacagtt ttattcgcag catcctccgc attagctgca    60
ccagctcctaa tgcaaagaag ggacataagt tctacagtac ttgacaacat agaccttttt   120
gctcagtatt ccgcagcagc ttattgttca tccaacatag agtctacggg taccacattg   180
acgtgtgatg tgggtaattg tccattggtt gaagccgctg gtgcaactac cattgatgag   240
tttgatgata gtagttctta cggtgaccca acaggattca ttgcagttga tcctacaaat   300
gagttgattg tgttagccct gagagggttcc tccgacattt caaattggat cgcagattta   360
gatttcggct tgactagtgt ttcagacatt tgtgacggtt gtgagatgca caagggcttg   420
tatgaggctt gggaagttat tgcagacaca ataactagca agttgaagc agctgttcc    480
tcatatccag actattccat tgtcttact ggtcacagtt atggcgctgc cttgcagcc    540
atcgcagcta cagtattgag aaatgctggg tacacactag acttatacaa cttcggtcaa   600
ccaaggattg gcaacttagc actagcagac tacataacg accaaaacat gggatccaac   660
tatagagtta cacatacaga tgatatagtc ccgaagcttc cacccaagtt acttggttat   720
caccacttt cccctgagta ctggatcaca tcaggcaatg atgttactgt gacaacctca   780
gatgttactg aagttgtggg tgtggattca acagatggca acgacggtac cctgttagat   840
tcaacaactg ctcatagatg gtacaccatt tacatttccg agtgtagtta a            891

SEQ ID NO: 387          moltype = DNA  length = 1110
FEATURE                 Location/Qualifiers
source                  1..1110
                        mol_type = genomic DNA
                        organism = Bacillus acidiceler
SEQUENCE: 387
atgagatttc cttcaattt tactacagtt ttattcgcag catcctccgc attagctatc    60
acatccttgt tttcaaacga tcagaaggct tttgcctggt ccgacgaaga tgtacataat   120
caagatcata gcacccatca cttcatagtc aacggctctg tcaaattgat tgcagacaat   180
acaaaccctg ccatcaacaa acctactacg ttgttgaatc agtttagaga tagatgggaa   240
caaggcttat acgacgcaga tcatatcaac cctttctatg acaccggtac tttcatgagc   300
cacttttacg atccagacac acaaaccaat tacacaggcg tttcatatcc aactgctcgt   360
caaagcggtg gcaagtattt caaccttgca tccgactact acaagaaagg tgacttctac   420
aatgccttct attactgtgg cgtgtcacta cactacttta cagatgtgac ccaaccttta   480
catgcctcca cattcaaaa cctgaccat aacgctcccg gataccctcc taagtttgag   540
aactatgcag agtctattca gaatcagatg gccattccag attccggttt gtacaactgg   600
attagtagca ccgatcctga ggcctggata caccaagccg ctgtacaagc taaatctgtt   660
ctgccacagg tttggaatga caccatcatc aactttttct ggcaggctgc atattccaac   720
tattacagtt ccatgtggaa gaatgaagta aagaatccaa ctttagttca attgaatcaa   780
```

```
gccgagaggg agactgctgg tttcattgat atgttctttc gtgtcaatgg cgtagagatg  840
cccgtgaaag tgtacaaaga gaatgctttt ggtggtgcct cagagatttt gggtctaggc  900
aactatgatt atgaccaatt cgtaaaagga ataggaaatg atactatatc ttcaattcat  960
attgccccag ctaccaagt caccttattc tccgacgcca actacaaagg cactagcacc  1020
gttttgactg gggatgtaaa cgacttgggc aactttaacc atcaagttag tagtcttaag  1080
attgtcaaga tatccgcaat atcaaaataa                                   1110

SEQ ID NO: 388           moltype = DNA   length = 837
FEATURE                  Location/Qualifiers
source                   1..837
                         mol_type = genomic DNA
                         organism = Lysinibacillus xylanilyticus
SEQUENCE: 388
atgagatttc cttcaatttt tactacagtt ttattcgcag catcctccgc attagctcac   60
gagaattgct accaagatcc tcccatacct ttgaagtgga gtgccgaaag tatccacaac  120
gagggcgtat cctcccatct gtggattgtc aatagagcta tagacataat gtctcagaat  180
actactatcg ttaaacaaca tgaaacagac tactgaatga gtggagaaac agatttggag  240
gaaggcatct attctgcaga ttatcaaaac ccatactgta acaattccac gtttgctagt  300
cacttctatg atccagattc cggcaaaacc tacattccct ttgctaagca agctaaacaa  360
accggtgcca aatacttcaa actagccggt gaagcttatc agaacaaaga cttgaaaaac  420
gcattcttct atttgggcct aagtttgcac tatttggggg atgttaatca acctatgcat  480
gctgccaact ttaccaacat atcccatcca ttccgttttcc actccaagta tgagaacttt  540
gtagatactg tcaaggataa ctatcgtgtt acagatggaa atggttactg gaattggaaa  600
tctgccaatc cagaagaatg ggtgcatgcc agtgctgttg ccgcaaaggc cgacttcttg  660
ttgattgtta atgataacac cgaaagtggt tttctaaaag ccgctgtttc tcaagattca  720
gcagataagt ggagagctga gtaacacct gttacgggaa aagattgat ggaagctcaa   780
agaattactg caggatacat ccacttatgg ttcgacacat acgtaaacaa caaataa     837

SEQ ID NO: 389           moltype = DNA   length = 837
FEATURE                  Location/Qualifiers
source                   1..837
                         mol_type = genomic DNA
                         organism = Bacillus toyonensis
SEQUENCE: 389
atgagatttc cttcaatttt tactacagtt ttattcgcag catcctccgc attagctcac   60
gagaatgaag acgtcaacta taacgcacct attcttagat ggagtgctga ggacaagcac  120
aaggaaggtg tcaactctca cttatggatc gtcaatagaa gtatagatat gatgtccaga  180
aatactacca ttgtaaagaa gaatcaagtg gcactgttaa acgagtggag aactgaactt  240
gaaaacggca tctacaatgc agatcatgag aatccgtatt tcgataactt cacttttgcc  300
tctcacttct atgatccaga aaccggttcc acctatatcc cattagtgtc tactcaagca  360
aaggaagccg gttccaagta tttcaagttg gcaggtgaat cctacaaaaa gaatgatatg  420
aaacaggcct tcttttacct aggcttgtca ttgcattact gggtgatgt caaccagcca  480
atgcatgctg ccaactttac aaacttgtct tacccacagg gcttccactc taagtatgaa  540
aactttgttg acaccataaa ggataactac aaagtaaatg atggtaacgg ttattggaat  600
tggaagggtt caaatccagg tgactggatc cacggtgctg ccgttgctgc caagaaagac  660
tatactggta ttgttaacga cacaaccaaa gattggttcg tcaaagctgc tatatcatca  720
gaatatgcag acaaatggag agcagaagtc actccggcaa caggtaaaag attgatgaa  780
gcacaaagaa taacagcagg gtacatacaa ctttggtttg acacatacgc caattaa     837

SEQ ID NO: 390           moltype = DNA   length = 837
FEATURE                  Location/Qualifiers
source                   1..837
                         mol_type = genomic DNA
                         organism = Bacillus wiedmannii
SEQUENCE: 390
atgagatttc cttcaatttt tactacagtt ttattcgcag catcctccgc attagctcac   60
gagaatgacg gaggttccaa aatcaagatt gttcacagat ggagtgctga ggacaagcac  120
aaggaaggtg tcaactctca cttatggatc gtcaatagag caatagacat tatgtccaga  180
aatactacct tggtaaagca agatagagtg acccagttaa acgagtggag aactgaactt  240
gaaaacggca tctatgcagc agattatgag aatccgtatt acgataacag cacttttgcc  300
tctcacttct atgatccaga caacggtaaa acctatatcc cattagccaa acaagcaaag  360
gaaactgggc taagtacttt aagcttgct ggagaatctt acaagaataa ggatatgaag  420
caagccttct tctatcttgg cctatcttta cattatctgg gtgatgtaaa ccaacctatg  480
catgcagcaa actttacaaa tctatcttat ccccaaggct tccactccaa atacgagaac  540
tttgttgata ccatcaagga caattacaaa gttacagatg gtaatggcta ttggaactgg  600
aaaggcacaa atcctgaaga atggatacat ggcgctgctg tcgtcgccaa gcaagactat  660
tcaggtattg ttaatgacaa cacaaaggat tggttcgtca aggctgctgt tcccaagaa  720
tatgcagata agtggagagc agaagtaacc caatgaccg gaaaaggtt aatggatgca  780
caaagagtta cagcaggata catacagtta tggttcgata ccctatgggga cagataa     837

SEQ ID NO: 391           moltype = DNA   length = 864
FEATURE                  Location/Qualifiers
source                   1..864
                         mol_type = genomic DNA
                         organism = Listeria seeligeri
SEQUENCE: 391
atgagatttc cttcaatttt tactacagtt ttattcgcag catcctccgc attagcttgt   60
ggcgacgagt ccattaagga ccaaatcgct ccacacgcta ttcaaaacaa gttaccatct  120
aagttgggtt ggagtgctga acatccatcc aaagacgaga tcaatacccca cttgtggttg  180
```

```
tttaaccaag cagagaagat cttagctaaa gatgtgactg gggctcagtt agatctggtt    240
agagagttga agaactacaa caaagaaatc gctcaaggca ttttcgatgc agaccacaag    300
aatccttact atgacaaaaa cacttttcta agtcatttct acaatcctaa acacacaaa     360
acttacatac cagggtttcc aaacgcaaag gatacaggta ctaagtactt caacatatcc    420
gtcgaagaat accaagatgg caatttcgaa aaagtttct ataacctagg cctagctatc     480
cactactata cagatgtcag tcaacctatg cacgccaaca actttacagc tctatcacat    540
cctgttggtt accattgtgc atatgaaaac tatgtggaca cctttaagca aatcttccaa    600
gcttcagctg aatctgaagc taagtggttt tgcacagatg acataagtga atggtatcac    660
gaaaatgcta aaagggcaca agcagattat cctaagattg tgaacgccat catcaagaaa    720
tcctacatac aaggtctatc agacagccaa aaagatagga cctggaagaa agccgtcaga    780
gctgcaacag ggaagagact tagagatagt caagaaactt tagccggatt cttagagttt    840
tggtatgcta agacaaacga ataa                                           864

SEQ ID NO: 392              moltype = DNA  length = 885
FEATURE                     Location/Qualifiers
source                      1..885
                            mol_type = genomic DNA
                            organism = Penicillium swiecickii
SEQUENCE: 392
atgagatttc cttcaattt tactacagtt ttattcgcag catcctccgc attagctgct      60
cctagtagac ctgttccaag ggatgtttct acctctgtct tatctcagtt aagtctattc    120
gcagagtact ctgctgcttc ttactgctcc aacaacatca attcaactgg aaacgctctg    180
tcttgcgaag cagggaattg tccctctgta caatctgcag atactaccac tttgtgggaa    240
ttcgatagaa cgtgttctta tggaaacgtt gccggtttct tggcagtcga caaaaccaac    300
aaaactattag tagtctcttt tcgtggaagc cgttctatta gtaactggat tgccaacatt    360
aactttggtt taacagatgc accatctcta tgttcaggtt gtgaagcaca ttctggcttt    420
ctagagtcct gggaaaccgt agcagatgac ttaactacca acatcaaaag cgctcaatca    480
acatattctg gctatactct agttttgacc ggtcattcat ttggtggggc agttgccgct    540
ttaggcggaa ccgccttaag aaatggtggt tctactttga acgtctatac ctatggacag    600
cctagggttg gtaatggagc attagcttca tacataacaa atcaaggatc actatggcgt    660
gtcacacata cagatgatat tgtacccaag ttacctcctt ccagctttgg atttagtcac    720
cctagtcctg agtactggat tacctccgag aacgaagtca cagttacctc atccgatgtt    780
gaggtaatcg aaggtgttgg ttctaaaagc ggtaacgctg gtaccttaaa ccccgacgta    840
gaggcccaca attggtattt gggctacatt gatgggtgtc aataa                    885

SEQ ID NO: 393              moltype = DNA  length = 888
FEATURE                     Location/Qualifiers
source                      1..888
                            mol_type = genomic DNA
                            organism = Talaromyces boninensis
SEQUENCE: 393
atgagatttc cttcaattt tactacagtt ttattcgcag catcctccgc attagctgtc      60
cctacaccag ttacaagaag aactgtctct acagcattgt tagatacgct agacttattc    120
gcccagtatt ctgctgccgc atactgtcct gccaacttca attcaagctc tacgtctctt    180
gcatgtagcg ctggtaactg tcctactgtt caagctgcag acactaccat cttatactca    240
tttgacaaat ctgcaagttt cggtgacgct accggttatg tcgccgttga caatacaaac    300
cagttgatag ttattgcctt tcgtgggtct tcagacctat ccaattggat tgcaaacttg    360
gatgtacctt tcaccgatgc tggcaacatt tgttcaggat gcgaagttca ctctggcttc    420
tacgacactt ggcaaactgt agcttcagac atcacagcaa ctgtggattc tgcattatca    480
acttaccctg gttacactgt tgtcgctact ggacattcac tgggaggtgc cttggctgcc    540
ataggtgcca cagtcttaag atcttctggt caagtggtca aactatatga ttacggacag    600
ccaagaattg gcaacttagc tttagcagac ttcattacaa gtgaaaccgc tgggtccaac    660
tatagagtaa ctcatagtga tgatattgtc cctaagctgc ctcctgaatt cctaggatac    720
gcacacttct ctccagagta ttggatcaca tccggtgata acgtagcagt tacagacgca    780
gacattgttg aagttattgg tgtggatagc actgcaggta atgacggcac gtttggcgac    840
tccatcaatg cacatttgtg gtactttgag gctattagtg cttgctaa                 888

SEQ ID NO: 394              moltype = DNA  length = 891
FEATURE                     Location/Qualifiers
source                      1..891
                            mol_type = genomic DNA
                            organism = Hamigera striata
SEQUENCE: 394
atgagatttc cttcaattt tactacagtt ttattcgcag catcctccgc attagctgct      60
cccgcaccta ttctacgtag agatgtcagt gcaagtgtcc ttaatgaact agatttgttt    120
gctcagtatt ctgcagctgc ttactgttcc tcaaacatag gttccacagg aaacaagttg    180
atgtgcaatt ttgaaattg tcccagagtc gaagcctccg acacagtaac catcgatgag    240
ttcaatgagt ctgcaagtta cggggatgtc gctgggtaca ttgcagtgga caacacaaat    300
caacttctgg ttttgtcttt tagagggtcc agctcctat caaattggat cgccaacatt    360
gatgttgatt tgcacagacgc ctccagttta tgttcaggtt gcgaagtaca ctctgggttc    420
tggagcgcat ggcaaacagt acaaggaact attacctcta gttagaatc agccagagca    480
tcatatccag gttatacgtt ggtctttacg ggtcacagtt atggtgccgc tctggctggc    540
ttagccgcta caaccttgag ggacgctggt tggactatac agttgtacaa ttacggtcaa    600
ccgagattga gtaacttagc cttggcacag tacatacagt ctcaaacaca gggttccaat    660
tacagagtga cgcacacaga cgatattgta cctaagcttc ctcctgagtt cttaggatat    720
gaccattact ctccagagta ttggataaca tccggtgata acgtcactgt taccacttca    780
gacgtacagg ttatcgaagg gattgactcc gtcgctggaa atgacggaac ttcagatgat    840
tccactgaag ctcatcaatg gtatttcatc tatatcagtg aatgttcata a             891
```

```
SEQ ID NO: 395          moltype = DNA  length = 1113
FEATURE                 Location/Qualifiers
source                  1..1113
                        mol_type = genomic DNA
                        organism = Bacillus sp.
SEQUENCE: 395
atgagatttc cttcaatttt tactacagtt ttattcgcag catcctccgc attagctatt  60
acatccttat tcggaagctt ccaaaaagcc ttcgcctggt catgtgatga tccacataat  120
caagaccagt caacccactt attcatagtc aacaatggtg tcaagttgat ttcaggaaac  180
gcagatcctg ccataaacaa accgtccaca ttgttggaac agtttagaga tagatgggaa  240
caaggactgt atgatgcaga ccacataaac cctttctacg atactagtac attcatgtca  300
cacttctatg acccagatac tcaaaccaat tacgctggta gatcttatcc aacggctcgt  360
caatcaggtg ctaagtactt caatctagcc tccgactact acaagaatgg agacttttac  420
aatgctttct attaccttgg tgtctcatta cactacttta ccgacgcaac aatgccactt  480
catgcatcca atatcagcaa cttagaccat caggcaccag ggtatcattc taagttggaa  540
tcatactctg aaagcattca ggaccaggtt acagtccccg attctggact attcaattgg  600
gtgagttcta cagacccgga actatggatt caccaagcag ctgttcaagc taaaagcgtt  660
cttccacagg tttggaatga ctccatcatt tcctggttct ggcaagctgc atactcaaac  720
tattactcag atatgtggaa atccgcagtt aaagctccca ttttgaatca gttaaaccag  780
gcagagagag aaactgcagg cttcatagac atgttcttca gactaaatgg ggtcgagatg  840
ccagtgacag tttactcaga aactgctttt gggggagctt ctgaattgct aggctcaggc  900
aactatgact atgaccaatt ggtaaaagga ataggaaatg atgctatttc atctattcac  960
attgctcccg gttaccaggt aacgcttttc gccgattcca attactcagg tgcctctaaa  1020
gttttgacag cagatgcctc agatttggat aacttcaaca aaaccataag ttccttaaag  1080
attgaaaaga tacaacctgt aaacgttcac taa                             1113

SEQ ID NO: 396          moltype = DNA  length = 837
FEATURE                 Location/Qualifiers
source                  1..837
                        mol_type = genomic DNA
                        organism = Bacillus thuringiensis
SEQUENCE: 396
atgagatttc cttcaatttt tactacagtt ttattcgcag catcctccgc attagctcac  60
gagaatgcag gaggtcaaag agtgggcgta attcccagat ggagtgctga ggacaagcac  120
aaggaaggtg tcaactctca cttatggatc gtcaatagag caatagacat tatgtccaga  180
aatactacca ttgtaaagca agatcaagtg gcactgttaa acgagtggag aacagatctt  240
gaaaacggca tctattcagc agattttgag aatccgtatt acgataacag cacttttgcc  300
tctcacttct atgatccaga cagtgagaaa acctatatcc cattagccaa acaagcaaag  360
gaaactgggg ctaagtactt taagcttgct ggagaatctt accagaataa cgatatgaag  420
caagccttct tctatcttgg cctatcttta cattatctgg gtgatgtaaa ccaacctatg  480
catgcagcca actttacaaa tctatcttat ccccaaggct tccactccaa atacgagaac  540
tttgttgata ccatcaagga caattacaaa gttacagatg gtactggcta ttggaactgg  600
aaaggcacaa atcctgaaga ttggatacat ggcgctgctg tcgtcgccaa gcaagactat  660
tcaggtattg tcaataacaa cacaaaggaa tggttcgtca aggctgctgt ttcccaagaa  720
tatgcagata agtggagagc agaagtaacc ccaatgaccg gaaaaaggtt gattgatgca  780
caaagaatta cagcaggata catacagtta tggttcgata cctatgtgaa cagataa     837

SEQ ID NO: 397          moltype = DNA  length = 837
FEATURE                 Location/Qualifiers
source                  1..837
                        mol_type = genomic DNA
                        organism = Bacillus mycoides
SEQUENCE: 397
atgagatttc cttcaatttt tactacagtt ttattcgcag catcctccgc attagctcac  60
gagaattgtc accaagatcc tcccatagca ttgaagtggt ctgccgaatc catccacaac  120
gagggcgtaa gtagtcatct gtggattgtc aacaaagcta tagacataat gtctcagaat  180
actactgtcg ttaaacaaaa tgaaacagcc ctactgaatg agtggagaac agatttggag  240
aagggcatct attctgcaga ttatcaaaac ccatactatg acaatagtac gtttgcttcc  300
cacttctatg atccagatag tggcaaaacc tacattccct ttgctaagca agctaaacaa  360
accggtgcca aatacttcaa actagccggt gaagcttatc agaacaaaga catgaaaaac  420
gcattcttct atttgggcct atccttgcac tatttggggg atgttaatca acctatgcat  480
gctgccaact ttaccaacat aagtcatcca ttcggtttcc acagtaagta tgagaacttt  540
gtagatactg tcaaggataa ctatcgtgtt acagatggaa atggttactg gaattggcaa  600
tctaccaatc cagaagattg ggtgcatgcc tccgcttctg ccgcaaaggc cgatttttcct  660
tcaattgtta atgataacac caaaaactgg tttctaaaag ccgctgtttc tcaagattca  720
gcagataagt ggagagctga agtaacacct gttacgggaa aaagattgat agaagctcaa  780
agaattactg caggatacat ccacttatgg ttcgacacat acgtaaacaa caaataa     837

SEQ ID NO: 398          moltype = DNA  length = 837
FEATURE                 Location/Qualifiers
source                  1..837
                        mol_type = genomic DNA
                        organism = Fictibacillus macauensis
SEQUENCE: 398
atgagatttc cttcaatttt tactacagtt ttattcgcag catcctccgc attagctcat  60
gagaatgaag gggtaacaa agttagggta atacagtatt ggtctgccga agatccacat  120
catgaagaca caaacactca cttatggata gtccgtcatg caatggagat tatggccaac  180
aacaaagatg ttgtgaaacc aggcgaagtc gagcaactaa aacaatggca atcagaccta  240
gaacaaggca tttacgatgc agatcatgcc aacccgtatt acgataacgc aacgttcgct  300
```

```
tcccatttct atgatccaga cactggtaag tcatacatcc ccttggcagc acacgcaaaa   360
acaaccagcg tcaaatactt caaaagagct ggggaagcat accaaaaggg tgatcataaa   420
caagcctttt acaatcttgg tctggctctg cattacatag gtgatctaaa ccagccaatg   480
catgcagcca atttcacaaa cttatcttat cctcaaggat tccattccaa gtatgagaac   540
tatgttgata gcttcaagga ggattatgct gtcaaagatg gagagggtta ctggcattgg   600
aaagggacca acccggaaga ctggttgcac ggtacagctg ttgctgccaa gaaagattat   660
ccagacatcg taaatgatac aaccaaagcc tggtttgtaa aagcagcagt ctcaaactct   720
tatgcagcta aatggagagc tgccgttgtt cccgcaacgg gcaagaggtt aacagaagcc   780
caacgtatct tggctggtta catgcaacta tggtttgata cttatgtgaa caaataa      837

SEQ ID NO: 399           moltype = DNA   length = 864
FEATURE                  Location/Qualifiers
source                   1..864
                         mol_type = genomic DNA
                         organism = Listeria seeligeri
SEQUENCE: 399
atgagatttc cttcaatttt tactacagtt ttattcgcag catcctccgc attagcttgt   60
ggcgacgaga gtgtaaagga ccaaatcgct ccacacgata ttcaaaacaa gttaccatct   120
aagtttgggtt ggtccgctga acatccatcc aaaaacgaga tcaataccca cttgtggttg   180
tttaaccaag cagagaagat cttagctaaa gatgtgactg gggctcagtt agatctggtt   240
agagagttga agaactacaa caaagaaatc gctcaaggca ttttcgatgc agaccacaag   300
aatccttact atgacaaaaa cactttttcta tcccatttct acaatcctaa aacacacaaa   360
acttacatag ctgggttttcc aaacgcaaag gatacaggta ctaagtactt caacataagt   420
atagaagaat accaagatgg caatttcgaa aaagcttttct ataacctagg cctagctatc   480
cactactata cagacatatc ccaacctatg cacgccaaca actttacagc tctatcacat   540
cctgttggtt accattgtgc atatgaaaac tatgtgacac tttaagca aatcttccaa   600
gcttcagctg aatctgaagc taagtggttt tgcacagatg acgtctccga atggtttcac   660
gaaaatgcta aaagggcaca agcagattat cctaagattg tgaacaccat catcaagaaa   720
tcctacatac aaggtctatc agacagccaa aaagatagga cctggaagaa agccgtcaga   780
gctgcaacag ggaagagact tagagattcc caagaaactt tagccggact tttagagttt   840
tggtatacaa agacaaacga ataa                                          864

SEQ ID NO: 400           moltype = DNA   length = 885
FEATURE                  Location/Qualifiers
source                   1..885
                         mol_type = genomic DNA
                         organism = Penicillium donkii
SEQUENCE: 400
atgagatttc cttcaatttt tactacagtt ttattcgcag catcctccgc attagctgct   60
cctgcaagac ctgttccaag ggacatttct tcctccttgt tagatgagtt aacgctattc   120
gcagagtacg ctgctgcttc ttactgctcc aacaacattg attcaactgg agacgctgtg   180
acttgctcag gagactattg tcccttggta caatctgctg gtgcaaagac tttgtatgaa   240
ttcaatgata gcactgaatg gggagacgtt gccggttctc tggcagtcga cactaccaac   300
aaattgattg tactatcttt tcgtggaagc cgttctattt ccactggat tgccaatttg   360
gactttggtt taacagatac ctcttctcta tgtgatgatt gtgaagcaca ttctggcttt   420
tggaagagtt gggaaaccgt agcagatgat atgactgccc aaatagaaag cgctcaatca   480
agttatccat cctatactct agttttgacc ggtcattcat ttggtgccgc agttgccgct   540
ttaggcgcaa ccgccttaag aaatgctggt tatactttgg acttgtatac ctatggacag   600
cctaggggttg gtaatgaagc attagctact tacatgacat ctcaaggatc actatggcgt   660
gtcacacatg aagatgatat tgtacccaag ttacctcctta tgagctgggg atttttccac   720
gcatcccctg agtactgggt taccagtgac agcgatgtca cagttaccac aagtgatgtt   780
gaggaagtgg ttggtgttga ttctacagcc ggtaacgctg gtacttcagg cgagtccatt   840
tctgcccaca attggtactt tgttgaaatt gatgggtgtg attaa                   885

SEQ ID NO: 401           moltype = DNA   length = 888
FEATURE                  Location/Qualifiers
source                   1..888
                         mol_type = genomic DNA
                         organism = Hamigera paravellanea
SEQUENCE: 401
atgagatttc cttcaatttt tactacagtt ttattcgcag catcctccgc attagctgct   60
cccgcagcag ttaggcgtga tgtaagtgca ggagtcctag ccaacttaga cttgtttgct   120
cagtattctg ctgcagctta ttgcgattcc aatttgaatt cagacggtac aaagcttact   180
tgccaggacg gtaattgtcc acttgtagaa gctgccgaca ccgaaaacact tgacgaaaaac   240
gatatgaccg ctacatacgg gaacgtagca ggttacatcg ctgtagaccg taccaataga   300
ttacttgtgt tggcttttag aggtagcgcc agcatctcaa attggattgc aacttgaac    360
ttaggtttaa cggatgcctc tgccctatgt gcaggttgtc gtgttcattc cggtttctgg   420
gaagcctggc aaacagcaga agctacaatg tcagacatta tcgcttcagc agcccaaaca   480
tatccaggtt atactctggt tgcactgggg catagttacg tgtcgcctt agccgctatc   540
gctgctacca aattcagaaa cgagggttat gctgttgaac tttacgatta tggacaacct   600
cgtataggaa atctagctct ggctcaatac atcacaaacc aatcttctgg tggcaacttt   660
cgtgttacgc acaccaatga cattgttccc aagttacccc cagattggtt aggatactct   720
cactttggac cagaatactg gattacatca ggcgatggta tccctgttac taccgcagat   780
gtggaagtga ttagtggagt ggatgcaact ggcggtaatg atggcgcaga aggtacttca   840
gtggatgcac atagatggta ctttgtgtac attagtcaat gtgaataa                888

SEQ ID NO: 402           moltype = DNA   length = 891
FEATURE                  Location/Qualifiers
source                   1..891
```

```
                         mol_type = genomic DNA
                         organism = Talaromyces lecycettanus
SEQUENCE: 402
atgagatttc cttcaatttt tactacagtt ttattcgcag catcctccgc attagctgct  60
ccagctccag ttcttaggag agatgtatct tcctctgtat tgtctgagct ggacttattc  120
gctcagtact ctgccgctgc atattgctct tccaatatcg gttctccggg tacgaagctt  180
acttgtagtg tcggtaattg tccccgtgtt gaagctgccg atacagagac gttgatagag  240
tttaacgaat catcttcttt tggtgatgtg actggctata tcgctgtgga taggaccaat  300
tcactactgg tgttggcatt taggggctct tccacagtgt caaattggga agcagatcta  360
gattttccat taacagatgc ttctagtctg tgcagtggct gtgaaattca ctctggtttt  420
tgggctgcct ggcaaaccgt acaggcatcc atcactagca cattggagtc agctattgct  480
tcttaccctg gttatacttt ggtcttcaca ggtcattcat acggtgccgc tttggcagca  540
atagcagcaa ctacattgag aaatgctggt tacacaatcc agttgtacga ctatggccag  600
ccgaggttag gtaatcttgc tctggcccag tacattacgg cacaaacaca gggtgccaac  660
tatcgtgtta ctcataccga tgacatcgta cccaaactac cccctgagtt gtttggctat  720
caccacttct ccccagagta ttggataacg tcaggcgata atgttacagt tacaactagc  780
gatgtgcaag tagtcactgg aattgacagt acagctggaa atgatgggac tttgcttgat  840
tctacaagtg cccatgattg gtacattgtc tacattgatg ggtgcgatta a           891

SEQ ID NO: 403           moltype = DNA  length = 1407
FEATURE                  Location/Qualifiers
source                   1..1407
                         mol_type = genomic DNA
                         organism = Paenibacillus sp.
SEQUENCE: 403
atgagatttc cttcaatttt tactacagtt ttattcgcag catcctccgc attagctatt  60
acttctatct ttggcaatag ccaagacgct tacgcatggt cagcagacga cccacattct  120
caggactttt ccacacactt gttcattgta aatggaggcg tcaaattgat ttctggtaat  180
gttgatagcg ccataaacaa atcttctacc ttgttggaac agtttcgtgg aagatgggaa  240
cagggccttt acgatgccga tcatcttaat cccttctatg atagctcaac ctttatgtca  300
cacttctatg atccagatac ccaaacgaac tatgcaggat tatcataccc aacagctaga  360
caatctggtt ccaaatactt caaagtcgcc tcaaactact acaagaatgg tgatttctca  420
aacgccttct actatctggg agtaagtctt cactacttta cagactcaac tatgcctcta  480
cacgcatcag acattagtaa cctagatcat agagccccag gctaccacgc caaattggaa  540
gaatatgcca catccataca aaatcagatc aatgttccgg atagcggctt attcaattgg  600
atttccagta cagatcctga actatggatt catcaggctg ctgtacaagc caaatctgtg  660
atgccagaag tcttcaatga cacgattacc gattggtttt ggaaagccgc tttttcctat  720
tactattccg atatgtggaa atccgctgtc aaaatcccta tactaaatca gcttaatcaa  780
gcagaaagag aaacagccgg ttacattgac ttgttcttta ggttaaacgg tgtggatatg  840
ccggttgccg tgtacaaagg gactgcattt ggtggggcac tacaacttct gggtttcggc  900
aactatgatt acgaccaact tgttaaaggt ataggtaatg atacagttag ttcaattagg  960
atagcaccgg gttaccaagt aactttgttc gcagattcca attactcagg agttagcaag  1020
gtgttaacgg cagacgcttc agatttgggt aacttcaata agacaacatc ttccttgaag  1080
attgagaaga ttcaaccagt tactgtctat acagatgctt catttagtgg gagtagccaa  1140
tcattttccg taggaaatca tgattacaac gaaatcgtta acagaaagtt gaatgatact  1200
atttcttcta taagaatagc ccctgggtat caagtcacct tgtttagaga cagcaactat  1260
tctggggttt ctactgtagt taccggtgat gtgtatggtt tatcaaactt aaacgaccaa  1320
acaagtagcc taaaagtgga ggttattcca acaaatccgg caccatccca aacgaaacag  1380
tccatctttt ccaatccctt gaattaa                                      1407

SEQ ID NO: 404           moltype = DNA  length = 837
FEATURE                  Location/Qualifiers
source                   1..837
                         mol_type = genomic DNA
                         organism = Bacillus toyonensis
SEQUENCE: 404
atgagatttc cttcaatttt tactacagtt ttattcgcag catcctccgc attagctcac  60
gagaatgacg gaggtcaaag agtgggcgta attcccagat ggtccgctga ggacaagcac  120
aaggaaggtg tcaactctca cttatggatc gtcaatagag caatggacat tatgagtaga  180
aatactacct tggtaaagca agatagagtg gcactgttaa acgagtggag aactgaactt  240
gaaaacggca tctatgcagc agattatgag aatctgtatt acgataacag cacttttgcc  300
tctcacttct atgatccaga caacggtaaa acctatatcc catatgccaa acaagcaaag  360
gaaactgggg ctaagtactt taagcttgct ggagaatctt acaagaataa ggatatgaag  420
caagccttct tctatcttgg cctatcttta cattatctgg gtgatgtaaa ccaacctatg  480
catgcagcca actttacaaa tctatcttat cttcaaggct tccactccaa atacgagaac  540
tttgttgata ccatcaagga caattacaaa gttacagatg gtaatggcta ttggaactgg  600
aaaggcacaa atcctgaaga ttggatacat ggcgctgctg tcgtcgccaa gcaagattat  660
gctggtattg ttaatgacaa cacaaaggat tggttcgtca gggctgctgt tagtcaagaa  720
tatgcagata agtggagagt agaagtaacc ccaatgaccg gaaaaaggtt aatggatgca  780
caaagagtta cagcaggata catacagtta tggttcgata cctatgggaa cagataa     837

SEQ ID NO: 405           moltype = DNA  length = 837
FEATURE                  Location/Qualifiers
source                   1..837
                         mol_type = genomic DNA
                         organism = Bacillus thuringiensis
SEQUENCE: 405
atgagatttc cttcaatttt tactacagtt ttattcgcag catcctccgc attagctgat  60
gagcacacca caaacaacaa gattgacata ttccaacctt ggtcaaatga agaaaatcat  120
```

```
aaagaaggca agaattcaca tctttggatc gtaaacggag caatcgacat aatgagtaga  180
aacaccacaa ttgtaaaaca agagaatcta gctctgcttc agcaatggag gacccatctt  240
gaaaatggct tgtatgtcgc cgactatgag aatccgtact atgatagcgg gacctttgca  300
tcacacttct acaatccaga tacagacagt acgtacttac catttgctaa gcacgccaaa  360
gaaactggtg ccacttactt caccctagca ggtgaagctt accaacataa gaatatccaa  420
caagccttct tctacttagg tgtttcattg cattacttgg gggacatcaa tcagccaatg  480
catgctgcca actttacgaa cttatcttac ccattcggat ttcactccaa atacgaacac  540
tttgtcgata ccatcaaaca gaactatgag attatggatg gcgagggata ttggaattgg  600
aagggaaggg atcctgaaga ctggatacac caggcagccg ttgctgcaaa ccaagacttt  660
agtgatatcg tgaactcaga caccaagaat tggttcgtca aggcagctgt ttcacaaact  720
tacgcagata gatggagagc tgctgtaaca cccattactg gcaagagatt gatcgaagct  780
cagagaatca ctgccggata cattcaactt tggtttgata catacataca tcaataa     837
```

```
SEQ ID NO: 406          moltype = DNA  length = 837
FEATURE                 Location/Qualifiers
source                  1..837
                        mol_type = genomic DNA
                        organism = Bacillus thuringiensis
SEQUENCE: 406
atgagatttc cttcaatttt tactacagtt ttattcgcag catcctccgc attagctcat  60
gagaatgatg gggttccaa gattaagatc atacatagat ggtctgccga agataaacat  120
aaagaagggg ttaactctca cttatggata gtcaacagag caatcgacat tatgtcaaga  180
aatacaactt tagtgaaaca agacagagtc gcccaactaa atgaatggag aactgagcta  240
gaaaatggca tttacgctgc agattatgag aacccgtatt acgataactc cacgttcgct  300
tcccatttct atgatccaga caatggtaag acatacatcc cctttgcaaa gcaggcaaaa  360
gaaactggtg ccaaatactt caagttagct ggggaatcct acaaaaacaa agatatgaaa  420
caagcctttt tctatcttgg tctgtctctg cattacctag gtgatgtcaa ccagccaatg  480
catgcagcca atttcacaaa cttatcttat cctcaaggat tccattccaa gtatgagaac  540
tttgttgata cgatcaagga caactacaaa gtcacagatg gaaacggtta ctggaattgg  600
aaagggacca acccggaaga ctggattcac ggtgctgctg ttgttgccaa acaagactat  660
tcaggaatcg taaatgacaa taccaaagac tggtttgtaa aagcagcagt ctctcaagaa  720
tatgcagaca aatggagagc cgaggttaca cccatgacgg gcaagaggtt aatggatgcc  780
caacgtgtca ctgctggtta catacaacta tggtttgata cttatgggga tagataa     837
```

```
SEQ ID NO: 407          moltype = DNA  length = 867
FEATURE                 Location/Qualifiers
source                  1..867
                        mol_type = genomic DNA
                        organism = Talaromyces rugulosus
SEQUENCE: 407
atgagatttc cttcaatttt tactacagtt ttattcgcag catcctccgc attagctgac  60
gtcaccacag cagtcttgga cgacttaacc ttgttttcac agtattcagc tgctgcatat  120
tgttctacca acttgaattc tacaggtgtg gcagtgacat gcagtgttgg taattgtccc  180
ctagtcgaag cagcagatac acaaatactg tatgactttg acgaatcctg caagtttggc  240
gatgcatctg gcttcattgc agtggacaat accaataact tgattgtgtt gtcttttagg  300
ggatctcacg atctttcaaa ttggatcgca aacttagatt tcttcttagt cgaaactgcc  360
tcaatctgcg aaggttgcta catgcatggt ggtttttggg aaacttggca aacagtcgct  420
gcaaacgtta cagaacaatt agaagctgct atcactgcaa accctggata taccttagtt  480
atgactggtc acagtctagg agctgccttg gctgcaatag ttgctaccga gtttaggaat  540
gaaggcattg atgtagaaat gtacaattac ggccaaccaa ggctaggcaa cttagcttta  600
gctcagtata tgacaaacca gacacagact tcaaactaca gggttactca ttccgatgat  660
attgttccta agcttccacc tagagtacta gatttcgacc actattctcc tgagtattgg  720
ataacttcag ccaataacgt gtcagtatca gacgcagatg tcgtacaggt cgttggtata  780
gatagcacgg atggcaatga tggcaccatc ttagatgaca tagaggctca tagatggtac  840
ttagggtata tctctgaatg ttcataa                                    867
```

```
SEQ ID NO: 408          moltype = DNA  length = 885
FEATURE                 Location/Qualifiers
source                  1..885
                        mol_type = genomic DNA
                        organism = Penicillium sp.
SEQUENCE: 408
atgagatttc cttcaatttt tactacagtt ttattcgcag catcctccgc attagctgct  60
cctgcaagac ctgttccaag ggatgtttct agtgctacat tatctgagtt aacgctattc  120
gcagagtacg ctgctgctgc ttactgctcc aacaacattg attcaactgg agacgctctg  180
tcttgctcag gagggtattg tcccgaagta caatctgctg gtgcaaccac tttgtatgaa  240
ttcgaagata gcacagattt tggagacgtt acgggtttct ttgcagtcga caataccaac  300
aaactattag tactatcttt tcgtggaagc agctctatta gtaactggat tgccaatttg  360
gactttggtt taacagatgc atcttctcta tgttcaggtt gtgaagcaca ttctggcttt  420
tacaagtcct ggggtgtcgt agcagatact ttaactgccc aagtcgctag cgctgtttca  480
acatatccaa gttatactct agttgttacc ggtcattcat tgggtggggc attagccgct  540
ttaggcggaa ccgccttaag aaatgctggt tatactttgg acatctatac ctatggacag  600
cctagggttg gtaataccgc attagcagat tacatgacaa atcaaggatc actatggcgt  660
gtcacacatt caaatgatat tgtacccaag ttacctcctg caagctgggg atttaccccac  720
gcaagtcctg agtactggat tacctccggg aacgatgtca cagttaccac atccgatgtt  780
accgaagtga ctggtgttgg ttcttcagac ggtaacgctg gttcatcagg cgacagtgta  840
agtgcccaca attggtacat tgttgatatt gatgggtgtt cttaa                885
```

```
SEQ ID NO: 409          moltype = DNA  length = 888
```

| FEATURE | Location/Qualifiers |
|---|---|
| source | 1..888 |
| | mol_type = genomic DNA |
| | organism = Hamigera avellanea |

SEQUENCE: 409

```
atgagatttc cttcaattttt tactacagtt ttattcgcag catcctccgc attagctgct   60
cccgcacctg ttaggcgtga tgtaagtgca ggagtcctag ccaacttaga cttgtttgct  120
cagtattctg ctgcagctta ttgcgattcc aatttgaatt cagacggtac aaagcttact  180
tgtgccgctg gtaattgtcc acttgtagaa gctgccgaca ccgaaacact tgacgaattc  240
gatatgaccg ctacatacgg gaacgtagca ggttacatcg ctgtagaccg taccaataga  300
ttacttgtgt tggcttttag aggtagcgcc agcatctcaa attggattgc caacttgaac  360
ttaggtttaa cggatgcctc tgccctatgt gcaggttgtg aggttcattc cggtttctgg  420
gaagcctggc aaacagcaga agctacaatt tcagacatta tcgcttcagc agcccaaaca  480
tatccaggtt atactctggt tgtaactggg catagttacg gtgctgcctt agccgctatc  540
gctgccacta gattcagaaa cgagggttat gctgttgaac tttacgatta tggacaacct  600
cgtataggaa atctagctct ggctcaatac atcacaaacc aatctggagg tggcaacttt  660
cgtgttacgc acaccaatga cattgttccc aagttacccc cagattggtt aggatactct  720
cacttggac cagaatactg gattacatca ggcgatggtg tgcctgttac taccgcagat  780
gtggaagtga ttagtggagt ggatgcaact ggcggtaatg atggcgcaga aggtacttca  840
gtggatgcac atagatggta ctttgtgtac attagtcaat gtgaataa              888
```

| SEQ ID NO: 410 | moltype = DNA length = 894 |
|---|---|
| FEATURE | Location/Qualifiers |
| source | 1..894 |
| | mol_type = genomic DNA |
| | organism = Penicillium spikei |

SEQUENCE: 410

```
atgagatttc cttcaattttt tactacagtt ttattcgcag catcctccgc attagctgct   60
cctactagat tgcttattcc tagggacata tcaagtgacg tgttagccga gttgactttg  120
tttgccgaat actctgcagc tgcatattgt tcagccaata tcgatagtgc atctgccgat  180
tctgccttga catgtgaatc tggtaactgc ccagaagtac aaagtgcaga tacgtctacc  240
ttatacgaat ttgacgaaac cacagattac ggcgatgtag ctggttttctt tgctgtcgac  300
aaaacgaatg agctgttggt tcttagttc agaggttcta gaacgatttc aaattgggtc  360
gccaatttgg attttgactt aacagatgca tcttctcttt gtagtgactg cgaagctcac  420
tcaggttttt ggaaatcctg ggaaacagtt gccgatgagt taacaacaca aatagaatct  480
gcacagaata gttatccaga ttatcaactg gtattgaccg gtcatagtct aggtgccgca  540
ttggcagctt tggctggtac tgccctaaga aacgctggat acacccttga tttgtatacc  600
tttggtcaac caagggtcgg caacttagca ttagcagatt acatgacaga tcaaggatca  660
ttatggagag ttactcatac agacgacata gtaccaaggg tccctcccga aagcttcggt  720
tatgcacatg ccagccctga gtattggatc acatccggta atgacgtaac cgttactaca  780
tcagatgttg aggaaatcgt tggtgtcaat tccagtgccg gtaatgccgg agaagcagat  840
ttgtcaatag atgctcacaa ttggtacatt gtctacattg atgaatgtga ataa        894
```

| SEQ ID NO: 411 | moltype = DNA length = 1500 |
|---|---|
| FEATURE | Location/Qualifiers |
| source | 1..1500 |
| | mol_type = genomic DNA |
| | organism = Paenibacillus alginolyticus |

SEQUENCE: 411

```
atgagatttc cttcaattttt tactacagtt ttattcgcag catcctccgc attagctatt   60
acctccgtct ttggcaacta tcaaaacgca tacgcatgga gtgcagatga cgttcataat  120
caagactatt ctacacactt attcattgtc aatggcggag taaagttgat aagtggcaat  180
gccgactcag ccatcaacaa aagttcaaca ttactggagc agttcagaga caggtgggag  240
caaggtcttt atgatgcaga ccacttaaac ccattctacg attcaagcac gttcatgtca  300
catttctacg atccagatac tcaaaacgaac tatgccgatt tatcttatcc gaccgccaga  360
caatctggta gcaaatactt caaggtcgca tcagactatt acaagaatgg agatttctcc  420
aacgccttct actacttagg tatttcattg cattacttta cggattcaac aatgccatta  480
catgcttcag acattagcaa cttagatcac agagcacctg gttaccacgc taagttggag  540
gaatacacta caagtattca gaaccagatt acagttccag acagtggcct gttcaattgg  600
atctcctcca cagacccaga gttgtgatc caccaagccg ctgttcaagc caaatccgtc  660
atgccacagg tgttcaatga ctctattaca gattggttct ggaaggctgc tgtatcctat  720
tactattccg atatgtggaa gaatacagtt aagactcaaa tcctaaatca acttaatcaa  780
gccgaacgtg aaaccgcagg gtacatagac ttgttctttta gacttaacgg tgttgatatg  840
cccgttacag tctacaatgg tactgccttt ggtggcgcat ctcaattact aggtttcggc  900
aattacgatt acaatcagtt ggtgaagggc ataggtaatg atacaattag ttccattagg  960
attgctccag gctaccaagt tacactttt gcagactcca attactctgg cgttagtacg 1020
gtcgtcacac gaaatgttta cgggttatca aacttgaatg accagacaag cagtttgaaa 1080
gttggtgtta taccaaccaa cccagctcca tctccaacaa tccaggcaga atctttctct 1140
gggtcccagg ggatcttgac tcacagtgca gggagtggga ccgttgtcgg caacattaac 1200
agtggttctt ggctttctta tgataatgta gactttggta ccggtaagac caagtttgta 1260
gcttctgttg aatggatcc cgctttcgct gctataggta agcagttgga gttaaggtta 1320
gacagtccca cagggacctt gattggtacg tttacaatat cttcatctgg tggtttgggat 1380
gcttatacga ctcagaattg ctacgtaaca tctgcatctg gtactcataa gctttacatc 1440
atcacaaaag gtaacggtc tggatttggt aacatagatt ggtttacttt ttctagttaa 1500
```

| SEQ ID NO: 412 | moltype = DNA length = 837 |
|---|---|
| FEATURE | Location/Qualifiers |
| source | 1..837 |
| | mol_type = genomic DNA |

```
                           organism = Bacillus mycoides
SEQUENCE: 412
atgagatttc cttcaatttt tactacagtt ttattcgcag catcctccgc attagctcat   60
gagaacgacg gtggcagcag gattaacata gtccataggt ggtctgcaga agataaacat  120
aaagaaggtg tcaattccaca tctttggatc gtaaacagaa caatggacat aatgagtaga  180
aacaccacat tggtaaaaca agaccaagtc gctctgctta acgaatggag gaccgaactt  240
gaaaatggca tctatgcagc cgactatgag aatccgtact atgataacag cacctttgca  300
tcacacttct atgatccaga taatgggaag acgtacattc catttgctaa gcaggccaaa  360
gaaactggtg ccaaatactt caagctagca ggtgaattac acaagaataa ggatatgaag  420
caagccttct tctacttagg tttgtcattg cattacttgg gggatgtaaa tcagccaatg  480
catgctgcca actttacgaa cttatcttac ccacagggat ttcactccaa atacgaaaac  540
tttgtcgata ccatcaaaga caactacaaa gttacagatg caacggata  ttggaattgg  600
aagggaacaa atcctgaaga ctggatacat ggcgcagccg ttgctgcaaa gcaagactat  660
agtggtatcg tgaacgataa cactaaagat tggttcgtca aggcagctgt ttcacaagga  720
tacgcagaca aatggagagc tgaagtaaca cccatgactg gcacaagatt gatggatgct  780
cagagagtga ctgccggata cattcaactt tggtttgata catacggaaa tagataa    837

SEQ ID NO: 413         moltype = DNA    length = 837
FEATURE                Location/Qualifiers
source                 1..837
                       mol_type = genomic DNA
                       organism = Bacillus bingmayongensis
SEQUENCE: 413
atgagatttc cttcaatttt tactacagtt ttattcgcag catcctccgc attagctcac   60
gagaatgaag gaggcaacaa aatcagggta attcagtatt ggtccgctga ggacaagcac  120
gcagaaggtg tcaactctca cttatggatc gtcaatagaa caatagacat tatgagtaga  180
aatactacca ttgtaaagca agatgaagtg gcactgttaa acgagtggag aactgaactt  240
gaaacggca  tctatgcagc agattatgag aatccgtatt acgataacag cacttttgcc  300
tctcacttct atgatccaga ctccggtaaa acctatatcc catttgccaa acaagcaaag  360
gaaactgggg ctaagtactt taagcttgct ggagaatctt accaaaaaca ggaaatgaag  420
caagccttct tctatcttgg cctatcttta cattatctgg gtgatgtaaa ccaacctatg  480
catgtagcca actttacaaa tctatcttat ccccaaggct tccactccaa atacgagaac  540
tttgttgata ccatcaagga caattacaaa gctattgatg gtaatggcta ttggaactgg  600
aaaggcacaa atcctgaaga ttggatacat ggcgctgctg tcgcagccaa gcaagaatat  660
gctggtattg ttaatgacac cacaaaggat tggttcgtct gggctgctgt tagtcaagaa  720
tatgcagata agtggagagc agaagtaacc ccagctaccg aaaaagatt  agttgaagca  780
caaagagtta cagcaggata catacagtta tggttcgata cctatgggaa cagataa    837

SEQ ID NO: 414         moltype = DNA    length = 840
FEATURE                Location/Qualifiers
source                 1..840
                       mol_type = genomic DNA
                       organism = Bacillus mycoides
SEQUENCE: 414
atgagatttc cttcaatttt tactacagtt ttattcgcag catcctccgc attagctcat   60
gagaacagtg atcagaacgg aatttccttt ggacataagt ggtctgcaga agctattcat  120
gatgaaggtg ttagtactca tctttggatc gtaaacgat  caatcgaagt aatggcccaa  180
aacaagacag ttgtacaacc aaacgagata tcactgctta acgaatggag agccgatctt  240
gaaaaaggca tctatagtgc cgactatgac aatccgtact ttgataacgg gaccctttgca  300
tcacacttct atgatccaga tactggtggc acgtacttac cattggctaa gcacgccaaa  360
gaaactggtg ccaaatactt caagctagca ggtgaagctt accagaataa cgatctgaag  420
aacgccttct tctacttagg tttgtcattg cattacttgg gggatgtaaa tcagccaatg  480
catgctgcca actttacgaa tgtatctctg ccagtcgcat acactccaa  atacgaaaac  540
tttgtcgata cagtcaaaga caactacaaa gttaagatg  caacggata  ttggaattgg  600
aagagtgtaa atcctgaaga ctgggtacac gcctcagccg ttggtgcaaa ggcagatttt  660
cccttgatcg tgaacgataa gaccaagaaa tggttccttg acgcagctat ttcacaagat  720
gcagcagaca aatggagagc tgaagtaaca cccgttactg gcaagagatt gatggaagct  780
cagagaatca ctgccggata cattcacctt tggtttgata catacgtcaa ctacaaataa  840

SEQ ID NO: 415         moltype = DNA    length = 867
FEATURE                Location/Qualifiers
source                 1..867
                       mol_type = genomic DNA
                       organism = Brevibacillus sp.
SEQUENCE: 415
atgagatttc cttcaatttt tactacagtt ttattcgcag catcctccgc attagctaag   60
aaggagtata aggtcaaata ccatggtaag actattacaa gtcccacaa  gattgatcca  120
agatggagtg aagaatcccc acatgaagag ggccacgcaa cccacttgtg gattgttaac  180
agggcaattg acatcttatc aagaacaagc aataaggatg tgaattccaa ggaaactgaa  240
atgttgaatg cttggagatc cagttgggaa caaggtcttt atgatgccga tcatacaaac  300
ccctattaca atttcggtac attcgcctct cacttctatg atccagatac caaatcaaac  360
tggctgaca cttctggcac cgcattgaca gaaggtagca ggtactttgc actagcaggc  420
aaatactatc aaaatggtga taaggaaaaa gcctttttact acctaggatt gagtttacac  480
tatttgacag acgtcacaca accaatgcat gctgccaact ttacttggtt gaattggaca  540
actagttttc atgcaagtt  tgaggattac accgatgata tccaaggcaa ctatgctgta  600
acagatggtg aaggttactg ggatttccaa gatagtaacc ccgaacttg  gatacatcaa  660
gctgctgtcg acgcaaaagc agaatttccc aatatccaca catcagacat aactaaatgg  720
ttttggctg  cagcagtcag cgactactat agtgacaaat ggcataaggc cgttcaacct  780
acaatcgagc ataggttaac tgaggcacaa agaattaccg caggctactt acatttgtgg  840
```

```
tttaagactt acgttgataa tcaataa                                          867

SEQ ID NO: 416            moltype = DNA   length = 885
FEATURE                   Location/Qualifiers
source                    1..885
                          mol_type = genomic DNA
                          organism = Penicilliumvasconiae
SEQUENCE: 416
atgagatttc cttcaatttt tactacagtt ttattcgcag catcctccgc attagctgct       60
cccgcaaggc cagtcccgag agatgtcagt agtgcaaccc tttctgaatt gactttgttt      120
tcacaatatg ctgcagctgc ttactgtacc aataacgtca attccgcagg agacgccgtt      180
agctgctcag gtggatattg tcccgaagtc caatctgctg cgcaacaac cctttatgag       240
tttgatgact ctacagattt cggggatgtc gctgggttct ttgcagtgga cgcaaccaac      300
aaacttctgg ttttgtcttt tagagggtcc cgtaccattt caaattggat cgccaactta      360
gattttggtc agacagacgc ctccagttta tgttcaggtt gcgaagcaca ctctgggttc      420
ttcaaggcat gggaagcagt agcagatact ttaaccgctc agattgcatc agccgttgca      480
acttatccat catatacgtt ggtattgacg ggtcacagtt ttggtggcgc tgtggctgcc      540
ttaggcggta cagcattgag gaacgctggt tatactttag acttgtatac atacggtcaa      600
ccgagagtag gtaacacagc cttggcagac tacatgacga atcaaggatc cttatgagaa      660
gtgactcaca gcgacgatat cgttcccaag cttccaccca ccagttgggg ttttacccat      720
gcatctcctg agtattggat tacatcaggt gacgatgtta ccgtcactac ttccgatgtt      780
acggaagtga ctggcgtcgg gtcaagtggt ggcaatgcag gtaccagtgg tgattctgtt      840
tccgctcaca attggtacat tgttgacatt gatggctgtc aataa                      885

SEQ ID NO: 417            moltype = DNA   length = 891
FEATURE                   Location/Qualifiers
source                    1..891
                          mol_type = genomic DNA
                          organism = Talaromyces diversus
SEQUENCE: 417
atgagatttc cttcaatttt tactacagtt ttattcgcag catcctccgc attagctgct       60
atcgacccct tgaaccgtag aacaataagt gaaagtctac ttgatgaact agatttgttt      120
gctcagtatt ctgcagctgc ttactgttcc gcaaacttag attccacagg atccgccttg      180
gcctgcgatg ttggaaattg tcccttagtc gaagctgcct ccacaacaat cctttatgac      240
tttgatgaga caaatgattt cggggatgca actgggtaca ttgcagtgga caccacaaat      300
gaatacatca ttttgtcttt tagagggacc gacgacttag agaattggat cgccaactta      360
gattttccat tgattgacgc ctccgacatt tgttcaggtt gcgaaataca cgaagggtgg      420
tgggacagtt gggaaacagt agcttcagac attaccgctc agattgaatc agccgtttca      480
acttatccag actatacgtt ggtagctacg ggtcacagtt taggtgccgc tctggctgcc      540
attgccgcta cagtcttgag gctagatggt tatactgtac agttgtacaa ttacggtgaa      600
ccgagaatag gtaacttagc cttggcagac tacataacga ctgaaacaat gggttccaat      660
tacagagtga cgcacacaga cgatattgta cctaagcttc ctcctgagtt gttaggatat      720
gaccatttct ctccagagta ttggataaca tccggtagtc acgcactgt tcttgataca      780
gacgtaaccg aagtcgtcgg ggtagactcc accgctggaa atgacggaac tttgttggat      840
tccattgatg ctccatagatg gtatttcgtc tatatcagtg aatgttcata a              891

SEQ ID NO: 418            moltype = DNA   length = 900
FEATURE                   Location/Qualifiers
source                    1..900
                          mol_type = genomic DNA
                          organism = Aspergillus wentii
SEQUENCE: 418
atgagatttc cttcaatttt tactacagtt ttattcgcag catcctccgc attagctgct       60
cccagtcctg ttaggcgtga tgtagacagt agtgtcctaa caacttaga cttgtttgct       120
cagtattctg ctgcatcata ttgcttggag aatttgaatt catccaatac aaagcttgaa      180
tgctccgtag gtaattgtcc acttgtagaa gctgcctcca ccgtcacact tgacgaattc      240
gatgaatcct cttcattcgg ggacgtaacc ggtttcatcg ctgcagacga gaccaacaag      300
ttacttgtgt tgtcttttag aggtagctcc gacatcgcaa attggattgc cgaccttgat      360
ttcggtttaa cggatgggag cgacctatgt tcaggttgta aggttcatag tggtttctgg      420
gaagcctggg gaacagtatc agacaacagtt acatccatta tcgaatcagc aaccgccaag      480
tatcccaact atgaactggc ttttactggg cattcctacg gtgctgcctt agccgctgtg      540
gctgccgttg tattcagaaa ctccggttat acagttcaac tttacaacta tggacaacct      600
cgtataggaa atctagctct ggcagattac atcacaaacg ttacagataa gggtgacaat      660
tacagagtga cgcacacaga cgatattgta cctaagcttc ctcccaagtt gttaggatat      720
caccatgcat ctccagagta ttggataaca tccggcaata acgtcactgt taccactgca      780
gacgtagacg ttgtcacagg ggtagactcc accgatggaa atgacggaac tactgcagat      840
tccagaacag ctcatagatg gtatttcggc tatatcagtg aatgttcaac cttgtactaa      900

SEQ ID NO: 419            moltype = DNA   length = 1500
FEATURE                   Location/Qualifiers
source                    1..1500
                          mol_type = genomic DNA
                          organism = Bacillus acidiceler
SEQUENCE: 419
atgagatttc cttcaatttt tactacagtt ttattcgcag catcctccgc attagctata       60
accagctgt tcggcaatta ccaaagagct tttgcttggt cagatgaaga tgttcacaac       120
caagatcatt caacccatca cttcattgta aatggaggag tcaaattgat tgcagacaat      180
acagacccag ccatcaataa gcccacaacg cttctgaacc agtttagaga cagatgggag      240
caaggtttgt acgatgcaga tcacatcaat cccttttacg atactggtac cttcatgtcc      300
```

```
catttctatg atcccgatac acaaacaaac tattccggac tatcctatcc aacagctaga    360
cagtcaggtg gcaagtactt caacttagct agcgattact acaaaaaggg tgactttaac    420
aacgccttt  actatctagg ggtttctctt cactacttta cagacgttac tcagccgttg    480
catgcttcca atatcagcaa tctagatcat aatgctccag gctatcattc caaatacgaa    540
acctacgctg aatctataca atcacaaatc atttgtccta attccggctt gtacaactgg    600
acagatagta cggatcccga agcctggata cataaagcag ccattcaggc aaaaagcgtt    660
ctgcccttgg tttggaatga taccatcatc aactggtttt ggcaggctgc ctattccaac    720
tattactccg caatgtggaa gaatgaagtc aagaatccaa ctctagctca acttaaccaa    780
gccgaacgtg aaacagctgg tttcattgat atgtttttca ggttgaatgg ggttgagatg    840
ccggtaacgg tctacaatga aaatgccttt ggtggagcaa gtgaactttt gggttctggc    900
aactatgatt atgatcaatt gattaagtgt attggtaatg atacgataag ctctattcat    960
atcgcacctg gttatcaagt caccttattc gcagacgcaa actacaaagg tgcttcaatt   1020
gttttgacag gagacgtcaa cgatttgggc aacttcaatc atcaggtgag ttcattgaag   1080
attgagaaga tatctaccaa tccagcctct tctcctacaa tccaagcaga gtctttcata   1140
agcagtaaag gcatcttgac tcataatgtt gggtcaggta ccgttgtggg taacataaac   1200
tcaggctcat ggattggata tgataacgtc gatttcggaa ctggaaaaac caaattcata   1260
gctagggttg gtatggaccc ctcttacgcc atattcgata aacagttgga attgaggttg   1320
gattctccta caggtaccat cattggaacc tttaccatca acatactgg  aggttgggac   1380
acatatgcta ctcagacgag catacttcct ggcgcaactg gtaccacaa  attgtacata   1440
gtttcaaaag ggtctggtga tggatttggc aacattgatt ggataacatt ctctccttaa   1500

SEQ ID NO: 420           moltype = DNA   length = 837
FEATURE                  Location/Qualifiers
source                   1..837
                         mol_type = genomic DNA
                         organism = Bacillus luti
SEQUENCE: 420
atgagatttc cttcaatttt tactacagtt ttattcgcag catcctccgc attagctcac     60
gagaaaaacg aaggtaatgt acccatcatt actcagtatt ggagtgctga ggacacccac    120
agtgaaggtg tcaactctca cttatggatc gtcaatagaa caatagacat tatgtccaga    180
aatactacct tggtaaggca agatgaagtg gcactgttaa acgcctggag aacagatctt    240
gaaaagggca tctatgcagc agattatgag aatccgtatt acgataacag cacttttacc    300
tctcacttct atgatccaga caccggtaaa acatatgtcg gttagccaa  acaagcaaag    360
gaaactggga ataagtactt taagcttgct ggagaatctt acaagaataa ggatatgaag    420
caagccttct tctatcttgg cctatctttat cattatctgg gtgatgtaaa ccaacctatg    480
catgcagcca acttacaaa  tctatcttat ccccaaggct tccactccaa atacgagaac    540
tttgttgata ccatcaagga caattacaaa gttacagatg taatggcta  ttggaactgg    600
aaaggcatga atcctgaaga atggatacat ggcgctgctg tcgcagccaa gcaagactat    660
tcaggtattg tcaatagcaa cacaaagtct tggttcgtca aggctgctgt ttcccaatca    720
tatgcagata agtggagagc agaagtaacc ccaacgaccg aaaaaggtt  aatgaaagca    780
caaagagtta cagcaggata catacagtta tggttcgata cctatgggaa cagataa       837

SEQ ID NO: 421           moltype = DNA   length = 837
FEATURE                  Location/Qualifiers
source                   1..837
                         mol_type = genomic DNA
                         organism = Bacillus pseudomycoides
SEQUENCE: 421
atgagatttc cttcaatttt tactacagtt ttattcgcag catcctccgc attagctcat     60
accaacgact gtggcaacga agctcctgta ctaaagtggt ccgctgaaga caaacataat    120
gaaggtagaa atagtcactt atggattgtc aataggcaa  ttgacattat gtccaggagt    180
aagaccgtag ttaagccaaa tgagacagca ttactgaacg agtggagaga cgacttagag    240
aatggtatct attcagcaga ctacgaaaac ccatacttcg ataatgggac gttcgcatca    300
catttctacg atccagatac tcaaaagtcc tacatcccctt tgctaaaca  cgccaaggaa    360
acaggtgcta agtatttcaa gcttgcaggt gaagcttaca agaacaaaga tatgaagcaa    420
gcattcttct acttaggatt atctttacat tatcttggtg acgttaatca acccatgcat    480
gctgccaact ttacaaacat tagtactgag gctcccatct ttcactccaa atacgaaaac    540
tttgtcgata ccatcaaaga caactacaaa gttgcagatg gcaacggata ttggaattgg    600
aagggaacaa atagtgaaga ctggataccat ggcgcagccg ttgctagtaa gcaagactat    660
tcctctatcg tgaacgatac cactactagt tggttccta  aggcagctac atcacaagaa    720
tacgcaaaca aatggagagc tgaagtaaca cccacttctg gcaagagatt gatcgaagct    780
cagagagtga ctgccggata cattcacctt tggtttgata catacgtcaa tagataa       837

SEQ ID NO: 422           moltype = DNA   length = 840
FEATURE                  Location/Qualifiers
source                   1..840
                         mol_type = genomic DNA
                         organism = Bacillus mycoides
SEQUENCE: 422
atgagatttc cttcaatttt tactacagtt ttattcgcag catcctccgc attagctcat     60
gaaaacgatg tcaattcga  ccctccaatc gctcagaggt ggagtgccga gagcatccac    120
aatgaaggcg ttagctcaca tctttggatt gtaaacagca aattgacat  aatgtctcaa    180
aacactacag tagttaaaca aaacgagacg gcacttctta atgaatggag aaccaaccta    240
gaagaaggca tctattcagc agactataag aatcccctatt acgaccattc tacctttgca    300
tctcacttct atgaccccga ttctggaaaa acctacattc cgtttgctaa caagcaaaa     360
cagactggtg ccaaatactt caaactagct ggtgaagctt atcagaacaa agacatgaag    420
aacgccttt  tctacctagg tttatctttg cactatttgg gagatgtcaa ccaaccaatg    480
catgctgcca atttcaccaa cattagtcat cctttcggct tccattccaa gtatgagaac    540
tttgtcgaca cagtcaaaga caactataga gtaacagatg gcgatggtta ctggaattgg    600
```

```
aaatctgcaa atccagagga atgggtccat gctagtgcaa gtgccgcaaa agcagatttt  660
ccatctattg tgaacgataa caccaaaaac tggttcttga agctaccgt atcacaagat  720
tccgcagaca aatggagagc agaggttacg cctgtaactg gtaaaaggtt aatgaaagct  780
caaaggataa ctgctggcta cattcaccta tggttcgata cgtacgtcaa taacaaataa  840
```

SEQ ID NO: 423              moltype = DNA   length = 876
FEATURE                     Location/Qualifiers
source                      1..876
                            mol_type = genomic DNA
                            organism = Penicillium cinnamopurpureum
SEQUENCE: 423
```
atgagatttc cttcaatttt tactacagtt ttattcgcag catcctccgc attagctgtt  60
ccgttaagaa gggatgtttc atccgatgat ttgaaacaat tgactttgtt cgctgaatac  120
gctagtgcat cctactgcac aaacaacatc aattctactg gcgacgcatt gtcatgtgca  180
gaaggtaatt gcccagccgt tcagtcagca acgactaaaa ccttgtatga gttcaatgat  240
agtaccgaat ttggagatgt cgctggtttc ttggctgcag acgaaacaaa cgaacttttg  300
gtactatcct ttagggggtc taggacaatt tccacttggg tggcaaacct ggattttggc  360
ttgaccgata catcagatct gtgttctgga tgcgaagcac atggtggatt ttggaaatca  420
tggcagactg ttaccgatga cataacctcc aaaatcgatg ctggtttgaa aagtcaccct  480
ggatatacgg ttgtcttaac aggtcattcc tttggtgcag ctatgccaca ttgggaggt  540
acagccttac gtaacgctgg ttacaagatc aagttgtata catatggtga accaagagtg  600
ggcaatgagg ctttagcaaa gtacattact aaacaaggtg atttgtatag ggtcacacat  660
gcagatgatg tcgttccgaa ggttccacca gcatcatttg gattttctca tgcatccct  720
gagtattgga ttacctccgg aaacaataag accgtttcta ccagtgacat caaagtcatt  780
caaggcgtag gatcaaaaga cggaaacgct ggtaccatca atccagacat tgaggctcac  840
aattggtaca tcgtgcatat agacggatgt caataa                            876
```

SEQ ID NO: 424              moltype = DNA   length = 885
FEATURE                     Location/Qualifiers
source                      1..885
                            mol_type = genomic DNA
                            organism = Talaromyces verruculosus
SEQUENCE: 424
```
atgagatttc cttcaatttt tactacagtt ttattcgcag catcctccgc attagctgaa  60
cccatctata gaaggaagat agctacttct cttttggata gtttggactt attcgcacag  120
tattctgccg ctgcttattg ttccgcaaac ttggatacta caggtactgc actggcttgc  180
aatgtgggta actgcccagc tgtggaagca gcagatacta ccatattgta ttctttgat  240
tcctcatcaa gctttggtga tgcaaccggt tacattgccg ttgatgaatc ccatggctac  300
atcatcttat cattcagagg tacgtcaaac ctggagaatt tcatcgcaac tttagatatg  360
cagttgattg atgcaagttc catttgtagt ggttgtaaag ttcataaggg ttttttggaat  420
acctgggaaa ccgttgcctc agatgtaact tcacaaatca aggcagctct gtctgcttat  480
ccagactata ccttagttgc aactggtcac tcattgggag ctgctctggc agccatcgct  540
gctaccgtct tccgtgcatc tggatatact gttcaattgt acaactatgg cgaacctagg  600
ataggcaatt tggctctagc agacttcatt acaagtgaaa cttcaggaac aaactatcgt  660
gtcacacatt caaatgacat cataccaag ttacctcctg gactgttagg atatcaccac  720
ttttcccctg agtactggat taccagtaag gacaatgtca cagttaccga tagtgatgtt  780
gtggaaatca aaggtgttga ttctacagac ggtaacgatg gtactgctgg tgcctccatt  840
gaggcccata cttggtactt tgtctacatt tcagagtgtt tgtaa                  885
```

SEQ ID NO: 425              moltype = DNA   length = 891
FEATURE                     Location/Qualifiers
source                      1..891
                            mol_type = genomic DNA
                            organism = Talaromyces cellulolyticus
SEQUENCE: 425
```
atgagatttc cttcaatttt tactacagtt ttattcgcag catcctccgc attagctgca  60
ccaaaaccta ttcatagaag gactataacct acttccttac ttgacaactt agaccttttt  120
gctcagtata gtgcagcagc ttattgttca gccaacttag agactacggg taccgcacta  180
gcctgtaatg tgggtaattg tccagctgtt gaagccgaca ataccattat cttgtatagc  240
tttgattcat cctcctcttt cggtgacgct acaggatacg ttgcagttga tgaatcaaat  300
gagtacatta tcttaagctt cagaggtagt agtaacttgg agaattggat cgccaactta  360
gatataccctt tgattgatgc ttcatcaatt tgttccggtt gtaccgttca cgagggcttc  420
tgggacacat gggaaactgt tgcaagtgat gtcactagca aaattgaatc cgcttttgagt  480
acatatccca actatacctt agttgcaact ggtcactcac taggcggtgc tcttgcaag  540
atcgcagcta cagtctttag agcttctggg tacacagtcc agttatacaa ctacggtcaa  600
ccaaggattg gcaacttagc actagcagac ttcataacaa gtgaaacgtc cggaaccaac  660
tatagagtta cacattcaga tgatatagtc ccgaagcttc cacccgagtt acttggttat  720
caccactta gtcctgagta ctggatcaca tcaaacgata atgttactgt gacagactca  780
gatgttgttg aaattcaggg tgtggattca actgctggca acgacggtac cagcggagat  840
tcaattgatg ctcattcttg gtactttgtt tccattagtg agtgttccta a            891
```

SEQ ID NO: 426              moltype = DNA   length = 900
FEATURE                     Location/Qualifiers
source                      1..900
                            mol_type = genomic DNA
                            organism = Penicillium megasporum
SEQUENCE: 426
```
atgagatttc cttcaatttt tactacagtt ttattcgcag catcctccgc attagctggt  60
cccgtttcag tattgagaag agacgaggac gtatccgcct ctgttttgtc tgagctagac  120
```

```
ttctttctc agtattcagc agccgcttac tgttccacaa acatcaattc tgccggtacc    180
aaattgactt gtagtgaggg tatttgtcca cttgttgaaa acgcagatac agaaaccttg    240
gacgaattcg atgaaagtgc ctcttacggt gatgtcgctg gtttcattgc tgtggatcgt    300
acgaatgaac ttctagtctt gtcatttaga gggtctgcta gtttcagtaa ctggttggcc    360
aacattgact tattcctaga tgatgcctct tccgtctgca gtggttgcga agttcattct    420
ggtttctggg atgcatggca gactgttgaa ggacagatta ccacagctct aggttctgcc    480
atggaaacat atccagggta tacgcttgtc tttaccggac acagctatgg tgcagctttg    540
gctgctattg ccgcaaccat ctttagaaac agtggctata ctgttgagtt gtacaactat    600
ggacaaccta gaattggaaa tctagctctg gcagagtaca ttacaaatca gaacaaaggt    660
ggtaactata gggtgacaca tacagacgac atagtcccta aggtcccacc aaagataacg    720
gggtatcacc atgcttcccc tgagtattgg atcacatccg gcaacaatgt tactgttacg    780
actagcgatg tacagttgat aactggcgta gacagcacat ctggtaatga tggtacatca    840
gatgactctg ttgaagctca caggtggtac tttgtacaca tttctatgtg cacaatataa    900

SEQ ID NO: 427        moltype = DNA  length = 837
FEATURE               Location/Qualifiers
source                1..837
                      mol_type = genomic DNA
                      organism = Bacillus toyonensis
SEQUENCE: 427
atgagatttc cttcaattt tactacagtt ttattcgcag catcctccgc attagctcac     60
gagaaaaccg aaggtcataa tgtgaacatc attcagtatt ggagtgctga ggacaagcac    120
agtgaaggtg tcaactctca cttatggatc gtcaatagaa caatagacat tatgtccaga    180
aatactaagt tggtaaagca agatcaaatc atactgttaa acgagtggag aacagatctt    240
gaaaacggca tctattcagc agatcatgag aatccgtatt acgataacag cactttggtg    300
tctcacttct atgatccaga cgacggttct acctatatcc catttgccaa acaagcaaag    360
gaaactgggg ctaagtactt taagcttgct ggagaatctt acaagaataa ggatatgaag    420
caagccttct tctatcttgg cgtctcttta cattatctgg gtgatgtaaa ccaacctatg    480
catgcagcca actttacaaa tctatcttat ccccaaggct tccactccaa atacgagaac    540
tttgttgata ccatcaagga caattacaaa gttacagatg gtaatggcta ttggaactgg    600
aaaggcattc atcctgaaga ttggatacat ggcgctgctg tcggagccaa gcaagctttt    660
tcaggtattg tcaatagcaa cacaaagtct tggttcgtca aggctgctgt tcccaatca     720
tatgcagata agtggagagc agaagtaacc ccaatgaccg gaaaaaggtt gattgaagca    780
caaagagtta cagcaggata catacagtta tggttcgata cctatgtgaa cagataa      837

SEQ ID NO: 428        moltype = DNA  length = 837
FEATURE               Location/Qualifiers
source                1..837
                      mol_type = genomic DNA
                      organism = Bacillus sp.
SEQUENCE: 428
atgagatttc cttcaattt tactacagtt ttattcgcag catcctccgc attagctcac     60
gaggatacc accaagatcc tcccatagca ttgaagtgga gtgccgaaag tgtgcacaac    120
gagggcgtat cctcccatct gtggattgtc aatagagcta tagacataat gtctcagaat    180
actactgtcg ttaaacaaaa tgaaacagcc tactgaatg actggagaac caatttggag    240
gaaggcatct attctgcaga ctacaaaaac ccatactatg acaattccac gtttgctagt    300
cacttctatg atccagattc cgagaaaacc tacattccct tgctaagca agctaaacaa    360
accggtgcca aatacttcaa actagccggt gaagcttatc agaacaaaga catgaaaaac    420
gcattcttct atttgggcct aagtttgcac tatttggggg atgttaatca acctatgcat    480
gctgccaact taccaacat atcccatcca ttcggtttcc actccaagta tgagaacttt    540
gtagatactg tcaaggataa ctatcgtgtt acagatggaa atggttactg gaattggaaa    600
tctgccaatc cagaagaatg ggtgcatgag agtgctgctg ccgcaaaggc cgatttttcct    660
tcaattgtta atgataacac caaaagttgg tttctaaaag ccgctgtttc tcaagattca    720
gcagataagt ggagagctga agtaacacct gttacgggaa aagattgat agaagctcaa    780
agaattactg caggatacat ccacttatgg ttcgacacat acgtaaacaa caaataa      837

SEQ ID NO: 429        moltype = DNA  length = 846
FEATURE               Location/Qualifiers
source                1..846
                      mol_type = genomic DNA
                      organism = Bacillus manliponensis
SEQUENCE: 429
atgagatttc cttcaattt tactacagtt ttattcgcag catcctccgc attagctcat     60
ggcaaccacg atgcaagcaa tgattccgga ataagtatat ccccaagatg gtctgctgaa    120
gaaatgcatg ctgaaggcaa aaactctcac ttatggatag taaacagagc aatcgacatt    180
atggccagag atacaactgt tgtgaaagaa atgaggtgg ccttgttaaa cgagtggagg    240
acagatcttg aagatggaat ctacacagca gattacgaga tccttactac gacaattca     300
acattcgcct ctcacttcta tgatccggac acggacgata cctacattcc gttcgccaaa    360
aacgctaaag tgactggtgc caagtacttc aagttagctg gggaagcata cgaacagcaa    420
gatatgcaac aagccttctt ctacttaggt ttatccttgc actactttgg agacatcaat    480
caaccaatgc atgctagcaa cttacaaac atttcccatc cattcggctt tcactctaag    540
tatgagaact ttgtcgatac catcaaagct ccatatgcag tcaccgattc aaaaggttac    600
tggaactttg caggaggtac gccagaagag tggttacaca ctgctgcagt ggctgccaaa    660
aaggctgctc caggcattgt gaatgaaaca acaaagtggt tcttgaa agcaagtgtt    720
tcccaagaat atgccaatat gtggagagct gaggttactc ccgaaactgg tgccagattg    780
atggaagccc aaagggcaat ggcaggatac atccacttat ggttcgatac ttatgttaat    840
cgttaa                                                                846

SEQ ID NO: 430        moltype = DNA  length = 882
```

| FEATURE | Location/Qualifiers |
| --- | --- |
| source | 1..882 |
| | mol_type = genomic DNA |
| | organism = Penicillium simplicissimum |

SEQUENCE: 430

```
atgagatttc cttcaatttt tactacagtt ttattcgcag catcctccgc attagctgcc   60
ccagctagat ccgtacctag agatgtatct gcttctgtct tggaacagtt taccttatac  120
gcacagtggg ctgccgctgc ttattgttcc aacaacttgg attctacagg tgatgcaatc  180
acttgcgctg gcggttactg cccagaagtg aatcatcta ctactattag tctttctgag   240
ttcaatgaca caaatgactt tggtgatacc gcaggtttcg ttgccgttga taagaccaat  300
aagcaaattg tcgttgcttt cagaggtagc aaaagcatct caaattggat cgcagattta  360
gattttgggt tgacagatgc aagtaacttg tgtagtggtt gtgaagctca taccggtttt  420
cttgaagcat gggaaaccgt tgccgattct attacttcac aaatcggagc agctatgaaa  480
acttatagtg gttatacctt agttgtcact ggtcactcat tgggaggtgc tatcgcagcc  540
atcggtgcta ccgtccttcg taatgctgga tatactttgg atttgtacac ctttggccaa  600
cctagggtcg gcaatttggc tctagcaacc ttcttaacaa agcaaggcaa aatagaatg   660
actcacctaa atgatattgt accaagatta cctccaacta gttttggatt ctcacattca  720
tctcccgaat actggatcac ctctgcccagac gatgtgaatc tgggaggtgc tatcgcagcc  780
gttattgagg gaatcgattc aacagctggt aatgccggtg agttgattga atcagttgct  840
gcccatgcat ggtacatcat tgatattgat ggatgtgaat aa                    882
```

| SEQ ID NO: 431 | moltype = DNA length = 888 |
| --- | --- |
| FEATURE | Location/Qualifiers |
| source | 1..888 |
| | mol_type = genomic DNA |
| | organism = Penicillium arenicola |

SEQUENCE: 431

```
atgagatttc cttcaatttt tactacagtt ttattcgcag catcctccgc attagctgca   60
cctttcaat tgtggtctag agctgtcact ccttccgtct tatcaaagct agacttatac   120
ggccaatatg ctattgccgc atactgtgat gacaacattg cttcagccgg tacggaagtg  180
acatgtagcg ctggtaactg tcctttggtt caagctgcaa ccacaaatac attaagtgag  240
tttaacgaat caaatgaatt cggtgacgtt gctggctttt tcgccgttga tacaacaaac  300
caagctctag ttttgagctt tcgtgggtct catacgatcg acaattggat tgcaaacttg  360
gattttggat tgacctctgt ttccacttta tgttcaggat gcaaagctca cactggcttc  420
tggaaggctt ggaatactgt agcttcagac atcgcaagac ctgtggatgc tgcacaagat  480
acttacccct cttacccccat tatctttact ggacattcat acggagctgc cttggctgcc  540
ctagctgcca caactatgag aaatgctggt tatagcatag aattgtatac atacggacag  600
ccaagaattg gaaatacagc tttagcaacc tacattacaa atcaaaacaa aggtggcaac  660
tatagagtaa ctcatacaaa tgatattgtc cctaggctgg tacctagact tctaggatac  720
tcacacttct ctccagagta ttggatcaca agtggcaata acgtaacagt tactgcctcc  780
gacattactt tagttactgg tatcgatagc aatggtggta atgcaggcga gttactcag   840
tccgttgaac ctcactattg gtactttgtg aagttgaag attgctaa                888
```

| SEQ ID NO: 432 | moltype = DNA length = 891 |
| --- | --- |
| FEATURE | Location/Qualifiers |
| source | 1..891 |
| | mol_type = genomic DNA |
| | organism = Aspergillus aculeatus |

SEQUENCE: 432

```
atgagatttc cttcaatttt tactacagtt ttattcgcag catcctccgc attagctgct   60
cccgcaccta ttgagcgtag atcagtctcc acaacactac ttgatcaaat ggatttgttt  120
gctcagtatt ctgcagctgc ttactgtagt acaaacatag atagtgcatc aaccgccttg  180
agctgctcag cagacaattg tcccttagtc gttgctgctg cccctacagt ccttgatgag  240
ttcaatgaga ctgcagaatt cggggatacc gctgggttcg ttgcagtgga cagtaccaac  300
aaagccatcg ttgttgcttt tagagggagt agcgacttat caaattggat cgccaacatt  360
gattttggtt tgacagacgc cagttccatt tgtacaggtt gcgaaataca ctctgggttc  420
tggaaggcat gggaaacagt agcttccaact attgcctcta aggttgaagc agccgttaca  480
acttattcag attatgacgt tgtctttacg ggtcactcct taggtgccgc tctgctgcc   540
attggcgcta cagtcttgag gaacgatggt tatactgtag acttgtacaa ctttggtcaa  600
ccgagaatag gtaacttagc cttggcagac tacataacgg atcagaataa gggttccaat  660
tacagagtga cgcacacaga cgatattgta cctaaggtcc ctcctgagtt gttaggatat  720
caccattcct ctccagagta ttgataaca agtgataatg acgtcactgt taccacttca  780
gacattaccg aagtcacagg ggtagacagt accgctgaa atgacggaac tttgttggat  840
agtgtttccg ctcacaagtt ctatttcgag tatatctccg cttgtgatta a            891
```

| SEQ ID NO: 433 | moltype = DNA length = 1107 |
| --- | --- |
| FEATURE | Location/Qualifiers |
| source | 1..1107 |
| | mol_type = genomic DNA |
| | organism = Bacillus acidiceler |

SEQUENCE: 433

```
atgagatttc cttcaatttt tactacagtt ttattcgcag catcctccgc attagctatt   60
acttccttct ttggcaacta tcagaaagcc ttcgcttgga gtgatgagga cgtacataat  120
caagatcatt ctactccaca cttcatagtt aatggctccg tcaaattgat tgcagacaat  180
acaaatcctg ccatcaacaa acctacaacc ttgctgaacc agtttagaga tagatgggaa  240
caaggcttat acgatgcaga ccacatcaat cccttctacg acacagggac ctttatgagt  300
catttctacg atcccgatac tcagaccaac tatactggcg caagttatcc aacagctaga  360
caaagcggtg ccaagtactt caatctagcc agtgattact acaagaaagg tgacttcaac  420
aatgcctttt actatttggg cgttagtctt cattactta cagatgttac tcagccttta  480
```

```
catgcatcaa acatttccaa tttggatcac cacgctcccg gttaccacag caagtatgaa   540
acttacgctg aatcaatcca aaatgagatg acgatgcccg attccggatt gtacaattgg   600
atagcctcaa cagaccccga agcatggatc catcaagccg ctgtgcaagc aaaatctgtt   660
ttgccacagg tttggaatga cactatcatt aactactttt ggcaagctgc ctattccaat   720
tactactctg ccatgtggaa atctgaagtc aagaatccta ctttggatca attgaatcaa   780
gctgaacgtg agaccgcagg cttcattgac atgttctttc gtgttaacgg agtagaaatg   840
ccggtcaccg tgtataagga aaatgccttt tcaggtgctt ctgagttatt gggttctggt   900
aactacgatt atgatcaact tgttaagggt attggaaatg atacaatatc ttccattcat   960
attgctccag gctatcaggt gactctattc tcagacgcca actacaaagg tgctagtact  1020
gtgcttacaa atgatgtgca cgatctaggc aactttctc atcaggtttc ttccataaag  1080
gtcgccaaaa tctcagcact taagtaa                                      1107

SEQ ID NO: 434        moltype = DNA   length = 21
FEATURE               Location/Qualifiers
misc_feature          1..21
                      note = Artificial DNA Primer
source                1..21
                      mol_type = other DNA
                      organism = synthetic construct
SEQUENCE: 434
tcttttcgcg ccctggaaag g                                              21

SEQ ID NO: 435        moltype = DNA   length = 49
FEATURE               Location/Qualifiers
misc_feature          1..49
                      note = Artificial DNA Primer
source                1..49
                      mol_type = other DNA
                      organism = synthetic construct
SEQUENCE: 435
tgttttatat ttgttgtaaa aagtagataa ttacttcctt gatgatctg                49

SEQ ID NO: 436        moltype = DNA   length = 22
FEATURE               Location/Qualifiers
misc_feature          1..22
                      note = Artificial DNA Primer
source                1..22
                      mol_type = other DNA
                      organism = synthetic construct
SEQUENCE: 436
gtgacaacaa cagcctgttc tc                                             22

SEQ ID NO: 437        moltype = DNA   length = 21
FEATURE               Location/Qualifiers
misc_feature          1..21
                      note = Artificial DNA Primer
source                1..21
                      mol_type = other DNA
                      organism = synthetic construct
SEQUENCE: 437
agctaatgcg gaggatgctg c                                              21

SEQ ID NO: 438        moltype = DNA   length = 22
FEATURE               Location/Qualifiers
misc_feature          1..22
                      note = Artificial DNA Primer
source                1..22
                      mol_type = other DNA
                      organism = synthetic construct
SEQUENCE: 438
acagaagacg ggagacacta gc                                             22

SEQ ID NO: 439        moltype = DNA   length = 18
FEATURE               Location/Qualifiers
misc_feature          1..18
                      note = Artificial DNA Primer
source                1..18
                      mol_type = other DNA
                      organism = synthetic construct
SEQUENCE: 439
ggggtcgcaa cttttccc                                                  18
```